US007585656B2

(12) United States Patent
Minoprio et al.

(10) Patent No.: US 7,585,656 B2
(45) Date of Patent: Sep. 8, 2009

(54) CRYSTALLOGRAPHIC STRUCTURE OF TCPRACA AND USES THEREFOR

(75) Inventors: Paola Minoprio, Villiers sur Marne (FR); Pedro Alzari, Paris (FR); Alejandro Buschiazzo, Paris (FR); Christophe Grégoire, Parede PaVegol (FR); Armand Berneman, Paris (FR); Wim M. Degrave, Rio de Janeiro (BR)

(73) Assignees: Institute Pasteur, Paris (FR); Centre National de la Recherche Scientifique (CNRS), Paris (FR)

( * ) Notice: Subject to any disclaimer, the term of this patent is extended or adjusted under 35 U.S.C. 154(b) by 821 days.

(21) Appl. No.: 10/853,533

(22) Filed: May 26, 2004

(65) Prior Publication Data

US 2005/0250195 A1    Nov. 10, 2005

Related U.S. Application Data

(63) Continuation-in-part of application No. 10/775,339, filed on Feb. 11, 2004, now abandoned.

(60) Provisional application No. 60/484,661, filed on Jul. 7, 2003, provisional application No. 60/474,238, filed on May 30, 2003, provisional application No. 60/446,263, filed on Feb. 11, 2003.

(51) Int. Cl.
*C12N 9/90* (2006.01)
*C30B 7/00* (2006.01)

(52) U.S. Cl. ......................................... 435/233; 117/70
(58) Field of Classification Search ....................... None
See application file for complete search history.

(56) References Cited

U.S. PATENT DOCUMENTS

| 6,459,996 B1 | 10/2002 | Somers et al. |
| 6,524,589 B1 | 2/2003 | Reichert et al. |
| 6,546,074 B1 | 4/2003 | Blundell et al. |
| 2006/0014162 A1 | 1/2006 | Minoprio et al. |

FOREIGN PATENT DOCUMENTS

| JP | 55-081595 | 6/1980 |
| WO | WO-01/40449 A2 | 6/2001 |
| WO | WO-01/40449 A3 | 6/2001 |
| WO | WO-2004-072223 A2 | 8/2004 |
| WO | WO-2004/106506 A2 | 12/2004 |

OTHER PUBLICATIONS

Branden et al., "Introduction to Protein Structure Second Edition", Garland Publishing Inc., New York, 1999, pp. 374-375.*
Drenth et al., "Principles of X-ray Crystallography," Springer, New York, 1999, p. 1.*
Kierzek et al., Biophys Chem 91:1-20, 2001.*
Wiencek, Ann Rev Biomed Eng 1:505-534, 1999.*
Buts et al., Acta Cryst D61:1149-1159, 2005.*
Skarzynski et al., Acta Cryst D62:102-107, 2006.*
Kundrot et al., Cell. Mol. Life Sci. 61: 525-536, 2004.*
Weber, Methods in Enzymology, 276:13-22, 1997.*
Cudney, Rigaku Journal, 16:1-7, 1999.*
McPherson et al., Eur. J. Biochem. 189:1-23, 1990.*
Amersham Protein Purification Handbook, Oct. 2001, p. 59.*
Cardinale, G.J. et al., "Purification and Mechanism of Action of Proline Racemase," *Biochemistry*, vol. 7, No. 11, pp. 3970-3978 (1968).
Chamond, N. et al., "Biochemical Characterization of Proline Racemases from the Human Protozoan Parasite *Trypanosoma cruzi* and Definition of Putative Protein Signatures," *The Journal of Biological Chemistry*, vol. 278, No. 18, pp. 15484-15494 (May 2, 2003).
Chamond et al.; "Immunotherapy of *Trypanosoma cruzi* Infections"; *Current Drug Targets—Immune, Endocrine & Metabollic Disorders*, vol. 2, No. 3, pp. 247-254 (2002).
Delvecchio, V.G. et al., "The Genome Sequence of the Facultative Intracellular Pathogen *Brucella melitensis*," *Proc. Natl. Acad. Sci. U.S.A.*, vol. 99, No. 1, pp. 443-448 (Jan. 8, 2002).
Minoprio, P. et al., U.S. Appl. No. 10/545,149, filed Aug. 10, 2004, as a national stage application of International Application No. WO 2004/072223 A2, and published as WO 2004/072223 A2.
Minoprio, P. et al., U.S. Appl. No. 10/558,371, filed Nov. 29, 2005, as a national stage application of PCT/IB04/002062, filed Feb. 11, 2004, and published as WO 2004/106506 A2.
Reina-San-Martin, B. et al., "A B-Cell Mitogen From a Pathogenic Trypanosome is a Eukaryotic Proline Racemase," *Nature Medicine*, vol. 6, No. 8, pp. 890-897 (Aug. 2000).
Rudnick, G. et al., "Reaction Mechanism and Structure of the Active Site of Proline Racemase," *Biochemistry*, vol. 14, No. 20, pp. 4515-4522 (1975).
Delvecchio, V. G. et al., "The Genome Sequence of the Facultative Intracellular Pathogen *Brucella melitensis*," Abstract of *Proc. Natl. Acad. Sci. U.S.A.*, vol. 99, No. 1, pp. 443-448, XP002290326 (2002).
Office Action mailed Apr. 5, 2006, in U.S. Appl. No. 11/008,570, filed Dec. 10, 2004 (published as US-2006-0014162-A1).

* cited by examiner

*Primary Examiner*—David J Steadman
(74) *Attorney, Agent, or Firm*—Finnegan, Henderson, Farabow, Garrett & Dunner LLP

(57) ABSTRACT

The present invention provides the crystal structure of the *Trypanosoma cruzi* PRACA proline racemase. Methods of modelling drugs that treat or prevent infection by *T. cruzi* are also provided, as are the drugs that are identified.

8 Claims, 1 Drawing Sheet

SEQUENCE LISTING

<160> NUMBER OF SEQ ID NOS: 3

<210> SEQ ID NO 1
<211> LENGTH: 1665
<212> TYPE: DNA
<213> ORGANISM: Trypanosoma cruzi

<400> SEQUENCE: 1

```
ccttttctct tttaaaaaca aaaaaattc cggggggaat atggaacagg gtatatgcgt      60
aaaagtgtct gtcccaaaca aaatttttt ttttccgcct tcccatttt tttttttttt     120 tgtgtgtttc ccttgatctc tcgaacaggg caggaaaagc ttctgtttga ccaaaaatat    180
aaaattatta agggcgagaa aaaagaaaag aaaaaaaatc aacgagcaaa caggagagaa    240
caccaacaaa aaagggaaat tatgcgattt aagaaatcat tcacatgcat cgacatgcat    300
acggaaggtg aagcagcacg gattgtgacg agtggtttgc cacacattcc aggttcgaat    360
atggcggaga agaaagcata cctgcaggaa aacatggatt atttgaggcg tggcataatg    420
ctggaaccac gtggtcatga tgatatgttt ggagccttt tatttgaccc tattgaagaa    480
ggcgctgact tgggcatggt attcatggat accggtggct atttaaatat gtgtggacat    540
aactcaattg cagcggttac ggcggcagtt gaaacgggaa ttgtgagcgt gccggcgaag    600
gcaacaaatg ttccggttgt cctggacaca cctgcgggt tggtgcgcgg tacggcacac    660
cttcagagtg gtactgagag tgaggtgtca aatgcgagta ttatcaatgt accctcattt    720
ttgtatcagc aggatgtggt ggttgtgttg ccaaagccct atggtgaagt acgggttgat    780
```

```
attgcatttg gaggcaattt tttcgccatt gttcccgcgg agcagttggg aattgatatc      840
tccgttcaaa acctctccag gctgcaggag gcaggagaac ttctgcgtac tgaaatcaat      900
cgcagtgtga aggttcagca ccctcagctg ccccatatta acactgtgga ctgtgttgag      960
atatacggtc cgccaacgaa cccggaggca aactacaaga acgttgtgat atttggcaat     1020
cgccaggcgg atcgctctcc atgtgggaca ggcaccagcg ccaagatggc aacactttat     1080
gccaaaggcc agcttcgcat cggagagact tttgtgtacg agagcatact cggctcactc     1140
ttccagggca gggtacttgg ggaggagcga ataccggggg tgaaggtgcc ggtgaccaaa     1200
gatgccgagg aagggatgct cgttgtaacg gcagaaatta ctggaaaggc ttttatcatg     1260
ggtttcaaca ccatgctgtt tgacccaacg gatccgttta agaacggatt cacattaaag     1320
cagtagatct ggtagagcac agaaactatt ggggaacacg tgcgaacagg tgctgctacg     1380
tgaagggtat tgaatgaatc gttttttttt attttattt ttattttta ttagtgcatt     1440 attattaaat ttttttttg ttttggggtt tcaacggtac cgcgttggga gcagggaagc     1500
gatagcggcc ggacaatttt ttgcttttat tttcattttc atcttcctac ccaacccccct   1560 tggttccacc ggtcgcggcg gggtcttgtg ggtggaggag tcctaaatcc cgcacctcgg     1620
aggaataaac atatttcaat ttcatatctt ggaatcaaaa ggcat                     1665
```

<210> SEQ ID NO 2
<211> LENGTH: 423
<212> TYPE: PRT
<213> ORGANISM: Trypanosoma cruzi

<400> SEQUENCE: 2

```
Met Arg Lys Ser Val Cys Pro Lys Gln Lys Phe Phe Ser Ala Phe
 1               5                  10                  15

Pro Phe Phe Phe Phe Cys Val Phe Pro Leu Ile Ser Arg Thr Gly
                20                  25                  30

Gln Glu Lys Leu Leu Phe Asp Gln Lys Tyr Lys Ile Ile Lys Gly Glu
            35                  40                  45

Lys Lys Glu Lys Lys Lys Asn Gln Arg Ala Asn Arg Arg Glu His Gln
        50                  55                  60

Gln Lys Arg Glu Ile Met Arg Phe Lys Lys Ser Phe Thr Cys Ile Asp
    65                  70                  75                  80

Met His Thr Glu Gly Glu Ala Ala Arg Ile Val Thr Ser Gly Leu Pro
                85                  90                  95

His Ile Pro Gly Ser Asn Met Ala Glu Lys Lys Ala Tyr Leu Gln Glu
            100                 105                 110

Asn Met Asp Tyr Leu Arg Arg Gly Ile Met Leu Glu Pro Arg Gly His
        115                 120                 125

Asp Asp Met Phe Gly Ala Phe Leu Phe Asp Pro Ile Glu Glu Gly Ala
    130                 135                 140

Asp Leu Gly Met Val Phe Met Asp Thr Gly Gly Tyr Leu Asn Met Cys
145                 150                 155                 160

Gly His Asn Ser Ile Ala Ala Val Thr Ala Ala Val Glu Thr Gly Ile
                165                 170                 175

Val Ser Val Pro Ala Lys Ala Thr Asn Val Pro Val Val Leu Asp Thr
            180                 185                 190

Pro Ala Gly Leu Val Arg Gly Thr Ala His Leu Gln Ser Gly Thr Glu
        195                 200                 205

Ser Glu Val Ser Asn Ala Ser Ile Ile Asn Val Pro Ser Phe Leu Tyr
    210                 215                 220
```

```
Gln Gln Asp Val Val Val Leu Pro Lys Pro Tyr Gly Glu Val Arg
225                 230                 235                 240

Val Asp Ile Ala Phe Gly Gly Asn Phe Phe Ala Ile Val Pro Ala Glu
            245                 250                 255

Gln Leu Gly Ile Asp Ile Ser Val Gln Asn Leu Ser Arg Leu Gln Glu
            260                 265                 270

Ala Gly Glu Leu Leu Arg Thr Glu Ile Asn Arg Ser Val Lys Val Gln
            275                 280                 285

His Pro Gln Leu Pro His Ile Asn Thr Val Asp Cys Val Glu Ile Tyr
            290                 295                 300

Gly Pro Pro Thr Asn Pro Glu Ala Asn Tyr Lys Asn Val Val Ile Phe
305                 310                 315                 320

Gly Asn Arg Gln Ala Asp Arg Ser Pro Cys Gly Thr Gly Thr Ser Ala
            325                 330                 335

Lys Met Ala Thr Leu Tyr Ala Lys Gly Gln Leu Arg Ile Gly Glu Thr
            340                 345                 350

Phe Val Tyr Glu Ser Ile Leu Gly Ser Leu Phe Gln Gly Arg Val Leu
            355                 360                 365

Gly Glu Glu Arg Ile Pro Gly Val Lys Val Pro Val Thr Lys Asp Ala
            370                 375                 380

Glu Glu Gly Met Leu Val Val Thr Ala Glu Ile Thr Gly Lys Ala Phe
385                 390                 395                 400

Ile Met Gly Phe Asn Thr Met Leu Phe Asp Pro Thr Asp Pro Phe Lys
            405                 410                 415

Asn Gly Phe Thr Leu Lys Gln
            420

<210> SEQ ID NO 3
<211> LENGTH: 399
<212> TYPE: PRT
<213> ORGANISM: Artificial Sequence
<220> FEATURE:
<223> OTHER INFORMATION: Description of Artificial Sequence: Recombinant
      TcPRACA having a 6-His tag replacing wild-type
      N-terminal 30 residues

<400> SEQUENCE: 3

His His His His His His Thr Gly Gln Glu Lys Leu Leu Phe Asp Gln
  1               5                  10                  15

Lys Tyr Lys Ile Ile Lys Gly Glu Lys Lys Glu Lys Lys Lys Asn Gln
            20                  25                  30

Arg Ala Asn Arg Arg Glu His Gln Gln Lys Arg Glu Ile Met Arg Phe
            35                  40                  45

Lys Lys Ser Phe Thr Cys Ile Asp Met His Thr Glu Gly Glu Ala Ala
        50                  55                  60

Arg Ile Val Thr Ser Gly Leu Pro His Ile Pro Gly Ser Asn Met Ala
 65                  70                  75                  80

Glu Lys Lys Ala Tyr Leu Gln Glu Asn Met Asp Tyr Leu Arg Arg Gly
                85                  90                  95

Ile Met Leu Glu Pro Arg Gly His Asp Asp Met Phe Gly Ala Phe Leu
            100                 105                 110

Phe Asp Pro Ile Glu Glu Gly Ala Asp Leu Gly Met Val Phe Met Asp
            115                 120                 125

Thr Gly Gly Tyr Leu Asn Met Cys Gly His Asn Ser Ile Ala Ala Val
    130                 135                 140
```

-continued

```
Thr Ala Ala Val Glu Thr Gly Ile Val Ser Val Pro Ala Lys Ala Thr
145                 150                 155                 160

Asn Val Pro Val Val Leu Asp Thr Pro Ala Gly Leu Val Arg Gly Thr
                165                 170                 175

Ala His Leu Gln Ser Gly Thr Glu Ser Glu Val Ser Asn Ala Ser Ile
                180                 185                 190

Ile Asn Val Pro Ser Phe Leu Tyr Gln Gln Asp Val Val Val Val Leu
                195                 200                 205

Pro Lys Pro Tyr Gly Glu Val Arg Val Asp Ile Ala Phe Gly Gly Asn
                210                 215                 220

Phe Phe Ala Ile Val Pro Ala Glu Gln Leu Gly Ile Asp Ile Ser Val
225                 230                 235                 240

Gln Asn Leu Ser Arg Leu Gln Glu Ala Gly Glu Leu Leu Arg Thr Glu
                245                 250                 255

Ile Asn Arg Ser Val Lys Val Gln His Pro Gln Leu Pro His Ile Asn
                260                 265                 270

Thr Val Asp Cys Val Glu Ile Tyr Gly Pro Pro Thr Asn Pro Glu Ala
                275                 280                 285

Asn Tyr Lys Asn Val Val Ile Phe Gly Asn Arg Gln Ala Asp Arg Ser
                290                 295                 300

Pro Cys Gly Thr Gly Thr Ser Ala Lys Met Ala Thr Leu Tyr Ala Lys
305                 310                 315                 320

Gly Gln Leu Arg Ile Gly Glu Thr Phe Val Tyr Glu Ser Ile Leu Gly
                325                 330                 335

Ser Leu Phe Gln Gly Arg Val Leu Gly Glu Glu Arg Ile Pro Gly Val
                340                 345                 350

Lys Val Pro Val Thr Lys Asp Ala Glu Glu Gly Met Leu Val Val Thr
                355                 360                 365

Ala Glu Ile Thr Gly Lys Ala Phe Ile Met Gly Phe Asn Thr Met Leu
                370                 375                 380

Phe Asp Pro Thr Asp Pro Phe Lys Asn Gly Phe Thr Leu Lys Gln
385                 390                 395
```

CRYSTALLOGRAPHIC STRUCTURE OF TCPRACA AND USES THEREFOR

CROSS-REFERENCE TO RELATED APPLICATIONS

Figure 1:
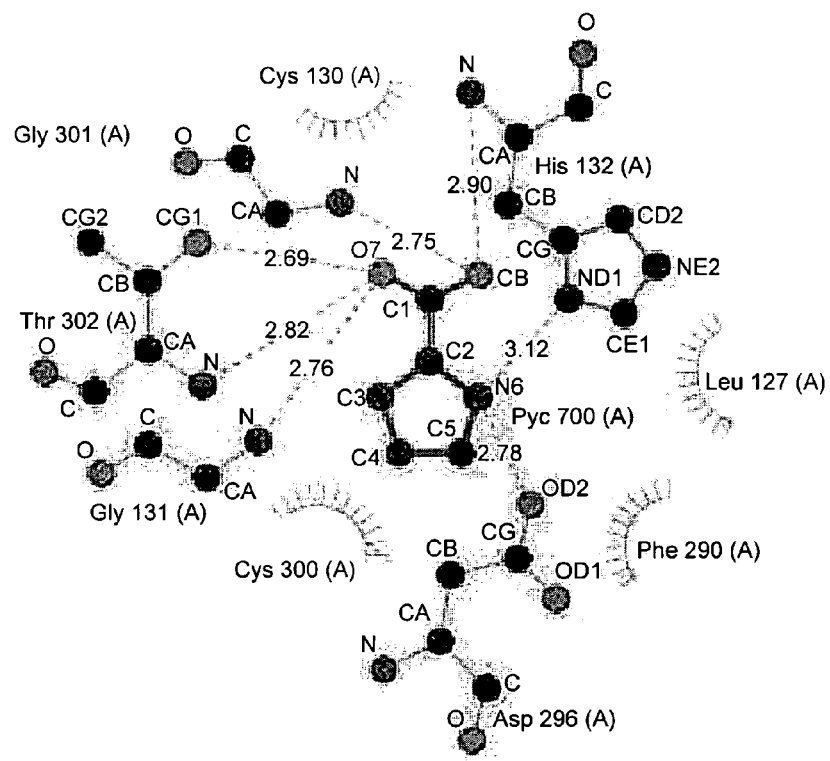

This application is based on and claims the benefit of U.S. Provisional Application No. 60/484,661, filed Jul. 7, 2003 and U.S. Provisional Application No. 60/474,238, filed May 30, 2003. The entire disclosures of these provisional applications are relied upon and incorporated by reference herein. This application is also based on and is a continuation-in-part of application Ser. No. 10/775,339, filed Feb. 11, 2004, now abandoned, which claims the benefit of U.S. Provisional Application No. 60/446,263, filed Feb. 11, 2003.

BACKGROUND OF THE INVENTION

1. Field of the Invention

The present invention relates to the *Trypanosoma cruzi* proline racemase, a 45 kDa polyclonal activator. More specifically, the present invention relates to the crystal structure of the TcPA45 (TcPRAC) protein of *T. cruzi*, methods of obtaining crystals and crystal structures of the TcPA45 (TcPRAC) protein of *T. cruzi*, and methods of using the crystal structure of the TcPA45 (TcPRAC) protein of *T. cruzi* to identify drugs that affect the pathogenicity of *T. cruzi*.

2. Description of the Related Art

D-amino acids have long been described in the cell wall of eubacteria, where they constitute essential elements of the peptidoglycan and act as substitutes of cell wall teichoic acids (4), and in other parts of eubacteria as part of small peptides made by non-ribosomal protein synthesis (3, 4). In contrast, until recently it was believed that only L-amino acid enantiomers were present in eukaryotes (apart from a very low level of D-amino acids from spontaneous racemization due to aging) (1). However, recently an increasing number of studies have reported the presence of various D-amino acids (D-aa) in both protein-bound (5) and free forms (6) in a wide variety of eukaryotes, including mammals. The origin of free D-aa can be exogenous (9) or endogenous (7, 8, 10-12) to the eukaryote.

Proline racemase catalyzes the interconversion of L- and D-proline enantiomers, and has, to date, been described in only two species, *Clostridium sticklandii* and *Trypanosoma cruzi*. The enzyme from the eubacterium *C. sticklandii* contains cysteine residues in the active site, and does not require co-factors or known co-enzymes for activity. As disclosed in U.S. Provisional Patent Application No. 60/446,263, and U.S. patent application Ser. No. 09/725,945, now U.S. Pat. No. 6,713,617, the entire disclosures of which are hereby incorporated by reference, the enzyme from the parasitic eukaryote *T. cruzi*, which causes Chagas' Disease in humans, exists in two forms, TcPRACA and TcPRACB, encoded by two independent genes, respectively. The *T. cruzi* TcPRACB enzyme represents an intracellular form of the enzyme that is present in non-infective forms of the organism. The *T. cruzi* TcPRACA enzyme represents a membrane-bound or secreted form of the enzyme that is present in infective forms of the organism. TcPRACA may also originate an intracellular version of proline racemase by a mechanism of alternative splicing. The two forms of the enzyme share a high level of homology, and appear to be a result of gene duplication. A cysteine at residue 330 of the TcPRACA enzyme is located in the active site of the enzyme. A cysteine at position 160 of the TcPRACA is also involved in the active site of the enzyme. The TcPRACA enzyme is a potent host B-cell mitogen that supports parasite evasion of specific immune responses, and has been implicated in persistence of the parasite through polyclonal lymphocyte activation (10). The mitogenic properties of the *T. cruzi* proline racemase are dependent on the integrity of the enzyme active site (2).

In view of the importance of both forms of the TcPRAC enzyme (i.e., TcPRACA and TcPRACB) to the growth and infectivity of *T. cruzi*, structural and biochemical information on the enzyme is needed to provide new drugs and methods for treating *T. cruzi* infection.

SUMMARY OF THE INVENTION

The present invention addresses the needs of the art for information on the TcPRAC enzyme by providing the three-dimensional structure of the TcPRACA enzyme. The three-dimensional structure of the TcPRACA can be used as a model for rational drug design to design and develop drugs that affect the biological activity of the TcPRACA, and that affect the ability of *T. cruzi* to establish and perpetuate the process of infection. It also can be used to model drugs that affect proline racemases of other organisms.

In one aspect of the invention, a crystal comprising *Trypanosoma cruzi* PRACA proline racemase (TcPRACA) is provided. In another aspect, the TcPRACA has the sequence of SEQ ID NO:3, while in a further aspect the TcPRACA is encoded by SEQ ID NO:1. In another aspect of the invention the crystal has a three-dimensional structure defined by the data set listed in Table 2.

The crystal can be provided in multiple forms, including as a component of a composition. Accordingly, in another aspect the invention provides a composition comprising a crystal comprising (TcPRACA) and a salt.

In another aspect, the invention provides a method of making a crystal comprising TcPRACA. In general, the method comprises providing TcPRACA in a solution and at a concentration suitable for the process of crystallization, and allowing the TcPRACA to crystallize from the solution. In one aspect, the method comprises providing TcPRACA at a concentration of 5-6 mg/ml in 25 mM sodium acetate, pH 5.2, to provide a protein solution; mixing the protein solution with an equal volume of a buffer comprising 0.2 M ammonium acetate, 50 mM trisodium citrate dihydrate, pH 5.6, and 15% (w/v) polyethylene glycol 4000; and allowing a crystal comprising TcPRACA to form.

In yet another aspect, the invention provides a method of identifying a substance that affects the biological activity of TcPRACA. The method comprises providing a model of TcPRACA that includes the proline binding site of the TcPRACA, and using the model to determine the structure of a substance that binds to the TcPRACA. In one aspect, the substance interacts with residue Cys160 of TcPRACA. In another aspect, using the model may comprise providing a model of the structure of the substance that binds to the TcPRACA; fitting the model of the structure of the substance into a binding site on the modeled TcPRACA; and selecting a substance whose model structure fits into a binding site on the modeled TcPRACA. In another aspect, the method may further comprise providing the TcPRACA; providing the substance; combining the TcPRACA with the substance; and determining the effect of the substance on the biological activity of the TcPRACA. In a further aspect, determining the effect of the substance on the biological activity of the TcPRACA may comprise modulating TcPRACA activity by means of a molecule being tested in the presence of an equimolar mixture of a L- and D-proline and of TcPRACA to be modulated; oxidatively deaminating the D-proline generated in step (A) by means of a D-amino oxidase with a prosthetic group; and detecting the hydrogen peroxide generated by the oxidative deamination; where modulation of the hydrogen peroxide is indicative of the capability of the tested molecule to modulate TcPRACA activity. In one aspect, the molecule inhibits said racemase activity. In a further aspect, the method identifies a substance that affects the infectivity of *T. cruzi*.

In a further aspect, the invention provides a substance that affects the enzymatic activity of the TcPRACA racemase. In one aspect, the substance interacts with residue Cys160 of TcPRACA. The substance that affects the enzymatic activity of the TcPRACA can affect the mitogenicity of the TcPRACA as well. In addition, the substance can affect the parasitic activity or infectivity of *T. cruzi*.

In still another aspect, the invention provides a computer readable medium that contains information that can be used to create a model, such as a molecular model, of the TcPRACA. In one aspect, the computer readable medium has recorded thereon the data set listed in Table 2. The computer readable medium may be, for example, a computer diskette, a compact disk, a digital video disk, or a computer hard drive.

In a further aspect, the invention provides a computer system comprising a central processing unit and a video display unit. According to the invention, the computer system, and in particular the combination of the central processing unit and the video display unit, is capable of converting data regarding the positions of atoms in the TcPRACA crystal into a model of TcPRACA. In one aspect, the central processing unit and the video display unit are physically attached. In another aspect, the computer system comprises a central processing unit and a video display unit, where the combination of the central processing unit and the video display unit is capable of converting the data set listed in Table 2 into a model of TcPRACA.

In a still further aspect, the invention provides a method for designing a molecule that affects the biological activity of TcPRACA. The method comprises using the data set listed in Table 2. In another aspect, the invention provides a molecule designed by this method. In another aspect of the method, the method comprises using residue Cys330 as a interaction target for the designed substance.

BRIEF DESCRIPTION OF THE DRAWING

FIG. 1 depicts the active site of the TcPRACA enzyme. In crystallographic studies presented in FIG. 1, the residue Cys330 and the residue Cys160 of the TcPRACA peptide sequence are represented as Cys300 and Cys130, respectively.

DETAILED DESCRIPTION OF VARIOUS EMBODIMENTS

Reference will now be made in detail to specific exemplary embodiments of the invention. The following specific embodiments are not to be construed as limiting the full scope of the invention, but are presented merely to exemplify and explain in detail aspects and embodiments of the invention.

In one aspect of the invention, a crystal comprising *Trypanosoma cruzi* PRACA proline racemase (TcPRACA) is provided. The crystal can be provided alone, or as part of a composition. If provided as part of a composition, the composition can comprise one or more other components, such as proteins, salts, solvents, etc. The other components can be selected by those of skill in the art based on the intended use of the crystal.

In embodiments of this aspect of the invention, the TcPRACA has the sequence of SEQ ID NO:3. In other embodiments, the TcPRACA has the sequence of SEQ ID NO:2 (GenBank Accession: AAF97423.1). In other embodiments, the TcPRACA is encoded by SEQ ID NO:1 (GenBank Accession: AF195522). In yet other embodiments, the crystal has a three-dimensional structure that can be defined by the data set listed in Table 2.

The TcPRACA proteins that are crystallized can be produced using any known technique. For example, TcPRACA can be overexpressed in *E. coli* and purified as an excreted protein or from cell lysates. Likewise, it can be expressed in eukaryotic systems, such as a baculovirus system. Those of skill in the art are aware of numerous systems that are suitable for expression of proteins for purification. Thus, the techniques need not be detailed here. Likewise, protein purification techniques are well known to those of skill in the art, and thus need not be detailed here. An exemplary expression and purification scheme is disclosed below in the Examples.

It is now widely recognized that the crystal structure of a protein is a powerful tool for identifying substances that bind to the protein. Indeed, the three-dimensional structure of a protein can be used to model molecular interactions between the protein and various substances, permitting one to design molecules that specifically bind to the protein without having to first chemically synthesize the molecules. The present invention provides such an advantage for the TcPRACA racemase by providing, for the first time, the crystal structure of the racemase. The crystal structure includes the proline binding site, which acts not only as the active site of the enzyme, but whose integrity is involved in the mitogenic activity. Furthermore, the crystal structure provides a plethora of data about the exterior surface of the TcPRACA, which, like the active site, can be used to design and create therapeutic molecules for preventing or treating *T. cruzi* infection. The crystals of the invention are useful not only for modelling of the racemase and substances that bind to it, but also for modelling the three-dimensional structures of related proteins. Although a powerful use of the crystals of the invention is as a model for drug design, the process of crystallization can also be used as a purification step for the protein.

In a second aspect, the invention provides a method of making a crystal comprising TcPRACA. The method comprises providing TcPRACA at a concentration of 5-6 mg/ml in 25 mM sodium acetate, pH 5.2, to provide a protein solution; mixing the protein solution with an equal volume of a buffer comprising 0.2 M ammonium acetate, 50 mM trisodium citrate dihydrate, pH 5.6, and 15% (w/v) polyethylene glycol 4000; and allowing a crystal to form. It is well within the abilities of those of skill in the art to modify these conditions to obtain crystals according to the invention. For example, the pH of the solutions can be modified within about one unit, the protein can be provided in a concentration that is more or less than 5-6 mg/ml, and the concentrations of the salt components in the protein solution and buffer can be varied. Thus, the invention contemplates crystallization conditions that are not identical to those disclosed herein, but that are similar and result in a crystal of TcPRACA.

Once the crystal forms, it can be analyzed to determine its three-dimensional structure using any number of techniques. For example, the three-dimensional structure of the crystal can be determined using x-ray diffraction using, for example, synchrotron radiation or the sealed tube or rotating anode methods. In addition, neutron diffraction analysis can be used to determine the three-dimensional structure of the crystal.

Data can be collected using any suitable technique, including precession photography, oscillation photography, and diffractometer data collection.

Electron density maps can be calculated using programs such as those from the CCP4 computing package (13) and the modelling program O (14). Docking programs, such as GRAM, DOCK, and AUTODOCK (15, 16) are available for identification of substances that interact with TcPRACA. Other well-known computer programs for model building and analysis include HKL, MOSFILM, XDS, SHARP, PHASES, HEAVY, XPLOR, TNT, NMRCOMPASS, NMRPIPE, DIANA, NMRDRAW, FELIX, VNMR, MADIGRAS, BUSTER, SOLVE, FRODO, RASMOL, INSIGHT, MCSS/HOOK, CHARMM, LEAPFROG, CAVEAT (UC Berkeley), CAVEAT (MSI), MODELLER, CATALYST, ISIS, and CHAIN.

In a third aspect, the invention provides a method of identifying a substance that affects the biological activity of TcPRACA. In general, the method comprises providing a model of the TcPRACA, or a portion of the TcPRACA, and using the model to determine the structure of a substance that binds to the TcPRACA. Crystal structure information presented here is useful in designing inhibitors or activators of TcPRACA by modelling their interaction with TcPRACA. In embodiments, the model of TcPRACA includes the proline binding site (the active site). The substance can be a substance having a structure that is designed using the TcPRACA structure, or can be a structure that exists in a computer database. Alternatively, the substance can be identified by first designing a substance using the three-dimensional structure of the TcPRACA, then using the structure of that substance to probe databases for other compounds having similar structures. Those structures can then be modelled with the TcPRACA to determine if they will bind. The method thus can be a method of rational drug design.

The data set disclosed in Table 2 provides a relative set of positions that define a shape in three dimensions. It is to be understood that an entirely different set of positions having a different origin or axes can define a similar three-dimensional shape. Likewise, manipulation of the data set to increase or decrease the distances between various atoms, or to add or subtract solvent molecules, might not significantly alter the overall three-dimensional structure defined by the data set in Table 2. Accordingly, reference to the data set in Table 2 should be understood to include coordinate sets that define the same general structure of TcPRACA, or in which minor variations have been made to the data set. Coordinate sets that are not identical, but define a similar structure as that defined by the data set of Table 2 can be identified using various computer programs, such as the Molecular Similarity application of QUANTA (Molecular Simulations Inc., San Diego, Calif.).

In addition, it is to be understood that the three-dimensional structure defined by the data set in Table 2 encompasses three-dimensional structures of TcPRACA proteins in which one or more amino acids have been altered or deleted, or in which one or more amino acids have been added, without affecting the general three-dimensional structure of the protein. More specifically, it is well known in the art that many changes can be made in a protein's primary amino acid sequence without changing its overall three-dimensional structure or its activity. Such mutations can include a single mutation or multiple mutations within the same primary amino acid sequence. Indeed, with the information provided by the three-dimensional structure of the present invention, those of skill in the art can readily identify numerous amino acids that do not play any apparent role in enzyme activity or folding/structure. It is to be understood that mutants that do not significantly affect the general three-dimensional structure or the activity of the resulting enzyme are encompassed by reference to the data set of Table 2.

In embodiments, the method of identifying a substance also comprises providing the TcPRACA; providing the substance; combining the TcPRACA with the substance; and determining the effect of the substance on the biological activity of the TcPRACA. For example, the method can include contacting the TcPRACA with the substance, assaying the racemase activity of the TcPRACA, and comparing the activity to the activity of an equal amount of TcPRACA assayed under the same conditions, but in the absence of the substance.

An effect of the substance can be an inhibitory effect or an activating effect. In embodiments, the substance inhibits the activity of the TcPRACA at least 80%. That is, the activity of the TcPRACA in the presence of the substance is 20% or less of the activity of the racemase in the absence of the substance, when present at a concentration that provides maximal inhibition. Inhibition can be 80%, 90%, 95%, 98%, or 99% or greater, such as 100%. Alternatively, the activity of the TcPRACA can be activated. For example, it can be 80% more active, 90% more active, 95% more active, or 99% or greater more active. In embodiments, it is twice as active (i.e., 100% more active) or greater.

In embodiments, the method of identifying a substance comprises providing a model of the structure of the substance that binds to the TcPRACA; fitting the model of the structure of the substance into a binding site on the modelled TcPRACA; and selecting a substance whose model structure fits into a binding site on the modelled TcPRACA.

According to the method of identifying a substance, the model of TcPRACA preferably includes the active site of the enzyme. As discussed above, the conformation of the enzyme has been linked to the mitogenic activity of the enzyme, and appears to be involved in the parasitic activity of *T. cruzi*. The occupation of the active site by a specific inhibitor induces a conformational change affecting completely the mitogenic activity of the protein. Thus, the active site of the enzyme is a logical target for binding of a substance that affects, and in particular, inhibits, the activity of TcPRACA.

However, the invention also includes identifying a substance that binds to a site on the TcPRACA that is not part of the active site. Based on the three-dimensional structure disclosed herein, multiple binding sites for substances can be envisioned. It is well known that binding of a molecule at a site that is distant from an active site of an enzyme can, in some instances, affect the activity of the enzyme by causing a change in the three-dimensional structure of the enzyme, which results in a change in the three-dimensional structure of the active site. Modelling of binding in such a way is encompassed by the present invention. Thus, sites other than those that are part of the active site of the enzyme can be used to identify substances, such as inhibitors, according to the invention.

The method of the invention permits one to identify a substance that affects the enzymatic activity of the TcPRACA racemase. The substance can affect the mitogenicity of the TcPRACA as well. In addition, the substance can affect the parasitic activity of *T. cruzi*. Further, the substance can affect the infectivity of *T. cruzi*. Such substances constitute part of the present invention. The effect of the substance can be an inhibiting effect or an activating effect, i.e., it can decrease or increase the activity of the TcPRACA racemase, the mitogenicity of the TcPRACA, and the parasitic activity of *T. cruzi*, and can decrease or increase the infectivity of *T. cruzi*.

When used to affect the mitogenicity, parasitic activity, or infectivity of *T. cruzi*, the substance is considered to be a drug, in accordance with the broad definition of drug used in the art. The term thus includes antibodies (polyclonal or monoclonal) or fragments of antibodies that are designed using the three-dimensional structure of TcPRACA. The drug can be administered to a subject, such as a human, using any mode of administration that is suitable and that is known in the art for administration of drugs. Thus, for example, the drug can be administered to the subject orally or parenterally, such as by intravenous or intramuscular injection. Other modes of administration can also be employed, such as intrasplenic, intradermal, and mucosal administration (e.g., by inhalation). For purposes of injection, the drug can be prepared in the form of a solution, suspension, or emulsion in vehicles conventionally employed for this purpose. Other dosage forms are well known to those of skill in the art and need not be detailed here.

It is preferred that the drug affect the mitogenicity, or parasitic activity or infectivity by inhibiting or reducing these biological activities. When such a drug is used, it thus can be used to treat or prevent *T. cruzi* infection. To do so, the drug should be administered in an amount sufficient to reduce, inhibit, or prevent infection or the infectious process of *T. cruzi*. The amount administered to each individual subject will depend on various physical and physiological traits of the particular individual, including size, absorption, distribution, and clearance by the individual's body.

Thus, the dosage of the drug can vary over wide limits. For example, the dosage of the drug can vary from about 50 ng per kg of body weight to about 1 μg per kg of body weight per dose. Thus, suitable dosages include, but are not limited to, about 100 ng per kg of body weight, and about 500 ng per kg of body weight per dose. Multiple doses can be administered over a suitable time period. Frequency and duration of dosing can also vary depending on such things as the severity of infection, the age of the individual, and the presence or absence of other infections or health problems. Those of skill in the medical art can determine the appropriate dosing regimen using routine techniques without undue experimentation.

The term "about" as used herein in describing dosage ranges means an amount that is equivalent to the numerically stated amount as indicated by the biological effect in the host to whom the drug is administered. It is used to recognize that equivalents, while not necessarily encompassed by the values recited, exist and are included within the spirit and scope of the invention.

The drug can be provided in any suitable form, including, but not limited to, pills, tablets, lozenges, troches, capsules, suppositories, injectable solutions, ingestable solutions, and the like.

Appropriate pharmaceutically acceptable carriers, diluents, and adjuvants can be combined with the drug in order to prepare the drug for use in the treatment or prevention of *T. cruzi* infection. Such carriers, diluents, and adjuvants are known to those of skill in the art, and need not be detailed here. Thus, drug compositions of this invention can contain the active drug together with a solid or liquid pharmaceutically acceptable nontoxic carrier. Non-limiting examples of pharmaceutical carriers are sterile liquids, such as water and oils, including those of petroleum, animal, vegetable, or synthetic origin. Non-limiting examples of suitable liquids are peanut oil, soybean oil, mineral oil, sesame oil, and the like. Physiological solutions can also be employed as liquid carriers, particularly for injectable solutions.

Suitable pharmaceutical excipients include, but are not limited to, starch, glucose, lactose, sucrose, gelatine, malt, rice, flour, chalk, silica gel, magnesium carbonate, magnesium stearate, sodium stearate, glycerol monostearate, talc, sodium chloride, dried skim milk, glycerol, propylene glycol, water, ethanol, and the like. These compositions can take the form of solutions, suspensions, tablets, pills, capsules, powders, sustained-release formulations, and the like. Suitable pharmaceutical carriers are described in "Remington's Pharmaceutical Sciences" by E. W. Martin.

The subject to whom the drug is administered can be an animal susceptible to infection by *T. cruzi*. In embodiments, the subject is a mammal. For example, the mammal can be a human, a dog, a cat, a bovine, a pig, or a horse. In particular, the mammal can be a human.

It is to be understood that the drugs identified by practicing this invention can be used in combination with other drugs. For example, mixtures of different drugs can be employed in a single composition. Likewise, multiple compositions comprising one or more drugs can be employed. Indeed, the drugs of the present invention can be administered in conjunction with a vaccine designed to elicit a protective response against *T. cruzi*.

In yet another aspect of the invention, a computer readable medium having recorded thereon the data set listed in Table 2, or a portion of the data set listed in Table 2, is provided. By computer readable medium it is meant any media that can be read and accessed directly or indirectly by a computer. An example of a computer readable medium is one that is suitable for use in a computer system, as described below. Non-limiting examples of the computer readable medium include magnetic storage media, such as a computer diskette, a computer hard drive, and a magnetic tape; and optical storage media, such as an optical disk, a compact disk, a digital video disk; and hybrids of these two types of media.

In yet a further aspect, the invention is directed to a computer system comprising at least a central processing unit and a video display unit. The combination of the central processing unit and the video display unit is capable of converting the data set listed in Table 2 into a model of TcPRACA that can be viewed by a person. Likewise, the computer system is capable of converting some, but not all, of the data into a model of a portion of TcPRACA that can be viewed and/or manipulated by a person. It is envisioned that, when less than the entire TcPRACA protein is modelled, a sufficient number of atoms are included in the model to permit a person to determine whether a substance of interest can bind to the TcPRACA. In embodiments, the computer system is used to generate and display a three-dimensional model of TcPRACA, alone or with a model of one or more substances that can bind the TcPRACA. It is preferred that the model or models can be manipulated by a person while being displayed by the computer system.

A computer system according to the invention can comprise hardware, software, and at least one data storage element that are used to collect, store, and analyze information. Hardware includes, but is not limited to, a central processing unit. Software includes all computer programs, whether they be contained within the hardware or provided by way of externally supplied media, that control the activity of the computer system. Data storage elements include, but are not limited to, random access memory (RAM). Computer systems include personal computers, servers, mainframes, and the like, and can be purchased as one unit or in parts from commercial vendors such as Silicon Graphics Inc., Sun Microsystems, and Apple Computer. One particular example of a computer system according to the present invention is a device that is used to analyze atomic coordinate data, including the data set listed in Table 2, or a portion of that data set.

In view of the power of the internet, wide area networks, and local area networks, and the interconnectedness of computers throughout the world, it is not necessary that all of the elements of the computer system be located in physical proximity. Indeed, the elements of the computer system need not be physically connected at all. For example, a central processing unit can be located in one physical location, for example, at a laboratory, while a video display unit can be located in another physical location, for example, an office. The two elements can communicate through any suitable element that is capable of transmitting data, such as electrical, optical, or audio signals.

EXAMPLES

The invention will be further clarified by the following examples, which are intended to be purely exemplary of the invention and should not be construed as limiting the scope of the invention in any way.

Example 1

Recombinant Protein Production and Purification

A TcPRACA gene fragment starting at codon 30 was obtained by PCR using Hi- and Bg-45 primers (17), and cloned in frame with a C-terminal six-histidine tag into the pET28b(+) expression vector, following the protocol described by Reina-San-Martin et al. (10). The sequence of the engineered protein is given as SEQ ID NO:3.

Recombinant TcPRACA was produced in E. coli BL21 (DE3) and purified using Immobilized Metal Affinity Chromatography on nickel columns. Recombinant TcPRACA was purified using an anion exchange column (Mono-Q) and an FPLC system. Elution was performed at a constant flow rate of 0.5 ml/min. Protein fractions of 0.5 ml were collected and the absorbance was monitored at 280 nm. The fraction containing recombinant TcPRACA was recovered and precipitated with 75% ammonium sulfate. The pellet was resuspended in 25 mM NaOAc pH 5.2 with or without 1 mM pyrrole-2-carboxylic acid (PAC). The protein was desalted using PD10 columns previously equilibrated with 25 mM NaOAc pH 5.2. Recombinant TcPRACA was finally submitted to ultra filtration using 25 mM NaOAc pH 5.2.

Example 2

Enzyme Assays

TcPRACA racemization activity was assayed polarimetrically as described previously (10). Briefly, a 500 µl reaction mixture was prepared containing 0.25 µM purified enzyme and 40 mM L-proline in 0.2 M sodium acetate, 20 MM β-mercaptoethanol, pH 6.0. Racemization was assayed at 37EC. The reaction was stopped by incubating for 10 minutes at 80EC and then freezing. Water (1 ml) was then added. The percent racemization was determined by measuring the optical rotation in a polarimeter, such as a model 241 MC, made by Perkin Elmer, Montigny le Bretonneux, France, at a wavelength of 365 nm in a cell with a path length of 10 cm at a precision of 0.001 degree Using this assay, compounds that affect the mitogenic activity of TcPRACA can be confirmed, their relative anti-parasite activity determined, and useful in vivo doses identified. .

Example 3

Mitogenicity Assays

TcPRACA is a parasite mitogen because it is capable of activating a non-specific polyclonal response in lymphocytes. It is not clear whether TcPRACA itself is a mitogen, whether it acts as a mitogen by binding to host molecules, or whether its enzymatic product is, or constitutes part of, a mitogen. Regardless, the non-specific lymphocyte activation by TcPRACA is a functional result that can be assayed.

As disclosed in co-pending U.S. patent application Ser. No. 09/725,945, now U.S. Pat. No. 6,713,617, TcPRACA mitogenic activity can be assayed in vitro as follows: $5 \times 10^5$ naive spleen cells/well (96 well plate) are stimulated in vitro with different doses of TcPRACA (ranging from about 0.8 to 200 µg/ml final) for 24, 48, and 72 hours at 37EC, 5% $CO_2$. Cultures are pulsed with $^3$H-thymidine (1 µCi/well) for 16-18 hours before harvesting. $^3$H-thymidine incorporation is determined by counting using a beta-plate and the ELISPOT technique.

As disclosed in co-pending U.S. patent application Ser. No. 09/725,945, now U.S. Pat. No. 6,713,617, TcPRACA mitogenic activity can be assayed in vivo as follows: BALB/c mice are injected (i.p.) with 50 µg of TcPRACA, and spleen cells assayed day 7 after injection. Results are expressed as total numbers of spleen cells, total number of B cells producing IgM, IgG2a, and IgG2b isotypes, and total number of isotype-producing B cells specific to the TcPRACA. The control run is mice that are not injected with the protein.

Using this assay, compounds that affect the mitogenic activity of TcPRACA can be confirmed, their relative anti-parasite activity determined, and useful in vivo doses identified.

Example 4

Crystallization Buffers

The following buffers can be used to crystallize the TcPRACA protein:
  Buffer 1: 100 mM NaOAc, pH 5.6-5.8; and 10% polyethylene glycol 1500 with or without 1 mM PAC;
  Buffer 2: 0.2 M ammonium acetate; 50 mM trisodium citrate dihydrate, pH 5.6; 15% (w/v) polyethylene glycol 4000, equilibrated over the buffer;
  Buffer 3: 100 mM ammonium acetate; 50 mM trisodium citrate dihydrate, pH 5.6; and 15% w/v polyethylene glycol 4000 with or without 1 mM PAC.

Example 5

Crystallization of the TcPRACA Protein

A protein drop was set by mixing 2-3 µl (6 µg) of the protein solution obtained in Example 1 with an equal volume of crystallization buffer 2. Crystals grew to a final size of 0.2× 0.2×0.05 mm in 3-4 days. For X-ray diffraction experiments, the crystals were frozen in liquid nitrogen using the crystallization buffer plus 30% glycerol (used as a cryoprotectant).

Example 6

Crystallographic Studies

X ray diffraction data sets were collected from single crystals at 110K at the ESRF synchrotron, Grenoble, France, on beamlines BM14 and ID29. Diffraction was isotropic. Data were processed (Table 1) using the programs MOSFLM, SCALA, and TRUNCATE from the CCP4 program suite (13). Crystals proved to be monoclinic (C2) with unit cell dimensions (Å): a=134.0651 Å; b=91.618 Å; c=86.0307 Å; β=123.3735°. No significant non-origin peaks were detected in the native Patterson map.

Initial molecular replacement calculations using low homology models such as diaminopimelate epimerase (PDB1bwz) proved unsuccessful.

TABLE 1

| Data Set | Data collection statistics | |
|---|---|---|
| | Native | SAD anomalous peak |
| Wavelength (Å) | 1.0072 | 0.9795 |
| $D_{min}$ (Å) | 2.1 | 2.9 |
| Completeness (%) | 98.8 | 98 |
| Multiplicity | 3.7 | 6.3 |
| $R_{sym}$ (%) | 6.9 | 8.9 |

BEAM-LINE BM14 European Synchrotron Radiation Facility (Grenoble)
Project/Protein name: Proline racemase from *Trypanosoma cruzi*.
Method of Structure Solution: SAD
MAD/SAD absorption edge: Se SAD Δf″ peak12.657 KeV
Unit cell dimensions (Å): a = 134.0651 Å; b = 91.618 Å; c = 86.0307 Å; β = 123.3735°
Space group: C2

Example 7

Seleno-Methionine Incorporation

The plasmid expressing the recombinant TcPRACA having the amino acid sequence SEQ ID NO:3 was used to transform strain B834 (DE3) *Escherichia coli* cells (same genotype as BL21 but met). These transformed bacteria were cultured in M9 minimal medium supplemented with amino acids (seleno-methionine replacing methionine), nucleosides, vitamins, and oligoelements, as described previously (18). Recombinant protein overexpression was induced as usual with IPTG. Cells were harvested, and protein purification was achieved with the same protocols as for the Met wild-type TcPRACA.

The structure was solved by single-wavelength anomalous diffraction methods (highly redundant data set was measured at 12.657 KeV, corresponding to the Se Δf″ peak) combined with electron density modification strategies that took into account the 2-fold non-crystallographic symmetry. Twenty-two (out of 26) Se sites were determined by direct methods using the program Shake'n'Bake (19), and refined with the program SHARP (20). Electron density improvement was performed with the program SOLOMON (21).

The coordinates of the resulting TcPRACA crystal are given in Table 2.

Example 8

Enzyme Assay

One can use a simple test to rapidly screen putative modulators, such as inhibitors, of TcPRAC. TcPRAC constructs allowing for the production of high amounts of the recombinant active enzyme can be used together with the knowledge of a specific inhibitor of proline racemases (such as, for example, pyrrole carboxylic acid, PAC) to provide a medium/high throughput microplate test to easily screen a high number of inhibitor candidates (i.e. 100-1000). Such a test is based on colorimetric reactions that are a simpler alternative to polarimetry and other time-consuming tests.

More particularly, the test is based on the detection of D-proline originated through racemization of L-proline by TcPRAC, in the presence or in the absence of known concentrations of PAC inhibitor as positive and negative controls of racemization, respectively. For that purpose, this test utilizes another enzyme, D-amino acid oxidase (D-AAO), which has the ability to specifically oxidize D-amino acids in the presence of a donor/acceptor of electrons and yield hydrogen peroxide. The advantage of this strategy is that hydrogen peroxide can be classically quantified by peroxidase in a very sensitive reaction involving ortho-phenylenediamine, for example, ultimately offering a chromogenic reaction that is visualized by colorimetry at 490 nm.

Since D-amino acid oxidase reacts indiscriminately with any "D-amino acid", and not with their L-stereoisomers, such a test is not only helpful to identify proline racemase inhibitors, but also applicable, if slightly modified, to detect any alterations in levels of free D-aa in various fluids to make a diagnosis of some pathogenic processes.

A. Basics for a D-amino-acid Quantitative Test

The following test allows detection and quantitation of D-Amino acids. A first reaction involves a D-amino-oxidase. This enzyme specifically catalyses an oxidative deamination of D-amino-acids, together with a prosthetic group, either Flavin-Adenin-Dinucleotide (FAD) or Flavin-Mononuclotide (FMN), according to the origin of the Enzyme. (Obs. FAD if the enzyme comes from porcine kidney).

The general reaction is as follows:

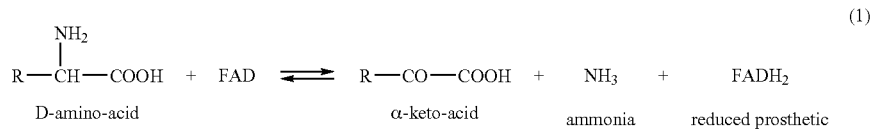

In (1), the D-amino acid is deaminated and oxidized, releasing ammonia and the reduced prosthetic group. If the amino group is not a primary group, the amino group remains untouched and no ammonia is released.

In (2), the reduced prosthetic group reduces oxygen, and generates hydrogen peroxide.

Either a catalase or a peroxidase can decompose hydrogen peroxide. A catalase activity is written as:

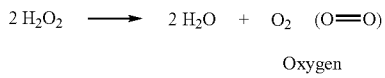
Oxygen whereas a peroxidase activity is

wherein R' is any carbon chain.

Thus, detection of hydrogen peroxide can be done with the use of catalase and a reagent sensitive to oxygen, such as by destaining reduced methylene blue, for instance, with oxygen or with the use of peroxidase with a change in color of the reagent indicated by:

B. Application of such a Test for Evaluating the *T. Cruzi* Racemase Activity and the Modulation of this Racemase.

II-1-Test for Racemase Activity

The *T. cruzi* racemase activity converts reversibly L-Pro into D-Pro. Since these two forms can induce polarized light deviation, this conversion can be measured by optical polarized light deviation. But the presence of the D-form allows also the use of D-amino-acid oxidase in order to assess the amount of D-Proline in racemase kinetics. In this test, the following reactions are involved:

1) Proline-Racemase activity.

2) D-amino-acid oxidase

(Obs: There is no ammonia formed in the case of Proline, because the nitrogen of Proline is involved in a secondary amine.)

3) Detection of hydrogen peroxide with peroxidase

The chromogenic reagent can be, for example, orthophenylenediamine (OPD), or 3,3',5,5' tetramethyl benzidine (TMB), or 5-aminosalicylic acid (ASA).

These reactions can be carried out using the following exemplary, but preferred, materials and methods.

| Materials | Comments |
|---|---|
| Proline-racemase (TcPRAC) (1 mg/ml Stock) | |
| L-Proline, Sigma, Ref. P-0380 (1M Stock) | An equimolar of D- and L-Proline is made by mixing equal volumes of 2M D-Proline with 2M L-Proline |
| D-Proline, Aldrich, réf. 85 891-9 (1M Stock) | |
| Orthophenylenediamine (OPD) Sigma refP-8287 lot 119H8200 | 10 mg tablets. Extemporaneously used as a 20 mg/ml stock solution in water. |
| D-AAO from swine kidney (Sigma) ref. A-5222 lot 102K1287 | Powder dissolved into 1 ml Buffer* + 1 ml 100% glycerol. The resulting activity is 50 U/ml. Stored at −20° C. |
| Horse radish peroxidase (HRP) Sigma ref P8375 lot 69F95002 | Powder dissolved into 2.5 ml Buffer* + 2.5 ml 100% glycerol. The resulting activity is 5042 U/ml. Stored at −20° C. |
| Sodium acetate 0.2M Ph6.0 | |
| Flavine-adenine-dinucleotide (FAD) (Sigma) ref. F-6625 | Stock solution of $10^{-1}$M in water. Stored at −20° C. Used as a $10^{-3}$M sub-stock solution. |
| Sodium pyrophosphate (Pop) 0.235M | Not soluble at a higher concentration. Must be stored at 4° C. and gently heated before use in order to solubilize crystals which may occur. |

-continued

| Materials | |
|---|---|
| Materials | Comments |
| Buffer* = 10 ml of 0.2M sodium acetate buffer pH6.0 + 680 µl 0.235M Pop | The final pH is 8.3. |
| Microplates (96 wells) | With adhesive coverlid |
| ELISA reader for microplates | With a wavelength filter at 490 nm for OPD substrate. |

Methods

Racemisation in Microplates:

(1) The volumes are indicated for a single well, but duplicates are mandatory. Leave enough raws of the microplate empty for standard and controls to be used in further steps. Distribute the following volumes per well reactions:
  a) without inhibitor (Vol=QS 81 µl)

| TcPRAC 1 mg/ml | 2 µl | 2 µl | 2 µl | 2 µl |
|---|---|---|---|---|
| L-Proline 0.1M | 32 µl | 16 µl | 8 µl | 4 µl |
| Proline Final concentration | (40 mM) | (20 mM) | (10 mM) | (5 mM) |
| Sodium acetate buffer 0.2M pH6 | 47 µl | 63 µl | 71 µl | 75 µl | b) with inhibitor (Vol=QS 81 µl):

A range of concentrations between 5 mM and 1 mM can be planned for the inhibitor. It should be diluted in sodium acetate buffer 0.2 M pH 6.0. Hence, the volume of inhibitor is substracted from the volume of buffer added in order to reach a final volume of 81 µl. For instance, 50% inhibition of racemisation of 10 mM L-proline is obtained with 45 µM Pyrrole carboxylic acid (PAC, specific inhibitor of proline racemase), when 36.5 µl PAC+44.5 µl buffer are used.

Table 3 is provided for 10 mM L-Proline as a substrate.

(2) Cover the microplate with an adhesive coverlid and leave for 30 nm at 37° C.

(3) At the end of racemisation, 5.5 µl of 0.235M Pop are added in each reaction well of the microplate in order to shift pH from pH6.0 to pH 8.3.

Quantitation of formed D-Proline: Standards and Controls.

(1) Prepare Standard and Controls:

Standard: An equimolar mixture of L- and D-Proline is used as a standard in a range from 0.05 mM to 50 mM (final concentration in the assay). It is used for assessing the amount of D-Proline formed after racemization. The standard range is made in microtubes, as follows:

In tube 1, mix Proline and buffer according to the described proportions.

Then, add 500 µl of the obtained mixture to 500 µl of buffer in next tube, and so on.

TABLE 3

| TcPrac 1 mg/ml | 2 µl | 2 µl | 2 µl | 2 µl | 2 µl | 2 µl | 2 µl | 2 µl | 2 µl | 2 µl |
|---|---|---|---|---|---|---|---|---|---|---|
| L-Proline 0.1M | 8 µl | 8 µl | 8 µl | 8 µl | 8 µl | 8 µl | 8 µl | 8 µl | 8 µl | 8 µl |
| PAC 0.1 mM/1 mM**/10 mM*** | 0 µl | 5.4 µl | 11 µl | 22 µl | 43 µl | 9 µl** | 17 µl** | 35 µl** | 69 µl** | 14 µl** |
| Final concentration (µM) | 0 | 6.7 | 13.5 | 27 | 54 | 107 | 214 | 429 | 858 | 1715 |
| Sodium acetate buffer 0.2 M pH6 QS 81 µl | 71 µl | 65.6 µl | 60 µl | 49 µl | 28 µl | 62 µl | 54 µl | 36 µl | 2 µl | 57 µl |

| Tube # | 1 | 2 | 3 | 4 | 5 | 6 | 7 | 8 | 9 | 10 | 11 | 12 |
|---|---|---|---|---|---|---|---|---|---|---|---|---|
| L-& D-Pro 1M | 250 µl | 500 µl | 500 µl | 500 µl | ... | | | | | | | 0 |
| Final Concentration (mM) in assay | 50 | 25 | 12.5 | 6.25 | 3.125 | 1.56 | 0.78 | 0.39 | 0.19 | 0.097 | 0.049 | 0 |
| Buffer* | 750 µl | 500 µl | 500 µl | 500 µl | ... | | | | | | | 1 ml |

Negative control: is prepared in an other microtube, as follows:

| L-Proline (1M) | 200 µl |
|---|---|
| Buffer* | 800 µl |
| Final concentration | 40 ml |

Blank = Buffer*.

(2) Dispense in the empty wells of the microplate (see step II-1-2.1):

| Buffer* | 67 µl |
|---|---|
| Standard dilutions or negative control | 20 µl |

Obs: For the blank dispense 87 µl of Buffer* only:

(3) Prepare a mixture containing the enzymes (D-AAO/HRP Mix), as follows:

The amounts are given for one well, provided that the final volume will be 100 µl with the racemase products or the substrate:

| | For 13 µl: |
|---|---|
| Buffer* | 6.5 µl |
| D-AAO 50 U/ml | 1.7 µl |
| OPD (20 mg/ml) | 2.5 µl |
| HRP 5000 U/ml | 0.75 µl |
| FAD $10^{-3}$M (4.5 µl $10^{-1}$M + 446 µl buffer) | 1.5 µl |

This mixture is kept in the ice until use.

(4) The quantitation reaction starts when 13 µl of D-AAO/HRP mix is added to the reaction well.

(5) The microplate is covered with an adhesive coverlid and it is left in the dark at 37° C. between 30 nm and 2 hours. The reaction can be monitored by eye whenever a color gradient matches the D-amino acid concentration of the standard dilutions.

(6) The microplate is read with a microplate spectrophotometer using a filter of at 490 nm.

In conclusion, D-AAO/HRP evaluation is more sensitive than D-Proline quantitation by polarimeter since it can discriminate PAC inhibition at a lower concentration than evaluation with the polarimeter. Furthermore, inhibition is logically conversely proportional to L-Proline concentration, which can be assessed with the D-AAO/HRP method, but not with the polarimeter measurement. Such a test is useful for the screening of new modulators, such as inhibitors, for instance, of TcPRAC in a medium/high throughput test.

A preferred technological platform to perform the above test and to select appropriate inhibitors contains at least the following products:

L-Proline, D-Proline, a proline-racemase

A peroxidase, a substrate of a peroxidase

A D-amino-acid oxidase

And optionally a battery of potential inhibitory molecules.

Example 9

A Medium/High Throughput Test Using the D-AAO Microplate Test

Table 4 is an Example of a medium/high throughput test using the D-AAO microplate test.

TABLE 4

| 1 D-Pro (mM) | 2 | 3 | 4 | 5 | 6 | 7 | 8 | 9 | 10 | 11 | 12 |
|---|---|---|---|---|---|---|---|---|---|---|---|
| A 10*[1] | L-Pro*[2] | T1 | T2 | T3 | T4 | T5 | T6 | T7 | T8 | T9 | T10 |
| B 5*[1] | L-Pro*[2] | " | " | " | " | " | " | " | " | " | " |
| C 2.5*[1] | L-Pro + PAC*[3] | T11 | T12 | T13 | T14 | T15 | T16 | T17 | T18 | T19 | T20 |
| D 1.25*[1] | L-Pro + PAC*[3] | " | " | " | " | " | " | " | " | " | " |
| E 0.62*[1] | Blank 1 | T21 | T22 | T23 | T24 | T25 | T26 | T27 | T28 | T29 | T30 |
| F 0.31*[1] | Blank 2 | " | " | " | " | " | " | " | " | " | " |
| G 0.15*[1] | L-Pro*[4] | T31 | T32 | T33 | T34 | T35 | T36 | T37 | T38 | T39 | T40 |
| H 0.07*[1] | L-Pro*[4] | " | " | " | " | " | " | " | " | " | " |

*[1]D-proline standard (column 1)
*[2]Positive control of racemization using avec 10 mM substate (column 2, line A and B)
*[3]control for inhibition of racemization reaction by PAC using 10 mM substrate (column 2, line C and D)
Blank 1: mix with racemase (column 2, line E)
Blank 2: mix without racemase (column 2, line F)
*[4]Negative control for specificity of (without racemase + 40 mM L-proline) (column 2, line G and H)
Other wells: with Inhibitors (T1, T2, T3, . . . T40): in duplicates The use of a microplate test based on D-amino-acid oxidase together with a peroxidase, such as horseradish peroxidase, can be used to detect and quantitate any D-amino acid in any biological or chemical sample. For example, since D-amino acids are described to be involved in several pathological processes or neurological diseases, such as Alzheimer disease, Parkinson, or renal diseases, their detection can be an important marker or parameter for the diagnosis and the follow-up of these pathologies. This technology can be also extended to the detection and quantification of D-amino acids in eukaryotic organisms, such as plants or fungi, and in bacteria.

The D-AAO/HRP test described here above can also be used for this purpose with slight modifications. For that purpose, the racemase reaction step should be skipped and the microplate test should start straightforward at "Racemisation in microplates" step (2) described above with the following remarks:

1) Standard: It should not be an equimolar mixture of D- and L-amino acid, but rather a serial dilution of D-Amino acids. The choice of amino acid is made according to the interest of the D-amino acid under investigation. The final volume in wells should be of 87 µl.

2) Negative control: It is made with the L-enantiomer of the D-amino acid under investigation. The final volume should be 87 µl.

3) Blank: It is made with 87 µl buffer*. (See paragraph II.1.1 Materials.)

4) Samples: The samples to be tested should be adjusted to pH 8,3 with buffer* and their final volumes should be of 87 µl per well.

Obs: Standards, negative controls, samples to test and blanks should be made in duplicates. They are dispensed into the wells of the microplate.

5) Then, the procedure follows steps 3) to 6), as above.

A preferred platform to search and quantitate the presence of a D-Amino acid in samples contains at least the following products:

A D-amino acid,

A peroxidase and a substrate of a peroxidase

A D-amino-acid oxidase

And optionally, a L-amino acid enantiomer, as control.

Thus, for example, the test for screening a molecule, which can modulate a racemase activity can comprise:

(A) modulating a racemase activity by means of a molecule being tested in the presence of an equimolar mixture of a L- and D-amino acid and of a racemase to be modulated;

(B) oxidatively deaminating the D-amino acid generated in step (A) by means of a D-amino oxidase in a prosthetic group; and (C) detecting the hydrogen peroxide generated by the oxidative deamination;

wherein modulation of the hydrogen peroxide is indicative of the capability of the tested molecule to modulate racemase activity. Preferably the molecule inhibits racemase activity, and more preferably the racemase is a proline racemase, for example, *Tripanosoma curzi* proline racemase.

The test can include a technological platform and all reagents and devices necessary to perform the test. The technological platform can comprise:

a) L-amino acid, D-amino acid, and a racemase;

b) a peroxydase and a substrate of a peroxydase, or a catalase and a reagent sensitive to oxygen;

c) a D-amino acid oxidase; and d) optionally, one or more molecules to be screened for inhibitory activity of said racemase.

Preferably, the racemase is a proline racemase and the L-amino acid and D-amino acid are L-proline and D-proline, respectively.

It will be apparent to those skilled in the art that various modifications and other variations can be made in the practice of the present invention without departing from the scope or spirit of the invention. Thus, other embodiments of the invention will be apparent to those skilled in the art from consideration of the specification and practice of the invention disclosed herein. It is intended that the disclosure of specific embodiments be considered as exemplary only, with the true scope and spirit of the invention being indicated by the following claims.

TABLE 2

REMARK coordinates from minimization and B-factor refinement
REMARK refinement resolution: 29 - 2.1 A
REMARK starting r = 0.1896 free_r = 0.2226
REMARK final      r = 0.1742 free_r = 0.2165
REMARK rmsd bonds = 0.016237 rmsd angles = 1.85196
REMARK B rmsd for bonded mainchain atoms = 1.802 target = 1.5
REMARK B rmsd for bonded sidechain atoms = 2.822 target = 2.0
REMARK B rmsd for angle mainchain atoms = 2.613 target = 2.0
REMARK B rmsd for angle sidechain atoms = 3.801 target = 2.5
REMARK target = mlf final wa = 5
REMARK final rweight = 0.1600 (with wa = 5)
REMARK md-method = torsion annealing schedule = slowcool
REMARK starting temperature = 5000   total md steps = 100 * 6
REMARK cycles = 2 coordinate steps = 100 B-factor steps = 50
REMARK sg = C2 a = 131.1528 b = 91.2088 c = 85.9827 alpha = 90 beta = 126.5217 gamma = 90
REMARK topology file 1: CNS_TOPPAR:protein.top
REMARK topology file 2: CNS_TOPPAR:dna-rna.top
REMARK topology file 3: CNS_TOPPAR:water.top
REMARK topology file 4: CNS_TOPPAR:ion.top
REMARK topology file 5: pac.top
REMARK parameter file 1: CNS_TOPPAR:protein_rep.param
REMARK parameter file 2: CNS_TOPPAR:dna-rna_rep.param
REMARK parameter file 3: CNS_TOPPAR:water_rep.param
REMARK parameter file 4: CNS_TOPPAR:ion.param
REMARK parameter file 5: pac.par
REMARK molecular structure file: water_pick.mtf
REMARK input coordinates: water_pick.pdb
REMARK reflection file = p45nat_free2.1.hkl
REMARK ncs = none
REMARK B-correction resolution: 6.0 - 2.1
REMARK initial B-factor correction applied to fobs:
REMARK B11 = −6.502 B22 =  4.876 B33 = 1.626

TABLE 2-continued

REMARK B12 = 0.000 B13 = −4.520 B23 = 0.000
REMARK B-factor correction applied to coordinate array B: −0.136
REMARK bulk solvent: density level = 0.364053 e/A^3, B-factor = 47.0089 A^2
REMARK reflections with |Fobs|/sigma__F < 0.0 rejected
REMARK reflections with |Fobs| > 10000 * rms (Fobs) rejected
REMARK theoretical total number of refl. in resol. range:      47515 (100.0%)
REMARK number of unobserved reflections (no entry or |F|= 0):   3534 (7.4%)
REMARK number of reflections rejected:                             0 (0.0%)
REMARK total number of reflections used:                       43981 (92.6%)
REMARK number of reflections in working set:                   41780 (87.9%)
REMARK number of reflections in test set:                       2201 (4.6%)
CRYST1 131.153   91.209   85.983   90.00 126.52   90.00 C 2
REMARK FILENAME = "/home/da/alebus/Grenoble0207/Nativa/Refine/Cns/refine__ultimo"
REMARK DATE: Nov. 3, 2002   00:23:10    created by user: alebus
REMARK VERSION:1.1

| ATOM | 1 | CB | LYS | A | 44 | 20.615 | 6.288 | −2.953 | 1.00 | 43.29 | A |
|---|---|---|---|---|---|---|---|---|---|---|---|
| ATOM | 2 | CG | LYS | A | 44 | 20.649 | 7.594 | −3.721 | 1.00 | 45.66 | A |
| ATOM | 3 | CD | LYS | A | 44 | 20.631 | 7.304 | −5.234 | 1.00 | 46.84 | A |
| ATOM | 4 | CE | LYS | A | 44 | 21.147 | 8.499 | −6.087 | 1.00 | 45.34 | A |
| ATOM | 5 | NZ | LYS | A | 44 | 22.581 | 8.809 | −5.825 | 1.00 | 43.53 | A |
| ATOM | 6 | C | LYS | A | 44 | 19.693 | 7.028 | −0.721 | 1.00 | 41.08 | A |
| ATOM | 7 | O | LYS | A | 44 | 19.606 | 8.262 | −0.567 | 1.00 | 42.77 | A |
| ATOM | 8 | N | LYS | A | 44 | 21.185 | 5.059 | −0.889 | 1.00 | 42.83 | A |
| ATOM | 9 | CA | LYS | A | 44 | 20.898 | 6.411 | −1.463 | 1.00 | 41.97 | A |
| ATOM | 10 | N | SER | A | 45 | 18.770 | 6.179 | −0.277 | 1.00 | 35.27 | A |
| ATOM | 11 | CA | SER | A | 45 | 17.619 | 6.627 | 0.499 | 1.00 | 32.35 | A |
| ATOM | 12 | CB | SER | A | 45 | 16.526 | 7.122 | −0.404 | 1.00 | 34.26 | A |
| ATOM | 13 | OG | SER | A | 45 | 16.035 | 6.043 | −1.151 | 1.00 | 36.65 | A |
| ATOM | 14 | C | SER | A | 45 | 17.044 | 5.514 | 1.399 | 1.00 | 31.37 | A |
| ATOM | 15 | O | SER | A | 45 | 17.249 | 4.324 | 1.150 | 1.00 | 29.02 | A |
| ATOM | 16 | N | PHE | A | 46 | 16.319 | 5.918 | 2.442 | 1.00 | 27.54 | A |
| ATOM | 17 | CA | PHE | A | 46 | 15.697 | 4.986 | 3.372 | 1.00 | 23.33 | A |
| ATOM | 18 | CB | PHE | A | 46 | 16.461 | 4.918 | 4.703 | 1.00 | 24.39 | A |
| ATOM | 19 | CG | PHE | A | 46 | 17.718 | 4.150 | 4.631 | 1.00 | 24.94 | A |
| ATOM | 20 | CD1 | PHE | A | 46 | 18.903 | 4.772 | 4.320 | 1.00 | 27.54 | A |
| ATOM | 21 | CD2 | PHE | A | 46 | 17.715 | 2.786 | 4.842 | 1.00 | 24.61 | A |
| ATOM | 22 | CE1 | PHE | A | 46 | 20.079 | 4.047 | 4.218 | 1.00 | 28.38 | A |
| ATOM | 23 | CE2 | PHE | A | 46 | 18.871 | 2.062 | 4.745 | 1.00 | 25.80 | A |
| ATOM | 24 | CZ | PHE | A | 46 | 20.059 | 2.687 | 4.432 | 1.00 | 28.78 | A |
| ATOM | 25 | C | PHE | A | 46 | 14.353 | 5.561 | 3.663 | 1.00 | 22.42 | A |
| ATOM | 26 | O | PHE | A | 46 | 14.228 | 6.766 | 3.763 | 1.00 | 24.31 | A |
| ATOM | 27 | N | THR | A | 47 | 13.362 | 4.705 | 3.831 | 1.00 | 20.85 | A |
| ATOM | 28 | CA | THR | A | 47 | 12.005 | 5.110 | 4.145 | 1.00 | 19.91 | A |
| ATOM | 29 | CB | THR | A | 47 | 11.003 | 4.255 | 3.323 | 1.00 | 23.60 | A |
| ATOM | 30 | OG1 | THR | A | 47 | 11.101 | 4.621 | 1.931 | 1.00 | 30.92 | A |
| ATOM | 31 | CG2 | THR | A | 47 | 9.602 | 4.518 | 3.756 | 1.00 | 28.40 | A |
| ATOM | 32 | C | THR | A | 47 | 11.838 | 4.847 | 5.658 | 1.00 | 20.08 | A |
| ATOM | 33 | O | THR | A | 47 | 12.207 | 3.773 | 6.147 | 1.00 | 17.57 | A |
| ATOM | 34 | N | CYS | A | 48 | 11.249 | 5.800 | 6.373 | 1.00 | 18.11 | A |
| ATOM | 35 | CA | CYS | A | 48 | 11.063 | 5.691 | 7.823 | 1.00 | 18.60 | A |
| ATOM | 36 | CB | CYS | A | 48 | 11.954 | 6.680 | 8.572 | 1.00 | 18.20 | A |
| ATOM | 37 | SG | CYS | A | 48 | 13.661 | 6.540 | 8.248 | 1.00 | 32.01 | A |
| ATOM | 38 | C | CYS | A | 48 | 9.690 | 6.080 | 8.235 | 1.00 | 18.84 | A |
| ATOM | 39 | O | CYS | A | 48 | 9.106 | 7.001 | 7.652 | 1.00 | 17.62 | A |
| ATOM | 40 | N | ILE | A | 49 | 9.181 | 5.386 | 9.249 | 1.00 | 17.10 | A |
| ATOM | 41 | CA | ILE | A | 49 | 7.924 | 5.761 | 9.868 | 1.00 | 14.94 | A |
| ATOM | 42 | CB | ILE | A | 49 | 7.060 | 4.561 | 10.259 | 1.00 | 16.49 | A |
| ATOM | 43 | CG2 | ILE | A | 49 | 5.765 | 5.056 | 10.922 | 1.00 | 15.09 | A |
| ATOM | 44 | CG1 | ILE | A | 49 | 6.766 | 3.697 | 9.018 | 1.00 | 19.56 | A |
| ATOM | 45 | CD1 | ILE | A | 49 | 5.714 | 2.712 | 9.244 | 1.00 | 18.95 | A |
| ATOM | 46 | C | ILE | A | 49 | 8.523 | 6.390 | 11.164 | 1.00 | 17.73 | A |
| ATOM | 47 | O | ILE | A | 49 | 9.053 | 5.677 | 12.037 | 1.00 | 14.13 | A |
| ATOM | 48 | N | ASP | A | 50 | 8.503 | 7.714 | 11.254 | 1.00 | 17.01 | A |
| ATOM | 49 | CA | ASP | A | 50 | 9.048 | 8.388 | 12.440 | 1.00 | 17.48 | A |
| ATOM | 50 | CB | ASP | A | 50 | 9.531 | 9.822 | 12.136 | 1.00 | 13.12 | A |
| ATOM | 51 | CG | ASP | A | 50 | 10.953 | 9.859 | 11.578 | 1.00 | 21.06 | A |
| ATOM | 52 | OD1 | ASP | A | 50 | 11.710 | 8.846 | 11.640 | 1.00 | 27.30 | A |
| ATOM | 53 | OD2 | ASP | A | 50 | 11.359 | 10.907 | 11.055 | 1.00 | 24.19 | A |
| ATOM | 54 | C | ASP | A | 50 | 7.972 | 8.422 | 13.491 | 1.00 | 18.22 | A |
| ATOM | 55 | O | ASP | A | 50 | 6.865 | 8.952 | 13.293 | 1.00 | 20.05 | A |
| ATOM | 56 | N | MET | A | 51 | 8.277 | 7.835 | 14.628 | 1.00 | 15.21 | A |
| ATOM | 57 | CA | MET | A | 51 | 7.299 | 7.826 | 15.681 | 1.00 | 15.55 | A |
| ATOM | 58 | CB | MET | A | 51 | 6.834 | 6.418 | 15.875 | 1.00 | 18.11 | A |
| ATOM | 59 | CG | MET | A | 51 | 6.226 | 5.852 | 14.581 | 1.00 | 22.02 | A |
| ATOM | 60 | SD | MET | A | 51 | 5.667 | 4.271 | 14.916 | 1.00 | 25.65 | A |
| ATOM | 61 | CE | MET | A | 51 | 4.098 | 4.685 | 15.860 | 1.00 | 20.93 | A |
| ATOM | 62 | C | MET | A | 51 | 7.913 | 8.301 | 16.971 | 1.00 | 11.93 | A |
| ATOM | 63 | O | MET | A | 51 | 9.099 | 8.508 | 17.027 | 1.00 | 13.17 | A |
| ATOM | 64 | N | HIS | A | 52 | 7.091 | 8.490 | 17.989 | 1.00 | 10.52 | A |

TABLE 2-continued

| ATOM | 65 | CA | HIS | A | 52 | 7.649 | 8.765 | 19.312 | 1.00 | 12.27 | A |
| --- | --- | --- | --- | --- | --- | --- | --- | --- | --- | --- | --- |
| ATOM | 66 | CB | HIS | A | 52 | 7.710 | 10.305 | 19.630 | 1.00 | 9.72 | A |
| ATOM | 67 | CG | HIS | A | 52 | 6.391 | 10.949 | 19.953 | 1.00 | 12.04 | A |
| ATOM | 68 | CD2 | HIS | A | 52 | 5.489 | 11.596 | 19.162 | 1.00 | 9.69 | A |
| ATOM | 69 | ND1 | HIS | A | 52 | 5.881 | 11.001 | 21.233 | 1.00 | 12.85 | A |
| ATOM | 70 | CE1 | HIS | A | 52 | 4.725 | 11.647 | 21.222 | 1.00 | 11.94 | A |
| ATOM | 71 | NE2 | HIS | A | 52 | 4.466 | 12.021 | 19.979 | 1.00 | 13.12 | A |
| ATOM | 72 | C | HIS | A | 52 | 6.724 | 8.018 | 20.270 | 1.00 | 12.54 | A |
| ATOM | 73 | O | HIS | A | 52 | 5.535 | 7.852 | 20.002 | 1.00 | 13.79 | A |
| ATOM | 74 | N | THR | A | 53 | 7.270 | 7.533 | 21.369 | 1.00 | 14.00 | A |
| ATOM | 75 | CA | THR | A | 53 | 6.456 | 6.881 | 22.369 | 1.00 | 12.69 | A |
| ATOM | 76 | CB | THR | A | 53 | 7.006 | 5.499 | 22.693 | 1.00 | 14.08 | A |
| ATOM | 77 | OG1 | THR | A | 53 | 7.018 | 4.713 | 21.499 | 1.00 | 14.10 | A |
| ATOM | 78 | CG2 | THR | A | 53 | 6.163 | 4.814 | 23.776 | 1.00 | 11.71 | A |
| ATOM | 79 | C | THR | A | 53 | 6.562 | 7.785 | 23.611 | 1.00 | 16.26 | A |
| ATOM | 80 | O | THR | A | 53 | 7.574 | 7.728 | 24.334 | 1.00 | 13.58 | A |
| ATOM | 81 | N | GLU | A | 54 | 5.546 | 8.628 | 23.821 | 1.00 | 16.02 | A |
| ATOM | 82 | CA | GLU | A | 54 | 5.474 | 9.550 | 24.953 | 1.00 | 17.70 | A |
| ATOM | 83 | CB | GLU | A | 54 | 5.226 | 8.751 | 26.257 | 1.00 | 17.93 | A |
| ATOM | 84 | CG | GLU | A | 54 | 3.931 | 7.897 | 26.155 | 1.00 | 19.27 | A |
| ATOM | 85 | CD | GLU | A | 54 | 3.605 | 7.086 | 27.390 | 1.00 | 26.18 | A |
| ATOM | 86 | OE1 | GLU | A | 54 | 3.942 | 7.555 | 28.514 | 1.00 | 27.93 | A |
| ATOM | 87 | OE2 | GLU | A | 54 | 2.990 | 5.983 | 27.250 | 1.00 | 23.64 | A |
| ATOM | 88 | C | GLU | A | 54 | 6.725 | 10.434 | 25.044 | 1.00 | 20.11 | A |
| ATOM | 89 | O | GLU | A | 54 | 7.308 | 10.619 | 26.117 | 1.00 | 19.57 | A |
| ATOM | 90 | N | GLY | A | 55 | 7.152 | 10.953 | 23.892 | 1.00 | 16.98 | A |
| ATOM | 91 | CA | GLY | A | 55 | 8.291 | 11.848 | 23.866 | 1.00 | 14.52 | A |
| ATOM | 92 | C | GLY | A | 55 | 9.597 | 11.265 | 23.389 | 1.00 | 13.92 | A |
| ATOM | 93 | O | GLY | A | 55 | 10.487 | 12.010 | 22.978 | 1.00 | 17.15 | A |
| ATOM | 94 | N | GLU | A | 56 | 9.733 | 9.947 | 23.449 | 1.00 | 12.64 | A |
| ATOM | 95 | CA | GLU | A | 56 | 10.957 | 9.305 | 23.012 | 1.00 | 12.64 | A |
| ATOM | 96 | CB | GLU | A | 56 | 11.291 | 8.108 | 23.926 | 1.00 | 12.43 | A |
| ATOM | 97 | CG | GLU | A | 56 | 12.538 | 7.340 | 23.546 | 1.00 | 13.31 | A |
| ATOM | 98 | CD | GLU | A | 56 | 13.833 | 8.066 | 23.845 | 1.00 | 13.36 | A |
| ATOM | 99 | OE1 | GLU | A | 56 | 13.805 | 9.147 | 24.447 | 1.00 | 13.61 | A |
| ATOM | 100 | OE2 | GLU | A | 56 | 14.916 | 7.554 | 23.465 | 1.00 | 15.37 | A |
| ATOM | 101 | C | GLU | A | 56 | 10.807 | 8.838 | 21.575 | 1.00 | 13.28 | A |
| ATOM | 102 | O | GLU | A | 56 | 9.881 | 8.099 | 21.242 | 1.00 | 14.77 | A |
| ATOM | 103 | N | ALA | A | 57 | 11.759 | 9.240 | 20.759 | 1.00 | 12.77 | A |
| ATOM | 104 | CA | ALA | A | 57 | 11.773 | 8.933 | 19.356 | 1.00 | 13.88 | A |
| ATOM | 105 | CB | ALA | A | 57 | 12.899 | 9.682 | 18.678 | 1.00 | 14.18 | A |
| ATOM | 106 | C | ALA | A | 57 | 11.924 | 7.483 | 19.073 | 1.00 | 16.02 | A |
| ATOM | 107 | O | ALA | A | 57 | 12.583 | 6.717 | 19.810 | 1.00 | 14.16 | A |
| ATOM | 108 | N | ALA | A | 58 | 11.326 | 7.092 | 17.960 | 1.00 | 14.72 | A |
| ATOM | 109 | CA | ALA | A | 58 | 11.439 | 5.708 | 17.519 | 1.00 | 14.82 | A |
| ATOM | 110 | CB | ALA | A | 58 | 10.277 | 4.899 | 18.065 | 1.00 | 16.68 | A |
| ATOM | 111 | C | ALA | A | 58 | 11.371 | 5.783 | 15.976 | 1.00 | 15.38 | A |
| ATOM | 112 | O | ALA | A | 58 | 10.283 | 5.714 | 15.394 | 1.00 | 14.57 | A |
| ATOM | 113 | N | ARG | A | 59 | 12.523 | 5.992 | 15.353 | 1.00 | 14.25 | A |
| ATOM | 114 | CA | ARG | A | 59 | 12.630 | 6.087 | 13.891 | 1.00 | 15.71 | A |
| ATOM | 115 | CB | ARG | A | 59 | 13.896 | 6.835 | 13.534 | 1.00 | 14.51 | A |
| ATOM | 116 | CG | ARG | A | 59 | 14.306 | 6.885 | 12.049 | 1.00 | 17.75 | A |
| ATOM | 117 | CD | ARG | A | 59 | 15.248 | 8.083 | 11.816 | 1.00 | 16.44 | A |
| ATOM | 118 | NE | ARG | A | 59 | 14.497 | 9.340 | 11.944 | 1.00 | 18.31 | A |
| ATOM | 119 | CZ | ARG | A | 59 | 15.055 | 10.559 | 12.063 | 1.00 | 18.86 | A |
| ATOM | 120 | NH1 | ARG | A | 59 | 16.363 | 10.721 | 12.082 | 1.00 | 17.30 | A |
| ATOM | 121 | NH2 | ARG | A | 59 | 14.292 | 11.628 | 12.146 | 1.00 | 19.95 | A |
| ATOM | 122 | C | ARG | A | 59 | 12.679 | 4.670 | 13.314 | 1.00 | 14.31 | A |
| ATOM | 123 | O | ARG | A | 59 | 13.710 | 4.015 | 13.359 | 1.00 | 11.88 | A |
| ATOM | 124 | N | ILE | A | 60 | 11.563 | 4.224 | 12.761 | 1.00 | 12.93 | A |
| ATOM | 125 | CA | ILE | A | 60 | 11.502 | 2.876 | 12.206 | 1.00 | 14.14 | A |
| ATOM | 126 | CB | ILE | A | 60 | 10.145 | 2.282 | 12.498 | 1.00 | 16.01 | A |
| ATOM | 127 | CG2 | ILE | A | 60 | 10.080 | 0.837 | 11.933 | 1.00 | 16.40 | A |
| ATOM | 128 | CG1 | ILE | A | 60 | 9.938 | 2.257 | 14.030 | 1.00 | 14.56 | A |
| ATOM | 129 | CD1 | ILE | A | 60 | 8.512 | 1.875 | 14.500 | 1.00 | 13.94 | A |
| ATOM | 130 | C | ILE | A | 60 | 11.817 | 2.839 | 10.718 | 1.00 | 13.44 | A |
| ATOM | 131 | O | ILE | A | 60 | 11.047 | 3.321 | 9.896 | 1.00 | 15.63 | A |
| ATOM | 132 | N | VAL | A | 61 | 12.959 | 2.283 | 10.373 | 1.00 | 13.90 | A |
| ATOM | 133 | CA | VAL | A | 61 | 13.373 | 2.220 | 8.986 | 1.00 | 18.11 | A |
| ATOM | 134 | CB | VAL | A | 61 | 14.885 | 2.099 | 8.905 | 1.00 | 17.61 | A |
| ATOM | 135 | CG1 | VAL | A | 61 | 15.345 | 2.012 | 7.447 | 1.00 | 16.23 | A |
| ATOM | 136 | CG2 | VAL | A | 61 | 15.508 | 3.296 | 9.565 | 1.00 | 14.84 | A |
| ATOM | 137 | C | VAL | A | 61 | 12.698 | 1.014 | 8.332 | 1.00 | 21.61 | A |
| ATOM | 138 | O | VAL | A | 61 | 12.988 | −0.130 | 8.681 | 1.00 | 22.60 | A |
| ATOM | 139 | N | THR | A | 62 | 11.787 | 1.293 | 7.399 | 1.00 | 22.58 | A |
| ATOM | 140 | CA | THR | A | 62 | 11.016 | 0.270 | 6.717 | 1.00 | 22.33 | A |
| ATOM | 141 | CB | THR | A | 62 | 9.602 | 0.754 | 6.430 | 1.00 | 21.33 | A |
| ATOM | 142 | OG1 | THR | A | 62 | 9.684 | 1.915 | 5.617 | 1.00 | 26.78 | A |
| ATOM | 143 | CG2 | THR | A | 62 | 8.863 | 1.088 | 7.716 | 1.00 | 23.19 | A |

TABLE 2-continued

| | | | | | | | | | | |
|---|---|---|---|---|---|---|---|---|---|---|
| ATOM | 144 | C | THR | A | 62 | 11.598 | −0.231 | 5.398 | 1.00 | 24.06 A |
| ATOM | 145 | O | THR | A | 62 | 11.228 | −1.321 | 4.941 | 1.00 | 24.17 A |
| ATOM | 146 | N | SER | A | 63 | 12.475 | 0.535 | 4.773 | 1.00 | 21.99 A |
| ATOM | 147 | CA | SER | A | 63 | 13.098 | 0.088 | 3.527 | 1.00 | 23.76 A |
| ATOM | 148 | CB | SER | A | 63 | 12.151 | 0.246 | 2.312 | 1.00 | 26.04 A |
| ATOM | 149 | OG | SER | A | 63 | 12.349 | 1.516 | 1.696 | 1.00 | 33.16 A |
| ATOM | 150 | C | SER | A | 63 | 14.367 | 0.869 | 3.248 | 1.00 | 22.10 A |
| ATOM | 151 | O | SER | A | 63 | 14.538 | 1.983 | 3.722 | 1.00 | 22.92 A |
| ATOM | 152 | N | GLY | A | 64 | 15.272 | 0.252 | 2.506 | 1.00 | 20.57 A |
| ATOM | 153 | CA | GLY | A | 64 | 16.499 | 0.911 | 2.124 | 1.00 | 21.51 A |
| ATOM | 154 | C | GLY | A | 64 | 17.704 | 0.021 | 2.329 | 1.00 | 21.96 A |
| ATOM | 155 | O | GLY | A | 64 | 18.740 | 0.213 | 1.690 | 1.00 | 21.33 A |
| ATOM | 156 | N | LEU | A | 65 | 17.591 | −0.938 | 3.248 | 1.00 | 21.03 A |
| ATOM | 157 | CA | LEU | A | 65 | 18.716 | −1.821 | 3.515 | 1.00 | 21.89 A |
| ATOM | 158 | CB | LEU | A | 65 | 18.524 | −2.545 | 4.858 | 1.00 | 23.31 A |
| ATOM | 159 | CG | LEU | A | 65 | 18.805 | −1.852 | 6.195 | 1.00 | 21.07 A |
| ATOM | 160 | CD1 | LEU | A | 65 | 18.461 | −2.854 | 7.286 | 1.00 | 18.87 A |
| ATOM | 161 | CD2 | LEU | A | 65 | 20.274 | −1.400 | 6.286 | 1.00 | 17.46 A |
| ATOM | 162 | C | LEU | A | 65 | 18.927 | −2.906 | 2.468 | 1.00 | 21.41 A |
| ATOM | 163 | O | LEU | A | 65 | 17.979 | −3.377 | 1.858 | 1.00 | 23.58 A |
| ATOM | 164 | N | PRO | A | 66 | 20.182 | −3.291 | 2.227 | 1.00 | 23.00 A |
| ATOM | 165 | CD | PRO | A | 66 | 21.437 | −2.632 | 2.657 | 1.00 | 19.77 A |
| ATOM | 166 | CA | PRO | A | 66 | 20.444 | −4.372 | 1.252 | 1.00 | 22.04 A |
| ATOM | 167 | CB | PRO | A | 66 | 21.933 | −4.214 | 0.960 | 1.00 | 21.76 A |
| ATOM | 168 | CG | PRO | A | 66 | 22.480 | −3.668 | 2.306 | 1.00 | 22.66 A |
| ATOM | 169 | C | PRO | A | 66 | 20.197 | −5.648 | 2.076 | 1.00 | 25.01 A |
| ATOM | 170 | O | PRO | A | 66 | 19.774 | −5.562 | 3.233 | 1.00 | 24.41 A |
| ATOM | 171 | N | HIS | A | 67 | 20.445 | −6.828 | 1.516 | 1.00 | 27.46 A |
| ATOM | 172 | CA | HIS | A | 67 | 20.303 | −8.042 | 2.327 | 1.00 | 28.25 A |
| ATOM | 173 | CB | HIS | A | 67 | 20.597 | −9.296 | 1.506 | 1.00 | 30.96 A |
| ATOM | 174 | CG | HIS | A | 67 | 20.636 | −10.545 | 2.328 | 1.00 | 32.96 A |
| ATOM | 175 | CD2 | HIS | A | 67 | 19.645 | −11.256 | 2.914 | 1.00 | 32.55 A |
| ATOM | 176 | ND1 | HIS | A | 67 | 21.818 | −11.166 | 2.686 | 1.00 | 36.69 A |
| ATOM | 177 | CE1 | HIS | A | 67 | 21.549 | −12.203 | 3.457 | 1.00 | 33.28 A |
| ATOM | 178 | NE2 | HIS | A | 67 | 20.238 | −12.279 | 3.610 | 1.00 | 33.49 A |
| ATOM | 179 | C | HIS | A | 67 | 21.367 | −7.935 | 3.430 | 1.00 | 27.80 A |
| ATOM | 180 | O | HIS | A | 67 | 22.466 | −7.496 | 3.158 | 1.00 | 27.68 A |
| ATOM | 181 | N | ILE | A | 68 | 21.028 | −8.319 | 4.661 | 1.00 | 26.99 A |
| ATOM | 182 | CA | ILE | A | 68 | 21.965 | −8.285 | 5.782 | 1.00 | 24.94 A |
| ATOM | 183 | CB | ILE | A | 68 | 21.404 | −7.433 | 6.968 | 1.00 | 22.93 A |
| ATOM | 184 | CG2 | ILE | A | 68 | 22.319 | −7.549 | 8.147 | 1.00 | 19.99 A |
| ATOM | 185 | CG1 | ILE | A | 68 | 21.261 | −5.953 | 6.543 | 1.00 | 20.08 A |
| ATOM | 186 | CD1 | ILE | A | 68 | 22.594 | −5.284 | 6.161 | 1.00 | 20.15 A |
| ATOM | 187 | C | ILE | A | 68 | 22.142 | −9.747 | 6.246 | 1.00 | 26.15 A |
| ATOM | 188 | O | ILE | A | 68 | 21.206 | −10.377 | 6.742 | 1.00 | 25.93 A |
| ATOM | 189 | N | PRO | A | 69 | 23.347 | −10.298 | 6.103 | 1.00 | 26.77 A |
| ATOM | 190 | CD | PRO | A | 69 | 24.504 | −9.912 | 5.282 | 1.00 | 27.67 A |
| ATOM | 191 | CA | PRO | A | 69 | 23.448 | −11.683 | 6.552 | 1.00 | 28.58 A |
| ATOM | 192 | CB | PRO | A | 69 | 24.800 | −12.132 | 5.989 | 1.00 | 28.02 A |
| ATOM | 193 | CG | PRO | A | 69 | 25.537 | −10.891 | 5.716 | 1.00 | 30.49 A |
| ATOM | 194 | C | PRO | A | 69 | 23.301 | −11.914 | 8.064 | 1.00 | 28.45 A |
| ATOM | 195 | O | PRO | A | 69 | 23.574 | −11.031 | 8.879 | 1.00 | 27.11 A |
| ATOM | 196 | N | GLY | A | 70 | 22.833 | −13.112 | 8.407 | 1.00 | 27.37 A |
| ATOM | 197 | CA | GLY | A | 70 | 22.664 | −13.499 | 9.798 | 1.00 | 27.72 A |
| ATOM | 198 | C | GLY | A | 70 | 21.548 | −14.515 | 9.885 | 1.00 | 28.99 A |
| ATOM | 199 | O | GLY | A | 70 | 20.503 | −14.327 | 9.251 | 1.00 | 29.07 A |
| ATOM | 200 | N | SER | A | 71 | 21.723 | −15.582 | 10.661 | 1.00 | 28.80 A |
| ATOM | 201 | CA | SER | A | 71 | 20.642 | −16.564 | 10.717 | 1.00 | 31.13 A |
| ATOM | 202 | CB | SER | A | 71 | 21.198 | −17.985 | 10.918 | 1.00 | 31.64 A |
| ATOM | 203 | OG | SER | A | 71 | 21.813 | −18.137 | 12.189 | 1.00 | 37.34 A |
| ATOM | 204 | C | SER | A | 71 | 19.581 | −16.229 | 11.766 | 1.00 | 31.53 A |
| ATOM | 205 | O | SER | A | 71 | 18.564 | −16.919 | 11.863 | 1.00 | 31.74 A |
| ATOM | 206 | N | ASN | A | 72 | 19.810 | −15.170 | 12.549 | 1.00 | 29.98 A |
| ATOM | 207 | CA | ASN | A | 72 | 18.818 | −14.723 | 13.532 | 1.00 | 27.95 A |
| ATOM | 208 | CB | ASN | A | 72 | 18.978 | −15.432 | 14.889 | 1.00 | 27.77 A |
| ATOM | 209 | CG | ASN | A | 72 | 20.367 | −15.274 | 15.471 | 1.00 | 28.15 A |
| ATOM | 210 | OD1 | ASN | A | 72 | 20.971 | −14.222 | 15.376 | 1.00 | 29.74 A |
| ATOM | 211 | ND2 | ASN | A | 72 | 20.872 | −16.327 | 16.093 | 1.00 | 30.36 A |
| ATOM | 212 | C | ASN | A | 72 | 18.994 | −13.217 | 13.698 | 1.00 | 26.29 A |
| ATOM | 213 | O | ASN | A | 72 | 19.937 | −12.640 | 13.182 | 1.00 | 25.46 A |
| ATOM | 214 | N | MET | A | 73 | 18.084 | −12.587 | 14.421 | 1.00 | 25.13 A |
| ATOM | 215 | CA | MET | A | 73 | 18.137 | −11.145 | 14.577 | 1.00 | 25.69 A |
| ATOM | 216 | CB | MET | A | 73 | 16.862 | −10.712 | 15.298 | 1.00 | 26.70 A |
| ATOM | 217 | CG | MET | A | 73 | 16.066 | −9.589 | 14.629 | 1.00 | 31.37 A |
| ATOM | 218 | SD | MET | A | 73 | 16.059 | −9.539 | 12.826 | 1.00 | 28.71 A |
| ATOM | 219 | CE | MET | A | 73 | 14.998 | −10.868 | 12.484 | 1.00 | 29.39 A |
| ATOM | 220 | C | MET | A | 73 | 19.426 | −10.651 | 15.265 | 1.00 | 25.28 A |
| ATOM | 221 | O | MET | A | 73 | 19.987 | −9.601 | 14.892 | 1.00 | 25.94 A |
| ATOM | 222 | N | ALA | A | 74 | 19.929 | −11.408 | 16.235 | 1.00 | 23.64 A |

TABLE 2-continued

| | | | | | | | | | | |
|---|---|---|---|---|---|---|---|---|---|---|
| ATOM | 223 | CA | ALA | A | 74 | 21.168 | −11.020 | 16.906 | 1.00 | 22.23 A |
| ATOM | 224 | CB | ALA | A | 74 | 21.453 | −11.956 | 18.102 | 1.00 | 22.03 A |
| ATOM | 225 | C | ALA | A | 74 | 22.364 | −11.018 | 15.943 | 1.00 | 21.64 A |
| ATOM | 226 | O | ALA | A | 74 | 23.283 | −10.184 | 16.063 | 1.00 | 21.49 A |
| ATOM | 227 | N | GLU | A | 75 | 22.394 | −11.940 | 14.992 | 1.00 | 20.77 A |
| ATOM | 228 | CA | GLU | A | 75 | 23.532 | −11.933 | 14.071 | 1.00 | 22.04 A |
| ATOM | 229 | CB | GLU | A | 75 | 23.641 | −13.262 | 13.322 | 1.00 | 24.69 A |
| ATOM | 230 | CG | GLU | A | 75 | 24.048 | −14.407 | 14.235 | 1.00 | 29.64 A |
| ATOM | 231 | CD | GLU | A | 75 | 24.196 | −15.750 | 13.502 | 1.00 | 36.55 A |
| ATOM | 232 | OE1 | GLU | A | 75 | 24.396 | −16.761 | 14.214 | 1.00 | 35.91 A |
| ATOM | 233 | OE2 | GLU | A | 75 | 24.109 | −15.795 | 12.238 | 1.00 | 36.81 A |
| ATOM | 234 | C | GLU | A | 75 | 23.429 | −10.794 | 13.080 | 1.00 | 19.77 A |
| ATOM | 235 | O | GLU | A | 75 | 24.434 | −10.247 | 12.636 | 1.00 | 21.47 A |
| ATOM | 236 | N | LYS | A | 76 | 22.212 | −10.457 | 12.711 | 1.00 | 19.70 A |
| ATOM | 237 | CA | LYS | A | 76 | 21.988 | −9.368 | 11.772 | 1.00 | 20.97 A |
| ATOM | 238 | CB | LYS | A | 76 | 20.507 | −9.326 | 11.366 | 1.00 | 23.57 A |
| ATOM | 239 | CG | LYS | A | 76 | 20.093 | −10.486 | 10.463 | 1.00 | 26.56 A |
| ATOM | 240 | CD | LYS | A | 76 | 18.856 | −10.154 | 9.699 | 1.00 | 31.83 A |
| ATOM | 241 | CE | LYS | A | 76 | 18.567 | −11.228 | 8.690 | 1.00 | 36.06 A |
| ATOM | 242 | NZ | LYS | A | 76 | 17.800 | −10.601 | 7.593 | 1.00 | 40.32 A |
| ATOM | 243 | C | LYS | A | 76 | 22.381 | −8.093 | 12.484 | 1.00 | 18.46 A |
| ATOM | 244 | O | LYS | A | 76 | 22.919 | −7.196 | 11.878 | 1.00 | 21.85 A |
| ATOM | 245 | N | LYS | A | 77 | 22.103 | −8.015 | 13.783 | 1.00 | 18.56 A |
| ATOM | 246 | CA | LYS | A | 77 | 22.488 | −6.834 | 14.562 | 1.00 | 20.12 A |
| ATOM | 247 | CB | LYS | A | 77 | 21.955 | −6.936 | 15.993 | 1.00 | 20.58 A |
| ATOM | 248 | CG | LYS | A | 77 | 22.453 | −5.820 | 16.889 | 1.00 | 23.41 A |
| ATOM | 249 | CD | LYS | A | 77 | 22.270 | −6.191 | 18.374 | 1.00 | 27.57 A |
| ATOM | 250 | CE | LYS | A | 77 | 23.362 | −7.150 | 18.819 | 1.00 | 26.72 A |
| ATOM | 251 | NZ | LYS | A | 77 | 23.370 | −7.270 | 20.291 | 1.00 | 30.73 A |
| ATOM | 252 | C | LYS | A | 77 | 24.013 | −6.705 | 14.599 | 1.00 | 21.31 A |
| ATOM | 253 | O | LYS | A | 77 | 24.581 | −5.607 | 14.380 | 1.00 | 19.27 A |
| ATOM | 254 | N | ALA | A | 78 | 24.690 | −7.822 | 14.890 | 1.00 | 22.65 A |
| ATOM | 255 | CA | ALA | A | 78 | 26.151 | −7.824 | 14.951 | 1.00 | 21.66 A |
| ATOM | 256 | CB | ALA | A | 78 | 26.681 | −9.198 | 15.437 | 1.00 | 20.69 A |
| ATOM | 257 | C | ALA | A | 78 | 26.703 | −7.506 | 13.557 | 1.00 | 21.46 A |
| ATOM | 258 | O | ALA | A | 78 | 27.716 | −6.848 | 13.417 | 1.00 | 23.60 A |
| ATOM | 259 | N | TYR | A | 79 | 26.044 | −7.963 | 12.515 | 1.00 | 23.23 A |
| ATOM | 260 | CA | TYR | A | 79 | 26.538 | −7.647 | 11.159 | 1.00 | 24.48 A |
| ATOM | 261 | CB | TYR | A | 79 | 25.702 | −8.347 | 10.087 | 1.00 | 23.95 A |
| ATOM | 262 | CG | TYR | A | 79 | 26.324 | −8.216 | 8.723 | 1.00 | 27.94 A |
| ATOM | 263 | CD1 | TYR | A | 79 | 27.183 | −9.219 | 8.230 | 1.00 | 30.43 A |
| ATOM | 264 | CE1 | TYR | A | 79 | 27.825 | −9.089 | 6.991 | 1.00 | 32.06 A |
| ATOM | 265 | CD2 | TYR | A | 79 | 26.110 | −7.073 | 7.943 | 1.00 | 26.91 A |
| ATOM | 266 | CE2 | TYR | A | 79 | 26.739 | −6.918 | 6.706 | 1.00 | 29.70 A |
| ATOM | 267 | CZ | TYR | A | 79 | 27.597 | −7.935 | 6.231 | 1.00 | 33.31 A |
| ATOM | 268 | OH | TYR | A | 79 | 28.213 | −7.821 | 5.004 | 1.00 | 31.81 A |
| ATOM | 269 | C | TYR | A | 79 | 26.476 | −6.124 | 10.925 | 1.00 | 22.69 A |
| ATOM | 270 | O | TYR | A | 79 | 27.462 | −5.504 | 10.540 | 1.00 | 23.34 A |
| ATOM | 271 | N | LEU | A | 80 | 25.319 | −5.527 | 11.160 | 1.00 | 22.46 A |
| ATOM | 272 | CA | LEU | A | 80 | 25.187 | −4.078 | 10.988 | 1.00 | 23.85 A |
| ATOM | 273 | CB | LEU | A | 80 | 23.801 | −3.617 | 11.455 | 1.00 | 22.25 A |
| ATOM | 274 | CG | LEU | A | 80 | 22.743 | −4.066 | 10.433 | 1.00 | 22.54 A |
| ATOM | 275 | CD1 | LEU | A | 80 | 21.349 | −4.078 | 11.069 | 1.00 | 24.63 A |
| ATOM | 276 | CD2 | LEU | A | 80 | 22.788 | −3.126 | 9.213 | 1.00 | 20.87 A |
| ATOM | 277 | C | LEU | A | 80 | 26.278 | −3.373 | 11.773 | 1.00 | 22.91 A |
| ATOM | 278 | O | LEU | A | 80 | 27.001 | −2.522 | 11.248 | 1.00 | 22.48 A |
| ATOM | 279 | N | GLN | A | 81 | 26.452 | −3.778 | 13.025 | 1.00 | 24.64 A |
| ATOM | 280 | CA | GLN | A | 81 | 27.446 | −3.137 | 13.867 | 1.00 | 24.12 A |
| ATOM | 281 | CB | GLN | A | 81 | 27.336 | −3.641 | 15.297 | 1.00 | 26.17 A |
| ATOM | 282 | CG | GLN | A | 81 | 28.324 | −2.974 | 16.237 | 1.00 | 34.02 A |
| ATOM | 283 | CD | GLN | A | 81 | 27.922 | −3.169 | 17.682 | 1.00 | 39.76 A |
| ATOM | 284 | OE1 | GLN | A | 81 | 27.987 | −2.243 | 18.495 | 1.00 | 42.80 A |
| ATOM | 285 | NE2 | GLN | A | 81 | 27.485 | −4.384 | 18.013 | 1.00 | 42.11 A |
| ATOM | 286 | C | GLN | A | 81 | 28.882 | −3.289 | 13.425 | 1.00 | 25.91 A |
| ATOM | 287 | O | GLN | A | 81 | 29.688 | −2.349 | 13.545 | 1.00 | 24.54 A |
| ATOM | 288 | N | GLU | A | 82 | 29.238 | −4.477 | 12.942 | 1.00 | 26.23 A |
| ATOM | 289 | CA | GLU | A | 82 | 30.621 | −4.694 | 12.547 | 1.00 | 27.94 A |
| ATOM | 290 | CB | GLU | A | 82 | 30.989 | −6.192 | 12.668 | 1.00 | 27.33 A |
| ATOM | 291 | CG | GLU | A | 82 | 30.834 | −6.750 | 14.083 | 1.00 | 34.38 A |
| ATOM | 292 | CD | GLU | A | 82 | 30.963 | −8.283 | 14.165 | 1.00 | 37.63 A |
| ATOM | 293 | OE1 | GLU | A | 82 | 30.675 | −8.832 | 15.253 | 1.00 | 40.42 A |
| ATOM | 294 | OE2 | GLU | A | 82 | 31.348 | −8.937 | 13.159 | 1.00 | 38.38 A |
| ATOM | 295 | C | GLU | A | 82 | 30.945 | −4.206 | 11.133 | 1.00 | 26.64 A |
| ATOM | 296 | O | GLU | A | 82 | 32.063 | −3.775 | 10.884 | 1.00 | 27.50 A |
| ATOM | 297 | N | ASN | A | 83 | 29.977 | −4.247 | 10.224 | 1.00 | 24.69 A |
| ATOM | 298 | CA | ASN | A | 83 | 30.261 | −3.874 | 8.839 | 1.00 | 25.21 A |
| ATOM | 299 | CB | ASN | A | 83 | 30.003 | −5.089 | 7.963 | 1.00 | 25.28 A |
| ATOM | 300 | CG | ASN | A | 83 | 30.679 | −6.333 | 8.514 | 1.00 | 27.39 A |
| ATOM | 301 | OD1 | ASN | A | 83 | 31.901 | −6.371 | 8.646 | 1.00 | 28.14 A |

TABLE 2-continued

| ATOM | 302 | ND2 | ASN | A | 83 | 29.879 | −7.333 | 8.888 | 1.00 | 27.65 | A |
|---|---|---|---|---|---|---|---|---|---|---|---|
| ATOM | 303 | C | ASN | A | 83 | 29.569 | −2.677 | 8.197 | 1.00 | 26.32 | A |
| ATOM | 304 | O | ASN | A | 83 | 29.982 | −2.236 | 7.099 | 1.00 | 25.85 | A |
| ATOM | 305 | N | MET | A | 84 | 28.530 | −2.153 | 8.848 | 1.00 | 24.24 | A |
| ATOM | 306 | CA | MET | A | 84 | 27.776 | −1.031 | 8.278 | 1.00 | 23.55 | A |
| ATOM | 307 | CB | MET | A | 84 | 26.574 | −1.583 | 7.518 | 1.00 | 20.89 | A |
| ATOM | 308 | CG | MET | A | 84 | 26.934 | −2.691 | 6.504 | 1.00 | 26.55 | A |
| ATOM | 309 | SD | MET | A | 84 | 25.498 | −3.241 | 5.536 | 1.00 | 30.67 | A |
| ATOM | 310 | CE | MET | A | 84 | 25.283 | −1.794 | 4.446 | 1.00 | 28.24 | A |
| ATOM | 311 | C | MET | A | 84 | 27.321 | −0.045 | 9.351 | 1.00 | 21.14 | A |
| ATOM | 312 | O | MET | A | 84 | 26.220 | 0.486 | 9.320 | 1.00 | 22.98 | A |
| ATOM | 313 | N | ASP | A | 85 | 28.210 | 0.251 | 10.271 | 1.00 | 21.65 | A |
| ATOM | 314 | CA | ASP | A | 85 | 27.862 | 1.114 | 11.383 | 1.00 | 21.92 | A |
| ATOM | 315 | CB | ASP | A | 85 | 28.939 | 1.061 | 12.446 | 1.00 | 23.59 | A |
| ATOM | 316 | CG | ASP | A | 85 | 28.453 | 1.623 | 13.754 | 1.00 | 26.12 | A |
| ATOM | 317 | OD1 | ASP | A | 85 | 29.172 | 2.460 | 14.357 | 1.00 | 27.42 | A |
| ATOM | 318 | OD2 | ASP | A | 85 | 27.343 | 1.223 | 14.174 | 1.00 | 25.97 | A |
| ATOM | 319 | C | ASP | A | 85 | 27.616 | 2.548 | 11.006 | 1.00 | 22.06 | A |
| ATOM | 320 | O | ASP | A | 85 | 26.977 | 3.275 | 11.747 | 1.00 | 19.57 | A |
| ATOM | 321 | N | TYR | A | 86 | 28.119 | 2.951 | 9.847 | 1.00 | 21.34 | A |
| ATOM | 322 | CA | TYR | A | 86 | 27.915 | 4.316 | 9.376 | 1.00 | 21.09 | A |
| ATOM | 323 | CB | TYR | A | 86 | 28.813 | 4.559 | 8.144 | 1.00 | 22.25 | A |
| ATOM | 324 | CG | TYR | A | 86 | 28.466 | 3.685 | 6.966 | 1.00 | 22.22 | A |
| ATOM | 325 | CD1 | TYR | A | 86 | 27.550 | 4.113 | 6.012 | 1.00 | 21.01 | A |
| ATOM | 326 | CE1 | TYR | A | 86 | 27.170 | 3.293 | 4.950 | 1.00 | 22.57 | A |
| ATOM | 327 | CD2 | TYR | A | 86 | 29.012 | 2.398 | 6.830 | 1.00 | 20.83 | A |
| ATOM | 328 | CE2 | TYR | A | 86 | 28.639 | 1.573 | 5.773 | 1.00 | 22.92 | A |
| ATOM | 329 | CZ | TYR | A | 86 | 27.713 | 2.026 | 4.845 | 1.00 | 20.81 | A |
| ATOM | 330 | OH | TYR | A | 86 | 27.252 | 1.209 | 3.858 | 1.00 | 24.84 | A |
| ATOM | 331 | C | TYR | A | 86 | 26.418 | 4.558 | 9.046 | 1.00 | 20.01 | A |
| ATOM | 332 | O | TYR | A | 86 | 25.962 | 5.709 | 8.997 | 1.00 | 19.86 | A |
| ATOM | 333 | N | LEU | A | 87 | 25.654 | 3.489 | 8.841 | 1.00 | 18.58 | A |
| ATOM | 334 | CA | LEU | A | 87 | 24.236 | 3.635 | 8.546 | 1.00 | 19.32 | A |
| ATOM | 335 | CB | LEU | A | 87 | 23.601 | 2.299 | 8.152 | 1.00 | 20.93 | A |
| ATOM | 336 | CG | LEU | A | 87 | 23.970 | 1.731 | 6.753 | 1.00 | 23.72 | A |
| ATOM | 337 | CD1 | LEU | A | 87 | 23.110 | 0.467 | 6.459 | 1.00 | 21.09 | A |
| ATOM | 338 | CD2 | LEU | A | 87 | 23.730 | 2.798 | 5.684 | 1.00 | 21.56 | A |
| ATOM | 339 | C | LEU | A | 87 | 23.557 | 4.168 | 9.802 | 1.00 | 22.57 | A |
| ATOM | 340 | O | LEU | A | 87 | 22.881 | 5.219 | 9.761 | 1.00 | 23.70 | A |
| ATOM | 341 | N | ARG | A | 88 | 23.728 | 3.446 | 10.914 | 1.00 | 18.66 | A |
| ATOM | 342 | CA | ARG | A | 88 | 23.178 | 3.868 | 12.200 | 1.00 | 17.18 | A |
| ATOM | 343 | CB | ARG | A | 88 | 23.791 | 3.035 | 13.340 | 1.00 | 16.82 | A |
| ATOM | 344 | CG | ARG | A | 88 | 23.393 | 3.500 | 14.755 | 1.00 | 15.73 | A |
| ATOM | 345 | CD | ARG | A | 88 | 24.192 | 2.736 | 15.841 | 1.00 | 14.74 | A |
| ATOM | 346 | NE | ARG | A | 88 | 25.638 | 2.992 | 15.790 | 1.00 | 14.51 | A |
| ATOM | 347 | CZ | ARG | A | 88 | 26.248 | 4.048 | 16.335 | 1.00 | 18.63 | A |
| ATOM | 348 | NH1 | ARG | A | 88 | 25.548 | 4.977 | 16.987 | 1.00 | 15.86 | A |
| ATOM | 349 | NH2 | ARG | A | 88 | 27.570 | 4.168 | 16.236 | 1.00 | 16.53 | A |
| ATOM | 350 | C | ARG | A | 88 | 23.538 | 5.342 | 12.444 | 1.00 | 17.32 | A |
| ATOM | 351 | O | ARG | A | 88 | 22.691 | 6.165 | 12.773 | 1.00 | 17.20 | A |
| ATOM | 352 | N | ARG | A | 89 | 24.805 | 5.663 | 12.275 | 1.00 | 18.21 | A |
| ATOM | 353 | CA | ARG | A | 89 | 25.245 | 7.011 | 12.527 | 1.00 | 17.70 | A |
| ATOM | 354 | CB | ARG | A | 89 | 26.752 | 7.055 | 12.448 | 1.00 | 17.76 | A |
| ATOM | 355 | CG | ARG | A | 89 | 27.360 | 6.118 | 13.470 | 1.00 | 23.83 | A |
| ATOM | 356 | CD | ARG | A | 89 | 28.759 | 6.521 | 13.831 | 1.00 | 25.48 | A |
| ATOM | 357 | NE | ARG | A | 89 | 29.600 | 6.742 | 12.654 | 1.00 | 29.29 | A |
| ATOM | 358 | CZ | ARG | A | 89 | 30.261 | 5.795 | 11.977 | 1.00 | 33.21 | A |
| ATOM | 359 | NH1 | ARG | A | 89 | 30.196 | 4.508 | 12.339 | 1.00 | 31.83 | A |
| ATOM | 360 | NH2 | ARG | A | 89 | 31.023 | 6.152 | 10.946 | 1.00 | 29.73 | A |
| ATOM | 361 | C | ARG | A | 89 | 24.597 | 8.055 | 11.633 | 1.00 | 16.73 | A |
| ATOM | 362 | O | ARG | A | 89 | 24.228 | 9.130 | 12.114 | 1.00 | 16.87 | A |
| ATOM | 363 | N | GLY | A | 90 | 24.405 | 7.751 | 10.349 | 1.00 | 16.66 | A |
| ATOM | 364 | CA | GLY | A | 90 | 23.763 | 8.748 | 9.489 | 1.00 | 15.65 | A |
| ATOM | 365 | C | GLY | A | 90 | 22.267 | 8.905 | 9.742 | 1.00 | 16.02 | A |
| ATOM | 366 | O | GLY | A | 90 | 21.684 | 9.955 | 9.519 | 1.00 | 17.00 | A |
| ATOM | 367 | N | ILE | A | 91 | 21.630 | 7.836 | 10.207 | 1.00 | 16.42 | A |
| ATOM | 368 | CA | ILE | A | 91 | 20.203 | 7.833 | 10.463 | 1.00 | 14.69 | A |
| ATOM | 369 | CB | ILE | A | 91 | 19.684 | 6.385 | 10.366 | 1.00 | 15.27 | A |
| ATOM | 370 | CG2 | ILE | A | 91 | 18.211 | 6.313 | 10.782 | 1.00 | 15.69 | A |
| ATOM | 371 | CG1 | ILE | A | 91 | 19.944 | 5.872 | 8.937 | 1.00 | 17.64 | A |
| ATOM | 372 | CD1 | ILE | A | 91 | 19.610 | 4.380 | 8.737 | 1.00 | 16.19 | A |
| ATOM | 373 | C | ILE | A | 91 | 19.869 | 8.405 | 11.844 | 1.00 | 15.63 | A |
| ATOM | 374 | O | ILE | A | 91 | 18.827 | 9.025 | 12.038 | 1.00 | 15.86 | A |
| ATOM | 375 | N | MET | A | 92 | 20.758 | 8.178 | 12.798 | 1.00 | 14.75 | A |
| ATOM | 376 | CA | MET | A | 92 | 20.555 | 8.611 | 14.170 | 1.00 | 15.17 | A |
| ATOM | 377 | CB | MET | A | 92 | 21.213 | 7.624 | 15.137 | 1.00 | 14.47 | A |
| ATOM | 378 | CG | MET | A | 92 | 20.601 | 6.219 | 15.213 | 1.00 | 13.01 | A |
| ATOM | 379 | SD | MET | A | 92 | 18.978 | 6.209 | 15.930 | 1.00 | 17.19 | A |
| ATOM | 380 | CE | MET | A | 92 | 17.835 | 6.183 | 14.338 | 1.00 | 16.35 | A |

TABLE 2-continued

| | | | | | | | | | | |
|---|---|---|---|---|---|---|---|---|---|---|
| ATOM | 381 | C | MET | A | 92 | 21.102 | 9.981 | 14.525 | 1.00 | 15.24 A |
| ATOM | 382 | O | MET | A | 92 | 20.505 | 10.675 | 15.324 | 1.00 | 17.97 A |
| ATOM | 383 | N | LEU | A | 93 | 22.236 | 10.372 | 13.951 | 1.00 | 16.45 A |
| ATOM | 384 | CA | LEU | A | 93 | 22.873 | 11.622 | 14.359 | 1.00 | 17.69 A |
| ATOM | 385 | CB | LEU | A | 93 | 24.392 | 11.427 | 14.372 | 1.00 | 17.36 A |
| ATOM | 386 | CG | LEU | A | 93 | 24.907 | 10.217 | 15.139 | 1.00 | 18.15 A |
| ATOM | 387 | CD1 | LEU | A | 93 | 26.467 | 10.218 | 15.074 | 1.00 | 20.38 A |
| ATOM | 388 | CD2 | LEU | A | 93 | 24.468 | 10.331 | 16.617 | 1.00 | 19.39 A |
| ATOM | 389 | C | LEU | A | 93 | 22.533 | 12.815 | 13.483 | 1.00 | 18.28 A |
| ATOM | 390 | O | LEU | A | 93 | 21.978 | 12.644 | 12.398 | 1.00 | 16.95 A |
| ATOM | 391 | N | GLU | A | 94 | 22.859 | 14.018 | 13.966 | 1.00 | 16.83 A |
| ATOM | 392 | CA | GLU | A | 94 | 22.636 | 15.231 | 13.185 | 1.00 | 17.55 A |
| ATOM | 393 | CB | GLU | A | 94 | 23.241 | 16.445 | 13.889 | 1.00 | 16.93 A |
| ATOM | 394 | CG | GLU | A | 94 | 22.509 | 16.931 | 15.139 | 1.00 | 15.03 A |
| ATOM | 395 | CD | GLU | A | 94 | 23.126 | 18.232 | 15.644 | 1.00 | 18.68 A |
| ATOM | 396 | OE1 | GLU | A | 94 | 23.146 | 19.212 | 14.874 | 1.00 | 14.75 A |
| ATOM | 397 | OE2 | GLU | A | 94 | 23.594 | 18.274 | 16.799 | 1.00 | 20.51 A |
| ATOM | 398 | C | GLU | A | 94 | 23.397 | 15.008 | 11.881 | 1.00 | 17.15 A |
| ATOM | 399 | O | GLU | A | 94 | 24.399 | 14.302 | 11.867 | 1.00 | 19.87 A |
| ATOM | 400 | N | PRO | A | 95 | 22.981 | 15.657 | 10.785 | 1.00 | 17.47 A |
| ATOM | 401 | CD | PRO | A | 95 | 23.728 | 15.618 | 9.500 | 1.00 | 13.75 A |
| ATOM | 402 | CA | PRO | A | 95 | 21.837 | 16.587 | 10.724 | 1.00 | 14.31 A |
| ATOM | 403 | CB | PRO | A | 95 | 22.173 | 17.466 | 9.521 | 1.00 | 12.04 A |
| ATOM | 404 | CG | PRO | A | 95 | 22.811 | 16.440 | 8.547 | 1.00 | 14.31 A |
| ATOM | 405 | C | PRO | A | 95 | 20.461 | 15.914 | 10.569 | 1.00 | 14.91 A |
| ATOM | 406 | O | PRO | A | 95 | 19.433 | 16.587 | 10.759 | 1.00 | 13.85 A |
| ATOM | 407 | N | ARG | A | 96 | 20.416 | 14.608 | 10.255 | 1.00 | 14.35 A |
| ATOM | 408 | CA | ARG | A | 96 | 19.107 | 13.939 | 10.059 | 1.00 | 14.78 A |
| ATOM | 409 | CB | ARG | A | 96 | 19.226 | 12.720 | 9.125 | 1.00 | 17.07 A |
| ATOM | 410 | CG | ARG | A | 96 | 19.741 | 13.101 | 7.724 | 1.00 | 16.75 A |
| ATOM | 411 | CD | ARG | A | 96 | 20.191 | 11.906 | 6.917 | 1.00 | 14.98 A |
| ATOM | 412 | NE | ARG | A | 96 | 20.844 | 12.328 | 5.665 | 1.00 | 16.89 A |
| ATOM | 413 | CZ | ARG | A | 96 | 22.085 | 12.801 | 5.598 | 1.00 | 18.63 A |
| ATOM | 414 | NH1 | ARG | A | 96 | 22.821 | 12.916 | 6.701 | 1.00 | 15.91 A |
| ATOM | 415 | NH2 | ARG | A | 96 | 22.599 | 13.163 | 4.428 | 1.00 | 16.81 A |
| ATOM | 416 | C | ARG | A | 96 | 18.460 | 13.497 | 11.353 | 1.00 | 13.78 A |
| ATOM | 417 | O | ARG | A | 96 | 17.250 | 13.289 | 11.389 | 1.00 | 14.58 A |
| ATOM | 418 | N | GLY | A | 97 | 19.267 | 13.318 | 12.400 | 1.00 | 14.31 A |
| ATOM | 419 | CA | GLY | A | 97 | 18.744 | 12.906 | 13.706 | 1.00 | 10.79 A |
| ATOM | 420 | C | GLY | A | 97 | 19.316 | 13.888 | 14.739 | 1.00 | 15.14 A |
| ATOM | 421 | O | GLY | A | 97 | 19.489 | 15.079 | 14.429 | 1.00 | 7.59 A |
| ATOM | 422 | N | HIS | A | 98 | 19.646 | 13.406 | 15.941 | 1.00 | 10.85 A |
| ATOM | 423 | CA | HIS | A | 98 | 20.198 | 14.288 | 16.958 | 1.00 | 14.07 A |
| ATOM | 424 | CB | HIS | A | 98 | 19.178 | 15.337 | 17.466 | 1.00 | 8.74 A |
| ATOM | 425 | CG | HIS | A | 98 | 17.937 | 14.760 | 18.073 | 1.00 | 13.09 A |
| ATOM | 426 | CD2 | HIS | A | 98 | 16.764 | 14.370 | 17.504 | 1.00 | 14.21 A |
| ATOM | 427 | ND1 | HIS | A | 98 | 17.770 | 14.604 | 19.433 | 1.00 | 13.11 A |
| ATOM | 428 | CE1 | HIS | A | 98 | 16.552 | 14.148 | 19.677 | 1.00 | 14.59 A |
| ATOM | 429 | NE2 | HIS | A | 98 | 15.921 | 13.996 | 18.523 | 1.00 | 13.08 A |
| ATOM | 430 | C | HIS | A | 98 | 20.712 | 13.438 | 18.109 | 1.00 | 16.45 A |
| ATOM | 431 | O | HIS | A | 98 | 20.539 | 12.216 | 18.115 | 1.00 | 19.11 A |
| ATOM | 432 | N | ASP | A | 99 | 21.320 | 14.091 | 19.086 | 1.00 | 16.12 A |
| ATOM | 433 | CA | ASP | A | 99 | 21.931 | 13.403 | 20.203 | 1.00 | 17.48 A |
| ATOM | 434 | CB | ASP | A | 99 | 22.668 | 14.418 | 21.094 | 1.00 | 15.66 A |
| ATOM | 435 | CG | ASP | A | 99 | 23.915 | 14.952 | 20.440 | 1.00 | 16.01 A |
| ATOM | 436 | OD1 | ASP | A | 99 | 24.427 | 14.349 | 19.465 | 1.00 | 18.90 A |
| ATOM | 437 | OD2 | ASP | A | 99 | 24.417 | 15.988 | 20.899 | 1.00 | 23.85 A |
| ATOM | 438 | C | ASP | A | 99 | 21.060 | 12.511 | 21.052 | 1.00 | 18.60 A |
| ATOM | 439 | O | ASP | A | 99 | 21.584 | 11.708 | 21.823 | 1.00 | 19.70 A |
| ATOM | 440 | N | ASP | A | 100 | 19.740 | 12.633 | 20.918 | 1.00 | 17.35 A |
| ATOM | 441 | CA | ASP | A | 100 | 18.827 | 11.814 | 21.702 | 1.00 | 15.56 A |
| ATOM | 442 | CB | ASP | A | 100 | 18.090 | 12.721 | 22.685 | 1.00 | 14.97 A |
| ATOM | 443 | CG | ASP | A | 100 | 19.047 | 13.235 | 23.761 | 1.00 | 19.99 A |
| ATOM | 444 | OD1 | ASP | A | 100 | 19.281 | 12.471 | 24.737 | 1.00 | 20.11 A |
| ATOM | 445 | OD2 | ASP | A | 100 | 19.597 | 14.355 | 23.601 | 1.00 | 13.67 A |
| ATOM | 446 | C | ASP | A | 100 | 17.848 | 11.000 | 20.838 | 1.00 | 15.48 A |
| ATOM | 447 | O | ASP | A | 100 | 16.791 | 10.568 | 21.308 | 1.00 | 12.21 A |
| ATOM | 448 | N | MET | A | 101 | 18.242 | 10.815 | 19.581 | 1.00 | 15.25 A |
| ATOM | 449 | CA | MET | A | 101 | 17.442 | 10.062 | 18.621 | 1.00 | 15.36 A |
| ATOM | 450 | CB | MET | A | 101 | 17.948 | 10.352 | 17.200 | 1.00 | 14.76 A |
| ATOM | 451 | CG | MET | A | 101 | 17.268 | 9.571 | 16.033 | 1.00 | 13.95 A |
| ATOM | 452 | SD | MET | A | 101 | 15.482 | 9.588 | 16.014 | 1.00 | 13.64 A |
| ATOM | 453 | CE | MET | A | 101 | 15.128 | 11.365 | 15.913 | 1.00 | 12.08 A |
| ATOM | 454 | C | MET | A | 101 | 17.566 | 8.566 | 18.942 | 1.00 | 15.87 A |
| ATOM | 455 | O | MET | A | 101 | 18.577 | 8.063 | 19.539 | 1.00 | 10.67 A |
| ATOM | 456 | N | PHE | A | 102 | 16.514 | 7.851 | 18.594 | 1.00 | 13.47 A |
| ATOM | 457 | CA | PHE | A | 102 | 16.529 | 6.390 | 18.796 | 1.00 | 13.24 A |
| ATOM | 458 | CB | PHE | A | 102 | 15.768 | 6.020 | 20.059 | 1.00 | 11.30 A |
| ATOM | 459 | CG | PHE | A | 102 | 15.970 | 4.596 | 20.495 | 1.00 | 14.49 A |

TABLE 2-continued

| | | | | | | | | | | |
|---|---|---|---|---|---|---|---|---|---|---|
| ATOM | 460 | CD1 | PHE | A | 102 | 16.932 | 4.285 | 21.443 | 1.00 | 17.54 A |
| ATOM | 461 | CD2 | PHE | A | 102 | 15.250 | 3.557 | 19.899 | 1.00 | 18.57 A |
| ATOM | 462 | CE1 | PHE | A | 102 | 17.199 | 2.936 | 21.795 | 1.00 | 17.59 A |
| ATOM | 463 | CE2 | PHE | A | 102 | 15.516 | 2.174 | 20.246 | 1.00 | 14.85 A |
| ATOM | 464 | CZ | PHE | A | 102 | 16.494 | 1.897 | 21.189 | 1.00 | 16.14 A |
| ATOM | 465 | C | PHE | A | 102 | 15.792 | 5.781 | 17.599 | 1.00 | 13.32 A |
| ATOM | 466 | O | PHE | A | 102 | 14.898 | 6.412 | 17.062 | 1.00 | 14.93 A |
| ATOM | 467 | N | GLY | A | 103 | 16.130 | 4.572 | 17.189 | 1.00 | 14.70 A |
| ATOM | 468 | CA | GLY | A | 103 | 15.386 | 3.990 | 16.074 | 1.00 | 16.20 A |
| ATOM | 469 | C | GLY | A | 103 | 15.584 | 2.487 | 15.907 | 1.00 | 18.65 A |
| ATOM | 470 | O | GLY | A | 103 | 16.136 | 1.835 | 16.784 | 1.00 | 17.53 A |
| ATOM | 471 | N | ALA | A | 104 | 15.111 | 1.934 | 14.790 | 1.00 | 15.29 A |
| ATOM | 472 | CA | ALA | A | 104 | 15.233 | 0.522 | 14.540 | 1.00 | 15.59 A |
| ATOM | 473 | CB | ALA | A | 104 | 14.145 | −0.160 | 15.241 | 1.00 | 11.49 A |
| ATOM | 474 | C | ALA | A | 104 | 15.124 | 0.206 | 13.042 | 1.00 | 19.00 A |
| ATOM | 475 | O | ALA | A | 104 | 14.524 | 0.976 | 12.265 | 1.00 | 19.13 A |
| ATOM | 476 | N | PHE | A | 105 | 15.705 | −0.925 | 12.662 | 1.00 | 18.37 A |
| ATOM | 477 | CA | PHE | A | 105 | 15.618 | −1.448 | 11.295 | 1.00 | 18.11 A |
| ATOM | 478 | CB | PHE | A | 105 | 16.944 | −1.976 | 10.815 | 1.00 | 16.70 A |
| ATOM | 479 | CG | PHE | A | 105 | 17.965 | −0.921 | 10.536 | 1.00 | 20.05 A |
| ATOM | 480 | CD1 | PHE | A | 105 | 19.143 | −0.871 | 11.283 | 1.00 | 20.65 A |
| ATOM | 481 | CD2 | PHE | A | 105 | 17.818 | −0.046 | 9.452 | 1.00 | 16.06 A |
| ATOM | 482 | CE1 | PHE | A | 105 | 20.162 | 0.009 | 10.950 | 1.00 | 20.60 A |
| ATOM | 483 | CE2 | PHE | A | 105 | 18.838 | 0.836 | 9.126 | 1.00 | 19.84 A |
| ATOM | 484 | CZ | PHE | A | 105 | 20.021 | 0.865 | 9.871 | 1.00 | 17.14 A |
| ATOM | 485 | C | PHE | A | 105 | 14.646 | −2.635 | 11.355 | 1.00 | 19.49 A |
| ATOM | 486 | O | PHE | A | 105 | 14.778 | −3.528 | 12.210 | 1.00 | 18.11 A |
| ATOM | 487 | N | LEU | A | 106 | 13.646 | −2.622 | 10.481 | 1.00 | 17.64 A |
| ATOM | 488 | CA | LEU | A | 106 | 12.699 | −3.717 | 10.375 | 1.00 | 19.09 A |
| ATOM | 489 | CB | LEU | A | 106 | 11.345 | −3.236 | 9.843 | 1.00 | 18.18 A |
| ATOM | 490 | CG | LEU | A | 106 | 10.537 | −2.315 | 10.725 | 1.00 | 19.53 A |
| ATOM | 491 | CD1 | LEU | A | 106 | 9.170 | −2.039 | 10.105 | 1.00 | 18.35 A |
| ATOM | 492 | CD2 | LEU | A | 106 | 10.371 | −3.012 | 12.107 | 1.00 | 14.58 A |
| ATOM | 493 | C | LEU | A | 106 | 13.257 | −4.756 | 9.395 | 1.00 | 20.13 A |
| ATOM | 494 | O | LEU | A | 106 | 13.975 | −4.414 | 8.447 | 1.00 | 21.09 A |
| ATOM | 495 | N | PHE | A | 107 | 12.923 | −6.025 | 9.632 | 1.00 | 19.65 A |
| ATOM | 496 | CA | PHE | A | 107 | 13.364 | −7.122 | 8.774 | 1.00 | 19.75 A |
| ATOM | 497 | CB | PHE | A | 107 | 14.557 | −7.863 | 9.378 | 1.00 | 19.25 A |
| ATOM | 498 | CG | PHE | A | 107 | 15.814 | −7.081 | 9.416 | 1.00 | 21.72 A |
| ATOM | 499 | CD1 | PHE | A | 107 | 16.189 | −6.397 | 10.565 | 1.00 | 18.65 A |
| ATOM | 500 | CD2 | PHE | A | 107 | 16.667 | −7.075 | 8.316 | 1.00 | 19.05 A |
| ATOM | 501 | CE1 | PHE | A | 107 | 17.420 | −5.718 | 10.615 | 1.00 | 17.88 A |
| ATOM | 502 | CE2 | PHE | A | 107 | 17.900 | −6.405 | 8.361 | 1.00 | 22.07 A |
| ATOM | 503 | CZ | PHE | A | 107 | 18.276 | −5.723 | 9.525 | 1.00 | 19.88 A |
| ATOM | 504 | C | PHE | A | 107 | 12.244 | −8.136 | 8.727 | 1.00 | 21.28 A |
| ATOM | 505 | O | PHE | A | 107 | 11.313 | −8.099 | 9.569 | 1.00 | 20.80 A |
| ATOM | 506 | N | ASP | A | 108 | 12.326 | −9.077 | 7.786 | 1.00 | 22.42 A |
| ATOM | 507 | CA | ASP | A | 108 | 11.318 | −10.149 | 7.779 | 1.00 | 23.81 A |
| ATOM | 508 | CB | ASP | A | 108 | 11.528 | −11.125 | 6.618 | 1.00 | 27.23 A |
| ATOM | 509 | CG | ASP | A | 108 | 11.260 | −10.502 | 5.247 | 1.00 | 33.34 A |
| ATOM | 510 | OD1 | ASP | A | 108 | 10.305 | −9.698 | 5.121 | 1.00 | 31.69 A |
| ATOM | 511 | OD2 | ASP | A | 108 | 12.013 | −10.852 | 4.306 | 1.00 | 35.16 A |
| ATOM | 512 | C | ASP | A | 108 | 11.581 | −10.967 | 9.071 | 1.00 | 22.73 A |
| ATOM | 513 | O | ASP | A | 108 | 12.729 | −11.114 | 9.500 | 1.00 | 21.59 A |
| ATOM | 514 | N | PRO | A | 109 | 10.535 | −11.534 | 9.674 | 1.00 | 24.11 A |
| ATOM | 515 | CD | PRO | A | 109 | 9.125 | −11.592 | 9.235 | 1.00 | 27.42 A |
| ATOM | 516 | CA | PRO | A | 109 | 10.742 | −12.321 | 10.889 | 1.00 | 26.64 A |
| ATOM | 517 | CB | PRO | A | 109 | 9.320 | −12.626 | 11.348 | 1.00 | 26.54 A |
| ATOM | 518 | CG | PRO | A | 109 | 8.574 | −12.761 | 10.062 | 1.00 | 27.76 A |
| ATOM | 519 | C | PRO | A | 109 | 11.533 | −13.582 | 10.536 | 1.00 | 27.91 A |
| ATOM | 520 | O | PRO | A | 109 | 11.531 | −13.995 | 9.386 | 1.00 | 28.57 A |
| ATOM | 521 | N | ILE | A | 110 | 12.278 | −14.129 | 11.496 | 1.00 | 27.71 A |
| ATOM | 522 | CA | ILE | A | 110 | 13.009 | −15.370 | 11.281 | 1.00 | 27.40 A |
| ATOM | 523 | CB | ILE | A | 110 | 14.533 | −15.210 | 11.509 | 1.00 | 26.59 A |
| ATOM | 524 | CG2 | ILE | A | 110 | 15.231 | −16.579 | 11.612 | 1.00 | 26.12 A |
| ATOM | 525 | CG1 | ILE | A | 110 | 15.138 | −14.452 | 10.339 | 1.00 | 23.91 A |
| ATOM | 526 | CD1 | ILE | A | 110 | 16.621 | −14.185 | 10.475 | 1.00 | 27.88 A |
| ATOM | 527 | C | ILE | A | 110 | 12.407 | −16.390 | 12.249 | 1.00 | 30.57 A |
| ATOM | 528 | O | ILE | A | 110 | 12.054 | −17.485 | 11.836 | 1.00 | 33.38 A |
| ATOM | 529 | N | GLU | A | 111 | 12.237 | −16.044 | 13.523 | 1.00 | 31.37 A |
| ATOM | 530 | CA | GLU | A | 111 | 11.668 | −17.002 | 14.455 | 1.00 | 34.74 A |
| ATOM | 531 | CB | GLU | A | 111 | 11.743 | −16.487 | 15.901 | 1.00 | 37.88 A |
| ATOM | 532 | CG | GLU | A | 111 | 13.163 | −16.199 | 16.388 | 1.00 | 39.88 A |
| ATOM | 533 | CD | GLU | A | 111 | 14.150 | −17.350 | 16.125 | 1.00 | 43.16 A |
| ATOM | 534 | OE1 | GLU | A | 111 | 13.790 | −18.508 | 16.449 | 1.00 | 41.26 A |
| ATOM | 535 | OE2 | GLU | A | 111 | 15.284 | −17.085 | 15.613 | 1.00 | 41.95 A |
| ATOM | 536 | C | GLU | A | 111 | 10.228 | −17.362 | 14.112 | 1.00 | 37.26 A |
| ATOM | 537 | O | GLU | A | 111 | 9.449 | −16.527 | 13.619 | 1.00 | 37.51 A |
| ATOM | 538 | N | GLU | A | 112 | 9.878 | −18.619 | 14.365 | 1.00 | 37.51 A |

TABLE 2-continued

| ATOM | 539 | CA | GLU | A | 112 | 8.538 | −19.096 | 14.087 | 1.00 | 39.20 | A |
| ATOM | 540 | CB | GLU | A | 112 | 8.423 | −20.618 | 14.343 | 1.00 | 44.94 | A |
| ATOM | 541 | CG | GLU | A | 112 | 7.136 | −21.231 | 13.740 | 1.00 | 52.80 | A |
| ATOM | 542 | CD | GLU | A | 112 | 7.049 | −22.757 | 13.884 | 1.00 | 58.10 | A |
| ATOM | 543 | OE1 | GLU | A | 112 | 6.132 | −23.369 | 13.268 | 1.00 | 60.88 | A |
| ATOM | 544 | OE2 | GLU | A | 112 | 7.887 | −23.340 | 14.613 | 1.00 | 59.93 | A |
| ATOM | 545 | C | GLU | A | 112 | 7.554 | −18.361 | 14.969 | 1.00 | 35.05 | A |
| ATOM | 546 | O | GLU | A | 112 | 7.761 | −18.229 | 16.154 | 1.00 | 35.71 | A |
| ATOM | 547 | N | GLY | A | 113 | 6.484 | −17.865 | 14.379 | 1.00 | 33.74 | A |
| ATOM | 548 | CA | GLY | A | 113 | 5.497 | −17.146 | 15.168 | 1.00 | 33.22 | A |
| ATOM | 549 | C | GLY | A | 113 | 5.650 | −15.632 | 15.164 | 1.00 | 31.00 | A |
| ATOM | 550 | O | GLY | A | 113 | 4.718 | −14.938 | 15.561 | 1.00 | 30.67 | A |
| ATOM | 551 | N | ALA | A | 114 | 6.789 | −15.111 | 14.706 | 1.00 | 27.90 | A |
| ATOM | 552 | CA | ALA | A | 114 | 6.968 | −13.665 | 14.707 | 1.00 | 27.93 | A |
| ATOM | 553 | CB | ALA | A | 114 | 8.449 | −13.315 | 14.829 | 1.00 | 25.37 | A |
| ATOM | 554 | C | ALA | A | 114 | 6.377 | −13.052 | 13.446 | 1.00 | 30.01 | A |
| ATOM | 555 | O | ALA | A | 114 | 6.295 | −13.708 | 12.389 | 1.00 | 29.87 | A |
| ATOM | 556 | N | ASP | A | 115 | 5.945 | −11.799 | 13.564 | 1.00 | 27.80 | A |
| ATOM | 557 | CA | ASP | A | 115 | 5.363 | −11.085 | 12.453 | 1.00 | 27.62 | A |
| ATOM | 558 | CB | ASP | A | 115 | 4.201 | −10.209 | 12.928 | 1.00 | 29.66 | A |
| ATOM | 559 | CG | ASP | A | 115 | 3.001 | −11.017 | 13.415 | 1.00 | 33.45 | A |
| ATOM | 560 | OD1 | ASP | A | 115 | 2.396 | −11.728 | 12.588 | 1.00 | 36.10 | A |
| ATOM | 561 | OD2 | ASP | A | 115 | 2.646 | −10.952 | 14.619 | 1.00 | 33.25 | A |
| ATOM | 562 | C | ASP | A | 115 | 6.416 | −10.192 | 11.859 | 1.00 | 27.45 | A |
| ATOM | 563 | O | ASP | A | 115 | 6.392 | −9.888 | 10.675 | 1.00 | 27.18 | A |
| ATOM | 564 | N | LEU | A | 116 | 7.363 | −9.769 | 12.691 | 1.00 | 25.66 | A |
| ATOM | 565 | CA | LEU | A | 116 | 8.381 | −8.846 | 12.236 | 1.00 | 22.36 | A |
| ATOM | 566 | CB | LEU | A | 116 | 7.955 | −7.410 | 12.513 | 1.00 | 22.77 | A |
| ATOM | 567 | CG | LEU | A | 116 | 7.179 | −6.525 | 11.570 | 1.00 | 29.91 | A |
| ATOM | 568 | CD1 | LEU | A | 116 | 6.802 | −5.250 | 12.337 | 1.00 | 27.25 | A |
| ATOM | 569 | CD2 | LEU | A | 116 | 8.055 | −6.208 | 10.310 | 1.00 | 29.47 | A |
| ATOM | 570 | C | LEU | A | 116 | 9.690 | −8.996 | 12.949 | 1.00 | 21.54 | A |
| ATOM | 571 | O | LEU | A | 116 | 9.723 | −9.166 | 14.173 | 1.00 | 21.94 | A |
| ATOM | 572 | N | GLY | A | 117 | 10.758 | −8.855 | 12.187 | 1.00 | 18.26 | A |
| ATOM | 573 | CA | GLY | A | 117 | 12.082 | −8.884 | 12.761 | 1.00 | 18.36 | A |
| ATOM | 574 | C | GLY | A | 117 | 12.443 | −7.426 | 12.993 | 1.00 | 20.69 | A |
| ATOM | 575 | O | GLY | A | 117 | 12.034 | −6.524 | 12.212 | 1.00 | 17.83 | A |
| ATOM | 576 | N | ILE | A | 118 | 13.183 | −7.172 | 14.071 | 1.00 | 19.56 | A |
| ATOM | 577 | CA | ILE | A | 118 | 13.582 | −5.814 | 14.401 | 1.00 | 19.75 | A |
| ATOM | 578 | CB | ILE | A | 118 | 12.449 | −5.115 | 15.235 | 1.00 | 17.66 | A |
| ATOM | 579 | CG2 | ILE | A | 118 | 12.214 | −5.843 | 16.528 | 1.00 | 11.10 | A |
| ATOM | 580 | CG1 | ILE | A | 118 | 12.780 | −3.626 | 15.482 | 1.00 | 16.73 | A |
| ATOM | 581 | CD1 | ILE | A | 118 | 11.554 | −2.826 | 15.983 | 1.00 | 11.45 | A |
| ATOM | 582 | C | ILE | A | 118 | 14.950 | −5.699 | 15.082 | 1.00 | 20.89 | A |
| ATOM | 583 | O | ILE | A | 118 | 15.336 | −6.523 | 15.911 | 1.00 | 22.69 | A |
| ATOM | 584 | N | VAL | A | 119 | 15.726 | −4.725 | 14.648 | 1.00 | 17.68 | A |
| ATOM | 585 | CA | VAL | A | 119 | 17.023 | −4.479 | 15.245 | 1.00 | 17.73 | A |
| ATOM | 586 | CB | VAL | A | 119 | 18.156 | −4.707 | 14.245 | 1.00 | 18.48 | A |
| ATOM | 587 | CG1 | VAL | A | 119 | 19.470 | −4.088 | 14.786 | 1.00 | 16.26 | A |
| ATOM | 588 | CG2 | VAL | A | 119 | 18.360 | −6.248 | 14.024 | 1.00 | 17.37 | A |
| ATOM | 589 | C | VAL | A | 119 | 16.995 | −3.007 | 15.703 | 1.00 | 19.67 | A |
| ATOM | 590 | O | VAL | A | 119 | 16.685 | −2.109 | 14.897 | 1.00 | 22.22 | A |
| ATOM | 591 | N | PHE | A | 120 | 17.264 | −2.783 | 16.990 | 1.00 | 17.05 | A |
| ATOM | 592 | CA | PHE | A | 120 | 17.268 | −1.451 | 17.601 | 1.00 | 17.35 | A |
| ATOM | 593 | CB | PHE | A | 120 | 16.913 | −1.575 | 19.071 | 1.00 | 14.79 | A |
| ATOM | 594 | CG | PHE | A | 120 | 15.575 | −2.162 | 19.296 | 1.00 | 14.74 | A |
| ATOM | 595 | CD1 | PHE | A | 120 | 15.446 | −3.471 | 19.743 | 1.00 | 18.44 | A |
| ATOM | 596 | CD2 | PHE | A | 120 | 14.431 | −1.455 | 18.942 | 1.00 | 11.88 | A |
| ATOM | 597 | CE1 | PHE | A | 120 | 14.205 | −4.072 | 19.822 | 1.00 | 17.97 | A |
| ATOM | 598 | CE2 | PHE | A | 120 | 13.184 | −2.036 | 19.024 | 1.00 | 8.38 | A |
| ATOM | 599 | CZ | PHE | A | 120 | 13.065 | −3.346 | 19.461 | 1.00 | 16.46 | A |
| ATOM | 600 | C | PHE | A | 120 | 18.587 | −0.704 | 17.489 | 1.00 | 16.31 | A |
| ATOM | 601 | O | PHE | A | 120 | 19.643 | −1.307 | 17.485 | 1.00 | 17.15 | A |
| ATOM | 602 | N | MET | A | 121 | 18.533 | 0.607 | 17.406 | 1.00 | 13.89 | A |
| ATOM | 603 | CA | MET | A | 121 | 19.784 | 1.373 | 17.332 | 1.00 | 15.68 | A |
| ATOM | 604 | CB | MET | A | 121 | 20.173 | 1.653 | 15.868 | 1.00 | 16.03 | A |
| ATOM | 605 | CG | MET | A | 121 | 19.064 | 2.347 | 15.026 | 1.00 | 14.51 | A |
| ATOM | 606 | SD | MET | A | 121 | 19.630 | 2.803 | 13.354 | 1.00 | 18.48 | A |
| ATOM | 607 | CE | MET | A | 121 | 17.989 | 2.729 | 12.387 | 1.00 | 14.43 | A |
| ATOM | 608 | C | MET | A | 121 | 19.628 | 2.699 | 18.085 | 1.00 | 15.20 | A |
| ATOM | 609 | O | MET | A | 121 | 18.511 | 3.156 | 18.271 | 1.00 | 15.74 | A |
| ATOM | 610 | N | ASP | A | 122 | 20.738 | 3.311 | 18.511 | 1.00 | 16.13 | A |
| ATOM | 611 | CA | ASP | A | 122 | 20.695 | 4.596 | 19.228 | 1.00 | 15.51 | A |
| ATOM | 612 | CB | ASP | A | 122 | 20.602 | 4.380 | 20.743 | 1.00 | 16.13 | A |
| ATOM | 613 | CG | ASP | A | 122 | 21.662 | 3.387 | 21.252 | 1.00 | 17.19 | A |
| ATOM | 614 | OD1 | ASP | A | 122 | 21.302 | 2.301 | 21.738 | 1.00 | 17.17 | A |
| ATOM | 615 | OD2 | ASP | A | 122 | 22.859 | 3.668 | 21.110 | 1.00 | 18.95 | A |
| ATOM | 616 | C | ASP | A | 122 | 21.940 | 5.393 | 18.875 | 1.00 | 16.30 | A |
| ATOM | 617 | O | ASP | A | 122 | 22.659 | 5.021 | 17.927 | 1.00 | 16.43 | A |

TABLE 2-continued

| ATOM | 618 | N | THR | A | 123 | 22.232 | 6.476 | 19.606 | 1.00 | 14.64 | A |
|---|---|---|---|---|---|---|---|---|---|---|---|
| ATOM | 619 | CA | THR | A | 123 | 23.405 | 7.296 | 19.248 | 1.00 | 16.34 | A |
| ATOM | 620 | CB | THR | A | 123 | 23.377 | 8.666 | 19.948 | 1.00 | 20.16 | A |
| ATOM | 621 | OG1 | THR | A | 123 | 23.433 | 8.452 | 21.359 | 1.00 | 20.03 | A |
| ATOM | 622 | CG2 | THR | A | 123 | 22.050 | 9.420 | 19.651 | 1.00 | 15.91 | A |
| ATOM | 623 | C | THR | A | 123 | 24.765 | 6.654 | 19.543 | 1.00 | 18.44 | A |
| ATOM | 624 | O | THR | A | 123 | 25.788 | 7.105 | 19.045 | 1.00 | 17.71 | A |
| ATOM | 625 | N | GLY | A | 124 | 24.783 | 5.575 | 20.314 | 1.00 | 19.83 | A |
| ATOM | 626 | CA | GLY | A | 124 | 26.067 | 4.937 | 20.620 | 1.00 | 19.03 | A |
| ATOM | 627 | C | GLY | A | 124 | 26.151 | 3.518 | 20.111 | 1.00 | 20.74 | A |
| ATOM | 628 | O | GLY | A | 124 | 27.210 | 3.095 | 19.684 | 1.00 | 23.11 | A |
| ATOM | 629 | N | GLY | A | 125 | 25.044 | 2.779 | 20.111 | 1.00 | 21.72 | A |
| ATOM | 630 | CA | GLY | A | 125 | 25.112 | 1.398 | 19.639 | 1.00 | 20.92 | A |
| ATOM | 631 | C | GLY | A | 125 | 23.774 | 0.755 | 19.288 | 1.00 | 21.20 | A |
| ATOM | 632 | O | GLY | A | 125 | 22.910 | 1.390 | 18.701 | 1.00 | 15.13 | A |
| ATOM | 633 | N | TYR | A | 126 | 23.627 | −0.520 | 19.659 | 1.00 | 20.42 | A |
| ATOM | 634 | CA | TYR | A | 126 | 22.434 | −1.309 | 19.376 | 1.00 | 18.95 | A |
| ATOM | 635 | CB | TYR | A | 126 | 22.769 | −2.346 | 18.304 | 1.00 | 18.10 | A |
| ATOM | 636 | CG | TYR | A | 126 | 23.407 | −1.769 | 17.039 | 1.00 | 21.30 | A |
| ATOM | 637 | CD1 | TYR | A | 126 | 24.746 | −1.391 | 17.022 | 1.00 | 20.88 | A |
| ATOM | 638 | CE1 | TYR | A | 126 | 25.335 | −0.852 | 15.891 | 1.00 | 20.12 | A |
| ATOM | 639 | CD2 | TYR | A | 126 | 22.658 | −1.582 | 15.866 | 1.00 | 19.45 | A |
| ATOM | 640 | CE2 | TYR | A | 126 | 23.255 | −1.023 | 14.718 | 1.00 | 19.36 | A |
| ATOM | 641 | CZ | TYR | A | 126 | 24.591 | −0.670 | 14.752 | 1.00 | 19.84 | A |
| ATOM | 642 | OH | TYR | A | 126 | 25.200 | −0.139 | 13.643 | 1.00 | 22.55 | A |
| ATOM | 643 | C | TYR | A | 126 | 21.962 | −2.039 | 20.636 | 1.00 | 20.67 | A |
| ATOM | 644 | O | TYR | A | 126 | 22.664 | −2.923 | 21.122 | 1.00 | 21.83 | A |
| ATOM | 645 | N | LEU | A | 127 | 20.817 | −1.668 | 21.199 | 1.00 | 18.90 | A |
| ATOM | 646 | CA | LEU | A | 127 | 20.333 | −2.396 | 22.378 | 1.00 | 19.94 | A |
| ATOM | 647 | CB | LEU | A | 127 | 19.293 | −1.565 | 23.136 | 1.00 | 16.69 | A |
| ATOM | 648 | CG | LEU | A | 127 | 19.833 | −0.296 | 23.778 | 1.00 | 15.15 | A |
| ATOM | 649 | CD1 | LEU | A | 127 | 18.687 | 0.434 | 24.454 | 1.00 | 15.62 | A |
| ATOM | 650 | CD2 | LEU | A | 127 | 20.917 | −0.693 | 24.813 | 1.00 | 14.77 | A |
| ATOM | 651 | C | LEU | A | 127 | 19.679 | −3.714 | 21.922 | 1.00 | 22.15 | A |
| ATOM | 652 | O | LEU | A | 127 | 19.087 | −3.789 | 20.807 | 1.00 | 19.94 | A |
| ATOM | 653 | N | ASN | A | 128 | 19.729 | −4.731 | 22.784 | 1.00 | 19.78 | A |
| ATOM | 654 | CA | ASN | A | 128 | 19.146 | −6.008 | 22.442 | 1.00 | 17.69 | A |
| ATOM | 655 | CB | ASN | A | 128 | 19.718 | −7.129 | 23.329 | 1.00 | 17.30 | A |
| ATOM | 656 | CG | ASN | A | 128 | 21.132 | −7.510 | 22.910 | 1.00 | 20.21 | A |
| ATOM | 657 | OD1 | ASN | A | 128 | 21.321 | −8.172 | 21.911 | 1.00 | 21.69 | A |
| ATOM | 658 | ND2 | ASN | A | 128 | 22.130 | −7.046 | 23.653 | 1.00 | 20.77 | A |
| ATOM | 659 | C | ASN | A | 128 | 17.652 | −5.951 | 22.489 | 1.00 | 16.66 | A |
| ATOM | 660 | O | ASN | A | 128 | 16.979 | −6.726 | 21.820 | 1.00 | 16.07 | A |
| ATOM | 661 | N | MET | A | 129 | 17.105 | −5.049 | 23.286 | 1.00 | 17.43 | A |
| ATOM | 662 | CA | MET | A | 129 | 15.644 | −4.891 | 23.293 | 1.00 | 17.78 | A |
| ATOM | 663 | CB | MET | A | 129 | 14.945 | −5.836 | 24.304 | 1.00 | 18.80 | A |
| ATOM | 664 | CG | MET | A | 129 | 13.855 | −6.743 | 23.656 | 1.00 | 17.74 | A |
| ATOM | 665 | SD | MET | A | 129 | 12.478 | −5.794 | 22.876 | 1.00 | 19.04 | A |
| ATOM | 666 | CE | MET | A | 129 | 11.555 | −5.342 | 24.274 | 1.00 | 13.77 | A |
| ATOM | 667 | C | MET | A | 129 | 15.329 | −3.450 | 23.649 | 1.00 | 17.45 | A |
| ATOM | 668 | O | MET | A | 129 | 16.169 | −2.749 | 24.196 | 1.00 | 17.29 | A |
| ATOM | 669 | N | CYS | A | 130 | 14.118 | −3.004 | 23.339 | 1.00 | 15.99 | A |
| ATOM | 670 | CA | CYS | A | 130 | 13.711 | −1.636 | 23.660 | 1.00 | 15.23 | A |
| ATOM | 671 | CB | CYS | A | 130 | 14.154 | −0.643 | 22.570 | 1.00 | 15.57 | A |
| ATOM | 672 | SG | CYS | A | 130 | 13.513 | 1.020 | 22.846 | 1.00 | 19.18 | A |
| ATOM | 673 | C | CYS | A | 130 | 12.227 | −1.675 | 23.760 | 1.00 | 16.14 | A |
| ATOM | 674 | O | CYS | A | 130 | 11.503 | −2.026 | 22.790 | 1.00 | 15.93 | A |
| ATOM | 675 | N | GLY | A | 131 | 11.750 | −1.357 | 24.951 | 1.00 | 14.58 | A |
| ATOM | 676 | CA | GLY | A | 131 | 10.337 | −1.379 | 25.170 | 1.00 | 12.01 | A |
| ATOM | 677 | C | GLY | A | 131 | 9.573 | −0.282 | 24.444 | 1.00 | 14.99 | A |
| ATOM | 678 | O | GLY | A | 131 | 8.529 | −0.572 | 23.833 | 1.00 | 13.87 | A |
| ATOM | 679 | N | HIS | A | 132 | 10.047 | 0.968 | 24.507 | 1.00 | 14.36 | A |
| ATOM | 680 | CA | HIS | A | 132 | 9.278 | 2.065 | 23.885 | 1.00 | 13.54 | A |
| ATOM | 681 | CB | HIS | A | 132 | 9.854 | 3.463 | 24.279 | 1.00 | 11.91 | A |
| ATOM | 682 | CG | HIS | A | 132 | 10.898 | 3.974 | 23.343 | 1.00 | 13.25 | A |
| ATOM | 683 | CD2 | HIS | A | 132 | 10.783 | 4.677 | 22.190 | 1.00 | 13.24 | A |
| ATOM | 684 | ND1 | HIS | A | 132 | 12.237 | 3.688 | 23.486 | 1.00 | 9.99 | A |
| ATOM | 685 | CE1 | HIS | A | 132 | 12.898 | 4.175 | 22.455 | 1.00 | 11.19 | A |
| ATOM | 686 | NE2 | HIS | A | 132 | 12.037 | 4.776 | 21.649 | 1.00 | 11.37 | A |
| ATOM | 687 | C | HIS | A | 132 | 9.222 | 1.914 | 22.365 | 1.00 | 13.22 | A |
| ATOM | 688 | O | HIS | A | 132 | 8.201 | 2.253 | 21.763 | 1.00 | 17.33 | A |
| ATOM | 689 | N | ASN | A | 133 | 10.285 | 1.399 | 21.755 | 1.00 | 12.92 | A |
| ATOM | 690 | CA | ASN | A | 133 | 10.317 | 1.208 | 20.309 | 1.00 | 14.55 | A |
| ATOM | 691 | CB | ASN | A | 133 | 11.730 | 1.128 | 19.793 | 1.00 | 15.34 | A |
| ATOM | 692 | CG | ASN | A | 133 | 11.835 | 1.479 | 18.305 | 1.00 | 16.38 | A |
| ATOM | 693 | OD1 | ASN | A | 133 | 10.980 | 1.085 | 17.438 | 1.00 | 20.05 | A |
| ATOM | 694 | ND2 | ASN | A | 133 | 12.879 | 2.178 | 17.983 | 1.00 | 6.24 | A |
| ATOM | 695 | C | ASN | A | 133 | 9.560 | −0.061 | 19.895 | 1.00 | 18.07 | A |
| ATOM | 696 | O | ASN | A | 133 | 9.135 | −0.173 | 18.735 | 1.00 | 18.98 | A |

TABLE 2-continued

| | | | | | | | | | | |
|---|---|---|---|---|---|---|---|---|---|---|
| ATOM | 697 | N | SER | A | 134 | 9.374 | −1.011 | 20.828 | 1.00 | 16.69 A |
| ATOM | 698 | CA | SER | A | 134 | 8.596 | −2.218 | 20.504 | 1.00 | 15.31 A |
| ATOM | 699 | CB | SER | A | 134 | 8.807 | −3.360 | 21.507 | 1.00 | 10.54 A |
| ATOM | 700 | OG | SER | A | 134 | 10.111 | −3.909 | 21.364 | 1.00 | 13.79 A |
| ATOM | 701 | C | SER | A | 134 | 7.141 | −1.785 | 20.533 | 1.00 | 14.52 A |
| ATOM | 702 | O | SER | A | 134 | 6.336 | −2.230 | 19.703 | 1.00 | 14.42 A |
| ATOM | 703 | N | ILE | A | 135 | 6.801 | −0.942 | 21.502 | 1.00 | 11.79 A |
| ATOM | 704 | CA | ILE | A | 135 | 5.441 | −0.420 | 21.596 | 1.00 | 13.50 A |
| ATOM | 705 | CB | ILE | A | 135 | 5.332 | 0.467 | 22.852 | 1.00 | 14.04 A |
| ATOM | 706 | CG2 | ILE | A | 135 | 4.193 | 1.501 | 22.747 | 1.00 | 9.42 A |
| ATOM | 707 | CG1 | ILE | A | 135 | 5.117 | −0.450 | 24.088 | 1.00 | 18.53 A |
| ATOM | 708 | CD1 | ILE | A | 135 | 5.311 | 0.285 | 25.427 | 1.00 | 17.58 A |
| ATOM | 709 | C | ILE | A | 135 | 5.134 | 0.396 | 20.301 | 1.00 | 14.43 A |
| ATOM | 710 | O | ILE | A | 135 | 4.027 | 0.327 | 19.742 | 1.00 | 15.61 A |
| ATOM | 711 | N | ALA | A | 136 | 6.109 | 1.168 | 19.826 | 1.00 | 13.39 A |
| ATOM | 712 | CA | ALA | A | 136 | 5.900 | 1.957 | 18.597 | 1.00 | 15.96 A |
| ATOM | 713 | CB | ALA | A | 136 | 7.045 | 2.923 | 18.385 | 1.00 | 13.90 A |
| ATOM | 714 | C | ALA | A | 136 | 5.766 | 1.043 | 17.349 | 1.00 | 14.98 A |
| ATOM | 715 | O | ALA | A | 136 | 4.943 | 1.316 | 16.498 | 1.00 | 17.14 A |
| ATOM | 716 | N | ALA | A | 137 | 6.606 | 0.009 | 17.241 | 1.00 | 14.19 A |
| ATOM | 717 | CA | ALA | A | 137 | 6.588 | −0.926 | 16.113 | 1.00 | 16.25 A |
| ATOM | 718 | CB | ALA | A | 137 | 7.739 | −1.897 | 16.211 | 1.00 | 12.23 A |
| ATOM | 719 | C | ALA | A | 137 | 5.260 | −1.692 | 16.044 | 1.00 | 18.92 A |
| ATOM | 720 | O | ALA | A | 137 | 4.711 | −1.912 | 14.945 | 1.00 | 17.99 A |
| ATOM | 721 | N | VAL | A | 138 | 4.735 | −2.065 | 17.213 | 1.00 | 18.01 A |
| ATOM | 722 | CA | VAL | A | 138 | 3.464 | −2.764 | 17.324 | 1.00 | 18.72 A |
| ATOM | 723 | CB | VAL | A | 138 | 3.167 | −3.135 | 18.802 | 1.00 | 20.11 A |
| ATOM | 724 | CG1 | VAL | A | 138 | 1.730 | −3.592 | 18.960 | 1.00 | 16.49 A |
| ATOM | 725 | CG2 | VAL | A | 138 | 4.106 | −4.290 | 19.253 | 1.00 | 17.41 A |
| ATOM | 726 | C | VAL | A | 138 | 2.346 | −1.862 | 16.806 | 1.00 | 22.43 A |
| ATOM | 727 | O | VAL | A | 138 | 1.467 | −2.298 | 16.033 | 1.00 | 21.66 A |
| ATOM | 728 | N | THR | A | 139 | 2.370 | −0.608 | 17.269 | 1.00 | 19.76 A |
| ATOM | 729 | CA | THR | A | 139 | 1.416 | 0.394 | 16.874 | 1.00 | 17.43 A |
| ATOM | 730 | CB | THR | A | 139 | 1.679 | 1.716 | 17.613 | 1.00 | 17.77 A |
| ATOM | 731 | OG1 | THR | A | 139 | 1.590 | 1.501 | 19.035 | 1.00 | 19.95 A |
| ATOM | 732 | CG2 | THR | A | 139 | 0.622 | 2.763 | 17.217 | 1.00 | 15.20 A |
| ATOM | 733 | C | THR | A | 139 | 1.485 | 0.649 | 15.340 | 1.00 | 19.71 A |
| ATOM | 734 | O | THR | A | 139 | 0.451 | 0.656 | 14.676 | 1.00 | 17.61 A |
| ATOM | 735 | N | ALA | A | 140 | 2.688 | 0.843 | 14.807 | 1.00 | 16.15 A |
| ATOM | 736 | CA | ALA | A | 140 | 2.886 | 1.115 | 13.394 | 1.00 | 21.42 A |
| ATOM | 737 | CB | ALA | A | 140 | 4.344 | 1.509 | 13.124 | 1.00 | 16.14 A |
| ATOM | 738 | C | ALA | A | 140 | 2.488 | −0.091 | 12.509 | 1.00 | 24.04 A |
| ATOM | 739 | O | ALA | A | 140 | 1.934 | 0.102 | 11.430 | 1.00 | 23.58 A |
| ATOM | 740 | N | ALA | A | 141 | 2.791 | −1.315 | 12.956 | 1.00 | 24.46 A |
| ATOM | 741 | CA | ALA | A | 141 | 2.435 | −2.510 | 12.198 | 1.00 | 26.30 A |
| ATOM | 742 | CB | ALA | A | 141 | 2.874 | −3.762 | 12.948 | 1.00 | 22.70 A |
| ATOM | 743 | C | ALA | A | 141 | 0.907 | −2.517 | 11.954 | 1.00 | 28.47 A |
| ATOM | 744 | O | ALA | A | 141 | 0.455 | −2.817 | 10.864 | 1.00 | 30.58 A |
| ATOM | 745 | N | VAL | A | 142 | 0.113 | −2.147 | 12.951 | 1.00 | 28.68 A |
| ATOM | 746 | CA | VAL | A | 142 | −1.334 | −2.102 | 12.792 | 1.00 | 27.80 A |
| ATOM | 747 | CB | VAL | A | 142 | −1.992 | −2.213 | 14.162 | 1.00 | 28.54 A |
| ATOM | 748 | CG1 | VAL | A | 142 | −3.496 | −2.054 | 14.046 | 1.00 | 28.64 A |
| ATOM | 749 | CG2 | VAL | A | 142 | −1.676 | −3.598 | 14.741 | 1.00 | 27.60 A |
| ATOM | 750 | C | VAL | A | 142 | −1.844 | −0.862 | 12.031 | 1.00 | 29.31 A |
| ATOM | 751 | O | VAL | A | 142 | −2.619 | −0.984 | 11.068 | 1.00 | 27.43 A |
| ATOM | 752 | N | GLU | A | 143 | −1.380 | 0.322 | 12.422 | 1.00 | 26.70 A |
| ATOM | 753 | CA | GLU | A | 143 | −1.783 | 1.575 | 11.763 | 1.00 | 29.66 A |
| ATOM | 754 | CB | GLU | A | 143 | −1.119 | 2.802 | 12.419 | 1.00 | 30.43 A |
| ATOM | 755 | CG | GLU | A | 143 | −1.421 | 2.958 | 13.895 | 1.00 | 33.87 A |
| ATOM | 756 | CD | GLU | A | 143 | −2.592 | 3.867 | 14.168 | 1.00 | 38.51 A |
| ATOM | 757 | OE1 | GLU | A | 143 | −3.334 | 4.181 | 13.200 | 1.00 | 40.06 A |
| ATOM | 758 | OE2 | GLU | A | 143 | −2.782 | 4.256 | 15.354 | 1.00 | 39.48 A |
| ATOM | 759 | C | GLU | A | 143 | −1.432 | 1.613 | 10.279 | 1.00 | 29.62 A |
| ATOM | 760 | O | GLU | A | 143 | −2.192 | 2.155 | 9.490 | 1.00 | 30.72 A |
| ATOM | 761 | N | THR | A | 144 | −0.282 | 1.068 | 9.889 | 1.00 | 29.09 A |
| ATOM | 762 | CA | THR | A | 144 | 0.077 | 1.112 | 8.488 | 1.00 | 30.43 A |
| ATOM | 763 | CB | THR | A | 144 | 1.570 | 1.450 | 8.257 | 1.00 | 30.25 A |
| ATOM | 764 | OG1 | THR | A | 144 | 2.395 | 0.361 | 8.704 | 1.00 | 32.60 A |
| ATOM | 765 | CG2 | THR | A | 144 | 1.935 | 2.762 | 8.951 | 1.00 | 28.09 A |
| ATOM | 766 | C | THR | A | 144 | −0.229 | −0.179 | 7.741 | 1.00 | 32.73 A |
| ATOM | 767 | O | THR | A | 144 | 0.151 | −0.328 | 6.584 | 1.00 | 33.67 A |
| ATOM | 768 | N | GLY | A | 145 | −0.872 | −1.131 | 8.405 | 1.00 | 33.93 A |
| ATOM | 769 | CA | GLY | A | 145 | −1.244 | −2.361 | 7.722 | 1.00 | 35.69 A |
| ATOM | 770 | C | GLY | A | 145 | −0.244 | −3.469 | 7.486 | 1.00 | 37.01 A |
| ATOM | 771 | O | GLY | A | 145 | −0.490 | −4.326 | 6.641 | 1.00 | 36.31 A |
| ATOM | 772 | N | ILE | A | 146 | 0.874 | −3.478 | 8.210 | 1.00 | 37.48 A |
| ATOM | 773 | CA | ILE | A | 146 | 1.858 | −4.541 | 8.047 | 1.00 | 36.37 A |
| ATOM | 774 | CB | ILE | A | 146 | 3.141 | −4.218 | 8.819 | 1.00 | 36.57 A |
| ATOM | 775 | CG2 | ILE | A | 146 | 4.073 | −5.423 | 8.822 | 1.00 | 34.02 A |

TABLE 2-continued

| ATOM | 776 | CG1 | ILE | A | 146 | 3.829 | −3.014 | 8.180 | 1.00 | 34.32 | A |
|---|---|---|---|---|---|---|---|---|---|---|---|
| ATOM | 777 | CD1 | ILE | A | 146 | 5.092 | −2.620 | 8.908 | 1.00 | 32.45 | A |
| ATOM | 778 | C | ILE | A | 146 | 1.238 | −5.825 | 8.598 | 1.00 | 37.65 | A |
| ATOM | 779 | O | ILE | A | 146 | 1.548 | −6.929 | 8.165 | 1.00 | 40.20 | A |
| ATOM | 780 | N | VAL | A | 147 | 0.348 | −5.675 | 9.558 | 1.00 | 38.72 | A |
| ATOM | 781 | CA | VAL | A | 147 | −0.330 | −6.813 | 10.154 | 1.00 | 40.62 | A |
| ATOM | 782 | CB | VAL | A | 147 | 0.044 | −6.955 | 11.675 | 1.00 | 40.04 | A |
| ATOM | 783 | CG1 | VAL | A | 147 | −0.821 | −8.017 | 12.352 | 1.00 | 39.93 | A |
| ATOM | 784 | CG2 | VAL | A | 147 | 1.520 | −7.330 | 11.815 | 1.00 | 38.17 | A |
| ATOM | 785 | C | VAL | A | 147 | −1.817 | −6.516 | 9.974 | 1.00 | 43.05 | A |
| ATOM | 786 | O | VAL | A | 147 | −2.254 | −5.374 | 10.166 | 1.00 | 44.56 | A |
| ATOM | 787 | N | SER | A | 148 | −2.599 | −7.524 | 9.592 | 1.00 | 44.20 | A |
| ATOM | 788 | CA | SER | A | 148 | −4.028 | −7.310 | 9.394 | 1.00 | 44.71 | A |
| ATOM | 789 | CB | SER | A | 148 | −4.600 | −8.334 | 8.427 | 1.00 | 46.12 | A |
| ATOM | 790 | OG | SER | A | 148 | −4.180 | −8.030 | 7.118 | 1.00 | 48.86 | A |
| ATOM | 791 | C | SER | A | 148 | −4.834 | −7.351 | 10.649 | 1.00 | 44.87 | A |
| ATOM | 792 | O | SER | A | 148 | −4.465 | −8.000 | 11.620 | 1.00 | 45.30 | A |
| ATOM | 793 | N | VAL | A | 149 | −5.960 | −6.654 | 10.604 | 1.00 | 46.41 | A |
| ATOM | 794 | CA | VAL | A | 149 | −6.884 | −6.582 | 11.716 | 1.00 | 48.20 | A |
| ATOM | 795 | CB | VAL | A | 149 | −7.392 | −5.142 | 11.916 | 1.00 | 46.71 | A |
| ATOM | 796 | CG1 | VAL | A | 149 | −8.323 | −5.094 | 13.101 | 1.00 | 45.64 | A |
| ATOM | 797 | CG2 | VAL | A | 149 | −6.219 | −4.170 | 12.084 | 1.00 | 48.16 | A |
| ATOM | 798 | C | VAL | A | 149 | −8.111 | −7.454 | 11.425 | 1.00 | 51.06 | A |
| ATOM | 799 | O | VAL | A | 149 | −8.984 | −7.055 | 10.659 | 1.00 | 53.06 | A |
| ATOM | 800 | N | PRO | A | 150 | −8.190 | −8.662 | 12.002 | 1.00 | 52.69 | A |
| ATOM | 801 | CD | PRO | A | 150 | −7.169 | −9.483 | 12.671 | 1.00 | 52.70 | A |
| ATOM | 802 | CA | PRO | A | 150 | −9.395 | −9.451 | 11.702 | 1.00 | 53.09 | A |
| ATOM | 803 | CB | PRO | A | 150 | −9.232 | −10.702 | 12.568 | 1.00 | 52.52 | A |
| ATOM | 804 | CG | PRO | A | 150 | −8.020 | −10.402 | 13.485 | 1.00 | 52.87 | A |
| ATOM | 805 | C | PRO | A | 150 | −10.679 | −8.670 | 12.024 | 1.00 | 54.69 | A |
| ATOM | 806 | O | PRO | A | 150 | −10.787 | −8.024 | 13.072 | 1.00 | 54.58 | A |
| ATOM | 807 | N | ALA | A | 151 | −11.651 | −8.714 | 11.113 | 1.00 | 54.81 | A |
| ATOM | 808 | CA | ALA | A | 151 | −12.891 | −7.982 | 11.320 | 1.00 | 54.05 | A |
| ATOM | 809 | CB | ALA | A | 151 | −13.943 | −8.422 | 10.308 | 1.00 | 56.26 | A |
| ATOM | 810 | C | ALA | A | 151 | −13.407 | −8.179 | 12.736 | 1.00 | 53.12 | A |
| ATOM | 811 | O | ALA | A | 151 | −13.345 | −9.279 | 13.296 | 1.00 | 51.58 | A |
| ATOM | 812 | N | ALA | A | 152 | −13.893 | −7.092 | 13.320 | 1.00 | 52.38 | A |
| ATOM | 813 | CA | ALA | A | 152 | −14.425 | −7.138 | 14.669 | 1.00 | 51.75 | A |
| ATOM | 814 | CB | ALA | A | 152 | −15.429 | −8.307 | 14.786 | 1.00 | 52.36 | A |
| ATOM | 815 | C | ALA | A | 152 | −13.355 | −7.247 | 15.776 | 1.00 | 50.34 | A |
| ATOM | 816 | O | ALA | A | 152 | −13.688 | −7.210 | 16.956 | 1.00 | 50.43 | A |
| ATOM | 817 | N | ALA | A | 153 | −12.083 | −7.391 | 15.421 | 1.00 | 48.11 | A |
| ATOM | 818 | CA | ALA | A | 153 | −11.061 | −7.498 | 16.462 | 1.00 | 47.03 | A |
| ATOM | 819 | CB | ALA | A | 153 | −9.689 | −7.708 | 15.843 | 1.00 | 46.77 | A |
| ATOM | 820 | C | ALA | A | 153 | −11.034 | −6.271 | 17.365 | 1.00 | 44.94 | A |
| ATOM | 821 | O | ALA | A | 153 | −11.250 | −5.155 | 16.917 | 1.00 | 45.60 | A |
| ATOM | 822 | N | THR | A | 154 | −10.797 | −6.505 | 18.648 | 1.00 | 43.39 | A |
| ATOM | 823 | CA | THR | A | 154 | −10.688 | −5.436 | 19.630 | 1.00 | 42.09 | A |
| ATOM | 824 | CB | THR | A | 154 | −11.337 | −5.800 | 20.955 | 1.00 | 41.60 | A |
| ATOM | 825 | OG1 | THR | A | 154 | −12.755 | −5.799 | 20.810 | 1.00 | 46.14 | A |
| ATOM | 826 | CG2 | THR | A | 154 | −10.968 | −4.782 | 21.999 | 1.00 | 44.67 | A |
| ATOM | 827 | C | THR | A | 154 | −9.200 | −5.256 | 19.924 | 1.00 | 39.95 | A |
| ATOM | 828 | O | THR | A | 154 | −8.762 | −4.189 | 20.329 | 1.00 | 39.27 | A |
| ATOM | 829 | N | ASN | A | 155 | −8.449 | −6.334 | 19.737 | 1.00 | 37.44 | A |
| ATOM | 830 | CA | ASN | A | 155 | −7.013 | −6.353 | 19.985 | 1.00 | 36.59 | A |
| ATOM | 831 | CB | ASN | A | 155 | −6.708 | −7.011 | 21.339 | 1.00 | 34.65 | A |
| ATOM | 832 | CG | ASN | A | 155 | −7.267 | −6.209 | 22.498 | 1.00 | 35.35 | A |
| ATOM | 833 | OD1 | ASN | A | 155 | −6.763 | −5.151 | 22.832 | 1.00 | 36.67 | A |
| ATOM | 834 | ND2 | ASN | A | 155 | −8.337 | −6.695 | 23.097 | 1.00 | 37.88 | A |
| ATOM | 835 | C | ASN | A | 155 | −6.368 | −7.124 | 18.862 | 1.00 | 35.69 | A |
| ATOM | 836 | O | ASN | A | 155 | −6.966 | −8.064 | 18.319 | 1.00 | 37.33 | A |
| ATOM | 837 | N | VAL | A | 156 | −5.157 | −6.714 | 18.501 | 1.00 | 32.21 | A |
| ATOM | 838 | CA | VAL | A | 156 | −4.420 | −7.355 | 17.440 | 1.00 | 29.99 | A |
| ATOM | 839 | CB | VAL | A | 156 | −4.283 | −6.436 | 16.195 | 1.00 | 27.92 | A |
| ATOM | 840 | CG1 | VAL | A | 156 | −3.633 | −7.209 | 15.063 | 1.00 | 24.91 | A |
| ATOM | 841 | CG2 | VAL | A | 156 | −5.650 | −5.859 | 15.808 | 1.00 | 30.14 | A |
| ATOM | 842 | C | VAL | A | 156 | −3.012 | −7.718 | 17.893 | 1.00 | 29.61 | A |
| ATOM | 843 | O | VAL | A | 156 | −2.247 | −6.858 | 18.296 | 1.00 | 29.57 | A |
| ATOM | 844 | N | PRO | A | 157 | −2.647 | −9.000 | 17.794 | 1.00 | 30.55 | A |
| ATOM | 845 | CD | PRO | A | 157 | −3.471 | −10.155 | 17.370 | 1.00 | 30.65 | A |
| ATOM | 846 | CA | PRO | A | 157 | −1.305 | −9.415 | 18.206 | 1.00 | 30.07 | A |
| ATOM | 847 | CB | PRO | A | 157 | −1.400 | −10.954 | 18.335 | 1.00 | 31.51 | A |
| ATOM | 848 | CG | PRO | A | 157 | −2.882 | −11.276 | 18.184 | 1.00 | 32.25 | A |
| ATOM | 849 | C | PRO | A | 157 | −0.260 | −9.031 | 17.171 | 1.00 | 28.74 | A |
| ATOM | 850 | O | PRO | A | 157 | −0.529 | −9.037 | 15.980 | 1.00 | 26.95 | A |
| ATOM | 851 | N | VAL | A | 158 | 0.932 | −8.665 | 17.641 | 1.00 | 25.33 | A |
| ATOM | 852 | CA | VAL | A | 158 | 2.032 | −8.355 | 16.755 | 1.00 | 22.06 | A |
| ATOM | 853 | CB | VAL | A | 158 | 2.262 | −6.855 | 16.575 | 1.00 | 21.96 | A |
| ATOM | 854 | CG1 | VAL | A | 158 | 3.452 | −6.653 | 15.680 | 1.00 | 18.31 | A |

TABLE 2-continued

| | | | | | | | | | | |
|---|---|---|---|---|---|---|---|---|---|---|
| ATOM | 855 | CG2 | VAL | A | 158 | 1.022 | −6.171 | 16.035 | 1.00 | 20.19 A |
| ATOM | 856 | C | VAL | A | 158 | 3.231 | −8.905 | 17.508 | 1.00 | 22.69 A |
| ATOM | 857 | O | VAL | A | 158 | 3.607 | −8.372 | 18.559 | 1.00 | 23.00 A |
| ATOM | 858 | N | VAL | A | 159 | 3.839 | −9.948 | 16.964 | 1.00 | 20.54 A |
| ATOM | 859 | CA | VAL | A | 159 | 4.986 | −10.597 | 17.576 | 1.00 | 20.03 A |
| ATOM | 860 | CB | VAL | A | 159 | 4.888 | −12.152 | 17.414 | 1.00 | 19.22 A |
| ATOM | 861 | CG1 | VAL | A | 159 | 6.049 | −12.818 | 18.063 | 1.00 | 20.27 A |
| ATOM | 862 | CG2 | VAL | A | 159 | 3.612 | −12.655 | 18.026 | 1.00 | 19.26 A |
| ATOM | 863 | C | VAL | A | 159 | 6.287 | −10.126 | 16.978 | 1.00 | 20.72 A |
| ATOM | 864 | O | VAL | A | 159 | 6.496 | −10.302 | 15.778 | 1.00 | 21.19 A |
| ATOM | 865 | N | LEU | A | 160 | 7.170 | −9.533 | 17.803 | 1.00 | 19.86 A |
| ATOM | 866 | CA | LEU | A | 160 | 8.464 | −9.068 | 17.317 | 1.00 | 20.29 A |
| ATOM | 867 | CB | LEU | A | 160 | 8.854 | −7.715 | 17.953 | 1.00 | 19.30 A |
| ATOM | 868 | CG | LEU | A | 160 | 7.801 | −6.591 | 17.875 | 1.00 | 23.35 A |
| ATOM | 869 | CD1 | LEU | A | 160 | 8.272 | −5.346 | 18.677 | 1.00 | 20.63 A |
| ATOM | 870 | CD2 | LEU | A | 160 | 7.580 | −6.233 | 16.397 | 1.00 | 22.61 A |
| ATOM | 871 | C | LEU | A | 160 | 9.594 | −10.066 | 17.590 | 1.00 | 20.87 A |
| ATOM | 872 | O | LEU | A | 160 | 9.718 | −10.608 | 18.700 | 1.00 | 20.58 A |
| ATOM | 873 | N | ASP | A | 161 | 10.429 | −10.271 | 16.578 | 1.00 | 19.18 A |
| ATOM | 874 | CA | ASP | A | 161 | 11.572 | −11.151 | 16.671 | 1.00 | 21.03 A |
| ATOM | 875 | CB | ASP | A | 161 | 11.640 | −11.943 | 15.360 | 1.00 | 23.60 A |
| ATOM | 876 | CG | ASP | A | 161 | 12.920 | −12.741 | 15.186 | 1.00 | 28.50 A |
| ATOM | 877 | OD1 | ASP | A | 161 | 13.724 | −12.894 | 16.154 | 1.00 | 29.03 A |
| ATOM | 878 | OD2 | ASP | A | 161 | 13.114 | −13.224 | 14.032 | 1.00 | 28.50 A |
| ATOM | 879 | C | ASP | A | 161 | 12.756 | −10.193 | 16.874 | 1.00 | 21.02 A |
| ATOM | 880 | O | ASP | A | 161 | 13.194 | −9.514 | 15.931 | 1.00 | 20.75 A |
| ATOM | 881 | N | THR | A | 162 | 13.256 | −10.126 | 18.112 | 1.00 | 19.55 A |
| ATOM | 882 | CA | THR | A | 162 | 14.349 | −9.216 | 18.457 | 1.00 | 20.55 A |
| ATOM | 883 | CB | THR | A | 162 | 13.913 | −8.280 | 19.605 | 1.00 | 20.90 A |
| ATOM | 884 | OG1 | THR | A | 162 | 14.100 | −8.937 | 20.868 | 1.00 | 19.94 A |
| ATOM | 885 | CG2 | THR | A | 162 | 12.450 | −7.937 | 19.468 | 1.00 | 19.99 A |
| ATOM | 886 | C | THR | A | 162 | 15.655 | −9.910 | 18.895 | 1.00 | 20.99 A |
| ATOM | 887 | O | THR | A | 162 | 15.673 | −11.097 | 19.160 | 1.00 | 20.21 A |
| ATOM | 888 | N | PRO | A | 163 | 16.761 | −9.151 | 18.991 | 1.00 | 20.13 A |
| ATOM | 889 | CD | PRO | A | 163 | 16.955 | −7.743 | 18.578 | 1.00 | 18.75 A |
| ATOM | 890 | CA | PRO | A | 163 | 18.020 | −9.776 | 19.399 | 1.00 | 18.56 A |
| ATOM | 891 | CB | PRO | A | 163 | 19.037 | −8.635 | 19.323 | 1.00 | 19.07 A |
| ATOM | 892 | CG | PRO | A | 163 | 18.461 | −7.736 | 18.220 | 1.00 | 22.15 A |
| ATOM | 893 | C | PRO | A | 163 | 17.973 | −10.395 | 20.785 | 1.00 | 21.23 A |
| ATOM | 894 | O | PRO | A | 163 | 18.817 | −11.196 | 21.127 | 1.00 | 20.60 A |
| ATOM | 895 | N | ALA | A | 164 | 16.993 | −10.023 | 21.586 | 1.00 | 20.11 A |
| ATOM | 896 | CA | ALA | A | 164 | 16.911 | −10.595 | 22.912 | 1.00 | 23.47 A |
| ATOM | 897 | CB | ALA | A | 164 | 16.550 | −9.521 | 23.930 | 1.00 | 21.10 A |
| ATOM | 898 | C | ALA | A | 164 | 15.877 | −11.701 | 22.971 | 1.00 | 22.65 A |
| ATOM | 899 | O | ALA | A | 164 | 15.717 | −12.322 | 24.010 | 1.00 | 20.35 A |
| ATOM | 900 | N | GLY | A | 165 | 15.157 | −11.941 | 21.879 | 1.00 | 21.35 A |
| ATOM | 901 | CA | GLY | A | 165 | 14.147 | −12.994 | 21.932 | 1.00 | 20.84 A |
| ATOM | 902 | C | GLY | A | 165 | 12.812 | −12.455 | 21.479 | 1.00 | 21.92 A |
| ATOM | 903 | O | GLY | A | 165 | 12.700 | −11.277 | 21.111 | 1.00 | 20.27 A |
| ATOM | 904 | N | LEU | A | 166 | 11.793 | −13.299 | 21.526 | 1.00 | 23.31 A |
| ATOM | 905 | CA | LEU | A | 166 | 10.457 | −12.940 | 21.065 | 1.00 | 23.22 A |
| ATOM | 906 | CB | LEU | A | 166 | 9.625 | −14.202 | 20.802 | 1.00 | 26.06 A |
| ATOM | 907 | CG | LEU | A | 166 | 9.589 | −14.876 | 19.428 | 1.00 | 31.69 A |
| ATOM | 908 | CD1 | LEU | A | 166 | 10.644 | −14.308 | 18.484 | 1.00 | 30.71 A |
| ATOM | 909 | CD2 | LEU | A | 166 | 9.797 | −16.382 | 19.632 | 1.00 | 31.54 A |
| ATOM | 910 | C | LEU | A | 166 | 9.701 | −12.077 | 22.027 | 1.00 | 22.07 A |
| ATOM | 911 | O | LEU | A | 166 | 9.557 | −12.401 | 23.204 | 1.00 | 21.62 A |
| ATOM | 912 | N | VAL | A | 167 | 9.145 | −10.993 | 21.499 | 1.00 | 20.99 A |
| ATOM | 913 | CA | VAL | A | 167 | 8.376 | −10.064 | 22.301 | 1.00 | 18.35 A |
| ATOM | 914 | CB | VAL | A | 167 | 8.997 | −8.658 | 22.219 | 1.00 | 16.52 A |
| ATOM | 915 | CG1 | VAL | A | 167 | 8.103 | −7.632 | 22.936 | 1.00 | 11.30 A |
| ATOM | 916 | CG2 | VAL | A | 167 | 10.373 | −8.709 | 22.839 | 1.00 | 13.66 A |
| ATOM | 917 | C | VAL | A | 167 | 6.969 | −10.066 | 21.740 | 1.00 | 19.92 A |
| ATOM | 918 | O | VAL | A | 167 | 6.780 | −9.713 | 20.577 | 1.00 | 20.81 A |
| ATOM | 919 | N | ARG | A | 168 | 5.999 | −10.459 | 22.566 | 1.00 | 19.73 A |
| ATOM | 920 | CA | ARG | A | 168 | 4.604 | −10.562 | 22.154 | 1.00 | 22.66 A |
| ATOM | 921 | CB | ARG | A | 168 | 3.967 | −11.769 | 22.841 | 1.00 | 25.09 A |
| ATOM | 922 | CG | ARG | A | 168 | 4.749 | −13.054 | 22.497 | 1.00 | 31.29 A |
| ATOM | 923 | CD | ARG | A | 168 | 4.262 | −14.314 | 23.275 | 1.00 | 37.67 A |
| ATOM | 924 | NE | ARG | A | 168 | 5.111 | −15.466 | 22.927 | 1.00 | 46.49 A |
| ATOM | 925 | CZ | ARG | A | 168 | 6.304 | −15.737 | 23.476 | 1.00 | 50.99 A |
| ATOM | 926 | NH1 | ARG | A | 168 | 6.808 | −14.955 | 24.440 | 1.00 | 52.72 A |
| ATOM | 927 | NH2 | ARG | A | 168 | 7.038 | −16.748 | 23.014 | 1.00 | 51.17 A |
| ATOM | 928 | C | ARG | A | 168 | 3.806 | −9.315 | 22.433 | 1.00 | 22.76 A |
| ATOM | 929 | O | ARG | A | 168 | 3.425 | −9.030 | 23.575 | 1.00 | 21.01 A |
| ATOM | 930 | N | GLY | A | 169 | 3.525 | −8.574 | 21.369 | 1.00 | 22.38 A |
| ATOM | 931 | CA | GLY | A | 169 | 2.798 | −7.347 | 21.547 | 1.00 | 22.35 A |
| ATOM | 932 | C | GLY | A | 169 | 1.357 | −7.463 | 21.195 | 1.00 | 23.33 A |
| ATOM | 933 | O | GLY | A | 169 | 0.940 | −8.401 | 20.515 | 1.00 | 26.69 A |

TABLE 2-continued

| ATOM | 934 | N | THR | A | 170 | 0.607 | −6.483 | 21.664 | 1.00 | 21.16 | A |
|---|---|---|---|---|---|---|---|---|---|---|---|
| ATOM | 935 | CA | THR | A | 170 | −0.809 | −6.401 | 21.438 | 1.00 | 22.01 | A |
| ATOM | 936 | CB | THR | A | 170 | −1.578 | −6.933 | 22.658 | 1.00 | 25.05 | A |
| ATOM | 937 | OG1 | THR | A | 170 | −1.192 | −8.289 | 22.920 | 1.00 | 23.90 | A |
| ATOM | 938 | CG2 | THR | A | 170 | −3.066 | −6.854 | 22.409 | 1.00 | 24.90 | A |
| ATOM | 939 | C | THR | A | 170 | −1.219 | −4.939 | 21.209 | 1.00 | 21.97 | A |
| ATOM | 940 | O | THR | A | 170 | −0.990 | −4.069 | 22.066 | 1.00 | 19.17 | A |
| ATOM | 941 | N | ALA | A | 171 | −1.818 | −4.657 | 20.055 | 1.00 | 19.71 | A |
| ATOM | 942 | CA | ALA | A | 171 | −2.270 | −3.301 | 19.798 | 1.00 | 19.40 | A |
| ATOM | 943 | CB | ALA | A | 171 | −2.161 | −2.951 | 18.302 | 1.00 | 18.99 | A |
| ATOM | 944 | C | ALA | A | 171 | −3.711 | −3.324 | 20.247 | 1.00 | 22.64 | A |
| ATOM | 945 | O | ALA | A | 171 | −4.481 | −4.181 | 19.812 | 1.00 | 25.12 | A |
| ATOM | 946 | N | HIS | A | 172 | −4.072 | −2.403 | 21.124 | 1.00 | 22.11 | A |
| ATOM | 947 | CA | HIS | A | 172 | −5.433 | −2.311 | 21.646 | 1.00 | 26.51 | A |
| ATOM | 948 | CB | HIS | A | 172 | −5.392 | −1.842 | 23.100 | 1.00 | 26.20 | A |
| ATOM | 949 | CG | HIS | A | 172 | −4.564 | −2.722 | 23.976 | 1.00 | 28.68 | A |
| ATOM | 950 | CD2 | HIS | A | 172 | −3.371 | −2.513 | 24.581 | 1.00 | 27.13 | A |
| ATOM | 951 | ND1 | HIS | A | 172 | −4.913 | −4.028 | 24.254 | 1.00 | 31.39 | A |
| ATOM | 952 | CE1 | HIS | A | 172 | −3.968 | −4.587 | 24.989 | 1.00 | 31.23 | A |
| ATOM | 953 | NE2 | HIS | A | 172 | −3.020 | −3.688 | 25.201 | 1.00 | 31.70 | A |
| ATOM | 954 | C | HIS | A | 172 | −6.109 | −1.279 | 20.762 | 1.00 | 28.48 | A |
| ATOM | 955 | O | HIS | A | 172 | −5.671 | −0.131 | 20.691 | 1.00 | 27.56 | A |
| ATOM | 956 | N | LEU | A | 173 | −7.162 | −1.691 | 20.071 | 1.00 | 31.72 | A |
| ATOM | 957 | CA | LEU | A | 173 | −7.836 | −0.800 | 19.129 | 1.00 | 35.72 | A |
| ATOM | 958 | CB | LEU | A | 173 | −8.589 | −1.621 | 18.071 | 1.00 | 33.82 | A |
| ATOM | 959 | CG | LEU | A | 173 | −7.675 | −2.540 | 17.271 | 1.00 | 33.81 | A |
| ATOM | 960 | CD1 | LEU | A | 173 | −8.421 | −3.178 | 16.123 | 1.00 | 34.73 | A |
| ATOM | 961 | CD2 | LEU | A | 173 | −6.513 | −1.732 | 16.744 | 1.00 | 33.88 | A |
| ATOM | 962 | C | LEU | A | 173 | −8.771 | 0.231 | 19.718 | 1.00 | 38.58 | A |
| ATOM | 963 | O | LEU | A | 173 | −9.358 | 0.034 | 20.775 | 1.00 | 37.75 | A |
| ATOM | 964 | N | GLN | A | 174 | −8.881 | 1.343 | 19.006 | 1.00 | 42.97 | A |
| ATOM | 965 | CA | GLN | A | 174 | −9.759 | 2.436 | 19.379 | 1.00 | 49.44 | A |
| ATOM | 966 | CB | GLN | A | 174 | −9.426 | 3.662 | 18.504 | 1.00 | 53.22 | A |
| ATOM | 967 | CG | GLN | A | 174 | −10.077 | 4.957 | 18.944 | 1.00 | 57.53 | A |
| ATOM | 968 | CD | GLN | A | 174 | −10.144 | 5.039 | 20.449 | 1.00 | 61.01 | A |
| ATOM | 969 | OE1 | GLN | A | 174 | −11.148 | 4.653 | 21.052 | 1.00 | 62.25 | A |
| ATOM | 970 | NE2 | GLN | A | 174 | −9.057 | 5.509 | 21.075 | 1.00 | 62.63 | A |
| ATOM | 971 | C | GLN | A | 174 | −11.207 | 1.972 | 19.123 | 1.00 | 51.36 | A |
| ATOM | 972 | O | GLN | A | 174 | −11.538 | 1.544 | 18.018 | 1.00 | 49.38 | A |
| ATOM | 973 | N | SER | A | 175 | −12.045 | 2.051 | 20.154 | 1.00 | 54.64 | A |
| ATOM | 974 | CA | SER | A | 175 | −13.454 | 1.649 | 20.098 | 1.00 | 58.88 | A |
| ATOM | 975 | CB | SER | A | 175 | −14.326 | 2.657 | 20.839 | 1.00 | 58.85 | A |
| ATOM | 976 | OG | SER | A | 175 | −14.341 | 2.355 | 22.215 | 1.00 | 61.88 | A |
| ATOM | 977 | C | SER | A | 175 | −14.112 | 1.385 | 18.755 | 1.00 | 61.01 | A |
| ATOM | 978 | O | SER | A | 175 | −14.118 | 0.253 | 18.277 | 1.00 | 63.42 | A |
| ATOM | 979 | N | GLY | A | 176 | −14.683 | 2.425 | 18.158 | 1.00 | 61.70 | A |
| ATOM | 980 | CA | GLY | A | 176 | −15.378 | 2.240 | 16.897 | 1.00 | 63.37 | A |
| ATOM | 981 | C | GLY | A | 176 | −14.584 | 2.515 | 15.640 | 1.00 | 63.98 | A |
| ATOM | 982 | O | GLY | A | 176 | −15.079 | 3.178 | 14.725 | 1.00 | 64.88 | A |
| ATOM | 983 | N | THR | A | 177 | −13.359 | 2.010 | 15.578 | 1.00 | 63.31 | A |
| ATOM | 984 | CA | THR | A | 177 | −12.530 | 2.232 | 14.401 | 1.00 | 62.57 | A |
| ATOM | 985 | CB | THR | A | 177 | −11.271 | 3.053 | 14.744 | 1.00 | 63.55 | A |
| ATOM | 986 | OG1 | THR | A | 177 | −10.353 | 2.239 | 15.493 | 1.00 | 63.78 | A |
| ATOM | 987 | CG2 | THR | A | 177 | −11.653 | 4.283 | 15.564 | 1.00 | 62.43 | A |
| ATOM | 988 | C | THR | A | 177 | −12.103 | 0.890 | 13.839 | 1.00 | 61.58 | A |
| ATOM | 989 | O | THR | A | 177 | −12.386 | −0.153 | 14.437 | 1.00 | 62.24 | A |
| ATOM | 990 | N | ALA | A | 178 | −11.419 | 0.912 | 12.697 | 1.00 | 59.38 | A |
| ATOM | 991 | CA | ALA | A | 178 | −10.969 | −0.325 | 12.074 | 1.00 | 57.95 | A |
| ATOM | 992 | CB | ALA | A | 178 | −11.149 | −0.253 | 10.568 | 1.00 | 58.65 | A |
| ATOM | 993 | C | ALA | A | 178 | −9.518 | −0.660 | 12.407 | 1.00 | 56.56 | A |
| ATOM | 994 | O | ALA | A | 178 | −9.220 | −1.797 | 12.771 | 1.00 | 57.02 | A |
| ATOM | 995 | N | SER | A | 179 | −8.621 | 0.317 | 12.273 | 1.00 | 53.10 | A |
| ATOM | 996 | CA | SER | A | 179 | −7.206 | 0.091 | 12.566 | 1.00 | 49.87 | A |
| ATOM | 997 | CB | SER | A | 179 | −6.421 | −0.115 | 11.261 | 1.00 | 49.16 | A |
| ATOM | 998 | OG | SER | A | 179 | −6.350 | 1.075 | 10.499 | 1.00 | 51.02 | A |
| ATOM | 999 | C | SER | A | 179 | −6.548 | 1.205 | 13.400 | 1.00 | 47.04 | A |
| ATOM | 1000 | O | SER | A | 179 | −5.323 | 1.356 | 13.378 | 1.00 | 46.21 | A |
| ATOM | 1001 | N | GLU | A | 180 | −7.365 | 1.975 | 14.123 | 1.00 | 43.11 | A |
| ATOM | 1002 | CA | GLU | A | 180 | −6.881 | 3.060 | 14.964 | 1.00 | 40.75 | A |
| ATOM | 1003 | CB | GLU | A | 180 | −7.978 | 4.094 | 15.189 | 1.00 | 44.55 | A |
| ATOM | 1004 | CG | GLU | A | 180 | −8.371 | 4.823 | 13.933 | 1.00 | 51.79 | A |
| ATOM | 1005 | CD | GLU | A | 180 | −7.989 | 6.270 | 13.997 | 1.00 | 55.40 | A |
| ATOM | 1006 | OE1 | GLU | A | 180 | −8.486 | 6.964 | 14.919 | 1.00 | 59.31 | A |
| ATOM | 1007 | OE2 | GLU | A | 180 | −7.194 | 6.712 | 13.135 | 1.00 | 58.50 | A |
| ATOM | 1008 | C | GLU | A | 180 | −6.447 | 2.469 | 16.308 | 1.00 | 37.00 | A |
| ATOM | 1009 | O | GLU | A | 180 | −7.248 | 1.846 | 17.016 | 1.00 | 33.16 | A |
| ATOM | 1010 | N | VAL | A | 181 | −5.180 | 2.692 | 16.649 | 1.00 | 33.23 | A |
| ATOM | 1011 | CA | VAL | A | 181 | −4.610 | 2.136 | 17.872 | 1.00 | 28.76 | A |
| ATOM | 1012 | CB | VAL | A | 181 | −3.146 | 1.739 | 17.625 | 1.00 | 24.78 | A |

TABLE 2-continued

| ATOM | 1013 | CG1 | VAL | A | 181 | −2.476 | 1.316 | 18.911 | 1.00 | 20.13 | A |
|---|---|---|---|---|---|---|---|---|---|---|---|
| ATOM | 1014 | CG2 | VAL | A | 181 | −3.110 | 0.621 | 16.584 | 1.00 | 22.09 | A |
| ATOM | 1015 | C | VAL | A | 181 | −4.708 | 3.057 | 19.051 | 1.00 | 29.35 | A |
| ATOM | 1016 | O | VAL | A | 181 | −4.199 | 4.174 | 19.020 | 1.00 | 30.49 | A |
| ATOM | 1017 | N | SER | A | 182 | −5.385 | 2.592 | 20.092 | 1.00 | 28.63 | A |
| ATOM | 1018 | CA | SER | A | 182 | −5.538 | 3.377 | 21.309 | 1.00 | 28.46 | A |
| ATOM | 1019 | CB | SER | A | 182 | −6.674 | 2.799 | 22.142 | 1.00 | 28.15 | A |
| ATOM | 1020 | OG | SER | A | 182 | −6.662 | 3.370 | 23.429 | 1.00 | 32.23 | A |
| ATOM | 1021 | C | SER | A | 182 | −4.219 | 3.381 | 22.104 | 1.00 | 26.83 | A |
| ATOM | 1022 | O | SER | A | 182 | −3.757 | 4.435 | 22.539 | 1.00 | 26.77 | A |
| ATOM | 1023 | N | ASN | A | 183 | −3.626 | 2.204 | 22.300 | 1.00 | 24.30 | A |
| ATOM | 1024 | CA | ASN | A | 183 | −2.337 | 2.080 | 22.984 | 1.00 | 22.32 | A |
| ATOM | 1025 | CB | ASN | A | 183 | −2.416 | 2.474 | 24.478 | 1.00 | 25.42 | A |
| ATOM | 1026 | CG | ASN | A | 183 | −3.214 | 1.505 | 25.347 | 1.00 | 27.40 | A |
| ATOM | 1027 | OD1 | ASN | A | 183 | −3.791 | 0.537 | 24.892 | 1.00 | 31.49 | A |
| ATOM | 1028 | ND2 | ASN | A | 183 | −3.230 | 1.787 | 26.625 | 1.00 | 30.03 | A |
| ATOM | 1029 | C | ASN | A | 183 | −1.834 | 0.663 | 22.736 | 1.00 | 23.53 | A |
| ATOM | 1030 | O | ASN | A | 183 | −2.501 | −0.080 | 22.038 | 1.00 | 21.08 | A |
| ATOM | 1031 | N | ALA | A | 184 | −0.651 | 0.297 | 23.235 | 1.00 | 19.38 | A |
| ATOM | 1032 | CA | ALA | A | 184 | −0.113 | −1.016 | 22.963 | 1.00 | 19.22 | A |
| ATOM | 1033 | CB | ALA | A | 184 | 0.819 | −0.942 | 21.791 | 1.00 | 18.34 | A |
| ATOM | 1034 | C | ALA | A | 184 | 0.616 | −1.595 | 24.162 | 1.00 | 20.28 | A |
| ATOM | 1035 | O | ALA | A | 184 | 1.181 | −0.863 | 24.973 | 1.00 | 18.76 | A |
| ATOM | 1036 | N | SER | A | 185 | 0.587 | −2.917 | 24.259 | 1.00 | 20.14 | A |
| ATOM | 1037 | CA | SER | A | 185 | 1.230 | −3.636 | 25.345 | 1.00 | 21.79 | A |
| ATOM | 1038 | CB | SER | A | 185 | 0.190 | −4.446 | 26.151 | 1.00 | 21.49 | A |
| ATOM | 1039 | OG | SER | A | 185 | −0.692 | −3.607 | 26.891 | 1.00 | 26.71 | A |
| ATOM | 1040 | C | SER | A | 185 | 2.219 | −4.617 | 24.720 | 1.00 | 20.64 | A |
| ATOM | 1041 | O | SER | A | 185 | 2.022 | −5.082 | 23.579 | 1.00 | 20.27 | A |
| ATOM | 1042 | N | ILE | A | 186 | 3.277 | −4.905 | 25.459 | 1.00 | 18.13 | A |
| ATOM | 1043 | CA | ILE | A | 186 | 4.270 | −5.880 | 25.034 | 1.00 | 19.89 | A |
| ATOM | 1044 | CB | ILE | A | 186 | 5.605 | −5.261 | 24.535 | 1.00 | 20.55 | A |
| ATOM | 1045 | CG2 | ILE | A | 186 | 5.367 | −4.463 | 23.208 | 1.00 | 22.02 | A |
| ATOM | 1046 | CG1 | ILE | A | 186 | 6.190 | −4.330 | 25.593 | 1.00 | 22.80 | A |
| ATOM | 1047 | CD1 | ILE | A | 186 | 7.598 | −3.839 | 25.251 | 1.00 | 25.83 | A |
| ATOM | 1048 | C | ILE | A | 186 | 4.584 | −6.733 | 26.243 | 1.00 | 20.18 | A |
| ATOM | 1049 | O | ILE | A | 186 | 4.688 | −6.235 | 27.368 | 1.00 | 19.60 | A |
| ATOM | 1050 | N | ILE | A | 187 | 4.659 | −8.037 | 26.004 | 1.00 | 21.83 | A |
| ATOM | 1051 | CA | ILE | A | 187 | 5.044 | −8.987 | 27.024 | 1.00 | 20.11 | A |
| ATOM | 1052 | CB | ILE | A | 187 | 4.213 | −10.226 | 26.950 | 1.00 | 21.79 | A |
| ATOM | 1053 | CG2 | ILE | A | 187 | 4.813 | −11.315 | 27.905 | 1.00 | 22.53 | A |
| ATOM | 1054 | CG1 | ILE | A | 187 | 2.776 | −9.834 | 27.345 | 1.00 | 21.71 | A |
| ATOM | 1055 | CD1 | ILE | A | 187 | 1.744 | −10.923 | 27.251 | 1.00 | 23.99 | A |
| ATOM | 1056 | C | ILE | A | 187 | 6.494 | −9.202 | 26.625 | 1.00 | 19.69 | A |
| ATOM | 1057 | O | ILE | A | 187 | 6.827 | −9.739 | 25.545 | 1.00 | 16.11 | A |
| ATOM | 1058 | N | ASN | A | 188 | 7.357 | −8.692 | 27.505 | 1.00 | 18.39 | A |
| ATOM | 1059 | CA | ASN | A | 188 | 8.792 | −8.673 | 27.308 | 1.00 | 16.27 | A |
| ATOM | 1060 | CB | ASN | A | 188 | 9.386 | −7.742 | 28.356 | 1.00 | 18.81 | A |
| ATOM | 1061 | CG | ASN | A | 188 | 10.764 | −7.272 | 28.010 | 1.00 | 24.47 | A |
| ATOM | 1062 | OD1 | ASN | A | 188 | 11.297 | −7.550 | 26.923 | 1.00 | 23.63 | A |
| ATOM | 1063 | ND2 | ASN | A | 188 | 11.368 | −6.531 | 28.934 | 1.00 | 23.67 | A |
| ATOM | 1064 | C | ASN | A | 188 | 9.387 | −10.050 | 27.444 | 1.00 | 17.45 | A |
| ATOM | 1065 | O | ASN | A | 188 | 8.702 | −10.982 | 27.869 | 1.00 | 19.16 | A |
| ATOM | 1066 | N | VAL | A | 189 | 10.653 | −10.182 | 27.065 | 1.00 | 17.74 | A |
| ATOM | 1067 | CA | VAL | A | 189 | 11.369 | −11.439 | 27.255 | 1.00 | 18.04 | A |
| ATOM | 1068 | CB | VAL | A | 189 | 12.759 | −11.456 | 26.539 | 1.00 | 17.23 | A |
| ATOM | 1069 | CG1 | VAL | A | 189 | 12.567 | −11.291 | 25.012 | 1.00 | 20.32 | A |
| ATOM | 1070 | CG2 | VAL | A | 189 | 13.680 | −10.315 | 27.076 | 1.00 | 16.50 | A |
| ATOM | 1071 | C | VAL | A | 189 | 11.599 | −11.574 | 28.789 | 1.00 | 18.92 | A |
| ATOM | 1072 | O | VAL | A | 189 | 11.461 | −10.622 | 29.567 | 1.00 | 19.14 | A |
| ATOM | 1073 | N | PRO | A | 190 | 11.944 | −12.773 | 29.241 | 1.00 | 19.74 | A |
| ATOM | 1074 | CD | PRO | A | 190 | 12.043 | −14.035 | 28.478 | 1.00 | 16.63 | A |
| ATOM | 1075 | CA | PRO | A | 190 | 12.172 | −12.955 | 30.689 | 1.00 | 18.42 | A |
| ATOM | 1076 | CB | PRO | A | 190 | 12.708 | −14.386 | 30.787 | 1.00 | 18.28 | A |
| ATOM | 1077 | CG | PRO | A | 190 | 11.911 | −15.088 | 29.574 | 1.00 | 20.26 | A |
| ATOM | 1078 | C | PRO | A | 190 | 13.118 | −11.943 | 31.303 | 1.00 | 16.46 | A |
| ATOM | 1079 | O | PRO | A | 190 | 14.227 | −11.728 | 30.809 | 1.00 | 18.54 | A |
| ATOM | 1080 | N | SER | A | 191 | 12.673 | −11.338 | 32.399 | 1.00 | 17.82 | A |
| ATOM | 1081 | CA | SER | A | 191 | 13.452 | −10.349 | 33.101 | 1.00 | 19.02 | A |
| ATOM | 1082 | CB | SER | A | 191 | 12.559 | −9.127 | 33.391 | 1.00 | 23.36 | A |
| ATOM | 1083 | OG | SER | A | 191 | 12.081 | −8.520 | 32.180 | 1.00 | 26.09 | A |
| ATOM | 1084 | C | SER | A | 191 | 13.888 | −10.979 | 34.428 | 1.00 | 20.75 | A |
| ATOM | 1085 | O | SER | A | 191 | 13.208 | −11.858 | 34.916 | 1.00 | 19.49 | A |
| ATOM | 1086 | N | PHE | A | 192 | 15.007 | −10.518 | 34.998 | 1.00 | 19.04 | A |
| ATOM | 1087 | CA | PHE | A | 192 | 15.477 | −11.027 | 36.284 | 1.00 | 21.15 | A |
| ATOM | 1088 | CB | PHE | A | 192 | 16.103 | −12.425 | 36.115 | 1.00 | 15.89 | A |
| ATOM | 1089 | CG | PHE | A | 192 | 17.110 | −12.499 | 35.022 | 1.00 | 16.68 | A |
| ATOM | 1090 | CD1 | PHE | A | 192 | 18.431 | −12.177 | 35.247 | 1.00 | 12.61 | A |
| ATOM | 1091 | CD2 | PHE | A | 192 | 16.727 | −12.890 | 33.737 | 1.00 | 13.86 | A |

TABLE 2-continued

| ATOM | 1092 | CE1 | PHE | A | 192 | 19.371 | −12.249 | 34.218 | 1.00 | 12.89 | A |
|------|------|-----|-----|---|-----|--------|---------|--------|------|-------|---|
| ATOM | 1093 | CE2 | PHE | A | 192 | 17.642 | −12.958 | 32.727 | 1.00 | 13.50 | A |
| ATOM | 1094 | CZ | PHE | A | 192 | 18.969 | −12.644 | 32.944 | 1.00 | 13.74 | A |
| ATOM | 1095 | C | PHE | A | 192 | 16.498 | −10.151 | 37.011 | 1.00 | 19.66 | A |
| ATOM | 1096 | O | PHE | A | 192 | 17.350 | −9.530 | 36.398 | 1.00 | 16.83 | A |
| ATOM | 1097 | N | LEU | A | 193 | 16.380 | −10.091 | 38.336 | 1.00 | 22.72 | A |
| ATOM | 1098 | CA | LEU | A | 193 | 17.386 | −9.398 | 39.142 | 1.00 | 20.58 | A |
| ATOM | 1099 | CB | LEU | A | 193 | 16.965 | −9.418 | 40.606 | 1.00 | 23.85 | A |
| ATOM | 1100 | CG | LEU | A | 193 | 18.004 | −8.909 | 41.613 | 1.00 | 23.40 | A |
| ATOM | 1101 | CD1 | LEU | A | 193 | 18.479 | −7.496 | 41.213 | 1.00 | 23.22 | A |
| ATOM | 1102 | CD2 | LEU | A | 193 | 17.346 | −8.907 | 42.999 | 1.00 | 22.88 | A |
| ATOM | 1103 | C | LEU | A | 193 | 18.616 | −10.311 | 38.935 | 1.00 | 21.88 | A |
| ATOM | 1104 | O | LEU | A | 193 | 18.497 | −11.549 | 38.903 | 1.00 | 21.21 | A |
| ATOM | 1105 | N | TYR | A | 194 | 19.786 | −9.710 | 38.756 | 1.00 | 22.39 | A |
| ATOM | 1106 | CA | TYR | A | 194 | 21.004 | −10.447 | 38.518 | 1.00 | 22.95 | A |
| ATOM | 1107 | CB | TYR | A | 194 | 21.616 | −9.922 | 37.229 | 1.00 | 21.48 | A |
| ATOM | 1108 | CG | TYR | A | 194 | 22.869 | −10.612 | 36.795 | 1.00 | 19.73 | A |
| ATOM | 1109 | CD1 | TYR | A | 194 | 24.115 | −10.095 | 37.127 | 1.00 | 19.48 | A |
| ATOM | 1110 | CE1 | TYR | A | 194 | 25.266 | −10.676 | 36.666 | 1.00 | 20.31 | A |
| ATOM | 1111 | CD2 | TYR | A | 194 | 22.813 | −11.741 | 35.984 | 1.00 | 16.74 | A |
| ATOM | 1112 | CE2 | TYR | A | 194 | 23.951 | −12.322 | 35.510 | 1.00 | 16.40 | A |
| ATOM | 1113 | CZ | TYR | A | 194 | 25.186 | −11.788 | 35.856 | 1.00 | 22.33 | A |
| ATOM | 1114 | OH | TYR | A | 194 | 26.354 | −12.356 | 35.387 | 1.00 | 23.45 | A |
| ATOM | 1115 | C | TYR | A | 194 | 22.055 | −10.413 | 39.656 | 1.00 | 25.99 | A |
| ATOM | 1116 | O | TYR | A | 194 | 22.700 | −11.418 | 39.935 | 1.00 | 23.15 | A |
| ATOM | 1117 | N | GLN | A | 195 | 22.232 | −9.250 | 40.284 | 1.00 | 29.35 | A |
| ATOM | 1118 | CA | GLN | A | 195 | 23.208 | −9.062 | 41.360 | 1.00 | 29.01 | A |
| ATOM | 1119 | CB | GLN | A | 195 | 24.607 | −8.870 | 40.786 | 1.00 | 28.31 | A |
| ATOM | 1120 | CG | GLN | A | 195 | 25.684 | −8.967 | 41.851 | 1.00 | 28.76 | A |
| ATOM | 1121 | CD | GLN | A | 195 | 27.087 | −8.989 | 41.310 | 1.00 | 32.25 | A |
| ATOM | 1122 | OE1 | GLN | A | 195 | 27.375 | −9.540 | 40.229 | 1.00 | 33.70 | A |
| ATOM | 1123 | NE2 | GLN | A | 195 | 27.999 | −8.417 | 42.083 | 1.00 | 34.02 | A |
| ATOM | 1124 | C | GLN | A | 195 | 22.822 | −7.850 | 42.188 | 1.00 | 31.85 | A |
| ATOM | 1125 | O | GLN | A | 195 | 22.518 | −6.784 | 41.631 | 1.00 | 32.81 | A |
| ATOM | 1126 | N | GLN | A | 196 | 22.811 | −8.008 | 43.509 | 1.00 | 31.55 | A |
| ATOM | 1127 | CA | GLN | A | 196 | 22.446 | −6.914 | 44.402 | 1.00 | 33.01 | A |
| ATOM | 1128 | CB | GLN | A | 196 | 21.562 | −7.388 | 45.547 | 1.00 | 33.40 | A |
| ATOM | 1129 | CG | GLN | A | 196 | 20.197 | −7.792 | 45.169 | 1.00 | 36.87 | A |
| ATOM | 1130 | CD | GLN | A | 196 | 19.322 | −8.018 | 46.386 | 1.00 | 38.23 | A |
| ATOM | 1131 | OE1 | GLN | A | 196 | 18.952 | −7.077 | 47.070 | 1.00 | 43.30 | A |
| ATOM | 1132 | NE2 | GLN | A | 196 | 19.000 | −9.265 | 46.663 | 1.00 | 41.48 | A |
| ATOM | 1133 | C | GLN | A | 196 | 23.632 | −6.238 | 45.043 | 1.00 | 33.18 | A |
| ATOM | 1134 | O | GLN | A | 196 | 24.742 | −6.772 | 45.099 | 1.00 | 32.67 | A |
| ATOM | 1135 | N | ASP | A | 197 | 23.347 | −5.065 | 45.583 | 1.00 | 34.68 | A |
| ATOM | 1136 | CA | ASP | A | 197 | 24.320 | −4.239 | 46.278 | 1.00 | 37.04 | A |
| ATOM | 1137 | CB | ASP | A | 197 | 24.393 | −4.625 | 47.758 | 1.00 | 39.18 | A |
| ATOM | 1138 | CG | ASP | A | 197 | 23.035 | −4.794 | 48.375 | 1.00 | 43.72 | A |
| ATOM | 1139 | OD1 | ASP | A | 197 | 22.265 | −3.802 | 48.418 | 1.00 | 45.93 | A |
| ATOM | 1140 | OD2 | ASP | A | 197 | 22.724 | −5.935 | 48.807 | 1.00 | 48.86 | A |
| ATOM | 1141 | C | ASP | A | 197 | 25.719 | −4.272 | 45.719 | 1.00 | 36.93 | A |
| ATOM | 1142 | O | ASP | A | 197 | 26.672 | −4.542 | 46.455 | 1.00 | 35.50 | A |
| ATOM | 1143 | N | VAL | A | 198 | 25.856 | −4.007 | 44.432 | 1.00 | 34.21 | A |
| ATOM | 1144 | CA | VAL | A | 198 | 27.176 | −3.969 | 43.836 | 1.00 | 36.03 | A |
| ATOM | 1145 | CB | VAL | A | 198 | 27.096 | −4.132 | 42.323 | 1.00 | 35.46 | A |
| ATOM | 1146 | CG1 | VAL | A | 198 | 28.473 | −3.979 | 41.716 | 1.00 | 35.71 | A |
| ATOM | 1147 | CG2 | VAL | A | 198 | 26.517 | −5.498 | 41.992 | 1.00 | 35.80 | A |
| ATOM | 1148 | C | VAL | A | 198 | 27.735 | −2.583 | 44.161 | 1.00 | 38.78 | A |
| ATOM | 1149 | O | VAL | A | 198 | 27.034 | −1.571 | 44.011 | 1.00 | 38.01 | A |
| ATOM | 1150 | N | VAL | A | 199 | 28.983 | −2.523 | 44.621 | 1.00 | 40.43 | A |
| ATOM | 1151 | CA | VAL | A | 199 | 29.572 | −1.222 | 44.960 | 1.00 | 40.95 | A |
| ATOM | 1152 | CB | VAL | A | 199 | 30.403 | −1.279 | 46.261 | 1.00 | 41.60 | A |
| ATOM | 1153 | CG1 | VAL | A | 199 | 29.496 | −1.669 | 47.443 | 1.00 | 40.30 | A |
| ATOM | 1154 | CG2 | VAL | A | 199 | 31.554 | −2.262 | 46.094 | 1.00 | 43.87 | A |
| ATOM | 1155 | C | VAL | A | 199 | 30.435 | −0.755 | 43.816 | 1.00 | 39.75 | A |
| ATOM | 1156 | O | VAL | A | 199 | 31.327 | −1.465 | 43.363 | 1.00 | 40.53 | A |
| ATOM | 1157 | N | VAL | A | 200 | 30.132 | 0.439 | 43.332 | 1.00 | 39.38 | A |
| ATOM | 1158 | CA | VAL | A | 200 | 30.845 | 1.004 | 42.209 | 1.00 | 40.37 | A |
| ATOM | 1159 | CB | VAL | A | 200 | 29.870 | 1.357 | 41.036 | 1.00 | 40.73 | A |
| ATOM | 1160 | CG1 | VAL | A | 200 | 30.649 | 1.654 | 39.771 | 1.00 | 40.68 | A |
| ATOM | 1161 | CG2 | VAL | A | 200 | 28.931 | 0.212 | 40.780 | 1.00 | 38.82 | A |
| ATOM | 1162 | C | VAL | A | 200 | 31.524 | 2.258 | 42.694 | 1.00 | 41.59 | A |
| ATOM | 1163 | O | VAL | A | 200 | 30.902 | 3.118 | 43.307 | 1.00 | 41.85 | A |
| ATOM | 1164 | N | VAL | A | 201 | 32.814 | 2.357 | 42.418 | 1.00 | 44.74 | A |
| ATOM | 1165 | CA | VAL | A | 201 | 33.567 | 3.513 | 42.847 | 1.00 | 46.61 | A |
| ATOM | 1166 | CB | VAL | A | 201 | 34.965 | 3.106 | 43.355 | 1.00 | 47.23 | A |
| ATOM | 1167 | CG1 | VAL | A | 201 | 35.604 | 4.274 | 44.127 | 1.00 | 46.39 | A |
| ATOM | 1168 | CG2 | VAL | A | 201 | 34.848 | 1.883 | 44.257 | 1.00 | 48.12 | A |
| ATOM | 1169 | C | VAL | A | 201 | 33.711 | 4.442 | 41.666 | 1.00 | 47.35 | A |
| ATOM | 1170 | O | VAL | A | 201 | 34.384 | 4.107 | 40.704 | 1.00 | 46.77 | A |

TABLE 2-continued

| | | | | | | | | | | |
|---|---|---|---|---|---|---|---|---|---|---|
| ATOM | 1171 | N | LEU | A | 202 | 33.053 | 5.594 | 41.746 | 1.00 | 50.34 A |
| ATOM | 1172 | CA | LEU | A | 202 | 33.090 | 6.609 | 40.695 | 1.00 | 53.52 A |
| ATOM | 1173 | CB | LEU | A | 202 | 31.669 | 7.091 | 40.353 | 1.00 | 54.00 A |
| ATOM | 1174 | CG | LEU | A | 202 | 30.710 | 6.236 | 39.515 | 1.00 | 54.72 A |
| ATOM | 1175 | CD1 | LEU | A | 202 | 30.450 | 4.928 | 40.210 | 1.00 | 57.57 A |
| ATOM | 1176 | CD2 | LEU | A | 202 | 29.405 | 6.963 | 39.327 | 1.00 | 54.51 A |
| ATOM | 1177 | C | LEU | A | 202 | 33.905 | 7.818 | 41.164 | 1.00 | 56.11 A |
| ATOM | 1178 | O | LEU | A | 202 | 34.022 | 8.073 | 42.368 | 1.00 | 55.09 A |
| ATOM | 1179 | N | PRO | A | 203 | 34.460 | 8.591 | 40.211 | 1.00 | 58.37 A |
| ATOM | 1180 | CD | PRO | A | 203 | 34.466 | 8.303 | 38.762 | 1.00 | 59.65 A |
| ATOM | 1181 | CA | PRO | A | 203 | 35.262 | 9.781 | 40.500 | 1.00 | 59.68 A |
| ATOM | 1182 | CB | PRO | A | 203 | 35.468 | 10.407 | 39.123 | 1.00 | 59.41 A |
| ATOM | 1183 | CG | PRO | A | 203 | 35.579 | 9.214 | 38.239 | 1.00 | 59.82 A |
| ATOM | 1184 | C | PRO | A | 203 | 34.640 | 10.759 | 41.490 | 1.00 | 61.14 A |
| ATOM | 1185 | O | PRO | A | 203 | 33.433 | 10.731 | 41.773 | 1.00 | 61.10 A |
| ATOM | 1186 | N | LYS | A | 204 | 35.517 | 11.631 | 41.983 | 1.00 | 63.03 A |
| ATOM | 1187 | CA | LYS | A | 204 | 35.243 | 12.670 | 42.977 | 1.00 | 63.67 A |
| ATOM | 1188 | CB | LYS | A | 204 | 36.107 | 13.911 | 42.686 | 1.00 | 66.51 A |
| ATOM | 1189 | CG | LYS | A | 204 | 37.561 | 13.807 | 43.182 | 1.00 | 70.06 A |
| ATOM | 1190 | CD | LYS | A | 204 | 37.661 | 13.875 | 44.716 | 1.00 | 71.79 A |
| ATOM | 1191 | CE | LYS | A | 204 | 39.118 | 13.815 | 45.172 | 1.00 | 73.07 A |
| ATOM | 1192 | NZ | LYS | A | 204 | 39.941 | 14.903 | 44.542 | 1.00 | 74.42 A |
| ATOM | 1193 | C | LYS | A | 204 | 33.828 | 13.127 | 43.303 | 1.00 | 60.91 A |
| ATOM | 1194 | O | LYS | A | 204 | 33.341 | 12.840 | 44.398 | 1.00 | 64.02 A |
| ATOM | 1195 | N | PRO | A | 205 | 33.139 | 13.818 | 42.373 | 1.00 | 56.45 A |
| ATOM | 1196 | CD | PRO | A | 205 | 33.349 | 13.981 | 40.925 | 1.00 | 53.96 A |
| ATOM | 1197 | CA | PRO | A | 205 | 31.792 | 14.245 | 42.761 | 1.00 | 53.46 A |
| ATOM | 1198 | CB | PRO | A | 205 | 31.217 | 14.849 | 41.473 | 1.00 | 53.48 A |
| ATOM | 1199 | CG | PRO | A | 205 | 32.414 | 15.112 | 40.611 | 1.00 | 53.39 A |
| ATOM | 1200 | C | PRO | A | 205 | 30.914 | 13.121 | 43.292 | 1.00 | 52.72 A |
| ATOM | 1201 | O | PRO | A | 205 | 30.146 | 13.307 | 44.238 | 1.00 | 52.54 A |
| ATOM | 1202 | N | TYR | A | 206 | 31.057 | 11.935 | 42.713 | 1.00 | 51.10 A |
| ATOM | 1203 | CA | TYR | A | 206 | 30.183 | 10.842 | 43.099 | 1.00 | 49.77 A |
| ATOM | 1204 | CB | TYR | A | 206 | 29.697 | 10.147 | 41.821 | 1.00 | 48.49 A |
| ATOM | 1205 | CG | TYR | A | 206 | 29.037 | 11.126 | 40.858 | 1.00 | 46.57 A |
| ATOM | 1206 | CD1 | TYR | A | 206 | 27.894 | 11.844 | 41.234 | 1.00 | 45.67 A |
| ATOM | 1207 | CE1 | TYR | A | 206 | 27.335 | 12.798 | 40.387 | 1.00 | 43.87 A |
| ATOM | 1208 | CD2 | TYR | A | 206 | 29.593 | 11.387 | 39.609 | 1.00 | 45.18 A |
| ATOM | 1209 | CE2 | TYR | A | 206 | 29.044 | 12.337 | 38.762 | 1.00 | 44.21 A |
| ATOM | 1210 | CZ | TYR | A | 206 | 27.919 | 13.039 | 39.154 | 1.00 | 44.28 A |
| ATOM | 1211 | OH | TYR | A | 206 | 27.393 | 13.991 | 38.307 | 1.00 | 44.33 A |
| ATOM | 1212 | C | TYR | A | 206 | 30.672 | 9.828 | 44.124 | 1.00 | 49.50 A |
| ATOM | 1213 | O | TYR | A | 206 | 29.896 | 9.412 | 44.978 | 1.00 | 48.83 A |
| ATOM | 1214 | N | GLY | A | 207 | 31.935 | 9.415 | 44.045 | 1.00 | 48.23 A |
| ATOM | 1215 | CA | GLY | A | 207 | 32.437 | 8.458 | 45.013 | 1.00 | 47.40 A |
| ATOM | 1216 | C | GLY | A | 207 | 31.848 | 7.065 | 44.892 | 1.00 | 47.68 A |
| ATOM | 1217 | O | GLY | A | 207 | 31.680 | 6.550 | 43.780 | 1.00 | 49.02 A |
| ATOM | 1218 | N | GLU | A | 208 | 31.550 | 6.445 | 46.033 | 1.00 | 45.57 A |
| ATOM | 1219 | CA | GLU | A | 208 | 31.003 | 5.097 | 46.043 | 1.00 | 43.83 A |
| ATOM | 1220 | CB | GLU | A | 208 | 31.457 | 4.331 | 47.299 | 1.00 | 43.06 A |
| ATOM | 1221 | CG | GLU | A | 208 | 32.808 | 3.661 | 47.057 | 1.00 | 47.39 A |
| ATOM | 1222 | CD | GLU | A | 208 | 33.274 | 2.730 | 48.167 | 1.00 | 48.82 A |
| ATOM | 1223 | OE1 | GLU | A | 208 | 34.402 | 2.187 | 48.026 | 1.00 | 49.97 A |
| ATOM | 1224 | OE2 | GLU | A | 208 | 32.533 | 2.541 | 49.162 | 1.00 | 48.55 A |
| ATOM | 1225 | C | GLU | A | 208 | 29.495 | 5.088 | 45.945 | 1.00 | 41.80 A |
| ATOM | 1226 | O | GLU | A | 208 | 28.818 | 5.876 | 46.604 | 1.00 | 39.96 A |
| ATOM | 1227 | N | VAL | A | 209 | 28.971 | 4.188 | 45.113 | 1.00 | 40.07 A |
| ATOM | 1228 | CA | VAL | A | 209 | 27.525 | 4.072 | 44.916 | 1.00 | 38.21 A |
| ATOM | 1229 | CB | VAL | A | 209 | 27.107 | 4.779 | 43.571 | 1.00 | 39.80 A |
| ATOM | 1230 | CG1 | VAL | A | 209 | 27.575 | 3.956 | 42.361 | 1.00 | 37.58 A |
| ATOM | 1231 | CG2 | VAL | A | 209 | 25.614 | 4.989 | 43.538 | 1.00 | 42.93 A |
| ATOM | 1232 | C | VAL | A | 209 | 27.158 | 2.583 | 44.881 | 1.00 | 36.12 A |
| ATOM | 1233 | O | VAL | A | 209 | 27.896 | 1.782 | 44.317 | 1.00 | 37.85 A |
| ATOM | 1234 | N | ALA | A | 210 | 26.044 | 2.212 | 45.502 | 1.00 | 34.67 A |
| ATOM | 1235 | CA | ALA | A | 210 | 25.592 | 0.819 | 45.530 | 1.00 | 34.49 A |
| ATOM | 1236 | CB | ALA | A | 210 | 25.119 | 0.430 | 46.938 | 1.00 | 33.45 A |
| ATOM | 1237 | C | ALA | A | 210 | 24.422 | 0.677 | 44.539 | 1.00 | 33.82 A |
| ATOM | 1238 | O | ALA | A | 210 | 23.414 | 1.365 | 44.657 | 1.00 | 34.77 A |
| ATOM | 1239 | N | VAL | A | 211 | 24.547 | −0.253 | 43.606 | 1.00 | 32.02 A |
| ATOM | 1240 | CA | VAL | A | 211 | 23.529 | −0.454 | 42.596 | 1.00 | 29.15 A |
| ATOM | 1241 | CB | VAL | A | 211 | 24.070 | 0.001 | 41.220 | 1.00 | 27.40 A |
| ATOM | 1242 | CG1 | VAL | A | 211 | 24.705 | 1.368 | 41.326 | 1.00 | 26.38 A |
| ATOM | 1243 | CG2 | VAL | A | 211 | 25.095 | −0.971 | 40.724 | 1.00 | 24.04 A |
| ATOM | 1244 | C | VAL | A | 211 | 23.120 | −1.914 | 42.456 | 1.00 | 30.40 A |
| ATOM | 1245 | O | VAL | A | 211 | 23.853 | −2.820 | 42.886 | 1.00 | 28.98 A |
| ATOM | 1246 | N | ASP | A | 212 | 21.948 | −2.139 | 41.858 | 1.00 | 28.19 A |
| ATOM | 1247 | CA | ASP | A | 212 | 21.483 | −3.494 | 41.566 | 1.00 | 28.03 A |
| ATOM | 1248 | CB | ASP | A | 212 | 19.999 | −3.677 | 41.919 | 1.00 | 29.50 A |
| ATOM | 1249 | CG | ASP | A | 212 | 19.752 | −3.758 | 43.431 | 1.00 | 31.57 A |

TABLE 2-continued

| | | | | | | | | | | |
|---|---|---|---|---|---|---|---|---|---|---|
| ATOM | 1250 | OD1 | ASP | A | 212 | 20.709 | −4.058 | 44.162 | 1.00 | 34.76 A |
| ATOM | 1251 | OD2 | ASP | A | 212 | 18.615 | −3.537 | 43.896 | 1.00 | 32.63 A |
| ATOM | 1252 | C | ASP | A | 212 | 21.688 | −3.686 | 40.053 | 1.00 | 28.82 A |
| ATOM | 1253 | O | ASP | A | 212 | 21.599 | −2.726 | 39.262 | 1.00 | 28.01 A |
| ATOM | 1254 | N | ILE | A | 213 | 22.017 | −4.903 | 39.643 | 1.00 | 26.82 A |
| ATOM | 1255 | CA | ILE | A | 213 | 22.180 | −5.180 | 38.230 | 1.00 | 23.45 A |
| ATOM | 1256 | CB | ILE | A | 213 | 23.505 | −5.893 | 37.939 | 1.00 | 24.63 A |
| ATOM | 1257 | CG2 | ILE | A | 213 | 23.567 | −6.338 | 36.450 | 1.00 | 20.86 A |
| ATOM | 1258 | CG1 | ILE | A | 213 | 24.661 | −4.928 | 38.247 | 1.00 | 22.68 A |
| ATOM | 1259 | CD1 | ILE | A | 213 | 26.014 | −5.461 | 37.864 | 1.00 | 26.22 A |
| ATOM | 1260 | C | ILE | A | 213 | 21.002 | −6.073 | 37.924 | 1.00 | 25.43 A |
| ATOM | 1261 | O | ILE | A | 213 | 20.742 | −7.030 | 38.668 | 1.00 | 24.17 A |
| ATOM | 1262 | N | ALA | A | 214 | 20.241 | −5.731 | 36.876 | 1.00 | 23.85 A |
| ATOM | 1263 | CA | ALA | A | 214 | 19.074 | −6.525 | 36.500 | 1.00 | 22.54 A |
| ATOM | 1264 | CB | ALA | A | 214 | 17.835 | −5.976 | 37.170 | 1.00 | 16.51 A |
| ATOM | 1265 | C | ALA | A | 214 | 18.881 | −6.559 | 34.981 | 1.00 | 23.53 A |
| ATOM | 1266 | O | ALA | A | 214 | 19.274 | −5.620 | 34.259 | 1.00 | 24.53 A |
| ATOM | 1267 | N | PHE | A | 215 | 18.244 | −7.621 | 34.493 | 1.00 | 21.22 A |
| ATOM | 1268 | CA | PHE | A | 215 | 18.027 | −7.742 | 33.068 | 1.00 | 20.88 A |
| ATOM | 1269 | CB | PHE | A | 215 | 18.475 | −9.116 | 32.575 | 1.00 | 19.85 A |
| ATOM | 1270 | CG | PHE | A | 215 | 18.342 | −9.302 | 31.070 | 1.00 | 17.94 A |
| ATOM | 1271 | CD1 | PHE | A | 215 | 19.241 | −8.698 | 30.201 | 1.00 | 18.85 A |
| ATOM | 1272 | CD2 | PHE | A | 215 | 17.329 | −10.076 | 30.536 | 1.00 | 18.21 A |
| ATOM | 1273 | CE1 | PHE | A | 215 | 19.137 | −8.865 | 28.797 | 1.00 | 21.00 A |
| ATOM | 1274 | CE2 | PHE | A | 215 | 17.212 | −10.250 | 29.125 | 1.00 | 18.93 A |
| ATOM | 1275 | CZ | PHE | A | 215 | 18.131 | −9.635 | 28.265 | 1.00 | 16.86 A |
| ATOM | 1276 | C | PHE | A | 215 | 16.541 | −7.517 | 32.774 | 1.00 | 19.38 A |
| ATOM | 1277 | O | PHE | A | 215 | 15.671 | −8.055 | 33.448 | 1.00 | 20.46 A |
| ATOM | 1278 | N | GLY | A | 216 | 16.258 | −6.673 | 31.792 | 1.00 | 18.98 A |
| ATOM | 1279 | CA | GLY | A | 216 | 14.873 | −6.415 | 31.417 | 1.00 | 16.50 A |
| ATOM | 1280 | C | GLY | A | 216 | 14.826 | −6.367 | 29.881 | 1.00 | 17.77 A |
| ATOM | 1281 | O | GLY | A | 216 | 13.928 | −5.762 | 29.307 | 1.00 | 20.47 A |
| ATOM | 1282 | N | GLY | A | 217 | 15.777 | −7.023 | 29.230 | 1.00 | 16.37 A |
| ATOM | 1283 | CA | GLY | A | 217 | 15.868 | −7.004 | 27.770 | 1.00 | 16.96 A |
| ATOM | 1284 | C | GLY | A | 217 | 17.268 | −6.497 | 27.468 | 1.00 | 16.38 A |
| ATOM | 1285 | O | GLY | A | 217 | 17.881 | −6.850 | 26.452 | 1.00 | 19.81 A |
| ATOM | 1286 | N | ASN | A | 218 | 17.766 | −5.641 | 28.359 | 1.00 | 15.91 A |
| ATOM | 1287 | CA | ASN | A | 218 | 19.137 | −5.137 | 28.318 | 1.00 | 15.62 A |
| ATOM | 1288 | CB | ASN | A | 218 | 19.204 | −3.642 | 27.979 | 1.00 | 13.15 A |
| ATOM | 1289 | CG | ASN | A | 218 | 18.607 | −3.327 | 26.589 | 1.00 | 17.85 A |
| ATOM | 1290 | OD1 | ASN | A | 218 | 19.104 | −3.804 | 25.559 | 1.00 | 18.86 A |
| ATOM | 1291 | ND2 | ASN | A | 218 | 17.554 | −2.534 | 26.575 | 1.00 | 14.08 A |
| ATOM | 1292 | C | ASN | A | 218 | 19.552 | −5.293 | 29.783 | 1.00 | 16.88 A |
| ATOM | 1293 | O | ASN | A | 218 | 18.703 | −5.367 | 30.634 | 1.00 | 16.76 A |
| ATOM | 1294 | N | PHE | A | 219 | 20.844 | −5.352 | 30.061 | 1.00 | 17.60 A |
| ATOM | 1295 | CA | PHE | A | 219 | 21.278 | −5.390 | 31.445 | 1.00 | 20.81 A |
| ATOM | 1296 | CB | PHE | A | 219 | 22.693 | −5.984 | 31.547 | 1.00 | 20.77 A |
| ATOM | 1297 | CG | PHE | A | 219 | 22.706 | −7.453 | 31.800 | 1.00 | 21.46 A |
| ATOM | 1298 | CD1 | PHE | A | 219 | 23.270 | −8.325 | 30.885 | 1.00 | 23.13 A |
| ATOM | 1299 | CD2 | PHE | A | 219 | 22.217 | −7.954 | 32.984 | 1.00 | 21.01 A |
| ATOM | 1300 | CE1 | PHE | A | 219 | 23.352 | −9.690 | 31.151 | 1.00 | 24.36 A |
| ATOM | 1301 | CE2 | PHE | A | 219 | 22.298 | −9.311 | 33.261 | 1.00 | 23.60 A |
| ATOM | 1302 | CZ | PHE | A | 219 | 22.867 | −10.178 | 32.341 | 1.00 | 21.15 A |
| ATOM | 1303 | C | PHE | A | 219 | 21.296 | −3.948 | 31.907 | 1.00 | 19.22 A |
| ATOM | 1304 | O | PHE | A | 219 | 21.817 | −3.074 | 31.230 | 1.00 | 21.81 A |
| ATOM | 1305 | N | PHE | A | 220 | 20.722 | −3.696 | 33.063 | 1.00 | 20.27 A |
| ATOM | 1306 | CA | PHE | A | 220 | 20.668 | −2.360 | 33.627 | 1.00 | 19.58 A |
| ATOM | 1307 | CB | PHE | A | 220 | 19.225 | −1.993 | 33.967 | 1.00 | 20.34 A |
| ATOM | 1308 | CG | PHE | A | 220 | 18.408 | −1.500 | 32.793 | 1.00 | 21.87 A |
| ATOM | 1309 | CD1 | PHE | A | 220 | 18.187 | −0.129 | 32.610 | 1.00 | 20.61 A |
| ATOM | 1310 | CD2 | PHE | A | 220 | 17.858 | −2.410 | 31.881 | 1.00 | 16.67 A |
| ATOM | 1311 | CE1 | PHE | A | 220 | 17.419 | 0.340 | 31.525 | 1.00 | 19.99 A |
| ATOM | 1312 | CE2 | PHE | A | 220 | 17.107 | −1.956 | 30.812 | 1.00 | 19.03 A |
| ATOM | 1313 | CZ | PHE | A | 220 | 16.885 | −0.578 | 30.633 | 1.00 | 19.94 A |
| ATOM | 1314 | C | PHE | A | 220 | 21.414 | −2.307 | 34.972 | 1.00 | 22.98 A |
| ATOM | 1315 | O | PHE | A | 220 | 21.483 | −3.313 | 35.669 | 1.00 | 22.94 A |
| ATOM | 1316 | N | ALA | A | 221 | 21.968 | −1.147 | 35.309 | 1.00 | 21.90 A |
| ATOM | 1317 | CA | ALA | A | 221 | 22.528 | −0.932 | 36.641 | 1.00 | 22.48 A |
| ATOM | 1318 | CB | ALA | A | 221 | 23.891 | −0.180 | 36.590 | 1.00 | 21.08 A |
| ATOM | 1319 | C | ALA | A | 221 | 21.423 | 0.001 | 37.146 | 1.00 | 21.09 A |
| ATOM | 1320 | O | ALA | A | 221 | 21.142 | 1.012 | 36.511 | 1.00 | 24.87 A |
| ATOM | 1321 | N | ILE | A | 222 | 20.765 | −0.347 | 38.240 | 1.00 | 20.84 A |
| ATOM | 1322 | CA | ILE | A | 222 | 19.697 | 0.449 | 38.816 | 1.00 | 23.85 A |
| ATOM | 1323 | CB | ILE | A | 222 | 18.521 | −0.446 | 39.155 | 1.00 | 23.60 A |
| ATOM | 1324 | CG2 | ILE | A | 222 | 17.417 | 0.383 | 39.799 | 1.00 | 21.92 A |
| ATOM | 1325 | CG1 | ILE | A | 222 | 18.030 | −1.159 | 37.874 | 1.00 | 24.75 A |
| ATOM | 1326 | CD1 | ILE | A | 222 | 16.816 | −2.090 | 38.112 | 1.00 | 23.70 A |
| ATOM | 1327 | C | ILE | A | 222 | 20.226 | 1.151 | 40.088 | 1.00 | 25.99 A |
| ATOM | 1328 | O | ILE | A | 222 | 20.749 | 0.489 | 40.981 | 1.00 | 25.47 A |

TABLE 2-continued

| | | | | | | | | | | |
|---|---|---|---|---|---|---|---|---|---|---|
| ATOM | 1329 | N | VAL | A | 223 | 20.076 | 2.475 | 40.170 | 1.00 | 27.20 A |
| ATOM | 1330 | CA | VAL | A | 223 | 20.631 | 3.272 | 41.278 | 1.00 | 27.77 A |
| ATOM | 1331 | CB | VAL | A | 223 | 22.064 | 3.826 | 40.861 | 1.00 | 30.02 A |
| ATOM | 1332 | CG1 | VAL | A | 223 | 21.944 | 4.837 | 39.708 | 1.00 | 30.59 A |
| ATOM | 1333 | CG2 | VAL | A | 223 | 22.774 | 4.482 | 42.038 | 1.00 | 29.54 A |
| ATOM | 1334 | C | VAL | A | 223 | 19.714 | 4.430 | 41.678 | 1.00 | 28.94 A |
| ATOM | 1335 | O | VAL | A | 223 | 19.151 | 5.113 | 40.823 | 1.00 | 26.93 A |
| ATOM | 1336 | N | PRO | A | 224 | 19.513 | 4.634 | 42.993 | 1.00 | 28.66 A |
| ATOM | 1337 | CD | PRO | A | 224 | 20.022 | 3.845 | 44.133 | 1.00 | 28.59 A |
| ATOM | 1338 | CA | PRO | A | 224 | 18.652 | 5.725 | 43.443 | 1.00 | 26.78 A |
| ATOM | 1339 | CB | PRO | A | 224 | 18.617 | 5.545 | 44.965 | 1.00 | 27.89 A |
| ATOM | 1340 | CG | PRO | A | 224 | 18.954 | 4.067 | 45.156 | 1.00 | 28.55 A |
| ATOM | 1341 | C | PRO | A | 224 | 19.334 | 7.031 | 43.066 | 1.00 | 26.32 A |
| ATOM | 1342 | O | PRO | A | 224 | 20.555 | 7.101 | 43.100 | 1.00 | 27.49 A |
| ATOM | 1343 | N | ALA | A | 225 | 18.587 | 8.066 | 42.695 | 1.00 | 25.04 A |
| ATOM | 1344 | CA | ALA | A | 225 | 19.265 | 9.331 | 42.385 | 1.00 | 26.13 A |
| ATOM | 1345 | CB | ALA | A | 225 | 18.296 | 10.336 | 41.857 | 1.00 | 23.34 A |
| ATOM | 1346 | C | ALA | A | 225 | 19.881 | 9.875 | 43.693 | 1.00 | 28.41 A |
| ATOM | 1347 | O | ALA | A | 225 | 20.928 | 10.536 | 43.666 | 1.00 | 28.29 A |
| ATOM | 1348 | N | ALA | A | 226 | 19.194 | 9.620 | 44.806 | 1.00 | 30.40 A |
| ATOM | 1349 | CA | ALA | A | 226 | 19.635 | 10.051 | 46.144 | 1.00 | 36.35 A |
| ATOM | 1350 | CB | ALA | A | 226 | 18.767 | 9.354 | 47.237 | 1.00 | 34.64 A |
| ATOM | 1351 | C | ALA | A | 226 | 21.135 | 9.734 | 46.341 | 1.00 | 37.02 A |
| ATOM | 1352 | O | ALA | A | 226 | 21.890 | 10.549 | 46.843 | 1.00 | 41.07 A |
| ATOM | 1353 | N | GLN | A | 227 | 21.569 | 8.564 | 45.907 | 1.00 | 37.05 A |
| ATOM | 1354 | CA | GLN | A | 227 | 22.971 | 8.167 | 46.016 | 1.00 | 36.73 A |
| ATOM | 1355 | CB | GLN | A | 227 | 23.120 | 6.697 | 45.641 | 1.00 | 36.28 A |
| ATOM | 1356 | CG | GLN | A | 227 | 22.563 | 5.732 | 46.659 | 1.00 | 40.94 A |
| ATOM | 1357 | CD | GLN | A | 227 | 23.355 | 4.435 | 46.638 | 1.00 | 44.78 A |
| ATOM | 1358 | OE1 | GLN | A | 227 | 24.600 | 4.456 | 46.745 | 1.00 | 48.47 A |
| ATOM | 1359 | NE2 | GLN | A | 227 | 22.661 | 3.305 | 46.495 | 1.00 | 40.85 A |
| ATOM | 1360 | C | GLN | A | 227 | 23.970 | 8.956 | 45.165 | 1.00 | 37.38 A |
| ATOM | 1361 | O | GLN | A | 227 | 25.174 | 8.904 | 45.414 | 1.00 | 36.82 A |
| ATOM | 1362 | N | LEU | A | 228 | 23.499 | 9.656 | 44.139 | 1.00 | 35.30 A |
| ATOM | 1363 | CA | LEU | A | 228 | 24.407 | 10.388 | 43.277 | 1.00 | 35.17 A |
| ATOM | 1364 | CB | LEU | A | 228 | 23.926 | 10.329 | 41.815 | 1.00 | 35.67 A |
| ATOM | 1365 | CG | LEU | A | 228 | 23.879 | 8.981 | 41.087 | 1.00 | 36.18 A |
| ATOM | 1366 | CD1 | LEU | A | 228 | 22.996 | 9.107 | 39.838 | 1.00 | 36.51 A |
| ATOM | 1367 | CD2 | LEU | A | 228 | 25.283 | 8.535 | 40.728 | 1.00 | 36.62 A |
| ATOM | 1368 | C | LEU | A | 228 | 24.500 | 11.842 | 43.706 | 1.00 | 34.19 A |
| ATOM | 1369 | O | LEU | A | 228 | 25.261 | 12.592 | 43.140 | 1.00 | 34.44 A |
| ATOM | 1370 | N | GLY | A | 229 | 23.709 | 12.247 | 44.688 | 1.00 | 35.21 A |
| ATOM | 1371 | CA | GLY | A | 229 | 23.779 | 13.637 | 45.108 | 1.00 | 38.34 A |
| ATOM | 1372 | C | GLY | A | 229 | 22.916 | 14.593 | 44.294 | 1.00 | 41.43 A |
| ATOM | 1373 | O | GLY | A | 229 | 22.769 | 15.770 | 44.649 | 1.00 | 38.76 A |
| ATOM | 1374 | N | ILE | A | 230 | 22.337 | 14.087 | 43.201 | 1.00 | 41.92 A |
| ATOM | 1375 | CA | ILE | A | 230 | 21.480 | 14.899 | 42.371 | 1.00 | 41.59 A |
| ATOM | 1376 | CB | ILE | A | 230 | 22.100 | 15.155 | 41.016 | 1.00 | 42.74 A |
| ATOM | 1377 | CG2 | ILE | A | 230 | 23.186 | 16.266 | 41.165 | 1.00 | 45.58 A |
| ATOM | 1378 | CG1 | ILE | A | 230 | 22.632 | 13.849 | 40.436 | 1.00 | 42.36 A |
| ATOM | 1379 | CD1 | ILE | A | 230 | 23.596 | 14.053 | 39.267 | 1.00 | 40.18 A |
| ATOM | 1380 | C | ILE | A | 230 | 20.101 | 14.318 | 42.199 | 1.00 | 40.92 A |
| ATOM | 1381 | O | ILE | A | 230 | 19.895 | 13.110 | 42.142 | 1.00 | 43.20 A |
| ATOM | 1382 | N | ASP | A | 231 | 19.517 | 15.235 | 42.143 | 1.00 | 39.70 A |
| ATOM | 1383 | CA | ASP | A | 231 | 17.731 | 14.986 | 42.021 | 1.00 | 39.27 A |
| ATOM | 1384 | CB | ASP | A | 231 | 17.075 | 16.210 | 42.629 | 1.00 | 44.87 A |
| ATOM | 1385 | CG | ASP | A | 231 | 15.614 | 16.121 | 42.667 | 1.00 | 51.32 A |
| ATOM | 1386 | OD1 | ASP | A | 231 | 15.094 | 15.087 | 43.149 | 1.00 | 55.63 A |
| ATOM | 1387 | OD2 | ASP | A | 231 | 14.984 | 17.105 | 42.228 | 1.00 | 55.31 A |
| ATOM | 1388 | C | ASP | A | 231 | 17.375 | 14.816 | 40.531 | 1.00 | 36.01 A |
| ATOM | 1389 | O | ASP | A | 231 | 18.099 | 15.310 | 39.690 | 1.00 | 30.59 A |
| ATOM | 1390 | N | ILE | A | 232 | 16.282 | 14.125 | 40.198 | 1.00 | 34.78 A |
| ATOM | 1391 | CA | ILE | A | 232 | 15.930 | 13.951 | 38.778 | 1.00 | 33.85 A |
| ATOM | 1392 | CB | ILE | A | 232 | 15.081 | 12.664 | 38.562 | 1.00 | 33.96 A |
| ATOM | 1393 | CG2 | ILE | A | 232 | 14.695 | 12.543 | 37.094 | 1.00 | 31.54 A |
| ATOM | 1394 | CG1 | ILE | A | 232 | 15.894 | 11.426 | 38.954 | 1.00 | 33.28 A |
| ATOM | 1395 | CD1 | ILE | A | 232 | 15.050 | 10.137 | 39.020 | 1.00 | 33.21 A |
| ATOM | 1396 | C | ILE | A | 232 | 15.158 | 15.174 | 38.243 | 1.00 | 31.38 A |
| ATOM | 1397 | O | ILE | A | 232 | 14.000 | 15.385 | 38.586 | 1.00 | 33.23 A |
| ATOM | 1398 | N | SER | A | 233 | 15.805 | 15.984 | 37.413 | 1.00 | 31.64 A |
| ATOM | 1399 | CA | SER | A | 233 | 15.161 | 17.185 | 36.882 | 1.00 | 31.46 A |
| ATOM | 1400 | CB | SER | A | 233 | 15.226 | 18.284 | 37.943 | 1.00 | 32.19 A |
| ATOM | 1401 | OG | SER | A | 233 | 16.586 | 18.665 | 38.122 | 1.00 | 31.68 A |
| ATOM | 1402 | C | SER | A | 233 | 15.920 | 17.627 | 35.651 | 1.00 | 30.92 A |
| ATOM | 1403 | O | SER | A | 233 | 17.038 | 17.150 | 35.423 | 1.00 | 31.22 A |
| ATOM | 1404 | N | VAL | A | 234 | 15.354 | 18.555 | 34.872 | 1.00 | 32.37 A |
| ATOM | 1405 | CA | VAL | A | 234 | 16.047 | 19.023 | 33.667 | 1.00 | 32.42 A |
| ATOM | 1406 | CB | VAL | A | 234 | 15.132 | 19.907 | 32.719 | 1.00 | 35.31 A |
| ATOM | 1407 | CG1 | VAL | A | 234 | 13.800 | 19.210 | 32.461 | 1.00 | 31.97 A |

TABLE 2-continued

| | | | | | | | | | | |
|---|---|---|---|---|---|---|---|---|---|---|
| ATOM | 1408 | CG2 | VAL | A | 234 | 14.929 | 21.288 | 33.314 | 1.00 | 36.97 A |
| ATOM | 1409 | C | VAL | A | 234 | 17.312 | 19.814 | 34.000 | 1.00 | 32.09 A |
| ATOM | 1410 | O | VAL | A | 234 | 18.266 | 19.844 | 33.205 | 1.00 | 30.77 A |
| ATOM | 1411 | N | GLN | A | 235 | 17.326 | 20.448 | 35.174 | 1.00 | 31.75 A |
| ATOM | 1412 | CA | GLN | A | 235 | 18.484 | 21.223 | 35.631 | 1.00 | 28.16 A |
| ATOM | 1413 | CB | GLN | A | 235 | 18.205 | 21.872 | 36.986 | 1.00 | 33.85 A |
| ATOM | 1414 | CG | GLN | A | 235 | 16.998 | 22.768 | 37.043 | 1.00 | 41.63 A |
| ATOM | 1415 | CD | GLN | A | 235 | 15.700 | 22.061 | 36.671 | 1.00 | 47.44 A |
| ATOM | 1416 | OE1 | GLN | A | 235 | 15.665 | 20.837 | 36.491 | 1.00 | 51.31 A |
| ATOM | 1417 | NE2 | GLN | A | 235 | 14.616 | 22.835 | 36.559 | 1.00 | 50.11 A |
| ATOM | 1418 | C | GLN | A | 235 | 19.645 | 20.278 | 35.816 | 1.00 | 25.54 A |
| ATOM | 1419 | O | GLN | A | 235 | 20.789 | 20.622 | 35.559 | 1.00 | 22.27 A |
| ATOM | 1420 | N | ASN | A | 236 | 19.353 | 19.060 | 36.260 | 1.00 | 25.06 A |
| ATOM | 1421 | CA | ASN | A | 236 | 20.417 | 18.091 | 36.510 | 1.00 | 27.53 A |
| ATOM | 1422 | CB | ASN | A | 236 | 20.042 | 17.327 | 37.780 | 1.00 | 29.64 A |
| ATOM | 1423 | CG | ASN | A | 236 | 20.088 | 18.223 | 39.016 | 1.00 | 30.18 A |
| ATOM | 1424 | OD1 | ASN | A | 236 | 19.335 | 18.042 | 39.976 | 1.00 | 32.72 A |
| ATOM | 1425 | ND2 | ASN | A | 236 | 20.976 | 19.203 | 38.982 | 1.00 | 27.69 A |
| ATOM | 1426 | C | ASN | A | 236 | 20.725 | 17.123 | 35.368 | 1.00 | 30.21 A |
| ATOM | 1427 | O | ASN | A | 236 | 21.739 | 16.386 | 35.387 | 1.00 | 29.37 A |
| ATOM | 1428 | N | LEU | A | 237 | 19.873 | 17.153 | 34.347 | 1.00 | 30.39 A |
| ATOM | 1429 | CA | LEU | A | 237 | 20.017 | 16.217 | 33.229 | 1.00 | 29.36 A |
| ATOM | 1430 | CB | LEU | A | 237 | 19.094 | 16.630 | 32.049 | 1.00 | 28.33 A |
| ATOM | 1431 | CG | LEU | A | 237 | 18.979 | 15.614 | 30.897 | 1.00 | 30.71 A |
| ATOM | 1432 | CD1 | LEU | A | 237 | 18.959 | 14.171 | 31.426 | 1.00 | 28.27 A |
| ATOM | 1433 | CD2 | LEU | A | 237 | 17.711 | 15.936 | 30.104 | 1.00 | 29.89 A |
| ATOM | 1434 | C | LEU | A | 237 | 21.448 | 16.015 | 32.749 | 1.00 | 28.73 A |
| ATOM | 1435 | O | LEU | A | 237 | 21.898 | 14.878 | 32.609 | 1.00 | 25.78 A |
| ATOM | 1436 | N | SER | A | 238 | 22.187 | 17.096 | 32.518 | 1.00 | 26.18 A |
| ATOM | 1437 | CA | SER | A | 238 | 23.544 | 16.918 | 32.050 | 1.00 | 30.73 A |
| ATOM | 1438 | CB | SER | A | 238 | 24.145 | 18.270 | 31.680 | 1.00 | 34.33 A |
| ATOM | 1439 | OG | SER | A | 238 | 24.126 | 19.125 | 32.823 | 1.00 | 41.05 A |
| ATOM | 1440 | C | SER | A | 238 | 24.459 | 16.198 | 33.088 | 1.00 | 31.26 A |
| ATOM | 1441 | O | SER | A | 238 | 25.435 | 15.544 | 32.714 | 1.00 | 31.50 A |
| ATOM | 1442 | N | ARG | A | 239 | 24.158 | 16.310 | 34.372 | 1.00 | 30.67 A |
| ATOM | 1443 | CA | ARG | A | 239 | 24.993 | 15.617 | 35.354 | 1.00 | 32.78 A |
| ATOM | 1444 | CB | ARG | A | 239 | 24.910 | 16.318 | 36.723 | 1.00 | 36.06 A |
| ATOM | 1445 | CG | ARG | A | 239 | 25.872 | 17.529 | 36.808 | 1.00 | 42.05 A |
| ATOM | 1446 | CD | ARG | A | 239 | 25.836 | 18.212 | 38.173 | 1.00 | 49.32 A |
| ATOM | 1447 | NE | ARG | A | 239 | 24.558 | 18.869 | 38.445 | 1.00 | 54.33 A |
| ATOM | 1448 | CZ | ARG | A | 239 | 24.156 | 20.015 | 37.884 | 1.00 | 57.82 A |
| ATOM | 1449 | NH1 | ARG | A | 239 | 24.941 | 20.651 | 37.008 | 1.00 | 58.80 A |
| ATOM | 1450 | NH2 | ARG | A | 239 | 22.959 | 20.524 | 38.187 | 1.00 | 56.96 A |
| ATOM | 1451 | C | ARG | A | 239 | 24.525 | 14.165 | 35.420 | 1.00 | 30.93 A |
| ATOM | 1452 | O | ARG | A | 239 | 25.346 | 13.233 | 35.480 | 1.00 | 32.56 A |
| ATOM | 1453 | N | LEU | A | 240 | 23.212 | 13.965 | 35.362 | 1.00 | 27.72 A |
| ATOM | 1454 | CA | LEU | A | 240 | 22.686 | 12.606 | 35.363 | 1.00 | 24.97 A |
| ATOM | 1455 | CB | LEU | A | 240 | 21.175 | 12.637 | 35.222 | 1.00 | 23.21 A |
| ATOM | 1456 | CG | LEU | A | 240 | 20.491 | 13.169 | 36.478 | 1.00 | 23.01 A |
| ATOM | 1457 | CD1 | LEU | A | 240 | 19.064 | 13.617 | 36.194 | 1.00 | 25.03 A |
| ATOM | 1458 | CD2 | LEU | A | 240 | 20.476 | 12.072 | 37.518 | 1.00 | 24.59 A |
| ATOM | 1459 | C | LEU | A | 240 | 23.327 | 11.830 | 34.238 | 1.00 | 25.23 A |
| ATOM | 1460 | O | LEU | A | 240 | 23.770 | 10.694 | 34.442 | 1.00 | 25.65 A |
| ATOM | 1461 | N | GLN | A | 241 | 23.426 | 12.445 | 33.054 | 1.00 | 26.19 A |
| ATOM | 1462 | CA | GLN | A | 241 | 24.025 | 11.783 | 31.899 | 1.00 | 26.22 A |
| ATOM | 1463 | CB | GLN | A | 241 | 24.019 | 12.684 | 30.635 | 1.00 | 26.20 A |
| ATOM | 1464 | CG | GLN | A | 241 | 22.633 | 13.194 | 30.196 | 1.00 | 29.99 A |
| ATOM | 1465 | CD | GLN | A | 241 | 22.700 | 13.888 | 28.829 | 1.00 | 33.73 A |
| ATOM | 1466 | OE1 | GLN | A | 241 | 23.787 | 14.192 | 28.345 | 1.00 | 38.34 A |
| ATOM | 1467 | NE2 | GLN | A | 241 | 21.551 | 14.136 | 28.211 | 1.00 | 30.09 A |
| ATOM | 1468 | C | GLN | A | 241 | 25.454 | 11.428 | 32.200 | 1.00 | 26.83 A |
| ATOM | 1469 | O | GLN | A | 241 | 25.929 | 10.310 | 31.903 | 1.00 | 25.21 A |
| ATOM | 1470 | N | GLU | A | 242 | 26.170 | 12.402 | 32.752 | 1.00 | 28.33 A |
| ATOM | 1471 | CA | GLU | A | 242 | 27.569 | 12.184 | 33.088 | 1.00 | 29.85 A |
| ATOM | 1472 | CB | GLU | A | 242 | 28.204 | 13.474 | 33.641 | 1.00 | 32.89 A |
| ATOM | 1473 | CG | GLU | A | 242 | 28.698 | 14.392 | 32.513 | 1.00 | 38.22 A |
| ATOM | 1474 | CD | GLU | A | 242 | 28.867 | 15.858 | 32.950 | 1.00 | 41.38 A |
| ATOM | 1475 | OE1 | GLU | A | 242 | 28.881 | 16.112 | 34.185 | 1.00 | 40.63 A |
| ATOM | 1476 | OE2 | GLU | A | 242 | 28.981 | 16.739 | 32.047 | 1.00 | 40.29 A |
| ATOM | 1477 | C | GLU | A | 242 | 27.675 | 11.063 | 34.094 | 1.00 | 25.98 A |
| ATOM | 1478 | O | GLU | A | 242 | 28.465 | 10.157 | 33.909 | 1.00 | 28.02 A |
| ATOM | 1479 | N | ALA | A | 243 | 26.887 | 11.132 | 35.154 | 1.00 | 25.29 A |
| ATOM | 1480 | CA | ALA | A | 243 | 26.903 | 10.090 | 36.177 | 1.00 | 28.40 A |
| ATOM | 1481 | CB | ALA | A | 243 | 25.934 | 10.452 | 37.299 | 1.00 | 26.78 A |
| ATOM | 1482 | C | ALA | A | 243 | 26.545 | 8.705 | 35.590 | 1.00 | 30.26 A |
| ATOM | 1483 | O | ALA | A | 243 | 27.161 | 7.694 | 35.947 | 1.00 | 28.44 A |
| ATOM | 1484 | N | GLY | A | 244 | 25.575 | 8.675 | 34.666 | 1.00 | 29.10 A |
| ATOM | 1485 | CA | GLY | A | 244 | 25.161 | 7.419 | 34.071 | 1.00 | 27.11 A |
| ATOM | 1486 | C | GLY | A | 244 | 26.246 | 6.817 | 33.224 | 1.00 | 28.29 A |

TABLE 2-continued

| ATOM | 1487 | O   | GLY | A | 244 | 26.398 | 5.604  | 33.171 | 1.00 | 26.53 | A |
|------|------|-----|-----|---|-----|--------|--------|--------|------|-------|---|
| ATOM | 1488 | N   | GLU | A | 245 | 27.004 | 7.664  | 32.537 | 1.00 | 31.02 | A |
| ATOM | 1489 | CA  | GLU | A | 245 | 28.101 | 7.193  | 31.703 | 1.00 | 31.96 | A |
| ATOM | 1490 | CB  | GLU | A | 245 | 28.614 | 8.325  | 30.808 | 1.00 | 34.93 | A |
| ATOM | 1491 | CG  | GLU | A | 245 | 29.815 | 7.953  | 29.956 | 1.00 | 40.76 | A |
| ATOM | 1492 | CD  | GLU | A | 245 | 29.499 | 6.907  | 28.872 | 1.00 | 48.97 | A |
| ATOM | 1493 | OE1 | GLU | A | 245 | 30.455 | 6.236  | 28.398 | 1.00 | 48.75 | A |
| ATOM | 1494 | OE2 | GLU | A | 245 | 28.303 | 6.763  | 28.476 | 1.00 | 52.76 | A |
| ATOM | 1495 | C   | GLU | A | 245 | 29.256 | 6.666  | 32.590 | 1.00 | 32.44 | A |
| ATOM | 1496 | O   | GLU | A | 245 | 29.790 | 5.581  | 32.337 | 1.00 | 31.01 | A |
| ATOM | 1497 | N   | LEU | A | 246 | 29.649 | 7.444  | 33.604 | 1.00 | 30.38 | A |
| ATOM | 1498 | CA  | LEU | A | 246 | 30.725 | 7.041  | 34.520 | 1.00 | 28.75 | A |
| ATOM | 1499 | CB  | LEU | A | 246 | 30.869 | 8.053  | 35.666 | 1.00 | 26.18 | A |
| ATOM | 1500 | CG  | LEU | A | 246 | 31.392 | 9.406  | 35.184 | 1.00 | 27.88 | A |
| ATOM | 1501 | CD1 | LEU | A | 246 | 31.292 | 10.416 | 36.293 | 1.00 | 30.27 | A |
| ATOM | 1502 | CD2 | LEU | A | 246 | 32.817 | 9.263  | 34.676 | 1.00 | 28.65 | A |
| ATOM | 1503 | C   | LEU | A | 246 | 30.367 | 5.686  | 35.106 | 1.00 | 28.55 | A |
| ATOM | 1504 | O   | LEU | A | 246 | 31.174 | 4.765  | 35.116 | 1.00 | 29.12 | A |
| ATOM | 1505 | N   | LEU | A | 247 | 29.129 | 5.569  | 35.573 | 1.00 | 27.99 | A |
| ATOM | 1506 | CA  | LEU | A | 247 | 28.639 | 4.331  | 36.167 | 1.00 | 28.99 | A |
| ATOM | 1507 | CB  | LEU | A | 247 | 27.209 | 4.556  | 36.628 | 1.00 | 29.61 | A |
| ATOM | 1508 | CG  | LEU | A | 247 | 26.536 | 3.556  | 37.555 | 1.00 | 33.22 | A |
| ATOM | 1509 | CD1 | LEU | A | 247 | 27.526 | 2.747  | 38.348 | 1.00 | 36.07 | A |
| ATOM | 1510 | CD2 | LEU | A | 247 | 25.669 | 4.361  | 38.494 | 1.00 | 35.86 | A |
| ATOM | 1511 | C   | LEU | A | 247 | 28.723 | 3.112  | 35.246 | 1.00 | 29.37 | A |
| ATOM | 1512 | O   | LEU | A | 247 | 29.209 | 2.047  | 35.638 | 1.00 | 28.84 | A |
| ATOM | 1513 | N   | ARG | A | 248 | 28.285 | 3.269  | 34.007 | 1.00 | 27.06 | A |
| ATOM | 1514 | CA  | ARG | A | 248 | 28.292 | 2.163  | 33.054 | 1.00 | 27.52 | A |
| ATOM | 1515 | CB  | ARG | A | 248 | 27.517 | 2.585  | 31.784 | 1.00 | 24.82 | A |
| ATOM | 1516 | CG  | ARG | A | 248 | 27.552 | 1.625  | 30.629 | 1.00 | 27.12 | A |
| ATOM | 1517 | CD  | ARG | A | 248 | 27.019 | 2.387  | 29.406 | 1.00 | 30.53 | A |
| ATOM | 1518 | NE  | ARG | A | 248 | 26.991 | 1.618  | 28.180 | 1.00 | 33.84 | A |
| ATOM | 1519 | CZ  | ARG | A | 248 | 26.565 | 2.111  | 27.018 | 1.00 | 36.44 | A |
| ATOM | 1520 | NH1 | ARG | A | 248 | 26.138 | 3.361  | 26.948 | 1.00 | 34.64 | A |
| ATOM | 1521 | NH2 | ARG | A | 248 | 26.582 | 1.360  | 25.924 | 1.00 | 36.47 | A |
| ATOM | 1522 | C   | ARG | A | 248 | 29.704 | 1.730  | 32.681 | 1.00 | 28.74 | A |
| ATOM | 1523 | O   | ARG | A | 248 | 30.001 | 0.522  | 32.519 | 1.00 | 27.51 | A |
| ATOM | 1524 | N   | THR | A | 249 | 30.575 | 2.717  | 32.503 | 1.00 | 31.55 | A |
| ATOM | 1525 | CA  | THR | A | 249 | 31.962 | 2.442  | 32.138 | 1.00 | 33.51 | A |
| ATOM | 1526 | CB  | THR | A | 249 | 32.719 | 3.758  | 31.841 | 1.00 | 34.55 | A |
| ATOM | 1527 | OG1 | THR | A | 249 | 32.178 | 4.334  | 30.640 | 1.00 | 33.35 | A |
| ATOM | 1528 | CG2 | THR | A | 249 | 34.225 | 3.506  | 31.630 | 1.00 | 33.62 | A |
| ATOM | 1529 | C   | THR | A | 249 | 32.641 | 1.653  | 33.249 | 1.00 | 34.73 | A |
| ATOM | 1530 | O   | THR | A | 249 | 33.190 | 0.564  | 33.003 | 1.00 | 35.33 | A |
| ATOM | 1531 | N   | GLU | A | 250 | 32.553 | 2.176  | 34.469 | 1.00 | 36.28 | A |
| ATOM | 1532 | CA  | GLU | A | 250 | 33.153 | 1.517  | 35.623 | 1.00 | 38.71 | A |
| ATOM | 1533 | CB  | GLU | A | 250 | 33.012 | 2.379  | 36.892 | 1.00 | 40.35 | A |
| ATOM | 1534 | CG  | GLU | A | 250 | 33.515 | 1.736  | 38.224 | 1.00 | 42.45 | A |
| ATOM | 1535 | CD  | GLU | A | 250 | 34.964 | 1.220  | 38.169 | 1.00 | 45.04 | A |
| ATOM | 1536 | OE1 | GLU | A | 250 | 35.751 | 1.691  | 37.311 | 1.00 | 42.97 | A |
| ATOM | 1537 | OE2 | GLU | A | 250 | 35.319 | 0.342  | 39.002 | 1.00 | 45.05 | A |
| ATOM | 1538 | C   | GLU | A | 250 | 32.567 | 0.126  | 35.846 | 1.00 | 38.53 | A |
| ATOM | 1539 | O   | GLU | A | 250 | 33.335 | −0.837 | 35.922 | 1.00 | 38.97 | A |
| ATOM | 1540 | N   | ILE | A | 251 | 31.238 | −0.015 | 35.909 | 1.00 | 38.19 | A |
| ATOM | 1541 | CA  | ILE | A | 251 | 30.692 | −1.357 | 36.146 | 1.00 | 37.75 | A |
| ATOM | 1542 | CB  | ILE | A | 251 | 29.155 | −1.406 | 36.306 | 1.00 | 40.00 | A |
| ATOM | 1543 | CG2 | ILE | A | 251 | 28.755 | −2.677 | 37.078 | 1.00 | 41.73 | A |
| ATOM | 1544 | CG1 | ILE | A | 251 | 28.681 | −0.293 | 37.215 | 1.00 | 41.27 | A |
| ATOM | 1545 | CD1 | ILE | A | 251 | 27.162 | −0.244 | 37.373 | 1.00 | 42.50 | A |
| ATOM | 1546 | C   | ILE | A | 251 | 31.080 | −2.346 | 35.064 | 1.00 | 35.33 | A |
| ATOM | 1547 | O   | ILE | A | 251 | 31.315 | −3.498 | 35.370 | 1.00 | 34.74 | A |
| ATOM | 1548 | N   | ASN | A | 252 | 31.169 | −1.935 | 33.806 | 1.00 | 33.30 | A |
| ATOM | 1549 | CA  | ASN | A | 252 | 31.558 | −2.917 | 32.795 | 1.00 | 34.49 | A |
| ATOM | 1550 | CB  | ASN | A | 252 | 31.237 | −2.440 | 31.379 | 1.00 | 30.83 | A |
| ATOM | 1551 | CG  | ASN | A | 252 | 29.779 | −2.642 | 31.016 | 1.00 | 30.63 | A |
| ATOM | 1552 | OD1 | ASN | A | 252 | 29.211 | −3.714 | 31.243 | 1.00 | 27.33 | A |
| ATOM | 1553 | ND2 | ASN | A | 252 | 29.167 | −1.613 | 30.425 | 1.00 | 30.85 | A |
| ATOM | 1554 | C   | ASN | A | 252 | 33.034 | −3.261 | 32.864 | 1.00 | 37.28 | A |
| ATOM | 1555 | O   | ASN | A | 252 | 33.488 | −4.238 | 32.248 | 1.00 | 37.49 | A |
| ATOM | 1556 | N   | ARG | A | 253 | 33.796 | −2.448 | 33.599 | 1.00 | 41.22 | A |
| ATOM | 1557 | CA  | ARG | A | 253 | 35.230 | −2.700 | 33.727 | 1.00 | 44.52 | A |
| ATOM | 1558 | CB  | ARG | A | 253 | 35.998 | −1.381 | 33.940 | 1.00 | 45.36 | A |
| ATOM | 1559 | CG  | ARG | A | 253 | 37.516 | −1.512 | 33.955 | 1.00 | 49.66 | A |
| ATOM | 1560 | CD  | ARG | A | 253 | 38.162 | −0.256 | 34.552 | 1.00 | 52.71 | A |
| ATOM | 1561 | NE  | ARG | A | 253 | 37.788 | −0.080 | 35.966 | 1.00 | 57.16 | A |
| ATOM | 1562 | CZ  | ARG | A | 253 | 38.430 | −0.629 | 37.007 | 1.00 | 58.29 | A |
| ATOM | 1563 | NH1 | ARG | A | 253 | 39.499 | −1.391 | 36.810 | 1.00 | 57.42 | A |
| ATOM | 1564 | NH2 | ARG | A | 253 | 37.988 | −0.431 | 38.252 | 1.00 | 58.60 | A |
| ATOM | 1565 | C   | ARG | A | 253 | 35.499 | −3.642 | 34.886 | 1.00 | 44.01 | A |

TABLE 2-continued

| | | | | | | | | | | |
|---|---|---|---|---|---|---|---|---|---|---|
| ATOM | 1566 | O | ARG | A | 253 | 36.352 | −4.504 | 34.791 | 1.00 | 44.73 A |
| ATOM | 1567 | N | SER | A | 254 | 34.723 | −3.500 | 35.954 | 1.00 | 43.93 A |
| ATOM | 1568 | CA | SER | A | 254 | 34.931 | −4.272 | 37.153 | 1.00 | 44.32 A |
| ATOM | 1569 | CB | SER | A | 254 | 34.937 | −3.322 | 38.329 | 1.00 | 47.35 A |
| ATOM | 1570 | OG | SER | A | 254 | 33.613 | −2.888 | 38.566 | 1.00 | 51.38 A |
| ATOM | 1571 | C | SER | A | 254 | 33.959 | −5.393 | 37.470 | 1.00 | 44.95 A |
| ATOM | 1572 | O | SER | A | 254 | 34.218 | −6.181 | 38.385 | 1.00 | 44.40 A |
| ATOM | 1573 | N | VAL | A | 255 | 32.844 | −5.468 | 36.741 | 1.00 | 42.74 A |
| ATOM | 1574 | CA | VAL | A | 255 | 31.836 | −6.493 | 36.986 | 1.00 | 40.36 A |
| ATOM | 1575 | CB | VAL | A | 255 | 30.548 | −5.896 | 37.561 | 1.00 | 41.60 A |
| ATOM | 1576 | CG1 | VAL | A | 255 | 29.531 | −7.011 | 37.869 | 1.00 | 40.22 A |
| ATOM | 1577 | CG2 | VAL | A | 255 | 30.856 | −5.062 | 38.795 | 1.00 | 40.74 A |
| ATOM | 1578 | C | VAL | A | 255 | 31.462 | −7.102 | 35.669 | 1.00 | 41.39 A |
| ATOM | 1579 | O | VAL | A | 255 | 30.865 | −6.431 | 34.840 | 1.00 | 41.40 A |
| ATOM | 1580 | N | LYS | A | 256 | 31.790 | −8.365 | 35.454 | 1.00 | 40.55 A |
| ATOM | 1581 | CA | LYS | A | 256 | 31.424 | −8.972 | 34.193 | 1.00 | 40.79 A |
| ATOM | 1582 | CB | LYS | A | 256 | 32.497 | −9.969 | 33.753 | 1.00 | 43.85 A |
| ATOM | 1583 | CG | LYS | A | 256 | 33.870 | −9.316 | 33.465 | 1.00 | 46.96 A |
| ATOM | 1584 | CD | LYS | A | 256 | 33.817 | −8.333 | 32.274 | 1.00 | 47.53 A |
| ATOM | 1585 | CE | LYS | A | 256 | 35.181 | −7.706 | 32.025 | 1.00 | 48.53 A |
| ATOM | 1586 | NZ | LYS | A | 256 | 35.655 | −7.013 | 33.257 | 1.00 | 50.53 A |
| ATOM | 1587 | C | LYS | A | 256 | 30.059 | −9.631 | 34.390 | 1.00 | 39.84 A |
| ATOM | 1588 | O | LYS | A | 256 | 29.827 | −10.326 | 35.393 | 1.00 | 42.78 A |
| ATOM | 1589 | N | VAL | A | 257 | 29.138 | −9.367 | 33.471 | 1.00 | 33.08 A |
| ATOM | 1590 | CA | VAL | A | 257 | 27.817 | −9.922 | 33.593 | 1.00 | 28.16 A |
| ATOM | 1591 | CB | VAL | A | 257 | 26.742 | −8.810 | 33.564 | 1.00 | 30.56 A |
| ATOM | 1592 | CG1 | VAL | A | 257 | 27.038 | −7.774 | 34.661 | 1.00 | 28.05 A |
| ATOM | 1593 | CG2 | VAL | A | 257 | 26.701 | −8.136 | 32.174 | 1.00 | 26.92 A |
| ATOM | 1594 | C | VAL | A | 257 | 27.628 | −10.859 | 32.426 | 1.00 | 26.46 A |
| ATOM | 1595 | O | VAL | A | 257 | 28.268 | −10.707 | 31.400 | 1.00 | 25.87 A |
| ATOM | 1596 | N | GLN | A | 258 | 26.777 | −11.855 | 32.588 | 1.00 | 24.28 A |
| ATOM | 1597 | CA | GLN | A | 258 | 26.544 | −12.805 | 31.500 | 1.00 | 25.71 A |
| ATOM | 1598 | CB | GLN | A | 258 | 27.554 | −13.957 | 31.520 | 1.00 | 23.07 A |
| ATOM | 1599 | CG | GLN | A | 258 | 27.280 | −15.009 | 30.432 | 1.00 | 24.95 A |
| ATOM | 1600 | CD | GLN | A | 258 | 27.426 | −14.467 | 29.009 | 1.00 | 23.63 A |
| ATOM | 1601 | OE1 | GLN | A | 258 | 26.467 | −14.430 | 28.221 | 1.00 | 26.35 A |
| ATOM | 1602 | NE2 | GLN | A | 258 | 28.626 | −14.073 | 28.671 | 1.00 | 24.37 A |
| ATOM | 1603 | C | GLN | A | 258 | 25.146 | −13.364 | 31.589 | 1.00 | 24.53 A |
| ATOM | 1604 | O | GLN | A | 258 | 24.791 | −14.030 | 32.564 | 1.00 | 29.09 A |
| ATOM | 1605 | N | HIS | A | 259 | 24.343 | −13.053 | 30.585 | 1.00 | 22.69 A |
| ATOM | 1606 | CA | HIS | A | 259 | 22.979 | −13.524 | 30.533 | 1.00 | 22.57 A |
| ATOM | 1607 | CB | HIS | A | 259 | 22.296 | −13.070 | 29.243 | 1.00 | 19.75 A |
| ATOM | 1608 | CG | HIS | A | 259 | 20.818 | −13.316 | 29.235 | 1.00 | 20.16 A |
| ATOM | 1609 | CD2 | HIS | A | 259 | 19.769 | −12.452 | 29.227 | 1.00 | 17.37 A |
| ATOM | 1610 | ND1 | HIS | A | 259 | 20.272 | −14.584 | 29.179 | 1.00 | 19.89 A |
| ATOM | 1611 | CE1 | HIS | A | 259 | 18.954 | −14.493 | 29.124 | 1.00 | 17.62 A |
| ATOM | 1612 | NE2 | HIS | A | 259 | 18.621 | −13.212 | 29.156 | 1.00 | 20.17 A |
| ATOM | 1613 | C | HIS | A | 259 | 23.143 | −15.025 | 30.488 | 1.00 | 21.89 A |
| ATOM | 1614 | O | HIS | A | 259 | 23.808 | −15.532 | 29.588 | 1.00 | 21.64 A |
| ATOM | 1615 | N | PRO | A | 260 | 22.513 | −15.752 | 31.424 | 1.00 | 23.23 A |
| ATOM | 1616 | CD | PRO | A | 260 | 21.576 | −15.292 | 32.466 | 1.00 | 22.30 A |
| ATOM | 1617 | CA | PRO | A | 260 | 22.647 | −17.213 | 31.432 | 1.00 | 25.20 A |
| ATOM | 1618 | CB | PRO | A | 260 | 22.000 | −17.614 | 32.762 | 1.00 | 25.03 A |
| ATOM | 1619 | CG | PRO | A | 260 | 20.915 | −16.570 | 32.930 | 1.00 | 26.38 A |
| ATOM | 1620 | C | PRO | A | 260 | 22.043 | −17.957 | 30.225 | 1.00 | 27.63 A |
| ATOM | 1621 | O | PRO | A | 260 | 22.445 | −19.080 | 29.966 | 1.00 | 27.93 A |
| ATOM | 1622 | N | GLN | A | 261 | 21.102 | −17.378 | 29.472 | 1.00 | 27.97 A |
| ATOM | 1623 | CA | GLN | A | 261 | 20.570 | −18.137 | 28.316 | 1.00 | 29.82 A |
| ATOM | 1624 | CB | GLN | A | 261 | 19.033 | −18.240 | 28.364 | 1.00 | 31.75 A |
| ATOM | 1625 | CG | GLN | A | 261 | 18.476 | −18.970 | 29.589 | 1.00 | 33.93 A |
| ATOM | 1626 | CD | GLN | A | 261 | 18.468 | −18.109 | 30.872 | 1.00 | 40.13 A |
| ATOM | 1627 | OE1 | GLN | A | 261 | 18.531 | −18.629 | 32.008 | 1.00 | 38.65 A |
| ATOM | 1628 | NE2 | GLN | A | 261 | 18.366 | −16.795 | 30.695 | 1.00 | 39.37 A |
| ATOM | 1629 | C | GLN | A | 261 | 20.985 | −17.632 | 26.940 | 1.00 | 30.75 A |
| ATOM | 1630 | O | GLN | A | 261 | 20.812 | −18.343 | 25.939 | 1.00 | 32.79 A |
| ATOM | 1631 | N | LEU | A | 262 | 21.517 | −16.404 | 26.880 | 1.00 | 31.46 A |
| ATOM | 1632 | CA | LEU | A | 262 | 21.965 | −15.784 | 25.621 | 1.00 | 28.88 A |
| ATOM | 1633 | CB | LEU | A | 262 | 21.118 | −14.549 | 25.329 | 1.00 | 29.37 A |
| ATOM | 1634 | CG | LEU | A | 262 | 19.627 | −14.879 | 25.161 | 1.00 | 28.53 A |
| ATOM | 1635 | CD1 | LEU | A | 262 | 18.802 | −13.598 | 25.265 | 1.00 | 28.91 A |
| ATOM | 1636 | CD2 | LEU | A | 262 | 19.406 | −15.562 | 23.819 | 1.00 | 27.64 A |
| ATOM | 1637 | C | LEU | A | 262 | 23.407 | −15.369 | 25.766 | 1.00 | 29.36 A |
| ATOM | 1638 | O | LEU | A | 262 | 23.693 | −14.333 | 26.380 | 1.00 | 33.16 A |
| ATOM | 1639 | N | PRO | A | 263 | 24.347 | −16.133 | 25.175 | 1.00 | 29.27 A |
| ATOM | 1640 | CD | PRO | A | 263 | 24.175 | −17.356 | 24.377 | 1.00 | 28.75 A |
| ATOM | 1641 | CA | PRO | A | 263 | 25.773 | −15.794 | 25.285 | 1.00 | 28.84 A |
| ATOM | 1642 | CB | PRO | A | 263 | 26.467 | −16.905 | 24.487 | 1.00 | 28.05 A |
| ATOM | 1643 | CG | PRO | A | 263 | 25.495 | −18.045 | 24.616 | 1.00 | 30.83 A |
| ATOM | 1644 | C | PRO | A | 263 | 26.185 | −14.410 | 24.808 | 1.00 | 27.41 A |

TABLE 2-continued

| | | | | | | | | | | |
|---|---|---|---|---|---|---|---|---|---|---|
| ATOM | 1645 | O | PRO | A | 263 | 27.055 | −13.771 | 25.425 | 1.00 | 27.57 A |
| ATOM | 1646 | N | HIS | A | 264 | 25.558 | −13.934 | 23.740 | 1.00 | 25.61 A |
| ATOM | 1647 | CA | HIS | A | 264 | 25.921 | −12.616 | 23.194 | 1.00 | 26.98 A |
| ATOM | 1648 | CB | HIS | A | 264 | 25.252 | −12.399 | 21.816 | 1.00 | 28.12 A |
| ATOM | 1649 | CG | HIS | A | 264 | 23.783 | −12.060 | 21.868 | 1.00 | 29.00 A |
| ATOM | 1650 | CD2 | HIS | A | 264 | 23.145 | −10.860 | 21.825 | 1.00 | 27.83 A |
| ATOM | 1651 | ND1 | HIS | A | 264 | 22.788 | −13.018 | 21.924 | 1.00 | 26.68 A |
| ATOM | 1652 | CE1 | HIS | A | 264 | 21.607 | −12.426 | 21.910 | 1.00 | 26.97 A |
| ATOM | 1653 | NE2 | HIS | A | 264 | 21.795 | −11.117 | 21.850 | 1.00 | 27.70 A |
| ATOM | 1654 | C | HIS | A | 264 | 25.622 | −11.420 | 24.110 | 1.00 | 26.42 A |
| ATOM | 1655 | O | HIS | A | 264 | 26.113 | −10.326 | 23.865 | 1.00 | 29.11 A |
| ATOM | 1656 | N | ILE | A | 265 | 24.819 | −11.614 | 25.155 | 1.00 | 23.38 A |
| ATOM | 1657 | CA | ILE | A | 265 | 24.496 | −10.520 | 26.053 | 1.00 | 23.73 A |
| ATOM | 1658 | CB | ILE | A | 265 | 22.998 | −10.500 | 26.396 | 1.00 | 21.86 A |
| ATOM | 1659 | CG2 | ILE | A | 265 | 22.694 | −9.330 | 27.322 | 1.00 | 22.67 A |
| ATOM | 1660 | CG1 | ILE | A | 265 | 22.176 | −10.294 | 25.106 | 1.00 | 23.22 A |
| ATOM | 1661 | CD1 | ILE | A | 265 | 20.626 | −10.297 | 25.309 | 1.00 | 18.57 A |
| ATOM | 1662 | C | ILE | A | 265 | 25.359 | −10.597 | 27.304 | 1.00 | 26.04 A |
| ATOM | 1663 | O | ILE | A | 265 | 25.082 | −11.363 | 28.247 | 1.00 | 25.64 A |
| ATOM | 1664 | N | ASN | A | 266 | 26.390 | −9.755 | 27.309 | 1.00 | 26.84 A |
| ATOM | 1665 | CA | ASN | A | 266 | 27.389 | −9.742 | 28.373 | 1.00 | 28.18 A |
| ATOM | 1666 | CB | ASN | A | 266 | 28.527 | −10.684 | 27.959 | 1.00 | 29.99 A |
| ATOM | 1667 | CG | ASN | A | 266 | 29.026 | −10.392 | 26.554 | 1.00 | 31.62 A |
| ATOM | 1668 | OD1 | ASN | A | 266 | 29.123 | −11.290 | 25.717 | 1.00 | 37.75 A |
| ATOM | 1669 | ND2 | ASN | A | 266 | 29.328 | −9.145 | 26.286 | 1.00 | 29.47 A |
| ATOM | 1670 | C | ASN | A | 266 | 27.994 | −8.390 | 28.769 | 1.00 | 27.92 A |
| ATOM | 1671 | O | ASN | A | 266 | 29.180 | −8.325 | 29.137 | 1.00 | 25.80 A |
| ATOM | 1672 | N | THR | A | 267 | 27.206 | −7.317 | 28.659 | 1.00 | 26.94 A |
| ATOM | 1673 | CA | THR | A | 267 | 27.637 | −5.997 | 29.088 | 1.00 | 25.81 A |
| ATOM | 1674 | CB | THR | A | 267 | 28.156 | −5.103 | 27.938 | 1.00 | 26.99 A |
| ATOM | 1675 | OG1 | THR | A | 267 | 27.180 | −5.045 | 26.894 | 1.00 | 24.87 A |
| ATOM | 1676 | CG2 | THR | A | 267 | 29.452 | −5.650 | 27.386 | 1.00 | 29.83 A |
| ATOM | 1677 | C | THR | A | 267 | 26.433 | −5.311 | 29.670 | 1.00 | 25.85 A |
| ATOM | 1678 | O | THR | A | 267 | 25.296 | −5.709 | 29.401 | 1.00 | 24.26 A |
| ATOM | 1679 | N | VAL | A | 268 | 26.679 | −4.306 | 30.504 | 1.00 | 25.30 A |
| ATOM | 1680 | CA | VAL | A | 268 | 25.598 | −3.528 | 31.059 | 1.00 | 23.45 A |
| ATOM | 1681 | CB | VAL | A | 268 | 25.900 | −3.048 | 32.484 | 1.00 | 24.54 A |
| ATOM | 1682 | CG1 | VAL | A | 268 | 24.754 | −2.188 | 32.973 | 1.00 | 21.26 A |
| ATOM | 1683 | CG2 | VAL | A | 268 | 26.056 | −4.222 | 33.429 | 1.00 | 22.47 A |
| ATOM | 1684 | C | VAL | A | 268 | 25.530 | −2.328 | 30.096 | 1.00 | 25.88 A |
| ATOM | 1685 | O | VAL | A | 268 | 26.508 | −1.572 | 29.948 | 1.00 | 23.19 A |
| ATOM | 1686 | N | ASP | A | 269 | 24.381 | −2.173 | 29.433 | 1.00 | 23.34 A |
| ATOM | 1687 | CA | ASP | A | 269 | 24.184 | −1.123 | 28.421 | 1.00 | 22.13 A |
| ATOM | 1688 | CB | ASP | A | 269 | 23.485 | −1.738 | 27.182 | 1.00 | 24.25 A |
| ATOM | 1689 | CG | ASP | A | 269 | 24.340 | −2.781 | 26.487 | 1.00 | 29.46 A |
| ATOM | 1690 | OD1 | ASP | A | 269 | 25.534 | −2.837 | 26.841 | 1.00 | 32.96 A |
| ATOM | 1691 | OD2 | ASP | A | 269 | 23.848 | −3.542 | 25.598 | 1.00 | 29.89 A |
| ATOM | 1692 | C | ASP | A | 269 | 23.392 | 0.109 | 28.870 | 1.00 | 19.52 A |
| ATOM | 1693 | O | ASP | A | 269 | 23.433 | 1.145 | 28.217 | 1.00 | 19.36 A |
| ATOM | 1694 | N | CYS | A | 270 | 22.665 | 0.011 | 29.967 | 1.00 | 17.24 A |
| ATOM | 1695 | CA | CYS | A | 270 | 21.867 | 1.142 | 30.414 | 1.00 | 17.72 A |
| ATOM | 1696 | CB | CYS | A | 270 | 20.392 | 0.861 | 30.112 | 1.00 | 16.25 A |
| ATOM | 1697 | SG | CYS | A | 270 | 20.107 | 0.226 | 28.435 | 1.00 | 23.39 A |
| ATOM | 1698 | C | CYS | A | 270 | 21.999 | 1.362 | 31.914 | 1.00 | 18.33 A |
| ATOM | 1699 | O | CYS | A | 270 | 22.222 | 0.406 | 32.650 | 1.00 | 17.53 A |
| ATOM | 1700 | N | VAL | A | 271 | 21.797 | 2.605 | 32.355 | 1.00 | 18.64 A |
| ATOM | 1701 | CA | VAL | A | 271 | 21.811 | 2.955 | 33.788 | 1.00 | 17.75 A |
| ATOM | 1702 | CB | VAL | A | 271 | 22.991 | 3.950 | 34.145 | 1.00 | 16.37 A |
| ATOM | 1703 | CG1 | VAL | A | 271 | 22.861 | 4.502 | 35.546 | 1.00 | 14.51 A |
| ATOM | 1704 | CG2 | VAL | A | 271 | 24.284 | 3.250 | 33.981 | 1.00 | 18.13 A |
| ATOM | 1705 | C | VAL | A | 271 | 20.473 | 3.623 | 34.058 | 1.00 | 16.20 A |
| ATOM | 1706 | O | VAL | A | 271 | 20.128 | 4.601 | 33.438 | 1.00 | 21.87 A |
| ATOM | 1707 | N | GLU | A | 272 | 19.724 | 3.091 | 34.998 | 1.00 | 17.20 A |
| ATOM | 1708 | CA | GLU | A | 272 | 18.417 | 3.589 | 35.373 | 1.00 | 14.82 A |
| ATOM | 1709 | CB | GLU | A | 272 | 17.468 | 2.384 | 35.508 | 1.00 | 14.38 A |
| ATOM | 1710 | CG | GLU | A | 272 | 16.096 | 2.705 | 35.949 | 1.00 | 14.85 A |
| ATOM | 1711 | CD | GLU | A | 272 | 15.239 | 1.481 | 36.007 | 1.00 | 18.26 A |
| ATOM | 1712 | OE1 | GLU | A | 272 | 15.439 | 0.581 | 35.161 | 1.00 | 23.67 A |
| ATOM | 1713 | OE2 | GLU | A | 272 | 14.361 | 1.399 | 36.886 | 1.00 | 18.99 A |
| ATOM | 1714 | C | GLU | A | 272 | 18.581 | 4.275 | 36.715 | 1.00 | 20.19 A |
| ATOM | 1715 | O | GLU | A | 272 | 18.952 | 3.621 | 37.717 | 1.00 | 20.75 A |
| ATOM | 1716 | N | ILE | A | 273 | 18.334 | 5.587 | 36.750 | 1.00 | 20.33 A |
| ATOM | 1717 | CA | ILE | A | 273 | 18.446 | 6.365 | 37.978 | 1.00 | 19.63 A |
| ATOM | 1718 | CB | ILE | A | 273 | 19.185 | 7.665 | 37.698 | 1.00 | 20.13 A |
| ATOM | 1719 | CG2 | ILE | A | 273 | 19.135 | 8.571 | 38.944 | 1.00 | 18.48 A |
| ATOM | 1720 | CG1 | ILE | A | 273 | 20.544 | 7.307 | 37.107 | 1.00 | 17.74 A |
| ATOM | 1721 | CD1 | ILE | A | 273 | 21.391 | 8.488 | 36.553 | 1.00 | 17.08 A |
| ATOM | 1722 | C | ILE | A | 273 | 17.036 | 6.659 | 38.443 | 1.00 | 22.46 A |
| ATOM | 1723 | O | ILE | A | 273 | 16.252 | 7.239 | 37.701 | 1.00 | 21.95 A |

TABLE 2-continued

| | | | | | | | | | | |
|---|---|---|---|---|---|---|---|---|---|---|
| ATOM | 1724 | N | TYR | A | 274 | 16.672 | 6.279 | 39.663 | 1.00 | 20.99 A |
| ATOM | 1725 | CA | TYR | A | 274 | 15.296 | 6.528 | 40.032 | 1.00 | 22.00 A |
| ATOM | 1726 | CB | TYR | A | 274 | 14.530 | 5.197 | 40.175 | 1.00 | 21.54 A |
| ATOM | 1727 | CG | TYR | A | 274 | 14.929 | 4.416 | 41.395 | 1.00 | 24.87 A |
| ATOM | 1728 | CD1 | TYR | A | 274 | 14.190 | 4.510 | 42.590 | 1.00 | 26.54 A |
| ATOM | 1729 | CE1 | TYR | A | 274 | 14.583 | 3.802 | 43.737 | 1.00 | 26.46 A |
| ATOM | 1730 | CD2 | TYR | A | 274 | 16.069 | 3.609 | 41.372 | 1.00 | 26.21 A |
| ATOM | 1731 | CE2 | TYR | A | 274 | 16.475 | 2.910 | 42.497 | 1.00 | 29.43 A |
| ATOM | 1732 | CZ | TYR | A | 274 | 15.729 | 3.007 | 43.674 | 1.00 | 29.69 A |
| ATOM | 1733 | OH | TYR | A | 274 | 16.159 | 2.287 | 44.775 | 1.00 | 34.48 A |
| ATOM | 1734 | C | TYR | A | 274 | 15.156 | 7.344 | 41.285 | 1.00 | 23.82 A |
| ATOM | 1735 | O | TYR | A | 274 | 16.104 | 7.506 | 42.076 | 1.00 | 24.77 A |
| ATOM | 1736 | N | GLY | A | 275 | 13.945 | 7.831 | 41.475 | 1.00 | 24.36 A |
| ATOM | 1737 | CA | GLY | A | 275 | 13.666 | 8.655 | 42.619 | 1.00 | 25.88 A |
| ATOM | 1738 | C | GLY | A | 275 | 12.171 | 8.729 | 42.786 | 1.00 | 26.08 A |
| ATOM | 1739 | O | GLY | A | 275 | 11.430 | 8.131 | 42.023 | 1.00 | 25.15 A |
| ATOM | 1740 | N | PRO | A | 276 | 11.700 | 9.481 | 43.780 | 1.00 | 26.94 A |
| ATOM | 1741 | CD | PRO | A | 276 | 12.506 | 10.426 | 44.574 | 1.00 | 27.05 A |
| ATOM | 1742 | CA | PRO | A | 276 | 10.274 | 9.636 | 44.072 | 1.00 | 27.66 A |
| ATOM | 1743 | CB | PRO | A | 276 | 10.264 | 10.579 | 45.286 | 1.00 | 29.39 A |
| ATOM | 1744 | CG | PRO | A | 276 | 11.697 | 10.455 | 45.868 | 1.00 | 29.74 A |
| ATOM | 1745 | C | PRO | A | 276 | 9.508 | 10.226 | 42.885 | 1.00 | 30.26 A |
| ATOM | 1746 | O | PRO | A | 276 | 10.034 | 11.045 | 42.143 | 1.00 | 28.59 A |
| ATOM | 1747 | N | PRO | A | 277 | 8.239 | 9.841 | 42.727 | 1.00 | 31.13 A |
| ATOM | 1748 | CD | PRO | A | 277 | 7.480 | 9.015 | 43.690 | 1.00 | 30.88 A |
| ATOM | 1749 | CA | PRO | A | 277 | 7.376 | 10.308 | 41.641 | 1.00 | 32.26 A |
| ATOM | 1750 | CB | PRO | A | 277 | 6.197 | 9.356 | 41.713 | 1.00 | 31.83 A |
| ATOM | 1751 | CG | PRO | A | 277 | 6.017 | 9.233 | 43.242 | 1.00 | 32.56 A |
| ATOM | 1752 | C | PRO | A | 277 | 6.923 | 11.746 | 41.815 | 1.00 | 35.37 A |
| ATOM | 1753 | O | PRO | A | 277 | 6.830 | 12.249 | 42.939 | 1.00 | 36.26 A |
| ATOM | 1754 | N | THR | A | 278 | 6.664 | 12.409 | 40.695 | 1.00 | 35.39 A |
| ATOM | 1755 | CA | THR | A | 278 | 6.169 | 13.772 | 40.703 | 1.00 | 35.85 A |
| ATOM | 1756 | CB | THR | A | 278 | 6.768 | 14.592 | 39.570 | 1.00 | 37.14 A |
| ATOM | 1757 | OG1 | THR | A | 278 | 8.189 | 14.665 | 39.732 | 1.00 | 40.01 A |
| ATOM | 1758 | CG2 | THR | A | 278 | 6.167 | 15.980 | 39.544 | 1.00 | 36.22 A |
| ATOM | 1759 | C | THR | A | 278 | 4.685 | 13.568 | 40.467 | 1.00 | 35.62 A |
| ATOM | 1760 | O | THR | A | 278 | 3.866 | 14.107 | 41.181 | 1.00 | 35.55 A |
| ATOM | 1761 | N | ASN | A | 279 | 4.338 | 12.738 | 39.486 | 1.00 | 36.85 A |
| ATOM | 1762 | CA | ASN | A | 279 | 2.930 | 12.468 | 39.205 | 1.00 | 37.04 A |
| ATOM | 1763 | CB | ASN | A | 279 | 2.790 | 11.824 | 37.837 | 1.00 | 37.56 A |
| ATOM | 1764 | CG | ASN | A | 279 | 1.367 | 11.607 | 37.442 | 1.00 | 36.56 A |
| ATOM | 1765 | OD1 | ASN | A | 279 | 0.550 | 11.120 | 38.224 | 1.00 | 39.17 A |
| ATOM | 1766 | ND2 | ASN | A | 279 | 1.053 | 11.956 | 36.210 | 1.00 | 35.92 A |
| ATOM | 1767 | C | ASN | A | 279 | 2.306 | 11.549 | 40.259 | 1.00 | 40.11 A |
| ATOM | 1768 | O | ASN | A | 279 | 2.794 | 10.442 | 40.515 | 1.00 | 39.15 A |
| ATOM | 1769 | N | ALA | A | 280 | 1.209 | 12.023 | 40.850 | 1.00 | 43.01 A |
| ATOM | 1770 | CA | ALA | A | 280 | 0.438 | 11.306 | 41.867 | 1.00 | 42.19 A |
| ATOM | 1771 | CB | ALA | A | 280 | −0.907 | 12.034 | 42.046 | 1.00 | 41.76 A |
| ATOM | 1772 | C | ALA | A | 280 | 0.172 | 9.810 | 41.561 | 1.00 | 41.12 A |
| ATOM | 1773 | O | ALA | A | 280 | 0.237 | 8.954 | 42.453 | 1.00 | 41.34 A |
| ATOM | 1774 | N | ALA | A | 281 | −0.133 | 9.509 | 40.298 | 1.00 | 38.84 A |
| ATOM | 1775 | CA | ALA | A | 281 | −0.456 | 8.153 | 39.855 | 1.00 | 34.05 A |
| ATOM | 1776 | CB | ALA | A | 281 | −1.221 | 8.231 | 38.531 | 1.00 | 36.24 A |
| ATOM | 1777 | C | ALA | A | 281 | 0.715 | 7.180 | 39.714 | 1.00 | 32.61 A |
| ATOM | 1778 | O | ALA | A | 281 | 0.502 | 5.978 | 39.588 | 1.00 | 34.54 A |
| ATOM | 1779 | N | ALA | A | 282 | 1.938 | 7.689 | 39.738 | 1.00 | 30.16 A |
| ATOM | 1780 | CA | ALA | A | 282 | 3.145 | 6.872 | 39.594 | 1.00 | 28.98 A |
| ATOM | 1781 | CB | ALA | A | 282 | 4.161 | 7.612 | 38.771 | 1.00 | 24.92 A |
| ATOM | 1782 | C | ALA | A | 282 | 3.809 | 6.441 | 40.913 | 1.00 | 30.47 A |
| ATOM | 1783 | O | ALA | A | 282 | 3.811 | 7.164 | 41.908 | 1.00 | 28.03 A |
| ATOM | 1784 | N | ASN | A | 283 | 4.429 | 5.268 | 40.870 | 1.00 | 28.97 A |
| ATOM | 1785 | CA | ASN | A | 283 | 5.105 | 4.709 | 42.014 | 1.00 | 27.62 A |
| ATOM | 1786 | CB | ASN | A | 283 | 5.194 | 3.194 | 41.826 | 1.00 | 26.90 A |
| ATOM | 1787 | CG | ASN | A | 283 | 3.842 | 2.548 | 41.886 | 1.00 | 29.65 A |
| ATOM | 1788 | OD1 | ASN | A | 283 | 3.273 | 2.393 | 42.982 | 1.00 | 32.86 A |
| ATOM | 1789 | ND2 | ASN | A | 283 | 3.278 | 2.203 | 40.724 | 1.00 | 22.77 A |
| ATOM | 1790 | C | ASN | A | 283 | 6.478 | 5.338 | 42.197 | 1.00 | 28.79 A |
| ATOM | 1791 | O | ASN | A | 283 | 6.897 | 5.609 | 43.325 | 1.00 | 29.55 A |
| ATOM | 1792 | N | TYR | A | 284 | 7.159 | 5.606 | 41.085 | 1.00 | 27.44 A |
| ATOM | 1793 | CA | TYR | A | 284 | 8.500 | 6.196 | 41.084 | 1.00 | 25.24 A |
| ATOM | 1794 | CB | TYR | A | 284 | 9.566 | 5.107 | 41.128 | 1.00 | 27.49 A |
| ATOM | 1795 | CG | TYR | A | 284 | 9.621 | 4.316 | 42.400 | 1.00 | 31.90 A |
| ATOM | 1796 | CD1 | TYR | A | 284 | 10.224 | 4.853 | 43.547 | 1.00 | 33.90 A |
| ATOM | 1797 | CE1 | TYR | A | 284 | 10.237 | 4.156 | 44.742 | 1.00 | 36.62 A |
| ATOM | 1798 | CD2 | TYR | A | 284 | 9.035 | 3.056 | 42.481 | 1.00 | 31.89 A |
| ATOM | 1799 | CE2 | TYR | A | 284 | 9.037 | 2.340 | 43.670 | 1.00 | 36.37 A |
| ATOM | 1800 | CZ | TYR | A | 284 | 9.642 | 2.899 | 44.806 | 1.00 | 39.52 A |
| ATOM | 1801 | OH | TYR | A | 284 | 9.641 | 2.218 | 46.008 | 1.00 | 40.61 A |
| ATOM | 1802 | C | TYR | A | 284 | 8.717 | 6.951 | 39.789 | 1.00 | 24.14 A |

TABLE 2-continued

| | | | | | | | | | | |
|---|---|---|---|---|---|---|---|---|---|---|
| ATOM | 1803 | O | TYR | A | 284 | 7.943 | 6.821 | 38.835 | 1.00 | 21.53 A |
| ATOM | 1804 | N | LYS | A | 285 | 9.818 | 7.690 | 39.736 | 1.00 | 23.69 A |
| ATOM | 1805 | CA | LYS | A | 285 | 10.191 | 8.422 | 38.530 | 1.00 | 23.08 A |
| ATOM | 1806 | CB | LYS | A | 285 | 10.246 | 9.916 | 38.815 | 1.00 | 26.03 A |
| ATOM | 1807 | CG | LYS | A | 285 | 10.760 | 10.738 | 37.667 | 1.00 | 31.12 A |
| ATOM | 1808 | CD | LYS | A | 285 | 11.190 | 12.168 | 38.080 | 1.00 | 31.68 A |
| ATOM | 1809 | CE | LYS | A | 285 | 10.052 | 13.061 | 38.489 | 1.00 | 33.32 A |
| ATOM | 1810 | NZ | LYS | A | 285 | 10.425 | 14.504 | 38.222 | 1.00 | 30.04 A |
| ATOM | 1811 | C | LYS | A | 285 | 11.578 | 7.937 | 38.151 | 1.00 | 22.32 A |
| ATOM | 1812 | O | LYS | A | 285 | 12.337 | 7.486 | 39.020 | 1.00 | 22.03 A |
| ATOM | 1813 | N | ASN | A | 286 | 11.925 | 7.975 | 36.870 | 1.00 | 17.42 A |
| ATOM | 1814 | CA | ASN | A | 286 | 13.275 | 7.598 | 36.530 | 1.00 | 16.88 A |
| ATOM | 1815 | CB | ASN | A | 286 | 13.399 | 6.079 | 36.404 | 1.00 | 19.06 A |
| ATOM | 1816 | CG | ASN | A | 286 | 12.946 | 5.571 | 35.029 | 1.00 | 18.80 A |
| ATOM | 1817 | OD1 | ASN | A | 286 | 11.760 | 5.440 | 34.756 | 1.00 | 19.90 A |
| ATOM | 1818 | ND2 | ASN | A | 286 | 13.884 | 5.322 | 34.182 | 1.00 | 14.52 A |
| ATOM | 1819 | C | ASN | A | 286 | 13.768 | 8.201 | 35.250 | 1.00 | 17.89 A |
| ATOM | 1820 | O | ASN | A | 286 | 12.996 | 8.712 | 34.448 | 1.00 | 17.84 A |
| ATOM | 1821 | N | VAL | A | 287 | 15.079 | 8.165 | 35.060 | 1.00 | 20.96 A |
| ATOM | 1822 | CA | VAL | A | 287 | 15.629 | 8.583 | 33.788 | 1.00 | 20.28 A |
| ATOM | 1823 | CB | VAL | A | 287 | 16.283 | 9.987 | 33.799 | 1.00 | 21.60 A |
| ATOM | 1824 | CG1 | VAL | A | 287 | 17.447 | 10.041 | 34.799 | 1.00 | 22.48 A |
| ATOM | 1825 | CG2 | VAL | A | 287 | 16.848 | 10.275 | 32.371 | 1.00 | 20.79 A |
| ATOM | 1826 | C | VAL | A | 287 | 16.672 | 7.511 | 33.510 | 1.00 | 19.85 A |
| ATOM | 1827 | O | VAL | A | 287 | 17.397 | 7.084 | 34.406 | 1.00 | 20.21 A |
| ATOM | 1828 | N | VAL | A | 288 | 16.706 | 7.016 | 32.284 | 1.00 | 17.36 A |
| ATOM | 1829 | CA | VAL | A | 288 | 17.680 | 6.007 | 31.901 | 1.00 | 14.40 A |
| ATOM | 1830 | CB | VAL | A | 288 | 16.981 | 4.835 | 31.182 | 1.00 | 15.48 A |
| ATOM | 1831 | CG1 | VAL | A | 288 | 18.009 | 3.953 | 30.479 | 1.00 | 17.37 A |
| ATOM | 1832 | CG2 | VAL | A | 288 | 16.147 | 4.049 | 32.149 | 1.00 | 12.26 A |
| ATOM | 1833 | C | VAL | A | 288 | 18.704 | 6.660 | 30.959 | 1.00 | 18.84 A |
| ATOM | 1834 | O | VAL | A | 288 | 18.327 | 7.341 | 29.988 | 1.00 | 15.71 A |
| ATOM | 1835 | N | ILE | A | 289 | 19.989 | 6.430 | 31.248 | 1.00 | 19.59 A |
| ATOM | 1836 | CA | ILE | A | 289 | 21.105 | 6.942 | 30.469 | 1.00 | 19.86 A |
| ATOM | 1837 | CB | ILE | A | 289 | 22.198 | 7.533 | 31.390 | 1.00 | 22.17 A |
| ATOM | 1838 | CG2 | ILE | A | 289 | 23.273 | 8.209 | 30.563 | 1.00 | 22.19 A |
| ATOM | 1839 | CG1 | ILE | A | 289 | 21.563 | 8.503 | 32.394 | 1.00 | 23.89 A |
| ATOM | 1840 | CD1 | ILE | A | 289 | 20.819 | 9.680 | 31.767 | 1.00 | 25.27 A |
| ATOM | 1841 | C | ILE | A | 289 | 21.696 | 5.775 | 29.692 | 1.00 | 19.13 A |
| ATOM | 1842 | O | ILE | A | 289 | 22.042 | 4.752 | 30.280 | 1.00 | 17.93 A |
| ATOM | 1843 | N | PHE | A | 290 | 21.836 | 5.930 | 28.373 | 1.00 | 18.30 A |
| ATOM | 1844 | CA | PHE | A | 290 | 22.357 | 4.852 | 27.542 | 1.00 | 18.38 A |
| ATOM | 1845 | CB | PHE | A | 290 | 21.197 | 3.883 | 27.213 | 1.00 | 17.27 A |
| ATOM | 1846 | CG | PHE | A | 290 | 20.120 | 4.493 | 26.342 | 1.00 | 16.26 A |
| ATOM | 1847 | CD1 | PHE | A | 290 | 20.093 | 4.231 | 24.965 | 1.00 | 14.12 A |
| ATOM | 1848 | CD2 | PHE | A | 290 | 19.180 | 5.373 | 26.882 | 1.00 | 13.82 A |
| ATOM | 1849 | CE1 | PHE | A | 290 | 19.120 | 4.860 | 24.125 | 1.00 | 15.22 A |
| ATOM | 1850 | CE2 | PHE | A | 290 | 18.213 | 5.998 | 26.065 | 1.00 | 18.66 A |
| ATOM | 1851 | CZ | PHE | A | 290 | 18.196 | 5.726 | 24.665 | 1.00 | 14.09 A |
| ATOM | 1852 | C | PHE | A | 290 | 22.964 | 5.426 | 26.275 | 1.00 | 21.43 A |
| ATOM | 1853 | O | PHE | A | 290 | 23.087 | 6.648 | 26.147 | 1.00 | 23.12 A |
| ATOM | 1854 | N | GLY | A | 291 | 23.377 | 4.568 | 25.347 | 1.00 | 22.25 A |
| ATOM | 1855 | CA | GLY | A | 291 | 23.956 | 5.064 | 24.099 | 1.00 | 23.92 A |
| ATOM | 1856 | C | GLY | A | 291 | 25.146 | 5.987 | 24.330 | 1.00 | 25.52 A |
| ATOM | 1857 | O | GLY | A | 291 | 25.970 | 5.682 | 25.205 | 1.00 | 25.30 A |
| ATOM | 1858 | N | ASN | A | 292 | 25.276 | 7.086 | 23.571 | 1.00 | 21.04 A |
| ATOM | 1859 | CA | ASN | A | 292 | 26.392 | 8.032 | 23.795 | 1.00 | 22.18 A |
| ATOM | 1860 | CB | ASN | A | 292 | 26.808 | 8.647 | 22.457 | 1.00 | 25.00 A |
| ATOM | 1861 | CG | ASN | A | 292 | 27.985 | 9.594 | 22.585 | 1.00 | 30.83 A |
| ATOM | 1862 | OD1 | ASN | A | 292 | 28.708 | 9.551 | 23.559 | 1.00 | 27.52 A |
| ATOM | 1863 | ND2 | ASN | A | 292 | 28.171 | 10.462 | 21.584 | 1.00 | 32.23 A |
| ATOM | 1864 | C | ASN | A | 292 | 25.804 | 9.064 | 24.802 | 1.00 | 23.69 A |
| ATOM | 1865 | O | ASN | A | 292 | 25.537 | 10.238 | 24.489 | 1.00 | 19.53 A |
| ATOM | 1866 | N | ARG | A | 293 | 25.643 | 8.579 | 26.038 | 1.00 | 20.48 A |
| ATOM | 1867 | CA | ARG | A | 293 | 24.988 | 9.281 | 27.130 | 1.00 | 21.42 A |
| ATOM | 1868 | CB | ARG | A | 293 | 25.959 | 10.057 | 28.070 | 1.00 | 22.90 A |
| ATOM | 1869 | CG | ARG | A | 293 | 26.918 | 11.034 | 27.517 | 1.00 | 27.98 A |
| ATOM | 1870 | CD | ARG | A | 293 | 27.667 | 11.715 | 28.695 | 1.00 | 29.22 A |
| ATOM | 1871 | NE | ARG | A | 293 | 28.257 | 12.992 | 28.297 | 1.00 | 30.64 A |
| ATOM | 1872 | CZ | ARG | A | 293 | 29.248 | 13.127 | 27.413 | 1.00 | 27.57 A |
| ATOM | 1873 | NH1 | ARG | A | 293 | 29.785 | 12.074 | 26.828 | 1.00 | 23.78 A |
| ATOM | 1874 | NH2 | ARG | A | 293 | 29.684 | 14.336 | 27.079 | 1.00 | 30.48 A |
| ATOM | 1875 | C | ARG | A | 293 | 23.767 | 10.122 | 26.747 | 1.00 | 21.38 A |
| ATOM | 1876 | O | ARG | A | 293 | 23.639 | 11.296 | 27.091 | 1.00 | 22.12 A |
| ATOM | 1877 | N | GLN | A | 294 | 22.830 | 9.478 | 26.049 | 1.00 | 19.61 A |
| ATOM | 1878 | CA | GLN | A | 294 | 21.574 | 10.141 | 25.734 | 1.00 | 15.56 A |
| ATOM | 1879 | CB | GLN | A | 294 | 21.047 | 9.649 | 24.378 | 1.00 | 16.96 A |
| ATOM | 1880 | CG | GLN | A | 294 | 20.766 | 8.153 | 24.240 | 1.00 | 12.45 A |
| ATOM | 1881 | CD | GLN | A | 294 | 20.403 | 7.794 | 22.806 | 1.00 | 16.44 A |

TABLE 2-continued

| | | | | | | | | | | |
|---|---|---|---|---|---|---|---|---|---|---|
| ATOM | 1882 | OE1 | GLN | A | 294 | 21.250 | 7.319 | 22.022 | 1.00 | 19.24 A |
| ATOM | 1883 | NE2 | GLN | A | 294 | 19.130 | 8.052 | 22.444 | 1.00 | 15.52 A |
| ATOM | 1884 | C | GLN | A | 294 | 20.667 | 9.727 | 26.899 | 1.00 | 16.98 A |
| ATOM | 1885 | O | GLN | A | 294 | 21.023 | 8.831 | 27.666 | 1.00 | 16.47 A |
| ATOM | 1886 | N | ALA | A | 295 | 19.522 | 10.377 | 27.068 | 1.00 | 16.71 A |
| ATOM | 1887 | CA | ALA | A | 295 | 18.610 | 10.055 | 28.150 | 1.00 | 15.79 A |
| ATOM | 1888 | CB | ALA | A | 295 | 18.397 | 11.274 | 29.040 | 1.00 | 14.11 A |
| ATOM | 1889 | C | ALA | A | 295 | 17.292 | 9.703 | 27.503 | 1.00 | 17.48 A |
| ATOM | 1890 | O | ALA | A | 295 | 16.907 | 10.343 | 26.531 | 1.00 | 17.63 A |
| ATOM | 1891 | N | ASP | A | 296 | 16.597 | 8.715 | 28.058 | 1.00 | 16.47 A |
| ATOM | 1892 | CA | ASP | A | 296 | 15.311 | 8.300 | 27.568 | 1.00 | 16.57 A |
| ATOM | 1893 | CB | ASP | A | 296 | 14.976 | 6.921 | 28.137 | 1.00 | 18.10 A |
| ATOM | 1894 | CG | ASP | A | 296 | 13.747 | 6.250 | 27.473 | 1.00 | 22.91 A |
| ATOM | 1895 | OD1 | ASP | A | 296 | 13.014 | 6.920 | 26.684 | 1.00 | 18.88 A |
| ATOM | 1896 | OD2 | ASP | A | 296 | 13.527 | 5.038 | 27.776 | 1.00 | 21.05 A |
| ATOM | 1897 | C | ASP | A | 296 | 14.296 | 9.314 | 28.074 | 1.00 | 18.63 A |
| ATOM | 1898 | O | ASP | A | 296 | 14.295 | 9.634 | 29.256 | 1.00 | 18.09 A |
| ATOM | 1899 | N | ARG | A | 297 | 13.425 | 9.813 | 27.186 | 1.00 | 14.83 A |
| ATOM | 1900 | CA | ARG | A | 297 | 12.357 | 10.733 | 27.579 | 1.00 | 13.48 A |
| ATOM | 1901 | CB | ARG | A | 297 | 11.950 | 11.644 | 26.392 | 1.00 | 15.86 A |
| ATOM | 1902 | CG | ARG | A | 297 | 12.986 | 12.719 | 26.071 | 1.00 | 13.58 A |
| ATOM | 1903 | CD | ARG | A | 297 | 14.068 | 12.262 | 25.140 | 1.00 | 17.33 A |
| ATOM | 1904 | NE | ARG | A | 297 | 14.810 | 13.446 | 24.741 | 1.00 | 15.75 A |
| ATOM | 1905 | CZ | ARG | A | 297 | 15.910 | 13.909 | 25.340 | 1.00 | 20.23 A |
| ATOM | 1906 | NH1 | ARG | A | 297 | 16.468 | 13.261 | 26.389 | 1.00 | 13.67 A |
| ATOM | 1907 | NH2 | ARG | A | 297 | 16.406 | 15.081 | 24.941 | 1.00 | 13.96 A |
| ATOM | 1908 | C | ARG | A | 297 | 11.148 | 9.944 | 28.047 | 1.00 | 12.76 A |
| ATOM | 1909 | O | ARG | A | 297 | 10.257 | 10.502 | 28.686 | 1.00 | 12.35 A |
| ATOM | 1910 | N | SER | A | 298 | 11.071 | 8.652 | 27.690 | 1.00 | 12.87 A |
| ATOM | 1911 | CA | SER | A | 298 | 9.948 | 7.820 | 28.150 | 1.00 | 11.04 A |
| ATOM | 1912 | CB | SER | A | 298 | 9.624 | 6.673 | 27.156 | 1.00 | 11.56 A |
| ATOM | 1913 | OG | SER | A | 298 | 10.543 | 5.567 | 27.271 | 1.00 | 13.30 A |
| ATOM | 1914 | C | SER | A | 298 | 10.415 | 7.173 | 29.445 | 1.00 | 13.44 A |
| ATOM | 1915 | O | SER | A | 298 | 11.602 | 7.272 | 29.804 | 1.00 | 15.33 A |
| ATOM | 1916 | N | PRO | A | 299 | 9.506 | 6.485 | 30.152 | 1.00 | 14.80 A |
| ATOM | 1917 | CD | PRO | A | 299 | 8.049 | 6.508 | 29.913 | 1.00 | 11.75 A |
| ATOM | 1918 | CA | PRO | A | 299 | 9.826 | 5.795 | 31.425 | 1.00 | 15.88 A |
| ATOM | 1919 | CB | PRO | A | 299 | 8.472 | 5.337 | 31.922 | 1.00 | 15.36 A |
| ATOM | 1920 | CG | PRO | A | 299 | 7.511 | 6.373 | 31.306 | 1.00 | 17.10 A |
| ATOM | 1921 | C | PRO | A | 299 | 10.780 | 4.601 | 31.203 | 1.00 | 19.82 A |
| ATOM | 1922 | O | PRO | A | 299 | 11.376 | 4.094 | 32.171 | 1.00 | 19.55 A |
| ATOM | 1923 | N | CYS | A | 300 | 10.965 | 4.203 | 29.935 | 1.00 | 15.95 A |
| ATOM | 1924 | CA | CYS | A | 300 | 11.850 | 3.091 | 29.530 | 1.00 | 16.95 A |
| ATOM | 1925 | CB | CYS | A | 300 | 13.208 | 3.147 | 30.248 | 1.00 | 15.86 A |
| ATOM | 1926 | SG | CYS | A | 300 | 14.450 | 2.046 | 29.512 | 1.00 | 20.02 A |
| ATOM | 1927 | C | CYS | A | 300 | 11.178 | 1.763 | 29.815 | 1.00 | 18.14 A |
| ATOM | 1928 | O | CYS | A | 300 | 10.962 | 1.407 | 30.972 | 1.00 | 19.63 A |
| ATOM | 1929 | N | GLY | A | 301 | 10.850 | 1.031 | 28.754 | 1.00 | 15.84 A |
| ATOM | 1930 | CA | GLY | A | 301 | 10.142 | −0.230 | 28.893 | 1.00 | 14.34 A |
| ATOM | 1931 | C | GLY | A | 301 | 11.011 | −1.358 | 29.428 | 1.00 | 15.88 A |
| ATOM | 1932 | O | GLY | A | 301 | 10.552 | −2.130 | 30.258 | 1.00 | 16.82 A |
| ATOM | 1933 | N | THR | A | 302 | 12.243 | −1.490 | 28.942 | 1.00 | 15.36 A |
| ATOM | 1934 | CA | THR | A | 302 | 13.099 | −2.539 | 29.451 | 1.00 | 15.43 A |
| ATOM | 1935 | CB | THR | A | 302 | 14.307 | −2.839 | 28.488 | 1.00 | 14.86 A |
| ATOM | 1936 | OG1 | THR | A | 302 | 15.120 | −1.677 | 28.299 | 1.00 | 13.76 A |
| ATOM | 1937 | CG2 | THR | A | 302 | 13.793 | −3.288 | 27.066 | 1.00 | 14.81 A |
| ATOM | 1938 | C | THR | A | 302 | 13.546 | −2.140 | 30.887 | 1.00 | 17.35 A |
| ATOM | 1939 | O | THR | A | 302 | 13.701 | −2.996 | 31.746 | 1.00 | 20.05 A |
| ATOM | 1940 | N | GLY | A | 303 | 13.717 | −0.851 | 31.148 | 1.00 | 17.14 A |
| ATOM | 1941 | CA | GLY | A | 303 | 14.105 | −0.408 | 32.479 | 1.00 | 19.74 A |
| ATOM | 1942 | C | GLY | A | 303 | 12.953 | −0.617 | 33.436 | 1.00 | 20.64 A |
| ATOM | 1943 | O | GLY | A | 303 | 13.152 | −0.885 | 34.623 | 1.00 | 20.62 A |
| ATOM | 1944 | N | THR | A | 304 | 11.723 | −0.509 | 32.929 | 1.00 | 17.17 A |
| ATOM | 1945 | CA | THR | A | 304 | 10.582 | −0.715 | 33.759 | 1.00 | 15.86 A |
| ATOM | 1946 | CB | THR | A | 304 | 9.272 | −0.241 | 33.089 | 1.00 | 18.98 A |
| ATOM | 1947 | OG1 | THR | A | 304 | 9.254 | 1.197 | 32.985 | 1.00 | 17.47 A |
| ATOM | 1948 | CG2 | THR | A | 304 | 8.097 | −0.646 | 33.901 | 1.00 | 16.75 A |
| ATOM | 1949 | C | THR | A | 304 | 10.539 | −2.216 | 34.068 | 1.00 | 20.55 A |
| ATOM | 1950 | O | THR | A | 304 | 10.235 | −2.607 | 35.206 | 1.00 | 17.94 A |
| ATOM | 1951 | N | SER | A | 305 | 10.861 | −3.063 | 33.088 | 1.00 | 19.20 A |
| ATOM | 1952 | CA | SER | A | 305 | 10.866 | −4.511 | 33.334 | 1.00 | 21.24 A |
| ATOM | 1953 | CB | SER | A | 305 | 11.150 | −5.325 | 32.059 | 1.00 | 20.30 A |
| ATOM | 1954 | OG | SER | A | 305 | 10.160 | −5.061 | 31.113 | 1.00 | 25.75 A |
| ATOM | 1955 | C | SER | A | 305 | 11.922 | −4.914 | 34.349 | 1.00 | 19.43 A |
| ATOM | 1956 | O | SER | A | 305 | 11.672 | −5.773 | 35.204 | 1.00 | 19.19 A |
| ATOM | 1957 | N | ALA | A | 306 | 13.109 | −4.324 | 34.244 | 1.00 | 17.52 A |
| ATOM | 1958 | CA | ALA | A | 306 | 14.202 | −4.676 | 35.181 | 1.00 | 17.97 A |
| ATOM | 1959 | CB | ALA | A | 306 | 15.531 | −4.017 | 34.751 | 1.00 | 14.00 A |
| ATOM | 1960 | C | ALA | A | 306 | 13.813 | −4.228 | 36.564 | 1.00 | 19.14 A |

TABLE 2-continued

| | | | | | | | | | | |
|---|---|---|---|---|---|---|---|---|---|---|
| ATOM | 1961 | O | ALA | A | 306 | 14.084 | −4.929 | 37.550 | 1.00 | 20.34 A |
| ATOM | 1962 | N | LYS | A | 307 | 13.153 | −3.070 | 36.651 | 1.00 | 19.53 A |
| ATOM | 1963 | CA | LYS | A | 307 | 12.728 | −2.549 | 37.946 | 1.00 | 18.39 A |
| ATOM | 1964 | CB | LYS | A | 307 | 12.181 | −1.125 | 37.827 | 1.00 | 19.79 A |
| ATOM | 1965 | CG | LYS | A | 307 | 11.719 | −0.476 | 39.166 | 1.00 | 20.72 A |
| ATOM | 1966 | CD | LYS | A | 307 | 12.893 | −0.148 | 40.071 | 1.00 | 22.15 A |
| ATOM | 1967 | CE | LYS | A | 307 | 12.404 | 0.574 | 41.320 | 1.00 | 26.69 A |
| ATOM | 1968 | NZ | LYS | A | 307 | 13.566 | 1.007 | 42.204 | 1.00 | 29.70 A |
| ATOM | 1969 | C | LYS | A | 307 | 11.691 | −3.443 | 38.604 | 1.00 | 21.93 A |
| ATOM | 1970 | O | LYS | A | 307 | 11.830 | −3.746 | 39.802 | 1.00 | 20.75 A |
| ATOM | 1971 | N | MET | A | 308 | 10.646 | −3.840 | 37.851 | 1.00 | 17.19 A |
| ATOM | 1972 | CA | MET | A | 308 | 9.608 | −4.708 | 38.359 | 1.00 | 18.29 A |
| ATOM | 1973 | CB | MET | A | 308 | 8.438 | −4.910 | 37.357 | 1.00 | 16.54 A |
| ATOM | 1974 | CG | MET | A | 308 | 7.635 | −3.639 | 37.099 | 1.00 | 18.29 A |
| ATOM | 1975 | SD | MET | A | 308 | 6.163 | −4.045 | 36.086 | 1.00 | 23.99 A |
| ATOM | 1976 | CE | MET | A | 308 | 7.003 | −4.399 | 34.684 | 1.00 | 17.81 A |
| ATOM | 1977 | C | MET | A | 308 | 10.179 | −6.080 | 38.707 | 1.00 | 19.02 A |
| ATOM | 1978 | O | MET | A | 308 | 9.690 | −6.711 | 39.631 | 1.00 | 20.04 A |
| ATOM | 1979 | N | ALA | A | 309 | 11.180 | −6.558 | 37.970 | 1.00 | 17.72 A |
| ATOM | 1980 | CA | ALA | A | 309 | 11.757 | −7.855 | 38.302 | 1.00 | 19.75 A |
| ATOM | 1981 | CB | ALA | A | 309 | 12.690 | −8.311 | 37.231 | 1.00 | 14.38 A |
| ATOM | 1982 | C | ALA | A | 309 | 12.539 | −7.723 | 39.634 | 1.00 | 21.52 A |
| ATOM | 1983 | O | ALA | A | 309 | 12.598 | −8.664 | 40.400 | 1.00 | 21.56 A |
| ATOM | 1984 | N | THR | A | 310 | 13.189 | −6.582 | 39.852 | 1.00 | 22.35 A |
| ATOM | 1985 | CA | THR | A | 310 | 13.935 | −6.361 | 41.079 | 1.00 | 22.57 A |
| ATOM | 1986 | CB | THR | A | 310 | 14.810 | −5.107 | 41.002 | 1.00 | 21.10 A |
| ATOM | 1987 | OG1 | THR | A | 310 | 15.688 | −5.259 | 39.900 | 1.00 | 21.25 A |
| ATOM | 1988 | CG2 | THR | A | 310 | 15.683 | −4.934 | 42.280 | 1.00 | 19.81 A |
| ATOM | 1989 | C | THR | A | 310 | 12.942 | −6.220 | 42.222 | 1.00 | 23.00 A |
| ATOM | 1990 | O | THR | A | 310 | 13.130 | −6.815 | 43.278 | 1.00 | 25.35 A |
| ATOM | 1991 | N | LEU | A | 311 | 11.879 | −5.456 | 42.023 | 1.00 | 21.75 A |
| ATOM | 1992 | CA | LEU | A | 311 | 10.886 | −5.306 | 43.071 | 1.00 | 21.63 A |
| ATOM | 1993 | CB | LEU | A | 311 | 9.821 | −4.289 | 42.662 | 1.00 | 21.40 A |
| ATOM | 1994 | CG | LEU | A | 311 | 10.257 | −2.831 | 42.560 | 1.00 | 24.01 A |
| ATOM | 1995 | CD1 | LEU | A | 311 | 9.065 | −2.006 | 42.131 | 1.00 | 21.73 A |
| ATOM | 1996 | CD2 | LEU | A | 311 | 10.761 | −2.319 | 43.901 | 1.00 | 25.88 A |
| ATOM | 1997 | C | LEU | A | 311 | 10.208 | −6.661 | 43.406 | 1.00 | 25.01 A |
| ATOM | 1998 | O | LEU | A | 311 | 9.961 | −6.984 | 44.592 | 1.00 | 23.01 A |
| ATOM | 1999 | N | TYR | A | 312 | 9.876 | −7.428 | 42.366 | 1.00 | 22.08 A |
| ATOM | 2000 | CA | TYR | A | 312 | 9.244 | −8.724 | 42.529 | 1.00 | 22.17 A |
| ATOM | 2001 | CB | TYR | A | 312 | 8.952 | −9.366 | 41.177 | 1.00 | 20.80 A |
| ATOM | 2002 | CG | TYR | A | 312 | 8.099 | −10.600 | 41.303 | 1.00 | 22.27 A |
| ATOM | 2003 | CD1 | TYR | A | 312 | 6.732 | −10.485 | 41.437 | 1.00 | 24.46 A |
| ATOM | 2004 | CE1 | TYR | A | 312 | 5.927 | −11.585 | 41.595 | 1.00 | 26.55 A |
| ATOM | 2005 | CD2 | TYR | A | 312 | 8.661 | −11.879 | 41.325 | 1.00 | 23.25 A |
| ATOM | 2006 | CE2 | TYR | A | 312 | 7.851 | −13.021 | 41.483 | 1.00 | 25.77 A |
| ATOM | 2007 | CZ | TYR | A | 312 | 6.485 | −12.855 | 41.617 | 1.00 | 27.12 A |
| ATOM | 2008 | OH | TYR | A | 312 | 5.617 | −13.926 | 41.776 | 1.00 | 30.79 A |
| ATOM | 2009 | C | TYR | A | 312 | 10.138 | −9.686 | 43.317 | 1.00 | 22.02 A |
| ATOM | 2010 | O | TYR | A | 312 | 9.666 | −10.431 | 44.168 | 1.00 | 21.42 A |
| ATOM | 2011 | N | ALA | A | 313 | 11.420 | −9.691 | 42.998 | 1.00 | 23.34 A |
| ATOM | 2012 | CA | ALA | A | 313 | 12.357 | −10.550 | 43.702 | 1.00 | 24.71 A |
| ATOM | 2013 | CB | ALA | A | 313 | 13.746 | −10.451 | 43.074 | 1.00 | 21.96 A |
| ATOM | 2014 | C | ALA | A | 313 | 12.397 | −10.140 | 45.204 | 1.00 | 26.11 A |
| ATOM | 2015 | O | ALA | A | 313 | 12.567 | −11.006 | 46.069 | 1.00 | 27.03 A |
| ATOM | 2016 | N | LYS | A | 314 | 12.210 | −8.848 | 45.509 | 1.00 | 24.31 A |
| ATOM | 2017 | CA | LYS | A | 314 | 12.248 | −8.372 | 46.911 | 1.00 | 26.72 A |
| ATOM | 2018 | CB | LYS | A | 314 | 12.788 | −6.937 | 47.016 | 1.00 | 23.01 A |
| ATOM | 2019 | CG | LYS | A | 314 | 14.216 | −6.828 | 46.576 | 1.00 | 23.25 A |
| ATOM | 2020 | CD | LYS | A | 314 | 14.797 | −5.404 | 46.643 | 1.00 | 24.01 A |
| ATOM | 2021 | CE | LYS | A | 314 | 16.179 | −5.465 | 45.999 | 1.00 | 25.50 A |
| ATOM | 2022 | NZ | LYS | A | 314 | 16.914 | −4.157 | 45.860 | 1.00 | 33.57 A |
| ATOM | 2023 | C | LYS | A | 314 | 10.913 | −8.447 | 47.619 | 1.00 | 26.12 A |
| ATOM | 2024 | O | LYS | A | 314 | 10.761 | −7.945 | 48.732 | 1.00 | 30.75 A |
| ATOM | 2025 | N | GLY | A | 315 | 9.956 | −9.089 | 46.979 | 1.00 | 25.97 A |
| ATOM | 2026 | CA | GLY | A | 315 | 8.632 | −9.242 | 47.547 | 1.00 | 26.25 A |
| ATOM | 2027 | C | GLY | A | 315 | 7.717 | −8.029 | 47.544 | 1.00 | 29.03 A |
| ATOM | 2028 | O | GLY | A | 315 | 6.694 | −8.053 | 48.230 | 1.00 | 26.41 A |
| ATOM | 2029 | N | GLN | A | 316 | 8.035 | −6.990 | 46.769 | 1.00 | 30.10 A |
| ATOM | 2030 | CA | GLN | A | 316 | 7.219 | −5.777 | 46.799 | 1.00 | 32.61 A |
| ATOM | 2031 | CB | GLN | A | 316 | 8.079 | −4.517 | 46.712 | 1.00 | 34.46 A |
| ATOM | 2032 | CG | GLN | A | 316 | 9.524 | −4.682 | 47.077 | 1.00 | 42.07 A |
| ATOM | 2033 | CD | GLN | A | 316 | 9.813 | −4.340 | 48.520 | 1.00 | 46.90 A |
| ATOM | 2034 | OE1 | GLN | A | 316 | 8.997 | −4.621 | 49.414 | 1.00 | 49.05 A |
| ATOM | 2035 | NE2 | GLN | A | 316 | 10.993 | −3.751 | 48.769 | 1.00 | 45.95 A |
| ATOM | 2036 | C | GLN | A | 316 | 6.190 | −5.666 | 45.712 | 1.00 | 32.22 A |
| ATOM | 2037 | O | GLN | A | 316 | 5.494 | −4.669 | 45.637 | 1.00 | 33.69 A |
| ATOM | 2038 | N | LEU | A | 317 | 6.064 | −6.678 | 44.879 | 1.00 | 30.12 A |
| ATOM | 2039 | CA | LEU | A | 317 | 5.109 | −6.561 | 43.814 | 1.00 | 30.73 A |

TABLE 2-continued

| | | | | | | | | | | |
|---|---|---|---|---|---|---|---|---|---|---|
| ATOM | 2040 | CB | LEU | A | 317 | 5.884 | −6.085 | 42.574 | 1.00 | 31.09 A |
| ATOM | 2041 | CG | LEU | A | 317 | 5.307 | −5.266 | 41.433 | 1.00 | 28.28 A |
| ATOM | 2042 | CD1 | LEU | A | 317 | 4.613 | −4.070 | 41.938 | 1.00 | 23.24 A |
| ATOM | 2043 | CD2 | LEU | A | 317 | 6.452 | −4.875 | 40.470 | 1.00 | 26.85 A |
| ATOM | 2044 | C | LEU | A | 317 | 4.534 | −7.942 | 43.630 | 1.00 | 32.43 A |
| ATOM | 2045 | O | LEU | A | 317 | 5.285 | −8.921 | 43.624 | 1.00 | 31.65 A |
| ATOM | 2046 | N | ARG | A | 318 | 3.216 | −8.064 | 43.510 | 1.00 | 29.97 A |
| ATOM | 2047 | CA | ARG | A | 318 | 2.676 | −9.402 | 43.320 | 1.00 | 31.00 A |
| ATOM | 2048 | CB | ARG | A | 318 | 1.551 | −9.758 | 44.361 | 1.00 | 29.39 A |
| ATOM | 2049 | CG | ARG | A | 318 | 0.364 | −8.833 | 44.438 | 1.00 | 28.90 A |
| ATOM | 2050 | CD | ARG | A | 318 | −0.689 | −9.212 | 45.524 | 1.00 | 22.30 A |
| ATOM | 2051 | NE | ARG | A | 318 | −1.214 | −10.593 | 45.475 | 1.00 | 22.48 A |
| ATOM | 2052 | CZ | ARG | A | 318 | −2.299 | −10.990 | 44.793 | 1.00 | 25.15 A |
| ATOM | 2053 | NH1 | ARG | A | 318 | −2.997 | −10.113 | 44.054 | 1.00 | 19.70 A |
| ATOM | 2054 | NH2 | ARG | A | 318 | −2.746 | −12.250 | 44.922 | 1.00 | 19.22 A |
| ATOM | 2055 | C | ARG | A | 318 | 2.166 | −9.480 | 41.909 | 1.00 | 30.22 A |
| ATOM | 2056 | O | ARG | A | 318 | 1.963 | −8.459 | 41.264 | 1.00 | 33.46 A |
| ATOM | 2057 | N | ILE | A | 319 | 2.001 | −10.693 | 41.422 | 1.00 | 27.73 A |
| ATOM | 2058 | CA | ILE | A | 319 | 1.504 | −10.931 | 40.076 | 1.00 | 27.20 A |
| ATOM | 2059 | CB | ILE | A | 319 | 1.247 | −12.448 | 39.862 | 1.00 | 26.32 A |
| ATOM | 2060 | CG2 | ILE | A | 319 | 0.536 | −12.704 | 38.523 | 1.00 | 28.21 A |
| ATOM | 2061 | CG1 | ILE | A | 319 | 2.560 | −13.238 | 40.010 | 1.00 | 30.23 A |
| ATOM | 2062 | CD1 | ILE | A | 319 | 3.483 | −13.203 | 38.843 | 1.00 | 28.53 A |
| ATOM | 2063 | C | ILE | A | 319 | 0.190 | −10.147 | 39.798 | 1.00 | 26.87 A |
| ATOM | 2064 | O | ILE | A | 319 | −0.769 | −10.199 | 40.568 | 1.00 | 27.43 A |
| ATOM | 2065 | N | GLY | A | 320 | 0.158 | −9.440 | 38.677 | 1.00 | 25.19 A |
| ATOM | 2066 | CA | GLY | A | 320 | −1.036 | −8.719 | 38.284 | 1.00 | 24.49 A |
| ATOM | 2067 | C | GLY | A | 320 | −1.101 | −7.329 | 38.835 | 1.00 | 21.71 A |
| ATOM | 2068 | O | GLY | A | 320 | −1.921 | −6.541 | 38.409 | 1.00 | 22.68 A |
| ATOM | 2069 | N | GLU | A | 321 | −0.237 | −7.024 | 39.787 | 1.00 | 21.52 A |
| ATOM | 2070 | CA | GLU | A | 321 | −0.225 | −5.702 | 40.385 | 1.00 | 21.14 A |
| ATOM | 2071 | CB | GLU | A | 321 | 0.628 | −5.688 | 41.652 | 1.00 | 19.03 A |
| ATOM | 2072 | CG | GLU | A | 321 | 0.470 | −4.405 | 42.476 | 1.00 | 23.27 A |
| ATOM | 2073 | CD | GLU | A | 321 | 1.325 | −4.412 | 43.754 | 1.00 | 27.85 A |
| ATOM | 2074 | OE1 | GLU | A | 321 | 1.555 | −3.317 | 44.347 | 1.00 | 29.39 A |
| ATOM | 2075 | OE2 | GLU | A | 321 | 1.763 | −5.519 | 44.151 | 1.00 | 27.03 A |
| ATOM | 2076 | C | GLU | A | 321 | 0.333 | −4.650 | 39.408 | 1.00 | 20.70 A |
| ATOM | 2077 | O | GLU | A | 321 | 1.438 | −4.785 | 38.875 | 1.00 | 19.53 A |
| ATOM | 2078 | N | THR | A | 322 | −0.411 | −3.582 | 39.206 | 1.00 | 20.24 A |
| ATOM | 2079 | CA | THR | A | 322 | 0.068 | −2.555 | 38.288 | 1.00 | 20.95 A |
| ATOM | 2080 | CB | THR | A | 322 | −1.091 | −1.639 | 37.822 | 1.00 | 19.80 A |
| ATOM | 2081 | OG1 | THR | A | 322 | −2.014 | −2.393 | 37.016 | 1.00 | 21.59 A |
| ATOM | 2082 | CG2 | THR | A | 322 | −0.544 | −0.455 | 37.017 | 1.00 | 21.75 A |
| ATOM | 2083 | C | THR | A | 322 | 1.127 | −1.680 | 38.957 | 1.00 | 20.24 A |
| ATOM | 2084 | O | THR | A | 322 | 0.922 | −1.190 | 40.054 | 1.00 | 22.77 A |
| ATOM | 2085 | N | PHE | A | 323 | 2.238 | −1.478 | 38.266 | 1.00 | 19.40 A |
| ATOM | 2086 | CA | PHE | A | 323 | 3.325 | −0.621 | 38.705 | 1.00 | 20.91 A |
| ATOM | 2087 | CB | PHE | A | 323 | 4.616 | −1.420 | 38.649 | 1.00 | 18.66 A |
| ATOM | 2088 | CG | PHE | A | 323 | 5.832 | −0.624 | 38.915 | 1.00 | 20.61 A |
| ATOM | 2089 | CD1 | PHE | A | 323 | 6.154 | −0.219 | 40.223 | 1.00 | 20.46 A |
| ATOM | 2090 | CD2 | PHE | A | 323 | 6.667 | −0.265 | 37.872 | 1.00 | 20.38 A |
| ATOM | 2091 | CE1 | PHE | A | 323 | 7.282 | 0.522 | 40.466 | 1.00 | 20.48 A |
| ATOM | 2092 | CE2 | PHE | A | 323 | 7.808 | 0.494 | 38.108 | 1.00 | 21.91 A |
| ATOM | 2093 | CZ | PHE | A | 323 | 8.121 | 0.889 | 39.413 | 1.00 | 24.48 A |
| ATOM | 2094 | C | PHE | A | 323 | 3.340 | 0.539 | 37.669 | 1.00 | 21.08 A |
| ATOM | 2095 | O | PHE | A | 323 | 3.239 | 0.300 | 36.460 | 1.00 | 19.64 A |
| ATOM | 2096 | N | VAL | A | 324 | 3.445 | 1.784 | 38.129 | 1.00 | 20.22 A |
| ATOM | 2097 | CA | VAL | A | 324 | 3.432 | 2.927 | 37.211 | 1.00 | 17.99 A |
| ATOM | 2098 | CB | VAL | A | 324 | 2.215 | 3.894 | 37.501 | 1.00 | 19.55 A |
| ATOM | 2099 | CG1 | VAL | A | 324 | 2.198 | 5.053 | 36.505 | 1.00 | 17.30 A |
| ATOM | 2100 | CG2 | VAL | A | 324 | 0.881 | 3.154 | 37.390 | 1.00 | 15.69 A |
| ATOM | 2101 | C | VAL | A | 324 | 4.752 | 3.648 | 37.371 | 1.00 | 20.30 A |
| ATOM | 2102 | O | VAL | A | 324 | 5.146 | 4.066 | 38.485 | 1.00 | 18.30 A |
| ATOM | 2103 | N | TYR | A | 325 | 5.472 | 3.755 | 36.257 | 1.00 | 16.62 A |
| ATOM | 2104 | CA | TYR | A | 325 | 6.764 | 4.419 | 36.229 | 1.00 | 17.19 A |
| ATOM | 2105 | CB | TYR | A | 325 | 7.767 | 3.506 | 35.549 | 1.00 | 16.29 A |
| ATOM | 2106 | CG | TYR | A | 325 | 9.116 | 3.410 | 36.228 | 1.00 | 16.54 A |
| ATOM | 2107 | CD1 | TYR | A | 325 | 9.451 | 4.234 | 37.321 | 1.00 | 15.57 A |
| ATOM | 2108 | CE1 | TYR | A | 325 | 10.690 | 4.093 | 37.985 | 1.00 | 16.89 A |
| ATOM | 2109 | CD2 | TYR | A | 325 | 10.035 | 2.468 | 35.806 | 1.00 | 12.57 A |
| ATOM | 2110 | CE2 | TYR | A | 325 | 11.252 | 2.322 | 36.438 | 1.00 | 16.53 A |
| ATOM | 2111 | CZ | TYR | A | 325 | 11.577 | 3.130 | 37.533 | 1.00 | 18.32 A |
| ATOM | 2112 | OH | TYR | A | 325 | 12.787 | 2.924 | 38.155 | 1.00 | 19.91 A |
| ATOM | 2113 | C | TYR | A | 325 | 6.649 | 5.745 | 35.459 | 1.00 | 19.60 A |
| ATOM | 2114 | O | TYR | A | 325 | 6.014 | 5.809 | 34.382 | 1.00 | 16.48 A |
| ATOM | 2115 | N | GLU | A | 326 | 7.228 | 6.810 | 36.019 | 1.00 | 19.56 A |
| ATOM | 2116 | CA | GLU | A | 326 | 7.167 | 8.133 | 35.398 | 1.00 | 17.58 A |
| ATOM | 2117 | CB | GLU | A | 326 | 6.672 | 9.163 | 36.429 | 1.00 | 20.07 A |
| ATOM | 2118 | CG | GLU | A | 326 | 6.635 | 10.622 | 35.926 | 1.00 | 20.89 A |

TABLE 2-continued

| | | | | | | | | | | |
|---|---|---|---|---|---|---|---|---|---|---|
| ATOM | 2119 | CD | GLU | A | 326 | 6.359 | 11.654 | 37.019 | 1.00 | 25.27 A |
| ATOM | 2120 | OE1 | GLU | A | 326 | 6.249 | 11.306 | 38.223 | 1.00 | 26.59 A |
| ATOM | 2121 | OE2 | GLU | A | 326 | 6.242 | 12.847 | 36.679 | 1.00 | 27.97 A |
| ATOM | 2122 | C | GLU | A | 326 | 8.535 | 8.506 | 34.864 | 1.00 | 18.25 A |
| ATOM | 2123 | O | GLU | A | 326 | 9.536 | 8.080 | 35.407 | 1.00 | 20.12 A |
| ATOM | 2124 | N | SER | A | 327 | 8.596 | 9.274 | 33.773 | 1.00 | 17.84 A |
| ATOM | 2125 | CA | SER | A | 327 | 9.866 | 9.672 | 33.201 | 1.00 | 17.03 A |
| ATOM | 2126 | CB | SER | A | 327 | 9.831 | 9.564 | 31.666 | 1.00 | 20.28 A |
| ATOM | 2127 | OG | SER | A | 327 | 9.168 | 10.713 | 31.160 | 1.00 | 19.41 A |
| ATOM | 2128 | C | SER | A | 327 | 10.174 | 11.139 | 33.563 | 1.00 | 16.98 A |
| ATOM | 2129 | O | SER | A | 327 | 9.347 | 11.844 | 34.126 | 1.00 | 16.81 A |
| ATOM | 2130 | N | ILE | A | 328 | 11.363 | 11.585 | 33.177 | 1.00 | 19.48 A |
| ATOM | 2131 | CA | ILE | A | 328 | 11.796 | 12.937 | 33.446 | 1.00 | 20.83 A |
| ATOM | 2132 | CB | ILE | A | 328 | 13.231 | 13.102 | 32.939 | 1.00 | 22.78 A |
| ATOM | 2133 | CG2 | ILE | A | 328 | 13.255 | 13.263 | 31.422 | 1.00 | 20.86 A |
| ATOM | 2134 | CG1 | ILE | A | 328 | 13.870 | 14.329 | 33.587 | 1.00 | 25.35 A |
| ATOM | 2135 | CD1 | ILE | A | 328 | 15.295 | 14.540 | 33.152 | 1.00 | 25.98 A |
| ATOM | 2136 | C | ILE | A | 328 | 10.846 | 13.939 | 32.790 | 1.00 | 24.54 A |
| ATOM | 2137 | O | ILE | A | 328 | 10.750 | 15.092 | 33.186 | 1.00 | 25.62 A |
| ATOM | 2138 | N | LEU | A | 329 | 10.055 | 13.467 | 31.836 | 1.00 | 25.46 A |
| ATOM | 2139 | CA | LEU | A | 329 | 9.141 | 14.338 | 31.112 | 1.00 | 25.84 A |
| ATOM | 2140 | CB | LEU | A | 329 | 9.212 | 13.933 | 29.637 | 1.00 | 27.88 A |
| ATOM | 2141 | CG | LEU | A | 329 | 8.816 | 14.822 | 28.469 | 1.00 | 32.12 A |
| ATOM | 2142 | CD1 | LEU | A | 329 | 9.372 | 16.220 | 28.618 | 1.00 | 30.41 A |
| ATOM | 2143 | CD2 | LEU | A | 329 | 9.341 | 14.147 | 27.194 | 1.00 | 29.12 A |
| ATOM | 2144 | C | LEU | A | 329 | 7.731 | 14.259 | 31.643 | 1.00 | 26.05 A |
| ATOM | 2145 | O | LEU | A | 329 | 6.857 | 15.027 | 31.237 | 1.00 | 25.53 A |
| ATOM | 2146 | N | GLY | A | 330 | 7.488 | 13.331 | 32.564 | 1.00 | 24.08 A |
| ATOM | 2147 | CA | GLY | A | 330 | 6.144 | 13.208 | 33.110 | 1.00 | 21.73 A |
| ATOM | 2148 | C | GLY | A | 330 | 5.325 | 12.127 | 32.419 | 1.00 | 19.70 A |
| ATOM | 2149 | O | GLY | A | 330 | 4.159 | 11.900 | 32.741 | 1.00 | 23.39 A |
| ATOM | 2150 | N | SER | A | 331 | 5.923 | 11.434 | 31.474 | 1.00 | 20.40 A |
| ATOM | 2151 | CA | SER | A | 331 | 5.186 | 10.363 | 30.778 | 1.00 | 22.86 A |
| ATOM | 2152 | CB | SER | A | 331 | 5.931 | 9.876 | 29.528 | 1.00 | 21.11 A |
| ATOM | 2153 | OG | SER | A | 331 | 6.431 | 10.941 | 28.778 | 1.00 | 26.43 A |
| ATOM | 2154 | C | SER | A | 331 | 5.098 | 9.167 | 31.714 | 1.00 | 20.81 A |
| ATOM | 2155 | O | SER | A | 331 | 5.999 | 8.940 | 32.542 | 1.00 | 21.77 A |
| ATOM | 2156 | N | LEU | A | 332 | 4.048 | 8.383 | 31.530 | 1.00 | 18.60 A |
| ATOM | 2157 | CA | LEU | A | 332 | 3.825 | 7.179 | 32.316 | 1.00 | 18.97 A |
| ATOM | 2158 | CB | LEU | A | 332 | 2.505 | 7.301 | 33.030 | 1.00 | 18.99 A |
| ATOM | 2159 | CG | LEU | A | 332 | 2.260 | 8.609 | 33.745 | 1.00 | 19.51 A |
| ATOM | 2160 | CD1 | LEU | A | 332 | 0.847 | 8.581 | 34.238 | 1.00 | 21.18 A |
| ATOM | 2161 | CD2 | LEU | A | 332 | 3.244 | 8.770 | 34.924 | 1.00 | 17.75 A |
| ATOM | 2162 | C | LEU | A | 332 | 3.755 | 5.887 | 31.524 | 1.00 | 19.35 A |
| ATOM | 2163 | O | LEU | A | 332 | 3.188 | 5.879 | 30.414 | 1.00 | 20.14 A |
| ATOM | 2164 | N | PHE | A | 333 | 4.344 | 4.806 | 32.061 | 1.00 | 17.44 A |
| ATOM | 2165 | CA | PHE | A | 333 | 4.203 | 3.458 | 31.481 | 1.00 | 14.82 A |
| ATOM | 2166 | CB | PHE | A | 333 | 5.533 | 2.761 | 31.133 | 1.00 | 12.51 A |
| ATOM | 2167 | CG | PHE | A | 333 | 6.123 | 3.135 | 29.778 | 1.00 | 13.15 A |
| ATOM | 2168 | CD1 | PHE | A | 333 | 5.376 | 3.830 | 28.824 | 1.00 | 15.15 A |
| ATOM | 2169 | CD2 | PHE | A | 333 | 7.411 | 2.748 | 29.460 | 1.00 | 8.85 A |
| ATOM | 2170 | CE1 | PHE | A | 333 | 5.925 | 4.122 | 27.571 | 1.00 | 14.83 A |
| ATOM | 2171 | CE2 | PHE | A | 333 | 7.962 | 3.019 | 28.233 | 1.00 | 14.68 A |
| ATOM | 2172 | CZ | PHE | A | 333 | 7.203 | 3.722 | 27.266 | 1.00 | 14.99 A |
| ATOM | 2173 | C | PHE | A | 333 | 3.563 | 2.653 | 32.605 | 1.00 | 17.99 A |
| ATOM | 2174 | O | PHE | A | 333 | 3.831 | 2.905 | 33.819 | 1.00 | 17.33 A |
| ATOM | 2175 | N | GLN | A | 334 | 2.708 | 1.700 | 32.231 | 1.00 | 16.15 A |
| ATOM | 2176 | CA | GLN | A | 334 | 2.073 | 0.821 | 33.217 | 1.00 | 19.09 A |
| ATOM | 2177 | CB | GLN | A | 334 | 0.548 | 0.748 | 33.055 | 1.00 | 19.52 A |
| ATOM | 2178 | CG | GLN | A | 334 | −0.233 | 2.077 | 33.240 | 1.00 | 24.47 A |
| ATOM | 2179 | CD | GLN | A | 334 | −0.022 | 3.042 | 32.040 | 1.00 | 26.93 A |
| ATOM | 2180 | OE1 | GLN | A | 334 | −0.116 | 2.638 | 30.890 | 1.00 | 29.49 A |
| ATOM | 2181 | NE2 | GLN | A | 334 | 0.251 | 4.300 | 32.320 | 1.00 | 27.42 A |
| ATOM | 2182 | C | GLN | A | 334 | 2.666 | −0.578 | 32.992 | 1.00 | 21.41 A |
| ATOM | 2183 | O | GLN | A | 334 | 2.788 | −1.036 | 31.842 | 1.00 | 22.36 A |
| ATOM | 2184 | N | GLY | A | 335 | 3.073 | −1.239 | 34.075 | 1.00 | 20.48 A |
| ATOM | 2185 | CA | GLY | A | 335 | 3.639 | −2.583 | 33.962 | 1.00 | 21.62 A |
| ATOM | 2186 | C | GLY | A | 335 | 2.941 | −3.553 | 34.887 | 1.00 | 23.01 A |
| ATOM | 2187 | O | GLY | A | 335 | 2.341 | −3.149 | 35.905 | 1.00 | 22.08 A |
| ATOM | 2188 | N | ARG | A | 336 | 2.960 | −4.829 | 34.534 | 1.00 | 22.00 A |
| ATOM | 2189 | CA | ARG | A | 336 | 2.372 | −5.823 | 35.415 | 1.00 | 22.02 A |
| ATOM | 2190 | CB | ARG | A | 336 | 0.996 | −6.293 | 34.931 | 1.00 | 23.20 A |
| ATOM | 2191 | CG | ARG | A | 336 | −0.120 | −5.301 | 34.988 | 1.00 | 27.17 A |
| ATOM | 2192 | CD | ARG | A | 336 | −1.429 | −6.013 | 34.766 | 1.00 | 25.93 A |
| ATOM | 2193 | NE | ARG | A | 336 | −1.550 | −6.514 | 33.399 | 1.00 | 29.18 A |
| ATOM | 2194 | CZ | ARG | A | 336 | −2.611 | −7.179 | 32.944 | 1.00 | 31.96 A |
| ATOM | 2195 | NH1 | ARG | A | 336 | −3.626 | −7.427 | 33.765 | 1.00 | 28.93 A |
| ATOM | 2196 | NH2 | ARG | A | 336 | −2.691 | −7.550 | 31.661 | 1.00 | 31.14 A |
| ATOM | 2197 | C | ARG | A | 336 | 3.296 | −7.016 | 35.285 | 1.00 | 22.85 A |

TABLE 2-continued

| ATOM | 2198 | O   | ARG | A | 336 | 3.805  | −7.269  | 34.187 | 1.00 | 19.28 | A |
|------|------|-----|-----|---|-----|--------|---------|--------|------|-------|---|
| ATOM | 2199 | N   | VAL | A | 337 | 3.533  | −7.748  | 36.376 | 1.00 | 19.68 | A |
| ATOM | 2200 | CA  | VAL | A | 337 | 4.320  | −8.979  | 36.250 | 1.00 | 18.60 | A |
| ATOM | 2201 | CB  | VAL | A | 337 | 5.094  | −9.353  | 37.544 | 1.00 | 18.22 | A |
| ATOM | 2202 | CG1 | VAL | A | 337 | 5.790  | −10.717 | 37.352 | 1.00 | 16.37 | A |
| ATOM | 2203 | CG2 | VAL | A | 337 | 6.178  | −8.328  | 37.820 | 1.00 | 16.50 | A |
| ATOM | 2204 | C   | VAL | A | 337 | 3.227  | −9.992  | 36.024 | 1.00 | 17.78 | A |
| ATOM | 2205 | O   | VAL | A | 337 | 2.290  | −10.066 | 36.825 | 1.00 | 21.86 | A |
| ATOM | 2206 | N   | LEU | A | 338 | 3.308  | −10.786 | 34.965 | 1.00 | 18.50 | A |
| ATOM | 2207 | CA  | LEU | A | 338 | 2.236  | −11.755 | 34.710 | 1.00 | 20.96 | A |
| ATOM | 2208 | CB  | LEU | A | 338 | 1.828  | −11.751 | 33.223 | 1.00 | 22.53 | A |
| ATOM | 2209 | CG  | LEU | A | 338 | 1.361  | −10.403 | 32.692 | 1.00 | 23.74 | A |
| ATOM | 2210 | CD1 | LEU | A | 338 | 1.044  | −10.528 | 31.211 | 1.00 | 25.84 | A |
| ATOM | 2211 | CD2 | LEU | A | 338 | 0.183  | −9.948  | 33.503 | 1.00 | 23.28 | A |
| ATOM | 2212 | C   | LEU | A | 338 | 2.569  | −13.197 | 35.092 | 1.00 | 24.05 | A |
| ATOM | 2213 | O   | LEU | A | 338 | 1.675  | −14.037 | 35.117 | 1.00 | 24.40 | A |
| ATOM | 2214 | N   | GLY | A | 339 | 3.838  | −13.479 | 35.369 | 1.00 | 24.56 | A |
| ATOM | 2215 | CA  | GLY | A | 339 | 4.231  | −14.820 | 35.743 | 1.00 | 23.69 | A |
| ATOM | 2216 | C   | GLY | A | 339 | 5.663  | −14.857 | 36.261 | 1.00 | 25.12 | A |
| ATOM | 2217 | O   | GLY | A | 339 | 6.475  | −13.968 | 35.975 | 1.00 | 21.74 | A |
| ATOM | 2218 | N   | GLU | A | 340 | 5.965  | −15.884 | 37.042 | 1.00 | 23.26 | A |
| ATOM | 2219 | CA  | GLU | A | 340 | 7.294  | −16.066 | 37.575 | 1.00 | 26.29 | A |
| ATOM | 2220 | CB  | GLU | A | 340 | 7.311  | −15.810 | 39.081 | 1.00 | 25.71 | A |
| ATOM | 2221 | CG  | GLU | A | 340 | 6.533  | −16.824 | 39.921 | 1.00 | 30.77 | A |
| ATOM | 2222 | CD  | GLU | A | 340 | 7.177  | −16.961 | 41.293 | 1.00 | 34.78 | A |
| ATOM | 2223 | OE1 | GLU | A | 340 | 7.867  | −17.970 | 41.537 | 1.00 | 37.88 | A |
| ATOM | 2224 | OE2 | GLU | A | 340 | 7.031  | −16.038 | 42.114 | 1.00 | 36.85 | A |
| ATOM | 2225 | C   | GLU | A | 340 | 7.721  | −17.493 | 37.320 | 1.00 | 27.28 | A |
| ATOM | 2226 | O   | GLU | A | 340 | 6.885  | −18.365 | 37.101 | 1.00 | 27.19 | A |
| ATOM | 2227 | N   | GLU | A | 341 | 9.021  | −17.731 | 37.375 | 1.00 | 28.56 | A |
| ATOM | 2228 | CA  | GLU | A | 341 | 9.548  | −19.061 | 37.172 | 1.00 | 31.30 | A |
| ATOM | 2229 | CB  | GLU | A | 341 | 9.573  | −19.371 | 35.684 | 1.00 | 33.64 | A |
| ATOM | 2230 | CG  | GLU | A | 341 | 9.857  | −20.803 | 35.352 | 1.00 | 38.66 | A |
| ATOM | 2231 | CD  | GLU | A | 341 | 9.978  | −20.976 | 33.859 | 1.00 | 44.82 | A |
| ATOM | 2232 | OE1 | GLU | A | 341 | 9.148  | −20.362 | 33.141 | 1.00 | 47.09 | A |
| ATOM | 2233 | OE2 | GLU | A | 341 | 10.890 | −21.699 | 33.399 | 1.00 | 44.78 | A |
| ATOM | 2234 | C   | GLU | A | 341 | 10.967 | −19.178 | 37.719 | 1.00 | 30.61 | A |
| ATOM | 2235 | O   | GLU | A | 341 | 11.753 | −18.219 | 37.636 | 1.00 | 29.95 | A |
| ATOM | 2236 | N   | ARG | A | 342 | 11.281 | −20.348 | 38.279 | 1.00 | 29.23 | A |
| ATOM | 2237 | CA  | ARG | A | 342 | 12.629 | −20.642 | 38.760 | 1.00 | 27.84 | A |
| ATOM | 2238 | CB  | ARG | A | 342 | 12.601 | −21.110 | 40.225 | 1.00 | 26.45 | A |
| ATOM | 2239 | CG  | ARG | A | 342 | 12.738 | −19.878 | 41.132 | 1.00 | 28.80 | A |
| ATOM | 2240 | CD  | ARG | A | 342 | 12.472 | −20.089 | 42.618 | 1.00 | 30.93 | A |
| ATOM | 2241 | NE  | ARG | A | 342 | 12.600 | −18.845 | 43.412 | 1.00 | 31.05 | A |
| ATOM | 2242 | CZ  | ARG | A | 342 | 13.718 | −18.105 | 43.574 | 1.00 | 32.80 | A |
| ATOM | 2243 | NH1 | ARG | A | 342 | 14.884 | −18.433 | 43.004 | 1.00 | 29.02 | A |
| ATOM | 2244 | NH2 | ARG | A | 342 | 13.664 | −16.996 | 44.327 | 1.00 | 31.86 | A |
| ATOM | 2245 | C   | ARG | A | 342 | 13.157 | −21.712 | 37.821 | 1.00 | 27.25 | A |
| ATOM | 2246 | O   | ARG | A | 342 | 12.439 | −22.638 | 37.478 | 1.00 | 27.76 | A |
| ATOM | 2247 | N   | ILE | A | 343 | 14.393 | −21.555 | 37.365 | 1.00 | 27.87 | A |
| ATOM | 2248 | CA  | ILE | A | 343 | 14.997 | −22.496 | 36.432 | 1.00 | 28.78 | A |
| ATOM | 2249 | CB  | ILE | A | 343 | 15.575 | −21.745 | 35.235 | 1.00 | 30.53 | A |
| ATOM | 2250 | CG2 | ILE | A | 343 | 15.773 | −22.707 | 34.090 | 1.00 | 30.06 | A |
| ATOM | 2251 | CG1 | ILE | A | 343 | 14.606 | −20.638 | 34.774 | 1.00 | 30.64 | A |
| ATOM | 2252 | CD1 | ILE | A | 343 | 15.285 | −19.655 | 33.797 | 1.00 | 31.26 | A |
| ATOM | 2253 | C   | ILE | A | 343 | 16.120 | −23.266 | 37.185 | 1.00 | 29.98 | A |
| ATOM | 2254 | O   | ILE | A | 343 | 17.235 | −22.771 | 37.368 | 1.00 | 25.59 | A |
| ATOM | 2255 | N   | PRO | A | 344 | 15.819 | −24.503 | 37.602 | 1.00 | 29.90 | A |
| ATOM | 2256 | CD  | PRO | A | 344 | 14.554 | −25.191 | 37.298 | 1.00 | 31.23 | A |
| ATOM | 2257 | CA  | PRO | A | 344 | 16.723 | −25.382 | 38.346 | 1.00 | 31.90 | A |
| ATOM | 2258 | CB  | PRO | A | 344 | 15.938 | −26.690 | 38.439 | 1.00 | 32.97 | A |
| ATOM | 2259 | CG  | PRO | A | 344 | 14.486 | −26.202 | 38.428 | 1.00 | 32.84 | A |
| ATOM | 2260 | C   | PRO | A | 344 | 18.078 | −25.573 | 37.726 | 1.00 | 32.48 | A |
| ATOM | 2261 | O   | PRO | A | 344 | 18.206 | −25.820 | 36.537 | 1.00 | 32.08 | A |
| ATOM | 2262 | N   | GLY | A | 345 | 19.109 | −25.439 | 38.536 | 1.00 | 34.45 | A |
| ATOM | 2263 | CA  | GLY | A | 345 | 20.439 | −25.664 | 38.001 | 1.00 | 35.77 | A |
| ATOM | 2264 | C   | GLY | A | 345 | 21.028 | −24.512 | 37.219 | 1.00 | 36.47 | A |
| ATOM | 2265 | O   | GLY | A | 345 | 22.072 | −24.659 | 36.570 | 1.00 | 37.85 | A |
| ATOM | 2266 | N   | VAL | A | 346 | 20.362 | −23.371 | 37.228 | 1.00 | 34.13 | A |
| ATOM | 2267 | CA  | VAL | A | 346 | 20.934 | −22.235 | 36.527 | 1.00 | 33.93 | A |
| ATOM | 2268 | CB  | VAL | A | 346 | 20.117 | −21.836 | 35.273 | 1.00 | 34.56 | A |
| ATOM | 2269 | CG1 | VAL | A | 346 | 20.707 | −20.580 | 34.660 | 1.00 | 34.47 | A |
| ATOM | 2270 | CG2 | VAL | A | 346 | 20.096 | −22.999 | 34.251 | 1.00 | 31.69 | A |
| ATOM | 2271 | C   | VAL | A | 346 | 20.842 | −21.130 | 37.540 | 1.00 | 33.88 | A |
| ATOM | 2272 | O   | VAL | A | 346 | 19.777 | −20.915 | 38.117 | 1.00 | 34.02 | A |
| ATOM | 2273 | N   | LYS | A | 347 | 21.952 | −20.454 | 37.798 | 1.00 | 33.67 | A |
| ATOM | 2274 | CA  | LYS | A | 347 | 21.893 | −19.361 | 38.744 | 1.00 | 34.72 | A |
| ATOM | 2275 | CB  | LYS | A | 347 | 22.362 | −19.806 | 40.129 | 1.00 | 37.72 | A |
| ATOM | 2276 | CG  | LYS | A | 347 | 23.748 | −20.375 | 40.194 | 1.00 | 43.18 | A |

TABLE 2-continued

| ATOM | 2277 | CD | LYS | A | 347 | 23.809 | −21.349 | 41.386 | 1.00 | 47.44 | A |
|---|---|---|---|---|---|---|---|---|---|---|---|
| ATOM | 2278 | CE | LYS | A | 347 | 25.239 | −21.599 | 41.817 | 1.00 | 49.22 | A |
| ATOM | 2279 | NZ | LYS | A | 347 | 25.838 | −20.326 | 42.340 | 1.00 | 51.49 | A |
| ATOM | 2280 | C | LYS | A | 347 | 22.668 | −18.141 | 38.297 | 1.00 | 32.11 | A |
| ATOM | 2281 | O | LYS | A | 347 | 23.474 | −18.198 | 37.372 | 1.00 | 28.94 | A |
| ATOM | 2282 | N | VAL | A | 348 | 22.361 | −17.023 | 38.934 | 1.00 | 29.06 | A |
| ATOM | 2283 | CA | VAL | A | 348 | 23.050 | −15.779 | 38.653 | 1.00 | 26.24 | A |
| ATOM | 2284 | CB | VAL | A | 348 | 22.076 | −14.770 | 38.004 | 1.00 | 22.25 | A |
| ATOM | 2285 | CG1 | VAL | A | 348 | 21.707 | −15.277 | 36.588 | 1.00 | 17.75 | A |
| ATOM | 2286 | CG2 | VAL | A | 348 | 20.830 | −14.630 | 38.840 | 1.00 | 19.28 | A |
| ATOM | 2287 | C | VAL | A | 348 | 23.566 | −15.336 | 40.030 | 1.00 | 25.52 | A |
| ATOM | 2288 | O | VAL | A | 348 | 23.184 | −15.928 | 41.049 | 1.00 | 26.03 | A |
| ATOM | 2289 | N | PRO | A | 349 | 24.433 | −14.314 | 40.079 | 1.00 | 24.92 | A |
| ATOM | 2290 | CD | PRO | A | 349 | 25.154 | −13.641 | 38.987 | 1.00 | 24.89 | A |
| ATOM | 2291 | CA | PRO | A | 349 | 24.953 | −13.891 | 41.377 | 1.00 | 26.91 | A |
| ATOM | 2292 | CB | PRO | A | 349 | 25.723 | −12.618 | 41.046 | 1.00 | 26.83 | A |
| ATOM | 2293 | CG | PRO | A | 349 | 26.354 | −13.002 | 39.715 | 1.00 | 26.19 | A |
| ATOM | 2294 | C | PRO | A | 349 | 23.947 | −13.717 | 42.476 | 1.00 | 28.45 | A |
| ATOM | 2295 | O | PRO | A | 349 | 24.229 | −14.074 | 43.615 | 1.00 | 32.28 | A |
| ATOM | 2296 | N | VAL | A | 350 | 22.757 | −13.218 | 42.191 | 1.00 | 25.90 | A |
| ATOM | 2297 | CA | VAL | A | 350 | 21.852 | −13.055 | 43.314 | 1.00 | 25.37 | A |
| ATOM | 2298 | CB | VAL | A | 350 | 20.731 | −12.027 | 43.017 | 1.00 | 25.38 | A |
| ATOM | 2299 | CG1 | VAL | A | 350 | 19.664 | −12.641 | 42.093 | 1.00 | 24.57 | A |
| ATOM | 2300 | CG2 | VAL | A | 350 | 20.116 | −11.541 | 44.336 | 1.00 | 26.42 | A |
| ATOM | 2301 | C | VAL | A | 350 | 21.193 | −14.334 | 43.800 | 1.00 | 26.89 | A |
| ATOM | 2302 | O | VAL | A | 350 | 20.578 | −14.314 | 44.860 | 1.00 | 27.74 | A |
| ATOM | 2303 | N | THR | A | 351 | 21.304 | −15.432 | 43.041 | 1.00 | 25.74 | A |
| ATOM | 2304 | CA | THR | A | 351 | 20.649 | −16.667 | 43.426 | 1.00 | 27.19 | A |
| ATOM | 2305 | CB | THR | A | 351 | 20.774 | −17.727 | 42.342 | 1.00 | 32.32 | A |
| ATOM | 2306 | OG1 | THR | A | 351 | 20.397 | −17.175 | 41.073 | 1.00 | 32.13 | A |
| ATOM | 2307 | CG2 | THR | A | 351 | 19.880 | −18.937 | 42.699 | 1.00 | 31.39 | A |
| ATOM | 2308 | C | THR | A | 351 | 21.240 | −17.307 | 44.689 | 1.00 | 26.98 | A |
| ATOM | 2309 | O | THR | A | 351 | 22.401 | −17.699 | 44.683 | 1.00 | 25.39 | A |
| ATOM | 2310 | N | LYS | A | 352 | 20.427 | −17.448 | 45.731 | 1.00 | 27.84 | A |
| ATOM | 2311 | CA | LYS | A | 352 | 20.882 | −18.056 | 46.994 | 1.00 | 31.21 | A |
| ATOM | 2312 | CB | LYS | A | 352 | 19.981 | −17.603 | 48.129 | 1.00 | 30.66 | A |
| ATOM | 2313 | CG | LYS | A | 352 | 20.109 | −16.107 | 48.292 | 1.00 | 34.76 | A |
| ATOM | 2314 | CD | LYS | A | 352 | 19.066 | −15.513 | 49.184 | 1.00 | 38.62 | A |
| ATOM | 2315 | CE | LYS | A | 352 | 19.451 | −14.065 | 49.440 | 1.00 | 41.73 | A |
| ATOM | 2316 | NZ | LYS | A | 352 | 18.428 | −13.358 | 50.216 | 1.00 | 43.53 | A |
| ATOM | 2317 | C | LYS | A | 352 | 20.951 | −19.569 | 46.971 | 1.00 | 30.19 | A |
| ATOM | 2318 | O | LYS | A | 352 | 20.219 | −20.236 | 46.234 | 1.00 | 29.91 | A |
| ATOM | 2319 | N | ASP | A | 353 | 21.841 | −20.085 | 47.799 | 1.00 | 30.00 | A |
| ATOM | 2320 | CA | ASP | A | 353 | 22.065 | −21.507 | 47.957 | 1.00 | 30.30 | A |
| ATOM | 2321 | CB | ASP | A | 353 | 23.085 | −21.745 | 49.053 | 1.00 | 37.47 | A |
| ATOM | 2322 | CG | ASP | A | 353 | 24.486 | −21.427 | 48.605 | 1.00 | 43.97 | A |
| ATOM | 2323 | OD1 | ASP | A | 353 | 24.998 | −22.184 | 47.737 | 1.00 | 48.17 | A |
| ATOM | 2324 | OD2 | ASP | A | 353 | 25.060 | −20.426 | 49.113 | 1.00 | 48.28 | A |
| ATOM | 2325 | C | ASP | A | 353 | 20.788 | −22.189 | 48.349 | 1.00 | 28.19 | A |
| ATOM | 2326 | O | ASP | A | 353 | 20.498 | −23.292 | 47.912 | 1.00 | 27.41 | A |
| ATOM | 2327 | N | ALA | A | 354 | 20.014 | −21.517 | 49.176 | 1.00 | 26.37 | A |
| ATOM | 2328 | CA | ALA | A | 354 | 18.770 | −22.086 | 49.623 | 1.00 | 28.33 | A |
| ATOM | 2329 | CB | ALA | A | 354 | 18.238 | −21.276 | 50.837 | 1.00 | 26.85 | A |
| ATOM | 2330 | C | ALA | A | 354 | 17.695 | −22.169 | 48.512 | 1.00 | 29.76 | A |
| ATOM | 2331 | O | ALA | A | 354 | 16.692 | −22.844 | 48.714 | 1.00 | 30.31 | A |
| ATOM | 2332 | N | GLU | A | 355 | 17.891 | −21.490 | 47.371 | 1.00 | 28.90 | A |
| ATOM | 2333 | CA | GLU | A | 355 | 16.887 | −21.531 | 46.282 | 1.00 | 32.70 | A |
| ATOM | 2334 | CB | GLU | A | 355 | 16.807 | −20.200 | 45.488 | 1.00 | 30.77 | A |
| ATOM | 2335 | CG | GLU | A | 355 | 16.979 | −18.910 | 46.264 | 1.00 | 38.87 | A |
| ATOM | 2336 | CD | GLU | A | 355 | 15.681 | −18.189 | 46.581 | 1.00 | 41.05 | A |
| ATOM | 2337 | OE1 | GLU | A | 355 | 15.739 | −16.946 | 46.760 | 1.00 | 43.22 | A |
| ATOM | 2338 | OE2 | GLU | A | 355 | 14.615 | −18.847 | 46.656 | 1.00 | 42.99 | A |
| ATOM | 2339 | C | GLU | A | 355 | 17.182 | −22.618 | 45.237 | 1.00 | 31.53 | A |
| ATOM | 2340 | O | GLU | A | 355 | 18.340 | −22.925 | 44.954 | 1.00 | 31.27 | A |
| ATOM | 2341 | N | GLU | A | 356 | 16.126 | −23.162 | 44.642 | 1.00 | 33.70 | A |
| ATOM | 2342 | CA | GLU | A | 356 | 16.265 | −24.175 | 43.596 | 1.00 | 36.13 | A |
| ATOM | 2343 | CB | GLU | A | 356 | 15.069 | −25.141 | 43.598 | 1.00 | 38.00 | A |
| ATOM | 2344 | CG | GLU | A | 356 | 15.166 | −26.340 | 44.545 | 1.00 | 47.18 | A |
| ATOM | 2345 | CD | GLU | A | 356 | 16.379 | −27.241 | 44.262 | 1.00 | 50.12 | A |
| ATOM | 2346 | OE1 | GLU | A | 356 | 16.697 | −27.480 | 43.069 | 1.00 | 51.50 | A |
| ATOM | 2347 | OE2 | GLU | A | 356 | 17.006 | −27.720 | 45.239 | 1.00 | 53.20 | A |
| ATOM | 2348 | C | GLU | A | 356 | 16.234 | −23.426 | 42.273 | 1.00 | 36.13 | A |
| ATOM | 2349 | O | GLU | A | 356 | 15.191 | −23.408 | 41.629 | 1.00 | 40.29 | A |
| ATOM | 2350 | N | GLY | A | 357 | 17.318 | −22.774 | 41.871 | 1.00 | 32.38 | A |
| ATOM | 2351 | CA | GLY | A | 357 | 17.290 | −22.089 | 40.591 | 1.00 | 29.57 | A |
| ATOM | 2352 | C | GLY | A | 357 | 16.995 | −20.595 | 40.570 | 1.00 | 26.44 | A |
| ATOM | 2353 | O | GLY | A | 357 | 16.314 | −20.059 | 41.453 | 1.00 | 24.81 | A |
| ATOM | 2354 | N | MET | A | 358 | 17.514 | −19.926 | 39.537 | 1.00 | 25.03 | A |
| ATOM | 2355 | CA | MET | A | 358 | 17.334 | −18.483 | 39.413 | 1.00 | 23.73 | A |

TABLE 2-continued

| ATOM | 2356 | CB  | MET | A | 358 | 18.197  | -17.912 | 38.299 | 1.00 | 24.66 | A |
| ---- | ---- | --- | --- | - | --- | ------- | ------- | ------ | ---- | ----- | - |
| ATOM | 2357 | CG  | MET | A | 358 | 17.740  | -18.327 | 36.886 | 1.00 | 23.91 | A |
| ATOM | 2358 | SD  | MET | A | 358 | 18.750  | -17.616 | 35.593 | 1.00 | 25.23 | A |
| ATOM | 2359 | CE  | MET | A | 358 | 18.219  | -15.909 | 35.710 | 1.00 | 24.07 | A |
| ATOM | 2360 | C   | MET | A | 358 | 15.890  | -18.159 | 39.118 | 1.00 | 23.88 | A |
| ATOM | 2361 | O   | MET | A | 358 | 15.205  | -18.903 | 38.417 | 1.00 | 26.76 | A |
| ATOM | 2362 | N   | LEU | A | 359 | 15.433  | -17.067 | 39.703 | 1.00 | 22.45 | A |
| ATOM | 2363 | CA  | LEU | A | 359 | 14.097  | -16.570 | 39.511 | 1.00 | 24.00 | A |
| ATOM | 2364 | CB  | LEU | A | 359 | 13.730  | -15.730 | 40.730 | 1.00 | 25.22 | A |
| ATOM | 2365 | CG  | LEU | A | 359 | 12.375  | -15.042 | 40.569 | 1.00 | 27.81 | A |
| ATOM | 2366 | CD1 | LEU | A | 359 | 11.251  | -16.079 | 40.469 | 1.00 | 23.28 | A |
| ATOM | 2367 | CD2 | LEU | A | 359 | 12.173  | -14.123 | 41.754 | 1.00 | 26.78 | A |
| ATOM | 2368 | C   | LEU | A | 359 | 14.052  | -15.657 | 38.229 | 1.00 | 22.85 | A |
| ATOM | 2369 | O   | LEU | A | 359 | 14.991  | -14.867 | 37.992 | 1.00 | 20.97 | A |
| ATOM | 2370 | N   | VAL | A | 360 | 13.027  | -15.806 | 37.386 | 1.00 | 23.44 | A |
| ATOM | 2371 | CA  | VAL | A | 360 | 12.866  | -14.922 | 36.207 | 1.00 | 21.29 | A |
| ATOM | 2372 | CB  | VAL | A | 360 | 13.158  | -15.590 | 34.854 | 1.00 | 20.64 | A |
| ATOM | 2373 | CG1 | VAL | A | 360 | 14.627  | -15.988 | 34.741 | 1.00 | 21.64 | A |
| ATOM | 2374 | CG2 | VAL | A | 360 | 12.200  | -16.762 | 34.618 | 1.00 | 20.34 | A |
| ATOM | 2375 | C   | VAL | A | 360 | 11.407  | -14.571 | 36.213 | 1.00 | 22.38 | A |
| ATOM | 2376 | O   | VAL | A | 360 | 10.605  | -15.336 | 36.745 | 1.00 | 22.65 | A |
| ATOM | 2377 | N   | VAL | A | 361 | 11.039  | -13.413 | 35.664 | 1.00 | 20.61 | A |
| ATOM | 2378 | CA  | VAL | A | 361 | 9.623   | -13.046 | 35.645 | 1.00 | 20.43 | A |
| ATOM | 2379 | CB  | VAL | A | 361 | 9.294   | -11.949 | 36.708 | 1.00 | 21.52 | A |
| ATOM | 2380 | CG1 | VAL | A | 361 | 9.888   | -12.362 | 38.090 | 1.00 | 22.78 | A |
| ATOM | 2381 | CG2 | VAL | A | 361 | 9.851   | -10.593 | 36.290 | 1.00 | 21.12 | A |
| ATOM | 2382 | C   | VAL | A | 361 | 9.164   | -12.565 | 34.245 | 1.00 | 19.89 | A |
| ATOM | 2383 | O   | VAL | A | 361 | 9.973   | -12.187 | 33.408 | 1.00 | 16.64 | A |
| ATOM | 2384 | N   | THR | A | 362 | 7.870   | -12.630 | 33.992 | 1.00 | 19.31 | A |
| ATOM | 2385 | CA  | THR | A | 362 | 7.342   | -12.175 | 32.729 | 1.00 | 21.14 | A |
| ATOM | 2386 | CB  | THR | A | 362 | 6.397   | -13.194 | 32.154 | 1.00 | 25.15 | A |
| ATOM | 2387 | OG1 | THR | A | 362 | 7.137   | -14.396 | 31.932 | 1.00 | 26.43 | A |
| ATOM | 2388 | CG2 | THR | A | 362 | 5.828   | -12.692 | 30.804 | 1.00 | 24.17 | A |
| ATOM | 2389 | C   | THR | A | 362 | 6.621   | -10.863 | 32.964 | 1.00 | 18.54 | A |
| ATOM | 2390 | O   | THR | A | 362 | 5.598   | -10.816 | 33.621 | 1.00 | 18.66 | A |
| ATOM | 2391 | N   | ALA | A | 363 | 7.214   | -9.802  | 32.446 | 1.00 | 18.27 | A |
| ATOM | 2392 | CA  | ALA | A | 363 | 6.699   | -8.440  | 32.591 | 1.00 | 21.61 | A |
| ATOM | 2393 | CB  | ALA | A | 363 | 7.868   | -7.494  | 32.802 | 1.00 | 22.47 | A |
| ATOM | 2394 | C   | ALA | A | 363 | 5.914   | -7.953  | 31.363 | 1.00 | 20.37 | A |
| ATOM | 2395 | O   | ALA | A | 363 | 6.362   | -8.116  | 30.255 | 1.00 | 16.27 | A |
| ATOM | 2396 | N   | GLU | A | 364 | 4.761   | -7.335  | 31.590 | 1.00 | 20.97 | A |
| ATOM | 2397 | CA  | GLU | A | 364 | 3.970   | -6.761  | 30.510 | 1.00 | 21.75 | A |
| ATOM | 2398 | CB  | GLU | A | 364 | 2.510   | -7.160  | 30.626 | 1.00 | 21.12 | A |
| ATOM | 2399 | CG  | GLU | A | 364 | 1.622   | -6.398  | 29.619 | 1.00 | 23.86 | A |
| ATOM | 2400 | CD  | GLU | A | 364 | 0.148   | -6.458  | 29.974 | 1.00 | 25.20 | A |
| ATOM | 2401 | OE1 | GLU | A | 364 | -0.273  | -5.780  | 30.925 | 1.00 | 24.82 | A |
| ATOM | 2402 | OE2 | GLU | A | 364 | -0.597  | -7.197  | 29.319 | 1.00 | 30.79 | A |
| ATOM | 2403 | C   | GLU | A | 364 | 4.084   | -5.238  | 30.699 | 1.00 | 21.33 | A |
| ATOM | 2404 | O   | GLU | A | 364 | 3.896   | -4.749  | 31.814 | 1.00 | 20.68 | A |
| ATOM | 2405 | N   | ILE | A | 365 | 4.404   | -4.521  | 29.617 | 1.00 | 19.59 | A |
| ATOM | 2406 | CA  | ILE | A | 365 | 4.543   | -3.059  | 29.592 | 1.00 | 19.18 | A |
| ATOM | 2407 | CB  | ILE | A | 365 | 5.982   | -2.617  | 29.140 | 1.00 | 20.31 | A |
| ATOM | 2408 | CG2 | ILE | A | 365 | 6.192   | -1.095  | 29.408 | 1.00 | 20.09 | A |
| ATOM | 2409 | CG1 | ILE | A | 365 | 7.036   | -3.329  | 29.991 | 1.00 | 20.70 | A |
| ATOM | 2410 | CD1 | ILE | A | 365 | 6.891   | -2.938  | 31.453 | 1.00 | 19.70 | A |
| ATOM | 2411 | C   | ILE | A | 365 | 3.535   | -2.452  | 28.605 | 1.00 | 19.48 | A |
| ATOM | 2412 | O   | ILE | A | 365 | 3.432   | -2.918  | 27.446 | 1.00 | 20.26 | A |
| ATOM | 2413 | N   | THR | A | 366 | 2.807   | -1.427  | 29.060 | 1.00 | 17.29 | A |
| ATOM | 2414 | CA  | THR | A | 366 | 1.826   | -0.724  | 28.269 | 1.00 | 16.66 | A |
| ATOM | 2415 | CB  | THR | A | 366 | 0.420   | -0.835  | 28.847 | 1.00 | 21.20 | A |
| ATOM | 2416 | OG1 | THR | A | 366 | 0.072   | -2.212  | 28.978 | 1.00 | 19.38 | A |
| ATOM | 2417 | CG2 | THR | A | 366 | -0.621  | -0.138  | 27.883 | 1.00 | 19.31 | A |
| ATOM | 2418 | C   | THR | A | 366 | 2.145   | 0.777   | 28.150 | 1.00 | 18.94 | A |
| ATOM | 2419 | O   | THR | A | 366 | 2.510   | 1.445   | 29.157 | 1.00 | 17.80 | A |
| ATOM | 2420 | N   | GLY | A | 367 | 2.021   | 1.304   | 26.920 | 1.00 | 18.08 | A |
| ATOM | 2421 | CA  | GLY | A | 367 | 2.253   | 2.732   | 26.679 | 1.00 | 18.99 | A |
| ATOM | 2422 | C   | GLY | A | 367 | 1.626   | 3.154   | 25.365 | 1.00 | 19.65 | A |
| ATOM | 2423 | O   | GLY | A | 367 | 1.002   | 2.310   | 24.711 | 1.00 | 16.56 | A |
| ATOM | 2424 | N   | LYS | A | 368 | 1.799   | 4.408   | 24.944 | 1.00 | 17.19 | A |
| ATOM | 2425 | CA  | LYS | A | 368 | 1.178   | 4.854   | 23.674 | 1.00 | 18.96 | A |
| ATOM | 2426 | CB  | LYS | A | 368 | 0.066   | 5.891   | 23.956 | 1.00 | 20.79 | A |
| ATOM | 2427 | CG  | LYS | A | 368 | -0.755  | 6.320   | 22.720 | 1.00 | 19.09 | A |
| ATOM | 2428 | CD  | LYS | A | 368 | -2.026  | 7.081   | 23.166 | 1.00 | 26.40 | A |
| ATOM | 2429 | CE  | LYS | A | 368 | -2.857  | 7.554   | 21.980 | 1.00 | 25.98 | A |
| ATOM | 2430 | NZ  | LYS | A | 368 | -2.864  | 6.515   | 20.894 | 1.00 | 26.43 | A |
| ATOM | 2431 | C   | LYS | A | 368 | 2.201   | 5.466   | 22.759 | 1.00 | 17.77 | A |
| ATOM | 2432 | O   | LYS | A | 368 | 3.067   | 6.234   | 23.218 | 1.00 | 18.97 | A |
| ATOM | 2433 | N   | ALA | A | 369 | 2.143   | 5.126   | 21.473 | 1.00 | 15.93 | A |
| ATOM | 2434 | CA  | ALA | A | 369 | 3.078   | 5.689   | 20.500 | 1.00 | 15.21 | A |

TABLE 2-continued

| ATOM | 2435 | CB | ALA | A | 369 | 3.881 | 4.586 | 19.832 | 1.00 | 14.74 | A |
|------|------|-----|-----|---|-----|-------|-------|--------|------|-------|---|
| ATOM | 2436 | C | ALA | A | 369 | 2.298 | 6.478 | 19.435 | 1.00 | 18.33 | A |
| ATOM | 2437 | O | ALA | A | 369 | 1.147 | 6.169 | 19.135 | 1.00 | 19.74 | A |
| ATOM | 2438 | N | PHE | A | 370 | 2.938 | 7.489 | 18.852 | 1.00 | 19.47 | A |
| ATOM | 2439 | CA | PHE | A | 370 | 2.295 | 8.291 | 17.826 | 1.00 | 18.39 | A |
| ATOM | 2440 | CB | PHE | A | 370 | 2.116 | 9.738 | 18.283 | 1.00 | 18.50 | A |
| ATOM | 2441 | CG | PHE | A | 370 | 1.005 | 9.928 | 19.266 | 1.00 | 20.13 | A |
| ATOM | 2442 | CD1 | PHE | A | 370 | −0.294 | 10.171 | 18.825 | 1.00 | 25.52 | A |
| ATOM | 2443 | CD2 | PHE | A | 370 | 1.249 | 9.892 | 20.611 | 1.00 | 20.40 | A |
| ATOM | 2444 | CE1 | PHE | A | 370 | −1.327 | 10.389 | 19.724 | 1.00 | 24.88 | A |
| ATOM | 2445 | CE2 | PHE | A | 370 | 0.218 | 10.107 | 21.550 | 1.00 | 22.40 | A |
| ATOM | 2446 | CZ | PHE | A | 370 | −1.065 | 10.361 | 21.106 | 1.00 | 24.56 | A |
| ATOM | 2447 | C | PHE | A | 370 | 3.150 | 8.297 | 16.591 | 1.00 | 17.55 | A |
| ATOM | 2448 | O | PHE | A | 370 | 4.400 | 8.302 | 16.661 | 1.00 | 16.04 | A |
| ATOM | 2449 | N | ILE | A | 371 | 2.497 | 8.283 | 15.438 | 1.00 | 16.13 | A |
| ATOM | 2450 | CA | ILE | A | 371 | 3.287 | 8.398 | 14.210 | 1.00 | 16.03 | A |
| ATOM | 2451 | CB | ILE | A | 371 | 2.501 | 7.895 | 12.984 | 1.00 | 17.82 | A |
| ATOM | 2452 | CG2 | ILE | A | 371 | 3.230 | 8.308 | 11.715 | 1.00 | 15.54 | A |
| ATOM | 2453 | CG1 | ILE | A | 371 | 2.313 | 6.380 | 13.049 | 1.00 | 17.91 | A |
| ATOM | 2454 | CD1 | ILE | A | 371 | 1.728 | 5.770 | 11.704 | 1.00 | 21.75 | A |
| ATOM | 2455 | C | ILE | A | 371 | 3.506 | 9.929 | 14.077 | 1.00 | 12.83 | A |
| ATOM | 2456 | O | ILE | A | 371 | 2.562 | 10.680 | 14.153 | 1.00 | 17.07 | A |
| ATOM | 2457 | N | MET | A | 372 | 4.724 | 10.407 | 13.891 | 1.00 | 12.85 | A |
| ATOM | 2458 | CA | MET | A | 372 | 4.905 | 11.843 | 13.776 | 1.00 | 13.49 | A |
| ATOM | 2459 | CB | MET | A | 372 | 5.855 | 12.380 | 14.862 | 1.00 | 11.09 | A |
| ATOM | 2460 | CG | MET | A | 372 | 7.214 | 11.747 | 14.831 | 1.00 | 11.67 | A |
| ATOM | 2461 | SD | MET | A | 372 | 8.253 | 12.416 | 16.231 | 1.00 | 15.23 | A |
| ATOM | 2462 | CE | MET | A | 372 | 9.721 | 11.802 | 15.790 | 1.00 | 5.94 | A |
| ATOM | 2463 | C | MET | A | 372 | 5.441 | 12.215 | 12.400 | 1.00 | 13.02 | A |
| ATOM | 2464 | O | MET | A | 372 | 5.632 | 13.377 | 12.103 | 1.00 | 13.88 | A |
| ATOM | 2465 | N | GLY | A | 373 | 5.732 | 11.228 | 11.579 | 1.00 | 15.47 | A |
| ATOM | 2466 | CA | GLY | A | 373 | 6.177 | 11.541 | 10.225 | 1.00 | 15.39 | A |
| ATOM | 2467 | C | GLY | A | 373 | 6.390 | 10.299 | 9.376 | 1.00 | 17.81 | A |
| ATOM | 2468 | O | GLY | A | 373 | 6.580 | 9.226 | 9.938 | 1.00 | 13.49 | A |
| ATOM | 2469 | N | PHE | A | 374 | 6.279 | 10.438 | 8.048 | 1.00 | 16.92 | A |
| ATOM | 2470 | CA | PHE | A | 374 | 6.610 | 9.373 | 7.097 | 1.00 | 18.33 | A |
| ATOM | 2471 | CB | PHE | A | 374 | 5.454 | 9.063 | 6.135 | 1.00 | 18.23 | A |
| ATOM | 2472 | CG | PHE | A | 374 | 4.314 | 8.350 | 6.798 | 1.00 | 19.51 | A |
| ATOM | 2473 | CD1 | PHE | A | 374 | 4.422 | 6.997 | 7.152 | 1.00 | 20.79 | A |
| ATOM | 2474 | CD2 | PHE | A | 374 | 3.147 | 9.020 | 7.094 | 1.00 | 22.02 | A |
| ATOM | 2475 | CE1 | PHE | A | 374 | 3.371 | 6.328 | 7.787 | 1.00 | 19.41 | A |
| ATOM | 2476 | CE2 | PHE | A | 374 | 2.070 | 8.352 | 7.740 | 1.00 | 24.08 | A |
| ATOM | 2477 | CZ | PHE | A | 374 | 2.202 | 6.994 | 8.079 | 1.00 | 21.87 | A |
| ATOM | 2478 | C | PHE | A | 374 | 7.739 | 10.100 | 6.378 | 1.00 | 19.52 | A |
| ATOM | 2479 | O | PHE | A | 374 | 7.526 | 11.147 | 5.757 | 1.00 | 20.86 | A |
| ATOM | 2480 | N | ASN | A | 375 | 8.944 | 9.567 | 6.465 | 1.00 | 20.28 | A |
| ATOM | 2481 | CA | ASN | A | 375 | 10.084 | 10.244 | 5.885 | 1.00 | 21.96 | A |
| ATOM | 2482 | CB | ASN | A | 375 | 10.959 | 10.761 | 7.034 | 1.00 | 26.82 | A |
| ATOM | 2483 | CG | ASN | A | 375 | 12.020 | 11.752 | 6.572 | 1.00 | 32.64 | A |
| ATOM | 2484 | OD1 | ASN | A | 375 | 11.851 | 12.438 | 5.554 | 1.00 | 34.71 | A |
| ATOM | 2485 | ND2 | ASN | A | 375 | 13.111 | 11.851 | 7.329 | 1.00 | 33.11 | A |
| ATOM | 2486 | C | ASN | A | 375 | 10.943 | 9.456 | 4.938 | 1.00 | 20.81 | A |
| ATOM | 2487 | O | ASN | A | 375 | 11.168 | 8.261 | 5.105 | 1.00 | 22.34 | A |
| ATOM | 2488 | N | THR | A | 376 | 11.408 | 10.137 | 3.910 | 1.00 | 20.56 | A |
| ATOM | 2489 | CA | THR | A | 376 | 12.326 | 9.535 | 2.984 | 1.00 | 22.95 | A |
| ATOM | 2490 | CB | THR | A | 376 | 11.884 | 9.708 | 1.515 | 1.00 | 20.60 | A |
| ATOM | 2491 | OG1 | THR | A | 376 | 10.598 | 9.103 | 1.348 | 1.00 | 25.54 | A |
| ATOM | 2492 | CG2 | THR | A | 376 | 12.875 | 9.045 | 0.595 | 1.00 | 22.86 | A |
| ATOM | 2493 | C | THR | A | 376 | 13.623 | 10.278 | 3.224 | 1.00 | 22.82 | A |
| ATOM | 2494 | O | THR | A | 376 | 13.789 | 11.448 | 2.838 | 1.00 | 21.25 | A |
| ATOM | 2495 | N | MET | A | 377 | 14.542 | 9.571 | 3.869 | 1.00 | 23.60 | A |
| ATOM | 2496 | CA | MET | A | 377 | 15.853 | 10.075 | 4.223 | 1.00 | 22.90 | A |
| ATOM | 2497 | CB | MET | A | 377 | 16.317 | 9.284 | 5.428 | 1.00 | 25.46 | A |
| ATOM | 2498 | CG | MET | A | 377 | 17.134 | 10.072 | 6.412 | 1.00 | 32.82 | A |
| ATOM | 2499 | SD | MET | A | 377 | 17.355 | 9.160 | 7.965 | 1.00 | 36.16 | A |
| ATOM | 2500 | CE | MET | A | 377 | 15.837 | 8.619 | 8.218 | 1.00 | 26.44 | A |
| ATOM | 2501 | C | MET | A | 377 | 16.835 | 9.930 | 3.046 | 1.00 | 24.15 | A |
| ATOM | 2502 | O | MET | A | 377 | 16.950 | 8.847 | 2.451 | 1.00 | 25.02 | A |
| ATOM | 2503 | N | LEU | A | 378 | 17.556 | 11.005 | 2.736 | 1.00 | 21.52 | A |
| ATOM | 2504 | CA | LEU | A | 378 | 18.492 | 11.056 | 1.603 | 1.00 | 23.77 | A |
| ATOM | 2505 | CB | LEU | A | 378 | 18.139 | 12.237 | 0.684 | 1.00 | 23.01 | A |
| ATOM | 2506 | CG | LEU | A | 378 | 17.070 | 11.994 | −0.405 | 1.00 | 30.05 | A |
| ATOM | 2507 | CD1 | LEU | A | 378 | 16.028 | 11.009 | 0.022 | 1.00 | 28.18 | A |
| ATOM | 2508 | CD2 | LEU | A | 378 | 16.412 | 13.323 | −0.762 | 1.00 | 31.19 | A |
| ATOM | 2509 | C | LEU | A | 378 | 19.942 | 11.188 | 2.003 | 1.00 | 21.83 | A |
| ATOM | 2510 | O | LEU | A | 378 | 20.282 | 11.911 | 2.935 | 1.00 | 18.59 | A |
| ATOM | 2511 | N | PHE | A | 379 | 20.787 | 10.490 | 1.264 | 1.00 | 21.15 | A |
| ATOM | 2512 | CA | PHE | A | 379 | 22.199 | 10.474 | 1.498 | 1.00 | 23.32 | A |
| ATOM | 2513 | CB | PHE | A | 379 | 22.593 | 9.113 | 2.087 | 1.00 | 23.60 | A |

TABLE 2-continued

| | | | | | | | | | | |
|---|---|---|---|---|---|---|---|---|---|---|
| ATOM | 2514 | CG | PHE | A | 379 | 22.074 | 8.892 | 3.492 | 1.00 | 23.39 A |
| ATOM | 2515 | CD1 | PHE | A | 379 | 22.764 | 9.407 | 4.592 | 1.00 | 19.85 A |
| ATOM | 2516 | CD2 | PHE | A | 379 | 20.883 | 8.209 | 3.710 | 1.00 | 22.46 A |
| ATOM | 2517 | CE1 | PHE | A | 379 | 22.263 | 9.242 | 5.906 | 1.00 | 22.76 A |
| ATOM | 2518 | CE2 | PHE | A | 379 | 20.375 | 8.036 | 5.028 | 1.00 | 23.81 A |
| ATOM | 2519 | CZ | PHE | A | 379 | 21.085 | 8.564 | 6.118 | 1.00 | 18.24 A |
| ATOM | 2520 | C | PHE | A | 379 | 22.889 | 10.700 | 0.148 | 1.00 | 26.49 A |
| ATOM | 2521 | O | PHE | A | 379 | 22.981 | 9.794 | −0.688 | 1.00 | 28.51 A |
| ATOM | 2522 | N | ASP | A | 380 | 23.315 | 11.926 | −0.076 | 1.00 | 26.30 A |
| ATOM | 2523 | CA | ASP | A | 380 | 24.026 | 12.282 | −1.281 | 1.00 | 28.29 A |
| ATOM | 2524 | CB | ASP | A | 380 | 23.932 | 13.785 | −1.515 | 1.00 | 31.26 A |
| ATOM | 2525 | CG | ASP | A | 380 | 24.746 | 14.246 | −2.705 | 1.00 | 35.78 A |
| ATOM | 2526 | OD1 | ASP | A | 380 | 25.953 | 13.901 | −2.824 | 1.00 | 35.50 A |
| ATOM | 2527 | OD2 | ASP | A | 380 | 24.170 | 14.984 | −3.520 | 1.00 | 40.55 A |
| ATOM | 2528 | C | ASP | A | 380 | 25.452 | 11.916 | −0.946 | 1.00 | 28.54 A |
| ATOM | 2529 | O | ASP | A | 380 | 25.957 | 12.323 | 0.087 | 1.00 | 28.42 A |
| ATOM | 2530 | N | PRO | A | 381 | 26.130 | 11.170 | −1.836 | 1.00 | 29.66 A |
| ATOM | 2531 | CD | PRO | A | 381 | 25.529 | 10.736 | −3.111 | 1.00 | 30.64 A |
| ATOM | 2532 | CA | PRO | A | 381 | 27.510 | 10.686 | −1.730 | 1.00 | 27.72 A |
| ATOM | 2533 | CB | PRO | A | 381 | 27.750 | 10.023 | −3.089 | 1.00 | 32.71 A |
| ATOM | 2534 | CG | PRO | A | 381 | 26.375 | 9.552 | −3.477 | 1.00 | 31.83 A |
| ATOM | 2535 | C | PRO | A | 381 | 28.534 | 11.750 | −1.459 | 1.00 | 26.44 A |
| ATOM | 2536 | O | PRO | A | 381 | 29.579 | 11.460 | −0.872 | 1.00 | 23.50 A |
| ATOM | 2537 | N | THR | A | 382 | 28.259 | 12.973 | −1.916 | 1.00 | 25.73 A |
| ATOM | 2538 | CA | THR | A | 382 | 29.192 | 14.082 | −1.714 | 1.00 | 26.51 A |
| ATOM | 2539 | CB | THR | A | 382 | 29.217 | 15.026 | −2.948 | 1.00 | 28.88 A |
| ATOM | 2540 | OG1 | THR | A | 382 | 27.979 | 15.742 | −3.060 | 1.00 | 28.59 A |
| ATOM | 2541 | CG2 | THR | A | 382 | 29.402 | 14.187 | −4.214 | 1.00 | 31.70 A |
| ATOM | 2542 | C | THR | A | 382 | 28.896 | 14.887 | −0.449 | 1.00 | 25.79 A |
| ATOM | 2543 | O | THR | A | 382 | 29.664 | 15.766 | −0.065 | 1.00 | 26.15 A |
| ATOM | 2544 | N | ASP | A | 383 | 27.773 | 14.588 | 0.189 | 1.00 | 25.03 A |
| ATOM | 2545 | CA | ASP | A | 383 | 27.401 | 15.239 | 1.448 | 1.00 | 25.26 A |
| ATOM | 2546 | CB | ASP | A | 383 | 26.030 | 14.715 | 1.883 | 1.00 | 25.52 A |
| ATOM | 2547 | CG | ASP | A | 383 | 25.499 | 15.378 | 3.170 | 1.00 | 27.35 A |
| ATOM | 2548 | OD1 | ASP | A | 383 | 26.289 | 16.041 | 3.875 | 1.00 | 22.90 A |
| ATOM | 2549 | OD2 | ASP | A | 383 | 24.276 | 15.208 | 3.456 | 1.00 | 25.08 A |
| ATOM | 2550 | C | ASP | A | 383 | 28.457 | 14.887 | 2.508 | 1.00 | 23.23 A |
| ATOM | 2551 | O | ASP | A | 383 | 28.655 | 13.721 | 2.837 | 1.00 | 23.43 A |
| ATOM | 2552 | N | PRO | A | 384 | 29.130 | 15.890 | 3.073 | 1.00 | 23.44 A |
| ATOM | 2553 | CD | PRO | A | 384 | 28.925 | 17.327 | 2.815 | 1.00 | 25.02 A |
| ATOM | 2554 | CA | PRO | A | 384 | 30.157 | 15.687 | 4.096 | 1.00 | 22.57 A |
| ATOM | 2555 | CB | PRO | A | 384 | 30.661 | 17.110 | 4.385 | 1.00 | 26.48 A |
| ATOM | 2556 | CG | PRO | A | 384 | 30.297 | 17.885 | 3.109 | 1.00 | 28.16 A |
| ATOM | 2557 | C | PRO | A | 384 | 29.627 | 15.035 | 5.378 | 1.00 | 22.82 A |
| ATOM | 2558 | O | PRO | A | 384 | 30.406 | 14.450 | 6.140 | 1.00 | 23.15 A |
| ATOM | 2559 | N | PHE | A | 385 | 28.327 | 15.161 | 5.644 | 1.00 | 21.40 A |
| ATOM | 2560 | CA | PHE | A | 385 | 27.767 | 14.539 | 6.848 | 1.00 | 21.27 A |
| ATOM | 2561 | CB | PHE | A | 385 | 27.139 | 15.598 | 7.753 | 1.00 | 21.78 A |
| ATOM | 2562 | CG | PHE | A | 385 | 28.062 | 16.738 | 8.064 | 1.00 | 24.99 A |
| ATOM | 2563 | CD1 | PHE | A | 385 | 29.146 | 16.563 | 8.938 | 1.00 | 25.29 A |
| ATOM | 2564 | CD2 | PHE | A | 385 | 27.888 | 17.974 | 7.448 | 1.00 | 24.36 A |
| ATOM | 2565 | CE1 | PHE | A | 385 | 30.046 | 17.618 | 9.196 | 1.00 | 27.96 A |
| ATOM | 2566 | CE2 | PHE | A | 385 | 28.789 | 19.043 | 7.699 | 1.00 | 26.41 A |
| ATOM | 2567 | CZ | PHE | A | 385 | 29.863 | 18.868 | 8.572 | 1.00 | 22.72 A |
| ATOM | 2568 | C | PHE | A | 385 | 26.754 | 13.442 | 6.506 | 1.00 | 21.88 A |
| ATOM | 2569 | O | PHE | A | 385 | 25.733 | 13.259 | 7.215 | 1.00 | 22.73 A |
| ATOM | 2570 | N | LYS | A | 386 | 27.025 | 12.731 | 5.404 | 1.00 | 21.03 A |
| ATOM | 2571 | CA | LYS | A | 386 | 26.196 | 11.598 | 5.006 | 1.00 | 22.03 A |
| ATOM | 2572 | CB | LYS | A | 386 | 26.667 | 10.955 | 3.680 | 1.00 | 21.87 A |
| ATOM | 2573 | CG | LYS | A | 386 | 28.115 | 10.474 | 3.622 | 1.00 | 24.75 A |
| ATOM | 2574 | CD | LYS | A | 386 | 28.460 | 10.008 | 2.182 | 1.00 | 25.18 A |
| ATOM | 2575 | CE | LYS | A | 386 | 29.840 | 9.343 | 2.079 | 1.00 | 26.61 A |
| ATOM | 2576 | NZ | LYS | A | 386 | 30.174 | 8.992 | 0.658 | 1.00 | 21.10 A |
| ATOM | 2577 | C | LYS | A | 386 | 26.280 | 10.571 | 6.119 | 1.00 | 20.27 A |
| ATOM | 2578 | O | LYS | A | 386 | 25.387 | 9.739 | 6.245 | 1.00 | 23.80 A |
| ATOM | 2579 | N | ASN | A | 387 | 27.332 | 10.612 | 6.937 | 1.00 | 20.30 A |
| ATOM | 2580 | CA | ASN | A | 387 | 27.425 | 9.639 | 8.034 | 1.00 | 20.44 A |
| ATOM | 2581 | CB | ASN | A | 387 | 28.808 | 8.951 | 8.069 | 1.00 | 21.89 A |
| ATOM | 2582 | CG | ASN | A | 387 | 29.079 | 8.100 | 6.825 | 1.00 | 23.30 A |
| ATOM | 2583 | OD1 | ASN | A | 387 | 30.240 | 7.882 | 6.469 | 1.00 | 27.15 A |
| ATOM | 2584 | ND2 | ASN | A | 387 | 28.010 | 7.617 | 6.153 | 1.00 | 21.07 A |
| ATOM | 2585 | C | ASN | A | 387 | 27.107 | 10.269 | 9.383 | 1.00 | 21.45 A |
| ATOM | 2586 | O | ASN | A | 387 | 27.336 | 9.658 | 10.416 | 1.00 | 22.31 A |
| ATOM | 2587 | N | GLY | A | 388 | 26.577 | 11.498 | 9.366 | 1.00 | 21.38 A |
| ATOM | 2588 | CA | GLY | A | 388 | 26.192 | 12.196 | 10.586 | 1.00 | 19.34 A |
| ATOM | 2589 | C | GLY | A | 388 | 27.321 | 12.737 | 11.447 | 1.00 | 21.22 A |
| ATOM | 2590 | O | GLY | A | 388 | 28.514 | 12.527 | 11.146 | 1.00 | 23.80 A |
| ATOM | 2591 | N | PHE | A | 389 | 26.968 | 13.467 | 12.510 | 1.00 | 18.74 A |
| ATOM | 2592 | CA | PHE | A | 389 | 27.982 | 13.964 | 13.434 | 1.00 | 17.79 A |

TABLE 2-continued

| | | | | | | | | | | |
|---|---|---|---|---|---|---|---|---|---|---|
| ATOM | 2593 | CB | PHE | A | 389 | 28.649 | 15.247 | 12.885 | 1.00 | 17.04 A |
| ATOM | 2594 | CG | PHE | A | 389 | 27.714 | 16.432 | 12.822 | 1.00 | 18.32 A |
| ATOM | 2595 | CD1 | PHE | A | 389 | 27.512 | 17.232 | 13.941 | 1.00 | 18.28 A |
| ATOM | 2596 | CD2 | PHE | A | 389 | 27.008 | 16.733 | 11.632 | 1.00 | 15.12 A |
| ATOM | 2597 | CE1 | PHE | A | 389 | 26.619 | 18.346 | 13.898 | 1.00 | 19.48 A |
| ATOM | 2598 | CE2 | PHE | A | 389 | 26.120 | 17.832 | 11.577 | 1.00 | 17.11 A |
| ATOM | 2599 | CZ | PHE | A | 389 | 25.929 | 18.638 | 12.712 | 1.00 | 17.18 A |
| ATOM | 2600 | C | PHE | A | 389 | 27.359 | 14.768 | 14.259 | 1.00 | 19.18 A |
| ATOM | 2601 | O | PHE | A | 389 | 26.134 | 14.320 | 14.909 | 1.00 | 21.09 A |
| ATOM | 2602 | N | THR | A | 390 | 28.201 | 14.403 | 15.781 | 1.00 | 19.69 A |
| ATOM | 2603 | CA | THR | A | 390 | 27.724 | 14.797 | 17.088 | 1.00 | 21.13 A |
| ATOM | 2604 | CB | THR | A | 390 | 27.584 | 13.627 | 18.089 | 1.00 | 21.00 A |
| ATOM | 2605 | OG1 | THR | A | 390 | 27.237 | 14.175 | 19.363 | 1.00 | 19.82 A |
| ATOM | 2606 | CG2 | THR | A | 390 | 28.879 | 12.808 | 18.217 | 1.00 | 22.94 A |
| ATOM | 2607 | C | THR | A | 390 | 28.745 | 15.792 | 17.635 | 1.00 | 24.09 A |
| ATOM | 2608 | O | THR | A | 390 | 29.933 | 15.666 | 17.365 | 1.00 | 22.68 A |
| ATOM | 2609 | N | LEU | A | 391 | 28.261 | 16.782 | 18.375 | 1.00 | 26.12 A |
| ATOM | 2610 | CA | LEU | A | 391 | 29.106 | 17.785 | 18.984 | 1.00 | 28.88 A |
| ATOM | 2611 | CB | LEU | A | 391 | 28.552 | 19.180 | 18.713 | 1.00 | 26.23 A |
| ATOM | 2612 | CG | LEU | A | 391 | 28.688 | 19.677 | 17.276 | 1.00 | 26.31 A |
| ATOM | 2613 | CD1 | LEU | A | 391 | 28.067 | 21.014 | 17.147 | 1.00 | 26.01 A |
| ATOM | 2614 | CD2 | LEU | A | 391 | 30.136 | 19.788 | 16.908 | 1.00 | 28.41 A |
| ATOM | 2615 | C | LEU | A | 391 | 29.122 | 17.542 | 20.491 | 1.00 | 31.62 A |
| ATOM | 2616 | O | LEU | A | 391 | 29.577 | 18.386 | 21.252 | 1.00 | 32.24 A |
| ATOM | 2617 | N | LYS | A | 392 | 28.603 | 16.394 | 20.912 | 1.00 | 33.34 A |
| ATOM | 2618 | CA | LYS | A | 392 | 28.546 | 16.073 | 22.323 | 1.00 | 34.57 A |
| ATOM | 2619 | CB | LYS | A | 392 | 27.766 | 14.780 | 22.549 | 1.00 | 33.29 A |
| ATOM | 2620 | CG | LYS | A | 392 | 27.738 | 14.379 | 23.993 | 1.00 | 34.77 A |
| ATOM | 2621 | CD | LYS | A | 392 | 26.619 | 13.425 | 24.307 | 1.00 | 34.56 A |
| ATOM | 2622 | CE | LYS | A | 392 | 25.318 | 14.133 | 24.426 | 1.00 | 33.28 A |
| ATOM | 2623 | NZ | LYS | A | 392 | 24.299 | 13.198 | 24.994 | 1.00 | 33.67 A |
| ATOM | 2624 | C | LYS | A | 392 | 29.936 | 15.984 | 22.947 | 1.00 | 38.13 A |
| ATOM | 2625 | O | LYS | A | 392 | 30.821 | 15.272 | 22.454 | 1.00 | 36.18 A |
| ATOM | 2626 | N | GLN | A | 393 | 30.090 | 16.746 | 24.034 | 1.00 | 42.81 A |
| ATOM | 2627 | CA | GLN | A | 393 | 31.311 | 16.868 | 24.823 | 1.00 | 46.40 A |
| ATOM | 2628 | CB | GLN | A | 393 | 30.980 | 17.198 | 26.304 | 1.00 | 49.81 A |
| ATOM | 2629 | CG | GLN | A | 393 | 30.051 | 18.413 | 26.602 | 1.00 | 53.16 A |
| ATOM | 2630 | CD | GLN | A | 393 | 28.543 | 18.152 | 26.351 | 1.00 | 55.09 A |
| ATOM | 2631 | OE1 | GLN | A | 393 | 28.016 | 18.484 | 25.281 | 1.00 | 54.47 A |
| ATOM | 2632 | NE2 | GLN | A | 393 | 27.851 | 17.558 | 27.349 | 1.00 | 54.52 A |
| ATOM | 2633 | C | GLN | A | 393 | 32.110 | 15.573 | 24.769 | 1.00 | 47.02 A |
| ATOM | 2634 | O | GLN | A | 393 | 33.239 | 15.641 | 24.241 | 1.00 | 47.43 A |
| ATOM | 2635 | OXT | GLN | A | 393 | 31.604 | 14.523 | 25.259 | 1.00 | 46.13 A |
| ATOM | 2636 | CB | LYS | B | 44 | −3.895 | 17.367 | 10.930 | 1.00 | 40.26 B |
| ATOM | 2637 | CG | LYS | B | 44 | −3.878 | 15.921 | 11.439 | 1.00 | 44.51 B |
| ATOM | 2638 | CD | LYS | B | 44 | −5.260 | 15.273 | 11.545 | 1.00 | 43.81 B |
| ATOM | 2639 | CE | LYS | B | 44 | −6.060 | 15.764 | 12.744 | 1.00 | 45.37 B |
| ATOM | 2640 | NZ | LYS | B | 44 | −6.512 | 17.191 | 12.732 | 1.00 | 46.86 B |
| ATOM | 2641 | C | LYS | B | 44 | −1.430 | 17.413 | 10.215 | 1.00 | 37.97 B |
| ATOM | 2642 | O | LYS | B | 44 | −0.781 | 16.450 | 10.675 | 1.00 | 37.22 B |
| ATOM | 2643 | N | LYS | B | 44 | −2.717 | 19.537 | 10.824 | 1.00 | 39.54 B |
| ATOM | 2644 | CA | LYS | B | 44 | −2.543 | 18.082 | 11.083 | 1.00 | 38.58 B |
| ATOM | 2645 | N | SER | B | 45 | −1.181 | 17.915 | 8.996 | 1.00 | 32.98 B |
| ATOM | 2646 | CA | SER | B | 45 | −0.119 | 17.359 | 8.146 | 1.00 | 29.60 B |
| ATOM | 2647 | CB | SER | B | 45 | −0.721 | 16.333 | 7.204 | 1.00 | 31.39 B |
| ATOM | 2648 | OG | SER | B | 45 | 0.290 | 15.796 | 6.386 | 1.00 | 36.45 B |
| ATOM | 2649 | C | SER | B | 45 | 0.682 | 18.394 | 7.319 | 1.00 | 27.30 B |
| ATOM | 2650 | O | SER | B | 45 | 0.076 | 19.151 | 6.553 | 1.00 | 27.94 B |
| ATOM | 2651 | N | PHE | B | 46 | 2.021 | 18.418 | 7.438 | 1.00 | 21.85 B |
| ATOM | 2652 | CA | PHE | B | 46 | 2.865 | 19.370 | 6.688 | 1.00 | 19.64 B |
| ATOM | 2653 | CB | PHE | B | 46 | 3.648 | 20.358 | 7.592 | 1.00 | 20.10 B |
| ATOM | 2654 | CG | PHE | B | 46 | 2.812 | 21.115 | 8.573 | 1.00 | 24.21 B |
| ATOM | 2655 | CD1 | PHE | B | 46 | 1.500 | 21.446 | 8.304 | 1.00 | 29.13 B |
| ATOM | 2656 | CD2 | PHE | B | 46 | 3.346 | 21.506 | 9.792 | 1.00 | 29.91 B |
| ATOM | 2657 | CE1 | PHE | B | 46 | 0.728 | 22.151 | 9.238 | 1.00 | 31.63 B |
| ATOM | 2658 | CE2 | PHE | B | 46 | 2.569 | 22.214 | 10.725 | 1.00 | 30.48 B |
| ATOM | 2659 | CZ | PHE | B | 46 | 1.268 | 22.529 | 10.447 | 1.00 | 26.55 B |
| ATOM | 2660 | C | PHE | B | 46 | 3.934 | 18.646 | 5.903 | 1.00 | 20.23 B |
| ATOM | 2661 | O | PHE | B | 46 | 4.516 | 17.661 | 6.385 | 1.00 | 18.88 B |
| ATOM | 2662 | N | THR | B | 47 | 4.240 | 19.169 | 4.722 | 1.00 | 15.03 B |
| ATOM | 2663 | CA | THR | B | 47 | 5.281 | 18.620 | 3.887 | 1.00 | 18.20 B |
| ATOM | 2664 | CB | THR | B | 47 | 4.849 | 18.682 | 2.362 | 1.00 | 20.20 B |
| ATOM | 2665 | OG1 | THR | B | 47 | 3.830 | 17.692 | 2.127 | 1.00 | 26.52 B |
| ATOM | 2666 | CG2 | THR | B | 47 | 5.996 | 18.358 | 1.496 | 1.00 | 23.55 B |
| ATOM | 2667 | C | THR | B | 47 | 6.550 | 19.450 | 4.115 | 1.00 | 15.89 B |
| ATOM | 2668 | O | THR | B | 47 | 6.485 | 20.669 | 4.141 | 1.00 | 14.37 B |
| ATOM | 2669 | N | CYS | B | 48 | 7.700 | 18.788 | 4.261 | 1.00 | 16.18 B |
| ATOM | 2670 | CA | CYS | B | 48 | 8.946 | 19.488 | 4.488 | 1.00 | 17.12 B |
| ATOM | 2671 | CB | CYS | B | 48 | 9.494 | 19.235 | 5.926 | 1.00 | 18.54 B |

TABLE 2-continued

| | | | | | | | | | | |
|---|---|---|---|---|---|---|---|---|---|---|
| ATOM | 2672 | SG | CYS | B | 48 | 8.389 | 19.800 | 7.152 | 1.00 | 27.91 B |
| ATOM | 2673 | C | CYS | B | 48 | 10.009 | 18.980 | 3.573 | 1.00 | 17.53 B |
| ATOM | 2674 | O | CYS | B | 48 | 10.087 | 17.774 | 3.318 | 1.00 | 17.05 B |
| ATOM | 2675 | N | ILE | B | 49 | 10.862 | 19.887 | 3.126 | 1.00 | 13.88 B |
| ATOM | 2676 | CA | ILE | B | 49 | 12.018 | 19.448 | 2.378 | 1.00 | 15.60 B |
| ATOM | 2677 | CB | ILE | B | 49 | 12.335 | 20.308 | 1.152 | 1.00 | 14.75 B |
| ATOM | 2678 | CG2 | ILE | B | 49 | 13.680 | 19.854 | 0.596 | 1.00 | 11.21 B |
| ATOM | 2679 | CG1 | ILE | B | 49 | 11.169 | 20.209 | 0.137 | 1.00 | 15.44 B |
| ATOM | 2680 | CD1 | ILE | B | 49 | 11.328 | 21.092 | −1.162 | 1.00 | 23.66 B |
| ATOM | 2681 | C | ILE | B | 49 | 13.073 | 19.709 | 3.434 | 1.00 | 16.35 B |
| ATOM | 2682 | O | ILE | B | 49 | 13.358 | 20.871 | 3.735 | 1.00 | 16.53 B |
| ATOM | 2683 | N | ASP | B | 50 | 13.595 | 18.636 | 4.033 | 1.00 | 16.66 B |
| ATOM | 2684 | CA | ASP | B | 50 | 14.627 | 18.724 | 5.068 | 1.00 | 19.15 B |
| ATOM | 2685 | CB | ASP | B | 50 | 14.600 | 17.503 | 6.029 | 1.00 | 18.41 B |
| ATOM | 2686 | CG | ASP | B | 50 | 13.511 | 17.608 | 7.093 | 1.00 | 19.55 B |
| ATOM | 2687 | OD1 | ASP | B | 50 | 12.903 | 18.676 | 7.252 | 1.00 | 22.93 B |
| ATOM | 2688 | OD2 | ASP | B | 50 | 13.256 | 16.636 | 7.812 | 1.00 | 24.62 B |
| ATOM | 2689 | C | ASP | B | 50 | 15.988 | 18.846 | 4.419 | 1.00 | 19.18 B |
| ATOM | 2690 | O | ASP | B | 50 | 16.442 | 18.009 | 3.610 | 1.00 | 20.35 B |
| ATOM | 2691 | N | MET | B | 51 | 16.648 | 19.931 | 4.746 | 1.00 | 19.24 B |
| ATOM | 2692 | CA | MET | B | 51 | 17.963 | 20.137 | 4.182 | 1.00 | 21.10 B |
| ATOM | 2693 | CB | MET | B | 51 | 17.902 | 21.253 | 3.177 | 1.00 | 22.58 B |
| ATOM | 2694 | CG | MET | B | 51 | 16.991 | 20.860 | 2.013 | 1.00 | 29.45 B |
| ATOM | 2695 | SD | MET | B | 51 | 16.967 | 22.192 | 0.962 | 1.00 | 35.46 B |
| ATOM | 2696 | CE | MET | B | 51 | 18.548 | 21.823 | 0.104 | 1.00 | 28.53 B |
| ATOM | 2697 | C | MET | B | 51 | 18.912 | 20.515 | 5.269 | 1.00 | 16.61 B |
| ATOM | 2698 | O | MET | B | 51 | 18.490 | 20.652 | 6.401 | 1.00 | 15.13 B |
| ATOM | 2699 | N | HIS | B | 52 | 20.188 | 20.627 | 4.905 | 1.00 | 15.80 B |
| ATOM | 2700 | CA | HIS | B | 52 | 21.213 | 21.144 | 5.812 | 1.00 | 15.68 B |
| ATOM | 2701 | CB | HIS | B | 52 | 21.898 | 20.048 | 6.694 | 1.00 | 13.58 B |
| ATOM | 2702 | CG | HIS | B | 52 | 22.889 | 19.185 | 5.971 | 1.00 | 12.15 B |
| ATOM | 2703 | CD2 | HIS | B | 52 | 22.734 | 18.021 | 5.281 | 1.00 | 10.68 B |
| ATOM | 2704 | ND1 | HIS | B | 52 | 24.236 | 19.467 | 5.950 | 1.00 | 12.26 B |
| ATOM | 2705 | CE1 | HIS | B | 52 | 24.874 | 18.515 | 5.281 | 1.00 | 13.59 B |
| ATOM | 2706 | NE2 | HIS | B | 52 | 23.986 | 17.626 | 4.866 | 1.00 | 14.03 B |
| ATOM | 2707 | C | HIS | B | 52 | 22.226 | 21.909 | 4.963 | 1.00 | 15.91 B |
| ATOM | 2708 | O | HIS | B | 52 | 22.485 | 21.601 | 3.777 | 1.00 | 14.81 B |
| ATOM | 2709 | N | THR | B | 53 | 22.769 | 22.950 | 5.558 | 1.00 | 14.81 B |
| ATOM | 2710 | CA | THR | B | 53 | 23.767 | 23.735 | 4.859 | 1.00 | 16.70 B |
| ATOM | 2711 | CB | THR | B | 53 | 23.388 | 25.216 | 4.816 | 1.00 | 16.27 B |
| ATOM | 2712 | OG1 | THR | B | 53 | 22.153 | 25.356 | 4.102 | 1.00 | 17.55 B |
| ATOM | 2713 | CG2 | THR | B | 53 | 24.489 | 26.023 | 4.139 | 1.00 | 16.30 B |
| ATOM | 2714 | C | THR | B | 53 | 25.034 | 23.552 | 5.661 | 1.00 | 17.07 B |
| ATOM | 2715 | O | THR | B | 53 | 25.173 | 24.130 | 6.711 | 1.00 | 16.97 B |
| ATOM | 2716 | N | GLU | B | 54 | 25.920 | 22.693 | 5.175 | 1.00 | 19.66 B |
| ATOM | 2717 | CA | GLU | B | 54 | 27.171 | 22.407 | 5.827 | 1.00 | 21.98 B |
| ATOM | 2718 | CB | GLU | B | 54 | 28.111 | 23.606 | 5.623 | 1.00 | 27.55 B |
| ATOM | 2719 | CG | GLU | B | 54 | 28.555 | 23.621 | 4.135 | 1.00 | 29.59 B |
| ATOM | 2720 | CD | GLU | B | 54 | 29.305 | 24.862 | 3.716 | 1.00 | 34.78 B |
| ATOM | 2721 | OE1 | GLU | B | 54 | 30.255 | 25.198 | 4.449 | 1.00 | 36.74 B |
| ATOM | 2722 | OE2 | GLU | B | 54 | 28.952 | 25.482 | 2.661 | 1.00 | 33.93 B |
| ATOM | 2723 | C | GLU | B | 54 | 26.995 | 22.019 | 7.277 | 1.00 | 22.64 B |
| ATOM | 2724 | O | GLU | B | 54 | 27.751 | 22.458 | 8.166 | 1.00 | 23.61 B |
| ATOM | 2725 | N | GLY | B | 55 | 25.978 | 21.185 | 7.513 | 1.00 | 19.39 B |
| ATOM | 2726 | CA | GLY | B | 55 | 25.719 | 20.725 | 8.872 | 1.00 | 22.16 B |
| ATOM | 2727 | C | GLY | B | 55 | 24.588 | 21.400 | 9.642 | 1.00 | 20.18 B |
| ATOM | 2728 | O | GLY | B | 55 | 24.066 | 20.831 | 10.612 | 1.00 | 21.32 B |
| ATOM | 2729 | N | GLU | B | 56 | 24.214 | 22.612 | 9.236 | 1.00 | 18.08 B |
| ATOM | 2730 | CA | GLU | B | 56 | 23.133 | 23.337 | 9.910 | 1.00 | 17.90 B |
| ATOM | 2731 | CB | GLU | B | 56 | 23.387 | 24.857 | 9.826 | 1.00 | 15.66 B |
| ATOM | 2732 | CG | GLU | B | 56 | 22.316 | 25.716 | 10.478 | 1.00 | 17.78 B |
| ATOM | 2733 | CD | GLU | B | 56 | 22.255 | 25.543 | 11.992 | 1.00 | 19.03 B |
| ATOM | 2734 | OE1 | GLU | B | 56 | 23.192 | 24.909 | 12.526 | 1.00 | 19.54 B |
| ATOM | 2735 | OE2 | GLU | B | 56 | 21.278 | 26.037 | 12.655 | 1.00 | 17.01 B |
| ATOM | 2736 | C | GLU | B | 56 | 21.782 | 23.002 | 9.250 | 1.00 | 17.16 B |
| ATOM | 2737 | O | GLU | B | 56 | 21.610 | 23.179 | 8.029 | 1.00 | 13.95 B |
| ATOM | 2738 | N | ALA | B | 57 | 20.823 | 22.557 | 10.050 | 1.00 | 17.49 B |
| ATOM | 2739 | CA | ALA | B | 57 | 19.529 | 22.205 | 9.492 | 1.00 | 19.53 B |
| ATOM | 2740 | CB | ALA | B | 57 | 18.647 | 21.565 | 10.510 | 1.00 | 19.15 B |
| ATOM | 2741 | C | ALA | B | 57 | 18.789 | 23.373 | 8.866 | 1.00 | 18.75 B |
| ATOM | 2742 | O | ALA | B | 57 | 18.973 | 24.532 | 9.222 | 1.00 | 16.43 B |
| ATOM | 2743 | N | ALA | B | 58 | 17.928 | 23.012 | 7.922 | 1.00 | 18.84 B |
| ATOM | 2744 | CA | ALA | B | 58 | 17.086 | 23.957 | 7.204 | 1.00 | 17.24 B |
| ATOM | 2745 | CB | ALA | B | 58 | 17.824 | 24.464 | 5.959 | 1.00 | 17.38 B |
| ATOM | 2746 | C | ALA | B | 58 | 15.830 | 23.179 | 6.812 | 1.00 | 14.53 B |
| ATOM | 2747 | O | ALA | B | 58 | 15.744 | 22.640 | 5.714 | 1.00 | 15.00 B |
| ATOM | 2748 | N | ARG | B | 59 | 14.862 | 23.144 | 7.716 | 1.00 | 15.19 B |
| ATOM | 2749 | CA | ARG | B | 59 | 13.611 | 22.437 | 7.498 | 1.00 | 15.97 B |
| ATOM | 2750 | CB | ARG | B | 59 | 13.024 | 21.943 | 8.847 | 1.00 | 13.98 B |

TABLE 2-continued

| | | | | | | | | | |
|---|---|---|---|---|---|---|---|---|---|
| ATOM | 2751 | CG | ARG | B | 59 | 11.585 | 21.468 | 8.813 | 1.00 16.23 B |
| ATOM | 2752 | CD | ARG | B | 59 | 11.251 | 20.594 | 10.031 | 1.00 15.13 B |
| ATOM | 2753 | NE | ARG | B | 59 | 12.080 | 19.404 | 9.963 | 1.00 15.99 B |
| ATOM | 2754 | CZ | ARG | B | 59 | 12.349 | 18.609 | 10.979 | 1.00 19.09 B |
| ATOM | 2755 | NH1 | ARG | B | 59 | 11.866 | 18.855 | 12.199 | 1.00 21.74 B |
| ATOM | 2756 | NH2 | ARG | B | 59 | 13.089 | 17.552 | 10.760 | 1.00 18.68 B |
| ATOM | 2757 | C | ARG | B | 59 | 12.655 | 23.378 | 6.803 | 1.00 16.30 B |
| ATOM | 2758 | O | ARG | B | 59 | 12.084 | 24.268 | 7.426 | 1.00 14.64 B |
| ATOM | 2759 | N | ILE | B | 60 | 12.464 | 23.154 | 5.502 | 1.00 17.44 B |
| ATOM | 2760 | CA | ILE | B | 60 | 11.589 | 24.028 | 4.713 | 1.00 14.54 B |
| ATOM | 2761 | CB | ILE | B | 60 | 12.224 | 24.302 | 3.341 | 1.00 14.79 B |
| ATOM | 2762 | CG2 | ILE | B | 60 | 11.309 | 25.206 | 2.480 | 1.00 17.69 B |
| ATOM | 2763 | CG1 | ILE | B | 60 | 13.549 | 24.991 | 3.566 | 1.00 15.38 B |
| ATOM | 2764 | CD1 | ILE | B | 60 | 14.481 | 25.009 | 2.372 | 1.00 16.72 B |
| ATOM | 2765 | C | ILE | B | 60 | 10.199 | 23.471 | 4.554 | 1.00 15.46 B |
| ATOM | 2766 | O | ILE | B | 60 | 9.985 | 22.497 | 3.844 | 1.00 15.09 B |
| ATOM | 2767 | N | VAL | B | 61 | 9.245 | 24.109 | 5.213 | 1.00 13.03 B |
| ATOM | 2768 | CA | VAL | B | 61 | 7.876 | 23.667 | 5.155 | 1.00 16.99 B |
| ATOM | 2769 | CB | VAL | B | 61 | 7.113 | 24.231 | 6.326 | 1.00 14.16 B |
| ATOM | 2770 | CG1 | VAL | B | 61 | 5.642 | 23.739 | 6.328 | 1.00 12.57 B |
| ATOM | 2771 | CG2 | VAL | B | 61 | 7.836 | 23.803 | 7.606 | 1.00 14.78 B |
| ATOM | 2772 | C | VAL | B | 61 | 7.280 | 24.189 | 3.834 | 1.00 17.71 B |
| ATOM | 2773 | O | VAL | B | 61 | 7.136 | 25.401 | 3.652 | 1.00 13.04 B |
| ATOM | 2774 | N | THR | B | 62 | 6.912 | 23.267 | 2.951 | 1.00 18.07 B |
| ATOM | 2775 | CA | THR | B | 62 | 6.392 | 23.619 | 1.626 | 1.00 17.61 B |
| ATOM | 2776 | CB | THR | B | 62 | 7.015 | 22.725 | 0.556 | 1.00 17.82 B |
| ATOM | 2777 | OG1 | THR | B | 62 | 6.807 | 21.357 | 0.927 | 1.00 17.48 B |
| ATOM | 2778 | CG2 | THR | B | 62 | 8.525 | 22.970 | 0.438 | 1.00 15.38 B |
| ATOM | 2779 | C | THR | B | 62 | 4.867 | 23.556 | 1.485 | 1.00 20.81 B |
| ATOM | 2780 | O | THR | B | 62 | 4.324 | 24.050 | 0.485 | 1.00 22.90 B |
| ATOM | 2781 | N | SER | B | 63 | 4.169 | 22.913 | 2.416 | 1.00 20.20 B |
| ATOM | 2782 | CA | SER | B | 63 | 2.717 | 22.920 | 2.374 | 1.00 22.57 B |
| ATOM | 2783 | CB | SER | B | 63 | 2.141 | 22.186 | 1.146 | 1.00 24.53 B |
| ATOM | 2784 | OG | SER | B | 63 | 2.452 | 20.829 | 1.129 | 1.00 29.31 B |
| ATOM | 2785 | C | SER | B | 63 | 2.087 | 22.378 | 3.614 | 1.00 23.17 B |
| ATOM | 2786 | O | SER | B | 63 | 2.767 | 21.814 | 4.481 | 1.00 23.98 B |
| ATOM | 2787 | N | GLY | B | 64 | 0.781 | 22.597 | 3.725 | 1.00 21.02 B |
| ATOM | 2788 | CA | GLY | B | 64 | 0.051 | 22.105 | 4.870 | 1.00 20.80 B |
| ATOM | 2789 | C | GLY | B | 64 | −0.236 | 23.144 | 5.925 | 1.00 19.04 B |
| ATOM | 2790 | O | GLY | B | 64 | −1.079 | 22.922 | 6.753 | 1.00 17.06 B |
| ATOM | 2791 | N | LEU | B | 65 | 0.429 | 24.293 | 5.873 | 1.00 21.03 B |
| ATOM | 2792 | CA | LEU | B | 65 | 0.172 | 25.371 | 6.821 | 1.00 21.79 B |
| ATOM | 2793 | CB | LEU | B | 65 | 1.180 | 26.492 | 6.627 | 1.00 23.81 B |
| ATOM | 2794 | CG | LEU | B | 65 | 2.624 | 26.002 | 6.721 | 1.00 31.25 B |
| ATOM | 2795 | CD1 | LEU | B | 65 | 3.587 | 27.183 | 6.412 | 1.00 33.04 B |
| ATOM | 2796 | CD2 | LEU | B | 65 | 2.886 | 25.418 | 8.131 | 1.00 31.57 B |
| ATOM | 2797 | C | LEU | B | 65 | −1.183 | 26.013 | 6.664 | 1.00 22.53 B |
| ATOM | 2798 | O | LEU | B | 65 | −1.692 | 26.147 | 5.552 | 1.00 23.83 B |
| ATOM | 2799 | N | PRO | B | 66 | −1.796 | 26.431 | 7.779 | 1.00 23.83 B |
| ATOM | 2800 | CD | PRO | B | 66 | −1.330 | 26.367 | 9.184 | 1.00 22.92 B |
| ATOM | 2801 | CA | PRO | B | 66 | −3.095 | 27.085 | 7.670 | 1.00 20.45 B |
| ATOM | 2802 | CB | PRO | B | 66 | −3.453 | 27.435 | 9.116 | 1.00 23.47 B |
| ATOM | 2803 | CG | PRO | B | 66 | −2.607 | 26.508 | 9.946 | 1.00 22.68 B |
| ATOM | 2804 | C | PRO | B | 66 | −2.816 | 28.383 | 6.901 | 1.00 22.07 B |
| ATOM | 2805 | O | PRO | B | 66 | −1.657 | 28.831 | 6.782 | 1.00 22.24 B |
| ATOM | 2806 | N | HIS | B | 67 | −3.877 | 29.011 | 6.423 | 1.00 22.84 B |
| ATOM | 2807 | CA | HIS | B | 67 | −3.782 | 30.269 | 5.696 | 1.00 24.81 B |
| ATOM | 2808 | CB | HIS | B | 67 | −5.035 | 30.411 | 4.849 | 1.00 25.33 B |
| ATOM | 2809 | CG | HIS | B | 67 | −4.959 | 29.596 | 3.600 | 1.00 24.38 B |
| ATOM | 2810 | CD2 | HIS | B | 67 | −5.666 | 28.522 | 3.185 | 1.00 23.83 B |
| ATOM | 2811 | ND1 | HIS | B | 67 | −3.984 | 29.806 | 2.647 | 1.00 26.91 B |
| ATOM | 2812 | CE1 | HIS | B | 67 | −4.097 | 28.895 | 1.695 | 1.00 24.42 B |
| ATOM | 2813 | NE2 | HIS | B | 67 | −5.113 | 28.106 | 1.999 | 1.00 23.01 B |
| ATOM | 2814 | C | HIS | B | 67 | −3.581 | 31.426 | 6.684 | 1.00 26.08 B |
| ATOM | 2815 | O | HIS | B | 67 | −4.302 | 31.558 | 7.675 | 1.00 27.39 B |
| ATOM | 2816 | N | ILE | B | 68 | −2.589 | 32.242 | 6.388 | 1.00 25.17 B |
| ATOM | 2817 | CA | ILE | B | 68 | −2.123 | 33.364 | 7.234 | 1.00 29.31 B |
| ATOM | 2818 | CB | ILE | B | 68 | −0.576 | 33.114 | 7.519 | 1.00 30.05 B |
| ATOM | 2819 | CG2 | ILE | B | 68 | 0.070 | 34.226 | 8.270 | 1.00 31.44 B |
| ATOM | 2820 | CG1 | ILE | B | 68 | −0.424 | 31.817 | 8.286 | 1.00 33.73 B |
| ATOM | 2821 | CD1 | ILE | B | 68 | −1.347 | 31.747 | 9.448 | 1.00 32.00 B |
| ATOM | 2822 | C | ILE | B | 68 | −2.281 | 34.753 | 6.576 | 1.00 27.45 B |
| ATOM | 2823 | O | ILE | B | 68 | −1.871 | 34.926 | 5.431 | 1.00 26.19 B |
| ATOM | 2824 | N | PRO | B | 69 | −2.845 | 35.757 | 7.296 | 1.00 27.51 B |
| ATOM | 2825 | CD | PRO | B | 69 | −3.318 | 35.680 | 8.689 | 1.00 28.93 B |
| ATOM | 2826 | CA | PRO | B | 69 | −3.017 | 37.119 | 6.758 | 1.00 24.72 B |
| ATOM | 2827 | CB | PRO | B | 69 | −3.853 | 37.834 | 7.820 | 1.00 28.44 B |
| ATOM | 2828 | CG | PRO | B | 69 | −4.361 | 36.717 | 8.724 | 1.00 30.40 B |
| ATOM | 2829 | C | PRO | B | 69 | −1.661 | 37.789 | 6.656 | 1.00 24.01 B |

TABLE 2-continued

| ATOM | 2830 | O | PRO | B | 69 | −0.639 | 37.181 | 6.941 | 1.00 | 25.75 | B |
| --- | --- | --- | --- | --- | --- | --- | --- | --- | --- | --- | --- |
| ATOM | 2831 | N | GLY | B | 70 | −1.642 | 39.059 | 6.276 | 1.00 | 27.17 | B |
| ATOM | 2832 | CA | GLY | B | 70 | −0.386 | 39.794 | 6.213 | 1.00 | 24.42 | B |
| ATOM | 2833 | C | GLY | B | 70 | −0.143 | 40.435 | 4.879 | 1.00 | 25.87 | B |
| ATOM | 2834 | O | GLY | B | 70 | −0.362 | 39.789 | 3.850 | 1.00 | 26.98 | B |
| ATOM | 2835 | N | SER | B | 71 | 0.330 | 41.682 | 4.879 | 1.00 | 22.99 | B |
| ATOM | 2836 | CA | SER | B | 71 | 0.575 | 42.368 | 3.623 | 1.00 | 24.10 | B |
| ATOM | 2837 | CB | SER | B | 71 | −0.076 | 43.770 | 3.659 | 1.00 | 27.25 | B |
| ATOM | 2838 | OG | SER | B | 71 | 0.501 | 44.598 | 4.638 | 1.00 | 30.35 | B |
| ATOM | 2839 | C | SER | B | 71 | 2.052 | 42.446 | 3.236 | 1.00 | 23.85 | B |
| ATOM | 2840 | O | SER | B | 71 | 2.420 | 43.091 | 2.262 | 1.00 | 23.56 | B |
| ATOM | 2841 | N | ASN | B | 72 | 2.905 | 41.808 | 4.028 | 1.00 | 21.63 | B |
| ATOM | 2842 | CA | ASN | B | 72 | 4.330 | 41.716 | 3.740 | 1.00 | 21.97 | B |
| ATOM | 2843 | CB | ASN | B | 72 | 5.049 | 43.073 | 3.933 | 1.00 | 23.34 | B |
| ATOM | 2844 | CG | ASN | B | 72 | 4.960 | 43.582 | 5.333 | 1.00 | 25.21 | B |
| ATOM | 2845 | OD1 | ASN | B | 72 | 5.221 | 42.854 | 6.284 | 1.00 | 24.44 | B |
| ATOM | 2846 | ND2 | ASN | B | 72 | 4.579 | 44.839 | 5.479 | 1.00 | 27.10 | B |
| ATOM | 2847 | C | ASN | B | 72 | 4.881 | 40.574 | 4.635 | 1.00 | 18.79 | B |
| ATOM | 2848 | O | ASN | B | 72 | 4.203 | 40.138 | 5.536 | 1.00 | 19.39 | B |
| ATOM | 2849 | N | MET | B | 73 | 6.053 | 40.032 | 4.308 | 1.00 | 21.09 | B |
| ATOM | 2850 | CA | MET | B | 73 | 6.602 | 38.919 | 5.037 | 1.00 | 20.53 | B |
| ATOM | 2851 | CB | MET | B | 73 | 7.883 | 38.409 | 4.351 | 1.00 | 21.73 | B |
| ATOM | 2852 | CG | MET | B | 73 | 7.660 | 37.504 | 3.118 | 1.00 | 26.09 | B |
| ATOM | 2853 | SD | MET | B | 73 | 6.349 | 36.315 | 3.372 | 1.00 | 24.28 | B |
| ATOM | 2854 | CE | MET | B | 73 | 7.254 | 34.956 | 3.846 | 1.00 | 37.90 | B |
| ATOM | 2855 | C | MET | B | 73 | 6.875 | 39.241 | 6.513 | 1.00 | 22.95 | B |
| ATOM | 2856 | O | MET | B | 73 | 6.856 | 38.327 | 7.330 | 1.00 | 22.05 | B |
| ATOM | 2857 | N | ALA | B | 74 | 7.155 | 40.510 | 6.850 | 1.00 | 22.95 | B |
| ATOM | 2858 | CA | ALA | B | 74 | 7.394 | 40.888 | 8.256 | 1.00 | 23.73 | B |
| ATOM | 2859 | CB | ALA | B | 74 | 7.910 | 42.352 | 8.374 | 1.00 | 22.58 | B |
| ATOM | 2860 | C | ALA | B | 74 | 6.075 | 40.734 | 8.993 | 1.00 | 24.38 | B |
| ATOM | 2861 | O | ALA | B | 74 | 6.063 | 40.296 | 10.140 | 1.00 | 21.32 | B |
| ATOM | 2862 | N | GLU | B | 75 | 4.942 | 41.058 | 8.350 | 1.00 | 22.42 | B |
| ATOM | 2863 | CA | GLU | B | 75 | 3.671 | 40.868 | 9.064 | 1.00 | 23.26 | B |
| ATOM | 2864 | CB | GLU | B | 75 | 2.510 | 41.632 | 8.434 | 1.00 | 21.51 | B |
| ATOM | 2865 | CG | GLU | B | 75 | 2.625 | 43.142 | 8.648 | 1.00 | 30.04 | B |
| ATOM | 2866 | CD | GLU | B | 75 | 1.533 | 43.935 | 7.922 | 1.00 | 34.70 | B |
| ATOM | 2867 | OE1 | GLU | B | 75 | 1.561 | 45.190 | 8.010 | 1.00 | 39.30 | B |
| ATOM | 2868 | OE2 | GLU | B | 75 | 0.660 | 43.310 | 7.269 | 1.00 | 34.22 | B |
| ATOM | 2869 | C | GLU | B | 75 | 3.283 | 39.398 | 9.158 | 1.00 | 21.95 | B |
| ATOM | 2870 | O | GLU | B | 75 | 2.601 | 38.998 | 10.098 | 1.00 | 23.57 | B |
| ATOM | 2871 | N | LYS | B | 76 | 3.685 | 38.593 | 8.183 | 1.00 | 19.88 | B |
| ATOM | 2872 | CA | LYS | B | 76 | 3.343 | 37.159 | 8.270 | 1.00 | 22.05 | B |
| ATOM | 2873 | CB | LYS | B | 76 | 3.677 | 36.423 | 6.960 | 1.00 | 21.17 | B |
| ATOM | 2874 | CG | LYS | B | 76 | 2.664 | 36.742 | 5.873 | 1.00 | 25.60 | B |
| ATOM | 2875 | CD | LYS | B | 76 | 2.543 | 35.595 | 4.865 | 1.00 | 26.77 | B |
| ATOM | 2876 | CE | LYS | B | 76 | 1.596 | 35.965 | 3.764 | 1.00 | 26.27 | B |
| ATOM | 2877 | NZ | LYS | B | 76 | 0.210 | 35.664 | 4.200 | 1.00 | 28.52 | B |
| ATOM | 2878 | C | LYS | B | 76 | 4.126 | 36.531 | 9.438 | 1.00 | 18.93 | B |
| ATOM | 2879 | O | LYS | B | 76 | 3.584 | 35.747 | 10.177 | 1.00 | 18.28 | B |
| ATOM | 2880 | N | LYS | B | 77 | 5.411 | 36.876 | 9.561 | 1.00 | 20.23 | B |
| ATOM | 2881 | CA | LYS | B | 77 | 6.227 | 36.403 | 10.673 | 1.00 | 20.30 | B |
| ATOM | 2882 | CB | LYS | B | 77 | 7.625 | 37.008 | 10.593 | 1.00 | 20.58 | B |
| ATOM | 2883 | CG | LYS | B | 77 | 8.515 | 36.695 | 11.805 | 1.00 | 24.45 | B |
| ATOM | 2884 | CD | LYS | B | 77 | 9.762 | 37.625 | 11.843 | 1.00 | 24.32 | B |
| ATOM | 2885 | CE | LYS | B | 77 | 9.486 | 38.814 | 12.697 | 1.00 | 29.37 | B |
| ATOM | 2886 | NZ | LYS | B | 77 | 10.665 | 39.704 | 12.697 | 1.00 | 31.25 | B |
| ATOM | 2887 | C | LYS | B | 77 | 5.568 | 36.818 | 11.991 | 1.00 | 19.06 | B |
| ATOM | 2888 | O | LYS | B | 77 | 5.415 | 35.990 | 12.891 | 1.00 | 22.30 | B |
| ATOM | 2889 | N | ALA | B | 78 | 5.166 | 38.085 | 12.120 | 1.00 | 20.24 | B |
| ATOM | 2890 | CA | ALA | B | 78 | 4.518 | 38.551 | 13.351 | 1.00 | 18.54 | B |
| ATOM | 2891 | CB | ALA | B | 78 | 4.301 | 40.136 | 13.321 | 1.00 | 20.71 | B |
| ATOM | 2892 | C | ALA | B | 78 | 3.203 | 37.834 | 13.637 | 1.00 | 19.22 | B |
| ATOM | 2893 | O | ALA | B | 78 | 2.884 | 37.496 | 14.803 | 1.00 | 17.38 | B |
| ATOM | 2894 | N | TYR | B | 79 | 2.418 | 37.566 | 12.598 | 1.00 | 17.23 | B |
| ATOM | 2895 | CA | TYR | B | 79 | 1.155 | 36.866 | 12.844 | 1.00 | 17.32 | B |
| ATOM | 2896 | CB | TYR | B | 79 | 0.344 | 36.667 | 11.553 | 1.00 | 18.14 | B |
| ATOM | 2897 | CG | TYR | B | 79 | −1.040 | 36.086 | 11.796 | 1.00 | 19.45 | B |
| ATOM | 2898 | CD1 | TYR | B | 79 | −2.107 | 36.915 | 12.136 | 1.00 | 19.81 | B |
| ATOM | 2899 | CE1 | TYR | B | 79 | −3.335 | 36.413 | 12.402 | 1.00 | 21.23 | B |
| ATOM | 2900 | CD2 | TYR | B | 79 | −1.265 | 34.711 | 11.733 | 1.00 | 21.03 | B |
| ATOM | 2901 | CE2 | TYR | B | 79 | −2.512 | 34.185 | 12.009 | 1.00 | 22.82 | B |
| ATOM | 2902 | CZ | TYR | B | 79 | −3.542 | 35.056 | 12.340 | 1.00 | 24.67 | B |
| ATOM | 2903 | OH | TYR | B | 79 | −4.800 | 34.575 | 12.577 | 1.00 | 29.09 | B |
| ATOM | 2904 | C | TYR | B | 79 | 1.449 | 35.475 | 13.425 | 1.00 | 16.70 | B |
| ATOM | 2905 | O | TYR | B | 79 | 0.727 | 35.030 | 14.292 | 1.00 | 17.53 | B |
| ATOM | 2906 | N | LEU | B | 80 | 2.484 | 34.793 | 12.919 | 1.00 | 15.64 | B |
| ATOM | 2907 | CA | LEU | B | 80 | 2.823 | 33.437 | 13.403 | 1.00 | 15.86 | B |
| ATOM | 2908 | CB | LEU | B | 80 | 3.943 | 32.809 | 12.554 | 1.00 | 13.89 | B |

TABLE 2-continued

| | | | | | | | | | | |
|---|---|---|---|---|---|---|---|---|---|---|
| ATOM | 2909 | CG | LEU | B | 80 | 3.541 | 32.471 | 11.089 | 1.00 | 15.35 B |
| ATOM | 2910 | CD1 | LEU | B | 80 | 4.787 | 32.093 | 10.245 | 1.00 | 15.67 B |
| ATOM | 2911 | CD2 | LEU | B | 80 | 2.530 | 31.343 | 11.114 | 1.00 | 18.07 B |
| ATOM | 2912 | C | LEU | B | 80 | 3.281 | 33.500 | 14.857 | 1.00 | 17.50 B |
| ATOM | 2913 | O | LEU | B | 80 | 2.801 | 32.737 | 15.714 | 1.00 | 18.00 B |
| ATOM | 2914 | N | GLN | B | 81 | 4.204 | 34.429 | 15.105 | 1.00 | 19.78 B |
| ATOM | 2915 | CA | GLN | B | 81 | 4.784 | 34.660 | 16.423 | 1.00 | 22.99 B |
| ATOM | 2916 | CB | GLN | B | 81 | 5.789 | 35.814 | 16.343 | 1.00 | 24.52 B |
| ATOM | 2917 | CG | GLN | B | 81 | 6.309 | 36.294 | 17.672 | 1.00 | 34.22 B |
| ATOM | 2918 | CD | GLN | B | 81 | 7.775 | 36.672 | 17.583 | 1.00 | 39.07 B |
| ATOM | 2919 | OE1 | GLN | B | 81 | 8.606 | 36.156 | 18.343 | 1.00 | 43.27 B |
| ATOM | 2920 | NE2 | GLN | B | 81 | 8.107 | 37.556 | 16.642 | 1.00 | 40.22 B |
| ATOM | 2921 | C | GLN | B | 81 | 3.722 | 34.947 | 17.463 | 1.00 | 23.63 B |
| ATOM | 2922 | O | GLN | B | 81 | 3.724 | 34.329 | 18.525 | 1.00 | 23.61 B |
| ATOM | 2923 | N | GLU | B | 82 | 2.796 | 35.850 | 17.143 | 1.00 | 22.09 B |
| ATOM | 2924 | CA | GLU | B | 82 | 1.728 | 36.219 | 18.059 | 1.00 | 23.23 B |
| ATOM | 2925 | CB | GLU | B | 82 | 1.226 | 37.641 | 17.734 | 1.00 | 25.57 B |
| ATOM | 2926 | CG | GLU | B | 82 | 2.341 | 38.721 | 17.855 | 1.00 | 32.60 B |
| ATOM | 2927 | CD | GLU | B | 82 | 2.073 | 40.036 | 17.076 | 1.00 | 35.87 B |
| ATOM | 2928 | OE1 | GLU | B | 82 | 0.910 | 40.472 | 16.988 | 1.00 | 39.19 B |
| ATOM | 2929 | OE2 | GLU | B | 82 | 3.043 | 40.638 | 16.565 | 1.00 | 38.90 B |
| ATOM | 2930 | C | GLU | B | 82 | 0.522 | 35.308 | 18.159 | 1.00 | 22.18 B |
| ATOM | 2931 | O | GLU | B | 82 | −0.059 | 35.201 | 19.226 | 1.00 | 25.71 B |
| ATOM | 2932 | N | ASN | B | 83 | 0.112 | 34.648 | 17.087 | 1.00 | 22.06 B |
| ATOM | 2933 | CA | ASN | B | 83 | −1.105 | 33.808 | 17.160 | 1.00 | 19.46 B |
| ATOM | 2934 | CB | ASN | B | 83 | −2.130 | 34.327 | 16.149 | 1.00 | 22.79 B |
| ATOM | 2935 | CG | ASN | B | 83 | −2.373 | 35.819 | 16.283 | 1.00 | 25.14 B |
| ATOM | 2936 | OD1 | ASN | B | 83 | −2.885 | 36.274 | 17.301 | 1.00 | 29.38 B |
| ATOM | 2937 | ND2 | ASN | B | 83 | −1.975 | 36.593 | 15.268 | 1.00 | 28.55 B |
| ATOM | 2938 | C | ASN | B | 83 | −0.950 | 32.303 | 16.922 | 1.00 | 19.81 B |
| ATOM | 2939 | O | ASN | B | 83 | −1.841 | 31.535 | 17.275 | 1.00 | 20.66 B |
| ATOM | 2940 | N | MET | B | 84 | 0.134 | 31.864 | 16.300 | 1.00 | 19.13 B |
| ATOM | 2941 | CA | MET | B | 84 | 0.267 | 30.412 | 16.031 | 1.00 | 21.56 B |
| ATOM | 2942 | CB | MET | B | 84 | −0.058 | 30.108 | 14.553 | 1.00 | 23.06 B |
| ATOM | 2943 | CG | MET | B | 84 | −1.324 | 30.804 | 14.080 | 1.00 | 30.92 B |
| ATOM | 2944 | SD | MET | B | 84 | −1.914 | 30.194 | 12.473 | 1.00 | 36.39 B |
| ATOM | 2945 | CE | MET | B | 84 | −3.423 | 29.460 | 12.986 | 1.00 | 35.29 B |
| ATOM | 2946 | C | MET | B | 84 | 1.661 | 29.921 | 16.309 | 1.00 | 18.45 B |
| ATOM | 2947 | O | MET | B | 84 | 2.240 | 29.181 | 15.481 | 1.00 | 17.30 B |
| ATOM | 2948 | N | ASP | B | 85 | 2.222 | 30.328 | 17.454 | 1.00 | 16.51 B |
| ATOM | 2949 | CA | ASP | B | 85 | 3.605 | 29.948 | 17.757 | 1.00 | 15.72 B |
| ATOM | 2950 | CB | ASP | B | 85 | 4.164 | 30.761 | 18.944 | 1.00 | 13.71 B |
| ATOM | 2951 | CG | ASP | B | 85 | 5.652 | 30.611 | 19.088 | 1.00 | 13.65 B |
| ATOM | 2952 | OD1 | ASP | B | 85 | 6.092 | 30.230 | 20.195 | 1.00 | 21.40 B |
| ATOM | 2953 | OD2 | ASP | B | 85 | 6.407 | 30.859 | 18.115 | 1.00 | 16.59 B |
| ATOM | 2954 | C | ASP | B | 85 | 3.719 | 28.468 | 18.027 | 1.00 | 14.08 B |
| ATOM | 2955 | O | ASP | B | 85 | 4.814 | 27.920 | 18.069 | 1.00 | 14.59 B |
| ATOM | 2956 | N | TYR | B | 86 | 2.599 | 27.802 | 18.210 | 1.00 | 14.71 B |
| ATOM | 2957 | CA | TYR | B | 86 | 2.668 | 26.360 | 18.445 | 1.00 | 16.89 B |
| ATOM | 2958 | CB | TYR | B | 86 | 1.334 | 25.853 | 18.968 | 1.00 | 17.61 B |
| ATOM | 2959 | CG | TYR | B | 86 | 0.181 | 26.250 | 18.089 | 1.00 | 25.22 B |
| ATOM | 2960 | CD1 | TYR | B | 86 | −0.166 | 25.489 | 16.997 | 1.00 | 22.80 B |
| ATOM | 2961 | CE1 | TYR | B | 86 | −1.238 | 25.850 | 16.162 | 1.00 | 30.23 B |
| ATOM | 2962 | CD2 | TYR | B | 86 | −0.557 | 27.409 | 18.355 | 1.00 | 28.72 B |
| ATOM | 2963 | CE2 | TYR | B | 86 | −1.622 | 27.779 | 17.539 | 1.00 | 31.23 B |
| ATOM | 2964 | CZ | TYR | B | 86 | −1.959 | 26.988 | 16.448 | 1.00 | 31.51 B |
| ATOM | 2965 | OH | TYR | B | 86 | −3.054 | 27.310 | 15.683 | 1.00 | 36.09 B |
| ATOM | 2966 | C | TYR | B | 86 | 3.085 | 25.591 | 17.166 | 1.00 | 17.90 B |
| ATOM | 2967 | O | TYR | B | 86 | 3.524 | 24.441 | 17.261 | 1.00 | 17.85 B |
| ATOM | 2968 | N | LEU | B | 87 | 2.961 | 26.205 | 15.985 | 1.00 | 15.55 B |
| ATOM | 2969 | CA | LEU | B | 87 | 3.387 | 25.518 | 14.747 | 1.00 | 16.00 B |
| ATOM | 2970 | CB | LEU | B | 87 | 2.914 | 26.284 | 13.493 | 1.00 | 16.39 B |
| ATOM | 2971 | CG | LEU | B | 87 | 1.388 | 26.390 | 13.320 | 1.00 | 18.77 B |
| ATOM | 2972 | CD1 | LEU | B | 87 | 1.104 | 27.272 | 12.069 | 1.00 | 23.28 B |
| ATOM | 2973 | CD2 | LEU | B | 87 | 0.731 | 24.991 | 13.116 | 1.00 | 21.10 B |
| ATOM | 2974 | C | LEU | B | 87 | 4.910 | 25.446 | 14.761 | 1.00 | 14.98 B |
| ATOM | 2975 | O | LEU | B | 87 | 5.498 | 24.399 | 14.512 | 1.00 | 16.96 B |
| ATOM | 2976 | N | ARG | B | 88 | 5.555 | 26.566 | 15.056 | 1.00 | 12.31 B |
| ATOM | 2977 | CA | ARG | B | 88 | 7.002 | 26.599 | 15.131 | 1.00 | 12.40 B |
| ATOM | 2978 | CB | ARG | B | 88 | 7.505 | 28.031 | 15.512 | 1.00 | 10.87 B |
| ATOM | 2979 | CG | ARG | B | 88 | 9.011 | 28.105 | 15.864 | 1.00 | 14.15 B |
| ATOM | 2980 | CD | ARG | B | 88 | 9.444 | 29.453 | 16.494 | 1.00 | 11.28 B |
| ATOM | 2981 | NE | ARG | B | 88 | 8.833 | 29.650 | 17.820 | 1.00 | 14.14 B |
| ATOM | 2982 | CZ | ARG | B | 88 | 9.340 | 29.174 | 18.967 | 1.00 | 14.03 B |
| ATOM | 2983 | NH1 | ARG | B | 88 | 10.480 | 28.473 | 18.965 | 1.00 | 13.10 B |
| ATOM | 2984 | NH2 | ARG | B | 88 | 8.696 | 29.377 | 20.109 | 1.00 | 11.86 B |
| ATOM | 2985 | C | ARG | B | 88 | 7.470 | 25.588 | 16.183 | 1.00 | 11.03 B |
| ATOM | 2986 | O | ARG | B | 88 | 8.392 | 24.795 | 15.968 | 1.00 | 13.86 B |
| ATOM | 2987 | N | ARG | B | 89 | 6.828 | 25.582 | 17.318 | 1.00 | 11.77 B |

TABLE 2-continued

| | | | | | | | | | | |
|---|---|---|---|---|---|---|---|---|---|---|
| ATOM | 2988 | CA | ARG | B | 89 | 7.288 | 24.664 | 18.368 | 1.00 | 14.54 B |
| ATOM | 2989 | CB | ARG | B | 89 | 6.540 | 24.942 | 19.669 | 1.00 | 11.21 B |
| ATOM | 2990 | CG | ARG | B | 89 | 6.949 | 26.245 | 20.341 | 1.00 | 17.33 B |
| ATOM | 2991 | CD | ARG | B | 89 | 6.138 | 26.435 | 21.631 | 1.00 | 22.04 B |
| ATOM | 2992 | NE | ARG | B | 89 | 5.029 | 27.377 | 21.482 | 1.00 | 31.04 B |
| ATOM | 2993 | CZ | ARG | B | 89 | 3.749 | 27.138 | 21.819 | 1.00 | 31.50 B |
| ATOM | 2994 | NH1 | ARG | B | 89 | 3.361 | 25.966 | 22.321 | 1.00 | 31.74 B |
| ATOM | 2995 | NH2 | ARG | B | 89 | 2.855 | 28.112 | 21.709 | 1.00 | 29.91 B |
| ATOM | 2996 | C | ARG | B | 89 | 7.141 | 23.191 | 17.997 | 1.00 | 12.87 B |
| ATOM | 2997 | O | ARG | B | 89 | 8.042 | 22.404 | 18.272 | 1.00 | 11.30 B |
| ATOM | 2998 | N | GLY | B | 90 | 6.007 | 22.829 | 17.390 | 1.00 | 10.76 B |
| ATOM | 2999 | CA | GLY | B | 90 | 5.806 | 21.452 | 17.017 | 1.00 | 12.35 B |
| ATOM | 3000 | C | GLY | B | 90 | 6.759 | 21.010 | 15.942 | 1.00 | 11.99 B |
| ATOM | 3001 | O | GLY | B | 90 | 7.139 | 19.847 | 15.870 | 1.00 | 14.46 B |
| ATOM | 3002 | N | ILE | B | 91 | 7.165 | 21.940 | 15.097 | 1.00 | 14.38 B |
| ATOM | 3003 | CA | ILE | B | 91 | 8.027 | 21.614 | 13.968 | 1.00 | 13.92 B |
| ATOM | 3004 | CB | ILE | B | 91 | 7.681 | 22.538 | 12.774 | 1.00 | 17.25 B |
| ATOM | 3005 | CG2 | ILE | B | 91 | 8.662 | 22.305 | 11.592 | 1.00 | 18.38 B |
| ATOM | 3006 | CG1 | ILE | B | 91 | 6.220 | 22.317 | 12.352 | 1.00 | 16.43 B |
| ATOM | 3007 | CD1 | ILE | B | 91 | 5.683 | 23.452 | 11.384 | 1.00 | 19.10 B |
| ATOM | 3008 | C | ILE | B | 91 | 9.507 | 21.717 | 14.263 | 1.00 | 14.95 B |
| ATOM | 3009 | O | ILE | B | 91 | 10.330 | 20.989 | 13.679 | 1.00 | 13.23 B |
| ATOM | 3010 | N | MET | B | 92 | 9.867 | 22.610 | 15.172 | 1.00 | 13.36 B |
| ATOM | 3011 | CA | MET | B | 92 | 11.275 | 22.779 | 15.503 | 1.00 | 14.20 B |
| ATOM | 3012 | CB | MET | B | 92 | 11.541 | 24.255 | 15.902 | 1.00 | 15.14 B |
| ATOM | 3013 | CG | MET | B | 92 | 11.381 | 25.299 | 14.736 | 1.00 | 14.52 B |
| ATOM | 3014 | SD | MET | B | 92 | 12.679 | 25.118 | 13.560 | 1.00 | 17.34 B |
| ATOM | 3015 | CE | MET | B | 92 | 11.857 | 24.037 | 12.319 | 1.00 | 9.40 B |
| ATOM | 3016 | C | MET | B | 92 | 11.822 | 21.886 | 16.629 | 1.00 | 12.93 B |
| ATOM | 3017 | O | MET | B | 92 | 12.987 | 21.435 | 16.585 | 1.00 | 12.02 B |
| ATOM | 3018 | N | LEU | B | 93 | 11.002 | 21.705 | 17.656 | 1.00 | 14.34 B |
| ATOM | 3019 | CA | LEU | B | 93 | 11.400 | 20.981 | 18.858 | 1.00 | 15.78 B |
| ATOM | 3020 | CB | LEU | B | 93 | 10.652 | 21.578 | 20.070 | 1.00 | 13.57 B |
| ATOM | 3021 | CG | LEU | B | 93 | 10.690 | 23.127 | 20.163 | 1.00 | 19.33 B |
| ATOM | 3022 | CD1 | LEU | B | 93 | 9.924 | 23.584 | 21.401 | 1.00 | 15.26 B |
| ATOM | 3023 | CD2 | LEU | B | 93 | 12.170 | 23.636 | 20.160 | 1.00 | 17.45 B |
| ATOM | 3024 | C | LEU | B | 93 | 11.137 | 19.481 | 18.832 | 1.00 | 17.68 B |
| ATOM | 3025 | O | LEU | B | 93 | 10.376 | 18.942 | 17.986 | 1.00 | 15.62 B |
| ATOM | 3026 | N | GLU | B | 94 | 11.738 | 18.814 | 19.805 | 1.00 | 14.03 B |
| ATOM | 3027 | CA | GLU | B | 94 | 11.553 | 17.381 | 19.952 | 1.00 | 13.77 B |
| ATOM | 3028 | CB | GLU | B | 94 | 12.277 | 16.865 | 21.221 | 1.00 | 12.90 B |
| ATOM | 3029 | CG | GLU | B | 94 | 13.778 | 16.689 | 21.012 | 1.00 | 12.37 B |
| ATOM | 3030 | CD | GLU | B | 94 | 14.461 | 16.007 | 22.244 | 1.00 | 18.93 B |
| ATOM | 3031 | OE1 | GLU | B | 94 | 14.073 | 14.847 | 22.588 | 1.00 | 17.09 B |
| ATOM | 3032 | OE2 | GLU | B | 94 | 15.378 | 16.644 | 22.830 | 1.00 | 16.53 B |
| ATOM | 3033 | C | GLU | B | 94 | 10.067 | 17.206 | 20.116 | 1.00 | 11.82 B |
| ATOM | 3034 | O | GLU | B | 94 | 9.418 | 18.078 | 20.654 | 1.00 | 12.83 B |
| ATOM | 3035 | N | PRO | B | 95 | 9.511 | 16.045 | 19.733 | 1.00 | 10.57 B |
| ATOM | 3036 | CD | PRO | B | 95 | 8.088 | 15.775 | 20.028 | 1.00 | 11.19 B |
| ATOM | 3037 | CA | PRO | B | 95 | 10.192 | 14.887 | 19.157 | 1.00 | 11.42 B |
| ATOM | 3038 | CB | PRO | B | 95 | 9.254 | 13.710 | 19.512 | 1.00 | 12.72 B |
| ATOM | 3039 | CG | PRO | B | 95 | 7.843 | 14.349 | 19.422 | 1.00 | 11.72 B |
| ATOM | 3040 | C | PRO | B | 95 | 10.437 | 15.004 | 17.629 | 1.00 | 13.53 B |
| ATOM | 3041 | O | PRO | B | 95 | 11.260 | 14.260 | 17.070 | 1.00 | 11.38 B |
| ATOM | 3042 | N | ARG | B | 96 | 9.726 | 15.908 | 16.953 | 1.00 | 12.44 B |
| ATOM | 3043 | CA | ARG | B | 96 | 9.921 | 16.041 | 15.478 | 1.00 | 14.68 B |
| ATOM | 3044 | CB | ARG | B | 96 | 8.709 | 16.765 | 14.820 | 1.00 | 15.11 B |
| ATOM | 3045 | CG | ARG | B | 96 | 7.419 | 15.916 | 14.917 | 1.00 | 10.29 B |
| ATOM | 3046 | CD | ARG | B | 96 | 6.173 | 16.792 | 14.809 | 1.00 | 9.53 B |
| ATOM | 3047 | NE | ARG | B | 96 | 4.963 | 16.064 | 15.181 | 1.00 | 11.15 B |
| ATOM | 3048 | CZ | ARG | B | 96 | 4.563 | 15.836 | 16.422 | 1.00 | 17.72 B |
| ATOM | 3049 | NH1 | ARG | B | 96 | 5.292 | 16.296 | 17.461 | 1.00 | 11.24 B |
| ATOM | 3050 | NH2 | ARG | B | 96 | 3.440 | 15.139 | 16.617 | 1.00 | 13.64 B |
| ATOM | 3051 | C | ARG | B | 96 | 11.196 | 16.769 | 15.148 | 1.00 | 13.90 B |
| ATOM | 3052 | O | ARG | B | 96 | 11.768 | 16.570 | 14.075 | 1.00 | 11.13 B |
| ATOM | 3053 | N | GLY | B | 97 | 11.646 | 17.647 | 16.054 | 1.00 | 12.77 B |
| ATOM | 3054 | CA | GLY | B | 97 | 12.919 | 18.323 | 15.797 | 1.00 | 12.77 B |
| ATOM | 3055 | C | GLY | B | 97 | 13.884 | 18.116 | 16.959 | 1.00 | 14.62 B |
| ATOM | 3056 | O | GLY | B | 97 | 13.925 | 17.021 | 17.523 | 1.00 | 11.85 B |
| ATOM | 3057 | N | HIS | B | 98 | 14.652 | 19.143 | 17.332 | 1.00 | 11.40 B |
| ATOM | 3058 | CA | HIS | B | 98 | 15.579 | 19.014 | 18.474 | 1.00 | 14.47 B |
| ATOM | 3059 | CB | HIS | B | 98 | 16.774 | 18.067 | 18.182 | 1.00 | 13.56 B |
| ATOM | 3060 | CG | HIS | B | 98 | 17.578 | 18.419 | 16.965 | 1.00 | 9.61 B |
| ATOM | 3061 | CD2 | HIS | B | 98 | 17.390 | 18.112 | 15.651 | 1.00 | 10.05 B |
| ATOM | 3062 | ND1 | HIS | B | 98 | 18.758 | 19.135 | 17.019 | 1.00 | 9.66 B |
| ATOM | 3063 | CE1 | HIS | B | 98 | 19.261 | 19.260 | 15.800 | 1.00 | 11.54 B |
| ATOM | 3064 | NE2 | HIS | B | 98 | 18.451 | 18.647 | 14.951 | 1.00 | 12.75 B |
| ATOM | 3065 | C | HIS | B | 98 | 16.069 | 20.396 | 18.818 | 1.00 | 17.08 B |
| ATOM | 3066 | O | HIS | B | 98 | 15.750 | 21.349 | 18.110 | 1.00 | 16.43 B |

TABLE 2-continued

| ATOM | 3067 | N   | ASP | B | 99  | 16.889 | 20.497 | 19.866 | 1.00 | 16.24 | B |
|------|------|-----|-----|---|-----|--------|--------|--------|------|-------|---|
| ATOM | 3068 | CA  | ASP | B | 99  | 17.345 | 21.804 | 20.365 | 1.00 | 13.35 | B |
| ATOM | 3069 | CB  | ASP | B | 99  | 18.104 | 21.628 | 21.693 | 1.00 | 14.50 | B |
| ATOM | 3070 | CG  | ASP | B | 99  | 17.203 | 21.162 | 22.820 | 1.00 | 17.36 | B |
| ATOM | 3071 | OD1 | ASP | B | 99  | 15.955 | 21.252 | 22.727 | 1.00 | 19.36 | B |
| ATOM | 3072 | OD2 | ASP | B | 99  | 17.739 | 20.705 | 23.841 | 1.00 | 21.08 | B |
| ATOM | 3073 | C   | ASP | B | 99  | 18.175 | 22.673 | 19.452 | 1.00 | 13.04 | B |
| ATOM | 3074 | O   | ASP | B | 99  | 18.403 | 23.842 | 19.774 | 1.00 | 14.23 | B |
| ATOM | 3075 | N   | ASP | B | 100 | 18.629 | 22.136 | 18.329 | 1.00 | 12.05 | B |
| ATOM | 3076 | CA  | ASP | B | 100 | 19.445 | 22.895 | 17.385 | 1.00 | 9.75  | B |
| ATOM | 3077 | CB  | ASP | B | 100 | 20.887 | 22.343 | 17.402 | 1.00 | 13.53 | B |
| ATOM | 3078 | CG  | ASP | B | 100 | 21.629 | 22.704 | 18.752 | 1.00 | 19.27 | B |
| ATOM | 3079 | OD1 | ASP | B | 100 | 22.144 | 23.833 | 18.871 | 1.00 | 15.89 | B |
| ATOM | 3080 | OD2 | ASP | B | 100 | 21.639 | 21.859 | 19.686 | 1.00 | 17.16 | B |
| ATOM | 3081 | C   | ASP | B | 100 | 18.867 | 22.883 | 15.960 | 1.00 | 10.00 | B |
| ATOM | 3082 | O   | ASP | B | 100 | 19.586 | 23.127 | 14.989 | 1.00 | 12.60 | B |
| ATOM | 3083 | N   | MET | B | 101 | 17.572 | 22.615 | 15.868 | 1.00 | 11.58 | B |
| ATOM | 3084 | CA  | MET | B | 101 | 16.846 | 22.534 | 14.602 | 1.00 | 11.02 | B |
| ATOM | 3085 | CB  | MET | B | 101 | 15.520 | 21.786 | 14.844 | 1.00 | 10.22 | B |
| ATOM | 3086 | CG  | MET | B | 101 | 14.521 | 21.670 | 13.626 | 1.00 | 11.45 | B |
| ATOM | 3087 | SD  | MET | B | 101 | 15.252 | 21.135 | 12.093 | 1.00 | 15.38 | B |
| ATOM | 3088 | CE  | MET | B | 101 | 15.915 | 19.442 | 12.492 | 1.00 | 15.52 | B |
| ATOM | 3089 | C   | MET | B | 101 | 16.599 | 23.974 | 14.134 | 1.00 | 13.90 | B |
| ATOM | 3090 | O   | MET | B | 101 | 16.526 | 24.919 | 14.958 | 1.00 | 12.10 | B |
| ATOM | 3091 | N   | PHE | B | 102 | 16.483 | 24.155 | 12.821 | 1.00 | 13.05 | B |
| ATOM | 3092 | CA  | PHE | B | 102 | 16.239 | 25.481 | 12.246 | 1.00 | 12.65 | B |
| ATOM | 3093 | CB  | PHE | B | 102 | 17.560 | 26.120 | 11.815 | 1.00 | 13.36 | B |
| ATOM | 3094 | CG  | PHE | B | 102 | 17.427 | 27.565 | 11.383 | 1.00 | 13.28 | B |
| ATOM | 3095 | CD1 | PHE | B | 102 | 17.757 | 28.597 | 12.266 | 1.00 | 15.69 | B |
| ATOM | 3096 | CD2 | PHE | B | 102 | 16.869 | 27.894 | 10.121 | 1.00 | 14.39 | B |
| ATOM | 3097 | CE1 | PHE | B | 102 | 17.536 | 29.970 | 11.923 | 1.00 | 14.81 | B |
| ATOM | 3098 | CE2 | PHE | B | 102 | 16.629 | 29.257 | 9.762  | 1.00 | 12.33 | B |
| ATOM | 3099 | CZ  | PHE | B | 102 | 16.967 | 30.292 | 10.667 | 1.00 | 20.33 | B |
| ATOM | 3100 | C   | PHE | B | 102 | 15.364 | 25.248 | 11.001 | 1.00 | 12.87 | B |
| ATOM | 3101 | O   | PHE | B | 102 | 15.454 | 24.190 | 10.391 | 1.00 | 14.63 | B |
| ATOM | 3102 | N   | GLY | B | 103 | 14.537 | 26.222 | 10.623 | 1.00 | 14.23 | B |
| ATOM | 3103 | CA  | GLY | B | 103 | 13.704 | 26.010 | 9.446  | 1.00 | 14.68 | B |
| ATOM | 3104 | C   | GLY | B | 103 | 13.023 | 27.268 | 8.927  | 1.00 | 16.05 | B |
| ATOM | 3105 | O   | GLY | B | 103 | 13.341 | 28.435 | 9.319  | 1.00 | 14.47 | B |
| ATOM | 3106 | N   | ALA | B | 104 | 12.047 | 27.044 | 8.056  | 1.00 | 14.15 | B |
| ATOM | 3107 | CA  | ALA | B | 104 | 11.382 | 28.167 | 7.426  | 1.00 | 13.51 | B |
| ATOM | 3108 | CB  | ALA | B | 104 | 12.315 | 28.715 | 6.340  | 1.00 | 9.30  | B |
| ATOM | 3109 | C   | ALA | B | 104 | 10.057 | 27.737 | 6.834  | 1.00 | 14.17 | B |
| ATOM | 3110 | O   | ALA | B | 104 | 9.891  | 26.581 | 6.519  | 1.00 | 15.19 | B |
| ATOM | 3111 | N   | PHE | B | 105 | 9.124  | 28.674 | 6.734  | 1.00 | 14.11 | B |
| ATOM | 3112 | CA  | PHE | B | 105 | 7.831  | 28.432 | 6.120  | 1.00 | 17.87 | B |
| ATOM | 3113 | CB  | PHE | B | 105 | 6.694  | 29.089 | 6.891  | 1.00 | 20.69 | B |
| ATOM | 3114 | CG  | PHE | B | 105 | 6.550  | 28.650 | 8.301  | 1.00 | 21.99 | B |
| ATOM | 3115 | CD1 | PHE | B | 105 | 6.938  | 29.487 | 9.340  | 1.00 | 25.85 | B |
| ATOM | 3116 | CD2 | PHE | B | 105 | 5.902  | 27.473 | 8.608  | 1.00 | 26.48 | B |
| ATOM | 3117 | CE1 | PHE | B | 105 | 6.651  | 29.147 | 10.671 | 1.00 | 27.88 | B |
| ATOM | 3118 | CE2 | PHE | B | 105 | 5.608  | 27.124 | 9.951  | 1.00 | 25.82 | B |
| ATOM | 3119 | CZ  | PHE | B | 105 | 5.970  | 27.948 | 10.957 | 1.00 | 24.10 | B |
| ATOM | 3120 | C   | PHE | B | 105 | 7.880  | 29.161 | 4.770  | 1.00 | 19.00 | B |
| ATOM | 3121 | O   | PHE | B | 105 | 8.374  | 30.312 | 4.701  | 1.00 | 16.48 | B |
| ATOM | 3122 | N   | LEU | B | 106 | 7.399  | 28.505 | 3.708  | 1.00 | 17.15 | B |
| ATOM | 3123 | CA  | LEU | B | 106 | 7.344  | 29.157 | 2.391  | 1.00 | 17.40 | B |
| ATOM | 3124 | CB  | LEU | B | 106 | 7.642  | 28.190 | 1.252  | 1.00 | 15.38 | B |
| ATOM | 3125 | CG  | LEU | B | 106 | 9.056  | 27.639 | 1.196  | 1.00 | 15.27 | B |
| ATOM | 3126 | CD1 | LEU | B | 106 | 9.212  | 26.884 | −0.090 | 1.00 | 13.58 | B |
| ATOM | 3127 | CD2 | LEU | B | 106 | 10.102 | 28.797 | 1.300  | 1.00 | 13.60 | B |
| ATOM | 3128 | C   | LEU | B | 106 | 5.959  | 29.727 | 2.187  | 1.00 | 16.51 | B |
| ATOM | 3129 | O   | LEU | B | 106 | 4.979  | 29.127 | 2.624  | 1.00 | 15.75 | B |
| ATOM | 3130 | N   | PHE | B | 107 | 5.903  | 30.899 | 1.541  | 1.00 | 17.32 | B |
| ATOM | 3131 | CA  | PHE | B | 107 | 4.651  | 31.622 | 1.210  | 1.00 | 16.78 | B |
| ATOM | 3132 | CB  | PHE | B | 107 | 4.432  | 32.840 | 2.114  | 1.00 | 17.59 | B |
| ATOM | 3133 | CG  | PHE | B | 107 | 4.221  | 32.509 | 3.568  | 1.00 | 21.65 | B |
| ATOM | 3134 | CD1 | PHE | B | 107 | 5.285  | 32.573 | 4.478  | 1.00 | 19.96 | B |
| ATOM | 3135 | CD2 | PHE | B | 107 | 2.963  | 32.087 | 4.022  | 1.00 | 21.02 | B |
| ATOM | 3136 | CE1 | PHE | B | 107 | 5.094  | 32.217 | 5.817  | 1.00 | 17.56 | B |
| ATOM | 3137 | CE2 | PHE | B | 107 | 2.756  | 31.725 | 5.386  | 1.00 | 19.92 | B |
| ATOM | 3138 | CZ  | PHE | B | 107 | 3.837  | 31.792 | 6.280  | 1.00 | 18.30 | B |
| ATOM | 3139 | C   | PHE | B | 107 | 4.755  | 32.207 | −0.204 | 1.00 | 17.62 | B |
| ATOM | 3140 | O   | PHE | B | 107 | 5.844  | 32.267 | −0.789 | 1.00 | 17.80 | B |
| ATOM | 3141 | N   | ASP | B | 108 | 3.618  | 32.651 | −0.739 | 1.00 | 15.56 | B |
| ATOM | 3142 | CA  | ASP | B | 108 | 3.621  | 33.349 | −2.004 | 1.00 | 17.74 | B |
| ATOM | 3143 | CB  | ASP | B | 108 | 2.201  | 33.809 | −2.370 | 1.00 | 18.05 | B |
| ATOM | 3144 | CG  | ASP | B | 108 | 1.372  | 32.706 | −2.988 | 1.00 | 20.49 | B |
| ATOM | 3145 | OD1 | ASP | B | 108 | 1.962  | 31.646 | −3.282 | 1.00 | 21.20 | B |

TABLE 2-continued

| | | | | | | | | | |
|---|---|---|---|---|---|---|---|---|---|
| ATOM | 3146 | OD2 | ASP | B | 108 | 0.138 | 32.907 | −3.173 | 1.00 | 23.28 | B |
| ATOM | 3147 | C | ASP | B | 108 | 4.436 | 34.611 | −1.786 | 1.00 | 16.97 | B |
| ATOM | 3148 | O | ASP | B | 108 | 4.354 | 35.231 | −0.723 | 1.00 | 16.00 | B |
| ATOM | 3149 | N | PRO | B | 109 | 5.223 | 35.019 | −2.784 | 1.00 | 19.99 | B |
| ATOM | 3150 | CD | PRO | B | 109 | 5.409 | 34.433 | −4.131 | 1.00 | 18.72 | B |
| ATOM | 3151 | CA | PRO | B | 109 | 6.004 | 36.246 | −2.621 | 1.00 | 20.09 | B |
| ATOM | 3152 | CB | PRO | B | 109 | 6.875 | 36.255 | −3.862 | 1.00 | 19.88 | B |
| ATOM | 3153 | CG | PRO | B | 109 | 5.944 | 35.592 | −4.905 | 1.00 | 19.20 | B |
| ATOM | 3154 | C | PRO | B | 109 | 4.996 | 37.419 | −2.660 | 1.00 | 21.67 | B |
| ATOM | 3155 | O | PRO | B | 109 | 3.939 | 37.302 | −3.294 | 1.00 | 21.73 | B |
| ATOM | 3156 | N | ILE | B | 110 | 5.326 | 38.527 | −1.986 | 1.00 | 21.64 | B |
| ATOM | 3157 | CA | ILE | B | 110 | 4.498 | 39.741 | −1.966 | 1.00 | 24.17 | B |
| ATOM | 3158 | CB | ILE | B | 110 | 4.083 | 40.152 | −0.530 | 1.00 | 23.18 | B |
| ATOM | 3159 | CG2 | ILE | B | 110 | 3.425 | 41.527 | −0.553 | 1.00 | 22.43 | B |
| ATOM | 3160 | CG1 | ILE | B | 110 | 3.120 | 39.118 | 0.047 | 1.00 | 23.36 | B |
| ATOM | 3161 | CD1 | ILE | B | 110 | 2.793 | 39.320 | 1.514 | 1.00 | 24.72 | B |
| ATOM | 3162 | C | ILE | B | 110 | 5.307 | 40.895 | −2.582 | 1.00 | 27.84 | B |
| ATOM | 3163 | O | ILE | B | 110 | 4.802 | 41.642 | −3.400 | 1.00 | 28.68 | B |
| ATOM | 3164 | N | GLU | B | 111 | 6.576 | 40.995 | −2.207 | 1.00 | 29.66 | B |
| ATOM | 3165 | CA | GLU | B | 111 | 7.474 | 42.027 | −2.686 | 1.00 | 32.69 | B |
| ATOM | 3166 | CB | GLU | B | 111 | 8.796 | 41.930 | −1.932 | 1.00 | 35.68 | B |
| ATOM | 3167 | CG | GLU | B | 111 | 9.693 | 43.110 | −2.117 | 1.00 | 41.39 | B |
| ATOM | 3168 | CD | GLU | B | 111 | 9.005 | 44.368 | −1.668 | 1.00 | 44.73 | B |
| ATOM | 3169 | OE1 | GLU | B | 111 | 8.366 | 44.337 | −0.587 | 1.00 | 48.52 | B |
| ATOM | 3170 | OE2 | GLU | B | 111 | 9.097 | 45.380 | −2.394 | 1.00 | 48.66 | B |
| ATOM | 3171 | C | GLU | B | 111 | 7.716 | 41.830 | −4.176 | 1.00 | 34.14 | B |
| ATOM | 3172 | O | GLU | B | 111 | 7.962 | 40.711 | −4.638 | 1.00 | 32.31 | B |
| ATOM | 3173 | N | GLU | B | 112 | 7.676 | 42.924 | −4.930 | 1.00 | 36.38 | B |
| ATOM | 3174 | CA | GLU | B | 112 | 7.845 | 42.845 | −6.389 | 1.00 | 36.42 | B |
| ATOM | 3175 | CB | GLU | B | 112 | 7.660 | 44.239 | −7.008 | 1.00 | 40.82 | B |
| ATOM | 3176 | CG | GLU | B | 112 | 7.541 | 44.237 | −8.534 | 1.00 | 50.01 | B |
| ATOM | 3177 | CD | GLU | B | 112 | 6.986 | 45.567 | −9.119 | 1.00 | 55.70 | B |
| ATOM | 3178 | OE1 | GLU | B | 112 | 7.033 | 45.733 | −10.364 | 1.00 | 56.98 | B |
| ATOM | 3179 | OE2 | GLU | B | 112 | 6.495 | 46.433 | −8.343 | 1.00 | 57.59 | B |
| ATOM | 3180 | C | GLU | B | 112 | 9.193 | 42.271 | −6.783 | 1.00 | 33.25 | B |
| ATOM | 3181 | O | GLU | B | 112 | 10.223 | 42.692 | −6.276 | 1.00 | 32.97 | B |
| ATOM | 3182 | N | GLY | B | 113 | 9.180 | 41.295 | −7.681 | 1.00 | 29.97 | B |
| ATOM | 3183 | CA | GLY | B | 113 | 10.421 | 40.696 | −8.129 | 1.00 | 29.24 | B |
| ATOM | 3184 | C | GLY | B | 113 | 10.854 | 39.459 | −7.356 | 1.00 | 27.93 | B |
| ATOM | 3185 | O | GLY | B | 113 | 11.863 | 38.842 | −7.694 | 1.00 | 28.34 | B |
| ATOM | 3186 | N | ALA | B | 114 | 10.104 | 39.084 | −6.325 | 1.00 | 26.08 | B |
| ATOM | 3187 | CA | ALA | B | 114 | 10.487 | 37.901 | −5.562 | 1.00 | 23.73 | B |
| ATOM | 3188 | CB | ALA | B | 114 | 10.103 | 38.083 | −4.069 | 1.00 | 21.16 | B |
| ATOM | 3189 | C | ALA | B | 114 | 9.826 | 36.650 | −6.120 | 1.00 | 20.49 | B |
| ATOM | 3190 | O | ALA | B | 114 | 8.721 | 36.711 | −6.637 | 1.00 | 22.09 | B |
| ATOM | 3191 | N | ASP | B | 115 | 10.497 | 35.515 | −5.987 | 1.00 | 19.60 | B |
| ATOM | 3192 | CA | ASP | B | 115 | 9.949 | 34.233 | −6.414 | 1.00 | 21.22 | B |
| ATOM | 3193 | CB | ASP | B | 115 | 11.087 | 33.338 | −6.898 | 1.00 | 21.99 | B |
| ATOM | 3194 | CG | ASP | B | 115 | 11.663 | 33.814 | −8.232 | 1.00 | 29.33 | B |
| ATOM | 3195 | OD1 | ASP | B | 115 | 10.843 | 33.917 | −9.192 | 1.00 | 29.52 | B |
| ATOM | 3196 | OD2 | ASP | B | 115 | 12.894 | 34.085 | −8.329 | 1.00 | 27.59 | B |
| ATOM | 3197 | C | ASP | B | 115 | 9.205 | 33.531 | −5.268 | 1.00 | 21.16 | B |
| ATOM | 3198 | O | ASP | B | 115 | 8.209 | 32.813 | −5.470 | 1.00 | 19.61 | B |
| ATOM | 3199 | N | LEU | B | 116 | 9.700 | 33.727 | −4.056 | 1.00 | 18.57 | B |
| ATOM | 3200 | CA | LEU | B | 116 | 9.124 | 33.054 | −2.902 | 1.00 | 20.02 | B |
| ATOM | 3201 | CB | LEU | B | 116 | 9.956 | 31.810 | −2.530 | 1.00 | 18.47 | B |
| ATOM | 3202 | CG | LEU | B | 116 | 10.015 | 30.620 | −3.484 | 1.00 | 23.55 | B |
| ATOM | 3203 | CD1 | LEU | B | 116 | 11.169 | 29.644 | −3.136 | 1.00 | 22.45 | B |
| ATOM | 3204 | CD2 | LEU | B | 116 | 8.679 | 29.929 | −3.366 | 1.00 | 20.45 | B |
| ATOM | 3205 | C | LEU | B | 116 | 9.176 | 33.948 | −1.711 | 1.00 | 19.28 | B |
| ATOM | 3206 | O | LEU | B | 116 | 10.174 | 34.654 | −1.526 | 1.00 | 19.41 | B |
| ATOM | 3207 | N | GLY | B | 117 | 8.112 | 33.895 | −0.914 | 1.00 | 18.20 | B |
| ATOM | 3208 | CA | GLY | B | 117 | 8.070 | 34.612 | 0.354 | 1.00 | 17.03 | B |
| ATOM | 3209 | C | GLY | B | 117 | 8.601 | 33.587 | 1.372 | 1.00 | 18.83 | B |
| ATOM | 3210 | O | GLY | B | 117 | 8.376 | 32.373 | 1.211 | 1.00 | 16.84 | B |
| ATOM | 3211 | N | ILE | B | 118 | 9.321 | 34.037 | 2.396 | 1.00 | 17.91 | B |
| ATOM | 3212 | CA | ILE | B | 118 | 9.908 | 33.094 | 3.366 | 1.00 | 17.96 | B |
| ATOM | 3213 | CB | ILE | B | 118 | 11.299 | 32.574 | 2.872 | 1.00 | 16.84 | B |
| ATOM | 3214 | CG2 | ILE | B | 118 | 12.346 | 33.706 | 2.857 | 1.00 | 16.92 | B |
| ATOM | 3215 | CG1 | ILE | B | 118 | 11.804 | 31.411 | 3.747 | 1.00 | 16.09 | B |
| ATOM | 3216 | CD1 | ILE | B | 118 | 13.066 | 30.742 | 3.147 | 1.00 | 14.59 | B |
| ATOM | 3217 | C | ILE | B | 118 | 10.024 | 33.735 | 4.731 | 1.00 | 18.80 | B |
| ATOM | 3218 | O | ILE | B | 118 | 10.341 | 34.934 | 4.842 | 1.00 | 20.74 | B |
| ATOM | 3219 | N | VAL | B | 119 | 9.663 | 32.944 | 5.738 | 1.00 | 16.15 | B |
| ATOM | 3220 | CA | VAL | B | 119 | 9.711 | 33.291 | 7.149 | 1.00 | 16.03 | B |
| ATOM | 3221 | CB | VAL | B | 119 | 8.328 | 33.325 | 7.756 | 1.00 | 15.82 | B |
| ATOM | 3222 | CG1 | VAL | B | 119 | 8.428 | 33.529 | 9.281 | 1.00 | 15.11 | B |
| ATOM | 3223 | CG2 | VAL | B | 119 | 7.515 | 34.475 | 7.115 | 1.00 | 18.56 | B |
| ATOM | 3224 | C | VAL | B | 119 | 10.559 | 32.219 | 7.879 | 1.00 | 18.50 | B |

TABLE 2-continued

| ATOM | 3225 | O | VAL | B | 119 | 10.267 | 30.992 | 7.821 | 1.00 | 15.89 | B |
|---|---|---|---|---|---|---|---|---|---|---|---|
| ATOM | 3226 | N | PHE | B | 120 | 11.618 | 32.686 | 8.541 | 1.00 | 16.22 | B |
| ATOM | 3227 | CA | PHE | B | 120 | 12.536 | 31.800 | 9.238 | 1.00 | 15.08 | B |
| ATOM | 3228 | CB | PHE | B | 120 | 13.919 | 32.413 | 9.205 | 1.00 | 17.53 | B |
| ATOM | 3229 | CG | PHE | B | 120 | 14.414 | 32.644 | 7.833 | 1.00 | 14.00 | B |
| ATOM | 3230 | CD1 | PHE | B | 120 | 14.463 | 33.938 | 7.307 | 1.00 | 14.97 | B |
| ATOM | 3231 | CD2 | PHE | B | 120 | 14.794 | 31.563 | 7.044 | 1.00 | 14.56 | B |
| ATOM | 3232 | CE1 | PHE | B | 120 | 14.888 | 34.147 | 5.989 | 1.00 | 16.92 | B |
| ATOM | 3233 | CE2 | PHE | B | 120 | 15.222 | 31.755 | 5.709 | 1.00 | 15.27 | B |
| ATOM | 3234 | CZ | PHE | B | 120 | 15.268 | 33.038 | 5.186 | 1.00 | 18.12 | B |
| ATOM | 3235 | C | PHE | B | 120 | 12.118 | 31.536 | 10.678 | 1.00 | 16.02 | B |
| ATOM | 3236 | O | PHE | B | 120 | 11.491 | 32.383 | 11.302 | 1.00 | 14.50 | B |
| ATOM | 3237 | N | MET | B | 121 | 12.476 | 30.368 | 11.213 | 1.00 | 14.96 | B |
| ATOM | 3238 | CA | MET | B | 121 | 12.085 | 30.034 | 12.597 | 1.00 | 14.05 | B |
| ATOM | 3239 | CB | MET | B | 121 | 10.754 | 29.263 | 12.602 | 1.00 | 13.80 | B |
| ATOM | 3240 | CG | MET | B | 121 | 10.803 | 27.906 | 11.834 | 1.00 | 13.67 | B |
| ATOM | 3241 | SD | MET | B | 121 | 9.276 | 26.999 | 12.007 | 1.00 | 22.65 | B |
| ATOM | 3242 | CE | MET | B | 121 | 9.109 | 26.208 | 10.361 | 1.00 | 22.43 | B |
| ATOM | 3243 | C | MET | B | 121 | 13.193 | 29.190 | 13.225 | 1.00 | 14.84 | B |
| ATOM | 3244 | O | MET | B | 121 | 14.039 | 28.649 | 12.509 | 1.00 | 13.98 | B |
| ATOM | 3245 | N | ASP | B | 122 | 13.219 | 29.098 | 14.553 | 1.00 | 16.05 | B |
| ATOM | 3246 | CA | ASP | B | 122 | 14.251 | 28.285 | 15.231 | 1.00 | 14.56 | B |
| ATOM | 3247 | CB | ASP | B | 122 | 15.556 | 29.070 | 15.385 | 1.00 | 16.40 | B |
| ATOM | 3248 | CG | ASP | B | 122 | 15.338 | 30.435 | 16.089 | 1.00 | 17.14 | B |
| ATOM | 3249 | OD1 | ASP | B | 122 | 15.593 | 31.495 | 15.466 | 1.00 | 18.16 | B |
| ATOM | 3250 | OD2 | ASP | B | 122 | 14.877 | 30.430 | 17.252 | 1.00 | 17.86 | B |
| ATOM | 3251 | C | ASP | B | 122 | 13.713 | 27.856 | 16.587 | 1.00 | 13.64 | B |
| ATOM | 3252 | O | ASP | B | 122 | 12.532 | 28.005 | 16.845 | 1.00 | 13.72 | B |
| ATOM | 3253 | N | THR | B | 123 | 14.569 | 27.357 | 17.476 | 1.00 | 13.54 | B |
| ATOM | 3254 | CA | THR | B | 123 | 14.060 | 26.864 | 18.765 | 1.00 | 13.21 | B |
| ATOM | 3255 | CB | THR | B | 123 | 15.142 | 26.038 | 19.482 | 1.00 | 13.98 | B |
| ATOM | 3256 | OG1 | THR | B | 123 | 16.294 | 26.875 | 19.727 | 1.00 | 13.78 | B |
| ATOM | 3257 | CG2 | THR | B | 123 | 15.592 | 24.911 | 18.537 | 1.00 | 12.57 | B |
| ATOM | 3258 | C | THR | B | 123 | 13.571 | 27.945 | 19.697 | 1.00 | 14.90 | B |
| ATOM | 3259 | O | THR | B | 123 | 12.849 | 27.644 | 20.639 | 1.00 | 17.35 | B |
| ATOM | 3260 | N | GLY | B | 124 | 13.921 | 29.198 | 19.438 | 1.00 | 13.04 | B |
| ATOM | 3261 | CA | GLY | B | 124 | 13.416 | 30.232 | 20.328 | 1.00 | 16.04 | B |
| ATOM | 3262 | C | GLY | B | 124 | 12.435 | 31.203 | 19.720 | 1.00 | 14.21 | B |
| ATOM | 3263 | O | GLY | B | 124 | 11.505 | 31.670 | 20.394 | 1.00 | 15.41 | B |
| ATOM | 3264 | N | GLY | B | 125 | 12.603 | 31.507 | 18.443 | 1.00 | 16.96 | B |
| ATOM | 3265 | CA | GLY | B | 125 | 11.685 | 32.449 | 17.825 | 1.00 | 14.99 | B |
| ATOM | 3266 | C | GLY | B | 125 | 11.875 | 32.551 | 16.304 | 1.00 | 16.45 | B |
| ATOM | 3267 | O | GLY | B | 125 | 12.004 | 31.536 | 15.629 | 1.00 | 13.60 | B |
| ATOM | 3268 | N | TYR | B | 126 | 11.943 | 33.778 | 15.781 | 1.00 | 14.89 | B |
| ATOM | 3269 | CA | TYR | B | 126 | 12.001 | 34.012 | 14.334 | 1.00 | 16.24 | B |
| ATOM | 3270 | CB | TYR | B | 126 | 10.621 | 34.491 | 13.862 | 1.00 | 16.59 | B |
| ATOM | 3271 | CG | TYR | B | 126 | 9.465 | 33.621 | 14.327 | 1.00 | 17.02 | B |
| ATOM | 3272 | CD1 | TYR | B | 126 | 8.965 | 33.696 | 15.657 | 1.00 | 15.28 | B |
| ATOM | 3273 | CE1 | TYR | B | 126 | 7.865 | 32.890 | 16.067 | 1.00 | 15.25 | B |
| ATOM | 3274 | CD2 | TYR | B | 126 | 8.851 | 32.730 | 13.429 | 1.00 | 16.86 | B |
| ATOM | 3275 | CE2 | TYR | B | 126 | 7.763 | 31.935 | 13.822 | 1.00 | 14.70 | B |
| ATOM | 3276 | CZ | TYR | B | 126 | 7.273 | 32.017 | 15.118 | 1.00 | 16.29 | B |
| ATOM | 3277 | OH | TYR | B | 126 | 6.176 | 31.246 | 15.429 | 1.00 | 13.26 | B |
| ATOM | 3278 | C | TYR | B | 126 | 12.994 | 35.039 | 13.888 | 1.00 | 16.63 | B |
| ATOM | 3279 | O | TYR | B | 126 | 12.797 | 36.206 | 14.149 | 1.00 | 22.61 | B |
| ATOM | 3280 | N | LEU | B | 127 | 14.048 | 34.629 | 13.200 | 1.00 | 17.28 | B |
| ATOM | 3281 | CA | LEU | B | 127 | 15.051 | 35.577 | 12.730 | 1.00 | 17.83 | B |
| ATOM | 3282 | CB | LEU | B | 127 | 16.329 | 34.826 | 12.412 | 1.00 | 15.68 | B |
| ATOM | 3283 | CG | LEU | B | 127 | 17.085 | 34.300 | 13.630 | 1.00 | 17.46 | B |
| ATOM | 3284 | CD1 | LEU | B | 127 | 18.245 | 33.477 | 13.133 | 1.00 | 13.73 | B |
| ATOM | 3285 | CD2 | LEU | B | 127 | 17.619 | 35.511 | 14.462 | 1.00 | 18.65 | B |
| ATOM | 3286 | C | LEU | B | 127 | 14.528 | 36.290 | 11.465 | 1.00 | 21.47 | B |
| ATOM | 3287 | O | LEU | B | 127 | 13.818 | 35.674 | 10.649 | 1.00 | 17.85 | B |
| ATOM | 3288 | N | ASN | B | 128 | 14.894 | 37.570 | 11.294 | 1.00 | 20.47 | B |
| ATOM | 3289 | CA | ASN | B | 128 | 14.434 | 38.334 | 10.137 | 1.00 | 18.68 | B |
| ATOM | 3290 | CB | ASN | B | 128 | 14.630 | 39.840 | 10.391 | 1.00 | 17.27 | B |
| ATOM | 3291 | CG | ASN | B | 128 | 13.611 | 40.391 | 11.386 | 1.00 | 19.71 | B |
| ATOM | 3292 | OD1 | ASN | B | 128 | 12.443 | 40.623 | 11.030 | 1.00 | 19.36 | B |
| ATOM | 3293 | ND2 | ASN | B | 128 | 14.038 | 40.582 | 12.646 | 1.00 | 13.45 | B |
| ATOM | 3294 | C | ASN | B | 128 | 15.112 | 37.897 | 8.837 | 1.00 | 19.45 | B |
| ATOM | 3295 | O | ASN | B | 128 | 14.558 | 38.096 | 7.760 | 1.00 | 18.70 | B |
| ATOM | 3296 | N | MET | B | 129 | 16.312 | 37.314 | 8.936 | 1.00 | 18.45 | B |
| ATOM | 3297 | CA | MET | B | 129 | 16.992 | 36.800 | 7.768 | 1.00 | 19.19 | B |
| ATOM | 3298 | CB | MET | B | 129 | 17.853 | 37.841 | 7.060 | 1.00 | 19.61 | B |
| ATOM | 3299 | CG | MET | B | 129 | 17.490 | 37.948 | 5.545 | 1.00 | 19.46 | B |
| ATOM | 3300 | SD | MET | B | 129 | 17.672 | 36.384 | 4.599 | 1.00 | 20.27 | B |
| ATOM | 3301 | CE | MET | B | 129 | 19.456 | 36.350 | 4.406 | 1.00 | 13.92 | B |
| ATOM | 3302 | C | MET | B | 129 | 17.855 | 35.651 | 8.229 | 1.00 | 20.29 | B |
| ATOM | 3303 | O | MET | B | 129 | 18.159 | 35.528 | 9.436 | 1.00 | 16.69 | B |

TABLE 2-continued

| | | | | | | | | | | |
|---|---|---|---|---|---|---|---|---|---|---|
| ATOM | 3304 | N | CYS | B | 130 | 18.222 | 34.793 | 7.281 | 1.00 | 14.53 B |
| ATOM | 3305 | CA | CYS | B | 130 | 19.060 | 33.659 | 7.600 | 1.00 | 13.66 B |
| ATOM | 3306 | CB | CYS | B | 130 | 18.245 | 32.468 | 8.100 | 1.00 | 15.73 B |
| ATOM | 3307 | SG | CYS | B | 130 | 19.316 | 31.057 | 8.372 | 1.00 | 18.46 B |
| ATOM | 3308 | C | CYS | B | 130 | 19.785 | 33.255 | 6.375 | 1.00 | 17.34 B |
| ATOM | 3309 | O | CYS | B | 130 | 19.181 | 32.844 | 5.354 | 1.00 | 18.61 B |
| ATOM | 3310 | N | GLY | B | 131 | 21.096 | 33.364 | 6.459 | 1.00 | 16.94 B |
| ATOM | 3311 | CA | GLY | B | 131 | 21.916 | 33.009 | 5.330 | 1.00 | 18.99 B |
| ATOM | 3312 | C | GLY | B | 131 | 21.930 | 31.539 | 4.914 | 1.00 | 19.83 B |
| ATOM | 3313 | O | GLY | B | 131 | 21.733 | 31.217 | 3.737 | 1.00 | 20.29 B |
| ATOM | 3314 | N | HIS | B | 132 | 22.178 | 30.637 | 5.844 | 1.00 | 17.57 B |
| ATOM | 3315 | CA | HIS | B | 132 | 22.294 | 29.242 | 5.457 | 1.00 | 17.84 B |
| ATOM | 3316 | CB | HIS | B | 132 | 22.842 | 28.401 | 6.619 | 1.00 | 16.45 B |
| ATOM | 3317 | CG | HIS | B | 132 | 21.775 | 27.891 | 7.528 | 1.00 | 14.73 B |
| ATOM | 3318 | CD2 | HIS | B | 132 | 20.983 | 26.794 | 7.438 | 1.00 | 18.88 B |
| ATOM | 3319 | ND1 | HIS | B | 132 | 21.342 | 28.584 | 8.637 | 1.00 | 18.66 B |
| ATOM | 3320 | CE1 | HIS | B | 132 | 20.328 | 27.940 | 9.191 | 1.00 | 17.97 B |
| ATOM | 3321 | NE2 | HIS | B | 132 | 20.087 | 26.849 | 8.482 | 1.00 | 16.80 B |
| ATOM | 3322 | C | HIS | B | 132 | 20.945 | 28.703 | 4.974 | 1.00 | 18.44 B |
| ATOM | 3323 | O | HIS | B | 132 | 20.890 | 27.859 | 4.056 | 1.00 | 22.20 B |
| ATOM | 3324 | N | ASN | B | 133 | 19.853 | 29.160 | 5.570 | 1.00 | 17.28 B |
| ATOM | 3325 | CA | ASN | B | 133 | 18.544 | 28.688 | 5.113 | 1.00 | 18.98 B |
| ATOM | 3326 | CB | ASN | B | 133 | 17.480 | 28.949 | 6.176 | 1.00 | 19.66 B |
| ATOM | 3327 | CG | ASN | B | 133 | 16.320 | 27.962 | 6.062 | 1.00 | 22.21 B |
| ATOM | 3328 | OD1 | ASN | B | 133 | 15.907 | 27.569 | 4.951 | 1.00 | 22.11 B |
| ATOM | 3329 | ND2 | ASN | B | 133 | 15.785 | 27.582 | 7.174 | 1.00 | 15.05 B |
| ATOM | 3330 | C | ASN | B | 133 | 18.115 | 29.305 | 3.739 | 1.00 | 19.26 B |
| ATOM | 3331 | O | ASN | B | 133 | 17.297 | 28.703 | 2.990 | 1.00 | 17.07 B |
| ATOM | 3332 | N | SER | B | 134 | 18.650 | 30.493 | 3.419 | 1.00 | 16.94 B |
| ATOM | 3333 | CA | SER | B | 134 | 18.405 | 31.115 | 2.120 | 1.00 | 17.36 B |
| ATOM | 3334 | CB | SER | B | 134 | 18.842 | 32.574 | 2.097 | 1.00 | 14.74 B |
| ATOM | 3335 | OG | SER | B | 134 | 17.987 | 33.329 | 2.941 | 1.00 | 13.64 B |
| ATOM | 3336 | C | SER | B | 134 | 19.197 | 30.324 | 1.066 | 1.00 | 16.67 B |
| ATOM | 3337 | O | SER | B | 134 | 18.685 | 30.012 | −0.008 | 1.00 | 18.11 B |
| ATOM | 3338 | N | ILE | B | 135 | 20.443 | 29.997 | 1.370 | 1.00 | 16.41 B |
| ATOM | 3339 | CA | ILE | B | 135 | 21.231 | 29.214 | 0.460 | 1.00 | 17.17 B |
| ATOM | 3340 | CB | ILE | B | 135 | 22.623 | 29.010 | 1.031 | 1.00 | 19.18 B |
| ATOM | 3341 | CG2 | ILE | B | 135 | 23.301 | 27.837 | 0.358 | 1.00 | 19.06 B |
| ATOM | 3342 | CG1 | ILE | B | 135 | 23.410 | 30.305 | 0.921 | 1.00 | 18.07 B |
| ATOM | 3343 | CD1 | ILE | B | 135 | 24.775 | 30.242 | 1.620 | 1.00 | 20.86 B |
| ATOM | 3344 | C | ILE | B | 135 | 20.535 | 27.852 | 0.252 | 1.00 | 19.28 B |
| ATOM | 3345 | O | ILE | B | 135 | 20.518 | 27.296 | −0.877 | 1.00 | 18.91 B |
| ATOM | 3346 | N | ALA | B | 136 | 19.931 | 27.317 | 1.313 | 1.00 | 17.04 B |
| ATOM | 3347 | CA | ALA | B | 136 | 19.215 | 26.036 | 1.183 | 1.00 | 18.05 B |
| ATOM | 3348 | CB | ALA | B | 136 | 18.861 | 25.447 | 2.582 | 1.00 | 15.60 B |
| ATOM | 3349 | C | ALA | B | 136 | 17.913 | 26.186 | 0.336 | 1.00 | 19.60 B |
| ATOM | 3350 | O | ALA | B | 136 | 17.599 | 25.312 | −0.450 | 1.00 | 16.66 B |
| ATOM | 3351 | N | ALA | B | 137 | 17.136 | 27.246 | 0.568 | 1.00 | 18.37 B |
| ATOM | 3352 | CA | ALA | B | 137 | 15.902 | 27.484 | −0.195 | 1.00 | 20.46 B |
| ATOM | 3353 | CB | ALA | B | 137 | 15.195 | 28.724 | 0.320 | 1.00 | 21.00 B |
| ATOM | 3354 | C | ALA | B | 137 | 16.156 | 27.654 | −1.717 | 1.00 | 21.34 B |
| ATOM | 3355 | O | ALA | B | 137 | 15.394 | 27.134 | −2.550 | 1.00 | 20.21 B |
| ATOM | 3356 | N | VAL | B | 138 | 17.206 | 28.406 | −2.047 | 1.00 | 20.85 B |
| ATOM | 3357 | CA | VAL | B | 138 | 17.617 | 28.642 | −3.427 | 1.00 | 21.90 B |
| ATOM | 3358 | CB | VAL | B | 138 | 18.850 | 29.570 | −3.434 | 1.00 | 22.55 B |
| ATOM | 3359 | CG1 | VAL | B | 138 | 19.525 | 29.595 | −4.795 | 1.00 | 21.36 B |
| ATOM | 3360 | CG2 | VAL | B | 138 | 18.401 | 30.967 | −3.012 | 1.00 | 18.99 B |
| ATOM | 3361 | C | VAL | B | 138 | 17.947 | 27.292 | −4.063 | 1.00 | 21.94 B |
| ATOM | 3362 | O | VAL | B | 138 | 17.449 | 26.974 | −5.141 | 1.00 | 22.22 B |
| ATOM | 3363 | N | THR | B | 139 | 18.754 | 26.490 | −3.370 | 1.00 | 21.41 B |
| ATOM | 3364 | CA | THR | B | 139 | 19.153 | 25.168 | −3.835 | 1.00 | 21.36 B |
| ATOM | 3365 | CB | THR | B | 139 | 20.113 | 24.477 | −2.818 | 1.00 | 21.83 B |
| ATOM | 3366 | OG1 | THR | B | 139 | 21.265 | 25.313 | −2.622 | 1.00 | 23.28 B |
| ATOM | 3367 | CG2 | THR | B | 139 | 20.589 | 23.089 | −3.328 | 1.00 | 16.99 B |
| ATOM | 3368 | C | THR | B | 139 | 17.934 | 24.256 | −4.065 | 1.00 | 23.71 B |
| ATOM | 3369 | O | THR | B | 139 | 17.808 | 23.601 | −5.121 | 1.00 | 21.66 B |
| ATOM | 3370 | N | ALA | B | 140 | 17.045 | 24.223 | −3.077 | 1.00 | 23.43 B |
| ATOM | 3371 | CA | ALA | B | 140 | 15.847 | 23.383 | −3.124 | 1.00 | 25.06 B |
| ATOM | 3372 | CB | ALA | B | 140 | 15.139 | 23.375 | −1.749 | 1.00 | 24.09 B |
| ATOM | 3373 | C | ALA | B | 140 | 14.868 | 23.841 | −4.195 | 1.00 | 26.55 B |
| ATOM | 3374 | O | ALA | B | 140 | 14.153 | 23.016 | −4.792 | 1.00 | 25.48 B |
| ATOM | 3375 | N | ALA | B | 141 | 14.817 | 25.154 | −4.428 | 1.00 | 25.06 B |
| ATOM | 3376 | CA | ALA | B | 141 | 13.921 | 25.694 | −5.438 | 1.00 | 25.64 B |
| ATOM | 3377 | CB | ALA | B | 141 | 13.977 | 27.228 | −5.425 | 1.00 | 24.92 B |
| ATOM | 3378 | C | ALA | B | 141 | 14.320 | 25.142 | −6.825 | 1.00 | 24.53 B |
| ATOM | 3379 | O | ALA | B | 141 | 13.468 | 24.722 | −7.596 | 1.00 | 26.15 B |
| ATOM | 3380 | N | VAL | B | 142 | 15.606 | 25.132 | −7.143 | 1.00 | 24.67 B |
| ATOM | 3381 | CA | VAL | B | 142 | 16.025 | 24.612 | −8.429 | 1.00 | 26.83 B |
| ATOM | 3382 | CB | VAL | B | 142 | 17.431 | 25.081 | −8.772 | 1.00 | 26.68 B |

TABLE 2-continued

| | | | | | | | | | | |
|---|---|---|---|---|---|---|---|---|---|---|
| ATOM | 3383 | CG1 | VAL | B | 142 | 17.922 | 24.382 | −10.044 | 1.00 | 28.13 B |
| ATOM | 3384 | CG2 | VAL | B | 142 | 17.435 | 26.603 | −8.937 | 1.00 | 28.27 B |
| ATOM | 3385 | C | VAL | B | 142 | 15.979 | 23.084 | −8.458 | 1.00 | 28.76 B |
| ATOM | 3386 | O | VAL | B | 142 | 15.421 | 22.499 | −9.369 | 1.00 | 29.04 B |
| ATOM | 3387 | N | GLU | B | 143 | 16.547 | 22.436 | −7.452 | 1.00 | 27.91 B |
| ATOM | 3388 | CA | GLU | B | 143 | 16.556 | 20.978 | −7.417 | 1.00 | 29.07 B |
| ATOM | 3389 | CB | GLU | B | 143 | 17.328 | 20.464 | −6.213 | 1.00 | 29.90 B |
| ATOM | 3390 | CG | GLU | B | 143 | 18.693 | 20.944 | −6.181 | 1.00 | 34.43 B |
| ATOM | 3391 | CD | GLU | B | 143 | 19.635 | 19.860 | −5.892 | 1.00 | 37.94 B |
| ATOM | 3392 | OE1 | GLU | B | 143 | 19.380 | 19.133 | −4.903 | 1.00 | 42.35 B |
| ATOM | 3393 | OE2 | GLU | B | 143 | 20.627 | 19.737 | −6.643 | 1.00 | 39.42 B |
| ATOM | 3394 | C | GLU | B | 143 | 15.214 | 20.297 | −7.391 | 1.00 | 28.14 B |
| ATOM | 3395 | O | GLU | B | 143 | 15.090 | 19.183 | −7.889 | 1.00 | 31.60 B |
| ATOM | 3396 | N | THR | B | 144 | 14.197 | 20.909 | −6.812 | 1.00 | 26.25 B |
| ATOM | 3397 | CA | THR | B | 144 | 12.927 | 20.219 | −6.790 | 1.00 | 25.53 B |
| ATOM | 3398 | CB | THR | B | 144 | 12.319 | 20.183 | −5.363 | 1.00 | 26.79 B |
| ATOM | 3399 | OG1 | THR | B | 144 | 11.882 | 21.499 | −4.998 | 1.00 | 25.58 B |
| ATOM | 3400 | CG2 | THR | B | 144 | 13.374 | 19.670 | −4.358 | 1.00 | 26.04 B |
| ATOM | 3401 | C | THR | B | 144 | 11.915 | 20.811 | −7.737 | 1.00 | 27.43 B |
| ATOM | 3402 | O | THR | B | 144 | 10.747 | 20.486 | −7.648 | 1.00 | 25.42 B |
| ATOM | 3403 | N | GLY | B | 145 | 12.350 | 21.693 | −8.631 | 1.00 | 30.17 B |
| ATOM | 3404 | CA | GLY | B | 145 | 11.430 | 22.253 | −9.613 | 1.00 | 33.69 B |
| ATOM | 3405 | C | GLY | B | 145 | 10.474 | 23.358 | −9.180 | 1.00 | 36.34 B |
| ATOM | 3406 | O | GLY | B | 145 | 9.420 | 23.545 | −9.800 | 1.00 | 35.36 B |
| ATOM | 3407 | N | ILE | B | 146 | 10.803 | 24.083 | −8.113 | 1.00 | 36.90 B |
| ATOM | 3408 | CA | ILE | B | 146 | 9.930 | 25.174 | −7.694 | 1.00 | 37.50 B |
| ATOM | 3409 | CB | ILE | B | 146 | 10.228 | 25.595 | −6.225 | 1.00 | 37.59 B |
| ATOM | 3410 | CG2 | ILE | B | 146 | 9.419 | 26.830 | −5.830 | 1.00 | 36.67 B |
| ATOM | 3411 | CG1 | ILE | B | 146 | 9.840 | 24.424 | −5.297 | 1.00 | 34.69 B |
| ATOM | 3412 | CD1 | ILE | B | 146 | 10.078 | 24.671 | −3.841 | 1.00 | 35.96 B |
| ATOM | 3413 | C | ILE | B | 146 | 10.158 | 26.287 | −8.723 | 1.00 | 38.72 B |
| ATOM | 3414 | O | ILE | B | 146 | 9.215 | 26.942 | −9.131 | 1.00 | 39.42 B |
| ATOM | 3415 | N | VAL | B | 147 | 11.396 | 26.503 | −9.160 | 1.00 | 40.40 B |
| ATOM | 3416 | CA | VAL | B | 147 | 11.614 | 27.491 | −10.216 | 1.00 | 43.31 B |
| ATOM | 3417 | CB | VAL | B | 147 | 12.561 | 28.662 | −9.825 | 1.00 | 41.32 B |
| ATOM | 3418 | CG1 | VAL | B | 147 | 12.086 | 29.327 | −8.540 | 1.00 | 40.94 B |
| ATOM | 3419 | CG2 | VAL | B | 147 | 13.982 | 28.178 | −9.733 | 1.00 | 40.93 B |
| ATOM | 3420 | C | VAL | B | 147 | 12.228 | 26.723 | −11.386 | 1.00 | 46.54 B |
| ATOM | 3421 | O | VAL | B | 147 | 12.945 | 25.735 | −11.196 | 1.00 | 46.96 B |
| ATOM | 3422 | N | SER | B | 148 | 11.944 | 27.155 | −12.607 | 1.00 | 49.75 B |
| ATOM | 3423 | CA | SER | B | 148 | 12.497 | 26.446 | −13.751 | 1.00 | 51.81 B |
| ATOM | 3424 | CB | SER | B | 148 | 11.530 | 26.508 | −14.938 | 1.00 | 53.22 B |
| ATOM | 3425 | OG | SER | B | 148 | 10.360 | 25.751 | −14.658 | 1.00 | 56.25 B |
| ATOM | 3426 | C | SER | B | 148 | 13.863 | 26.956 | −14.163 | 1.00 | 51.71 B |
| ATOM | 3427 | O | SER | B | 148 | 14.230 | 28.096 | −13.864 | 1.00 | 50.48 B |
| ATOM | 3428 | N | VAL | B | 149 | 14.611 | 26.088 | −14.840 | 1.00 | 51.94 B |
| ATOM | 3429 | CA | VAL | B | 149 | 15.938 | 26.426 | −15.316 | 1.00 | 53.72 B |
| ATOM | 3430 | CB | VAL | B | 149 | 16.935 | 25.276 | −15.099 | 1.00 | 52.89 B |
| ATOM | 3431 | CG1 | VAL | B | 149 | 18.334 | 25.717 | −15.520 | 1.00 | 51.41 B |
| ATOM | 3432 | CG2 | VAL | B | 149 | 16.923 | 24.844 | −13.647 | 1.00 | 52.99 B |
| ATOM | 3433 | C | VAL | B | 149 | 15.892 | 26.729 | −16.807 | 1.00 | 55.20 B |
| ATOM | 3434 | O | VAL | B | 149 | 15.491 | 25.880 | −17.601 | 1.00 | 54.20 B |
| ATOM | 3435 | N | PRO | B | 150 | 16.298 | 27.953 | −17.197 | 1.00 | 56.79 B |
| ATOM | 3436 | CD | PRO | B | 150 | 16.583 | 29.095 | −16.303 | 1.00 | 57.13 B |
| ATOM | 3437 | CA | PRO | B | 150 | 16.316 | 28.389 | −18.593 | 1.00 | 57.79 B |
| ATOM | 3438 | CB | PRO | B | 150 | 16.946 | 29.776 | −18.510 | 1.00 | 57.92 B |
| ATOM | 3439 | CG | PRO | B | 150 | 16.384 | 30.291 | −17.231 | 1.00 | 58.94 B |
| ATOM | 3440 | C | PRO | B | 150 | 17.097 | 27.460 | −19.502 | 1.00 | 58.46 B |
| ATOM | 3441 | O | PRO | B | 150 | 17.804 | 26.564 | −19.049 | 1.00 | 59.21 B |
| ATOM | 3442 | N | ALA | B | 151 | 16.960 | 27.691 | −20.801 | 1.00 | 59.07 B |
| ATOM | 3443 | CA | ALA | B | 151 | 17.639 | 26.890 | −21.800 | 1.00 | 58.12 B |
| ATOM | 3444 | CB | ALA | B | 151 | 17.212 | 27.355 | −23.204 | 1.00 | 58.67 B |
| ATOM | 3445 | C | ALA | B | 151 | 19.159 | 26.991 | −21.640 | 1.00 | 57.23 B |
| ATOM | 3446 | O | ALA | B | 151 | 19.741 | 28.082 | −21.739 | 1.00 | 56.76 B |
| ATOM | 3447 | N | ALA | B | 152 | 19.790 | 25.847 | −21.383 | 1.00 | 55.66 B |
| ATOM | 3448 | CA | ALA | B | 152 | 21.245 | 25.770 | −21.226 | 1.00 | 54.69 B |
| ATOM | 3449 | CB | ALA | B | 152 | 21.929 | 26.007 | −22.584 | 1.00 | 54.88 B |
| ATOM | 3450 | C | ALA | B | 152 | 21.834 | 26.724 | −20.175 | 1.00 | 53.31 B |
| ATOM | 3451 | O | ALA | B | 152 | 23.012 | 27.084 | −20.247 | 1.00 | 52.92 B |
| ATOM | 3452 | N | ALA | B | 153 | 21.020 | 27.121 | −19.201 | 1.00 | 51.83 B |
| ATOM | 3453 | CA | ALA | B | 153 | 21.475 | 28.026 | −18.154 | 1.00 | 49.75 B |
| ATOM | 3454 | CB | ALA | B | 153 | 20.292 | 28.474 | −17.302 | 1.00 | 49.39 B |
| ATOM | 3455 | C | ALA | B | 153 | 22.508 | 27.347 | −17.276 | 1.00 | 48.39 B |
| ATOM | 3456 | O | ALA | B | 153 | 22.451 | 26.139 | −17.063 | 1.00 | 48.67 B |
| ATOM | 3457 | N | THR | B | 154 | 23.466 | 28.125 | −16.787 | 1.00 | 46.99 B |
| ATOM | 3458 | CA | THR | B | 154 | 24.479 | 27.595 | −15.886 | 1.00 | 46.16 B |
| ATOM | 3459 | CB | THR | B | 154 | 25.925 | 27.932 | −16.340 | 1.00 | 47.69 B |
| ATOM | 3460 | OG1 | THR | B | 154 | 26.029 | 29.332 | −16.599 | 1.00 | 47.71 B |
| ATOM | 3461 | CG2 | THR | B | 154 | 26.307 | 27.147 | −17.605 | 1.00 | 49.85 B |

TABLE 2-continued

| | | | | | | | | | | |
|---|---|---|---|---|---|---|---|---|---|---|
| ATOM | 3462 | C | THR | B | 154 | 24.236 | 28.234 | −14.516 | 1.00 | 44.12 B |
| ATOM | 3463 | O | THR | B | 154 | 24.826 | 27.820 | −13.524 | 1.00 | 43.83 B |
| ATOM | 3464 | N | ASN | B | 155 | 23.369 | 29.245 | −14.483 | 1.00 | 40.84 B |
| ATOM | 3465 | CA | ASN | B | 155 | 23.033 | 29.949 | −13.244 | 1.00 | 39.51 B |
| ATOM | 3466 | CB | ASN | B | 155 | 23.846 | 31.234 | −13.111 | 1.00 | 37.17 B |
| ATOM | 3467 | CG | ASN | B | 155 | 25.324 | 30.957 | −12.970 | 1.00 | 40.83 B |
| ATOM | 3468 | OD1 | ASN | B | 155 | 26.128 | 31.322 | −13.836 | 1.00 | 44.25 B |
| ATOM | 3469 | ND2 | ASN | B | 155 | 25.696 | 30.285 | −11.892 | 1.00 | 36.63 B |
| ATOM | 3470 | C | ASN | B | 155 | 21.557 | 30.279 | −13.225 | 1.00 | 37.69 B |
| ATOM | 3471 | O | ASN | B | 155 | 21.004 | 30.736 | −14.232 | 1.00 | 38.02 B |
| ATOM | 3472 | N | VAL | B | 156 | 20.904 | 30.025 | −12.096 | 1.00 | 34.36 B |
| ATOM | 3473 | CA | VAL | B | 156 | 19.487 | 30.306 | −12.002 | 1.00 | 31.70 B |
| ATOM | 3474 | CB | VAL | B | 156 | 18.646 | 29.021 | −11.881 | 1.00 | 30.36 B |
| ATOM | 3475 | CG1 | VAL | B | 156 | 17.197 | 29.387 | −12.003 | 1.00 | 30.15 B |
| ATOM | 3476 | CG2 | VAL | B | 156 | 19.034 | 27.985 | −12.953 | 1.00 | 30.39 B |
| ATOM | 3477 | C | VAL | B | 156 | 19.184 | 31.177 | −10.790 | 1.00 | 33.16 B |
| ATOM | 3478 | O | VAL | B | 156 | 19.569 | 30.849 | −9.649 | 1.00 | 32.35 B |
| ATOM | 3479 | N | PRO | B | 157 | 18.516 | 32.320 | −11.028 | 1.00 | 32.62 B |
| ATOM | 3480 | CD | PRO | B | 157 | 18.341 | 32.926 | −12.361 | 1.00 | 32.91 B |
| ATOM | 3481 | CA | PRO | B | 157 | 18.134 | 33.271 | −9.980 | 1.00 | 29.88 B |
| ATOM | 3482 | CB | PRO | B | 157 | 17.789 | 34.553 | −10.748 | 1.00 | 29.97 B |
| ATOM | 3483 | CG | PRO | B | 157 | 18.521 | 34.395 | −12.040 | 1.00 | 34.80 B |
| ATOM | 3484 | C | PRO | B | 157 | 16.916 | 32.723 | −9.255 | 1.00 | 28.07 B |
| ATOM | 3485 | O | PRO | B | 157 | 16.046 | 32.042 | −9.836 | 1.00 | 26.47 B |
| ATOM | 3486 | N | VAL | B | 158 | 16.881 | 33.001 | −7.964 | 1.00 | 25.23 B |
| ATOM | 3487 | CA | VAL | B | 158 | 15.793 | 32.599 | −7.083 | 1.00 | 21.80 B |
| ATOM | 3488 | CB | VAL | B | 158 | 16.129 | 31.330 | −6.326 | 1.00 | 20.12 B |
| ATOM | 3489 | CG1 | VAL | B | 158 | 14.965 | 31.000 | −5.374 | 1.00 | 23.71 B |
| ATOM | 3490 | CG2 | VAL | B | 158 | 16.372 | 30.163 | −7.313 | 1.00 | 21.48 B |
| ATOM | 3491 | C | VAL | B | 158 | 15.789 | 33.761 | −6.112 | 1.00 | 21.25 B |
| ATOM | 3492 | O | VAL | B | 158 | 16.755 | 33.942 | −5.367 | 1.00 | 20.54 B |
| ATOM | 3493 | N | VAL | B | 159 | 14.726 | 34.557 | −6.114 | 1.00 | 19.96 B |
| ATOM | 3494 | CA | VAL | B | 159 | 14.699 | 35.736 | −5.229 | 1.00 | 20.32 B |
| ATOM | 3495 | CB | VAL | B | 159 | 14.304 | 36.989 | −6.031 | 1.00 | 22.57 B |
| ATOM | 3496 | CG1 | VAL | B | 159 | 14.359 | 38.209 | −5.167 | 1.00 | 18.83 B |
| ATOM | 3497 | CG2 | VAL | B | 159 | 15.261 | 37.126 | −7.264 | 1.00 | 22.85 B |
| ATOM | 3498 | C | VAL | B | 159 | 13.747 | 35.521 | −4.079 | 1.00 | 21.10 B |
| ATOM | 3499 | O | VAL | B | 159 | 12.595 | 35.127 | −4.270 | 1.00 | 22.48 B |
| ATOM | 3500 | N | LEU | B | 160 | 14.233 | 35.772 | −2.875 | 1.00 | 20.03 B |
| ATOM | 3501 | CA | LEU | B | 160 | 13.439 | 35.555 | −1.696 | 1.00 | 20.10 B |
| ATOM | 3502 | CB | LEU | B | 160 | 14.288 | 34.814 | −0.651 | 1.00 | 20.63 B |
| ATOM | 3503 | CG | LEU | B | 160 | 14.937 | 33.533 | −1.208 | 1.00 | 23.47 B |
| ATOM | 3504 | CD1 | LEU | B | 160 | 15.920 | 32.951 | −0.195 | 1.00 | 24.30 B |
| ATOM | 3505 | CD2 | LEU | B | 160 | 13.833 | 32.473 | −1.500 | 1.00 | 22.36 B |
| ATOM | 3506 | C | LEU | B | 160 | 12.933 | 36.840 | −1.108 | 1.00 | 18.11 B |
| ATOM | 3507 | O | LEU | B | 160 | 13.681 | 37.792 | −0.996 | 1.00 | 20.65 B |
| ATOM | 3508 | N | ASP | B | 161 | 11.659 | 36.848 | −0.732 | 1.00 | 16.91 B |
| ATOM | 3509 | CA | ASP | B | 161 | 10.997 | 37.952 | −0.075 | 1.00 | 18.70 B |
| ATOM | 3510 | CB | ASP | B | 161 | 9.540 | 38.034 | −0.591 | 1.00 | 21.90 B |
| ATOM | 3511 | CG | ASP | B | 161 | 8.732 | 39.110 | 0.092 | 1.00 | 23.80 B |
| ATOM | 3512 | OD1 | ASP | B | 161 | 9.331 | 39.837 | 0.907 | 1.00 | 25.02 B |
| ATOM | 3513 | OD2 | ASP | B | 161 | 7.500 | 39.229 | −0.171 | 1.00 | 23.82 B |
| ATOM | 3514 | C | ASP | B | 161 | 11.051 | 37.565 | 1.432 | 1.00 | 19.10 B |
| ATOM | 3515 | O | ASP | B | 161 | 10.319 | 36.699 | 1.884 | 1.00 | 16.38 B |
| ATOM | 3516 | N | THR | B | 162 | 11.946 | 38.199 | 2.196 | 1.00 | 21.04 B |
| ATOM | 3517 | CA | THR | B | 162 | 12.119 | 37.882 | 3.628 | 1.00 | 19.17 B |
| ATOM | 3518 | CB | THR | B | 162 | 13.619 | 37.604 | 3.974 | 1.00 | 16.98 B |
| ATOM | 3519 | OG1 | THR | B | 162 | 14.313 | 38.853 | 4.099 | 1.00 | 16.65 B |
| ATOM | 3520 | CG2 | THR | B | 162 | 14.318 | 36.796 | 2.898 | 1.00 | 13.77 B |
| ATOM | 3521 | C | THR | B | 162 | 11.673 | 39.022 | 4.553 | 1.00 | 20.82 B |
| ATOM | 3522 | O | THR | B | 162 | 11.456 | 40.153 | 4.099 | 1.00 | 22.61 B |
| ATOM | 3523 | N | PRO | B | 163 | 11.529 | 38.745 | 5.870 | 1.00 | 21.15 B |
| ATOM | 3524 | CD | PRO | B | 163 | 11.458 | 37.422 | 6.539 | 1.00 | 19.59 B |
| ATOM | 3525 | CA | PRO | B | 163 | 11.115 | 39.819 | 6.786 | 1.00 | 19.48 B |
| ATOM | 3526 | CB | PRO | B | 163 | 10.915 | 39.087 | 8.119 | 1.00 | 18.43 B |
| ATOM | 3527 | CG | PRO | B | 163 | 10.426 | 37.666 | 7.631 | 1.00 | 17.54 B |
| ATOM | 3528 | C | PRO | B | 163 | 12.132 | 40.980 | 6.891 | 1.00 | 19.63 B |
| ATOM | 3529 | O | PRO | B | 163 | 11.789 | 42.060 | 7.367 | 1.00 | 20.79 B |
| ATOM | 3530 | N | ALA | B | 164 | 13.362 | 40.757 | 6.444 | 1.00 | 18.72 B |
| ATOM | 3531 | CA | ALA | B | 164 | 14.395 | 41.802 | 6.459 | 1.00 | 21.68 B |
| ATOM | 3532 | CB | ALA | B | 164 | 15.793 | 41.223 | 6.888 | 1.00 | 17.32 B |
| ATOM | 3533 | C | ALA | B | 164 | 14.551 | 42.460 | 5.083 | 1.00 | 22.84 B |
| ATOM | 3534 | O | ALA | B | 164 | 15.340 | 43.389 | 4.952 | 1.00 | 20.27 B |
| ATOM | 3535 | N | GLY | B | 165 | 13.818 | 41.985 | 4.068 | 1.00 | 21.60 B |
| ATOM | 3536 | CA | GLY | B | 165 | 13.982 | 42.549 | 2.736 | 1.00 | 21.56 B |
| ATOM | 3537 | C | GLY | B | 165 | 14.259 | 41.520 | 1.635 | 1.00 | 22.44 B |
| ATOM | 3538 | O | GLY | B | 165 | 14.303 | 40.309 | 1.886 | 1.00 | 20.06 B |
| ATOM | 3539 | N | LEU | B | 166 | 14.460 | 42.015 | 0.417 | 1.00 | 22.49 B |
| ATOM | 3540 | CA | LEU | B | 166 | 14.700 | 41.188 | −0.774 | 1.00 | 24.05 B |

TABLE 2-continued

| ATOM | 3541 | CB | LEU | B | 166 | 14.437 | 42.023 | −2.042 | 1.00 | 28.16 | B |
| ATOM | 3542 | CG | LEU | B | 166 | 13.932 | 41.314 | −3.307 | 1.00 | 33.49 | B |
| ATOM | 3543 | CD1 | LEU | B | 166 | 12.568 | 40.662 | −3.005 | 1.00 | 31.68 | B |
| ATOM | 3544 | CD2 | LEU | B | 166 | 13.796 | 42.325 | −4.459 | 1.00 | 32.73 | B |
| ATOM | 3545 | C | LEU | B | 166 | 16.117 | 40.626 | −0.791 | 1.00 | 23.51 | B |
| ATOM | 3546 | O | LEU | B | 166 | 17.097 | 41.360 | −0.684 | 1.00 | 21.23 | B |
| ATOM | 3547 | N | VAL | B | 167 | 16.216 | 39.308 | −0.908 | 1.00 | 21.21 | B |
| ATOM | 3548 | CA | VAL | B | 167 | 17.483 | 38.617 | −0.924 | 1.00 | 19.79 | B |
| ATOM | 3549 | CB | VAL | B | 167 | 17.510 | 37.514 | 0.221 | 1.00 | 20.52 | B |
| ATOM | 3550 | CG1 | VAL | B | 167 | 18.758 | 36.572 | 0.050 | 1.00 | 21.30 | B |
| ATOM | 3551 | CG2 | VAL | B | 167 | 17.604 | 38.196 | 1.592 | 1.00 | 16.75 | B |
| ATOM | 3552 | C | VAL | B | 167 | 17.597 | 37.968 | −2.324 | 1.00 | 23.36 | B |
| ATOM | 3553 | O | VAL | B | 167 | 16.783 | 37.121 | −2.686 | 1.00 | 22.28 | B |
| ATOM | 3554 | N | ARG | B | 168 | 18.596 | 38.355 | −3.107 | 1.00 | 22.86 | B |
| ATOM | 3555 | CA | ARG | B | 168 | 18.722 | 37.773 | −4.446 | 1.00 | 26.01 | B |
| ATOM | 3556 | CB | ARG | B | 168 | 19.123 | 38.855 | −5.459 | 1.00 | 25.29 | B |
| ATOM | 3557 | CG | ARG | B | 168 | 18.017 | 39.900 | −5.600 | 1.00 | 29.89 | B |
| ATOM | 3558 | CD | ARG | B | 168 | 18.397 | 41.075 | −6.511 | 1.00 | 36.82 | B |
| ATOM | 3559 | NE | ARG | B | 168 | 17.202 | 41.890 | −6.756 | 1.00 | 44.36 | B |
| ATOM | 3560 | CZ | ARG | B | 168 | 16.272 | 41.631 | −7.683 | 1.00 | 45.86 | B |
| ATOM | 3561 | NH1 | ARG | B | 168 | 16.383 | 40.581 | −8.497 | 1.00 | 46.79 | B |
| ATOM | 3562 | NH2 | ARG | B | 168 | 15.197 | 42.408 | −7.768 | 1.00 | 49.79 | B |
| ATOM | 3563 | C | ARG | B | 168 | 19.700 | 36.623 | −4.505 | 1.00 | 25.13 | B |
| ATOM | 3564 | O | ARG | B | 168 | 20.906 | 36.824 | −4.427 | 1.00 | 26.32 | B |
| ATOM | 3565 | N | GLY | B | 169 | 19.173 | 35.415 | −4.664 | 1.00 | 23.45 | B |
| ATOM | 3566 | CA | GLY | B | 169 | 20.042 | 34.260 | −4.732 | 1.00 | 24.17 | B |
| ATOM | 3567 | C | GLY | B | 169 | 20.247 | 33.741 | −6.145 | 1.00 | 25.05 | B |
| ATOM | 3568 | O | GLY | B | 169 | 19.486 | 34.088 | −7.075 | 1.00 | 24.68 | B |
| ATOM | 3569 | N | THR | B | 170 | 21.276 | 32.908 | −6.295 | 1.00 | 24.50 | B |
| ATOM | 3570 | CA | THR | B | 170 | 21.626 | 32.296 | −7.574 | 1.00 | 25.20 | B |
| ATOM | 3571 | CB | THR | B | 170 | 22.833 | 33.029 | −8.273 | 1.00 | 25.09 | B |
| ATOM | 3572 | OG1 | THR | B | 170 | 22.546 | 34.415 | −8.404 | 1.00 | 25.53 | B |
| ATOM | 3573 | CG2 | THR | B | 170 | 23.097 | 32.455 | −9.684 | 1.00 | 26.85 | B |
| ATOM | 3574 | C | THR | B | 170 | 22.082 | 30.857 | −7.331 | 1.00 | 24.77 | B |
| ATOM | 3575 | O | THR | B | 170 | 23.003 | 30.620 | −6.546 | 1.00 | 26.30 | B |
| ATOM | 3576 | N | ALA | B | 171 | 21.432 | 29.893 | −7.969 | 1.00 | 24.50 | B |
| ATOM | 3577 | CA | ALA | B | 171 | 21.890 | 28.505 | −7.844 | 1.00 | 25.22 | B |
| ATOM | 3578 | CB | ALA | B | 171 | 20.740 | 27.548 | −8.070 | 1.00 | 25.22 | B |
| ATOM | 3579 | C | ALA | B | 171 | 22.916 | 28.354 | −8.969 | 1.00 | 27.75 | B |
| ATOM | 3580 | O | ALA | B | 171 | 22.616 | 28.723 | −10.129 | 1.00 | 27.37 | B |
| ATOM | 3581 | N | HIS | B | 172 | 24.118 | 27.868 | −8.648 | 1.00 | 26.80 | B |
| ATOM | 3582 | CA | HIS | B | 172 | 25.146 | 27.656 | −9.659 | 1.00 | 30.31 | B |
| ATOM | 3583 | CB | HIS | B | 172 | 26.509 | 28.027 | −9.097 | 1.00 | 30.88 | B |
| ATOM | 3584 | CG | HIS | B | 172 | 26.558 | 29.419 | −8.553 | 1.00 | 33.46 | B |
| ATOM | 3585 | CD2 | HIS | B | 172 | 26.765 | 29.885 | −7.295 | 1.00 | 34.34 | B |
| ATOM | 3586 | ND1 | HIS | B | 172 | 26.361 | 30.530 | −9.345 | 1.00 | 34.41 | B |
| ATOM | 3587 | CE1 | HIS | B | 172 | 26.451 | 31.620 | −8.598 | 1.00 | 34.92 | B |
| ATOM | 3588 | NE2 | HIS | B | 172 | 26.697 | 31.256 | −7.353 | 1.00 | 33.67 | B |
| ATOM | 3589 | C | HIS | B | 172 | 25.061 | 26.177 | −10.023 | 1.00 | 33.61 | B |
| ATOM | 3590 | O | HIS | B | 172 | 25.249 | 25.306 | −9.179 | 1.00 | 32.86 | B |
| ATOM | 3591 | N | LEU | B | 173 | 24.749 | 25.893 | −11.279 | 1.00 | 35.30 | B |
| ATOM | 3592 | CA | LEU | B | 173 | 24.558 | 24.511 | −11.686 | 1.00 | 39.94 | B |
| ATOM | 3593 | CB | LEU | B | 173 | 23.625 | 24.473 | −12.894 | 1.00 | 38.88 | B |
| ATOM | 3594 | CG | LEU | B | 173 | 22.308 | 25.249 | −12.780 | 1.00 | 40.04 | B |
| ATOM | 3595 | CD1 | LEU | B | 173 | 21.597 | 25.202 | −14.130 | 1.00 | 40.28 | B |
| ATOM | 3596 | CD2 | LEU | B | 173 | 21.415 | 24.646 | −11.701 | 1.00 | 38.11 | B |
| ATOM | 3597 | C | LEU | B | 173 | 25.797 | 23.671 | −11.961 | 1.00 | 43.11 | B |
| ATOM | 3598 | O | LEU | B | 173 | 26.865 | 24.176 | −12.300 | 1.00 | 42.30 | B |
| ATOM | 3599 | N | GLN | B | 174 | 25.641 | 22.368 | −11.778 | 1.00 | 48.56 | B |
| ATOM | 3600 | CA | GLN | B | 174 | 26.724 | 21.426 | −12.034 | 1.00 | 54.90 | B |
| ATOM | 3601 | CB | GLN | B | 174 | 26.392 | 20.071 | −11.387 | 1.00 | 58.00 | B |
| ATOM | 3602 | CG | GLN | B | 174 | 27.584 | 19.138 | −11.234 | 1.00 | 63.64 | B |
| ATOM | 3603 | CD | GLN | B | 174 | 28.784 | 19.836 | −10.598 | 1.00 | 67.39 | B |
| ATOM | 3604 | OE1 | GLN | B | 174 | 29.470 | 20.640 | −11.244 | 1.00 | 69.26 | B |
| ATOM | 3605 | NE2 | GLN | B | 174 | 29.033 | 19.545 | −9.319 | 1.00 | 68.38 | B |
| ATOM | 3606 | C | GLN | B | 174 | 26.841 | 21.285 | −13.564 | 1.00 | 57.02 | B |
| ATOM | 3607 | O | GLN | B | 174 | 25.848 | 20.988 | −14.243 | 1.00 | 55.17 | B |
| ATOM | 3608 | N | SER | B | 175 | 28.045 | 21.529 | −14.087 | 1.00 | 60.30 | B |
| ATOM | 3609 | CA | SER | B | 175 | 28.359 | 21.451 | −15.528 | 1.00 | 64.34 | B |
| ATOM | 3610 | CB | SER | B | 175 | 29.707 | 20.764 | −15.738 | 1.00 | 65.32 | B |
| ATOM | 3611 | OG | SER | B | 175 | 30.740 | 21.450 | −15.057 | 1.00 | 70.17 | B |
| ATOM | 3612 | C | SER | B | 175 | 27.346 | 20.747 | −16.421 | 1.00 | 65.30 | B |
| ATOM | 3613 | O | SER | B | 175 | 26.506 | 21.374 | −17.061 | 1.00 | 66.46 | B |
| ATOM | 3614 | N | GLY | B | 176 | 27.440 | 19.432 | −16.485 | 1.00 | 66.38 | B |
| ATOM | 3615 | CA | GLY | B | 176 | 26.515 | 18.704 | −17.327 | 1.00 | 68.88 | B |
| ATOM | 3616 | C | GLY | B | 176 | 25.218 | 18.276 | −16.657 | 1.00 | 69.36 | B |
| ATOM | 3617 | O | GLY | B | 176 | 24.995 | 17.079 | −16.440 | 1.00 | 70.97 | B |
| ATOM | 3618 | N | THR | B | 177 | 24.361 | 19.232 | −16.319 | 1.00 | 68.19 | B |
| ATOM | 3619 | CA | THR | B | 177 | 23.087 | 18.888 | −15.699 | 1.00 | 67.44 | B |

TABLE 2-continued

| ATOM | 3620 | CB | THR | B | 177 | 23.196 | 18.732 | −14.158 | 1.00 | 68.88 | B |
|---|---|---|---|---|---|---|---|---|---|---|---|
| ATOM | 3621 | OG1 | THR | B | 177 | 23.520 | 19.996 | −13.562 | 1.00 | 68.73 | B |
| ATOM | 3622 | CG2 | THR | B | 177 | 24.268 | 17.700 | −13.792 | 1.00 | 69.18 | B |
| ATOM | 3623 | C | THR | B | 177 | 22.050 | 19.946 | −15.991 | 1.00 | 65.83 | B |
| ATOM | 3624 | O | THR | B | 177 | 22.375 | 21.065 | −16.390 | 1.00 | 65.29 | B |
| ATOM | 3625 | N | ALA | B | 178 | 20.794 | 19.585 | −15.792 | 1.00 | 64.55 | B |
| ATOM | 3626 | CA | ALA | B | 178 | 19.708 | 20.518 | −16.025 | 1.00 | 63.40 | B |
| ATOM | 3627 | CB | ALA | B | 178 | 18.524 | 19.787 | −16.682 | 1.00 | 63.43 | B |
| ATOM | 3628 | C | ALA | B | 178 | 19.277 | 21.174 | −14.702 | 1.00 | 62.42 | B |
| ATOM | 3629 | O | ALA | B | 178 | 18.973 | 22.370 | −14.662 | 1.00 | 62.90 | B |
| ATOM | 3630 | N | SER | B | 179 | 19.268 | 20.404 | −13.615 | 1.00 | 59.73 | B |
| ATOM | 3631 | CA | SER | B | 179 | 18.852 | 20.962 | −12.337 | 1.00 | 56.34 | B |
| ATOM | 3632 | CB | SER | B | 179 | 17.379 | 20.629 | −12.080 | 1.00 | 56.87 | B |
| ATOM | 3633 | OG | SER | B | 179 | 17.118 | 19.249 | −12.291 | 1.00 | 56.80 | B |
| ATOM | 3634 | C | SER | B | 179 | 19.694 | 20.557 | −11.129 | 1.00 | 54.13 | B |
| ATOM | 3635 | O | SER | B | 179 | 19.246 | 20.694 | −9.982 | 1.00 | 52.99 | B |
| ATOM | 3636 | N | GLU | B | 180 | 20.905 | 20.060 | −11.376 | 1.00 | 50.55 | B |
| ATOM | 3637 | CA | GLU | B | 180 | 21.793 | 19.681 | −10.280 | 1.00 | 46.87 | B |
| ATOM | 3638 | CB | GLU | B | 180 | 22.818 | 18.639 | −10.725 | 1.00 | 49.20 | B |
| ATOM | 3639 | CG | GLU | B | 180 | 22.326 | 17.211 | −10.727 | 1.00 | 57.97 | B |
| ATOM | 3640 | CD | GLU | B | 180 | 23.426 | 16.227 | −10.299 | 1.00 | 61.97 | B |
| ATOM | 3641 | OE1 | GLU | B | 180 | 24.557 | 16.301 | −10.846 | 1.00 | 62.69 | B |
| ATOM | 3642 | OE2 | GLU | B | 180 | 23.154 | 15.382 | −9.408 | 1.00 | 64.41 | B |
| ATOM | 3643 | C | GLU | B | 180 | 22.534 | 20.945 | −9.816 | 1.00 | 41.07 | B |
| ATOM | 3644 | O | GLU | B | 180 | 23.184 | 21.620 | −10.611 | 1.00 | 39.10 | B |
| ATOM | 3645 | N | VAL | B | 181 | 22.455 | 21.249 | −8.533 | 1.00 | 34.98 | B |
| ATOM | 3646 | CA | VAL | B | 181 | 23.109 | 22.447 | −8.019 | 1.00 | 31.38 | B |
| ATOM | 3647 | CB | VAL | B | 181 | 22.172 | 23.137 | −7.021 | 1.00 | 29.36 | B |
| ATOM | 3648 | CG1 | VAL | B | 181 | 22.868 | 24.287 | −6.323 | 1.00 | 27.12 | B |
| ATOM | 3649 | CG2 | VAL | B | 181 | 20.938 | 23.589 | −7.736 | 1.00 | 25.04 | B |
| ATOM | 3650 | C | VAL | B | 181 | 24.454 | 22.166 | −7.353 | 1.00 | 31.06 | B |
| ATOM | 3651 | O | VAL | B | 181 | 24.522 | 21.316 | −6.453 | 1.00 | 29.88 | B |
| ATOM | 3652 | N | SER | B | 182 | 25.517 | 22.857 | −7.788 | 1.00 | 28.94 | B |
| ATOM | 3653 | CA | SER | B | 182 | 26.833 | 22.657 | −7.167 | 1.00 | 31.41 | B |
| ATOM | 3654 | CB | SER | B | 182 | 27.991 | 22.966 | −8.119 | 1.00 | 30.83 | B |
| ATOM | 3655 | OG | SER | B | 182 | 27.721 | 24.166 | −8.790 | 1.00 | 38.77 | B |
| ATOM | 3656 | C | SER | B | 182 | 26.993 | 23.500 | −5.914 | 1.00 | 30.33 | B |
| ATOM | 3657 | O | SER | B | 182 | 27.660 | 23.083 | −4.978 | 1.00 | 31.11 | B |
| ATOM | 3658 | N | ASN | B | 183 | 26.405 | 24.689 | −5.910 | 1.00 | 28.41 | B |
| ATOM | 3659 | CA | ASN | B | 183 | 26.431 | 25.574 | −4.737 | 1.00 | 28.22 | B |
| ATOM | 3660 | CB | ASN | B | 183 | 27.853 | 26.033 | −4.361 | 1.00 | 28.80 | B |
| ATOM | 3661 | CG | ASN | B | 183 | 28.582 | 26.720 | −5.501 | 1.00 | 31.71 | B |
| ATOM | 3662 | OD1 | ASN | B | 183 | 28.246 | 27.817 | −5.885 | 1.00 | 31.34 | B |
| ATOM | 3663 | ND2 | ASN | B | 183 | 29.584 | 26.051 | −6.053 | 1.00 | 36.11 | B |
| ATOM | 3664 | C | ASN | B | 183 | 25.514 | 26.762 | −5.043 | 1.00 | 27.08 | B |
| ATOM | 3665 | O | ASN | B | 183 | 24.967 | 26.885 | −6.158 | 1.00 | 22.50 | B |
| ATOM | 3666 | N | ALA | B | 184 | 25.300 | 27.614 | −4.060 | 1.00 | 23.13 | B |
| ATOM | 3667 | CA | ALA | B | 184 | 24.402 | 28.727 | −4.288 | 1.00 | 21.08 | B |
| ATOM | 3668 | CB | ALA | B | 184 | 23.037 | 28.422 | −3.729 | 1.00 | 21.32 | B |
| ATOM | 3669 | C | ALA | B | 184 | 24.976 | 29.901 | −3.566 | 1.00 | 22.75 | B |
| ATOM | 3670 | O | ALA | B | 184 | 25.694 | 29.761 | −2.592 | 1.00 | 24.83 | B |
| ATOM | 3671 | N | SER | B | 185 | 24.625 | 31.068 | −4.041 | 1.00 | 22.72 | B |
| ATOM | 3672 | CA | SER | B | 185 | 25.103 | 32.284 | −3.450 | 1.00 | 26.57 | B |
| ATOM | 3673 | CB | SER | B | 185 | 26.144 | 32.874 | −4.418 | 1.00 | 28.05 | B |
| ATOM | 3674 | OG | SER | B | 185 | 26.220 | 34.266 | −4.248 | 1.00 | 41.17 | B |
| ATOM | 3675 | C | SER | B | 185 | 23.879 | 33.198 | −3.245 | 1.00 | 25.15 | B |
| ATOM | 3676 | O | SER | B | 185 | 22.852 | 33.042 | −3.927 | 1.00 | 27.19 | B |
| ATOM | 3677 | N | ILE | B | 186 | 23.942 | 34.086 | −2.264 | 1.00 | 24.64 | B |
| ATOM | 3678 | CA | ILE | B | 186 | 22.843 | 35.005 | −2.027 | 1.00 | 23.33 | B |
| ATOM | 3679 | CB | ILE | B | 186 | 22.035 | 34.670 | −0.735 | 1.00 | 25.15 | B |
| ATOM | 3680 | CG2 | ILE | B | 186 | 21.287 | 33.323 | −0.888 | 1.00 | 23.30 | B |
| ATOM | 3681 | CG1 | ILE | B | 186 | 22.965 | 34.660 | 0.465 | 1.00 | 25.44 | B |
| ATOM | 3682 | CD1 | ILE | B | 186 | 22.267 | 34.359 | 1.756 | 1.00 | 27.40 | B |
| ATOM | 3683 | C | ILE | B | 186 | 23.404 | 36.419 | −1.851 | 1.00 | 24.37 | B |
| ATOM | 3684 | O | ILE | B | 186 | 24.489 | 36.601 | −1.290 | 1.00 | 23.24 | B |
| ATOM | 3685 | N | ILE | B | 187 | 22.697 | 37.403 | −2.391 | 1.00 | 23.02 | B |
| ATOM | 3686 | CA | ILE | B | 187 | 23.082 | 38.798 | −2.207 | 1.00 | 22.84 | B |
| ATOM | 3687 | CB | ILE | B | 187 | 22.846 | 39.621 | −3.486 | 1.00 | 24.39 | B |
| ATOM | 3688 | CG2 | ILE | B | 187 | 23.191 | 41.079 | −3.214 | 1.00 | 24.85 | B |
| ATOM | 3689 | CG1 | ILE | B | 187 | 23.755 | 39.069 | −4.601 | 1.00 | 26.00 | B |
| ATOM | 3690 | CD1 | ILE | B | 187 | 23.482 | 39.621 | −6.007 | 1.00 | 31.22 | B |
| ATOM | 3691 | C | ILE | B | 187 | 22.145 | 39.237 | −1.072 | 1.00 | 21.88 | B |
| ATOM | 3692 | O | ILE | B | 187 | 20.928 | 39.307 | −1.244 | 1.00 | 18.06 | B |
| ATOM | 3693 | N | ASN | B | 188 | 22.728 | 39.500 | 0.097 | 1.00 | 20.03 | B |
| ATOM | 3694 | CA | ASN | B | 188 | 21.969 | 39.867 | 1.298 | 1.00 | 20.82 | B |
| ATOM | 3695 | CB | ASN | B | 188 | 22.924 | 39.756 | 2.502 | 1.00 | 18.72 | B |
| ATOM | 3696 | CG | ASN | B | 188 | 22.203 | 39.619 | 3.831 | 1.00 | 20.78 | B |
| ATOM | 3697 | OD1 | ASN | B | 188 | 20.971 | 39.545 | 3.897 | 1.00 | 19.18 | B |
| ATOM | 3698 | ND2 | ASN | B | 188 | 22.986 | 39.565 | 4.913 | 1.00 | 22.75 | B |

TABLE 2-continued

| | | | | | | | | | | |
|---|---|---|---|---|---|---|---|---|---|---|
| ATOM | 3699 | C | ASN | B | 188 | 21.362 | 41.273 | 1.244 | 1.00 | 21.54 B |
| ATOM | 3700 | O | ASN | B | 188 | 21.694 | 42.057 | 0.361 | 1.00 | 23.70 B |
| ATOM | 3701 | N | VAL | B | 189 | 20.468 | 41.583 | 2.183 | 1.00 | 22.12 B |
| ATOM | 3702 | CA | VAL | B | 189 | 19.920 | 42.928 | 2.298 | 1.00 | 21.60 B |
| ATOM | 3703 | CB | VAL | B | 189 | 18.761 | 42.999 | 3.337 | 1.00 | 21.23 B |
| ATOM | 3704 | CG1 | VAL | B | 189 | 17.710 | 41.985 | 2.966 | 1.00 | 19.07 B |
| ATOM | 3705 | CG2 | VAL | B | 189 | 19.298 | 42.704 | 4.794 | 1.00 | 18.68 B |
| ATOM | 3706 | C | VAL | B | 189 | 21.118 | 43.728 | 2.800 | 1.00 | 21.80 B |
| ATOM | 3707 | O | VAL | B | 189 | 22.119 | 43.162 | 3.275 | 1.00 | 20.03 B |
| ATOM | 3708 | N | PRO | B | 190 | 21.058 | 45.067 | 2.683 | 1.00 | 23.62 B |
| ATOM | 3709 | CD | PRO | B | 190 | 19.952 | 45.927 | 2.196 | 1.00 | 22.76 B |
| ATOM | 3710 | CA | PRO | B | 190 | 22.212 | 45.863 | 3.149 | 1.00 | 20.85 B |
| ATOM | 3711 | CB | PRO | B | 190 | 21.714 | 47.317 | 2.999 | 1.00 | 21.69 B |
| ATOM | 3712 | CG | PRO | B | 190 | 20.673 | 47.221 | 1.827 | 1.00 | 24.78 B |
| ATOM | 3713 | C | PRO | B | 190 | 22.659 | 45.559 | 4.594 | 1.00 | 20.80 B |
| ATOM | 3714 | O | PRO | B | 190 | 21.832 | 45.438 | 5.495 | 1.00 | 18.40 B |
| ATOM | 3715 | N | SER | B | 191 | 23.964 | 45.458 | 4.799 | 1.00 | 20.03 B |
| ATOM | 3716 | CA | SER | B | 191 | 24.545 | 45.211 | 6.119 | 1.00 | 21.28 B |
| ATOM | 3717 | CB | SER | B | 191 | 25.562 | 44.058 | 6.045 | 1.00 | 19.59 B |
| ATOM | 3718 | OG | SER | B | 191 | 24.942 | 42.867 | 5.651 | 1.00 | 24.93 B |
| ATOM | 3719 | C | SER | B | 191 | 25.324 | 46.461 | 6.602 | 1.00 | 20.60 B |
| ATOM | 3720 | O | SER | B | 191 | 25.823 | 47.224 | 5.792 | 1.00 | 21.30 B |
| ATOM | 3721 | N | PHE | B | 192 | 25.515 | 46.609 | 7.904 | 1.00 | 19.63 B |
| ATOM | 3722 | CA | PHE | B | 192 | 26.282 | 47.745 | 8.393 | 1.00 | 21.84 B |
| ATOM | 3723 | CB | PHE | B | 192 | 25.417 | 49.033 | 8.285 | 1.00 | 18.92 B |
| ATOM | 3724 | CG | PHE | B | 192 | 23.981 | 48.865 | 8.823 | 1.00 | 21.72 B |
| ATOM | 3725 | CD1 | PHE | B | 192 | 23.697 | 49.027 | 10.184 | 1.00 | 20.59 B |
| ATOM | 3726 | CD2 | PHE | B | 192 | 22.923 | 48.545 | 7.953 | 1.00 | 22.45 B |
| ATOM | 3727 | CE1 | PHE | B | 192 | 22.397 | 48.885 | 10.674 | 1.00 | 23.50 B |
| ATOM | 3728 | CE2 | PHE | B | 192 | 21.609 | 48.394 | 8.426 | 1.00 | 22.94 B |
| ATOM | 3729 | CZ | PHE | B | 192 | 21.341 | 48.568 | 9.800 | 1.00 | 22.39 B |
| ATOM | 3730 | C | PHE | B | 192 | 26.795 | 47.623 | 9.824 | 1.00 | 21.60 B |
| ATOM | 3731 | O | PHE | B | 192 | 26.179 | 46.970 | 10.672 | 1.00 | 20.75 B |
| ATOM | 3732 | N | LEU | B | 193 | 27.931 | 48.254 | 10.092 | 1.00 | 22.13 B |
| ATOM | 3733 | CA | LEU | B | 193 | 28.428 | 48.330 | 11.459 | 1.00 | 22.04 B |
| ATOM | 3734 | CB | LEU | B | 193 | 29.835 | 48.921 | 11.465 | 1.00 | 23.72 B |
| ATOM | 3735 | CG | LEU | B | 193 | 30.502 | 49.181 | 12.815 | 1.00 | 22.77 B |
| ATOM | 3736 | CD1 | LEU | B | 193 | 30.406 | 47.931 | 13.686 | 1.00 | 22.50 B |
| ATOM | 3737 | CD2 | LEU | B | 193 | 31.970 | 49.572 | 12.558 | 1.00 | 23.46 B |
| ATOM | 3738 | C | LEU | B | 193 | 27.418 | 49.335 | 12.068 | 1.00 | 21.09 B |
| ATOM | 3739 | O | LEU | B | 193 | 27.066 | 50.322 | 11.423 | 1.00 | 22.33 B |
| ATOM | 3740 | N | TYR | B | 194 | 26.941 | 49.064 | 13.278 | 1.00 | 21.78 B |
| ATOM | 3741 | CA | TYR | B | 194 | 25.950 | 49.893 | 13.970 | 1.00 | 22.47 B |
| ATOM | 3742 | CB | TYR | B | 194 | 24.784 | 49.006 | 14.460 | 1.00 | 22.09 B |
| ATOM | 3743 | CG | TYR | B | 194 | 23.648 | 49.707 | 15.179 | 1.00 | 18.54 B |
| ATOM | 3744 | CD1 | TYR | B | 194 | 23.598 | 49.765 | 16.583 | 1.00 | 21.22 B |
| ATOM | 3745 | CE1 | TYR | B | 194 | 22.540 | 50.430 | 17.260 | 1.00 | 20.11 B |
| ATOM | 3746 | CD2 | TYR | B | 194 | 22.617 | 50.312 | 14.454 | 1.00 | 17.85 B |
| ATOM | 3747 | CE2 | TYR | B | 194 | 21.551 | 50.955 | 15.099 | 1.00 | 19.87 B |
| ATOM | 3748 | CZ | TYR | B | 194 | 21.519 | 51.025 | 16.492 | 1.00 | 21.49 B |
| ATOM | 3749 | OH | TYR | B | 194 | 20.517 | 51.761 | 17.098 | 1.00 | 21.29 B |
| ATOM | 3750 | C | TYR | B | 194 | 26.536 | 50.659 | 15.164 | 1.00 | 24.91 B |
| ATOM | 3751 | O | TYR | B | 194 | 26.299 | 51.874 | 15.337 | 1.00 | 23.36 B |
| ATOM | 3752 | N | GLN | B | 195 | 27.297 | 49.955 | 15.987 | 1.00 | 26.42 B |
| ATOM | 3753 | CA | GLN | B | 195 | 27.875 | 50.579 | 17.151 | 1.00 | 26.95 B |
| ATOM | 3754 | CB | GLN | B | 195 | 26.902 | 50.511 | 18.337 | 1.00 | 24.84 B |
| ATOM | 3755 | CG | GLN | B | 195 | 27.412 | 51.300 | 19.549 | 1.00 | 26.46 B |
| ATOM | 3756 | CD | GLN | B | 195 | 26.353 | 51.555 | 20.610 | 1.00 | 26.75 B |
| ATOM | 3757 | OE1 | GLN | B | 195 | 26.684 | 51.857 | 21.751 | 1.00 | 29.34 B |
| ATOM | 3758 | NE2 | GLN | B | 195 | 25.085 | 51.466 | 20.235 | 1.00 | 22.34 B |
| ATOM | 3759 | C | GLN | B | 195 | 29.142 | 49.819 | 17.409 | 1.00 | 28.24 B |
| ATOM | 3760 | O | GLN | B | 195 | 29.161 | 48.605 | 17.352 | 1.00 | 28.82 B |
| ATOM | 3761 | N | GLN | B | 196 | 30.196 | 50.567 | 17.707 | 1.00 | 28.60 B |
| ATOM | 3762 | CA | GLN | B | 196 | 31.554 | 50.075 | 17.921 | 1.00 | 28.90 B |
| ATOM | 3763 | CB | GLN | B | 196 | 32.470 | 51.030 | 17.156 | 1.00 | 32.89 B |
| ATOM | 3764 | CG | GLN | B | 196 | 33.820 | 50.583 | 16.775 | 1.00 | 36.95 B |
| ATOM | 3765 | CD | GLN | B | 196 | 34.379 | 51.519 | 15.721 | 1.00 | 39.73 B |
| ATOM | 3766 | OE1 | GLN | B | 196 | 34.820 | 51.077 | 14.661 | 1.00 | 43.26 B |
| ATOM | 3767 | NE2 | GLN | B | 196 | 34.329 | 52.828 | 15.993 | 1.00 | 40.01 B |
| ATOM | 3768 | C | GLN | B | 196 | 31.974 | 50.048 | 19.377 | 1.00 | 27.77 B |
| ATOM | 3769 | O | GLN | B | 196 | 31.527 | 50.851 | 20.161 | 1.00 | 27.32 B |
| ATOM | 3770 | N | ASP | B | 197 | 32.864 | 49.129 | 19.716 | 1.00 | 29.24 B |
| ATOM | 3771 | CA | ASP | B | 197 | 33.400 | 48.977 | 21.066 | 1.00 | 33.09 B |
| ATOM | 3772 | CB | ASP | B | 197 | 34.616 | 49.901 | 21.245 | 1.00 | 35.15 B |
| ATOM | 3773 | CG | ASP | B | 197 | 35.765 | 49.521 | 20.313 | 1.00 | 40.80 B |
| ATOM | 3774 | OD1 | ASP | B | 197 | 36.022 | 50.230 | 19.312 | 1.00 | 40.71 B |
| ATOM | 3775 | OD2 | ASP | B | 197 | 36.412 | 48.486 | 20.575 | 1.00 | 43.69 B |
| ATOM | 3776 | C | ASP | B | 197 | 32.424 | 49.172 | 22.220 | 1.00 | 33.74 B |
| ATOM | 3777 | O | ASP | B | 197 | 32.639 | 50.002 | 23.104 | 1.00 | 31.64 B |

TABLE 2-continued

| | | | | | | | | | | |
|---|---|---|---|---|---|---|---|---|---|---|
| ATOM | 3778 | N   | VAL | B | 198 | 31.348 | 48.399 | 22.210 | 1.00 | 33.10 B |
| ATOM | 3779 | CA  | VAL | B | 198 | 30.353 | 48.484 | 23.253 | 1.00 | 33.15 B |
| ATOM | 3780 | CB  | VAL | B | 198 | 28.989 | 47.983 | 22.743 | 1.00 | 33.80 B |
| ATOM | 3781 | CG1 | VAL | B | 198 | 27.971 | 48.060 | 23.851 | 1.00 | 27.97 B |
| ATOM | 3782 | CG2 | VAL | B | 198 | 28.557 | 48.812 | 21.541 | 1.00 | 30.42 B |
| ATOM | 3783 | C   | VAL | B | 198 | 30.819 | 47.579 | 24.382 | 1.00 | 35.35 B |
| ATOM | 3784 | O   | VAL | B | 198 | 31.116 | 46.405 | 24.145 | 1.00 | 35.20 B |
| ATOM | 3785 | N   | VAL | B | 199 | 30.896 | 48.097 | 25.606 | 1.00 | 34.56 B |
| ATOM | 3786 | CA  | VAL | B | 199 | 31.348 | 47.229 | 26.676 | 1.00 | 36.32 B |
| ATOM | 3787 | CB  | VAL | B | 199 | 32.483 | 47.880 | 27.528 | 1.00 | 38.23 B |
| ATOM | 3788 | CG1 | VAL | B | 199 | 33.684 | 48.177 | 26.644 | 1.00 | 40.61 B |
| ATOM | 3789 | CG2 | VAL | B | 199 | 31.993 | 49.132 | 28.197 | 1.00 | 39.10 B |
| ATOM | 3790 | C   | VAL | B | 199 | 30.188 | 46.854 | 27.569 | 1.00 | 36.00 B |
| ATOM | 3791 | O   | VAL | B | 199 | 29.429 | 47.709 | 28.001 | 1.00 | 35.56 B |
| ATOM | 3792 | N   | VAL | B | 200 | 30.030 | 45.561 | 27.806 | 1.00 | 34.64 B |
| ATOM | 3793 | CA  | VAL | B | 200 | 28.982 | 45.077 | 28.680 | 1.00 | 37.73 B |
| ATOM | 3794 | CB  | VAL | B | 200 | 27.979 | 44.195 | 27.933 | 1.00 | 39.32 B |
| ATOM | 3795 | CG1 | VAL | B | 200 | 27.082 | 45.059 | 27.079 | 1.00 | 42.45 B |
| ATOM | 3796 | CG2 | VAL | B | 200 | 28.716 | 43.198 | 27.094 | 1.00 | 37.56 B |
| ATOM | 3797 | C   | VAL | B | 200 | 29.622 | 44.228 | 29.768 | 1.00 | 36.92 B |
| ATOM | 3798 | O   | VAL | B | 200 | 30.689 | 43.643 | 29.580 | 1.00 | 37.21 B |
| ATOM | 3799 | N   | VAL | B | 201 | 28.966 | 44.156 | 30.909 | 1.00 | 36.03 B |
| ATOM | 3800 | CA  | VAL | B | 201 | 29.501 | 43.354 | 31.973 | 1.00 | 35.64 B |
| ATOM | 3801 | CB  | VAL | B | 201 | 29.529 | 44.154 | 33.299 | 1.00 | 38.23 B |
| ATOM | 3802 | CG1 | VAL | B | 201 | 29.931 | 43.238 | 34.446 | 1.00 | 36.70 B |
| ATOM | 3803 | CG2 | VAL | B | 201 | 30.501 | 45.331 | 33.169 | 1.00 | 38.09 B |
| ATOM | 3804 | C   | VAL | B | 201 | 28.622 | 42.126 | 32.111 | 1.00 | 34.41 B |
| ATOM | 3805 | O   | VAL | B | 201 | 27.428 | 42.237 | 32.362 | 1.00 | 33.60 B |
| ATOM | 3806 | N   | LEU | B | 202 | 29.213 | 40.953 | 31.928 | 1.00 | 35.90 B |
| ATOM | 3807 | CA  | LEU | B | 202 | 28.471 | 39.703 | 32.039 | 1.00 | 37.78 B |
| ATOM | 3808 | CB  | LEU | B | 202 | 28.951 | 38.728 | 30.971 | 1.00 | 35.05 B |
| ATOM | 3809 | CG  | LEU | B | 202 | 28.793 | 39.191 | 29.533 | 1.00 | 33.84 B |
| ATOM | 3810 | CD1 | LEU | B | 202 | 29.425 | 38.180 | 28.593 | 1.00 | 30.94 B |
| ATOM | 3811 | CD2 | LEU | B | 202 | 27.336 | 39.353 | 29.242 | 1.00 | 35.94 B |
| ATOM | 3812 | C   | LEU | B | 202 | 28.675 | 39.081 | 33.431 | 1.00 | 40.45 B |
| ATOM | 3813 | O   | LEU | B | 202 | 29.591 | 39.473 | 34.160 | 1.00 | 40.07 B |
| ATOM | 3814 | N   | PRO | B | 203 | 27.804 | 38.129 | 33.828 | 1.00 | 41.47 B |
| ATOM | 3815 | CD  | PRO | B | 203 | 26.463 | 37.810 | 33.290 | 1.00 | 41.41 B |
| ATOM | 3816 | CA  | PRO | B | 203 | 27.996 | 37.519 | 35.147 | 1.00 | 43.94 B |
| ATOM | 3817 | CB  | PRO | B | 203 | 26.958 | 36.402 | 35.164 | 1.00 | 41.84 B |
| ATOM | 3818 | CG  | PRO | B | 203 | 25.794 | 37.075 | 34.454 | 1.00 | 41.27 B |
| ATOM | 3819 | C   | PRO | B | 203 | 29.426 | 37.009 | 35.328 | 1.00 | 46.88 B |
| ATOM | 3820 | O   | PRO | B | 203 | 30.146 | 36.759 | 34.355 | 1.00 | 46.53 B |
| ATOM | 3821 | N   | LYS | B | 204 | 29.801 | 36.861 | 36.596 | 1.00 | 50.44 B |
| ATOM | 3822 | CA  | LYS | B | 204 | 31.119 | 36.439 | 37.043 | 1.00 | 52.55 B |
| ATOM | 3823 | CB  | LYS | B | 204 | 30.980 | 35.575 | 38.302 | 1.00 | 54.47 B |
| ATOM | 3824 | CG  | LYS | B | 204 | 30.516 | 36.350 | 39.527 | 1.00 | 58.74 B |
| ATOM | 3825 | CD  | LYS | B | 204 | 31.660 | 36.551 | 40.532 | 1.00 | 62.51 B |
| ATOM | 3826 | CE  | LYS | B | 204 | 32.839 | 37.334 | 39.944 | 1.00 | 65.55 B |
| ATOM | 3827 | NZ  | LYS | B | 204 | 32.432 | 38.713 | 39.490 | 1.00 | 66.87 B |
| ATOM | 3828 | C   | LYS | B | 204 | 32.066 | 35.753 | 36.070 | 1.00 | 53.04 B |
| ATOM | 3829 | O   | LYS | B | 204 | 33.050 | 36.357 | 35.615 | 1.00 | 56.07 B |
| ATOM | 3830 | N   | PRO | B | 205 | 31.776 | 34.494 | 35.713 | 1.00 | 51.38 B |
| ATOM | 3831 | CD  | PRO | B | 205 | 30.410 | 33.932 | 35.730 | 1.00 | 48.40 B |
| ATOM | 3832 | CA  | PRO | B | 205 | 32.645 | 33.744 | 34.795 | 1.00 | 48.13 B |
| ATOM | 3833 | CB  | PRO | B | 205 | 31.692 | 32.718 | 34.183 | 1.00 | 48.22 B |
| ATOM | 3834 | CG  | PRO | B | 205 | 30.640 | 32.549 | 35.238 | 1.00 | 49.33 B |
| ATOM | 3835 | C   | PRO | B | 205 | 33.337 | 34.572 | 33.717 | 1.00 | 46.87 B |
| ATOM | 3836 | O   | PRO | B | 205 | 34.540 | 34.442 | 33.476 | 1.00 | 48.54 B |
| ATOM | 3837 | N   | TYR | B | 206 | 32.569 | 35.450 | 33.092 | 1.00 | 44.86 B |
| ATOM | 3838 | CA  | TYR | B | 206 | 33.044 | 36.245 | 31.967 | 1.00 | 41.86 B |
| ATOM | 3839 | CB  | TYR | B | 206 | 31.966 | 36.187 | 30.879 | 1.00 | 39.01 B |
| ATOM | 3840 | CG  | TYR | B | 206 | 31.542 | 34.761 | 30.616 | 1.00 | 35.04 B |
| ATOM | 3841 | CD1 | TYR | B | 206 | 32.341 | 33.912 | 29.855 | 1.00 | 33.92 B |
| ATOM | 3842 | CE1 | TYR | B | 206 | 32.001 | 32.591 | 29.652 | 1.00 | 34.84 B |
| ATOM | 3843 | CD2 | TYR | B | 206 | 30.377 | 34.250 | 31.174 | 1.00 | 33.09 B |
| ATOM | 3844 | CE2 | TYR | B | 206 | 30.018 | 32.918 | 30.986 | 1.00 | 34.92 B |
| ATOM | 3845 | CZ  | TYR | B | 206 | 30.837 | 32.096 | 30.225 | 1.00 | 35.22 B |
| ATOM | 3846 | OH  | TYR | B | 206 | 30.508 | 30.776 | 30.064 | 1.00 | 36.75 B |
| ATOM | 3847 | C   | TYR | B | 206 | 33.465 | 37.679 | 32.218 | 1.00 | 41.31 B |
| ATOM | 3848 | O   | TYR | B | 206 | 34.363 | 38.186 | 31.534 | 1.00 | 42.16 B |
| ATOM | 3849 | N   | GLY | B | 207 | 32.812 | 38.341 | 33.165 | 1.00 | 40.65 B |
| ATOM | 3850 | CA  | GLY | B | 207 | 33.171 | 39.713 | 33.469 | 1.00 | 40.15 B |
| ATOM | 3851 | C   | GLY | B | 207 | 32.882 | 40.687 | 32.341 | 1.00 | 41.22 B |
| ATOM | 3852 | O   | GLY | B | 207 | 31.960 | 40.496 | 31.533 | 1.00 | 40.83 B |
| ATOM | 3853 | N   | GLU | B | 208 | 33.688 | 41.738 | 32.274 | 1.00 | 38.29 B |
| ATOM | 3854 | CA  | GLU | B | 208 | 33.490 | 42.758 | 31.272 | 1.00 | 37.17 B |
| ATOM | 3855 | CB  | GLU | B | 208 | 34.130 | 44.055 | 31.744 | 1.00 | 38.43 B |
| ATOM | 3856 | CG  | GLU | B | 208 | 34.041 | 45.163 | 30.751 | 1.00 | 39.93 B |

TABLE 2-continued

| | | | | | | | | | | |
|---|---|---|---|---|---|---|---|---|---|---|
| ATOM | 3857 | CD | GLU | B | 208 | 34.769 | 46.413 | 31.232 | 1.00 | 43.29 B |
| ATOM | 3858 | OE1 | GLU | B | 208 | 34.360 | 46.979 | 32.277 | 1.00 | 40.64 B |
| ATOM | 3859 | OE2 | GLU | B | 208 | 35.744 | 46.814 | 30.552 | 1.00 | 43.54 B |
| ATOM | 3860 | C | GLU | B | 208 | 34.064 | 42.347 | 29.933 | 1.00 | 35.54 B |
| ATOM | 3861 | O | GLU | B | 208 | 35.164 | 41.805 | 29.859 | 1.00 | 35.57 B |
| ATOM | 3862 | N | VAL | B | 209 | 33.333 | 42.645 | 28.868 | 1.00 | 33.17 B |
| ATOM | 3863 | CA | VAL | B | 209 | 33.769 | 42.259 | 27.534 | 1.00 | 33.03 B |
| ATOM | 3864 | CB | VAL | B | 209 | 33.029 | 40.936 | 27.175 | 1.00 | 34.46 B |
| ATOM | 3865 | CG1 | VAL | B | 209 | 31.710 | 41.234 | 26.475 | 1.00 | 31.11 B |
| ATOM | 3866 | CG2 | VAL | B | 209 | 33.937 | 40.014 | 26.407 | 1.00 | 38.25 B |
| ATOM | 3867 | C | VAL | B | 209 | 33.446 | 43.402 | 26.544 | 1.00 | 31.89 B |
| ATOM | 3868 | O | VAL | B | 209 | 32.485 | 44.128 | 26.745 | 1.00 | 32.72 B |
| ATOM | 3869 | N | ALA | B | 210 | 34.256 | 43.597 | 25.511 | 1.00 | 30.54 B |
| ATOM | 3870 | CA | ALA | B | 210 | 33.978 | 44.657 | 24.532 | 1.00 | 31.33 B |
| ATOM | 3871 | CB | ALA | B | 210 | 35.213 | 45.552 | 24.332 | 1.00 | 29.78 B |
| ATOM | 3872 | C | ALA | B | 210 | 33.543 | 44.036 | 23.195 | 1.00 | 29.61 B |
| ATOM | 3873 | O | ALA | B | 210 | 34.167 | 43.095 | 22.698 | 1.00 | 30.07 B |
| ATOM | 3874 | N | VAL | B | 211 | 32.483 | 44.573 | 22.607 | 1.00 | 27.92 B |
| ATOM | 3875 | CA | VAL | B | 211 | 31.962 | 44.018 | 21.357 | 1.00 | 26.48 B |
| ATOM | 3876 | CB | VAL | B | 211 | 30.717 | 43.108 | 21.639 | 1.00 | 26.81 B |
| ATOM | 3877 | CG1 | VAL | B | 211 | 30.979 | 42.152 | 22.836 | 1.00 | 25.54 B |
| ATOM | 3878 | CG2 | VAL | B | 211 | 29.492 | 43.974 | 21.928 | 1.00 | 24.69 B |
| ATOM | 3879 | C | VAL | B | 211 | 31.506 | 45.063 | 20.370 | 1.00 | 26.64 B |
| ATOM | 3880 | O | VAL | B | 211 | 31.354 | 46.213 | 20.721 | 1.00 | 28.66 B |
| ATOM | 3881 | N | ASP | B | 212 | 31.277 | 44.651 | 19.125 | 1.00 | 27.44 B |
| ATOM | 3882 | CA | ASP | B | 212 | 30.705 | 45.532 | 18.098 | 1.00 | 24.95 B |
| ATOM | 3883 | CB | ASP | B | 212 | 31.474 | 45.472 | 16.787 | 1.00 | 26.88 B |
| ATOM | 3884 | CG | ASP | B | 212 | 32.867 | 46.064 | 16.899 | 1.00 | 29.89 B |
| ATOM | 3885 | OD1 | ASP | B | 212 | 33.047 | 46.951 | 17.772 | 1.00 | 29.64 B |
| ATOM | 3886 | OD2 | ASP | B | 212 | 33.757 | 45.655 | 16.113 | 1.00 | 29.19 B |
| ATOM | 3887 | C | ASP | B | 212 | 29.299 | 45.008 | 17.823 | 1.00 | 26.59 B |
| ATOM | 3888 | O | ASP | B | 212 | 29.041 | 43.789 | 17.956 | 1.00 | 25.79 B |
| ATOM | 3889 | N | ILE | B | 213 | 28.386 | 45.909 | 17.448 | 1.00 | 22.74 B |
| ATOM | 3890 | CA | ILE | B | 213 | 27.033 | 45.519 | 17.135 | 1.00 | 21.19 B |
| ATOM | 3891 | CB | ILE | B | 213 | 25.999 | 46.328 | 17.917 | 1.00 | 20.29 B |
| ATOM | 3892 | CG2 | ILE | B | 213 | 24.548 | 45.999 | 17.423 | 1.00 | 16.92 B |
| ATOM | 3893 | CG1 | ILE | B | 213 | 26.142 | 46.016 | 19.414 | 1.00 | 16.96 B |
| ATOM | 3894 | CD1 | ILE | B | 213 | 25.177 | 46.778 | 20.308 | 1.00 | 18.18 B |
| ATOM | 3895 | C | ILE | B | 213 | 26.952 | 45.854 | 15.649 | 1.00 | 25.13 B |
| ATOM | 3896 | O | ILE | B | 213 | 27.286 | 46.989 | 15.243 | 1.00 | 22.61 B |
| ATOM | 3897 | N | ALA | B | 214 | 26.551 | 44.858 | 14.843 | 1.00 | 23.15 B |
| ATOM | 3898 | CA | ALA | B | 214 | 26.417 | 45.032 | 13.402 | 1.00 | 21.58 B |
| ATOM | 3899 | CB | ALA | B | 214 | 27.635 | 44.515 | 12.724 | 1.00 | 22.03 B |
| ATOM | 3900 | C | ALA | B | 214 | 25.191 | 44.295 | 12.872 | 1.00 | 22.41 B |
| ATOM | 3901 | O | ALA | B | 214 | 24.798 | 43.239 | 13.387 | 1.00 | 22.71 B |
| ATOM | 3902 | N | PHE | B | 215 | 24.576 | 44.863 | 11.844 | 1.00 | 20.74 B |
| ATOM | 3903 | CA | PHE | B | 215 | 23.406 | 44.257 | 11.257 | 1.00 | 19.52 B |
| ATOM | 3904 | CB | PHE | B | 215 | 22.398 | 45.338 | 10.852 | 1.00 | 20.22 B |
| ATOM | 3905 | CG | PHE | B | 215 | 21.127 | 44.784 | 10.222 | 1.00 | 17.78 B |
| ATOM | 3906 | CD1 | PHE | B | 215 | 20.140 | 44.178 | 11.025 | 1.00 | 18.65 B |
| ATOM | 3907 | CD2 | PHE | B | 215 | 20.916 | 44.875 | 8.848 | 1.00 | 16.90 B |
| ATOM | 3908 | CE1 | PHE | B | 215 | 18.936 | 43.667 | 10.463 | 1.00 | 18.69 B |
| ATOM | 3909 | CE2 | PHE | B | 215 | 19.701 | 44.364 | 8.248 | 1.00 | 14.91 B |
| ATOM | 3910 | CZ | PHE | B | 215 | 18.713 | 43.762 | 9.066 | 1.00 | 18.21 B |
| ATOM | 3911 | C | PHE | B | 215 | 23.818 | 43.484 | 10.017 | 1.00 | 18.87 B |
| ATOM | 3912 | O | PHE | B | 215 | 24.532 | 44.025 | 9.163 | 1.00 | 15.66 B |
| ATOM | 3913 | N | GLY | B | 216 | 23.399 | 42.221 | 9.924 | 1.00 | 18.99 B |
| ATOM | 3914 | CA | GLY | B | 216 | 23.710 | 41.438 | 8.732 | 1.00 | 18.82 B |
| ATOM | 3915 | C | GLY | B | 216 | 22.460 | 40.718 | 8.223 | 1.00 | 20.31 B |
| ATOM | 3916 | O | GLY | B | 216 | 22.555 | 39.722 | 7.526 | 1.00 | 20.48 B |
| ATOM | 3917 | N | GLY | B | 217 | 21.291 | 41.251 | 8.554 | 1.00 | 16.48 B |
| ATOM | 3918 | CA | GLY | B | 217 | 20.047 | 40.595 | 8.201 | 1.00 | 18.41 B |
| ATOM | 3919 | C | GLY | B | 217 | 19.377 | 40.410 | 9.562 | 1.00 | 18.48 B |
| ATOM | 3920 | O | GLY | B | 217 | 18.131 | 40.401 | 9.691 | 1.00 | 16.81 B |
| ATOM | 3921 | N | ASN | B | 218 | 20.239 | 40.252 | 10.573 | 1.00 | 14.32 B |
| ATOM | 3922 | CA | ASN | B | 218 | 19.854 | 40.188 | 11.992 | 1.00 | 17.64 B |
| ATOM | 3923 | CB | ASN | B | 218 | 20.047 | 38.776 | 12.579 | 1.00 | 13.91 B |
| ATOM | 3924 | CG | ASN | B | 218 | 19.194 | 37.751 | 11.873 | 1.00 | 13.87 B |
| ATOM | 3925 | OD1 | ASN | B | 218 | 17.977 | 37.878 | 11.872 | 1.00 | 17.25 B |
| ATOM | 3926 | ND2 | ASN | B | 218 | 19.814 | 36.757 | 11.262 | 1.00 | 10.85 B |
| ATOM | 3927 | C | ASN | B | 218 | 20.900 | 41.114 | 12.665 | 1.00 | 17.23 B |
| ATOM | 3928 | O | ASN | B | 218 | 21.974 | 41.341 | 12.079 | 1.00 | 19.41 B |
| ATOM | 3929 | N | PHE | B | 219 | 20.584 | 41.654 | 13.840 | 1.00 | 15.60 B |
| ATOM | 3930 | CA | PHE | B | 219 | 21.578 | 42.443 | 14.596 | 1.00 | 16.70 B |
| ATOM | 3931 | CB | PHE | B | 219 | 20.932 | 43.362 | 15.627 | 1.00 | 16.41 B |
| ATOM | 3932 | CG | PHE | B | 219 | 20.573 | 44.717 | 15.092 | 1.00 | 16.73 B |
| ATOM | 3933 | CD1 | PHE | B | 219 | 19.237 | 45.101 | 14.969 | 1.00 | 19.82 B |
| ATOM | 3934 | CD2 | PHE | B | 219 | 21.565 | 45.616 | 14.740 | 1.00 | 17.46 B |
| ATOM | 3935 | CE1 | PHE | B | 219 | 18.896 | 46.383 | 14.495 | 1.00 | 20.17 B |

TABLE 2-continued

| ATOM | 3936 | CE2 | PHE | B | 219 | 21.237 | 46.899 | 14.270 | 1.00 | 17.52 | B |
|---|---|---|---|---|---|---|---|---|---|---|---|
| ATOM | 3937 | CZ | PHE | B | 219 | 19.906 | 47.275 | 14.147 | 1.00 | 19.68 | B |
| ATOM | 3938 | C | PHE | B | 219 | 22.392 | 41.434 | 15.352 | 1.00 | 15.65 | B |
| ATOM | 3939 | O | PHE | B | 219 | 21.824 | 40.513 | 15.960 | 1.00 | 16.90 | B |
| ATOM | 3940 | N | PHE | B | 220 | 23.707 | 41.579 | 15.288 | 1.00 | 17.38 | B |
| ATOM | 3941 | CA | PHE | B | 220 | 24.647 | 40.686 | 15.990 | 1.00 | 17.36 | B |
| ATOM | 3942 | CB | PHE | B | 220 | 25.669 | 40.052 | 15.008 | 1.00 | 14.53 | B |
| ATOM | 3943 | CG | PHE | B | 220 | 25.140 | 38.895 | 14.183 | 1.00 | 18.08 | B |
| ATOM | 3944 | CD1 | PHE | B | 220 | 25.443 | 37.571 | 14.533 | 1.00 | 14.69 | B |
| ATOM | 3945 | CD2 | PHE | B | 220 | 24.368 | 39.130 | 13.052 | 1.00 | 18.82 | B |
| ATOM | 3946 | CE1 | PHE | B | 220 | 24.982 | 36.499 | 13.761 | 1.00 | 21.99 | B |
| ATOM | 3947 | CE2 | PHE | B | 220 | 23.888 | 38.049 | 12.259 | 1.00 | 18.50 | B |
| ATOM | 3948 | CZ | PHE | B | 220 | 24.194 | 36.737 | 12.616 | 1.00 | 19.93 | B |
| ATOM | 3949 | C | PHE | B | 220 | 25.535 | 41.482 | 16.979 | 1.00 | 20.92 | B |
| ATOM | 3950 | O | PHE | B | 220 | 25.857 | 42.652 | 16.740 | 1.00 | 21.11 | B |
| ATOM | 3951 | N | ALA | B | 221 | 25.949 | 40.814 | 18.054 | 1.00 | 20.42 | B |
| ATOM | 3952 | CA | ALA | B | 221 | 26.962 | 41.372 | 18.950 | 1.00 | 21.16 | B |
| ATOM | 3953 | CB | ALA | B | 221 | 26.652 | 41.098 | 20.431 | 1.00 | 20.21 | B |
| ATOM | 3954 | C | ALA | B | 221 | 28.129 | 40.473 | 18.492 | 1.00 | 20.00 | B |
| ATOM | 3955 | O | ALA | B | 221 | 28.021 | 39.259 | 18.526 | 1.00 | 18.54 | B |
| ATOM | 3956 | N | ILE | B | 222 | 29.218 | 41.058 | 18.028 | 1.00 | 20.84 | B |
| ATOM | 3957 | CA | ILE | B | 222 | 30.370 | 40.284 | 17.598 | 1.00 | 21.05 | B |
| ATOM | 3958 | CB | ILE | B | 222 | 30.872 | 40.813 | 16.270 | 1.00 | 19.03 | B |
| ATOM | 3959 | CG2 | ILE | B | 222 | 32.077 | 39.978 | 15.827 | 1.00 | 21.00 | B |
| ATOM | 3960 | CG1 | ILE | B | 222 | 29.695 | 40.812 | 15.258 | 1.00 | 19.75 | B |
| ATOM | 3961 | CD1 | ILE | B | 222 | 30.013 | 41.277 | 13.822 | 1.00 | 21.35 | B |
| ATOM | 3962 | C | ILE | B | 222 | 31.469 | 40.380 | 18.687 | 1.00 | 22.59 | B |
| ATOM | 3963 | O | ILE | B | 222 | 31.852 | 41.475 | 19.092 | 1.00 | 22.63 | B |
| ATOM | 3964 | N | VAL | B | 223 | 31.957 | 39.236 | 19.163 | 1.00 | 23.55 | B |
| ATOM | 3965 | CA | VAL | B | 223 | 32.949 | 39.223 | 20.229 | 1.00 | 23.54 | B |
| ATOM | 3966 | CB | VAL | B | 223 | 32.219 | 38.970 | 21.596 | 1.00 | 22.80 | B |
| ATOM | 3967 | CG1 | VAL | B | 223 | 31.568 | 37.621 | 21.576 | 1.00 | 24.59 | B |
| ATOM | 3968 | CG2 | VAL | B | 223 | 33.183 | 39.048 | 22.782 | 1.00 | 22.04 | B |
| ATOM | 3969 | C | VAL | B | 223 | 34.060 | 38.170 | 20.039 | 1.00 | 25.89 | B |
| ATOM | 3970 | O | VAL | B | 223 | 33.809 | 37.057 | 19.534 | 1.00 | 24.57 | B |
| ATOM | 3971 | N | PRO | B | 224 | 35.316 | 38.513 | 20.401 | 1.00 | 25.09 | B |
| ATOM | 3972 | CD | PRO | B | 224 | 35.889 | 39.854 | 20.644 | 1.00 | 24.97 | B |
| ATOM | 3973 | CA | PRO | B | 224 | 36.363 | 37.492 | 20.238 | 1.00 | 24.62 | B |
| ATOM | 3974 | CB | PRO | B | 224 | 37.671 | 38.282 | 20.393 | 1.00 | 27.03 | B |
| ATOM | 3975 | CG | PRO | B | 224 | 37.271 | 39.736 | 20.045 | 1.00 | 27.24 | B |
| ATOM | 3976 | C | PRO | B | 224 | 36.194 | 36.457 | 21.357 | 1.00 | 25.91 | B |
| ATOM | 3977 | O | PRO | B | 224 | 35.868 | 36.809 | 22.497 | 1.00 | 28.33 | B |
| ATOM | 3978 | N | ALA | B | 225 | 36.377 | 35.185 | 21.029 | 1.00 | 25.54 | B |
| ATOM | 3979 | CA | ALA | B | 225 | 36.274 | 34.117 | 21.997 | 1.00 | 27.25 | B |
| ATOM | 3980 | CB | ALA | B | 225 | 36.563 | 32.762 | 21.322 | 1.00 | 23.58 | B |
| ATOM | 3981 | C | ALA | B | 225 | 37.303 | 34.369 | 23.104 | 1.00 | 30.20 | B |
| ATOM | 3982 | O | ALA | B | 225 | 37.059 | 34.078 | 24.286 | 1.00 | 28.25 | B |
| ATOM | 3983 | N | GLU | B | 226 | 38.455 | 34.897 | 22.702 | 1.00 | 32.53 | B |
| ATOM | 3984 | CA | GLU | B | 226 | 39.522 | 35.188 | 23.637 | 1.00 | 36.92 | B |
| ATOM | 3985 | CB | GLU | B | 226 | 40.712 | 35.778 | 22.852 | 1.00 | 41.09 | B |
| ATOM | 3986 | CG | GLU | B | 226 | 41.594 | 36.739 | 23.597 | 1.00 | 47.67 | B |
| ATOM | 3987 | CD | GLU | B | 226 | 41.011 | 38.145 | 23.613 | 1.00 | 52.00 | B |
| ATOM | 3988 | OE1 | GLU | B | 226 | 40.606 | 38.635 | 22.517 | 1.00 | 54.29 | B |
| ATOM | 3989 | OE2 | GLU | B | 226 | 40.967 | 38.756 | 24.713 | 1.00 | 53.44 | B |
| ATOM | 3990 | C | GLU | B | 226 | 39.047 | 36.090 | 24.803 | 1.00 | 36.91 | B |
| ATOM | 3991 | O | GLU | B | 226 | 39.537 | 35.977 | 25.927 | 1.00 | 35.72 | B |
| ATOM | 3992 | N | GLN | B | 227 | 38.071 | 36.956 | 24.552 | 1.00 | 35.92 | B |
| ATOM | 3993 | CA | GLN | B | 227 | 37.572 | 37.817 | 25.618 | 1.00 | 37.80 | B |
| ATOM | 3994 | CB | GLN | B | 227 | 36.833 | 39.006 | 25.047 | 1.00 | 39.77 | B |
| ATOM | 3995 | CG | GLN | B | 227 | 37.747 | 40.146 | 24.734 | 1.00 | 43.88 | B |
| ATOM | 3996 | CD | GLN | B | 227 | 37.050 | 41.428 | 24.962 | 1.00 | 48.12 | B |
| ATOM | 3997 | OE1 | GLN | B | 227 | 36.188 | 41.806 | 24.175 | 1.00 | 50.21 | B |
| ATOM | 3998 | NE2 | GLN | B | 227 | 37.378 | 42.107 | 26.074 | 1.00 | 49.13 | B |
| ATOM | 3999 | C | GLN | B | 227 | 36.661 | 37.113 | 26.599 | 1.00 | 36.57 | B |
| ATOM | 4000 | O | GLN | B | 227 | 36.426 | 37.605 | 27.701 | 1.00 | 37.01 | B |
| ATOM | 4001 | N | LEU | B | 228 | 36.131 | 35.969 | 26.191 | 1.00 | 33.41 | B |
| ATOM | 4002 | CA | LEU | B | 228 | 35.247 | 35.204 | 27.037 | 1.00 | 32.10 | B |
| ATOM | 4003 | CB | LEU | B | 228 | 34.173 | 34.489 | 26.189 | 1.00 | 30.91 | B |
| ATOM | 4004 | CG | LEU | B | 228 | 33.275 | 35.378 | 25.343 | 1.00 | 30.21 | B |
| ATOM | 4005 | CD1 | LEU | B | 228 | 32.395 | 34.512 | 24.423 | 1.00 | 28.88 | B |
| ATOM | 4006 | CD2 | LEU | B | 228 | 32.422 | 36.246 | 26.279 | 1.00 | 29.70 | B |
| ATOM | 4007 | C | LEU | B | 228 | 36.127 | 34.179 | 27.720 | 1.00 | 31.97 | B |
| ATOM | 4008 | O | LEU | B | 228 | 35.664 | 33.425 | 28.557 | 1.00 | 32.83 | B |
| ATOM | 4009 | N | GLY | B | 229 | 37.400 | 34.152 | 27.343 | 1.00 | 34.37 | B |
| ATOM | 4010 | CA | GLY | B | 229 | 38.328 | 33.193 | 27.919 | 1.00 | 35.86 | B |
| ATOM | 4011 | C | GLY | B | 229 | 37.923 | 31.760 | 27.617 | 1.00 | 39.19 | B |
| ATOM | 4012 | O | GLY | B | 229 | 38.058 | 30.876 | 28.470 | 1.00 | 39.69 | B |
| ATOM | 4013 | N | ILE | B | 230 | 37.416 | 31.540 | 26.403 | 1.00 | 39.34 | B |
| ATOM | 4014 | CA | ILE | B | 230 | 36.973 | 30.222 | 25.946 | 1.00 | 39.93 | B |

TABLE 2-continued

| ATOM | 4015 | CB | ILE | B | 230 | 35.424 | 30.118 | 25.867 | 1.00 | 41.97 | B |
| ATOM | 4016 | CG2 | ILE | B | 230 | 35.008 | 28.728 | 25.307 | 1.00 | 43.55 | B |
| ATOM | 4017 | CG1 | ILE | B | 230 | 34.789 | 30.356 | 27.232 | 1.00 | 43.87 | B |
| ATOM | 4018 | CD1 | ILE | B | 230 | 33.258 | 30.354 | 27.175 | 1.00 | 42.99 | B |
| ATOM | 4019 | C | ILE | B | 230 | 37.459 | 30.033 | 24.512 | 1.00 | 39.54 | B |
| ATOM | 4020 | O | ILE | B | 230 | 37.307 | 30.927 | 23.684 | 1.00 | 39.70 | B |
| ATOM | 4021 | N | ASP | B | 231 | 38.042 | 28.884 | 24.203 | 1.00 | 39.51 | B |
| ATOM | 4022 | CA | ASP | B | 231 | 38.459 | 28.656 | 22.832 | 1.00 | 38.89 | B |
| ATOM | 4023 | CB | ASP | B | 231 | 39.581 | 27.633 | 22.765 | 1.00 | 45.03 | B |
| ATOM | 4024 | CG | ASP | B | 231 | 40.869 | 28.168 | 23.328 | 1.00 | 51.63 | B |
| ATOM | 4025 | OD1 | ASP | B | 231 | 41.325 | 29.220 | 22.823 | 1.00 | 55.97 | B |
| ATOM | 4026 | OD2 | ASP | B | 231 | 41.429 | 27.555 | 24.272 | 1.00 | 55.23 | B |
| ATOM | 4027 | C | ASP | B | 231 | 37.248 | 28.102 | 22.118 | 1.00 | 35.71 | B |
| ATOM | 4028 | O | ASP | B | 231 | 36.399 | 27.453 | 22.730 | 1.00 | 33.16 | B |
| ATOM | 4029 | N | ILE | B | 232 | 37.157 | 28.374 | 20.825 | 1.00 | 33.95 | B |
| ATOM | 4030 | CA | ILE | B | 232 | 36.061 | 27.860 | 20.026 | 1.00 | 31.83 | B |
| ATOM | 4031 | CB | ILE | B | 232 | 35.894 | 28.645 | 18.732 | 1.00 | 30.95 | B |
| ATOM | 4032 | CG2 | ILE | B | 232 | 34.927 | 27.907 | 17.808 | 1.00 | 27.81 | B |
| ATOM | 4033 | CG1 | ILE | B | 232 | 35.434 | 30.069 | 19.057 | 1.00 | 26.67 | B |
| ATOM | 4034 | CD1 | ILE | B | 232 | 35.468 | 31.012 | 17.875 | 1.00 | 28.24 | B |
| ATOM | 4035 | C | ILE | B | 232 | 36.453 | 26.440 | 19.659 | 1.00 | 33.88 | B |
| ATOM | 4036 | O | ILE | B | 232 | 37.388 | 26.237 | 18.872 | 1.00 | 36.07 | B |
| ATOM | 4037 | N | SER | B | 233 | 35.754 | 25.466 | 20.234 | 1.00 | 31.46 | B |
| ATOM | 4038 | CA | SER | B | 233 | 36.027 | 24.059 | 19.976 | 1.00 | 32.58 | B |
| ATOM | 4039 | CB | SER | B | 233 | 37.190 | 23.566 | 20.842 | 1.00 | 32.17 | B |
| ATOM | 4040 | OG | SER | B | 233 | 36.779 | 23.577 | 22.205 | 1.00 | 31.71 | B |
| ATOM | 4041 | C | SER | B | 233 | 34.782 | 23.308 | 20.399 | 1.00 | 32.73 | B |
| ATOM | 4042 | O | SER | B | 233 | 33.949 | 23.838 | 21.141 | 1.00 | 32.49 | B |
| ATOM | 4043 | N | VAL | B | 234 | 34.668 | 22.064 | 19.964 | 1.00 | 32.35 | B |
| ATOM | 4044 | CA | VAL | B | 234 | 33.510 | 21.278 | 20.326 | 1.00 | 34.27 | B |
| ATOM | 4045 | CB | VAL | B | 234 | 33.546 | 19.948 | 19.583 | 1.00 | 36.16 | B |
| ATOM | 4046 | CG1 | VAL | B | 234 | 32.335 | 19.078 | 19.957 | 1.00 | 34.94 | B |
| ATOM | 4047 | CG2 | VAL | B | 234 | 33.602 | 20.248 | 18.075 | 1.00 | 34.29 | B |
| ATOM | 4048 | C | VAL | B | 234 | 33.407 | 21.066 | 21.823 | 1.00 | 35.04 | B |
| ATOM | 4049 | O | VAL | B | 234 | 32.310 | 21.153 | 22.398 | 1.00 | 37.39 | B |
| ATOM | 4050 | N | GLN | B | 235 | 34.535 | 20.825 | 22.484 | 1.00 | 34.17 | B |
| ATOM | 4051 | CA | GLN | B | 235 | 34.496 | 20.615 | 23.928 | 1.00 | 35.01 | B |
| ATOM | 4052 | CB | GLN | B | 235 | 35.912 | 20.403 | 24.482 | 1.00 | 40.67 | B |
| ATOM | 4053 | CG | GLN | B | 235 | 36.584 | 19.102 | 24.082 | 1.00 | 46.21 | B |
| ATOM | 4054 | CD | GLN | B | 235 | 36.597 | 18.913 | 22.580 | 1.00 | 52.08 | B |
| ATOM | 4055 | OE1 | GLN | B | 235 | 36.986 | 19.825 | 21.826 | 1.00 | 53.72 | B |
| ATOM | 4056 | NE2 | GLN | B | 235 | 36.167 | 17.724 | 22.123 | 1.00 | 53.39 | B |
| ATOM | 4057 | C | GLN | B | 235 | 33.849 | 21.759 | 24.718 | 1.00 | 33.35 | B |
| ATOM | 4058 | O | GLN | B | 235 | 33.304 | 21.543 | 25.805 | 1.00 | 31.51 | B |
| ATOM | 4059 | N | ASN | B | 236 | 33.933 | 22.980 | 24.191 | 1.00 | 33.62 | B |
| ATOM | 4060 | CA | ASN | B | 236 | 33.405 | 24.150 | 24.883 | 1.00 | 32.03 | B |
| ATOM | 4061 | CB | ASN | B | 236 | 34.391 | 25.300 | 24.734 | 1.00 | 32.81 | B |
| ATOM | 4062 | CG | ASN | B | 236 | 35.688 | 25.062 | 25.500 | 1.00 | 33.53 | B |
| ATOM | 4063 | OD1 | ASN | B | 236 | 36.774 | 25.314 | 24.997 | 1.00 | 33.41 | B |
| ATOM | 4064 | ND2 | ASN | B | 236 | 35.569 | 24.589 | 26.723 | 1.00 | 34.88 | B |
| ATOM | 4065 | C | ASN | B | 236 | 32.020 | 24.655 | 24.495 | 1.00 | 31.94 | B |
| ATOM | 4066 | O | ASN | B | 236 | 31.602 | 25.711 | 24.982 | 1.00 | 31.07 | B |
| ATOM | 4067 | N | LEU | B | 237 | 31.303 | 23.902 | 23.666 | 1.00 | 30.74 | B |
| ATOM | 4068 | CA | LEU | B | 237 | 29.991 | 24.345 | 23.174 | 1.00 | 31.70 | B |
| ATOM | 4069 | CB | LEU | B | 237 | 29.424 | 23.294 | 22.232 | 1.00 | 30.14 | B |
| ATOM | 4070 | CG | LEU | B | 237 | 28.481 | 23.780 | 21.135 | 1.00 | 35.92 | B |
| ATOM | 4071 | CD1 | LEU | B | 237 | 28.819 | 25.213 | 20.688 | 1.00 | 32.89 | B |
| ATOM | 4072 | CD2 | LEU | B | 237 | 28.588 | 22.812 | 19.965 | 1.00 | 34.63 | B |
| ATOM | 4073 | C | LEU | B | 237 | 28.975 | 24.735 | 24.263 | 1.00 | 30.38 | B |
| ATOM | 4074 | O | LEU | B | 237 | 28.288 | 25.760 | 24.141 | 1.00 | 28.54 | B |
| ATOM | 4075 | N | SER | B | 238 | 28.870 | 23.946 | 25.327 | 1.00 | 27.87 | B |
| ATOM | 4076 | CA | SER | B | 238 | 27.968 | 24.332 | 26.398 | 1.00 | 30.23 | B |
| ATOM | 4077 | CB | SER | B | 238 | 27.987 | 23.307 | 27.514 | 1.00 | 31.81 | B |
| ATOM | 4078 | OG | SER | B | 238 | 27.245 | 22.173 | 27.099 | 1.00 | 39.22 | B |
| ATOM | 4079 | C | SER | B | 238 | 28.344 | 25.707 | 26.969 | 1.00 | 29.61 | B |
| ATOM | 4080 | O | SER | B | 238 | 27.473 | 26.548 | 27.245 | 1.00 | 29.19 | B |
| ATOM | 4081 | N | ARG | B | 239 | 29.639 | 25.934 | 27.137 | 1.00 | 29.84 | B |
| ATOM | 4082 | CA | ARG | B | 239 | 30.106 | 27.207 | 27.664 | 1.00 | 29.36 | B |
| ATOM | 4083 | CB | ARG | B | 239 | 31.609 | 27.143 | 27.967 | 1.00 | 31.87 | B |
| ATOM | 4084 | CG | ARG | B | 239 | 31.970 | 26.367 | 29.232 | 1.00 | 38.00 | B |
| ATOM | 4085 | CD | ARG | B | 239 | 33.474 | 25.991 | 29.231 | 1.00 | 41.82 | B |
| ATOM | 4086 | NE | ARG | B | 239 | 34.343 | 27.165 | 29.125 | 1.00 | 47.34 | B |
| ATOM | 4087 | CZ | ARG | B | 239 | 35.668 | 27.133 | 28.952 | 1.00 | 48.64 | B |
| ATOM | 4088 | NH1 | ARG | B | 239 | 36.307 | 25.975 | 28.864 | 1.00 | 48.73 | B |
| ATOM | 4089 | NH2 | ARG | B | 239 | 36.356 | 28.273 | 28.858 | 1.00 | 48.08 | B |
| ATOM | 4090 | C | ARG | B | 239 | 29.834 | 28.330 | 26.670 | 1.00 | 27.01 | B |
| ATOM | 4091 | O | ARG | B | 239 | 29.387 | 29.419 | 27.043 | 1.00 | 24.04 | B |
| ATOM | 4092 | N | LEU | B | 240 | 30.139 | 28.077 | 25.403 | 1.00 | 23.94 | B |
| ATOM | 4093 | CA | LEU | B | 240 | 29.901 | 29.102 | 24.397 | 1.00 | 23.32 | B |

TABLE 2-continued

| | | | | | | | | | | |
|---|---|---|---|---|---|---|---|---|---|---|
| ATOM | 4094 | CB | LEU | B | 240 | 30.448 | 28.654 | 23.034 | 1.00 | 22.20 B |
| ATOM | 4095 | CG | LEU | B | 240 | 31.989 | 28.602 | 22.975 | 1.00 | 22.16 B |
| ATOM | 4096 | CD1 | LEU | B | 240 | 32.390 | 27.645 | 21.895 | 1.00 | 25.36 B |
| ATOM | 4097 | CD2 | LEU | B | 240 | 32.599 | 29.958 | 22.683 | 1.00 | 24.14 B |
| ATOM | 4098 | C | LEU | B | 240 | 28.421 | 29.488 | 24.319 | 1.00 | 21.17 B |
| ATOM | 4099 | O | LEU | B | 240 | 28.102 | 30.676 | 24.179 | 1.00 | 22.02 B |
| ATOM | 4100 | N | GLN | B | 241 | 27.520 | 28.515 | 24.462 | 1.00 | 20.36 B |
| ATOM | 4101 | CA | GLN | B | 241 | 26.095 | 28.803 | 24.407 | 1.00 | 22.99 B |
| ATOM | 4102 | CB | GLN | B | 241 | 25.256 | 27.514 | 24.382 | 1.00 | 23.87 B |
| ATOM | 4103 | CG | GLN | B | 241 | 25.509 | 26.532 | 23.238 | 1.00 | 28.86 B |
| ATOM | 4104 | CD | GLN | B | 241 | 24.472 | 25.380 | 23.265 | 1.00 | 31.87 B |
| ATOM | 4105 | OE1 | GLN | B | 241 | 23.779 | 25.188 | 24.273 | 1.00 | 35.06 B |
| ATOM | 4106 | NE2 | GLN | B | 241 | 24.359 | 24.634 | 22.171 | 1.00 | 30.36 B |
| ATOM | 4107 | C | GLN | B | 241 | 25.638 | 29.652 | 25.597 | 1.00 | 23.20 B |
| ATOM | 4108 | O | GLN | B | 241 | 24.793 | 30.560 | 25.446 | 1.00 | 20.26 B |
| ATOM | 4109 | N | GLU | B | 242 | 26.156 | 29.337 | 26.792 | 1.00 | 22.88 B |
| ATOM | 4110 | CA | GLU | B | 242 | 25.788 | 30.087 | 27.964 | 1.00 | 22.42 B |
| ATOM | 4111 | CB | GLU | B | 242 | 26.355 | 29.421 | 29.221 | 1.00 | 28.71 B |
| ATOM | 4112 | CG | GLU | B | 242 | 25.483 | 28.260 | 29.702 | 1.00 | 36.67 B |
| ATOM | 4113 | CD | GLU | B | 242 | 26.188 | 27.371 | 30.721 | 1.00 | 41.80 B |
| ATOM | 4114 | OE1 | GLU | B | 242 | 26.823 | 27.915 | 31.658 | 1.00 | 46.86 B |
| ATOM | 4115 | OE2 | GLU | B | 242 | 26.101 | 26.129 | 30.581 | 1.00 | 43.93 B |
| ATOM | 4116 | C | GLU | B | 242 | 26.287 | 31.513 | 27.823 | 1.00 | 21.20 B |
| ATOM | 4117 | O | GLU | B | 242 | 25.525 | 32.440 | 28.048 | 1.00 | 25.61 B |
| ATOM | 4118 | N | ALA | B | 243 | 27.541 | 31.696 | 27.421 | 1.00 | 22.11 B |
| ATOM | 4119 | CA | ALA | B | 243 | 28.098 | 33.043 | 27.245 | 1.00 | 20.87 B |
| ATOM | 4120 | CB | ALA | B | 243 | 29.586 | 32.949 | 26.834 | 1.00 | 20.20 B |
| ATOM | 4121 | C | ALA | B | 243 | 27.313 | 33.824 | 26.187 | 1.00 | 21.83 B |
| ATOM | 4122 | O | ALA | B | 243 | 27.019 | 35.029 | 26.350 | 1.00 | 19.38 B |
| ATOM | 4123 | N | GLY | B | 244 | 26.974 | 33.125 | 25.099 | 1.00 | 19.83 B |
| ATOM | 4124 | CA | GLY | B | 244 | 26.220 | 33.749 | 24.019 | 1.00 | 17.96 B |
| ATOM | 4125 | C | GLY | B | 244 | 24.868 | 34.205 | 24.520 | 1.00 | 16.76 B |
| ATOM | 4126 | O | GLY | B | 244 | 24.438 | 35.301 | 24.192 | 1.00 | 18.51 B |
| ATOM | 4127 | N | GLU | B | 245 | 24.187 | 33.376 | 25.315 | 1.00 | 18.05 B |
| ATOM | 4128 | CA | GLU | B | 245 | 22.869 | 33.731 | 25.875 | 1.00 | 18.68 B |
| ATOM | 4129 | CB | GLU | B | 245 | 22.258 | 32.524 | 26.600 | 1.00 | 18.41 B |
| ATOM | 4130 | CG | GLU | B | 245 | 21.001 | 32.823 | 27.418 | 1.00 | 18.86 B |
| ATOM | 4131 | CD | GLU | B | 245 | 19.804 | 33.258 | 26.562 | 1.00 | 26.70 B |
| ATOM | 4132 | OE1 | GLU | B | 245 | 19.107 | 34.218 | 26.980 | 1.00 | 23.58 B |
| ATOM | 4133 | OE2 | GLU | B | 245 | 19.558 | 32.635 | 25.489 | 1.00 | 25.59 B |
| ATOM | 4134 | C | GLU | B | 245 | 22.972 | 34.921 | 26.857 | 1.00 | 20.93 B |
| ATOM | 4135 | O | GLU | B | 245 | 22.226 | 35.898 | 26.744 | 1.00 | 19.67 B |
| ATOM | 4136 | N | LEU | B | 246 | 23.901 | 34.837 | 27.817 | 1.00 | 22.15 B |
| ATOM | 4137 | CA | LEU | B | 246 | 24.115 | 35.932 | 28.791 | 1.00 | 21.85 B |
| ATOM | 4138 | CB | LEU | B | 246 | 25.220 | 35.524 | 29.799 | 1.00 | 22.31 B |
| ATOM | 4139 | CG | LEU | B | 246 | 24.855 | 34.275 | 30.619 | 1.00 | 23.50 B |
| ATOM | 4140 | CD1 | LEU | B | 246 | 25.985 | 33.932 | 31.618 | 1.00 | 22.59 B |
| ATOM | 4141 | CD2 | LEU | B | 246 | 23.523 | 34.524 | 31.370 | 1.00 | 23.93 B |
| ATOM | 4142 | C | LEU | B | 246 | 24.523 | 37.240 | 28.088 | 1.00 | 22.02 B |
| ATOM | 4143 | O | LEU | B | 246 | 24.093 | 38.310 | 28.477 | 1.00 | 22.87 B |
| ATOM | 4144 | N | LEU | B | 247 | 25.361 | 37.172 | 27.055 | 1.00 | 22.12 B |
| ATOM | 4145 | CA | LEU | B | 247 | 25.741 | 38.392 | 26.361 | 1.00 | 21.46 B |
| ATOM | 4146 | CB | LEU | B | 247 | 26.939 | 38.130 | 25.434 | 1.00 | 22.75 B |
| ATOM | 4147 | CG | LEU | B | 247 | 27.408 | 39.192 | 24.428 | 1.00 | 27.31 B |
| ATOM | 4148 | CD1 | LEU | B | 247 | 27.625 | 40.552 | 25.110 | 1.00 | 32.23 B |
| ATOM | 4149 | CD2 | LEU | B | 247 | 28.738 | 38.730 | 23.816 | 1.00 | 29.23 B |
| ATOM | 4150 | C | LEU | B | 247 | 24.541 | 38.974 | 25.569 | 1.00 | 23.36 B |
| ATOM | 4151 | O | LEU | B | 247 | 24.312 | 40.192 | 25.569 | 1.00 | 24.82 B |
| ATOM | 4152 | N | ARG | B | 248 | 23.767 | 38.131 | 24.896 | 1.00 | 21.35 B |
| ATOM | 4153 | CA | ARG | B | 248 | 22.611 | 38.626 | 24.151 | 1.00 | 18.39 B |
| ATOM | 4154 | CB | ARG | B | 248 | 21.886 | 37.441 | 23.486 | 1.00 | 20.48 B |
| ATOM | 4155 | CG | ARG | B | 248 | 20.497 | 37.773 | 22.940 | 1.00 | 19.16 B |
| ATOM | 4156 | CD | ARG | B | 248 | 19.895 | 36.500 | 22.342 | 1.00 | 18.96 B |
| ATOM | 4157 | NE | ARG | B | 248 | 18.614 | 36.734 | 21.687 | 1.00 | 18.46 B |
| ATOM | 4158 | CZ | ARG | B | 248 | 17.891 | 35.759 | 21.135 | 1.00 | 21.38 B |
| ATOM | 4159 | NH1 | ARG | B | 248 | 18.352 | 34.505 | 21.176 | 1.00 | 20.14 B |
| ATOM | 4160 | NH2 | ARG | B | 248 | 16.734 | 36.029 | 20.534 | 1.00 | 19.23 B |
| ATOM | 4161 | C | ARG | B | 248 | 21.627 | 39.331 | 25.112 | 1.00 | 19.61 B |
| ATOM | 4162 | O | ARG | B | 248 | 21.093 | 40.403 | 24.819 | 1.00 | 19.89 B |
| ATOM | 4163 | N | THR | B | 249 | 21.354 | 38.721 | 26.259 | 1.00 | 20.63 B |
| ATOM | 4164 | CA | THR | B | 249 | 20.411 | 39.320 | 27.210 | 1.00 | 20.30 B |
| ATOM | 4165 | CB | THR | B | 249 | 20.122 | 38.319 | 28.354 | 1.00 | 23.57 B |
| ATOM | 4166 | OG1 | THR | B | 249 | 19.580 | 37.120 | 27.769 | 1.00 | 26.35 B |
| ATOM | 4167 | CG2 | THR | B | 249 | 19.089 | 38.881 | 29.361 | 1.00 | 20.63 B |
| ATOM | 4168 | C | THR | B | 249 | 20.912 | 40.662 | 27.783 | 1.00 | 21.90 B |
| ATOM | 4169 | O | THR | B | 249 | 20.136 | 41.622 | 27.908 | 1.00 | 19.98 B |
| ATOM | 4170 | N | GLU | B | 250 | 22.214 | 40.737 | 28.071 | 1.00 | 24.06 B |
| ATOM | 4171 | CA | GLU | B | 250 | 22.811 | 41.935 | 28.670 | 1.00 | 25.90 B |
| ATOM | 4172 | CB | GLU | B | 250 | 24.212 | 41.612 | 29.214 | 1.00 | 25.21 B |

TABLE 2-continued

| ATOM | 4173 | CG  | GLU | B | 250 | 24.940 | 42.790 | 29.890 | 1.00 | 31.63 | B |
| ATOM | 4174 | CD  | GLU | B | 250 | 24.054 | 43.574 | 30.862 | 1.00 | 34.21 | B |
| ATOM | 4175 | OE1 | GLU | B | 250 | 23.225 | 42.970 | 31.585 | 1.00 | 33.95 | B |
| ATOM | 4176 | OE2 | GLU | B | 250 | 24.192 | 44.812 | 30.904 | 1.00 | 36.59 | B |
| ATOM | 4177 | C   | GLU | B | 250 | 22.873 | 43.075 | 27.676 | 1.00 | 24.35 | B |
| ATOM | 4178 | O   | GLU | B | 250 | 22.576 | 44.207 | 28.024 | 1.00 | 22.65 | B |
| ATOM | 4179 | N   | ILE | B | 251 | 23.251 | 42.754 | 26.438 | 1.00 | 24.24 | B |
| ATOM | 4180 | CA  | ILE | B | 251 | 23.317 | 43.732 | 25.366 | 1.00 | 25.38 | B |
| ATOM | 4181 | CB  | ILE | B | 251 | 23.776 | 43.085 | 24.008 | 1.00 | 27.37 | B |
| ATOM | 4182 | CG2 | ILE | B | 251 | 23.246 | 43.903 | 22.839 | 1.00 | 31.03 | B |
| ATOM | 4183 | CG1 | ILE | B | 251 | 25.297 | 43.091 | 23.890 | 1.00 | 31.42 | B |
| ATOM | 4184 | CD1 | ILE | B | 251 | 25.879 | 44.481 | 23.505 | 1.00 | 33.33 | B |
| ATOM | 4185 | C   | ILE | B | 251 | 21.943 | 44.357 | 25.166 | 1.00 | 22.90 | B |
| ATOM | 4186 | O   | ILE | B | 251 | 21.831 | 45.570 | 25.045 | 1.00 | 23.83 | B |
| ATOM | 4187 | N   | ASN | B | 252 | 20.888 | 43.545 | 25.126 | 1.00 | 22.96 | B |
| ATOM | 4188 | CA  | ASN | B | 252 | 19.551 | 44.101 | 24.929 | 1.00 | 21.88 | B |
| ATOM | 4189 | CB  | ASN | B | 252 | 18.555 | 42.994 | 24.574 | 1.00 | 23.11 | B |
| ATOM | 4190 | CG  | ASN | B | 252 | 18.746 | 42.468 | 23.147 | 1.00 | 23.37 | B |
| ATOM | 4191 | OD1 | ASN | B | 252 | 18.661 | 43.224 | 22.170 | 1.00 | 19.39 | B |
| ATOM | 4192 | ND2 | ASN | B | 252 | 19.013 | 41.169 | 23.031 | 1.00 | 23.05 | B |
| ATOM | 4193 | C   | ASN | B | 252 | 19.033 | 44.901 | 26.133 | 1.00 | 21.84 | B |
| ATOM | 4194 | O   | ASN | B | 252 | 18.172 | 45.765 | 25.985 | 1.00 | 23.05 | B |
| ATOM | 4195 | N   | ARG | B | 253 | 19.543 | 44.614 | 27.320 | 1.00 | 21.04 | B |
| ATOM | 4196 | CA  | ARG | B | 253 | 19.097 | 45.349 | 28.490 | 1.00 | 23.58 | B |
| ATOM | 4197 | CB  | ARG | B | 253 | 19.489 | 44.605 | 29.779 | 1.00 | 24.48 | B |
| ATOM | 4198 | CG  | ARG | B | 253 | 18.836 | 45.196 | 31.078 | 1.00 | 28.02 | B |
| ATOM | 4199 | CD  | ARG | B | 253 | 19.427 | 44.592 | 32.357 | 1.00 | 28.97 | B |
| ATOM | 4200 | NE  | ARG | B | 253 | 20.857 | 44.870 | 32.483 | 1.00 | 32.96 | B |
| ATOM | 4201 | CZ  | ARG | B | 253 | 21.369 | 46.008 | 32.981 | 1.00 | 37.54 | B |
| ATOM | 4202 | NH1 | ARG | B | 253 | 20.572 | 46.979 | 33.425 | 1.00 | 35.88 | B |
| ATOM | 4203 | NH2 | ARG | B | 253 | 22.684 | 46.206 | 32.990 | 1.00 | 36.48 | B |
| ATOM | 4204 | C   | ARG | B | 253 | 19.770 | 46.727 | 28.453 | 1.00 | 23.77 | B |
| ATOM | 4205 | O   | ARG | B | 253 | 19.126 | 47.735 | 28.699 | 1.00 | 23.90 | B |
| ATOM | 4206 | N   | SER | B | 254 | 21.061 | 46.728 | 28.105 | 1.00 | 25.94 | B |
| ATOM | 4207 | CA  | SER | B | 254 | 21.941 | 47.912 | 28.049 | 1.00 | 29.19 | B |
| ATOM | 4208 | CB  | SER | B | 254 | 23.372 | 47.469 | 28.310 | 1.00 | 30.04 | B |
| ATOM | 4209 | OG  | SER | B | 254 | 23.418 | 46.694 | 29.487 | 1.00 | 39.65 | B |
| ATOM | 4210 | C   | SER | B | 254 | 21.976 | 48.759 | 26.779 | 1.00 | 30.24 | B |
| ATOM | 4211 | O   | SER | B | 254 | 22.292 | 49.941 | 26.828 | 1.00 | 30.50 | B |
| ATOM | 4212 | N   | VAL | B | 255 | 21.704 | 48.161 | 25.629 | 1.00 | 29.60 | B |
| ATOM | 4213 | CA  | VAL | B | 255 | 21.746 | 48.935 | 24.408 | 1.00 | 29.50 | B |
| ATOM | 4214 | CB  | VAL | B | 255 | 22.986 | 48.578 | 23.585 | 1.00 | 29.07 | B |
| ATOM | 4215 | CG1 | VAL | B | 255 | 23.126 | 49.537 | 22.403 | 1.00 | 31.55 | B |
| ATOM | 4216 | CG2 | VAL | B | 255 | 24.221 | 48.628 | 24.464 | 1.00 | 30.70 | B |
| ATOM | 4217 | C   | VAL | B | 255 | 20.509 | 48.685 | 23.577 | 1.00 | 31.57 | B |
| ATOM | 4218 | O   | VAL | B | 255 | 20.288 | 47.575 | 23.100 | 1.00 | 31.11 | B |
| ATOM | 4219 | N   | LYS | B | 256 | 19.697 | 49.718 | 23.405 | 1.00 | 32.36 | B |
| ATOM | 4220 | CA  | LYS | B | 256 | 18.494 | 49.587 | 22.601 | 1.00 | 33.66 | B |
| ATOM | 4221 | CB  | LYS | B | 256 | 17.462 | 50.610 | 23.075 | 1.00 | 34.92 | B |
| ATOM | 4222 | CG  | LYS | B | 256 | 17.124 | 50.390 | 24.550 | 1.00 | 34.93 | B |
| ATOM | 4223 | CD  | LYS | B | 256 | 16.657 | 48.940 | 24.760 | 1.00 | 33.36 | B |
| ATOM | 4224 | CE  | LYS | B | 256 | 16.491 | 48.599 | 26.244 | 1.00 | 35.28 | B |
| ATOM | 4225 | NZ  | LYS | B | 256 | 15.997 | 47.185 | 26.450 | 1.00 | 32.21 | B |
| ATOM | 4226 | C   | LYS | B | 256 | 18.917 | 49.834 | 21.157 | 1.00 | 33.47 | B |
| ATOM | 4227 | O   | LYS | B | 256 | 19.480 | 50.875 | 20.861 | 1.00 | 36.27 | B |
| ATOM | 4228 | N   | VAL | B | 257 | 18.704 | 48.868 | 20.268 | 1.00 | 30.48 | B |
| ATOM | 4229 | CA  | VAL | B | 257 | 19.101 | 49.064 | 18.874 | 1.00 | 27.66 | B |
| ATOM | 4230 | CB  | VAL | B | 257 | 19.818 | 47.835 | 18.305 | 1.00 | 26.04 | B |
| ATOM | 4231 | CG1 | VAL | B | 257 | 21.084 | 47.582 | 19.097 | 1.00 | 27.45 | B |
| ATOM | 4232 | CG2 | VAL | B | 257 | 18.855 | 46.612 | 18.321 | 1.00 | 27.60 | B |
| ATOM | 4233 | C   | VAL | B | 257 | 17.852 | 49.286 | 18.062 | 1.00 | 25.25 | B |
| ATOM | 4234 | O   | VAL | B | 257 | 16.789 | 48.901 | 18.480 | 1.00 | 23.87 | B |
| ATOM | 4235 | N   | GLN | B | 258 | 17.982 | 49.912 | 16.907 | 1.00 | 22.62 | B |
| ATOM | 4236 | CA  | GLN | B | 258 | 16.818 | 50.116 | 16.049 | 1.00 | 26.35 | B |
| ATOM | 4237 | CB  | GLN | B | 258 | 16.068 | 51.403 | 16.429 | 1.00 | 26.85 | B |
| ATOM | 4238 | CG  | GLN | B | 258 | 14.861 | 51.743 | 15.554 | 1.00 | 29.53 | B |
| ATOM | 4239 | CD  | GLN | B | 258 | 13.767 | 50.664 | 15.554 | 1.00 | 31.93 | B |
| ATOM | 4240 | OE1 | GLN | B | 258 | 13.594 | 49.936 | 14.563 | 1.00 | 34.79 | B |
| ATOM | 4241 | NE2 | GLN | B | 258 | 13.026 | 50.571 | 16.639 | 1.00 | 29.21 | B |
| ATOM | 4242 | C   | GLN | B | 258 | 17.316 | 50.190 | 14.615 | 1.00 | 23.38 | B |
| ATOM | 4243 | O   | GLN | B | 258 | 18.140 | 51.039 | 14.284 | 1.00 | 24.45 | B |
| ATOM | 4244 | N   | HIS | B | 259 | 16.860 | 49.270 | 13.774 | 1.00 | 21.70 | B |
| ATOM | 4245 | CA  | HIS | B | 259 | 17.290 | 49.302 | 12.372 | 1.00 | 22.97 | B |
| ATOM | 4246 | CB  | HIS | B | 259 | 16.712 | 48.101 | 11.603 | 1.00 | 21.33 | B |
| ATOM | 4247 | CG  | HIS | B | 259 | 17.203 | 47.992 | 10.202 | 1.00 | 23.30 | B |
| ATOM | 4248 | CD2 | HIS | B | 259 | 18.065 | 47.120 | 9.623  | 1.00 | 25.91 | B |
| ATOM | 4249 | ND1 | HIS | B | 259 | 16.830 | 48.882 | 9.210  | 1.00 | 24.60 | B |
| ATOM | 4250 | CE1 | HIS | B | 259 | 17.445 | 48.560 | 8.081  | 1.00 | 25.30 | B |
| ATOM | 4251 | NE2 | HIS | B | 259 | 18.199 | 47.493 | 8.303  | 1.00 | 26.11 | B |

TABLE 2-continued

| | | | | | | | | | | |
|---|---|---|---|---|---|---|---|---|---|---|
| ATOM | 4252 | C | HIS | B | 259 | 16.714 | 50.636 | 11.859 | 1.00 | 23.12 B |
| ATOM | 4253 | O | HIS | B | 259 | 15.514 | 50.878 | 11.966 | 1.00 | 22.20 B |
| ATOM | 4254 | N | PRO | B | 260 | 17.562 | 51.518 | 11.301 | 1.00 | 24.86 B |
| ATOM | 4255 | CD | PRO | B | 260 | 19.001 | 51.404 | 10.981 | 1.00 | 23.76 B |
| ATOM | 4256 | CA | PRO | B | 260 | 17.005 | 52.789 | 10.831 | 1.00 | 27.33 B |
| ATOM | 4257 | CB | PRO | B | 260 | 18.250 | 53.593 | 10.451 | 1.00 | 26.50 B |
| ATOM | 4258 | CG | PRO | B | 260 | 19.216 | 52.535 | 9.965 | 1.00 | 23.82 B |
| ATOM | 4259 | C | PRO | B | 260 | 15.954 | 52.743 | 9.720 | 1.00 | 31.96 B |
| ATOM | 4260 | O | PRO | B | 260 | 15.220 | 53.712 | 9.522 | 1.00 | 32.79 B |
| ATOM | 4261 | N | GLN | B | 261 | 15.851 | 51.651 | 8.978 | 1.00 | 31.37 B |
| ATOM | 4262 | CA | GLN | B | 261 | 14.805 | 51.629 | 7.950 | 1.00 | 34.02 B |
| ATOM | 4263 | CB | GLN | B | 261 | 15.430 | 51.512 | 6.562 | 1.00 | 36.14 B |
| ATOM | 4264 | CG | GLN | B | 261 | 16.010 | 52.837 | 6.102 | 1.00 | 44.20 B |
| ATOM | 4265 | CD | GLN | B | 261 | 17.510 | 52.805 | 5.906 | 1.00 | 48.07 B |
| ATOM | 4266 | OE1 | GLN | B | 261 | 18.277 | 52.353 | 6.773 | 1.00 | 50.80 B |
| ATOM | 4267 | NE2 | GLN | B | 261 | 17.946 | 53.296 | 4.755 | 1.00 | 51.92 B |
| ATOM | 4268 | C | GLN | B | 261 | 13.714 | 50.570 | 8.135 | 1.00 | 33.51 B |
| ATOM | 4269 | O | GLN | B | 261 | 12.715 | 50.587 | 7.423 | 1.00 | 33.58 B |
| ATOM | 4270 | N | LEU | B | 262 | 13.902 | 49.652 | 9.092 | 1.00 | 31.68 B |
| ATOM | 4271 | CA | LEU | B | 262 | 12.918 | 48.595 | 9.370 | 1.00 | 28.52 B |
| ATOM | 4272 | CB | LEU | B | 262 | 13.514 | 47.210 | 9.076 | 1.00 | 26.54 B |
| ATOM | 4273 | CG | LEU | B | 262 | 14.007 | 47.092 | 7.632 | 1.00 | 28.52 B |
| ATOM | 4274 | CD1 | LEU | B | 262 | 14.918 | 45.886 | 7.483 | 1.00 | 26.92 B |
| ATOM | 4275 | CD2 | LEU | B | 262 | 12.776 | 47.015 | 6.669 | 1.00 | 26.96 B |
| ATOM | 4276 | C | LEU | B | 262 | 12.553 | 48.706 | 10.841 | 1.00 | 29.00 B |
| ATOM | 4277 | O | LEU | B | 262 | 13.271 | 48.217 | 11.715 | 1.00 | 29.11 B |
| ATOM | 4278 | N | PRO | B | 263 | 11.441 | 49.374 | 11.137 | 1.00 | 28.56 B |
| ATOM | 4279 | CD | PRO | B | 263 | 10.544 | 50.044 | 10.177 | 1.00 | 30.84 B |
| ATOM | 4280 | CA | PRO | B | 263 | 10.978 | 49.562 | 12.510 | 1.00 | 28.36 B |
| ATOM | 4281 | CB | PRO | B | 263 | 9.627 | 50.237 | 12.325 | 1.00 | 29.82 B |
| ATOM | 4282 | CG | PRO | B | 263 | 9.836 | 51.043 | 11.048 | 1.00 | 31.88 B |
| ATOM | 4283 | C | PRO | B | 263 | 10.856 | 48.282 | 13.342 | 1.00 | 28.05 B |
| ATOM | 4284 | O | PRO | B | 263 | 11.138 | 48.313 | 14.553 | 1.00 | 26.36 B |
| ATOM | 4285 | N | HIS | B | 264 | 10.455 | 47.166 | 12.723 | 1.00 | 22.96 B |
| ATOM | 4286 | CA | HIS | B | 264 | 10.273 | 45.926 | 13.503 | 1.00 | 23.58 B |
| ATOM | 4287 | CB | HIS | B | 264 | 9.393 | 44.896 | 12.736 | 1.00 | 22.48 B |
| ATOM | 4288 | CG | HIS | B | 264 | 10.043 | 44.328 | 11.502 | 1.00 | 25.10 B |
| ATOM | 4289 | CD2 | HIS | B | 264 | 10.634 | 43.126 | 11.278 | 1.00 | 23.98 B |
| ATOM | 4290 | ND1 | HIS | B | 264 | 10.206 | 45.055 | 10.339 | 1.00 | 20.42 B |
| ATOM | 4291 | CE1 | HIS | B | 264 | 10.878 | 44.332 | 9.460 | 1.00 | 23.47 B |
| ATOM | 4292 | NE2 | HIS | B | 264 | 11.150 | 43.157 | 10.005 | 1.00 | 23.28 B |
| ATOM | 4293 | C | HIS | B | 264 | 11.567 | 45.248 | 13.989 | 1.00 | 21.78 B |
| ATOM | 4294 | O | HIS | B | 264 | 11.516 | 44.331 | 14.813 | 1.00 | 21.79 B |
| ATOM | 4295 | N | ILE | B | 265 | 12.730 | 45.653 | 13.484 | 1.00 | 20.77 B |
| ATOM | 4296 | CA | ILE | B | 265 | 13.964 | 45.031 | 13.977 | 1.00 | 22.53 B |
| ATOM | 4297 | CB | ILE | B | 265 | 14.962 | 44.760 | 12.837 | 1.00 | 21.59 B |
| ATOM | 4298 | CG2 | ILE | B | 265 | 16.121 | 43.895 | 13.380 | 1.00 | 20.60 B |
| ATOM | 4299 | CG1 | ILE | B | 265 | 14.230 | 44.032 | 11.680 | 1.00 | 23.48 B |
| ATOM | 4300 | CD1 | ILE | B | 265 | 15.114 | 43.682 | 10.468 | 1.00 | 23.27 B |
| ATOM | 4301 | C | ILE | B | 265 | 14.552 | 45.978 | 15.024 | 1.00 | 24.24 B |
| ATOM | 4302 | O | ILE | B | 265 | 15.095 | 47.052 | 14.708 | 1.00 | 22.60 B |
| ATOM | 4303 | N | ASN | B | 266 | 14.406 | 45.585 | 16.284 | 1.00 | 26.26 B |
| ATOM | 4304 | CA | ASN | B | 266 | 14.862 | 46.423 | 17.369 | 1.00 | 25.37 B |
| ATOM | 4305 | CB | ASN | B | 266 | 13.697 | 47.307 | 17.814 | 1.00 | 28.78 B |
| ATOM | 4306 | CG | ASN | B | 266 | 12.423 | 46.511 | 18.044 | 1.00 | 29.78 B |
| ATOM | 4307 | OD1 | ASN | B | 266 | 11.333 | 46.917 | 17.636 | 1.00 | 34.47 B |
| ATOM | 4308 | ND2 | ASN | B | 266 | 12.549 | 45.378 | 18.705 | 1.00 | 30.29 B |
| ATOM | 4309 | C | ASN | B | 266 | 15.405 | 45.632 | 18.552 | 1.00 | 25.99 B |
| ATOM | 4310 | O | ASN | B | 266 | 15.225 | 46.025 | 19.716 | 1.00 | 23.39 B |
| ATOM | 4311 | N | THR | B | 267 | 16.053 | 44.508 | 18.262 | 1.00 | 23.46 B |
| ATOM | 4312 | CA | THR | B | 267 | 16.663 | 43.682 | 19.319 | 1.00 | 20.83 B |
| ATOM | 4313 | CB | THR | B | 267 | 15.712 | 42.555 | 19.814 | 1.00 | 22.37 B |
| ATOM | 4314 | OG1 | THR | B | 267 | 15.295 | 41.769 | 18.684 | 1.00 | 25.80 B |
| ATOM | 4315 | CG2 | THR | B | 267 | 14.473 | 43.123 | 20.507 | 1.00 | 20.88 B |
| ATOM | 4316 | C | THR | B | 267 | 17.871 | 43.004 | 18.663 | 1.00 | 20.33 B |
| ATOM | 4317 | O | THR | B | 267 | 17.905 | 42.832 | 17.426 | 1.00 | 19.55 B |
| ATOM | 4318 | N | VAL | B | 268 | 18.873 | 42.673 | 19.468 | 1.00 | 18.62 B |
| ATOM | 4319 | CA | VAL | B | 268 | 20.051 | 41.946 | 19.004 | 1.00 | 18.09 B |
| ATOM | 4320 | CB | VAL | B | 268 | 21.300 | 42.304 | 19.846 | 1.00 | 17.35 B |
| ATOM | 4321 | CG1 | VAL | B | 268 | 22.463 | 41.417 | 19.462 | 1.00 | 13.08 B |
| ATOM | 4322 | CG2 | VAL | B | 268 | 21.636 | 43.771 | 19.668 | 1.00 | 16.71 B |
| ATOM | 4323 | C | VAL | B | 268 | 19.650 | 40.457 | 19.241 | 1.00 | 19.11 B |
| ATOM | 4324 | O | VAL | B | 268 | 19.415 | 40.028 | 20.385 | 1.00 | 17.09 B |
| ATOM | 4325 | N | ASP | B | 269 | 19.549 | 39.687 | 18.160 | 1.00 | 17.98 B |
| ATOM | 4326 | CA | ASP | B | 269 | 19.114 | 38.295 | 18.242 | 1.00 | 20.37 B |
| ATOM | 4327 | CB | ASP | B | 269 | 18.050 | 38.012 | 17.163 | 1.00 | 23.09 B |
| ATOM | 4328 | CG | ASP | B | 269 | 16.841 | 38.912 | 17.274 | 1.00 | 29.74 B |
| ATOM | 4329 | OD1 | ASP | B | 269 | 16.661 | 39.532 | 18.355 | 1.00 | 31.79 B |
| ATOM | 4330 | OD2 | ASP | B | 269 | 16.045 | 38.994 | 16.284 | 1.00 | 28.20 B |

TABLE 2-continued

| ATOM | 4331 | C   | ASP | B | 269 | 20.179 | 37.231 | 18.108 | 1.00 | 18.62 | B |
| ATOM | 4332 | O   | ASP | B | 269 | 19.892 | 36.039 | 18.297 | 1.00 | 18.69 | B |
| ATOM | 4333 | N   | CYS | B | 270 | 21.397 | 37.633 | 17.776 | 1.00 | 18.19 | B |
| ATOM | 4334 | CA  | CYS | B | 270 | 22.468 | 36.670 | 17.568 | 1.00 | 16.63 | B |
| ATOM | 4335 | CB  | CYS | B | 270 | 22.682 | 36.460 | 16.061 | 1.00 | 20.16 | B |
| ATOM | 4336 | SG  | CYS | B | 270 | 21.149 | 36.098 | 15.141 | 1.00 | 21.54 | B |
| ATOM | 4337 | C   | CYS | B | 270 | 23.783 | 37.140 | 18.143 | 1.00 | 17.57 | B |
| ATOM | 4338 | O   | CYS | B | 270 | 24.080 | 38.338 | 18.129 | 1.00 | 17.58 | B |
| ATOM | 4339 | N   | VAL | B | 271 | 24.573 | 36.196 | 18.640 | 1.00 | 16.48 | B |
| ATOM | 4340 | CA  | VAL | B | 271 | 25.888 | 36.520 | 19.149 | 1.00 | 16.35 | B |
| ATOM | 4341 | CB  | VAL | B | 271 | 26.021 | 36.250 | 20.650 | 1.00 | 15.70 | B |
| ATOM | 4342 | CG1 | VAL | B | 271 | 27.469 | 36.437 | 21.075 | 1.00 | 15.92 | B |
| ATOM | 4343 | CG2 | VAL | B | 271 | 25.132 | 37.261 | 21.417 | 1.00 | 15.00 | B |
| ATOM | 4344 | C   | VAL | B | 271 | 26.875 | 35.690 | 18.382 | 1.00 | 16.93 | B |
| ATOM | 4345 | O   | VAL | B | 271 | 26.752 | 34.468 | 18.300 | 1.00 | 16.84 | B |
| ATOM | 4346 | N   | GLU | B | 272 | 27.853 | 36.381 | 17.810 | 1.00 | 18.81 | B |
| ATOM | 4347 | CA  | GLU | B | 272 | 28.897 | 35.797 | 16.996 | 1.00 | 20.90 | B |
| ATOM | 4348 | CB  | GLU | B | 272 | 29.005 | 36.617 | 15.703 | 1.00 | 21.15 | B |
| ATOM | 4349 | CG  | GLU | B | 272 | 30.112 | 36.184 | 14.731 | 1.00 | 24.76 | B |
| ATOM | 4350 | CD  | GLU | B | 272 | 30.067 | 36.995 | 13.429 | 1.00 | 26.53 | B |
| ATOM | 4351 | OE1 | GLU | B | 272 | 28.950 | 37.366 | 13.016 | 1.00 | 25.44 | B |
| ATOM | 4352 | OE2 | GLU | B | 272 | 31.129 | 37.252 | 12.819 | 1.00 | 28.19 | B |
| ATOM | 4353 | C   | GLU | B | 272 | 30.224 | 35.821 | 17.769 | 1.00 | 23.58 | B |
| ATOM | 4354 | O   | GLU | B | 272 | 30.779 | 36.892 | 18.040 | 1.00 | 22.03 | B |
| ATOM | 4355 | N   | ILE | B | 273 | 30.713 | 34.642 | 18.135 | 1.00 | 23.04 | B |
| ATOM | 4356 | CA  | ILE | B | 273 | 31.965 | 34.502 | 18.873 | 1.00 | 21.91 | B |
| ATOM | 4357 | CB  | ILE | B | 273 | 31.777 | 33.437 | 19.986 | 1.00 | 23.57 | B |
| ATOM | 4358 | CG2 | ILE | B | 273 | 33.066 | 33.291 | 20.802 | 1.00 | 19.24 | B |
| ATOM | 4359 | CG1 | ILE | B | 273 | 30.580 | 33.836 | 20.843 | 1.00 | 18.64 | B |
| ATOM | 4360 | CD1 | ILE | B | 273 | 30.153 | 32.848 | 21.878 | 1.00 | 19.58 | B |
| ATOM | 4361 | C   | ILE | B | 273 | 33.009 | 34.056 | 17.837 | 1.00 | 23.92 | B |
| ATOM | 4362 | O   | ILE | B | 273 | 32.866 | 33.003 | 17.218 | 1.00 | 22.57 | B |
| ATOM | 4363 | N   | TYR | B | 274 | 34.041 | 34.862 | 17.610 | 1.00 | 23.93 | B |
| ATOM | 4364 | CA  | TYR | B | 274 | 35.041 | 34.521 | 16.606 | 1.00 | 24.62 | B |
| ATOM | 4365 | CB  | TYR | B | 274 | 35.054 | 35.572 | 15.502 | 1.00 | 25.85 | B |
| ATOM | 4366 | CG  | TYR | B | 274 | 35.797 | 36.859 | 15.865 | 1.00 | 29.39 | B |
| ATOM | 4367 | CD1 | TYR | B | 274 | 37.135 | 37.059 | 15.471 | 1.00 | 32.27 | B |
| ATOM | 4368 | CE1 | TYR | B | 274 | 37.805 | 38.270 | 15.743 | 1.00 | 30.29 | B |
| ATOM | 4369 | CD2 | TYR | B | 274 | 35.153 | 37.890 | 16.547 | 1.00 | 27.51 | B |
| ATOM | 4370 | CE2 | TYR | B | 274 | 35.804 | 39.102 | 16.822 | 1.00 | 30.17 | B |
| ATOM | 4371 | CZ  | TYR | B | 274 | 37.128 | 39.286 | 16.412 | 1.00 | 32.06 | B |
| ATOM | 4372 | OH  | TYR | B | 274 | 37.750 | 40.500 | 16.628 | 1.00 | 34.51 | B |
| ATOM | 4373 | C   | TYR | B | 274 | 36.444 | 34.365 | 17.161 | 1.00 | 25.89 | B |
| ATOM | 4374 | O   | TYR | B | 274 | 36.741 | 34.779 | 18.280 | 1.00 | 27.89 | B |
| ATOM | 4375 | N   | GLY | B | 275 | 37.290 | 33.742 | 16.360 | 1.00 | 27.45 | B |
| ATOM | 4376 | CA  | GLY | B | 275 | 38.671 | 33.480 | 16.734 | 1.00 | 29.14 | B |
| ATOM | 4377 | C   | GLY | B | 275 | 39.493 | 33.009 | 15.544 | 1.00 | 29.69 | B |
| ATOM | 4378 | O   | GLY | B | 275 | 39.004 | 32.998 | 14.396 | 1.00 | 31.46 | B |
| ATOM | 4379 | N   | PRO | B | 276 | 40.749 | 32.603 | 15.779 | 1.00 | 30.70 | B |
| ATOM | 4380 | CD  | PRO | B | 276 | 41.391 | 32.636 | 17.104 | 1.00 | 30.52 | B |
| ATOM | 4381 | CA  | PRO | B | 276 | 41.689 | 32.119 | 14.757 | 1.00 | 30.59 | B |
| ATOM | 4382 | CB  | PRO | B | 276 | 42.913 | 31.695 | 15.571 | 1.00 | 30.54 | B |
| ATOM | 4383 | CG  | PRO | B | 276 | 42.858 | 32.651 | 16.745 | 1.00 | 32.78 | B |
| ATOM | 4384 | C   | PRO | B | 276 | 41.158 | 30.953 | 13.980 | 1.00 | 29.49 | B |
| ATOM | 4385 | O   | PRO | B | 276 | 40.557 | 30.060 | 14.540 | 1.00 | 29.97 | B |
| ATOM | 4386 | N   | PRO | B | 277 | 41.400 | 30.931 | 12.670 | 1.00 | 30.75 | B |
| ATOM | 4387 | CD  | PRO | B | 277 | 42.077 | 31.968 | 11.866 | 1.00 | 29.65 | B |
| ATOM | 4388 | CA  | PRO | B | 277 | 40.928 | 29.823 | 11.828 | 1.00 | 31.30 | B |
| ATOM | 4389 | CB  | PRO | B | 277 | 41.189 | 30.333 | 10.419 | 1.00 | 31.23 | B |
| ATOM | 4390 | CG  | PRO | B | 277 | 42.456 | 31.205 | 10.624 | 1.00 | 29.77 | B |
| ATOM | 4391 | C   | PRO | B | 277 | 41.744 | 28.552 | 12.112 | 1.00 | 33.09 | B |
| ATOM | 4392 | O   | PRO | B | 277 | 42.809 | 28.630 | 12.714 | 1.00 | 32.82 | B |
| ATOM | 4393 | N   | THR | B | 278 | 41.216 | 27.389 | 11.735 | 1.00 | 31.19 | B |
| ATOM | 4394 | CA  | THR | B | 278 | 41.957 | 26.152 | 11.879 | 1.00 | 33.37 | B |
| ATOM | 4395 | CB  | THR | B | 278 | 41.140 | 25.032 | 12.514 | 1.00 | 33.50 | B |
| ATOM | 4396 | OG1 | THR | B | 278 | 40.915 | 25.337 | 13.890 | 1.00 | 36.07 | B |
| ATOM | 4397 | CG2 | THR | B | 278 | 41.895 | 23.694 | 12.403 | 1.00 | 34.08 | B |
| ATOM | 4398 | C   | THR | B | 278 | 42.286 | 25.762 | 10.450 | 1.00 | 34.04 | B |
| ATOM | 4399 | O   | THR | B | 278 | 43.367 | 25.249 | 10.155 | 1.00 | 36.70 | B |
| ATOM | 4400 | N   | ASN | B | 279 | 41.345 | 26.001 | 9.550  | 1.00 | 33.97 | B |
| ATOM | 4401 | CA  | ASN | B | 279 | 41.596 | 25.690 | 8.173  | 1.00 | 34.44 | B |
| ATOM | 4402 | CB  | ASN | B | 279 | 40.302 | 25.586 | 7.392  | 1.00 | 36.17 | B |
| ATOM | 4403 | CG  | ASN | B | 279 | 40.539 | 25.170 | 5.964  | 1.00 | 35.93 | B |
| ATOM | 4404 | OD1 | ASN | B | 279 | 41.439 | 25.683 | 5.303  | 1.00 | 37.59 | B |
| ATOM | 4405 | ND2 | ASN | B | 279 | 39.736 | 24.242 | 5.475  | 1.00 | 37.18 | B |
| ATOM | 4406 | C   | ASN | B | 279 | 42.450 | 26.805 | 7.595  | 1.00 | 36.89 | B |
| ATOM | 4407 | O   | ASN | B | 279 | 42.139 | 27.986 | 7.719  | 1.00 | 35.90 | B |
| ATOM | 4408 | N   | ALA | B | 280 | 43.535 | 26.410 | 6.953  | 1.00 | 38.37 | B |
| ATOM | 4409 | CA  | ALA | B | 280 | 44.456 | 27.350 | 6.366  | 1.00 | 38.17 | B |

TABLE 2-continued

| ATOM | 4410 | CB | ALA | B | 280 | 45.602 | 26.576 | 5.722 | 1.00 | 41.11 | B |
|------|------|-----|-----|---|-----|--------|--------|--------|------|-------|---|
| ATOM | 4411 | C | ALA | B | 280 | 43.799 | 28.258 | 5.338 | 1.00 | 37.13 | B |
| ATOM | 4412 | O | ALA | B | 280 | 44.303 | 29.326 | 5.053 | 1.00 | 37.57 | B |
| ATOM | 4413 | N | ALA | B | 281 | 42.671 | 27.855 | 4.775 | 1.00 | 35.36 | B |
| ATOM | 4414 | CA | ALA | B | 281 | 42.053 | 28.702 | 3.765 | 1.00 | 33.49 | B |
| ATOM | 4415 | CB | ALA | B | 281 | 41.337 | 27.840 | 2.735 | 1.00 | 32.32 | B |
| ATOM | 4416 | C | ALA | B | 281 | 41.090 | 29.741 | 4.334 | 1.00 | 31.88 | B |
| ATOM | 4417 | O | ALA | B | 281 | 40.647 | 30.619 | 3.623 | 1.00 | 31.61 | B |
| ATOM | 4418 | N | ALA | B | 282 | 40.773 | 29.661 | 5.616 | 1.00 | 30.29 | B |
| ATOM | 4419 | CA | ALA | B | 282 | 39.836 | 30.613 | 6.191 | 1.00 | 29.41 | B |
| ATOM | 4420 | CB | ALA | B | 282 | 38.939 | 29.913 | 7.200 | 1.00 | 24.10 | B |
| ATOM | 4421 | C | ALA | B | 282 | 40.508 | 31.816 | 6.841 | 1.00 | 28.29 | B |
| ATOM | 4422 | O | ALA | B | 282 | 41.625 | 31.722 | 7.302 | 1.00 | 29.25 | B |
| ATOM | 4423 | N | ASN | B | 283 | 39.802 | 32.934 | 6.890 | 1.00 | 27.61 | B |
| ATOM | 4424 | CA | ASN | B | 283 | 40.329 | 34.141 | 7.523 | 1.00 | 29.10 | B |
| ATOM | 4425 | CB | ASN | B | 283 | 39.570 | 35.392 | 7.074 | 1.00 | 27.02 | B |
| ATOM | 4426 | CG | ASN | B | 283 | 39.837 | 35.744 | 5.650 | 1.00 | 30.78 | B |
| ATOM | 4427 | OD1 | ASN | B | 283 | 40.515 | 36.732 | 5.347 | 1.00 | 32.73 | B |
| ATOM | 4428 | ND2 | ASN | B | 283 | 39.310 | 34.940 | 4.749 | 1.00 | 29.57 | B |
| ATOM | 4429 | C | ASN | B | 283 | 40.144 | 34.001 | 9.018 | 1.00 | 28.49 | B |
| ATOM | 4430 | O | ASN | B | 283 | 41.035 | 34.350 | 9.778 | 1.00 | 27.23 | B |
| ATOM | 4431 | N | TYR | B | 284 | 38.970 | 33.503 | 9.419 | 1.00 | 28.27 | B |
| ATOM | 4432 | CA | TYR | B | 284 | 38.606 | 33.325 | 10.836 | 1.00 | 29.54 | B |
| ATOM | 4433 | CB | TYR | B | 284 | 37.879 | 34.580 | 11.383 | 1.00 | 30.63 | B |
| ATOM | 4434 | CG | TYR | B | 284 | 38.710 | 35.859 | 11.442 | 1.00 | 32.81 | B |
| ATOM | 4435 | CD1 | TYR | B | 284 | 39.758 | 36.000 | 12.358 | 1.00 | 36.40 | B |
| ATOM | 4436 | CE1 | TYR | B | 284 | 40.553 | 37.141 | 12.377 | 1.00 | 37.48 | B |
| ATOM | 4437 | CD2 | TYR | B | 284 | 38.475 | 36.902 | 10.545 | 1.00 | 36.01 | B |
| ATOM | 4438 | CE2 | TYR | B | 284 | 39.256 | 38.049 | 10.546 | 1.00 | 37.71 | B |
| ATOM | 4439 | CZ | TYR | B | 284 | 40.299 | 38.165 | 11.463 | 1.00 | 39.96 | B |
| ATOM | 4440 | OH | TYR | B | 284 | 41.094 | 39.302 | 11.440 | 1.00 | 41.93 | B |
| ATOM | 4441 | C | TYR | B | 284 | 37.659 | 32.143 | 11.010 | 1.00 | 28.79 | B |
| ATOM | 4442 | O | TYR | B | 284 | 37.183 | 31.562 | 10.032 | 1.00 | 27.79 | B |
| ATOM | 4443 | N | LYS | B | 285 | 37.383 | 31.812 | 12.265 | 1.00 | 26.45 | B |
| ATOM | 4444 | CA | LYS | B | 285 | 36.453 | 30.761 | 12.595 | 1.00 | 26.21 | B |
| ATOM | 4445 | CB | LYS | B | 285 | 37.177 | 29.612 | 13.291 | 1.00 | 27.59 | B |
| ATOM | 4446 | CG | LYS | B | 285 | 36.254 | 28.526 | 13.695 | 1.00 | 27.93 | B |
| ATOM | 4447 | CD | LYS | B | 285 | 36.844 | 27.558 | 14.733 | 1.00 | 33.21 | B |
| ATOM | 4448 | CE | LYS | B | 285 | 38.190 | 26.954 | 14.301 | 1.00 | 31.02 | B |
| ATOM | 4449 | NZ | LYS | B | 285 | 38.371 | 25.617 | 14.946 | 1.00 | 33.66 | B |
| ATOM | 4450 | C | LYS | B | 285 | 35.425 | 31.388 | 13.540 | 1.00 | 27.15 | B |
| ATOM | 4451 | O | LYS | B | 285 | 35.728 | 32.357 | 14.242 | 1.00 | 28.11 | B |
| ATOM | 4452 | N | ASN | B | 286 | 34.193 | 30.903 | 13.539 | 1.00 | 24.35 | B |
| ATOM | 4453 | CA | ASN | B | 286 | 33.224 | 31.474 | 14.458 | 1.00 | 24.30 | B |
| ATOM | 4454 | CB | ASN | B | 286 | 32.550 | 32.744 | 13.875 | 1.00 | 21.64 | B |
| ATOM | 4455 | CG | ASN | B | 286 | 31.381 | 32.421 | 12.901 | 1.00 | 26.71 | B |
| ATOM | 4456 | OD1 | ASN | B | 286 | 31.590 | 32.106 | 11.720 | 1.00 | 26.63 | B |
| ATOM | 4457 | ND2 | ASN | B | 286 | 30.163 | 32.481 | 13.403 | 1.00 | 24.63 | B |
| ATOM | 4458 | C | ASN | B | 286 | 32.134 | 30.488 | 14.801 | 1.00 | 22.31 | B |
| ATOM | 4459 | O | ASN | B | 286 | 31.977 | 29.465 | 14.121 | 1.00 | 21.10 | B |
| ATOM | 4460 | N | VAL | B | 287 | 31.409 | 30.792 | 15.876 | 1.00 | 20.11 | B |
| ATOM | 4461 | CA | VAL | B | 287 | 30.218 | 30.039 | 16.231 | 1.00 | 18.93 | B |
| ATOM | 4462 | CB | VAL | B | 287 | 30.459 | 29.019 | 17.352 | 1.00 | 21.57 | B |
| ATOM | 4463 | CG1 | VAL | B | 287 | 30.971 | 29.703 | 18.605 | 1.00 | 19.17 | B |
| ATOM | 4464 | CG2 | VAL | B | 287 | 29.161 | 28.302 | 17.643 | 1.00 | 19.46 | B |
| ATOM | 4465 | C | VAL | B | 287 | 29.187 | 31.117 | 16.619 | 1.00 | 20.42 | B |
| ATOM | 4466 | O | VAL | B | 287 | 29.492 | 32.061 | 17.336 | 1.00 | 18.29 | B |
| ATOM | 4467 | N | VAL | B | 288 | 27.973 | 31.026 | 16.087 | 1.00 | 20.78 | B |
| ATOM | 4468 | CA | VAL | B | 288 | 26.943 | 32.022 | 16.389 | 1.00 | 15.95 | B |
| ATOM | 4469 | CB | VAL | B | 288 | 26.265 | 32.488 | 15.063 | 1.00 | 15.19 | B |
| ATOM | 4470 | CG1 | VAL | B | 288 | 24.908 | 33.215 | 15.353 | 1.00 | 14.49 | B |
| ATOM | 4471 | CG2 | VAL | B | 288 | 27.210 | 33.414 | 14.276 | 1.00 | 11.34 | B |
| ATOM | 4472 | C | VAL | B | 288 | 25.925 | 31.362 | 17.320 | 1.00 | 16.29 | B |
| ATOM | 4473 | O | VAL | B | 288 | 25.488 | 30.260 | 17.049 | 1.00 | 20.46 | B |
| ATOM | 4474 | N | ILE | B | 289 | 25.575 | 32.027 | 18.418 | 1.00 | 14.70 | B |
| ATOM | 4475 | CA | ILE | B | 289 | 24.622 | 31.523 | 19.401 | 1.00 | 16.01 | B |
| ATOM | 4476 | CB | ILE | B | 289 | 25.124 | 31.740 | 20.858 | 1.00 | 16.66 | B |
| ATOM | 4477 | CG2 | ILE | B | 289 | 24.130 | 31.086 | 21.862 | 1.00 | 14.71 | B |
| ATOM | 4478 | CG1 | ILE | B | 289 | 26.514 | 31.130 | 21.020 | 1.00 | 17.58 | B |
| ATOM | 4479 | CD1 | ILE | B | 289 | 26.624 | 29.695 | 20.447 | 1.00 | 20.06 | B |
| ATOM | 4480 | C | ILE | B | 289 | 23.355 | 32.320 | 19.227 | 1.00 | 15.77 | B |
| ATOM | 4481 | O | ILE | B | 289 | 23.414 | 33.560 | 19.222 | 1.00 | 15.29 | B |
| ATOM | 4482 | N | PHE | B | 290 | 22.209 | 31.636 | 19.133 | 1.00 | 13.94 | B |
| ATOM | 4483 | CA | PHE | B | 290 | 20.953 | 32.339 | 18.883 | 1.00 | 14.57 | B |
| ATOM | 4484 | CB | PHE | B | 290 | 20.832 | 32.622 | 17.385 | 1.00 | 13.60 | B |
| ATOM | 4485 | CG | PHE | B | 290 | 20.684 | 31.345 | 16.517 | 1.00 | 15.09 | B |
| ATOM | 4486 | CD1 | PHE | B | 290 | 19.419 | 30.964 | 16.004 | 1.00 | 14.57 | B |
| ATOM | 4487 | CD2 | PHE | B | 290 | 21.790 | 30.558 | 16.210 | 1.00 | 15.36 | B |
| ATOM | 4488 | CE1 | PHE | B | 290 | 19.278 | 29.822 | 15.197 | 1.00 | 12.71 | B |

TABLE 2-continued

| ATOM | 4489 | CE2 | PHE | B | 290 | 21.662 | 29.374 | 15.390 | 1.00 | 17.26 | B |
|---|---|---|---|---|---|---|---|---|---|---|---|
| ATOM | 4490 | CZ | PHE | B | 290 | 20.400 | 29.021 | 14.890 | 1.00 | 13.79 | B |
| ATOM | 4491 | C | PHE | B | 290 | 19.821 | 31.438 | 19.307 | 1.00 | 16.95 | B |
| ATOM | 4492 | O | PHE | B | 290 | 20.076 | 30.362 | 19.843 | 1.00 | 17.81 | B |
| ATOM | 4493 | N | GLY | B | 291 | 18.583 | 31.842 | 19.020 | 1.00 | 16.05 | B |
| ATOM | 4494 | CA | GLY | B | 291 | 17.441 | 31.007 | 19.389 | 1.00 | 17.59 | B |
| ATOM | 4495 | C | GLY | B | 291 | 17.411 | 30.764 | 20.908 | 1.00 | 18.74 | B |
| ATOM | 4496 | O | GLY | B | 291 | 17.616 | 31.711 | 21.656 | 1.00 | 16.99 | B |
| ATOM | 4497 | N | ASN | B | 292 | 17.102 | 29.541 | 21.364 | 1.00 | 18.13 | B |
| ATOM | 4498 | CA | ASN | B | 292 | 17.126 | 29.239 | 22.813 | 1.00 | 18.85 | B |
| ATOM | 4499 | CB | ASN | B | 292 | 16.106 | 28.147 | 23.151 | 1.00 | 20.25 | B |
| ATOM | 4500 | CG | ASN | B | 292 | 16.003 | 27.892 | 24.639 | 1.00 | 23.65 | B |
| ATOM | 4501 | OD1 | ASN | B | 292 | 16.456 | 28.726 | 25.429 | 1.00 | 19.04 | B |
| ATOM | 4502 | ND2 | ASN | B | 292 | 15.399 | 26.740 | 25.036 | 1.00 | 19.43 | B |
| ATOM | 4503 | C | ASN | B | 292 | 18.571 | 28.751 | 23.007 | 1.00 | 17.43 | B |
| ATOM | 4504 | O | ASN | B | 292 | 18.849 | 27.568 | 23.273 | 1.00 | 18.97 | B |
| ATOM | 4505 | N | ARG | B | 293 | 19.483 | 29.697 | 22.844 | 1.00 | 15.39 | B |
| ATOM | 4506 | CA | ARG | B | 293 | 20.920 | 29.435 | 22.864 | 1.00 | 18.63 | B |
| ATOM | 4507 | CB | ARG | B | 293 | 21.537 | 29.478 | 24.297 | 1.00 | 16.99 | B |
| ATOM | 4508 | CG | ARG | B | 293 | 21.250 | 28.373 | 25.269 | 1.00 | 19.89 | B |
| ATOM | 4509 | CD | ARG | B | 293 | 21.912 | 28.746 | 26.662 | 1.00 | 20.37 | B |
| ATOM | 4510 | NE | ARG | B | 293 | 21.883 | 27.627 | 27.595 | 1.00 | 20.93 | B |
| ATOM | 4511 | CZ | ARG | B | 293 | 20.806 | 27.213 | 28.249 | 1.00 | 19.26 | B |
| ATOM | 4512 | NH1 | ARG | B | 293 | 19.651 | 27.841 | 28.095 | 1.00 | 18.57 | B |
| ATOM | 4513 | NH2 | ARG | B | 293 | 20.882 | 26.132 | 29.024 | 1.00 | 18.49 | B |
| ATOM | 4514 | C | ARG | B | 293 | 21.356 | 28.178 | 22.099 | 1.00 | 20.83 | B |
| ATOM | 4515 | O | ARG | B | 293 | 22.162 | 27.365 | 22.588 | 1.00 | 20.39 | B |
| ATOM | 4516 | N | GLN | B | 294 | 20.823 | 28.013 | 20.875 | 1.00 | 18.85 | B |
| ATOM | 4517 | CA | GLN | B | 294 | 21.277 | 26.896 | 20.049 | 1.00 | 15.16 | B |
| ATOM | 4518 | CB | GLN | B | 294 | 20.224 | 26.499 | 18.987 | 1.00 | 14.87 | B |
| ATOM | 4519 | CG | GLN | B | 294 | 19.803 | 27.618 | 18.021 | 1.00 | 12.74 | B |
| ATOM | 4520 | CD | GLN | B | 294 | 18.544 | 27.222 | 17.208 | 1.00 | 12.47 | B |
| ATOM | 4521 | OE1 | GLN | B | 294 | 17.409 | 27.581 | 17.567 | 1.00 | 13.63 | B |
| ATOM | 4522 | NE2 | GLN | B | 294 | 18.760 | 26.437 | 16.137 | 1.00 | 9.14 | B |
| ATOM | 4523 | C | GLN | B | 294 | 22.513 | 27.483 | 19.381 | 1.00 | 15.29 | B |
| ATOM | 4524 | O | GLN | B | 294 | 22.750 | 28.697 | 19.480 | 1.00 | 15.53 | B |
| ATOM | 4525 | N | ALA | B | 295 | 23.280 | 26.654 | 18.679 | 1.00 | 14.85 | B |
| ATOM | 4526 | CA | ALA | B | 295 | 24.494 | 27.107 | 18.021 | 1.00 | 17.36 | B |
| ATOM | 4527 | CB | ALA | B | 295 | 25.716 | 26.422 | 18.646 | 1.00 | 14.59 | B |
| ATOM | 4528 | C | ALA | B | 295 | 24.421 | 26.727 | 16.544 | 1.00 | 20.27 | B |
| ATOM | 4529 | O | ALA | B | 295 | 23.930 | 25.635 | 16.203 | 1.00 | 19.23 | B |
| ATOM | 4530 | N | ASP | B | 296 | 24.928 | 27.616 | 15.688 | 1.00 | 18.98 | B |
| ATOM | 4531 | CA | ASP | B | 296 | 24.971 | 27.376 | 14.246 | 1.00 | 18.23 | B |
| ATOM | 4532 | CB | ASP | B | 296 | 25.088 | 28.704 | 13.519 | 1.00 | 20.79 | B |
| ATOM | 4533 | CG | ASP | B | 296 | 24.908 | 28.578 | 12.007 | 1.00 | 24.56 | B |
| ATOM | 4534 | OD1 | ASP | B | 296 | 24.737 | 27.449 | 11.464 | 1.00 | 25.61 | B |
| ATOM | 4535 | OD2 | ASP | B | 296 | 24.934 | 29.638 | 11.357 | 1.00 | 26.22 | B |
| ATOM | 4536 | C | ASP | B | 296 | 26.195 | 26.499 | 13.936 | 1.00 | 17.14 | B |
| ATOM | 4537 | O | ASP | B | 296 | 27.300 | 26.770 | 14.387 | 1.00 | 17.35 | B |
| ATOM | 4538 | N | ARG | B | 297 | 25.968 | 25.421 | 13.201 | 1.00 | 17.43 | B |
| ATOM | 4539 | CA | ARG | B | 297 | 27.036 | 24.507 | 12.807 | 1.00 | 17.91 | B |
| ATOM | 4540 | CB | ARG | B | 297 | 26.479 | 23.082 | 12.536 | 1.00 | 17.11 | B |
| ATOM | 4541 | CG | ARG | B | 297 | 26.036 | 22.327 | 13.809 | 1.00 | 18.89 | B |
| ATOM | 4542 | CD | ARG | B | 297 | 24.594 | 22.590 | 14.265 | 1.00 | 20.24 | B |
| ATOM | 4543 | NE | ARG | B | 297 | 24.264 | 21.627 | 15.320 | 1.00 | 21.67 | B |
| ATOM | 4544 | CZ | ARG | B | 297 | 24.447 | 21.827 | 16.630 | 1.00 | 21.96 | B |
| ATOM | 4545 | NH1 | ARG | B | 297 | 24.927 | 22.981 | 17.097 | 1.00 | 19.62 | B |
| ATOM | 4546 | NH2 | ARG | B | 297 | 24.206 | 20.844 | 17.487 | 1.00 | 17.20 | B |
| ATOM | 4547 | C | ARG | B | 297 | 27.705 | 25.036 | 11.552 | 1.00 | 18.71 | B |
| ATOM | 4548 | O | ARG | B | 297 | 28.846 | 24.639 | 11.258 | 1.00 | 20.92 | B |
| ATOM | 4549 | N | SER | B | 298 | 26.986 | 25.902 | 10.806 | 1.00 | 17.13 | B |
| ATOM | 4550 | CA | SER | B | 298 | 27.507 | 26.520 | 9.578 | 1.00 | 17.99 | B |
| ATOM | 4551 | CB | SER | B | 298 | 26.374 | 26.921 | 8.612 | 1.00 | 18.97 | B |
| ATOM | 4552 | OG | SER | B | 298 | 25.818 | 28.216 | 8.936 | 1.00 | 19.93 | B |
| ATOM | 4553 | C | SER | B | 298 | 28.226 | 27.793 | 10.022 | 1.00 | 17.47 | B |
| ATOM | 4554 | O | SER | B | 298 | 28.109 | 28.183 | 11.168 | 1.00 | 18.59 | B |
| ATOM | 4555 | N | PRO | B | 299 | 28.997 | 28.437 | 9.128 | 1.00 | 17.66 | B |
| ATOM | 4556 | CD | PRO | B | 299 | 29.469 | 27.971 | 7.815 | 1.00 | 17.65 | B |
| ATOM | 4557 | CA | PRO | B | 299 | 29.692 | 29.666 | 9.556 | 1.00 | 18.49 | B |
| ATOM | 4558 | CB | PRO | B | 299 | 30.693 | 29.943 | 8.425 | 1.00 | 18.69 | B |
| ATOM | 4559 | CG | PRO | B | 299 | 30.909 | 28.547 | 7.776 | 1.00 | 18.31 | B |
| ATOM | 4560 | C | PRO | B | 299 | 28.725 | 30.830 | 9.781 | 1.00 | 19.81 | B |
| ATOM | 4561 | O | PRO | B | 299 | 29.138 | 31.853 | 10.306 | 1.00 | 23.79 | B |
| ATOM | 4562 | N | CYS | B | 300 | 27.452 | 30.668 | 9.389 | 1.00 | 19.74 | B |
| ATOM | 4563 | CA | CYS | B | 300 | 26.378 | 31.686 | 9.549 | 1.00 | 17.92 | B |
| ATOM | 4564 | CB | CYS | B | 300 | 26.418 | 32.318 | 10.959 | 1.00 | 21.70 | B |
| ATOM | 4565 | SG | CYS | B | 300 | 24.928 | 33.340 | 11.375 | 1.00 | 21.58 | B |
| ATOM | 4566 | C | CYS | B | 300 | 26.468 | 32.784 | 8.484 | 1.00 | 20.18 | B |
| ATOM | 4567 | O | CYS | B | 300 | 27.385 | 33.625 | 8.479 | 1.00 | 21.88 | B |

TABLE 2-continued

| ATOM | 4568 | N | GLY | B | 301 | 25.497 | 32.794 | 7.586 | 1.00 | 17.72 | B |
| ATOM | 4569 | CA | GLY | B | 301 | 25.521 | 33.761 | 6.504 | 1.00 | 19.12 | B |
| ATOM | 4570 | C | GLY | B | 301 | 25.235 | 35.192 | 6.909 | 1.00 | 19.66 | B |
| ATOM | 4571 | O | GLY | B | 301 | 25.846 | 36.105 | 6.364 | 1.00 | 20.82 | B |
| ATOM | 4572 | N | THR | B | 302 | 24.282 | 35.422 | 7.808 | 1.00 | 18.67 | B |
| ATOM | 4573 | CA | THR | B | 302 | 24.038 | 36.803 | 8.232 | 1.00 | 18.51 | B |
| ATOM | 4574 | CB | THR | B | 302 | 22.684 | 36.998 | 8.998 | 1.00 | 16.35 | B |
| ATOM | 4575 | OG1 | THR | B | 302 | 22.559 | 36.037 | 10.043 | 1.00 | 16.80 | B |
| ATOM | 4576 | CG2 | THR | B | 302 | 21.510 | 36.861 | 8.061 | 1.00 | 19.01 | B |
| ATOM | 4577 | C | THR | B | 302 | 25.220 | 37.241 | 9.129 | 1.00 | 18.62 | B |
| ATOM | 4578 | O | THR | B | 302 | 25.599 | 38.413 | 9.121 | 1.00 | 19.41 | B |
| ATOM | 4579 | N | GLY | B | 303 | 25.810 | 36.300 | 9.863 | 1.00 | 18.02 | B |
| ATOM | 4580 | CA | GLY | B | 303 | 26.950 | 36.606 | 10.734 | 1.00 | 20.18 | B |
| ATOM | 4581 | C | GLY | B | 303 | 28.174 | 36.981 | 9.908 | 1.00 | 23.29 | B |
| ATOM | 4582 | O | GLY | B | 303 | 28.927 | 37.888 | 10.274 | 1.00 | 22.50 | B |
| ATOM | 4583 | N | THR | B | 304 | 28.377 | 36.287 | 8.787 | 1.00 | 20.83 | B |
| ATOM | 4584 | CA | THR | B | 304 | 29.480 | 36.617 | 7.889 | 1.00 | 20.55 | B |
| ATOM | 4585 | CB | THR | B | 304 | 29.583 | 35.540 | 6.756 | 1.00 | 19.71 | B |
| ATOM | 4586 | OG1 | THR | B | 304 | 29.811 | 34.262 | 7.355 | 1.00 | 18.24 | B |
| ATOM | 4587 | CG2 | THR | B | 304 | 30.732 | 35.826 | 5.799 | 1.00 | 15.10 | B |
| ATOM | 4588 | C | THR | B | 304 | 29.209 | 38.039 | 7.296 | 1.00 | 22.24 | B |
| ATOM | 4589 | O | THR | B | 304 | 30.106 | 38.890 | 7.247 | 1.00 | 22.60 | B |
| ATOM | 4590 | N | SER | B | 305 | 27.972 | 38.319 | 6.884 | 1.00 | 22.31 | B |
| ATOM | 4591 | CA | SER | B | 305 | 27.669 | 39.641 | 6.319 | 1.00 | 23.06 | B |
| ATOM | 4592 | CB | SER | B | 305 | 26.201 | 39.803 | 5.958 | 1.00 | 21.16 | B |
| ATOM | 4593 | OG | SER | B | 305 | 25.815 | 38.801 | 5.058 | 1.00 | 28.01 | B |
| ATOM | 4594 | C | SER | B | 305 | 27.984 | 40.660 | 7.385 | 1.00 | 23.82 | B |
| ATOM | 4595 | O | SER | B | 305 | 28.637 | 41.650 | 7.118 | 1.00 | 24.28 | B |
| ATOM | 4596 | N | ALA | B | 306 | 27.490 | 40.426 | 8.595 | 1.00 | 22.72 | B |
| ATOM | 4597 | CA | ALA | B | 306 | 27.771 | 41.342 | 9.704 | 1.00 | 22.21 | B |
| ATOM | 4598 | CB | ALA | B | 306 | 27.052 | 40.841 | 11.005 | 1.00 | 19.38 | B |
| ATOM | 4599 | C | ALA | B | 306 | 29.284 | 41.504 | 9.957 | 1.00 | 21.86 | B |
| ATOM | 4600 | O | ALA | B | 306 | 29.799 | 42.612 | 10.174 | 1.00 | 20.95 | B |
| ATOM | 4601 | N | LYS | B | 307 | 30.004 | 40.403 | 9.952 | 1.00 | 21.22 | B |
| ATOM | 4602 | CA | LYS | B | 307 | 31.437 | 40.464 | 10.194 | 1.00 | 21.77 | B |
| ATOM | 4603 | CB | LYS | B | 307 | 31.984 | 39.039 | 10.279 | 1.00 | 19.90 | B |
| ATOM | 4604 | CG | LYS | B | 307 | 33.489 | 38.930 | 10.355 | 1.00 | 24.69 | B |
| ATOM | 4605 | CD | LYS | B | 307 | 34.023 | 39.346 | 11.723 | 1.00 | 27.38 | B |
| ATOM | 4606 | CE | LYS | B | 307 | 35.505 | 39.124 | 11.838 | 1.00 | 26.03 | B |
| ATOM | 4607 | NZ | LYS | B | 307 | 35.885 | 39.513 | 13.235 | 1.00 | 32.57 | B |
| ATOM | 4608 | C | LYS | B | 307 | 32.120 | 41.235 | 9.048 | 1.00 | 24.17 | B |
| ATOM | 4609 | O | LYS | B | 307 | 33.008 | 42.077 | 9.290 | 1.00 | 24.25 | B |
| ATOM | 4610 | N | MET | B | 308 | 31.691 | 40.986 | 7.800 | 1.00 | 22.18 | B |
| ATOM | 4611 | CA | MET | B | 308 | 32.324 | 41.690 | 6.675 | 1.00 | 22.84 | B |
| ATOM | 4612 | CB | MET | B | 308 | 31.918 | 41.109 | 5.304 | 1.00 | 20.43 | B |
| ATOM | 4613 | CG | MET | B | 308 | 32.532 | 39.721 | 5.037 | 1.00 | 21.75 | B |
| ATOM | 4614 | SD | MET | B | 308 | 32.164 | 39.133 | 3.379 | 1.00 | 31.01 | B |
| ATOM | 4615 | CE | MET | B | 308 | 30.453 | 39.025 | 3.438 | 1.00 | 20.19 | B |
| ATOM | 4616 | C | MET | B | 308 | 32.013 | 43.174 | 6.700 | 1.00 | 23.26 | B |
| ATOM | 4617 | O | MET | B | 308 | 32.856 | 43.971 | 6.305 | 1.00 | 20.96 | B |
| ATOM | 4618 | N | ALA | B | 309 | 30.807 | 43.543 | 7.146 | 1.00 | 22.55 | B |
| ATOM | 4619 | CA | ALA | B | 309 | 30.454 | 44.972 | 7.216 | 1.00 | 23.95 | B |
| ATOM | 4620 | CB | ALA | B | 309 | 29.019 | 45.157 | 7.573 | 1.00 | 21.81 | B |
| ATOM | 4621 | C | ALA | B | 309 | 31.328 | 45.648 | 8.258 | 1.00 | 24.65 | B |
| ATOM | 4622 | O | ALA | B | 309 | 31.773 | 46.781 | 8.047 | 1.00 | 25.05 | B |
| ATOM | 4623 | N | THR | B | 310 | 31.565 | 44.953 | 9.370 | 1.00 | 23.33 | B |
| ATOM | 4624 | CA | THR | B | 310 | 32.419 | 45.462 | 10.444 | 1.00 | 23.58 | B |
| ATOM | 4625 | CB | THR | B | 310 | 32.398 | 44.507 | 11.656 | 1.00 | 22.56 | B |
| ATOM | 4626 | OG1 | THR | B | 310 | 31.054 | 44.427 | 12.126 | 1.00 | 23.56 | B |
| ATOM | 4627 | CG2 | THR | B | 310 | 33.309 | 45.019 | 12.824 | 1.00 | 21.09 | B |
| ATOM | 4628 | C | THR | B | 310 | 33.862 | 45.654 | 9.947 | 1.00 | 23.79 | B |
| ATOM | 4629 | O | THR | B | 310 | 34.407 | 46.743 | 10.042 | 1.00 | 24.36 | B |
| ATOM | 4630 | N | LEU | B | 311 | 34.492 | 44.595 | 9.445 | 1.00 | 25.69 | B |
| ATOM | 4631 | CA | LEU | B | 311 | 35.852 | 44.704 | 8.918 | 1.00 | 24.81 | B |
| ATOM | 4632 | CB | LEU | B | 311 | 36.273 | 43.384 | 8.294 | 1.00 | 24.27 | B |
| ATOM | 4633 | CG | LEU | B | 311 | 36.558 | 42.204 | 9.218 | 1.00 | 26.60 | B |
| ATOM | 4634 | CD1 | LEU | B | 311 | 36.706 | 40.935 | 8.362 | 1.00 | 23.71 | B |
| ATOM | 4635 | CD2 | LEU | B | 311 | 37.839 | 42.476 | 10.032 | 1.00 | 23.33 | B |
| ATOM | 4636 | C | LEU | B | 311 | 35.966 | 45.814 | 7.848 | 1.00 | 26.76 | B |
| ATOM | 4637 | O | LEU | B | 311 | 36.949 | 46.571 | 7.801 | 1.00 | 25.18 | B |
| ATOM | 4638 | N | TYR | B | 312 | 34.966 | 45.888 | 6.974 | 1.00 | 27.78 | B |
| ATOM | 4639 | CA | TYR | B | 312 | 34.931 | 46.884 | 5.896 | 1.00 | 28.94 | B |
| ATOM | 4640 | CB | TYR | B | 312 | 33.673 | 46.694 | 5.042 | 1.00 | 29.61 | B |
| ATOM | 4641 | CG | TYR | B | 312 | 33.660 | 47.576 | 3.827 | 1.00 | 32.01 | B |
| ATOM | 4642 | CD1 | TYR | B | 312 | 34.315 | 47.182 | 2.671 | 1.00 | 33.32 | B |
| ATOM | 4643 | CE1 | TYR | B | 312 | 34.396 | 48.004 | 1.581 | 1.00 | 34.26 | B |
| ATOM | 4644 | CD2 | TYR | B | 312 | 33.070 | 48.830 | 3.855 | 1.00 | 32.13 | B |
| ATOM | 4645 | CE2 | TYR | B | 312 | 33.142 | 49.676 | 2.757 | 1.00 | 33.45 | B |
| ATOM | 4646 | CZ | TYR | B | 312 | 33.816 | 49.249 | 1.620 | 1.00 | 35.84 | B |

TABLE 2-continued

| | | | | | | | | | | |
|---|---|---|---|---|---|---|---|---|---|---|
| ATOM | 4647 | OH | TYR | B | 312 | 33.947 | 50.059 | 0.515 | 1.00 | 31.99 B |
| ATOM | 4648 | C | TYR | B | 312 | 34.915 | 48.299 | 6.470 | 1.00 | 28.47 B |
| ATOM | 4649 | O | TYR | B | 312 | 35.602 | 49.200 | 5.975 | 1.00 | 27.06 B |
| ATOM | 4650 | N | ALA | B | 313 | 34.088 | 48.507 | 7.487 | 1.00 | 26.53 B |
| ATOM | 4651 | CA | ALA | B | 313 | 34.005 | 49.826 | 8.113 | 1.00 | 30.02 B |
| ATOM | 4652 | CB | ALA | B | 313 | 32.928 | 49.836 | 9.231 | 1.00 | 28.00 B |
| ATOM | 4653 | C | ALA | B | 313 | 35.373 | 50.187 | 8.703 | 1.00 | 30.88 B |
| ATOM | 4654 | O | ALA | B | 313 | 35.748 | 51.349 | 8.722 | 1.00 | 30.75 B |
| ATOM | 4655 | N | LYS | B | 314 | 36.123 | 49.182 | 9.158 | 1.00 | 30.56 B |
| ATOM | 4656 | CA | LYS | B | 314 | 37.417 | 49.434 | 9.744 | 1.00 | 31.37 B |
| ATOM | 4657 | CB | LYS | B | 314 | 37.714 | 48.390 | 10.818 | 1.00 | 32.57 B |
| ATOM | 4658 | CG | LYS | B | 314 | 36.762 | 48.467 | 11.986 | 1.00 | 31.09 B |
| ATOM | 4659 | CD | LYS | B | 314 | 37.033 | 47.413 | 13.046 | 1.00 | 30.45 B |
| ATOM | 4660 | CE | LYS | B | 314 | 35.925 | 47.495 | 14.123 | 1.00 | 32.33 B |
| ATOM | 4661 | NZ | LYS | B | 314 | 36.157 | 46.592 | 15.258 | 1.00 | 35.69 B |
| ATOM | 4662 | C | LYS | B | 314 | 38.541 | 49.452 | 8.730 | 1.00 | 31.96 B |
| ATOM | 4663 | O | LYS | B | 314 | 39.689 | 49.586 | 9.104 | 1.00 | 34.08 B |
| ATOM | 4664 | N | GLY | B | 315 | 38.223 | 49.315 | 7.450 | 1.00 | 31.60 B |
| ATOM | 4665 | CA | GLY | B | 315 | 39.271 | 49.320 | 6.447 | 1.00 | 31.25 B |
| ATOM | 4666 | C | GLY | B | 315 | 40.020 | 48.000 | 6.331 | 1.00 | 32.58 B |
| ATOM | 4667 | O | GLY | B | 315 | 41.077 | 47.977 | 5.715 | 1.00 | 32.33 B |
| ATOM | 4668 | N | GLN | B | 316 | 39.502 | 46.905 | 6.901 | 1.00 | 32.50 B |
| ATOM | 4669 | CA | GLN | B | 316 | 40.196 | 45.608 | 6.838 | 1.00 | 32.70 B |
| ATOM | 4670 | CB | GLN | B | 316 | 39.925 | 44.730 | 8.045 | 1.00 | 36.50 B |
| ATOM | 4671 | CG | GLN | B | 316 | 39.383 | 45.414 | 9.219 | 1.00 | 43.19 B |
| ATOM | 4672 | CD | GLN | B | 316 | 40.502 | 45.899 | 10.014 | 1.00 | 46.21 B |
| ATOM | 4673 | OE1 | GLN | B | 316 | 41.420 | 46.504 | 9.456 | 1.00 | 49.89 B |
| ATOM | 4674 | NE2 | GLN | B | 316 | 40.477 | 45.641 | 11.321 | 1.00 | 45.38 B |
| ATOM | 4675 | C | GLN | B | 316 | 39.771 | 44.739 | 5.698 | 1.00 | 30.10 B |
| ATOM | 4676 | O | GLN | B | 316 | 40.277 | 43.643 | 5.567 | 1.00 | 29.81 B |
| ATOM | 4677 | N | LEU | B | 317 | 38.819 | 45.174 | 4.902 | 1.00 | 29.16 B |
| ATOM | 4678 | CA | LEU | B | 317 | 38.352 | 44.303 | 3.834 | 1.00 | 29.99 B |
| ATOM | 4679 | CB | LEU | B | 317 | 37.156 | 43.466 | 4.317 | 1.00 | 29.43 B |
| ATOM | 4680 | CG | LEU | B | 317 | 36.524 | 42.472 | 3.354 | 1.00 | 32.12 B |
| ATOM | 4681 | CD1 | LEU | B | 317 | 37.594 | 41.410 | 2.967 | 1.00 | 30.14 B |
| ATOM | 4682 | CD2 | LEU | B | 317 | 35.274 | 41.840 | 4.029 | 1.00 | 29.54 B |
| ATOM | 4683 | C | LEU | B | 317 | 37.935 | 45.202 | 2.737 | 1.00 | 28.56 B |
| ATOM | 4684 | O | LEU | B | 317 | 37.328 | 46.243 | 3.009 | 1.00 | 26.57 B |
| ATOM | 4685 | N | ARG | B | 318 | 38.253 | 44.834 | 1.496 | 1.00 | 26.91 B |
| ATOM | 4686 | CA | ARG | B | 318 | 37.872 | 45.720 | 0.417 | 1.00 | 26.64 B |
| ATOM | 4687 | CB | ARG | B | 318 | 39.134 | 46.180 | −0.344 | 1.00 | 32.04 B |
| ATOM | 4688 | CG | ARG | B | 318 | 40.001 | 45.085 | −0.921 | 1.00 | 38.25 B |
| ATOM | 4689 | CD | ARG | B | 318 | 41.522 | 45.382 | −0.805 | 1.00 | 43.23 B |
| ATOM | 4690 | NE | ARG | B | 318 | 41.918 | 46.658 | −1.414 | 1.00 | 45.64 B |
| ATOM | 4691 | CZ | ARG | B | 318 | 43.134 | 47.185 | −1.302 | 1.00 | 42.17 B |
| ATOM | 4692 | NH1 | ARG | B | 318 | 44.060 | 46.534 | −0.624 | 1.00 | 44.82 B |
| ATOM | 4693 | NH2 | ARG | B | 318 | 43.408 | 48.377 | −1.813 | 1.00 | 39.98 B |
| ATOM | 4694 | C | ARG | B | 318 | 36.830 | 45.116 | −0.494 | 1.00 | 26.71 B |
| ATOM | 4695 | O | ARG | B | 318 | 36.567 | 43.915 | −0.457 | 1.00 | 25.62 B |
| ATOM | 4696 | N | ILE | B | 319 | 36.196 | 45.954 | −1.285 | 1.00 | 25.30 B |
| ATOM | 4697 | CA | ILE | B | 319 | 35.205 | 45.462 | −2.200 | 1.00 | 26.04 B |
| ATOM | 4698 | CB | ILE | B | 319 | 34.666 | 46.601 | −3.063 | 1.00 | 27.65 B |
| ATOM | 4699 | CG2 | ILE | B | 319 | 33.928 | 46.042 | −4.275 | 1.00 | 26.56 B |
| ATOM | 4700 | CG1 | ILE | B | 319 | 33.730 | 47.474 | −2.228 | 1.00 | 29.26 B |
| ATOM | 4701 | CD1 | ILE | B | 319 | 33.125 | 48.635 | −2.992 | 1.00 | 29.86 B |
| ATOM | 4702 | C | ILE | B | 319 | 35.824 | 44.396 | −3.088 | 1.00 | 26.25 B |
| ATOM | 4703 | O | ILE | B | 319 | 36.952 | 44.545 | −3.541 | 1.00 | 25.57 B |
| ATOM | 4704 | N | GLY | B | 320 | 35.100 | 43.308 | −3.311 | 1.00 | 24.57 B |
| ATOM | 4705 | CA | GLY | B | 320 | 35.588 | 42.251 | −4.179 | 1.00 | 24.17 B |
| ATOM | 4706 | C | GLY | B | 320 | 36.583 | 41.265 | −3.617 | 1.00 | 24.87 B |
| ATOM | 4707 | O | GLY | B | 320 | 36.854 | 40.257 | −4.243 | 1.00 | 24.14 B |
| ATOM | 4708 | N | GLU | B | 321 | 37.132 | 41.547 | −2.444 | 1.00 | 26.10 B |
| ATOM | 4709 | CA | GLU | B | 321 | 38.092 | 40.660 | −1.813 | 1.00 | 28.59 B |
| ATOM | 4710 | CB | GLU | B | 321 | 38.823 | 41.434 | −0.708 | 1.00 | 28.42 B |
| ATOM | 4711 | CG | GLU | B | 321 | 39.815 | 40.640 | 0.090 | 1.00 | 32.87 B |
| ATOM | 4712 | CD | GLU | B | 321 | 40.566 | 41.497 | 1.123 | 1.00 | 35.36 B |
| ATOM | 4713 | OE1 | GLU | B | 321 | 41.328 | 40.914 | 1.926 | 1.00 | 33.16 B |
| ATOM | 4714 | OE2 | GLU | B | 321 | 40.404 | 42.750 | 1.120 | 1.00 | 36.41 B |
| ATOM | 4715 | C | GLU | B | 321 | 37.337 | 39.439 | −1.234 | 1.00 | 30.34 B |
| ATOM | 4716 | O | GLU | B | 321 | 36.265 | 39.588 | −0.637 | 1.00 | 30.59 B |
| ATOM | 4717 | N | THR | B | 322 | 37.882 | 38.237 | −1.406 | 1.00 | 28.71 B |
| ATOM | 4718 | CA | THR | B | 322 | 37.197 | 37.072 | −0.870 | 1.00 | 29.64 B |
| ATOM | 4719 | CB | THR | B | 322 | 37.495 | 35.789 | −1.676 | 1.00 | 29.32 B |
| ATOM | 4720 | OG1 | THR | B | 322 | 37.031 | 35.976 | −3.019 | 1.00 | 27.57 B |
| ATOM | 4721 | CG2 | THR | B | 322 | 36.720 | 34.626 | −1.097 | 1.00 | 29.40 B |
| ATOM | 4722 | C | THR | B | 322 | 37.550 | 36.840 | 0.582 | 1.00 | 27.88 B |
| ATOM | 4723 | O | THR | B | 322 | 38.706 | 36.779 | 0.924 | 1.00 | 30.49 B |
| ATOM | 4724 | N | PHE | B | 323 | 36.519 | 36.751 | 1.419 | 1.00 | 27.87 B |
| ATOM | 4725 | CA | PHE | B | 323 | 36.630 | 36.509 | 2.863 | 1.00 | 24.68 B |

TABLE 2-continued

| ATOM | 4726 | CB  | PHE | B | 323 | 35.765 | 37.535 | 3.596  | 1.00 | 23.96 | B |
|------|------|-----|-----|---|-----|--------|--------|--------|------|-------|---|
| ATOM | 4727 | CG  | PHE | B | 323 | 35.765 | 37.373 | 5.081  | 1.00 | 23.54 | B |
| ATOM | 4728 | CD1 | PHE | B | 323 | 36.865 | 37.767 | 5.842  | 1.00 | 21.76 | B |
| ATOM | 4729 | CD2 | PHE | B | 323 | 34.670 | 36.788 | 5.724  | 1.00 | 23.45 | B |
| ATOM | 4730 | CE1 | PHE | B | 323 | 36.877 | 37.579 | 7.227  | 1.00 | 22.68 | B |
| ATOM | 4731 | CE2 | PHE | B | 323 | 34.681 | 36.596 | 7.116  | 1.00 | 25.05 | B |
| ATOM | 4732 | CZ  | PHE | B | 323 | 35.782 | 36.990 | 7.865  | 1.00 | 22.57 | B |
| ATOM | 4733 | C   | PHE | B | 323 | 36.100 | 35.094 | 3.111  | 1.00 | 22.82 | B |
| ATOM | 4734 | O   | PHE | B | 323 | 35.036 | 34.748 | 2.648  | 1.00 | 23.15 | B |
| ATOM | 4735 | N   | VAL | B | 324 | 36.821 | 34.278 | 3.861  | 1.00 | 24.13 | B |
| ATOM | 4736 | CA  | VAL | B | 324 | 36.385 | 32.908 | 4.071  | 1.00 | 22.59 | B |
| ATOM | 4737 | CB  | VAL | B | 324 | 37.479 | 31.920 | 3.522  | 1.00 | 24.16 | B |
| ATOM | 4738 | CG1 | VAL | B | 324 | 37.079 | 30.469 | 3.767  | 1.00 | 19.93 | B |
| ATOM | 4739 | CG2 | VAL | B | 324 | 37.667 | 32.152 | 2.014  | 1.00 | 23.03 | B |
| ATOM | 4740 | C   | VAL | B | 324 | 36.183 | 32.734 | 5.564  | 1.00 | 23.70 | B |
| ATOM | 4741 | O   | VAL | B | 324 | 37.088 | 32.981 | 6.326  | 1.00 | 25.46 | B |
| ATOM | 4742 | N   | TYR | B | 325 | 35.007 | 32.280 | 5.979  | 1.00 | 22.02 | B |
| ATOM | 4743 | CA  | TYR | B | 325 | 34.716 | 32.129 | 7.397  | 1.00 | 21.09 | B |
| ATOM | 4744 | CB  | TYR | B | 325 | 33.427 | 32.887 | 7.724  | 1.00 | 21.65 | B |
| ATOM | 4745 | CG  | TYR | B | 325 | 33.431 | 33.662 | 9.026  | 1.00 | 21.19 | B |
| ATOM | 4746 | CD1 | TYR | B | 325 | 34.496 | 33.567 | 9.924  | 1.00 | 22.48 | B |
| ATOM | 4747 | CE1 | TYR | B | 325 | 34.516 | 34.294 | 11.111 | 1.00 | 23.13 | B |
| ATOM | 4748 | CD2 | TYR | B | 325 | 32.361 | 34.508 | 9.355  | 1.00 | 23.18 | B |
| ATOM | 4749 | CE2 | TYR | B | 325 | 32.361 | 35.257 | 10.548 | 1.00 | 23.80 | B |
| ATOM | 4750 | CZ  | TYR | B | 325 | 33.461 | 35.141 | 11.422 | 1.00 | 26.04 | B |
| ATOM | 4751 | OH  | TYR | B | 325 | 33.530 | 35.908 | 12.569 | 1.00 | 24.25 | B |
| ATOM | 4752 | C   | TYR | B | 325 | 34.523 | 30.641 | 7.691  | 1.00 | 22.00 | B |
| ATOM | 4753 | O   | TYR | B | 325 | 33.797 | 29.956 | 6.953  | 1.00 | 18.26 | B |
| ATOM | 4754 | N   | GLU | B | 326 | 35.156 | 30.160 | 8.762  | 1.00 | 19.41 | B |
| ATOM | 4755 | CA  | GLU | B | 326 | 35.066 | 28.756 | 9.139  | 1.00 | 20.68 | B |
| ATOM | 4756 | CB  | GLU | B | 326 | 36.469 | 28.221 | 9.467  | 1.00 | 20.27 | B |
| ATOM | 4757 | CG  | GLU | B | 326 | 36.551 | 26.727 | 9.712  | 1.00 | 23.54 | B |
| ATOM | 4758 | CD  | GLU | B | 326 | 37.935 | 26.272 | 10.251 | 1.00 | 27.42 | B |
| ATOM | 4759 | OE1 | GLU | B | 326 | 38.892 | 27.083 | 10.273 | 1.00 | 25.47 | B |
| ATOM | 4760 | OE2 | GLU | B | 326 | 38.069 | 25.087 | 10.641 | 1.00 | 29.39 | B |
| ATOM | 4761 | C   | GLU | B | 326 | 34.143 | 28.574 | 10.338 | 1.00 | 21.06 | B |
| ATOM | 4762 | O   | GLU | B | 326 | 34.138 | 29.418 | 11.234 | 1.00 | 20.32 | B |
| ATOM | 4763 | N   | SER | B | 327 | 33.363 | 27.481 | 10.363 | 1.00 | 21.23 | B |
| ATOM | 4764 | CA  | SER | B | 327 | 32.449 | 27.188 | 11.488 | 1.00 | 21.35 | B |
| ATOM | 4765 | CB  | SER | B | 327 | 31.173 | 26.465 | 11.007 | 1.00 | 19.86 | B |
| ATOM | 4766 | OG  | SER | B | 327 | 31.467 | 25.105 | 10.662 | 1.00 | 24.82 | B |
| ATOM | 4767 | C   | SER | B | 327 | 33.166 | 26.278 | 12.499 | 1.00 | 23.23 | B |
| ATOM | 4768 | O   | SER | B | 327 | 34.269 | 25.817 | 12.251 | 1.00 | 23.74 | B |
| ATOM | 4769 | N   | ILE | B | 328 | 32.514 | 26.020 | 13.627 | 1.00 | 24.81 | B |
| ATOM | 4770 | CA  | ILE | B | 328 | 33.054 | 25.160 | 14.655 | 1.00 | 26.71 | B |
| ATOM | 4771 | CB  | ILE | B | 328 | 32.108 | 25.170 | 15.877 | 1.00 | 28.57 | B |
| ATOM | 4772 | CG2 | ILE | B | 328 | 30.790 | 24.456 | 15.539 | 1.00 | 25.55 | B |
| ATOM | 4773 | CG1 | ILE | B | 328 | 32.791 | 24.519 | 17.076 | 1.00 | 30.14 | B |
| ATOM | 4774 | CD1 | ILE | B | 328 | 32.015 | 24.681 | 18.380 | 1.00 | 31.36 | B |
| ATOM | 4775 | C   | ILE | B | 328 | 33.218 | 23.722 | 14.123 | 1.00 | 30.18 | B |
| ATOM | 4776 | O   | ILE | B | 328 | 33.957 | 22.916 | 14.703 | 1.00 | 29.50 | B |
| ATOM | 4777 | N   | LEU | B | 329 | 32.530 | 23.402 | 13.018 | 1.00 | 28.53 | B |
| ATOM | 4778 | CA  | LEU | B | 329 | 32.596 | 22.063 | 12.420 | 1.00 | 27.58 | B |
| ATOM | 4779 | CB  | LEU | B | 329 | 31.250 | 21.698 | 11.784 | 1.00 | 28.35 | B |
| ATOM | 4780 | CG  | LEU | B | 329 | 30.375 | 20.622 | 12.390 | 1.00 | 31.33 | B |
| ATOM | 4781 | CD1 | LEU | B | 329 | 30.326 | 20.831 | 13.880 | 1.00 | 33.26 | B |
| ATOM | 4782 | CD2 | LEU | B | 329 | 29.010 | 20.660 | 11.757 | 1.00 | 26.48 | B |
| ATOM | 4783 | C   | LEU | B | 329 | 33.647 | 21.988 | 11.318 | 1.00 | 28.66 | B |
| ATOM | 4784 | O   | LEU | B | 329 | 33.913 | 20.905 | 10.794 | 1.00 | 28.04 | B |
| ATOM | 4785 | N   | GLY | B | 330 | 34.218 | 23.129 | 10.934 | 1.00 | 27.29 | B |
| ATOM | 4786 | CA  | GLY | B | 330 | 35.197 | 23.119 | 9.867  | 1.00 | 24.54 | B |
| ATOM | 4787 | C   | GLY | B | 330 | 34.565 | 23.478 | 8.520  | 1.00 | 25.24 | B |
| ATOM | 4788 | O   | GLY | B | 330 | 35.261 | 23.504 | 7.509  | 1.00 | 24.70 | B |
| ATOM | 4789 | N   | SER | B | 331 | 33.254 | 23.742 | 8.500  | 1.00 | 25.56 | B |
| ATOM | 4790 | CA  | SER | B | 331 | 32.542 | 24.144 | 7.257  | 1.00 | 25.38 | B |
| ATOM | 4791 | CB  | SER | B | 331 | 31.036 | 24.246 | 7.485  | 1.00 | 24.64 | B |
| ATOM | 4792 | OG  | SER | B | 331 | 30.506 | 23.026 | 7.933  | 1.00 | 29.63 | B |
| ATOM | 4793 | C   | SER | B | 331 | 33.017 | 25.538 | 6.863  | 1.00 | 22.80 | B |
| ATOM | 4794 | O   | SER | B | 331 | 33.348 | 26.342 | 7.722  | 1.00 | 20.67 | B |
| ATOM | 4795 | N   | LEU | B | 332 | 33.018 | 25.832 | 5.569  | 1.00 | 22.11 | B |
| ATOM | 4796 | CA  | LEU | B | 332 | 33.453 | 27.154 | 5.106  | 1.00 | 20.67 | B |
| ATOM | 4797 | CB  | LEU | B | 332 | 34.677 | 27.015 | 4.189  | 1.00 | 18.98 | B |
| ATOM | 4798 | CG  | LEU | B | 332 | 35.918 | 26.301 | 4.734  | 1.00 | 21.63 | B |
| ATOM | 4799 | CD1 | LEU | B | 332 | 36.944 | 26.133 | 3.604  | 1.00 | 19.80 | B |
| ATOM | 4800 | CD2 | LEU | B | 332 | 36.511 | 27.132 | 5.893  | 1.00 | 18.73 | B |
| ATOM | 4801 | C   | LEU | B | 332 | 32.373 | 27.865 | 4.300  | 1.00 | 20.52 | B |
| ATOM | 4802 | O   | LEU | B | 332 | 31.623 | 27.218 | 3.545  | 1.00 | 18.68 | B |
| ATOM | 4803 | N   | PHE | B | 333 | 32.312 | 29.188 | 4.445  | 1.00 | 19.09 | B |
| ATOM | 4804 | CA  | PHE | B | 333 | 31.410 | 30.022 | 3.642  | 1.00 | 19.79 | B |

TABLE 2-continued

| | | | | | | | | | | |
|---|---|---|---|---|---|---|---|---|---|---|
| ATOM | 4805 | CB | PHE | B | 333 | 30.401 | 30.834 | 4.503 | 1.00 | 20.49 B |
| ATOM | 4806 | CG | PHE | B | 333 | 29.075 | 30.137 | 4.746 | 1.00 | 22.21 B |
| ATOM | 4807 | CD1 | PHE | B | 333 | 28.791 | 28.890 | 4.162 | 1.00 | 22.88 B |
| ATOM | 4808 | CD2 | PHE | B | 333 | 28.121 | 30.714 | 5.594 | 1.00 | 20.25 B |
| ATOM | 4809 | CE1 | PHE | B | 333 | 27.585 | 28.227 | 4.418 | 1.00 | 19.19 B |
| ATOM | 4810 | CE2 | PHE | B | 333 | 26.905 | 30.057 | 5.858 | 1.00 | 20.18 B |
| ATOM | 4811 | CZ | PHE | B | 333 | 26.649 | 28.809 | 5.261 | 1.00 | 23.20 B |
| ATOM | 4812 | C | PHE | B | 333 | 32.352 | 31.022 | 2.981 | 1.00 | 20.58 B |
| ATOM | 4813 | O | PHE | B | 333 | 33.373 | 31.369 | 3.577 | 1.00 | 17.56 B |
| ATOM | 4814 | N | GLN | B | 334 | 32.033 | 31.455 | 1.754 | 1.00 | 21.12 B |
| ATOM | 4815 | CA | GLN | B | 334 | 32.826 | 32.486 | 1.066 | 1.00 | 23.93 B |
| ATOM | 4816 | CB | GLN | B | 334 | 33.195 | 32.093 | −0.388 | 1.00 | 26.06 B |
| ATOM | 4817 | CG | GLN | B | 334 | 34.088 | 30.833 | −0.538 | 1.00 | 30.48 B |
| ATOM | 4818 | CD | GLN | B | 334 | 33.316 | 29.542 | −0.206 | 1.00 | 34.25 B |
| ATOM | 4819 | OE1 | GLN | B | 334 | 32.215 | 29.317 | −0.732 | 1.00 | 33.30 B |
| ATOM | 4820 | NE2 | GLN | B | 334 | 33.887 | 28.695 | 0.666 | 1.00 | 33.45 B |
| ATOM | 4821 | C | GLN | B | 334 | 31.942 | 33.742 | 1.005 | 1.00 | 25.04 B |
| ATOM | 4822 | O | GLN | B | 334 | 30.758 | 33.657 | 0.736 | 1.00 | 24.24 B |
| ATOM | 4823 | N | GLY | B | 335 | 32.506 | 34.910 | 1.268 | 1.00 | 25.13 B |
| ATOM | 4824 | CA | GLY | B | 335 | 31.696 | 36.116 | 1.205 | 1.00 | 26.16 B |
| ATOM | 4825 | C | GLY | B | 335 | 32.463 | 37.233 | 0.510 | 1.00 | 25.94 B |
| ATOM | 4826 | O | GLY | B | 335 | 33.698 | 37.262 | 0.508 | 1.00 | 27.60 B |
| ATOM | 4827 | N | ARG | B | 336 | 31.758 | 38.151 | −0.101 | 1.00 | 25.69 B |
| ATOM | 4828 | CA | ARG | B | 336 | 32.451 | 39.253 | −0.740 | 1.00 | 28.54 B |
| ATOM | 4829 | CB | ARG | B | 336 | 32.640 | 39.004 | −2.234 | 1.00 | 29.72 B |
| ATOM | 4830 | CG | ARG | B | 336 | 33.508 | 37.853 | −2.617 | 1.00 | 41.04 B |
| ATOM | 4831 | CD | ARG | B | 336 | 34.016 | 38.112 | −4.041 | 1.00 | 45.99 B |
| ATOM | 4832 | NE | ARG | B | 336 | 32.926 | 38.617 | −4.875 | 1.00 | 50.83 B |
| ATOM | 4833 | CZ | ARG | B | 336 | 32.166 | 37.838 | −5.638 | 1.00 | 52.45 B |
| ATOM | 4834 | NH1 | ARG | B | 336 | 32.409 | 36.527 | −5.667 | 1.00 | 53.87 B |
| ATOM | 4835 | NH2 | ARG | B | 336 | 31.161 | 38.356 | −6.339 | 1.00 | 49.99 B |
| ATOM | 4836 | C | ARG | B | 336 | 31.622 | 40.506 | −0.617 | 1.00 | 26.06 B |
| ATOM | 4837 | O | ARG | B | 336 | 30.426 | 40.445 | −0.775 | 1.00 | 25.98 B |
| ATOM | 4838 | N | VAL | B | 337 | 32.246 | 41.636 | −0.333 | 1.00 | 25.86 B |
| ATOM | 4839 | CA | VAL | B | 337 | 31.485 | 42.886 | −0.318 | 1.00 | 25.70 B |
| ATOM | 4840 | CB | VAL | B | 337 | 32.180 | 43.942 | 0.507 | 1.00 | 24.01 B |
| ATOM | 4841 | CG1 | VAL | B | 337 | 31.429 | 45.271 | 0.368 | 1.00 | 20.96 B |
| ATOM | 4842 | CG2 | VAL | B | 337 | 32.228 | 43.448 | 1.986 | 1.00 | 20.15 B |
| ATOM | 4843 | C | VAL | B | 337 | 31.367 | 43.350 | −1.788 | 1.00 | 26.87 B |
| ATOM | 4844 | O | VAL | B | 337 | 32.368 | 43.522 | −2.483 | 1.00 | 27.63 B |
| ATOM | 4845 | N | LEU | B | 338 | 30.139 | 43.505 | −2.258 | 1.00 | 26.02 B |
| ATOM | 4846 | CA | LEU | B | 338 | 29.878 | 43.910 | −3.630 | 1.00 | 27.59 B |
| ATOM | 4847 | CB | LEU | B | 338 | 28.532 | 43.326 | −4.095 | 1.00 | 25.02 B |
| ATOM | 4848 | CG | LEU | B | 338 | 28.376 | 41.786 | −3.998 | 1.00 | 25.21 B |
| ATOM | 4849 | CD1 | LEU | B | 338 | 27.080 | 41.364 | −4.729 | 1.00 | 24.08 B |
| ATOM | 4850 | CD2 | LEU | B | 338 | 29.585 | 41.064 | −4.638 | 1.00 | 25.18 B |
| ATOM | 4851 | C | LEU | B | 338 | 29.891 | 45.429 | −3.833 | 1.00 | 29.31 B |
| ATOM | 4852 | O | LEU | B | 338 | 30.225 | 45.910 | −4.915 | 1.00 | 27.00 B |
| ATOM | 4853 | N | GLY | B | 339 | 29.539 | 46.184 | −2.799 | 1.00 | 29.30 B |
| ATOM | 4854 | CA | GLY | B | 339 | 29.517 | 47.624 | −2.939 | 1.00 | 30.47 B |
| ATOM | 4855 | C | GLY | B | 339 | 29.139 | 48.290 | −1.635 | 1.00 | 32.22 B |
| ATOM | 4856 | O | GLY | B | 339 | 28.634 | 47.635 | −0.717 | 1.00 | 30.51 B |
| ATOM | 4857 | N | GLU | B | 340 | 29.385 | 49.594 | −1.553 | 1.00 | 32.95 B |
| ATOM | 4858 | CA | GLU | B | 340 | 29.084 | 50.372 | −0.351 | 1.00 | 34.26 B |
| ATOM | 4859 | CB | GLU | B | 340 | 30.350 | 50.971 | 0.257 | 1.00 | 33.77 B |
| ATOM | 4860 | CG | GLU | B | 340 | 30.999 | 52.033 | −0.627 | 1.00 | 38.93 B |
| ATOM | 4861 | CD | GLU | B | 340 | 32.342 | 52.531 | −0.099 | 1.00 | 41.55 B |
| ATOM | 4862 | OE1 | GLU | B | 340 | 33.058 | 53.220 | −0.857 | 1.00 | 46.29 B |
| ATOM | 4863 | OE2 | GLU | B | 340 | 32.695 | 52.241 | 1.061 | 1.00 | 43.41 B |
| ATOM | 4864 | C | GLU | B | 340 | 28.178 | 51.491 | −0.781 | 1.00 | 35.19 B |
| ATOM | 4865 | O | GLU | B | 340 | 27.952 | 51.690 | −1.966 | 1.00 | 33.75 B |
| ATOM | 4866 | N | GLU | B | 341 | 27.663 | 52.216 | 0.198 | 1.00 | 37.68 B |
| ATOM | 4867 | CA | GLU | B | 341 | 26.771 | 53.322 | −0.064 | 1.00 | 39.25 B |
| ATOM | 4868 | CB | GLU | B | 341 | 25.484 | 52.805 | −0.678 | 1.00 | 42.62 B |
| ATOM | 4869 | CG | GLU | B | 341 | 24.465 | 53.872 | −0.951 | 1.00 | 47.03 B |
| ATOM | 4870 | CD | GLU | B | 341 | 23.247 | 53.306 | −1.619 | 1.00 | 51.21 B |
| ATOM | 4871 | OE1 | GLU | B | 341 | 23.379 | 52.861 | −2.779 | 1.00 | 55.60 B |
| ATOM | 4872 | OE2 | GLU | B | 341 | 22.166 | 53.285 | −0.988 | 1.00 | 52.72 B |
| ATOM | 4873 | C | GLU | B | 341 | 26.475 | 54.061 | 1.230 | 1.00 | 39.57 B |
| ATOM | 4874 | O | GLU | B | 341 | 26.391 | 53.450 | 2.295 | 1.00 | 40.02 B |
| ATOM | 4875 | N | ARG | B | 342 | 26.379 | 55.383 | 1.127 | 1.00 | 38.97 B |
| ATOM | 4876 | CA | ARG | B | 342 | 26.062 | 56.252 | 2.250 | 1.00 | 39.68 B |
| ATOM | 4877 | CB | ARG | B | 342 | 26.914 | 57.506 | 2.188 | 1.00 | 40.08 B |
| ATOM | 4878 | CG | ARG | B | 342 | 28.346 | 57.288 | 2.568 | 1.00 | 38.91 B |
| ATOM | 4879 | CD | ARG | B | 342 | 28.517 | 57.312 | 4.062 | 1.00 | 40.93 B |
| ATOM | 4880 | NE | ARG | B | 342 | 29.898 | 57.013 | 4.430 | 1.00 | 40.78 B |
| ATOM | 4881 | CZ | ARG | B | 342 | 30.331 | 56.971 | 5.683 | 1.00 | 40.62 B |
| ATOM | 4882 | NH1 | ARG | B | 342 | 29.486 | 57.213 | 6.682 | 1.00 | 39.03 B |
| ATOM | 4883 | NH2 | ARG | B | 342 | 31.600 | 56.681 | 5.933 | 1.00 | 39.87 B |

TABLE 2-continued

| ATOM | 4884 | C | ARG | B | 342 | 24.601 | 56.644 | 2.088 | 1.00 | 39.85 | B |
| ATOM | 4885 | O | ARG | B | 342 | 24.206 | 57.040 | 0.994 | 1.00 | 39.84 | B |
| ATOM | 4886 | N | ILE | B | 343 | 23.802 | 56.524 | 3.153 | 1.00 | 38.11 | B |
| ATOM | 4887 | CA | ILE | B | 343 | 22.388 | 56.884 | 3.080 | 1.00 | 39.86 | B |
| ATOM | 4888 | CB | ILE | B | 343 | 21.482 | 55.833 | 3.800 | 1.00 | 40.57 | B |
| ATOM | 4889 | CG2 | ILE | B | 343 | 20.048 | 56.325 | 3.849 | 1.00 | 39.53 | B |
| ATOM | 4890 | CG1 | ILE | B | 343 | 21.479 | 54.500 | 3.023 | 1.00 | 42.58 | B |
| ATOM | 4891 | CD1 | ILE | B | 343 | 22.839 | 53.867 | 2.829 | 1.00 | 44.12 | B |
| ATOM | 4892 | C | ILE | B | 343 | 22.248 | 58.266 | 3.732 | 1.00 | 40.64 | B |
| ATOM | 4893 | O | ILE | B | 343 | 22.334 | 58.414 | 4.956 | 1.00 | 39.61 | B |
| ATOM | 4894 | N | PRO | B | 344 | 22.052 | 59.304 | 2.907 | 1.00 | 40.68 | B |
| ATOM | 4895 | CD | PRO | B | 344 | 21.922 | 59.204 | 1.441 | 1.00 | 40.17 | B |
| ATOM | 4896 | CA | PRO | B | 344 | 21.912 | 60.697 | 3.357 | 1.00 | 40.04 | B |
| ATOM | 4897 | CB | PRO | B | 344 | 21.483 | 61.416 | 2.081 | 1.00 | 40.93 | B |
| ATOM | 4898 | CG | PRO | B | 344 | 22.193 | 60.618 | 1.000 | 1.00 | 42.76 | B |
| ATOM | 4899 | C | PRO | B | 344 | 20.983 | 60.994 | 4.543 | 1.00 | 37.82 | B |
| ATOM | 4900 | O | PRO | B | 344 | 19.808 | 60.657 | 4.540 | 1.00 | 37.61 | B |
| ATOM | 4901 | N | GLY | B | 345 | 21.544 | 61.624 | 5.568 | 1.00 | 40.04 | B |
| ATOM | 4902 | CA | GLY | B | 345 | 20.767 | 62.018 | 6.737 | 1.00 | 39.71 | B |
| ATOM | 4903 | C | GLY | B | 345 | 20.150 | 60.926 | 7.582 | 1.00 | 39.78 | B |
| ATOM | 4904 | O | GLY | B | 345 | 19.204 | 61.178 | 8.320 | 1.00 | 40.82 | B |
| ATOM | 4905 | N | VAL | B | 346 | 20.682 | 59.716 | 7.478 | 1.00 | 39.41 | B |
| ATOM | 4906 | CA | VAL | B | 346 | 20.204 | 58.565 | 8.250 | 1.00 | 36.79 | B |
| ATOM | 4907 | CB | VAL | B | 346 | 19.681 | 57.471 | 7.309 | 1.00 | 38.80 | B |
| ATOM | 4908 | CG1 | VAL | B | 346 | 19.197 | 56.254 | 8.108 | 1.00 | 35.85 | B |
| ATOM | 4909 | CG2 | VAL | B | 346 | 18.549 | 58.057 | 6.440 | 1.00 | 38.21 | B |
| ATOM | 4910 | C | VAL | B | 346 | 21.454 | 58.086 | 8.958 | 1.00 | 36.54 | B |
| ATOM | 4911 | O | VAL | B | 346 | 22.408 | 57.643 | 8.318 | 1.00 | 36.64 | B |
| ATOM | 4912 | N | LYS | B | 347 | 21.480 | 58.196 | 10.278 | 1.00 | 34.42 | B |
| ATOM | 4913 | CA | LYS | B | 347 | 22.661 | 57.797 | 10.998 | 1.00 | 34.09 | B |
| ATOM | 4914 | CB | LYS | B | 347 | 23.263 | 58.997 | 11.755 | 1.00 | 36.17 | B |
| ATOM | 4915 | CG | LYS | B | 347 | 23.561 | 60.211 | 10.886 | 1.00 | 38.07 | B |
| ATOM | 4916 | CD | LYS | B | 347 | 24.358 | 61.260 | 11.662 | 1.00 | 38.70 | B |
| ATOM | 4917 | CE | LYS | B | 347 | 24.728 | 62.460 | 10.777 | 1.00 | 39.52 | B |
| ATOM | 4918 | NZ | LYS | B | 347 | 26.053 | 63.049 | 11.184 | 1.00 | 41.11 | B |
| ATOM | 4919 | C | LYS | B | 347 | 22.348 | 56.716 | 11.990 | 1.00 | 32.99 | B |
| ATOM | 4920 | O | LYS | B | 347 | 21.178 | 56.486 | 12.317 | 1.00 | 32.79 | B |
| ATOM | 4921 | N | VAL | B | 348 | 23.417 | 56.065 | 12.453 | 1.00 | 30.95 | B |
| ATOM | 4922 | CA | VAL | B | 348 | 23.375 | 55.023 | 13.472 | 1.00 | 29.42 | B |
| ATOM | 4923 | CB | VAL | B | 348 | 23.626 | 53.578 | 12.889 | 1.00 | 30.26 | B |
| ATOM | 4924 | CG1 | VAL | B | 348 | 22.372 | 53.111 | 12.092 | 1.00 | 28.31 | B |
| ATOM | 4925 | CG2 | VAL | B | 348 | 24.902 | 53.568 | 12.007 | 1.00 | 25.77 | B |
| ATOM | 4926 | C | VAL | B | 348 | 24.528 | 55.433 | 14.396 | 1.00 | 30.34 | B |
| ATOM | 4927 | O | VAL | B | 348 | 25.385 | 56.217 | 14.004 | 1.00 | 28.38 | B |
| ATOM | 4928 | N | PRO | B | 349 | 24.569 | 54.898 | 15.624 | 1.00 | 30.96 | B |
| ATOM | 4929 | CD | PRO | B | 349 | 23.723 | 53.791 | 16.112 | 1.00 | 30.71 | B |
| ATOM | 4930 | CA | PRO | B | 349 | 25.619 | 55.230 | 16.600 | 1.00 | 30.90 | B |
| ATOM | 4931 | CB | PRO | B | 349 | 25.505 | 54.111 | 17.639 | 1.00 | 31.30 | B |
| ATOM | 4932 | CG | PRO | B | 349 | 24.020 | 53.776 | 17.615 | 1.00 | 32.51 | B |
| ATOM | 4933 | C | PRO | B | 349 | 27.035 | 55.377 | 16.085 | 1.00 | 32.47 | B |
| ATOM | 4934 | O | PRO | B | 349 | 27.780 | 56.256 | 16.530 | 1.00 | 32.64 | B |
| ATOM | 4935 | N | VAL | B | 350 | 27.432 | 54.523 | 15.157 | 1.00 | 32.92 | B |
| ATOM | 4936 | CA | VAL | B | 350 | 28.786 | 54.618 | 14.662 | 1.00 | 33.72 | B |
| ATOM | 4937 | CB | VAL | B | 350 | 29.258 | 53.232 | 14.058 | 1.00 | 34.37 | B |
| ATOM | 4938 | CG1 | VAL | B | 350 | 28.802 | 53.082 | 12.599 | 1.00 | 33.33 | B |
| ATOM | 4939 | CG2 | VAL | B | 350 | 30.772 | 53.088 | 14.198 | 1.00 | 34.51 | B |
| ATOM | 4940 | C | VAL | B | 350 | 28.929 | 55.761 | 13.638 | 1.00 | 34.67 | B |
| ATOM | 4941 | O | VAL | B | 350 | 30.031 | 56.147 | 13.278 | 1.00 | 33.68 | B |
| ATOM | 4942 | N | THR | B | 351 | 27.826 | 56.332 | 13.187 | 1.00 | 34.78 | B |
| ATOM | 4943 | CA | THR | B | 351 | 27.954 | 57.391 | 12.196 | 1.00 | 37.98 | B |
| ATOM | 4944 | CB | THR | B | 351 | 26.637 | 57.622 | 11.496 | 1.00 | 36.38 | B |
| ATOM | 4945 | OG1 | THR | B | 351 | 26.122 | 56.348 | 11.066 | 1.00 | 34.42 | B |
| ATOM | 4946 | CG2 | THR | B | 351 | 26.845 | 58.520 | 10.261 | 1.00 | 36.20 | B |
| ATOM | 4947 | C | THR | B | 351 | 28.483 | 58.698 | 12.819 | 1.00 | 40.94 | B |
| ATOM | 4948 | O | THR | B | 351 | 27.904 | 59.222 | 13.766 | 1.00 | 38.36 | B |
| ATOM | 4949 | N | LYS | B | 352 | 29.611 | 59.188 | 12.296 | 1.00 | 44.39 | B |
| ATOM | 4950 | CA | LYS | B | 352 | 30.242 | 60.418 | 12.806 | 1.00 | 49.45 | B |
| ATOM | 4951 | CB | LYS | B | 352 | 31.659 | 60.573 | 12.243 | 1.00 | 51.04 | B |
| ATOM | 4952 | CG | LYS | B | 352 | 32.650 | 59.621 | 12.898 | 1.00 | 54.39 | B |
| ATOM | 4953 | CD | LYS | B | 352 | 33.989 | 59.628 | 12.206 | 1.00 | 56.49 | B |
| ATOM | 4954 | CE | LYS | B | 352 | 34.800 | 58.413 | 12.625 | 1.00 | 58.70 | B |
| ATOM | 4955 | NZ | LYS | B | 352 | 36.112 | 58.345 | 11.911 | 1.00 | 62.06 | B |
| ATOM | 4956 | C | LYS | B | 352 | 29.441 | 61.673 | 12.516 | 1.00 | 50.40 | B |
| ATOM | 4957 | O | LYS | B | 352 | 28.717 | 61.748 | 11.515 | 1.00 | 50.31 | B |
| ATOM | 4958 | N | ASP | B | 353 | 29.560 | 62.651 | 13.410 | 1.00 | 52.66 | B |
| ATOM | 4959 | CA | ASP | B | 353 | 28.844 | 63.914 | 13.249 | 1.00 | 53.89 | B |
| ATOM | 4960 | CB | ASP | B | 353 | 29.237 | 64.890 | 14.357 | 1.00 | 56.77 | B |
| ATOM | 4961 | CG | ASP | B | 353 | 28.700 | 64.472 | 15.703 | 1.00 | 59.96 | B |
| ATOM | 4962 | OD1 | ASP | B | 353 | 27.611 | 63.849 | 15.703 | 1.00 | 61.27 | B |

TABLE 2-continued

| ATOM | 4963 | OD2 | ASP | B | 353 | 29.345 | 64.772 | 16.744 | 1.00 | 60.41 | B |
|---|---|---|---|---|---|---|---|---|---|---|---|
| ATOM | 4964 | C | ASP | B | 353 | 29.150 | 64.531 | 11.895 | 1.00 | 53.00 | B |
| ATOM | 4965 | O | ASP | B | 353 | 28.253 | 65.045 | 11.223 | 1.00 | 52.07 | B |
| ATOM | 4966 | N | ALA | B | 354 | 30.425 | 64.458 | 11.510 | 1.00 | 52.54 | B |
| ATOM | 4967 | CA | ALA | B | 354 | 30.909 | 64.999 | 10.245 | 1.00 | 51.99 | B |
| ATOM | 4968 | CB | ALA | B | 354 | 32.427 | 64.961 | 10.212 | 1.00 | 50.93 | B |
| ATOM | 4969 | C | ALA | B | 354 | 30.352 | 64.230 | 9.052 | 1.00 | 51.80 | B |
| ATOM | 4970 | O | ALA | B | 354 | 30.253 | 64.782 | 7.949 | 1.00 | 53.72 | B |
| ATOM | 4971 | N | GLU | B | 355 | 30.000 | 62.961 | 9.256 | 1.00 | 49.04 | B |
| ATOM | 4972 | CA | GLU | B | 355 | 29.452 | 62.155 | 8.172 | 1.00 | 46.93 | B |
| ATOM | 4973 | CB | GLU | B | 355 | 29.638 | 60.659 | 8.474 | 1.00 | 47.46 | B |
| ATOM | 4974 | CG | GLU | B | 355 | 31.086 | 60.183 | 8.244 | 1.00 | 46.52 | B |
| ATOM | 4975 | CD | GLU | B | 355 | 31.358 | 58.811 | 8.825 | 1.00 | 46.45 | B |
| ATOM | 4976 | OE1 | GLU | B | 355 | 32.353 | 58.159 | 8.410 | 1.00 | 45.51 | B |
| ATOM | 4977 | OE2 | GLU | B | 355 | 30.577 | 58.400 | 9.709 | 1.00 | 43.89 | B |
| ATOM | 4978 | C | GLU | B | 355 | 27.988 | 62.499 | 7.908 | 1.00 | 45.36 | B |
| ATOM | 4979 | O | GLU | B | 355 | 27.164 | 62.583 | 8.825 | 1.00 | 42.97 | B |
| ATOM | 4980 | N | GLU | B | 356 | 27.692 | 62.716 | 6.633 | 1.00 | 45.09 | B |
| ATOM | 4981 | CA | GLU | B | 356 | 26.358 | 63.096 | 6.186 | 1.00 | 46.60 | B |
| ATOM | 4982 | CB | GLU | B | 356 | 26.410 | 63.582 | 4.728 | 1.00 | 51.78 | B |
| ATOM | 4983 | CG | GLU | B | 356 | 27.388 | 64.747 | 4.443 | 1.00 | 59.66 | B |
| ATOM | 4984 | CD | GLU | B | 356 | 27.003 | 66.065 | 5.134 | 1.00 | 63.36 | B |
| ATOM | 4985 | OE1 | GLU | B | 356 | 25.796 | 66.423 | 5.143 | 1.00 | 66.13 | B |
| ATOM | 4986 | OE2 | GLU | B | 356 | 27.915 | 66.755 | 5.650 | 1.00 | 64.88 | B |
| ATOM | 4987 | C | GLU | B | 356 | 25.329 | 61.982 | 6.281 | 1.00 | 43.74 | B |
| ATOM | 4988 | O | GLU | B | 356 | 24.123 | 62.256 | 6.378 | 1.00 | 43.78 | B |
| ATOM | 4989 | N | GLY | B | 357 | 25.808 | 60.738 | 6.228 | 1.00 | 39.88 | B |
| ATOM | 4990 | CA | GLY | B | 357 | 24.921 | 59.586 | 6.280 | 1.00 | 37.14 | B |
| ATOM | 4991 | C | GLY | B | 357 | 25.615 | 58.279 | 6.613 | 1.00 | 34.47 | B |
| ATOM | 4992 | O | GLY | B | 357 | 26.818 | 58.132 | 6.447 | 1.00 | 34.26 | B |
| ATOM | 4993 | N | MET | B | 358 | 24.848 | 57.306 | 7.090 | 1.00 | 33.76 | B |
| ATOM | 4994 | CA | MET | B | 358 | 25.426 | 56.015 | 7.476 | 1.00 | 30.05 | B |
| ATOM | 4995 | CB | MET | B | 358 | 24.364 | 55.173 | 8.179 | 1.00 | 30.10 | B |
| ATOM | 4996 | CG | MET | B | 358 | 23.215 | 54.751 | 7.295 | 1.00 | 28.41 | B |
| ATOM | 4997 | SD | MET | B | 358 | 21.970 | 53.810 | 8.233 | 1.00 | 30.92 | B |
| ATOM | 4998 | CE | MET | B | 358 | 22.892 | 52.181 | 8.410 | 1.00 | 29.07 | B |
| ATOM | 4999 | C | MET | B | 358 | 26.007 | 55.223 | 6.302 | 1.00 | 28.66 | B |
| ATOM | 5000 | O | MET | B | 358 | 25.545 | 55.340 | 5.170 | 1.00 | 28.07 | B |
| ATOM | 5001 | N | LEU | B | 359 | 27.032 | 54.423 | 6.582 | 1.00 | 26.06 | B |
| ATOM | 5002 | CA | LEU | B | 359 | 27.640 | 53.568 | 5.569 | 1.00 | 26.98 | B |
| ATOM | 5003 | CB | LEU | B | 359 | 29.108 | 53.355 | 5.885 | 1.00 | 27.21 | B |
| ATOM | 5004 | CG | LEU | B | 359 | 29.867 | 52.329 | 5.045 | 1.00 | 27.90 | B |
| ATOM | 5005 | CD1 | LEU | B | 359 | 30.157 | 52.889 | 3.655 | 1.00 | 29.11 | B |
| ATOM | 5006 | CD2 | LEU | B | 359 | 31.195 | 52.002 | 5.746 | 1.00 | 30.24 | B |
| ATOM | 5007 | C | LEU | B | 359 | 26.936 | 52.198 | 5.632 | 1.00 | 27.27 | B |
| ATOM | 5008 | O | LEU | B | 359 | 26.710 | 51.702 | 6.729 | 1.00 | 24.72 | B |
| ATOM | 5009 | N | VAL | B | 360 | 26.561 | 51.628 | 4.477 | 1.00 | 26.99 | B |
| ATOM | 5010 | CA | VAL | B | 360 | 25.948 | 50.282 | 4.406 | 1.00 | 26.74 | B |
| ATOM | 5011 | CB | VAL | B | 360 | 24.435 | 50.277 | 4.014 | 1.00 | 24.35 | B |
| ATOM | 5012 | CG1 | VAL | B | 360 | 23.612 | 51.065 | 5.015 | 1.00 | 26.85 | B |
| ATOM | 5013 | CG2 | VAL | B | 360 | 24.245 | 50.821 | 2.606 | 1.00 | 28.14 | B |
| ATOM | 5014 | C | VAL | B | 360 | 26.700 | 49.573 | 3.297 | 1.00 | 27.27 | B |
| ATOM | 5015 | O | VAL | B | 360 | 27.190 | 50.247 | 2.387 | 1.00 | 28.61 | B |
| ATOM | 5016 | N | VAL | B | 361 | 26.823 | 48.241 | 3.374 | 1.00 | 26.68 | B |
| ATOM | 5017 | CA | VAL | B | 361 | 27.491 | 47.468 | 2.318 | 1.00 | 25.44 | B |
| ATOM | 5018 | CB | VAL | B | 361 | 28.864 | 46.867 | 2.767 | 1.00 | 27.07 | B |
| ATOM | 5019 | CG1 | VAL | B | 361 | 29.862 | 47.996 | 3.097 | 1.00 | 25.00 | B |
| ATOM | 5020 | CG2 | VAL | B | 361 | 28.684 | 45.912 | 3.966 | 1.00 | 24.63 | B |
| ATOM | 5021 | C | VAL | B | 361 | 26.596 | 46.321 | 1.854 | 1.00 | 26.05 | B |
| ATOM | 5022 | O | VAL | B | 361 | 25.695 | 45.903 | 2.566 | 1.00 | 27.10 | B |
| ATOM | 5023 | N | THR | B | 362 | 26.835 | 45.824 | 0.652 | 1.00 | 26.26 | B |
| ATOM | 5024 | CA | THR | B | 362 | 26.055 | 44.709 | 0.131 | 1.00 | 27.08 | B |
| ATOM | 5025 | CB | THR | B | 362 | 25.466 | 45.076 | −1.240 | 1.00 | 27.95 | B |
| ATOM | 5026 | OG1 | THR | B | 362 | 24.371 | 45.971 | −1.019 | 1.00 | 31.35 | B |
| ATOM | 5027 | CG2 | THR | B | 362 | 24.963 | 43.816 | −1.985 | 1.00 | 27.89 | B |
| ATOM | 5028 | C | THR | B | 362 | 26.973 | 43.494 | 0.047 | 1.00 | 26.27 | B |
| ATOM | 5029 | O | THR | B | 362 | 27.943 | 43.502 | −0.688 | 1.00 | 29.04 | B |
| ATOM | 5030 | N | ALA | B | 363 | 26.695 | 42.473 | 0.845 | 1.00 | 24.70 | B |
| ATOM | 5031 | CA | ALA | B | 363 | 27.506 | 41.253 | 0.862 | 1.00 | 24.15 | B |
| ATOM | 5032 | CB | ALA | B | 363 | 27.751 | 40.812 | 2.315 | 1.00 | 23.75 | B |
| ATOM | 5033 | C | ALA | B | 363 | 26.840 | 40.087 | 0.101 | 1.00 | 24.63 | B |
| ATOM | 5034 | O | ALA | B | 363 | 25.609 | 39.951 | 0.072 | 1.00 | 23.22 | B |
| ATOM | 5035 | N | GLU | B | 364 | 27.676 | 39.273 | −0.529 | 1.00 | 22.66 | B |
| ATOM | 5036 | CA | GLU | B | 364 | 27.230 | 38.093 | −1.214 | 1.00 | 23.99 | B |
| ATOM | 5037 | CB | GLU | B | 364 | 27.749 | 38.055 | −2.644 | 1.00 | 27.69 | B |
| ATOM | 5038 | CG | GLU | B | 364 | 27.155 | 36.902 | −3.443 | 1.00 | 33.48 | B |
| ATOM | 5039 | CD | GLU | B | 364 | 27.562 | 36.936 | −4.922 | 1.00 | 39.70 | B |
| ATOM | 5040 | OE1 | GLU | B | 364 | 28.779 | 37.089 | −5.183 | 1.00 | 42.02 | B |
| ATOM | 5041 | OE2 | GLU | B | 364 | 26.668 | 36.795 | −5.814 | 1.00 | 42.01 | B |

TABLE 2-continued

| ATOM | 5042 | C | GLU | B | 364 | 27.876 | 36.964 | −0.402 | 1.00 | 23.63 | B |
| ATOM | 5043 | O | GLU | B | 364 | 29.043 | 37.073 | −0.021 | 1.00 | 23.47 | B |
| ATOM | 5044 | N | ILE | B | 365 | 27.121 | 35.904 | −0.118 | 1.00 | 22.05 | B |
| ATOM | 5045 | CA | ILE | B | 365 | 27.606 | 34.761 | 0.659 | 1.00 | 20.67 | B |
| ATOM | 5046 | CB | ILE | B | 365 | 26.777 | 34.594 | 1.980 | 1.00 | 22.40 | B |
| ATOM | 5047 | CG2 | ILE | B | 365 | 27.274 | 33.352 | 2.781 | 1.00 | 23.38 | B |
| ATOM | 5048 | CG1 | ILE | B | 365 | 26.847 | 35.871 | 2.830 | 1.00 | 19.69 | B |
| ATOM | 5049 | CD1 | ILE | B | 365 | 28.257 | 36.253 | 3.366 | 1.00 | 20.19 | B |
| ATOM | 5050 | C | ILE | B | 365 | 27.382 | 33.525 | −0.235 | 1.00 | 22.67 | B |
| ATOM | 5051 | O | ILE | B | 365 | 26.338 | 33.404 | −0.913 | 1.00 | 21.12 | B |
| ATOM | 5052 | N | THR | B | 366 | 28.339 | 32.610 | −0.231 | 1.00 | 20.74 | B |
| ATOM | 5053 | CA | THR | B | 366 | 28.233 | 31.408 | −1.062 | 1.00 | 22.55 | B |
| ATOM | 5054 | CB | THR | B | 366 | 29.294 | 31.424 | −2.179 | 1.00 | 22.50 | B |
| ATOM | 5055 | OG1 | THR | B | 366 | 29.123 | 32.605 | −2.959 | 1.00 | 24.75 | B |
| ATOM | 5056 | CG2 | THR | B | 366 | 29.141 | 30.232 | −3.107 | 1.00 | 23.94 | B |
| ATOM | 5057 | C | THR | B | 366 | 28.475 | 30.196 | −0.181 | 1.00 | 22.86 | B |
| ATOM | 5058 | O | THR | B | 366 | 29.409 | 30.214 | 0.604 | 1.00 | 22.02 | B |
| ATOM | 5059 | N | GLY | B | 367 | 27.624 | 29.177 | −0.307 | 1.00 | 21.56 | B |
| ATOM | 5060 | CA | GLY | B | 367 | 27.741 | 27.951 | 0.467 | 1.00 | 21.48 | B |
| ATOM | 5061 | C | GLY | B | 367 | 27.050 | 26.816 | −0.284 | 1.00 | 22.21 | B |
| ATOM | 5062 | O | GLY | B | 367 | 26.565 | 27.017 | −1.404 | 1.00 | 21.84 | B |
| ATOM | 5063 | N | LYS | B | 368 | 27.006 | 25.610 | 0.283 | 1.00 | 22.66 | B |
| ATOM | 5064 | CA | LYS | B | 368 | 26.347 | 24.498 | −0.423 | 1.00 | 20.46 | B |
| ATOM | 5065 | CB | LYS | B | 368 | 27.398 | 23.485 | −0.916 | 1.00 | 24.29 | B |
| ATOM | 5066 | CG | LYS | B | 368 | 26.833 | 22.217 | −1.637 | 1.00 | 27.75 | B |
| ATOM | 5067 | CD | LYS | B | 368 | 27.990 | 21.314 | −2.153 | 1.00 | 29.26 | B |
| ATOM | 5068 | CE | LYS | B | 368 | 27.466 | 20.142 | −2.982 | 1.00 | 30.74 | B |
| ATOM | 5069 | NZ | LYS | B | 368 | 26.271 | 20.559 | −3.794 | 1.00 | 32.01 | B |
| ATOM | 5070 | C | LYS | B | 368 | 25.362 | 23.840 | 0.512 | 1.00 | 21.10 | B |
| ATOM | 5071 | O | LYS | B | 368 | 25.630 | 23.685 | 1.708 | 1.00 | 23.03 | B |
| ATOM | 5072 | N | ALA | B | 369 | 24.203 | 23.468 | −0.016 | 1.00 | 19.42 | B |
| ATOM | 5073 | CA | ALA | B | 369 | 23.202 | 22.825 | 0.788 | 1.00 | 17.75 | B |
| ATOM | 5074 | CB | ALA | B | 369 | 21.974 | 23.663 | 0.878 | 1.00 | 19.50 | B |
| ATOM | 5075 | C | ALA | B | 369 | 22.857 | 21.487 | 0.191 | 1.00 | 20.13 | B |
| ATOM | 5076 | O | ALA | B | 369 | 22.956 | 21.283 | −1.028 | 1.00 | 19.17 | B |
| ATOM | 5077 | N | PHE | B | 370 | 22.444 | 20.576 | 1.061 | 1.00 | 17.05 | B |
| ATOM | 5078 | CA | PHE | B | 370 | 22.079 | 19.247 | 0.630 | 1.00 | 18.83 | B |
| ATOM | 5079 | CB | PHE | B | 370 | 22.992 | 18.185 | 1.286 | 1.00 | 22.41 | B |
| ATOM | 5080 | CG | PHE | B | 370 | 24.396 | 18.173 | 0.761 | 1.00 | 26.25 | B |
| ATOM | 5081 | CD1 | PHE | B | 370 | 24.708 | 17.482 | −0.406 | 1.00 | 30.61 | B |
| ATOM | 5082 | CD2 | PHE | B | 370 | 25.395 | 18.876 | 1.403 | 1.00 | 27.98 | B |
| ATOM | 5083 | CE1 | PHE | B | 370 | 26.006 | 17.496 | −0.921 | 1.00 | 32.67 | B |
| ATOM | 5084 | CE2 | PHE | B | 370 | 26.715 | 18.895 | 0.888 | 1.00 | 28.34 | B |
| ATOM | 5085 | CZ | PHE | B | 370 | 27.011 | 18.208 | −0.264 | 1.00 | 28.75 | B |
| ATOM | 5086 | C | PHE | B | 370 | 20.688 | 18.943 | 1.057 | 1.00 | 17.51 | B |
| ATOM | 5087 | O | PHE | B | 370 | 20.259 | 19.311 | 2.172 | 1.00 | 16.63 | B |
| ATOM | 5088 | N | ILE | B | 371 | 19.968 | 18.243 | 0.198 | 1.00 | 16.90 | B |
| ATOM | 5089 | CA | ILE | B | 371 | 18.645 | 17.788 | 0.602 | 1.00 | 18.95 | B |
| ATOM | 5090 | CB | ILE | B | 371 | 17.781 | 17.437 | −0.627 | 1.00 | 21.54 | B |
| ATOM | 5091 | CG2 | ILE | B | 371 | 16.463 | 16.786 | −0.185 | 1.00 | 21.62 | B |
| ATOM | 5092 | CG1 | ILE | B | 371 | 17.547 | 18.720 | −1.437 | 1.00 | 22.68 | B |
| ATOM | 5093 | CD1 | ILE | B | 371 | 16.438 | 18.650 | −2.554 | 1.00 | 27.87 | B |
| ATOM | 5094 | C | ILE | B | 371 | 18.937 | 16.512 | 1.457 | 1.00 | 19.48 | B |
| ATOM | 5095 | O | ILE | B | 371 | 19.709 | 15.655 | 1.028 | 1.00 | 17.27 | B |
| ATOM | 5096 | N | MET | B | 372 | 18.401 | 16.434 | 2.690 | 1.00 | 17.92 | B |
| ATOM | 5097 | CA | MET | B | 372 | 18.613 | 15.256 | 3.506 | 1.00 | 18.60 | B |
| ATOM | 5098 | CB | MET | B | 372 | 19.274 | 15.623 | 4.850 | 1.00 | 19.34 | B |
| ATOM | 5099 | CG | MET | B | 372 | 18.419 | 16.435 | 5.758 | 1.00 | 18.11 | B |
| ATOM | 5100 | SD | MET | B | 372 | 19.301 | 16.869 | 7.267 | 1.00 | 19.21 | B |
| ATOM | 5101 | CE | MET | B | 372 | 18.041 | 17.789 | 8.107 | 1.00 | 12.91 | B |
| ATOM | 5102 | C | MET | B | 372 | 17.328 | 14.445 | 3.722 | 1.00 | 18.21 | B |
| ATOM | 5103 | O | MET | B | 372 | 17.376 | 13.308 | 4.195 | 1.00 | 17.66 | B |
| ATOM | 5104 | N | GLY | B | 373 | 16.184 | 15.009 | 3.360 | 1.00 | 19.33 | B |
| ATOM | 5105 | CA | GLY | B | 373 | 14.937 | 14.276 | 3.489 | 1.00 | 19.69 | B |
| ATOM | 5106 | C | GLY | B | 373 | 13.702 | 14.954 | 2.911 | 1.00 | 20.45 | B |
| ATOM | 5107 | O | GLY | B | 373 | 13.659 | 16.187 | 2.793 | 1.00 | 18.84 | B |
| ATOM | 5108 | N | PHE | B | 374 | 12.724 | 14.157 | 2.491 | 1.00 | 18.91 | B |
| ATOM | 5109 | CA | PHE | B | 374 | 11.433 | 14.694 | 2.051 | 1.00 | 21.32 | B |
| ATOM | 5110 | CB | PHE | B | 374 | 11.031 | 14.179 | 0.669 | 1.00 | 23.96 | B |
| ATOM | 5111 | CG | PHE | B | 374 | 11.868 | 14.742 | −0.434 | 1.00 | 23.84 | B |
| ATOM | 5112 | CD1 | PHE | B | 374 | 11.773 | 16.079 | −0.773 | 1.00 | 25.19 | B |
| ATOM | 5113 | CD2 | PHE | B | 374 | 12.770 | 13.941 | −1.115 | 1.00 | 25.02 | B |
| ATOM | 5114 | CE1 | PHE | B | 374 | 12.577 | 16.605 | −1.787 | 1.00 | 25.39 | B |
| ATOM | 5115 | CE2 | PHE | B | 374 | 13.568 | 14.451 | −2.120 | 1.00 | 24.17 | B |
| ATOM | 5116 | CZ | PHE | B | 374 | 13.474 | 15.784 | −2.460 | 1.00 | 23.47 | B |
| ATOM | 5117 | C | PHE | B | 374 | 10.544 | 14.108 | 3.132 | 1.00 | 22.93 | B |
| ATOM | 5118 | O | PHE | B | 374 | 10.378 | 12.885 | 3.208 | 1.00 | 23.92 | B |
| ATOM | 5119 | N | ASN | B | 375 | 9.952 | 14.961 | 3.955 | 1.00 | 21.77 | B |
| ATOM | 5120 | CA | ASN | B | 375 | 9.205 | 14.478 | 5.104 | 1.00 | 22.02 | B |

TABLE 2-continued

| ATOM | 5121 | CB | ASN | B | 375 | 9.982 | 14.973 | 6.335 | 1.00 | 26.98 | B |
| ATOM | 5122 | CG | ASN | B | 375 | 9.525 | 14.358 | 7.643 | 1.00 | 30.89 | B |
| ATOM | 5123 | OD1 | ASN | B | 375 | 8.939 | 13.266 | 7.691 | 1.00 | 34.61 | B |
| ATOM | 5124 | ND2 | ASN | B | 375 | 9.825 | 15.061 | 8.739 | 1.00 | 33.14 | B |
| ATOM | 5125 | C | ASN | B | 375 | 7.764 | 14.940 | 5.160 | 1.00 | 21.79 | B |
| ATOM | 5126 | O | ASN | B | 375 | 7.454 | 16.042 | 4.729 | 1.00 | 25.19 | B |
| ATOM | 5127 | N | THR | B | 376 | 6.861 | 14.073 | 5.603 | 1.00 | 18.65 | B |
| ATOM | 5128 | CA | THR | B | 376 | 5.491 | 14.481 | 5.788 | 1.00 | 18.70 | B |
| ATOM | 5129 | CB | THR | B | 376 | 4.528 | 13.602 | 5.008 | 1.00 | 19.42 | B |
| ATOM | 5130 | OG1 | THR | B | 376 | 4.792 | 13.773 | 3.602 | 1.00 | 24.49 | B |
| ATOM | 5131 | CG2 | THR | B | 376 | 3.117 | 14.005 | 5.292 | 1.00 | 20.36 | B |
| ATOM | 5132 | C | THR | B | 376 | 5.300 | 14.349 | 7.294 | 1.00 | 18.93 | B |
| ATOM | 5133 | O | THR | B | 376 | 5.206 | 13.254 | 7.846 | 1.00 | 20.07 | B |
| ATOM | 5134 | N | MET | B | 377 | 5.265 | 15.502 | 7.936 | 1.00 | 18.83 | B |
| ATOM | 5135 | CA | MET | B | 377 | 5.181 | 15.654 | 9.372 | 1.00 | 21.66 | B |
| ATOM | 5136 | CB | MET | B | 377 | 5.888 | 16.965 | 9.723 | 1.00 | 23.86 | B |
| ATOM | 5137 | CG | MET | B | 377 | 6.173 | 17.173 | 11.177 | 1.00 | 28.77 | B |
| ATOM | 5138 | SD | MET | B | 377 | 7.393 | 18.508 | 11.335 | 1.00 | 33.73 | B |
| ATOM | 5139 | CE | MET | B | 377 | 8.597 | 17.989 | 10.319 | 1.00 | 26.81 | B |
| ATOM | 5140 | C | MET | B | 377 | 3.745 | 15.633 | 9.840 | 1.00 | 20.80 | B |
| ATOM | 5141 | O | MET | B | 377 | 2.909 | 16.347 | 9.301 | 1.00 | 23.03 | B |
| ATOM | 5142 | N | LEU | B | 378 | 3.463 | 14.807 | 10.847 | 1.00 | 18.13 | B |
| ATOM | 5143 | CA | LEU | B | 378 | 2.122 | 14.628 | 11.377 | 1.00 | 17.58 | B |
| ATOM | 5144 | CB | LEU | B | 378 | 1.755 | 13.145 | 11.314 | 1.00 | 19.64 | B |
| ATOM | 5145 | CG | LEU | B | 378 | 1.890 | 12.441 | 9.960 | 1.00 | 23.99 | B |
| ATOM | 5146 | CD1 | LEU | B | 378 | 1.387 | 11.024 | 10.095 | 1.00 | 25.18 | B |
| ATOM | 5147 | CD2 | LEU | B | 378 | 1.058 | 13.167 | 8.929 | 1.00 | 22.82 | B |
| ATOM | 5148 | C | LEU | B | 378 | 1.904 | 15.123 | 12.807 | 1.00 | 20.28 | B |
| ATOM | 5149 | O | LEU | B | 378 | 2.805 | 15.047 | 13.671 | 1.00 | 18.55 | B |
| ATOM | 5150 | N | PHE | B | 379 | 0.679 | 15.573 | 13.060 | 1.00 | 19.42 | B |
| ATOM | 5151 | CA | PHE | B | 379 | 0.293 | 16.106 | 14.345 | 1.00 | 19.30 | B |
| ATOM | 5152 | CB | PHE | B | 379 | 0.251 | 17.642 | 14.275 | 1.00 | 17.57 | B |
| ATOM | 5153 | CG | PHE | B | 379 | 1.593 | 18.275 | 13.988 | 1.00 | 18.77 | B |
| ATOM | 5154 | CD1 | PHE | B | 379 | 2.493 | 18.546 | 15.035 | 1.00 | 16.65 | B |
| ATOM | 5155 | CD2 | PHE | B | 379 | 1.991 | 18.541 | 12.669 | 1.00 | 20.08 | B |
| ATOM | 5156 | CE1 | PHE | B | 379 | 3.765 | 19.068 | 14.776 | 1.00 | 16.88 | B |
| ATOM | 5157 | CE2 | PHE | B | 379 | 3.279 | 19.071 | 12.386 | 1.00 | 18.55 | B |
| ATOM | 5158 | CZ | PHE | B | 379 | 4.168 | 19.332 | 13.465 | 1.00 | 14.92 | B |
| ATOM | 5159 | C | PHE | B | 379 | −1.095 | 15.609 | 14.772 | 1.00 | 23.48 | B |
| ATOM | 5160 | O | PHE | B | 379 | −2.113 | 16.153 | 14.363 | 1.00 | 26.02 | B |
| ATOM | 5161 | N | ASP | B | 380 | −1.140 | 14.576 | 15.590 | 1.00 | 23.87 | B |
| ATOM | 5162 | CA | ASP | B | 380 | −2.403 | 14.091 | 16.101 | 1.00 | 24.28 | B |
| ATOM | 5163 | CB | ASP | B | 380 | −2.202 | 12.679 | 16.640 | 1.00 | 27.17 | B |
| ATOM | 5164 | CG | ASP | B | 380 | −3.490 | 12.045 | 17.131 | 1.00 | 29.28 | B |
| ATOM | 5165 | OD1 | ASP | B | 380 | −4.295 | 12.692 | 17.851 | 1.00 | 29.00 | B |
| ATOM | 5166 | OD2 | ASP | B | 380 | −3.671 | 10.870 | 16.795 | 1.00 | 32.48 | B |
| ATOM | 5167 | C | ASP | B | 380 | −2.830 | 15.044 | 17.240 | 1.00 | 25.93 | B |
| ATOM | 5168 | O | ASP | B | 380 | −2.044 | 15.371 | 18.112 | 1.00 | 25.21 | B |
| ATOM | 5169 | N | PRO | B | 381 | −4.088 | 15.521 | 17.221 | 1.00 | 29.19 | B |
| ATOM | 5170 | CD | PRO | B | 381 | −5.069 | 15.151 | 16.175 | 1.00 | 28.13 | B |
| ATOM | 5171 | CA | PRO | B | 381 | −4.686 | 16.433 | 18.210 | 1.00 | 27.16 | B |
| ATOM | 5172 | CB | PRO | B | 381 | −6.153 | 16.484 | 17.775 | 1.00 | 31.84 | B |
| ATOM | 5173 | CG | PRO | B | 381 | −6.089 | 16.237 | 16.288 | 1.00 | 29.58 | B |
| ATOM | 5174 | C | PRO | B | 381 | −4.559 | 15.894 | 19.647 | 1.00 | 28.24 | B |
| ATOM | 5175 | O | PRO | B | 381 | −4.549 | 16.675 | 20.634 | 1.00 | 26.10 | B |
| ATOM | 5176 | N | THR | B | 382 | −4.470 | 14.563 | 19.758 | 1.00 | 25.53 | B |
| ATOM | 5177 | CA | THR | B | 382 | −4.347 | 13.904 | 21.065 | 1.00 | 26.78 | B |
| ATOM | 5178 | CB | THR | B | 382 | −5.109 | 12.556 | 21.116 | 1.00 | 26.38 | B |
| ATOM | 5179 | OG1 | THR | B | 382 | −4.537 | 11.660 | 20.156 | 1.00 | 27.59 | B |
| ATOM | 5180 | CG2 | THR | B | 382 | −6.575 | 12.770 | 20.833 | 1.00 | 24.91 | B |
| ATOM | 5181 | C | THR | B | 382 | −2.904 | 13.615 | 21.491 | 1.00 | 25.71 | B |
| ATOM | 5182 | O | THR | B | 382 | −2.655 | 13.143 | 22.590 | 1.00 | 26.08 | B |
| ATOM | 5183 | N | ASP | B | 383 | −1.953 | 13.891 | 20.622 | 1.00 | 23.16 | B |
| ATOM | 5184 | CA | ASP | B | 383 | −0.559 | 13.678 | 20.951 | 1.00 | 22.99 | B |
| ATOM | 5185 | CB | ASP | B | 383 | 0.256 | 13.833 | 19.652 | 1.00 | 19.53 | B |
| ATOM | 5186 | CG | ASP | B | 383 | 1.727 | 13.629 | 19.861 | 1.00 | 20.29 | B |
| ATOM | 5187 | OD1 | ASP | B | 383 | 2.135 | 13.563 | 21.040 | 1.00 | 20.01 | B |
| ATOM | 5188 | OD2 | ASP | B | 383 | 2.465 | 13.548 | 18.863 | 1.00 | 17.16 | B |
| ATOM | 5189 | C | ASP | B | 383 | −0.175 | 14.767 | 21.987 | 1.00 | 23.38 | B |
| ATOM | 5190 | O | ASP | B | 383 | −0.247 | 15.963 | 21.681 | 1.00 | 22.31 | B |
| ATOM | 5191 | N | PRO | B | 384 | 0.219 | 14.372 | 23.229 | 1.00 | 24.61 | B |
| ATOM | 5192 | CD | PRO | B | 384 | 0.601 | 13.005 | 23.648 | 1.00 | 26.35 | B |
| ATOM | 5193 | CA | PRO | B | 384 | 0.605 | 15.362 | 24.258 | 1.00 | 22.33 | B |
| ATOM | 5194 | CB | PRO | B | 384 | 1.004 | 14.511 | 25.489 | 1.00 | 27.33 | B |
| ATOM | 5195 | CG | PRO | B | 384 | 0.534 | 13.093 | 25.160 | 1.00 | 28.78 | B |
| ATOM | 5196 | C | PRO | B | 384 | 1.796 | 16.184 | 23.805 | 1.00 | 19.14 | B |
| ATOM | 5197 | O | PRO | B | 384 | 2.037 | 17.230 | 24.339 | 1.00 | 21.49 | B |
| ATOM | 5198 | N | PHE | B | 385 | 2.560 | 15.691 | 22.832 | 1.00 | 15.43 | B |
| ATOM | 5199 | CA | PHE | B | 385 | 3.694 | 16.430 | 22.329 | 1.00 | 15.93 | B |

TABLE 2-continued

| | | | | | | | | | | |
|---|---|---|---|---|---|---|---|---|---|---|
| ATOM | 5200 | CB | PHE | B | 385 | 4.952 | 15.554 | 22.436 | 1.00 | 18.87 B |
| ATOM | 5201 | CG | PHE | B | 385 | 5.260 | 15.166 | 23.866 | 1.00 | 20.13 B |
| ATOM | 5202 | CD1 | PHE | B | 385 | 5.581 | 16.151 | 24.798 | 1.00 | 22.85 B |
| ATOM | 5203 | CD2 | PHE | B | 385 | 5.120 | 13.852 | 24.301 | 1.00 | 22.78 B |
| ATOM | 5204 | CE1 | PHE | B | 385 | 5.760 | 15.807 | 26.180 | 1.00 | 26.22 B |
| ATOM | 5205 | CE2 | PHE | B | 385 | 5.290 | 13.504 | 25.651 | 1.00 | 21.69 B |
| ATOM | 5206 | CZ | PHE | B | 385 | 5.608 | 14.471 | 26.579 | 1.00 | 19.44 B |
| ATOM | 5207 | C | PHE | B | 385 | 3.519 | 16.977 | 20.918 | 1.00 | 16.47 B |
| ATOM | 5208 | O | PHE | B | 385 | 4.507 | 17.204 | 20.205 | 1.00 | 15.60 B |
| ATOM | 5209 | N | LYS | B | 386 | 2.270 | 17.190 | 20.512 | 1.00 | 15.17 B |
| ATOM | 5210 | CA | LYS | B | 386 | 1.991 | 17.765 | 19.182 | 1.00 | 15.53 B |
| ATOM | 5211 | CB | LYS | B | 386 | 0.485 | 17.933 | 18.935 | 1.00 | 16.93 B |
| ATOM | 5212 | CG | LYS | B | 386 | −0.236 | 18.815 | 19.932 | 1.00 | 17.12 B |
| ATOM | 5213 | CD | LYS | B | 386 | −1.731 | 18.614 | 19.828 | 1.00 | 20.90 B |
| ATOM | 5214 | CE | LYS | B | 386 | −2.472 | 19.453 | 20.810 | 1.00 | 24.15 B |
| ATOM | 5215 | NZ | LYS | B | 386 | −3.923 | 19.103 | 20.662 | 1.00 | 31.40 B |
| ATOM | 5216 | C | LYS | B | 386 | 2.666 | 19.105 | 19.076 | 1.00 | 17.01 B |
| ATOM | 5217 | O | LYS | B | 386 | 3.011 | 19.529 | 17.974 | 1.00 | 16.30 B |
| ATOM | 5218 | N | ASN | B | 387 | 2.898 | 19.778 | 20.218 | 1.00 | 16.85 B |
| ATOM | 5219 | CA | ASN | B | 387 | 3.576 | 21.081 | 20.166 | 1.00 | 16.48 B |
| ATOM | 5220 | CB | ASN | B | 387 | 2.787 | 22.146 | 20.934 | 1.00 | 19.73 B |
| ATOM | 5221 | CG | ASN | B | 387 | 1.348 | 22.312 | 20.378 | 1.00 | 22.02 B |
| ATOM | 5222 | OD1 | ASN | B | 387 | 0.397 | 22.510 | 21.134 | 1.00 | 25.02 B |
| ATOM | 5223 | ND2 | ASN | B | 387 | 1.208 | 22.225 | 19.058 | 1.00 | 17.56 B |
| ATOM | 5224 | C | ASN | B | 387 | 5.021 | 21.079 | 20.629 | 1.00 | 16.78 B |
| ATOM | 5225 | O | ASN | B | 387 | 5.569 | 22.142 | 20.944 | 1.00 | 15.14 B |
| ATOM | 5226 | N | GLY | B | 388 | 5.637 | 19.896 | 20.653 | 1.00 | 15.66 B |
| ATOM | 5227 | CA | GLY | B | 388 | 7.041 | 19.784 | 21.032 | 1.00 | 13.64 B |
| ATOM | 5228 | C | GLY | B | 388 | 7.415 | 20.031 | 22.499 | 1.00 | 15.26 B |
| ATOM | 5229 | O | GLY | B | 388 | 6.596 | 20.447 | 23.275 | 1.00 | 13.96 B |
| ATOM | 5230 | N | PHE | B | 389 | 8.682 | 19.797 | 22.847 | 1.00 | 16.92 B |
| ATOM | 5231 | CA | PHE | B | 389 | 9.185 | 20.039 | 24.209 | 1.00 | 15.27 B |
| ATOM | 5232 | CB | PHE | B | 389 | 8.873 | 18.849 | 25.154 | 1.00 | 11.75 B |
| ATOM | 5233 | CG | PHE | B | 389 | 9.623 | 17.584 | 24.800 | 1.00 | 14.56 B |
| ATOM | 5234 | CD1 | PHE | B | 389 | 10.928 | 17.387 | 25.228 | 1.00 | 16.32 B |
| ATOM | 5235 | CD2 | PHE | B | 389 | 9.033 | 16.611 | 24.004 | 1.00 | 14.91 B |
| ATOM | 5236 | CE1 | PHE | B | 389 | 11.655 | 16.256 | 24.883 | 1.00 | 14.69 B |
| ATOM | 5237 | CE2 | PHE | B | 389 | 9.746 | 15.466 | 23.643 | 1.00 | 15.69 B |
| ATOM | 5238 | CZ | PHE | B | 389 | 11.074 | 15.288 | 24.090 | 1.00 | 16.98 B |
| ATOM | 5239 | C | PHE | B | 389 | 10.683 | 20.181 | 24.077 | 1.00 | 15.32 B |
| ATOM | 5240 | O | PHE | B | 389 | 11.263 | 19.859 | 23.039 | 1.00 | 16.57 B |
| ATOM | 5241 | N | THR | B | 390 | 11.303 | 20.753 | 25.101 | 1.00 | 13.16 B |
| ATOM | 5242 | CA | THR | B | 390 | 12.756 | 20.871 | 25.158 | 1.00 | 15.26 B |
| ATOM | 5243 | CB | THR | B | 390 | 13.289 | 22.292 | 24.842 | 1.00 | 11.40 B |
| ATOM | 5244 | OG1 | THR | B | 390 | 14.718 | 22.271 | 24.938 | 1.00 | 14.33 B |
| ATOM | 5245 | CG2 | THR | B | 390 | 12.764 | 23.347 | 25.830 | 1.00 | 11.90 B |
| ATOM | 5246 | C | THR | B | 390 | 13.128 | 20.554 | 26.610 | 1.00 | 16.50 B |
| ATOM | 5247 | O | THR | B | 390 | 12.373 | 20.868 | 27.529 | 1.00 | 14.49 B |
| ATOM | 5248 | N | LEU | B | 391 | 14.280 | 19.949 | 26.796 | 1.00 | 20.29 B |
| ATOM | 5249 | CA | LEU | B | 391 | 14.768 | 19.609 | 28.129 | 1.00 | 22.25 B |
| ATOM | 5250 | CB | LEU | B | 391 | 15.334 | 18.195 | 28.133 | 1.00 | 17.40 B |
| ATOM | 5251 | CG | LEU | B | 391 | 14.460 | 17.032 | 28.635 | 1.00 | 21.15 B |
| ATOM | 5252 | CD1 | LEU | B | 391 | 13.037 | 17.200 | 28.424 | 1.00 | 18.95 B |
| ATOM | 5253 | CD2 | LEU | B | 391 | 14.922 | 15.777 | 27.985 | 1.00 | 19.75 B |
| ATOM | 5254 | C | LEU | B | 391 | 15.865 | 20.624 | 28.468 | 1.00 | 25.38 B |
| ATOM | 5255 | O | LEU | B | 391 | 16.522 | 20.519 | 29.530 | 1.00 | 24.09 B |
| ATOM | 5256 | N | LYS | B | 392 | 16.069 | 21.608 | 27.579 | 1.00 | 21.77 B |
| ATOM | 5257 | CA | LYS | B | 392 | 17.087 | 22.618 | 27.857 | 1.00 | 25.23 B |
| ATOM | 5258 | CB | LYS | B | 392 | 17.467 | 23.442 | 26.611 | 1.00 | 22.83 B |
| ATOM | 5259 | CG | LYS | B | 392 | 18.670 | 24.379 | 26.879 | 1.00 | 25.42 B |
| ATOM | 5260 | CD | LYS | B | 392 | 19.140 | 25.171 | 25.646 | 1.00 | 22.17 B |
| ATOM | 5261 | CE | LYS | B | 392 | 19.709 | 24.248 | 24.642 | 1.00 | 18.21 B |
| ATOM | 5262 | NZ | LYS | B | 392 | 20.409 | 24.920 | 23.508 | 1.00 | 16.92 B |
| ATOM | 5263 | C | LYS | B | 392 | 16.553 | 23.552 | 28.957 | 1.00 | 25.50 B |
| ATOM | 5264 | O | LYS | B | 392 | 15.390 | 23.960 | 28.930 | 1.00 | 22.06 B |
| ATOM | 5265 | N | GLN | B | 393 | 17.393 | 23.891 | 29.930 | 1.00 | 27.99 B |
| ATOM | 5266 | CA | GLN | B | 393 | 16.912 | 24.769 | 30.987 | 1.00 | 31.46 B |
| ATOM | 5267 | CB | GLN | B | 393 | 17.537 | 24.451 | 32.356 | 1.00 | 38.27 B |
| ATOM | 5268 | CG | GLN | B | 393 | 18.587 | 23.361 | 32.408 | 1.00 | 45.31 B |
| ATOM | 5269 | CD | GLN | B | 393 | 19.853 | 23.635 | 31.584 | 1.00 | 51.08 B |
| ATOM | 5270 | OE1 | GLN | B | 393 | 19.854 | 23.508 | 30.330 | 1.00 | 48.97 B |
| ATOM | 5271 | NE2 | GLN | B | 393 | 20.953 | 23.986 | 32.287 | 1.00 | 50.04 B |
| ATOM | 5272 | C | GLN | B | 393 | 17.218 | 26.202 | 30.684 | 1.00 | 28.44 B |
| ATOM | 5273 | O | GLN | B | 393 | 18.222 | 26.513 | 30.061 | 1.00 | 27.03 B |
| ATOM | 5274 | N | TYR | B | 394 | 16.338 | 27.073 | 31.145 | 1.00 | 29.22 B |
| ATOM | 5275 | CA | TYR | B | 394 | 16.520 | 28.497 | 30.973 | 1.00 | 30.02 B |
| ATOM | 5276 | CB | TYR | B | 394 | 15.188 | 29.211 | 31.204 | 1.00 | 33.65 B |
| ATOM | 5277 | CG | TYR | B | 394 | 14.182 | 28.968 | 30.082 | 1.00 | 38.44 B |
| ATOM | 5278 | CD1 | TYR | B | 394 | 14.437 | 29.436 | 28.783 | 1.00 | 40.10 B |

TABLE 2-continued

| ATOM | 5279 | CE1 | TYR | B | 394 | 13.526 | 29.224 | 27.731 | 1.00 | 39.96 | B |
| --- | --- | --- | --- | --- | --- | --- | --- | --- | --- | --- | --- |
| ATOM | 5280 | CD2 | TYR | B | 394 | 12.979 | 28.272 | 30.308 | 1.00 | 39.87 | B |
| ATOM | 5281 | CE2 | TYR | B | 394 | 12.049 | 28.055 | 29.242 | 1.00 | 41.57 | B |
| ATOM | 5282 | CZ | TYR | B | 394 | 12.347 | 28.539 | 27.964 | 1.00 | 40.99 | B |
| ATOM | 5283 | OH | TYR | B | 394 | 11.497 | 28.329 | 26.901 | 1.00 | 42.49 | B |
| ATOM | 5284 | C | TYR | B | 394 | 17.567 | 28.970 | 31.969 | 1.00 | 28.81 | B |
| ATOM | 5285 | O | TYR | B | 394 | 17.621 | 28.495 | 33.104 | 1.00 | 29.44 | B |
| ATOM | 5286 | N | ILE | B | 395 | 18.415 | 29.884 | 31.534 | 1.00 | 27.82 | B |
| ATOM | 5287 | CA | ILE | B | 395 | 19.461 | 30.445 | 32.394 | 1.00 | 28.78 | B |
| ATOM | 5288 | CB | ILE | B | 395 | 20.879 | 30.096 | 31.895 | 1.00 | 27.79 | B |
| ATOM | 5289 | CG2 | ILE | B | 395 | 21.130 | 28.599 | 32.026 | 1.00 | 27.52 | B |
| ATOM | 5290 | CG1 | ILE | B | 395 | 21.018 | 30.587 | 30.449 | 1.00 | 27.16 | B |
| ATOM | 5291 | CD1 | ILE | B | 395 | 22.403 | 30.578 | 29.928 | 1.00 | 28.45 | B |
| ATOM | 5292 | C | ILE | B | 395 | 19.331 | 31.961 | 32.341 | 1.00 | 28.96 | B |
| ATOM | 5293 | O | ILE | B | 395 | 18.778 | 32.522 | 31.371 | 1.00 | 29.24 | B |
| ATOM | 5294 | N | TRP | B | 396 | 19.855 | 32.622 | 33.374 | 1.00 | 26.93 | B |
| ATOM | 5295 | CA | TRP | B | 396 | 19.815 | 34.080 | 33.471 | 1.00 | 28.76 | B |
| ATOM | 5296 | CB | TRP | B | 396 | 18.382 | 34.526 | 33.769 | 1.00 | 30.11 | B |
| ATOM | 5297 | CG | TRP | B | 396 | 17.832 | 34.000 | 35.089 | 1.00 | 32.00 | B |
| ATOM | 5298 | CD2 | TRP | B | 396 | 16.950 | 32.886 | 35.274 | 1.00 | 31.29 | B |
| ATOM | 5299 | CE2 | TRP | B | 396 | 16.694 | 32.782 | 36.662 | 1.00 | 32.00 | B |
| ATOM | 5300 | CE3 | TRP | B | 396 | 16.349 | 31.971 | 34.406 | 1.00 | 31.88 | B |
| ATOM | 5301 | CD1 | TRP | B | 396 | 18.070 | 34.511 | 36.344 | 1.00 | 32.40 | B |
| ATOM | 5302 | NE1 | TRP | B | 396 | 17.389 | 33.787 | 37.287 | 1.00 | 31.50 | B |
| ATOM | 5303 | CZ2 | TRP | B | 396 | 15.863 | 31.794 | 37.203 | 1.00 | 30.40 | B |
| ATOM | 5304 | CZ3 | TRP | B | 396 | 15.519 | 30.982 | 34.948 | 1.00 | 32.75 | B |
| ATOM | 5305 | CH2 | TRP | B | 396 | 15.287 | 30.908 | 36.338 | 1.00 | 30.75 | B |
| ATOM | 5306 | C | TRP | B | 396 | 20.775 | 34.580 | 34.577 | 1.00 | 30.49 | B |
| ATOM | 5307 | O | TRP | B | 396 | 21.119 | 33.835 | 35.520 | 1.00 | 29.07 | B |
| ATOM | 5308 | N | SER | B | 397 | 21.229 | 35.823 | 34.441 | 1.00 | 32.27 | B |
| ATOM | 5309 | CA | SER | B | 397 | 22.139 | 36.411 | 35.420 | 1.00 | 35.37 | B |
| ATOM | 5310 | CB | SER | B | 397 | 22.674 | 37.749 | 34.908 | 1.00 | 37.46 | B |
| ATOM | 5311 | OG | SER | B | 397 | 21.614 | 38.595 | 34.465 | 1.00 | 40.94 | B |
| ATOM | 5312 | C | SER | B | 397 | 21.395 | 36.643 | 36.720 | 1.00 | 38.16 | B |
| ATOM | 5313 | O | SER | B | 397 | 20.232 | 37.050 | 36.713 | 1.00 | 35.33 | B |
| ATOM | 5314 | N | SER | B | 398 | 22.042 | 36.364 | 37.843 | 1.00 | 43.16 | B |
| ATOM | 5315 | CA | SER | B | 398 | 21.375 | 36.606 | 39.116 | 1.00 | 48.81 | B |
| ATOM | 5316 | CB | SER | B | 398 | 22.085 | 35.870 | 40.247 | 1.00 | 50.31 | B |
| ATOM | 5317 | OG | SER | B | 398 | 23.299 | 36.531 | 40.556 | 1.00 | 53.01 | B |
| ATOM | 5318 | C | SER | B | 398 | 21.447 | 38.126 | 39.363 | 1.00 | 50.81 | B |
| ATOM | 5319 | O | SER | B | 398 | 20.376 | 38.786 | 39.470 | 1.00 | 52.12 | B |
| ATOM | 5320 | OXT | SER | B | 398 | 22.592 | 38.643 | 39.431 | 1.00 | 53.13 | B |
| ATOM | 5321 | O7 | PYC | A | 700 | 13.481 | −0.197 | 26.759 | 1.00 | 19.84 | A |
| ATOM | 5322 | O8 | PYC | A | 700 | 12.170 | 1.527 | 26.395 | 1.00 | 16.27 | A |
| ATOM | 5323 | C1 | PYC | A | 700 | 13.296 | 1.007 | 26.457 | 1.00 | 18.42 | A |
| ATOM | 5324 | C2 | PYC | A | 700 | 14.406 | 1.821 | 26.182 | 1.00 | 22.03 | A |
| ATOM | 5325 | C3 | PYC | A | 700 | 15.773 | 1.579 | 26.164 | 1.00 | 22.86 | A |
| ATOM | 5326 | C4 | PYC | A | 700 | 16.370 | 2.779 | 25.824 | 1.00 | 21.80 | A |
| ATOM | 5327 | C5 | PYC | A | 700 | 15.373 | 3.748 | 25.630 | 1.00 | 23.81 | A |
| ATOM | 5328 | N6 | PYC | A | 700 | 14.204 | 3.151 | 25.851 | 1.00 | 21.67 | A |
| ATOM | 5329 | O7 | PYC | B | 700 | 22.383 | 33.722 | 8.823 | 1.00 | 18.59 | B |
| ATOM | 5330 | O8 | PYC | B | 700 | 23.098 | 31.691 | 8.287 | 1.00 | 18.41 | B |
| ATOM | 5331 | C1 | PYC | B | 700 | 22.534 | 32.498 | 9.085 | 1.00 | 23.28 | B |
| ATOM | 5332 | C2 | PYC | B | 700 | 22.044 | 31.993 | 10.358 | 1.00 | 26.44 | B |
| ATOM | 5333 | C3 | PYC | B | 700 | 21.400 | 32.598 | 11.433 | 1.00 | 29.27 | B |
| ATOM | 5334 | C4 | PYC | B | 700 | 21.173 | 31.609 | 12.368 | 1.00 | 27.91 | B |
| ATOM | 5335 | C5 | PYC | B | 700 | 21.672 | 30.396 | 11.870 | 1.00 | 29.09 | B |
| ATOM | 5336 | N6 | PYC | B | 700 | 22.188 | 30.662 | 10.674 | 1.00 | 27.50 | B |
| ATOM | 5337 | O | HOH | W | 1 | 19.575 | 0.730 | 20.384 | 1.00 | 12.54 | W |
| ATOM | 5338 | O | HOH | W | 2 | 7.711 | 18.122 | 17.860 | 1.00 | 14.12 | W |
| ATOM | 5339 | O | HOH | W | 3 | 0.172 | 3.107 | 20.802 | 1.00 | 16.38 | W |
| ATOM | 5340 | O | HOH | W | 4 | 17.208 | 18.178 | 21.578 | 1.00 | 13.22 | W |
| ATOM | 5341 | O | HOH | W | 5 | 13.548 | 20.136 | 21.577 | 1.00 | 10.72 | W |
| ATOM | 5342 | O | HOH | W | 6 | 23.967 | 14.117 | 16.596 | 1.00 | 15.47 | W |
| ATOM | 5343 | O | HOH | W | 7 | 29.048 | 34.506 | 11.369 | 1.00 | 16.68 | W |
| ATOM | 5344 | O | HOH | W | 8 | 22.689 | 34.546 | 21.899 | 1.00 | 17.94 | W |
| ATOM | 5345 | O | HOH | W | 9 | 19.443 | −4.117 | 18.308 | 1.00 | 16.92 | W |
| ATOM | 5346 | O | HOH | W | 10 | 4.639 | 29.359 | 14.239 | 1.00 | 16.06 | W |
| ATOM | 5347 | O | HOH | W | 11 | 13.201 | 25.917 | 22.886 | 1.00 | 15.15 | W |
| ATOM | 5348 | O | HOH | W | 12 | 13.348 | 13.237 | 18.596 | 1.00 | 12.85 | W |
| ATOM | 5349 | O | HOH | W | 13 | 13.920 | 14.749 | 15.771 | 1.00 | 14.25 | W |
| ATOM | 5350 | O | HOH | W | 14 | 13.254 | 2.418 | 33.519 | 1.00 | 19.64 | W |
| ATOM | 5351 | O | HOH | W | 15 | 9.952 | −9.881 | 31.497 | 1.00 | 19.83 | W |
| ATOM | 5352 | O | HOH | W | 16 | 12.512 | 13.045 | 21.227 | 1.00 | 13.74 | W |
| ATOM | 5353 | O | HOH | W | 17 | 14.069 | 10.773 | 21.701 | 1.00 | 14.26 | W |
| ATOM | 5354 | O | HOH | W | 18 | 22.009 | 16.920 | 18.735 | 1.00 | 14.71 | W |
| ATOM | 5355 | O | HOH | W | 19 | 11.371 | 34.991 | 9.992 | 1.00 | 18.39 | W |
| ATOM | 5356 | O | HOH | W | 20 | 18.859 | 45.956 | 21.842 | 1.00 | 28.04 | W |
| ATOM | 5357 | O | HOH | W | 21 | 16.980 | 9.220 | 23.895 | 1.00 | 18.22 | W |

TABLE 2-continued

| | | | | | | | | | | |
|---|---|---|---|---|---|---|---|---|---|---|
| ATOM | 5358 | O | HOH | W | 22 | 24.954 | 6.992 | 6.611 | 1.00 | 18.55 W |
| ATOM | 5359 | O | HOH | W | 23 | 19.630 | 18.720 | 12.356 | 1.00 | 17.14 W |
| ATOM | 5360 | O | HOH | W | 24 | 14.717 | 31.845 | 12.903 | 1.00 | 16.35 W |
| ATOM | 5361 | O | HOH | W | 25 | 22.606 | 12.454 | 9.699 | 1.00 | 19.04 W |
| ATOM | 5362 | O | HOH | W | 26 | 17.447 | 16.403 | 12.909 | 1.00 | 16.47 W |
| ATOM | 5363 | O | HOH | W | 27 | 25.555 | 17.295 | 18.598 | 1.00 | 23.39 W |
| ATOM | 5364 | O | HOH | W | 28 | 17.423 | 41.770 | 27.801 | 1.00 | 21.32 W |
| ATOM | 5365 | O | HOH | W | 29 | 3.049 | −6.899 | 39.037 | 1.00 | 16.07 W |
| ATOM | 5366 | O | HOH | W | 30 | 15.225 | 33.564 | 19.567 | 1.00 | 26.87 W |
| ATOM | 5367 | O | HOH | W | 31 | 17.841 | 25.008 | 21.866 | 1.00 | 21.46 W |
| ATOM | 5368 | O | HOH | W | 32 | 24.759 | 23.206 | 19.981 | 1.00 | 20.53 W |
| ATOM | 5369 | O | HOH | W | 33 | 0.715 | −3.226 | 31.258 | 1.00 | 19.12 W |
| ATOM | 5370 | O | HOH | W | 34 | 22.550 | 14.109 | 1.550 | 1.00 | 23.43 W |
| ATOM | 5371 | O | HOH | W | 35 | 0.856 | 31.822 | 19.591 | 1.00 | 23.52 W |
| ATOM | 5372 | O | HOH | W | 36 | 1.110 | 13.342 | 16.458 | 1.00 | 24.25 W |
| ATOM | 5373 | O | HOH | W | 37 | 18.003 | 41.273 | 15.280 | 1.00 | 19.99 W |
| ATOM | 5374 | O | HOH | W | 38 | 22.078 | 19.725 | 12.381 | 1.00 | 16.80 W |
| ATOM | 5375 | O | HOH | W | 39 | 13.814 | 6.768 | 31.483 | 1.00 | 18.36 W |
| ATOM | 5376 | O | HOH | W | 40 | 18.317 | −8.777 | 5.412 | 1.00 | 28.08 W |
| ATOM | 5377 | O | HOH | W | 41 | 21.219 | 22.343 | 12.892 | 1.00 | 19.62 W |
| ATOM | 5378 | O | HOH | W | 42 | 18.656 | 30.286 | 26.470 | 1.00 | 21.12 W |
| ATOM | 5379 | O | HOH | W | 43 | 6.406 | 23.678 | 23.186 | 1.00 | 21.41 W |
| ATOM | 5380 | O | HOH | W | 44 | 20.570 | 19.256 | 19.409 | 1.00 | 15.70 W |
| ATOM | 5381 | O | HOH | W | 45 | 28.511 | 29.966 | 13.328 | 1.00 | 21.41 W |
| ATOM | 5382 | O | HOH | W | 46 | 1.841 | 9.384 | 30.007 | 1.00 | 21.68 W |
| ATOM | 5383 | O | HOH | W | 47 | 29.829 | 27.435 | 13.900 | 1.00 | 26.70 W |
| ATOM | 5384 | O | HOH | W | 48 | 2.476 | 22.051 | 16.314 | 1.00 | 18.26 W |
| ATOM | 5385 | O | HOH | W | 49 | 19.041 | 14.268 | 26.973 | 1.00 | 22.84 W |
| ATOM | 5386 | O | HOH | W | 50 | 7.480 | −12.341 | 24.926 | 1.00 | 24.22 W |
| ATOM | 5387 | O | HOH | W | 51 | 16.332 | 39.301 | 13.526 | 1.00 | 16.61 W |
| ATOM | 5388 | O | HOH | W | 52 | 16.242 | −14.165 | 15.655 | 1.00 | 26.55 W |
| ATOM | 5389 | O | HOH | W | 53 | 25.929 | 2.494 | 23.401 | 1.00 | 29.28 W |
| ATOM | 5390 | O | HOH | W | 54 | 15.339 | 24.525 | 23.133 | 1.00 | 23.56 W |
| ATOM | 5391 | O | HOH | W | 55 | 19.012 | 15.868 | 21.651 | 1.00 | 18.59 W |
| ATOM | 5392 | O | HOH | W | 56 | 23.149 | 52.942 | 20.995 | 1.00 | 33.11 W |
| ATOM | 5393 | O | HOH | W | 57 | 7.964 | 14.521 | 11.807 | 1.00 | 33.54 W |
| ATOM | 5394 | O | HOH | W | 58 | 17.164 | −13.916 | 39.473 | 1.00 | 21.00 W |
| ATOM | 5395 | O | HOH | W | 59 | 24.174 | 0.430 | 10.985 | 1.00 | 21.07 W |
| ATOM | 5396 | O | HOH | W | 60 | 15.268 | 33.839 | 16.997 | 1.00 | 14.54 W |
| ATOM | 5397 | O | HOH | W | 61 | 15.858 | −13.374 | 29.266 | 1.00 | 19.95 W |
| ATOM | 5398 | O | HOH | W | 62 | 15.585 | 18.782 | 24.703 | 1.00 | 21.00 W |
| ATOM | 5399 | O | HOH | W | 63 | 22.038 | 14.618 | 24.718 | 1.00 | 21.50 W |
| ATOM | 5400 | O | HOH | W | 65 | 7.445 | 41.308 | 2.151 | 1.00 | 24.44 W |
| ATOM | 5401 | O | HOH | W | 66 | 20.460 | 32.978 | 22.744 | 1.00 | 25.39 W |
| ATOM | 5402 | O | HOH | W | 67 | 8.615 | 42.215 | 4.941 | 1.00 | 28.44 W |
| ATOM | 5403 | O | HOH | W | 68 | 22.882 | −5.251 | 28.140 | 1.00 | 22.59 W |
| ATOM | 5404 | O | HOH | W | 69 | 23.585 | 1.299 | 22.927 | 1.00 | 22.06 W |
| ATOM | 5405 | O | HOH | W | 70 | 14.678 | −1.833 | 7.424 | 1.00 | 24.57 W |
| ATOM | 5406 | O | HOH | W | 71 | 22.568 | 36.211 | −6.316 | 1.00 | 23.20 W |
| ATOM | 5407 | O | HOH | W | 72 | 29.977 | 53.386 | 17.924 | 1.00 | 26.00 W |
| ATOM | 5408 | O | HOH | W | 73 | 5.079 | 30.480 | 22.852 | 1.00 | 30.93 W |
| ATOM | 5409 | O | HOH | W | 74 | 10.002 | −18.853 | 43.509 | 1.00 | 30.94 W |
| ATOM | 5410 | O | HOH | W | 75 | 4.640 | 26.616 | 3.081 | 1.00 | 28.98 W |
| ATOM | 5411 | O | HOH | W | 76 | 2.119 | 35.716 | 0.907 | 1.00 | 22.45 W |
| ATOM | 5412 | O | HOH | W | 77 | 34.942 | 41.656 | 0.293 | 1.00 | 24.03 W |
| ATOM | 5413 | O | HOH | W | 78 | 21.092 | 17.895 | −2.608 | 1.00 | 32.20 W |
| ATOM | 5414 | O | HOH | W | 79 | 26.638 | 6.888 | 3.483 | 1.00 | 32.81 W |
| ATOM | 5415 | O | HOH | W | 80 | 24.482 | −21.567 | 36.531 | 1.00 | 35.97 W |
| ATOM | 5416 | O | HOH | W | 81 | 2.934 | 33.607 | 20.748 | 1.00 | 23.15 W |
| ATOM | 5417 | O | HOH | W | 82 | 7.478 | 3.451 | 5.218 | 1.00 | 30.66 W |
| ATOM | 5418 | O | HOH | W | 83 | −1.102 | 37.264 | 2.808 | 1.00 | 31.26 W |
| ATOM | 5419 | O | HOH | W | 84 | 24.889 | 4.773 | 30.816 | 1.00 | 25.16 W |
| ATOM | 5420 | O | HOH | W | 85 | 19.436 | 35.034 | 29.941 | 1.00 | 29.97 W |
| ATOM | 5421 | O | HOH | W | 86 | −3.763 | −3.330 | 9.798 | 1.00 | 33.95 W |
| ATOM | 5422 | O | HOH | W | 87 | 0.070 | 29.723 | −4.420 | 1.00 | 20.98 W |
| ATOM | 5423 | O | HOH | W | 88 | 21.317 | 25.487 | 15.130 | 1.00 | 19.92 W |
| ATOM | 5424 | O | HOH | W | 89 | 29.507 | 9.736 | 12.251 | 1.00 | 31.78 W |
| ATOM | 5425 | O | HOH | W | 90 | 16.712 | 38.960 | 21.105 | 1.00 | 21.71 W |
| ATOM | 5426 | O | HOH | W | 91 | −3.537 | 41.000 | 5.604 | 1.00 | 27.09 W |
| ATOM | 5427 | O | HOH | W | 92 | 2.058 | 28.838 | 3.074 | 1.00 | 30.16 W |
| ATOM | 5428 | O | HOH | W | 93 | 22.828 | 38.394 | 30.972 | 1.00 | 28.01 W |
| ATOM | 5429 | O | HOH | W | 94 | 9.284 | 22.193 | 26.828 | 1.00 | 23.69 W |
| ATOM | 5430 | O | HOH | W | 95 | 3.985 | −18.017 | 36.098 | 1.00 | 32.32 W |
| ATOM | 5431 | O | HOH | W | 96 | 28.767 | 6.441 | 17.253 | 1.00 | 30.51 W |
| ATOM | 5432 | O | HOH | W | 97 | 39.368 | 35.015 | 19.824 | 1.00 | 34.80 W |
| ATOM | 5433 | O | HOH | W | 98 | 19.002 | 20.208 | 30.585 | 1.00 | 25.43 W |
| ATOM | 5434 | O | HOH | W | 99 | 0.860 | 3.535 | 41.135 | 1.00 | 31.34 W |
| ATOM | 5435 | O | HOH | W | 100 | −3.957 | −7.281 | 36.440 | 1.00 | 22.79 W |
| ATOM | 5436 | O | HOH | W | 101 | 25.636 | 11.661 | 20.100 | 1.00 | 23.96 W |

TABLE 2-continued

| | | | | | | | | | | |
|---|---|---|---|---|---|---|---|---|---|---|
| ATOM | 5437 | O | HOH | W | 102 | 14.563 | 26.171 | 27.857 | 1.00 | 25.50 W |
| ATOM | 5438 | O | HOH | W | 103 | 13.033 | 9.787 | 31.788 | 1.00 | 19.12 W |
| ATOM | 5439 | O | HOH | W | 104 | 13.671 | −22.210 | 45.078 | 1.00 | 32.32 W |
| ATOM | 5440 | O | HOH | W | 105 | 15.309 | −1.814 | 4.838 | 1.00 | 25.74 W |
| ATOM | 5441 | O | HOH | W | 106 | 23.286 | 17.123 | 22.699 | 1.00 | 32.55 W |
| ATOM | 5442 | O | HOH | W | 107 | 24.172 | 11.452 | 22.572 | 1.00 | 15.83 W |
| ATOM | 5443 | O | HOH | W | 108 | 8.296 | 7.770 | 2.718 | 1.00 | 43.73 W |
| ATOM | 5444 | O | HOH | W | 109 | 2.724 | 8.988 | 22.864 | 1.00 | 23.77 W |
| ATOM | 5445 | O | HOH | W | 110 | 21.667 | −4.838 | 25.392 | 1.00 | 18.94 W |
| ATOM | 5446 | O | HOH | W | 111 | 19.054 | 36.694 | −8.037 | 1.00 | 31.13 W |
| ATOM | 5447 | O | HOH | W | 112 | 19.954 | 42.665 | −4.614 | 1.00 | 33.84 W |
| ATOM | 5448 | O | HOH | W | 113 | 24.939 | −8.048 | 22.820 | 1.00 | 30.66 W |
| ATOM | 5449 | O | HOH | W | 114 | 3.058 | 13.336 | 34.670 | 1.00 | 36.40 W |
| ATOM | 5450 | O | HOH | W | 115 | 15.948 | 44.074 | 27.434 | 1.00 | 22.99 W |
| ATOM | 5451 | O | HOH | W | 116 | 13.993 | 23.239 | −11.578 | 1.00 | 30.94 W |
| ATOM | 5452 | O | HOH | W | 117 | −5.904 | 25.585 | 1.138 | 1.00 | 28.47 W |
| ATOM | 5453 | O | HOH | W | 118 | 35.355 | 42.252 | 13.575 | 1.00 | 35.41 W |
| ATOM | 5454 | O | HOH | W | 119 | −1.531 | 5.644 | 16.680 | 1.00 | 39.62 W |
| ATOM | 5455 | O | HOH | W | 120 | 26.452 | 15.032 | 29.043 | 1.00 | 40.51 W |
| ATOM | 5456 | O | HOH | W | 121 | 25.201 | −5.176 | 23.848 | 1.00 | 32.54 W |
| ATOM | 5457 | O | HOH | W | 122 | −0.624 | 27.222 | 3.157 | 1.00 | 36.61 W |
| ATOM | 5458 | O | HOH | W | 123 | 10.721 | −16.970 | 44.703 | 1.00 | 30.04 W |
| ATOM | 5459 | O | HOH | W | 124 | 27.180 | 9.713 | 19.059 | 1.00 | 21.96 W |
| ATOM | 5460 | O | HOH | W | 125 | 14.433 | −8.850 | 5.932 | 1.00 | 31.47 W |
| ATOM | 5461 | O | HOH | W | 126 | 23.876 | 24.249 | −2.724 | 1.00 | 21.42 W |
| ATOM | 5462 | O | HOH | W | 127 | −0.948 | 32.985 | −0.899 | 1.00 | 24.62 W |
| ATOM | 5463 | O | HOH | W | 128 | 7.801 | −16.307 | 33.953 | 1.00 | 31.29 W |
| ATOM | 5464 | O | HOH | W | 129 | 20.410 | 20.380 | 23.747 | 1.00 | 33.65 W |
| ATOM | 5465 | O | HOH | W | 131 | 14.030 | 44.772 | 0.063 | 1.00 | 26.62 W |
| ATOM | 5466 | O | HOH | W | 132 | 30.159 | 50.256 | −4.517 | 1.00 | 32.29 W |
| ATOM | 5467 | O | HOH | W | 133 | 26.508 | 21.268 | 2.601 | 1.00 | 28.60 W |
| ATOM | 5468 | O | HOH | W | 134 | 11.823 | 41.645 | 14.572 | 1.00 | 18.92 W |
| ATOM | 5469 | O | HOH | W | 135 | 24.762 | 42.790 | 2.730 | 1.00 | 23.32 W |
| ATOM | 5470 | O | HOH | W | 137 | 22.040 | 19.987 | −4.228 | 1.00 | 46.10 W |
| ATOM | 5471 | O | HOH | W | 138 | 42.354 | 44.107 | 2.423 | 1.00 | 43.23 W |
| ATOM | 5472 | O | HOH | W | 139 | −1.546 | 4.964 | 19.391 | 1.00 | 23.33 W |
| ATOM | 5473 | O | HOH | W | 140 | 17.786 | 34.186 | 17.907 | 1.00 | 21.15 W |
| ATOM | 5474 | O | HOH | W | 141 | 23.942 | −10.433 | 44.626 | 1.00 | 28.83 W |
| ATOM | 5475 | O | HOH | W | 142 | 14.103 | −11.214 | 39.418 | 1.00 | 26.66 W |
| ATOM | 5476 | O | HOH | W | 143 | 6.494 | 45.366 | −3.941 | 1.00 | 37.81 W |
| ATOM | 5477 | O | HOH | W | 144 | 1.145 | −11.093 | 21.122 | 1.00 | 30.40 W |
| ATOM | 5478 | O | HOH | W | 145 | 24.188 | −1.703 | 23.090 | 1.00 | 37.48 W |
| ATOM | 5479 | O | HOH | W | 146 | 19.956 | 18.125 | 42.965 | 1.00 | 31.86 W |
| ATOM | 5480 | O | HOH | W | 147 | 11.530 | 38.431 | 14.796 | 1.00 | 37.74 W |
| ATOM | 5481 | O | HOH | W | 148 | 34.094 | 42.825 | 15.848 | 1.00 | 31.85 W |
| ATOM | 5482 | O | HOH | W | 149 | −1.116 | 21.727 | 17.827 | 1.00 | 25.07 W |
| ATOM | 5483 | O | HOH | W | 150 | 36.884 | 48.719 | −1.273 | 1.00 | 29.60 W |
| ATOM | 5484 | O | HOH | W | 151 | −0.907 | −5.418 | 45.753 | 1.00 | 41.36 W |
| ATOM | 5485 | O | HOH | W | 153 | 14.564 | 36.418 | 16.445 | 1.00 | 32.21 W |
| ATOM | 5486 | O | HOH | W | 154 | 25.471 | −16.031 | 34.304 | 1.00 | 40.29 W |
| ATOM | 5487 | O | HOH | W | 155 | 9.101 | −22.454 | 38.744 | 1.00 | 35.78 W |
| ATOM | 5488 | O | HOH | W | 156 | −2.350 | −1.857 | 34.291 | 1.00 | 35.57 W |
| ATOM | 5489 | O | HOH | W | 157 | 13.668 | 14.445 | 11.210 | 1.00 | 34.96 W |
| ATOM | 5490 | O | HOH | W | 158 | 19.352 | 41.229 | −2.423 | 1.00 | 28.29 W |
| ATOM | 5491 | O | HOH | W | 159 | −0.734 | −1.890 | 44.440 | 1.00 | 31.74 W |
| ATOM | 5492 | O | HOH | W | 160 | 23.964 | 21.734 | −3.660 | 1.00 | 31.08 W |
| ATOM | 5493 | O | HOH | W | 161 | −10.017 | −8.814 | 19.418 | 1.00 | 40.16 W |
| ATOM | 5494 | O | HOH | W | 162 | 17.539 | −6.204 | 4.702 | 1.00 | 24.11 W |
| ATOM | 5495 | O | HOH | W | 163 | 29.741 | −5.988 | 32.677 | 1.00 | 31.42 W |
| ATOM | 5496 | O | HOH | W | 164 | 28.001 | −9.645 | 21.744 | 1.00 | 33.82 W |
| ATOM | 5497 | O | HOH | W | 165 | 0.760 | 40.602 | 11.593 | 1.00 | 30.23 W |
| ATOM | 5498 | O | HOH | W | 166 | 18.668 | 17.337 | 25.714 | 1.00 | 41.07 W |
| ATOM | 5499 | O | HOH | W | 168 | 7.720 | 41.267 | 12.098 | 1.00 | 26.51 W |
| ATOM | 5500 | O | HOH | W | 169 | 4.377 | 0.505 | 6.699 | 1.00 | 49.69 W |
| ATOM | 5501 | O | HOH | W | 170 | 16.156 | 12.924 | 6.910 | 1.00 | 33.21 W |
| ATOM | 5502 | O | HOH | W | 171 | 17.725 | 43.920 | −0.551 | 1.00 | 24.17 W |
| ATOM | 5503 | O | HOH | W | 172 | 0.459 | −12.235 | 47.031 | 1.00 | 33.75 W |
| ATOM | 5504 | O | HOH | W | 173 | 30.732 | 13.058 | 15.124 | 1.00 | 29.90 W |
| ATOM | 5505 | O | HOH | W | 174 | 11.356 | 35.894 | 17.493 | 1.00 | 25.46 W |
| ATOM | 5506 | O | HOH | W | 175 | 23.779 | 25.505 | 26.926 | 1.00 | 39.30 W |
| ATOM | 5507 | O | HOH | W | 176 | −0.665 | 7.937 | 15.517 | 1.00 | 30.68 W |
| ATOM | 5508 | O | HOH | W | 177 | 33.642 | 17.965 | 11.163 | 1.00 | 49.77 W |
| ATOM | 5509 | O | HOH | W | 178 | 12.538 | −15.968 | 22.560 | 1.00 | 25.37 W |
| ATOM | 5510 | O | HOH | W | 179 | 18.776 | −10.986 | 49.211 | 1.00 | 55.81 W |
| ATOM | 5511 | O | HOH | W | 180 | 0.483 | 5.084 | 28.763 | 1.00 | 37.57 W |
| ATOM | 5512 | O | HOH | W | 181 | 29.115 | 60.930 | 4.087 | 1.00 | 56.19 W |
| ATOM | 5513 | O | HOH | W | 182 | 9.546 | −3.129 | 6.126 | 1.00 | 43.37 W |
| ATOM | 5514 | O | HOH | W | 183 | 7.223 | −10.154 | 45.111 | 1.00 | 33.68 W |
| ATOM | 5515 | O | HOH | W | 184 | 21.609 | 22.844 | 22.266 | 1.00 | 23.54 W |

TABLE 2-continued

| | | | | | | | | | | |
|---|---|---|---|---|---|---|---|---|---|---|
| ATOM | 5516 | O | HOH | W | 185 | 25.045 | 40.463 | 33.659 | 1.00 | 43.23 W |
| ATOM | 5517 | O | HOH | W | 186 | 2.798 | 19.840 | 23.221 | 1.00 | 28.72 W |
| ATOM | 5518 | O | HOH | W | 187 | 35.149 | 45.916 | 19.323 | 1.00 | 46.96 W |
| ATOM | 5519 | O | HOH | W | 188 | 16.850 | 45.647 | 4.603 | 1.00 | 36.05 W |
| ATOM | 5520 | O | HOH | W | 189 | 31.164 | 12.579 | 2.121 | 1.00 | 36.80 W |
| ATOM | 5521 | O | HOH | W | 190 | 4.482 | 14.506 | 36.580 | 1.00 | 36.65 W |
| ATOM | 5522 | O | HOH | W | 191 | 30.060 | 21.331 | 25.530 | 1.00 | 28.14 W |
| ATOM | 5523 | O | HOH | W | 192 | 0.740 | −8.650 | 24.454 | 1.00 | 29.26 W |
| ATOM | 5524 | O | HOH | W | 193 | 29.066 | 49.529 | 7.946 | 1.00 | 25.56 W |
| ATOM | 5525 | O | HOH | W | 194 | 15.980 | −15.806 | 30.435 | 1.00 | 38.32 W |
| ATOM | 5526 | O | HOH | W | 195 | 14.674 | −1.144 | 42.845 | 1.00 | 38.18 W |
| ATOM | 5527 | O | HOH | W | 196 | 30.078 | 13.112 | 22.025 | 1.00 | 50.79 W |
| ATOM | 5528 | O | HOH | W | 197 | 13.401 | −13.755 | 45.484 | 1.00 | 36.75 W |
| ATOM | 5529 | O | HOH | W | 198 | −2.478 | −8.276 | 41.991 | 1.00 | 27.69 W |
| ATOM | 5530 | O | HOH | W | 199 | 24.180 | −4.901 | 21.333 | 1.00 | 27.65 W |
| ATOM | 5531 | O | HOH | W | 200 | 30.519 | 11.752 | 9.670 | 1.00 | 31.30 W |
| ATOM | 5532 | O | HOH | W | 201 | 27.815 | −1.263 | 26.975 | 1.00 | 34.58 W |
| ATOM | 5533 | O | HOH | W | 202 | 39.243 | 27.120 | 26.384 | 1.00 | 42.73 W |
| ATOM | 5534 | O | HOH | W | 203 | 7.031 | 39.708 | −8.535 | 1.00 | 43.10 W |
| ATOM | 5535 | O | HOH | W | 205 | 26.957 | −11.442 | 11.948 | 1.00 | 32.18 W |
| ATOM | 5536 | O | HOH | W | 206 | 2.139 | 25.701 | 3.586 | 1.00 | 24.66 W |
| ATOM | 5537 | O | HOH | W | 207 | −2.639 | −5.829 | 43.496 | 1.00 | 20.75 W |
| ATOM | 5538 | O | HOH | W | 208 | 10.766 | 25.886 | 23.937 | 1.00 | 26.10 W |
| ATOM | 5539 | O | HOH | W | 209 | 17.856 | −15.863 | 41.163 | 1.00 | 24.60 W |
| ATOM | 5540 | O | HOH | W | 210 | 29.134 | 9.212 | 17.294 | 1.00 | 27.68 W |
| ATOM | 5541 | O | HOH | W | 211 | 23.343 | 1.812 | 25.289 | 1.00 | 23.29 W |
| ATOM | 5542 | O | HOH | W | 212 | 27.741 | 54.838 | 9.595 | 1.00 | 24.89 W |
| ATOM | 5543 | O | HOH | W | 213 | 33.081 | 23.635 | 3.685 | 1.00 | 22.39 W |
| ATOM | 5544 | O | HOH | W | 214 | 20.368 | 36.865 | 31.789 | 1.00 | 31.59 W |
| ATOM | 5545 | O | HOH | W | 215 | 20.879 | 18.165 | 21.790 | 1.00 | 29.57 W |
| ATOM | 5546 | O | HOH | W | 216 | 1.269 | 21.473 | 13.930 | 1.00 | 32.04 W |
| ATOM | 5547 | O | HOH | W | 217 | 29.881 | 10.423 | 14.748 | 1.00 | 28.03 W |
| ATOM | 5548 | O | HOH | W | 218 | 18.056 | −13.596 | 17.921 | 1.00 | 31.04 W |
| ATOM | 5549 | O | HOH | W | 219 | 1.991 | −12.889 | 43.464 | 1.00 | 35.32 W |
| ATOM | 5550 | O | HOH | W | 220 | 15.759 | −12.503 | 41.417 | 1.00 | 28.33 W |
| ATOM | 5551 | O | HOH | W | 221 | 25.820 | 5.877 | 28.354 | 1.00 | 28.52 W |
| ATOM | 5552 | O | HOH | W | 222 | 4.982 | 32.970 | 22.441 | 1.00 | 39.46 W |
| ATOM | 5553 | O | HOH | W | 223 | 17.476 | 30.887 | 28.958 | 1.00 | 26.47 W |
| ATOM | 5554 | O | HOH | W | 224 | 11.291 | 41.349 | 1.417 | 1.00 | 37.24 W |
| ATOM | 5555 | O | HOH | W | 225 | 29.880 | 51.712 | 9.177 | 1.00 | 29.75 W |
| ATOM | 5556 | O | HOH | W | 226 | 40.211 | 32.579 | 20.654 | 1.00 | 30.21 W |
| ATOM | 5557 | O | HOH | W | 227 | 22.885 | 5.920 | 5.241 | 1.00 | 41.08 W |
| ATOM | 5558 | O | HOH | W | 228 | −6.490 | 28.305 | 6.799 | 1.00 | 30.25 W |
| ATOM | 5559 | O | HOH | W | 229 | 17.302 | −1.431 | 42.690 | 1.00 | 36.18 W |
| ATOM | 5560 | O | HOH | W | 230 | 0.125 | −11.638 | 23.724 | 1.00 | 35.78 W |
| ATOM | 5561 | O | HOH | W | 231 | 8.507 | 23.950 | 24.522 | 1.00 | 32.56 W |
| ATOM | 5562 | O | HOH | W | 232 | 26.160 | −1.690 | 20.722 | 1.00 | 29.53 W |
| ATOM | 5563 | O | HOH | W | 233 | 13.398 | 42.760 | 16.890 | 1.00 | 27.10 W |
| ATOM | 5564 | O | HOH | W | 234 | 22.357 | 40.731 | 32.179 | 1.00 | 30.74 W |
| ATOM | 5565 | O | HOH | W | 235 | 11.336 | −23.140 | 44.359 | 1.00 | 36.30 W |
| ATOM | 5566 | O | HOH | W | 236 | 17.508 | 38.327 | −9.628 | 1.00 | 35.63 W |
| ATOM | 5567 | O | HOH | W | 237 | 8.472 | 16.550 | 1.343 | 1.00 | 32.74 W |
| ATOM | 5568 | O | HOH | W | 238 | 31.364 | 23.487 | 27.239 | 1.00 | 31.19 W |
| ATOM | 5569 | O | HOH | W | 239 | 30.948 | 6.023 | 4.210 | 1.00 | 37.30 W |
| ATOM | 5570 | O | HOH | W | 240 | 26.615 | 45.872 | 30.472 | 1.00 | 39.41 W |
| ATOM | 5571 | O | HOH | W | 241 | 19.326 | 46.651 | 5.986 | 1.00 | 24.47 W |
| ATOM | 5572 | O | HOH | W | 242 | 40.219 | 38.031 | 2.750 | 1.00 | 41.15 W |
| ATOM | 5573 | O | HOH | W | 243 | 7.631 | 6.447 | 5.192 | 1.00 | 32.07 W |
| ATOM | 5574 | O | HOH | W | 244 | 14.947 | −4.945 | 5.698 | 1.00 | 46.51 W |
| ATOM | 5575 | O | HOH | W | 245 | 29.878 | 11.916 | 6.941 | 1.00 | 37.43 W |
| ATOM | 5576 | O | HOH | W | 246 | 13.119 | −15.352 | 25.333 | 1.00 | 31.96 W |
| ATOM | 5577 | O | HOH | W | 247 | 26.386 | −7.472 | 25.343 | 1.00 | 31.30 W |
| ATOM | 5578 | O | HOH | W | 248 | 30.165 | 34.873 | −2.447 | 1.00 | 37.59 W |
| ATOM | 5579 | O | HOH | W | 249 | 24.264 | 20.123 | 21.179 | 1.00 | 44.76 W |
| ATOM | 5580 | O | HOH | W | 250 | 33.782 | 14.688 | 27.127 | 1.00 | 48.15 W |
| ATOM | 5581 | O | HOH | W | 251 | 15.163 | 49.239 | 20.591 | 1.00 | 35.54 W |
| ATOM | 5582 | O | HOH | W | 252 | 14.290 | 3.113 | 0.051 | 1.00 | 44.21 W |
| ATOM | 5583 | O | HOH | W | 253 | 29.234 | 14.802 | 36.478 | 1.00 | 37.15 W |
| ATOM | 5584 | O | HOH | W | 254 | 1.939 | 17.834 | 27.020 | 1.00 | 36.48 W |
| ATOM | 5585 | O | HOH | W | 255 | 39.232 | 22.885 | 9.402 | 1.00 | 35.89 W |
| ATOM | 5586 | O | HOH | W | 256 | 16.614 | 47.670 | 30.134 | 1.00 | 30.62 W |
| ATOM | 5587 | O | HOH | W | 257 | 32.555 | −3.038 | 6.133 | 1.00 | 35.15 W |
| ATOM | 5588 | O | HOH | W | 258 | −2.289 | 19.140 | 4.977 | 1.00 | 39.69 W |
| ATOM | 5589 | O | HOH | W | 259 | 1.553 | −17.001 | 34.997 | 1.00 | 42.78 W |
| ATOM | 5590 | O | HOH | W | 260 | 15.155 | 12.430 | 41.749 | 1.00 | 32.11 W |
| ATOM | 5591 | O | HOH | W | 261 | 13.134 | 22.891 | 29.312 | 1.00 | 32.55 W |
| ATOM | 5592 | O | HOH | W | 262 | 1.356 | 29.398 | 0.186 | 1.00 | 39.92 W |
| ATOM | 5593 | O | HOH | W | 263 | 15.490 | −2.292 | 1.286 | 1.00 | 33.40 W |
| ATOM | 5594 | O | HOH | W | 264 | 24.801 | −17.578 | 28.195 | 1.00 | 37.92 W |

TABLE 2-continued

| | | | | | | | | | | |
|---|---|---|---|---|---|---|---|---|---|---|
| ATOM | 5595 | O | HOH | W | 265 | 40.969 | 36.681 | 18.857 | 1.00 | 34.76 W |
| ATOM | 5596 | O | HOH | W | 266 | −0.099 | −7.970 | 26.768 | 1.00 | 37.14 W |
| ATOM | 5597 | O | HOH | W | 267 | −5.600 | −4.895 | 36.300 | 1.00 | 28.04 W |
| ATOM | 5598 | O | HOH | W | 268 | 18.635 | 53.684 | 14.149 | 1.00 | 39.24 W |
| ATOM | 5599 | O | HOH | W | 269 | 21.160 | −22.110 | 44.292 | 1.00 | 31.93 W |
| ATOM | 5600 | O | HOH | W | 270 | 16.653 | 8.689 | 44.684 | 1.00 | 35.93 W |
| ATOM | 5601 | O | HOH | W | 271 | 8.044 | 30.381 | −7.362 | 1.00 | 36.73 W |
| ATOM | 5602 | O | HOH | W | 272 | 1.315 | 11.442 | 31.274 | 1.00 | 36.98 W |
| ATOM | 5603 | O | HOH | W | 273 | 8.987 | −21.995 | 41.278 | 1.00 | 43.76 W |
| ATOM | 5604 | O | HOH | W | 274 | 27.222 | −8.171 | 44.730 | 1.00 | 34.99 W |
| ATOM | 5605 | O | HOH | W | 275 | −3.218 | 10.852 | 23.922 | 1.00 | 38.19 W |
| ATOM | 5606 | O | HOH | W | 276 | 16.524 | 33.011 | 27.952 | 1.00 | 36.27 W |
| ATOM | 5607 | O | HOH | W | 277 | 13.566 | −15.726 | 47.855 | 1.00 | 39.75 W |
| ATOM | 5608 | O | HOH | W | 278 | 9.788 | 28.090 | 22.420 | 1.00 | 36.95 W |
| ATOM | 5609 | O | HOH | W | 279 | 2.038 | −0.985 | 42.549 | 1.00 | 29.62 W |
| ATOM | 5610 | O | HOH | W | 280 | −4.926 | 20.131 | 22.952 | 1.00 | 40.42 W |
| ATOM | 5611 | O | HOH | W | 281 | 13.468 | 39.982 | 16.142 | 1.00 | 40.09 W |
| ATOM | 5612 | O | HOH | W | 282 | 30.531 | 3.268 | 28.753 | 1.00 | 45.55 W |
| ATOM | 5613 | O | HOH | W | 283 | 20.900 | −19.423 | 51.054 | 1.00 | 38.60 W |
| ATOM | 5614 | O | HOH | W | 284 | 31.426 | 44.515 | −6.883 | 1.00 | 34.68 W |
| ATOM | 5615 | O | HOH | W | 285 | 13.964 | 35.075 | −10.523 | 1.00 | 43.27 W |
| ATOM | 5616 | O | HOH | W | 286 | −0.116 | 39.809 | 13.953 | 1.00 | 34.96 W |
| ATOM | 5617 | O | HOH | W | 287 | 21.093 | 0.363 | 45.524 | 1.00 | 38.08 W |
| ATOM | 5618 | O | HOH | W | 288 | 3.056 | 26.921 | 0.409 | 1.00 | 37.24 W |
| ATOM | 5619 | O | HOH | W | 289 | 15.649 | 14.637 | 8.810 | 1.00 | 41.00 W |
| ATOM | 5620 | O | HOH | W | 290 | 10.922 | 30.495 | 22.729 | 1.00 | 34.18 W |
| ATOM | 5621 | O | HOH | W | 291 | 31.775 | −6.708 | 30.429 | 1.00 | 43.95 W |
| ATOM | 5622 | O | HOH | W | 292 | −1.428 | 26.105 | 1.010 | 1.00 | 36.92 W |
| ATOM | 5623 | O | HOH | W | 293 | 24.971 | −17.752 | 42.875 | 1.00 | 35.76 W |
| ATOM | 5624 | O | HOH | W | 294 | 23.232 | 25.011 | 29.967 | 1.00 | 40.39 W |
| ATOM | 5625 | O | HOH | W | 295 | 12.419 | 35.901 | 20.319 | 1.00 | 38.87 W |
| ATOM | 5626 | O | HOH | W | 296 | 11.317 | 15.747 | 36.016 | 1.00 | 40.10 W |
| ATOM | 5627 | O | HOH | W | 297 | 3.160 | −3.418 | 46.260 | 1.00 | 42.94 W |
| ATOM | 5628 | O | HOH | W | 298 | −4.846 | −3.201 | 33.946 | 1.00 | 41.88 W |
| ATOM | 5629 | O | HOH | W | 299 | 1.910 | −14.630 | 12.849 | 1.00 | 47.08 W |
| ATOM | 5630 | O | HOH | W | 300 | 10.291 | −5.920 | 6.807 | 1.00 | 46.76 W |
| ATOM | 5631 | O | HOH | W | 301 | 26.461 | −10.577 | 44.997 | 1.00 | 36.54 W |
| ATOM | 5632 | O | HOH | W | 302 | −4.047 | 24.599 | 4.391 | 1.00 | 46.45 W |
| ATOM | 5633 | O | HOH | W | 303 | 14.690 | 25.613 | 32.659 | 1.00 | 51.09 W |
| ATOM | 5634 | O | HOH | W | 304 | 8.384 | 20.073 | 28.849 | 1.00 | 45.29 W |
| ATOM | 5635 | O | HOH | W | 305 | 9.442 | 12.765 | 10.381 | 1.00 | 42.60 W |
| ATOM | 5636 | O | HOH | W | 306 | 37.334 | 24.155 | 12.850 | 1.00 | 34.80 W |
| ATOM | 5637 | O | HOH | W | 307 | 23.914 | −20.195 | 27.220 | 1.00 | 43.22 W |
| ATOM | 5638 | O | HOH | W | 308 | 0.684 | −13.695 | 20.130 | 1.00 | 34.10 W |
| ATOM | 5639 | O | HOH | W | 309 | 16.030 | −13.142 | 44.203 | 1.00 | 38.82 W |
| ATOM | 5640 | O | HOH | W | 310 | 20.937 | 44.215 | −1.084 | 1.00 | 40.20 W |
| ATOM | 5641 | O | HOH | W | 311 | −3.355 | −4.210 | 38.115 | 1.00 | 32.38 W |
| ATOM | 5642 | O | HOH | W | 312 | −0.193 | −10.941 | 13.004 | 1.00 | 44.80 W |
| ATOM | 5643 | O | HOH | W | 313 | −1.398 | −9.899 | 9.421 | 1.00 | 42.24 W |
| ATOM | 5644 | O | HOH | W | 314 | 32.082 | 54.976 | 16.970 | 1.00 | 43.72 W |
| ATOM | 5645 | O | HOH | W | 315 | 10.534 | −14.518 | 25.108 | 1.00 | 38.70 W |
| ATOM | 5646 | O | HOH | W | 316 | 15.222 | −14.044 | 26.095 | 1.00 | 36.31 W |
| ATOM | 5647 | O | HOH | W | 317 | 39.673 | 32.342 | 23.136 | 1.00 | 43.10 W |
| ATOM | 5648 | O | HOH | W | 318 | 3.077 | −11.273 | 47.472 | 1.00 | 43.71 W |
| ATOM | 5649 | O | HOH | W | 319 | 0.005 | 11.290 | 14.724 | 1.00 | 46.16 W |
| ATOM | 5650 | O | HOH | W | 320 | 12.121 | 14.747 | 40.180 | 1.00 | 43.75 W |
| ATOM | 5651 | O | HOH | W | 321 | 16.889 | 20.109 | 40.511 | 1.00 | 41.01 W |
| ATOM | 5652 | O | HOH | W | 322 | 32.369 | 12.818 | 17.426 | 1.00 | 35.81 W |
| ATOM | 5653 | O | HOH | W | 323 | 26.413 | 13.788 | −5.898 | 1.00 | 52.65 W |
| ATOM | 5654 | O | HOH | W | 324 | 20.779 | 52.316 | 24.144 | 1.00 | 44.47 W |
| ATOM | 5655 | O | HOH | W | 325 | 2.891 | 11.216 | 27.584 | 1.00 | 39.00 W |
| ATOM | 5656 | O | HOH | W | 326 | 17.056 | −19.095 | 14.177 | 1.00 | 41.89 W |
| ATOM | 5657 | O | HOH | W | 327 | 30.349 | −2.177 | 26.445 | 1.00 | 51.16 W |
| ATOM | 5658 | O | HOH | W | 328 | 24.569 | 18.609 | −6.806 | 1.00 | 41.46 W |
| ATOM | 5659 | O | HOH | W | 329 | 8.480 | −13.826 | 27.951 | 1.00 | 43.20 W |
| ATOM | 5660 | O | HOH | W | 330 | 31.641 | 9.093 | 10.231 | 1.00 | 41.86 W |
| ATOM | 5661 | O | HOH | W | 331 | 10.366 | 44.118 | 2.341 | 1.00 | 39.86 W |
| ATOM | 5662 | O | HOH | W | 332 | 36.931 | 48.743 | 3.962 | 1.00 | 35.49 W |
| ATOM | 5663 | O | HOH | W | 333 | 26.668 | 19.551 | 28.746 | 1.00 | 45.32 W |
| ATOM | 5664 | O | HOH | W | 334 | 16.843 | 45.042 | −3.051 | 1.00 | 42.25 W |
| ATOM | 5665 | O | HOH | W | 335 | 42.140 | 50.797 | −2.692 | 1.00 | 41.41 W |
| ATOM | 5666 | O | HOH | W | 336 | 40.032 | 30.338 | 30.316 | 1.00 | 46.04 W |
| ATOM | 5667 | O | HOH | W | 337 | 26.941 | 16.456 | 40.201 | 1.00 | 42.67 W |
| ATOM | 5668 | O | HOH | W | 338 | 3.053 | −16.424 | 17.722 | 1.00 | 46.61 W |
| ATOM | 5669 | O | HOH | W | 339 | −2.774 | −5.761 | 28.409 | 1.00 | 39.39 W |
| ATOM | 5670 | O | HOH | W | 340 | 34.391 | 42.225 | 18.425 | 1.00 | 36.32 W |
| ATOM | 5671 | O | HOH | W | 341 | 34.199 | 56.068 | 4.324 | 1.00 | 41.66 W |
| ATOM | 5672 | O | HOH | W | 342 | 20.148 | −7.147 | −1.451 | 1.00 | 34.79 W |
| ATOM | 5673 | O | HOH | W | 343 | 29.115 | 54.457 | 19.899 | 1.00 | 40.93 W |

TABLE 2-continued

| ATOM | 5674 | O | HOH | W | 344 | 17.743 | 43.968 | -5.079 | 1.00 | 43.89 | W |
| ATOM | 5675 | O | HOH | W | 345 | 36.280 | 50.949 | -2.561 | 1.00 | 42.66 | W |
| ATOM | 5676 | O | HOH | W | 346 | 7.128 | 19.648 | -1.124 | 1.00 | 41.68 | W |
| ATOM | 5677 | O | HOH | W | 347 | 8.547 | 14.097 | 36.084 | 1.00 | 36.23 | W |
| ATOM | 5678 | O | HOH | W | 348 | 37.654 | 44.030 | 27.926 | 1.00 | 50.15 | W |
| ATOM | 5679 | O | HOH | W | 349 | 33.172 | 29.124 | 30.667 | 1.00 | 45.70 | W |
| ATOM | 5680 | O | HOH | W | 350 | 27.741 | 27.513 | -12.391 | 1.00 | 53.77 | W |
| ATOM | 5681 | O | HOH | W | 351 | 8.225 | -0.249 | 46.162 | 1.00 | 41.14 | W |
| END | | | | | | | | | | | |

REFERENCES

The following references are hereby incorporated by reference:

1. Fisher, G. H., *Exs.* 85:109-118, 1998.
2. Keenan, M. V., and Alworth, W. L., *Biochem. Biophys. Res. Commun.* 57:500-504, 1974.
3. Kleinkauf, H., and von Dohren, H., *Ann. Rev. Microbiol.* 41:259-289, 1987.
4. Lamzin, V. S., et al., *Curr. Opin. Struct. Biol.* 5:830-836, 1995.
5. Nagata, Y., et al., *Biochim. Biophys. Acta* 1379:76-82, 1998.
6. Nagata, Y., et al., *Biochim. Biophys. Acta* 1435:160-166, 1999.
7. Nagata, Y., et al., *FEBS* 454:317-320, 1999.
8. Neidle, A., and Dunlop, D. S., *Life Sci.* 46:1512-1522, 1990.
9. Oguri, S., et al., *Biochim. Biophys. Acta* 1472:107-114, 1999.
10. Reina-San-Martin, B., et al., *Nature Medicine* 6:890-897, 2000.
11. Schell, M. J., et al., *PNAS USA* 92:3948-3952, 1995.
12. Wolosker, H., et al., *PNAS USA* 96:13409-13414, 1999.
13. The CCP4 Suite: Programs for Protein Crystallography, *Acta Crystallographica* D40:760-763, 1994.
14. Jones et al., *Acta Crystallography* A47:110-119, 1991.
15. Walters et al., *Drug Discovery Today* 3(4):160-178, 1998.
16. Dunbrack et al., *Folding and Design* 2:27-42, 1997.
17. Chamond, N., et al., *J. Biol. Chem.* 278(18):15484-15494, 2003.
18. Current Protocols in Protein Science, Vol. 1. Edited by Coligan, J. et al. pp. 5.3.9-5.3.14. John Willey & Sons, Inc. New York.
19. Miller, R., et al, *J. Appl. Cryst.* 27:613-621, 1994.
20. La Fortelle, E. de & Bricogne, G., *Meth. Enzymol.* 216: 412-494, 1997.
21. Abrahams, J. P. & Leslie, A. G. W., *Act Cryst* D52:30-42, 1996.

What is claimed is:

1. A crystal of *Trypanosoma cruzi* proline racemase form A (TcPRACA) in complex with pyrrole-2-carboxylic acid, wherein the TcPRACA consists of the amino acid sequence of SEQ ID NO:3, except methionine is replaced with selenomethionine, and wherein the crystal has monoclinic space group C2 with unit cell dimensions: a=131.1528 Å, b=91.2088 Å, c=85.9827 Å, and β=126.5217°.

2. A composition comprising the crystal of claim 1 and a salt.

3. The crystal of claim 1, wherein the crystal diffracts X-rays for a determination of structure coordinates of the TcPRACA to a resolution of 2.1 Å.

4. The crystal of claim 3, wherein the structure coordinates of the TcPRACA are defined by the data set of Table 2.

5. A method of making a crystal comprising TcPRACA, said method comprising:
   providing TcPRACA at a concentration of 5-6 mg/ml and pyrrole-2-carboxylic acid at a concentration of 1 mM in 25 mM sodium acetate, pH 5.2 to provide a protein solution, wherein the TcPRACA consists of the amino acid sequence of SEQ ID NO:3, except methionine is replaced with selenomethionine;
   mixing the protein solution with an equal volume of a buffer comprising 0.2 M ammonium acetate, 50 mM trisodium citrate dihydrate, pH 5.6, and 15% (w/v) polyethylene glycol 4000; and
   allowing a crystal comprising the TcPRACA in complex with pyrrole-2-carboxylic acid to form, wherein the crystal has monoclinic space group C2 with unit cell dimensions: a=131.1528 Å, b=91.2088 Å, c=85.9827 Å, and β=126.5217°.

6. A crystal of *Trypanosoma cruzi* proline racemase form A (TcPRACA), wherein the TcPRACA consists of the amino acid sequence of SEQ ID NO:3, and wherein the crystal has monoclinic space group C2 with unit cell dimensions: a=134.0651 Å, b=91.618 Å, c=86.0307 Å, and β=123.3735°.

7. A composition comprising the crystal of claim 6 and a salt.

8. The crystal of claim 6, wherein the crystal exhibits the diffraction data listed in Table 1.

* * * * *

UNITED STATES PATENT AND TRADEMARK OFFICE
CERTIFICATE OF CORRECTION

PATENT NO. : 7,585,656 B2
APPLICATION NO. : 10/853533
DATED : September 8, 2009
INVENTOR(S) : Paolo Minoprio et al.

It is certified that error appears in the above-identified patent and that said Letters Patent is hereby corrected as shown below:

*On the title page, item (54) and Column 1, lines 1 and 2, delete the title in its entirety and insert therefor --CRYSTALS OF *TRYPANOSOMA CRUZI* PROLINE RACEMASE FORM A--.

*On the title page, item (75) Inventors, lines 4-5, "Parede PaVegol (FR);" should read --Parede (PT);--.

On the title page, item (73) Assignee, line 1, "Institute" should read --Institut--.

Signed and Sealed this

Fifteenth Day of December, 2009

David J. Kappos
*Director of the United States Patent and Trademark Office*